United States Patent
Charne et al.

(10) Patent No.: US 10,526,613 B2
(45) Date of Patent: Jan. 7, 2020

(54) QTLS ASSOCIATED WITH AND METHODS FOR IDENTIFYING SHATTER RESISTANCE IN CANOLA

(71) Applicant: PIONEER HI-BRED INTERNATIONAL, INC., Johnston, IA (US)

(72) Inventors: David George Charne, Guelph (CA); Igor Falak, Guelph (CA); Xiuqiang Huang, Mississauga (CA); Siva S. Ammiraju Jetty, Johnston, IA (US); Jayantilal Devabhai Patel, Thornhill (CA); Lomas Tulsieram, Mississauga (CA)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 0 days.

(21) Appl. No.: 15/325,918

(22) PCT Filed: Jul. 15, 2015

(86) PCT No.: PCT/US2015/040559
§ 371 (c)(1),
(2) Date: Jan. 12, 2017

(87) PCT Pub. No.: WO2016/011146
PCT Pub. Date: Jan. 21, 2016

(65) Prior Publication Data
US 2017/0159067 A1 Jun. 8, 2017

Related U.S. Application Data

(60) Provisional application No. 62/024,686, filed on Jul. 15, 2014, provisional application No. 62/162,301, filed on May 15, 2015.

(51) Int. Cl.
| | | |
|---|---|---|
| *C12N 15/82* | (2006.01) | |
| *A01H 1/04* | (2006.01) | |
| *A01H 5/00* | (2018.01) | |
| *A01H 1/02* | (2006.01) | |
| *A01H 5/10* | (2018.01) | |
| *C12Q 1/6895* | (2018.01) | |

(52) U.S. Cl.
CPC .......... *C12N 15/8266* (2013.01); *A01H 1/02* (2013.01); *A01H 1/04* (2013.01); *A01H 5/00* (2013.01); *A01H 5/10* (2013.01); *C12N 15/82* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2012/0023603 A1 1/2012 Laga et al.

FOREIGN PATENT DOCUMENTS

WO 2012/084742 A1 6/2012

OTHER PUBLICATIONS

Dong et al (2014 Nature Communications pp. 1-11, ncomms4352 (Year: 2014).*
*Brassica* Information, Linkage Groups Assignments, 2016.
Jose R. Dinneny et al., A genetic framework for fruit patterning in *Arabidopsis thaliana*, Development, 2005, pp. 4687-4696, vol. 132.
S. Hossain et al., Breeding *Brassica napus* for Shatter Resistance, Jan. 2012, Plant Breeding, pp. 313-332.
Zhiyong Hu et al., Discovery of Pod Shatter-Resistant Associated SNPs by Deep Sequencing of a Representative Library Followed by Bulk Segregant Analysis in Rapeseed, PLOSOne, Apr. 2012, pp. 1-7, vol. 7, Issue 4.
G. P. Kadkol et al., Breeding *Brassica napus* For Shatter Resistance, DSIR Plant Breeding Symposium, 1996, pp. 58-62, Paper 11, Special Publication No. 5.
Gururaj Kadkol, *Brassica* Shatter-resistance research update, 16th Australian Research Assembly on *Brassicas*, 2009, pp. 1-6.
Jia Liu et al., Multigenic Control of Pod Shattering Resistance in Chinese Rapeseed Germplasm Revealed by Genome-Wide Association and Linkage Analyses, Frontiers in Plant Science, Jul. 2016, pp. 1-14, vol. 7, Article 1058.
Mikihiro Ogawa et al., *Arabidopsis* Dehiscence Zone Polygalacturonase1 (ADPG1), ADPG2, and QUARTET2 Are Polygalacturonases Required for Cell Separation during Reproductive Development in *Arabidopsis*, The Plant Cell, Jan. 2009, pp. 216-233, vol. 21.
Shyam Prakash et al., Reconstruction of allopolyploid *Brassicas* through non-homologous recombination: introgression of resistance to pod shatter in *Brassica napus*, Genetical Research, 1990, pp. 1-2, vol. 56, Issue 01—Abstract Only.
Harsh Raman et al., Genome-Wide Delineation of Natural Variation for Pod Shatter Resistance in *Brassica napus*, PLOS One, Jul. 2014, pp. 1-13, vol. 9, Issue 7.
Y. C. Wen et al., Identification of QTLs involved in pod-shatter resistance in *Brassica napus* L., United States Department of Agriculture, National Agricultural Library, Crop & Pasture Science, 2012, pp. 1082-1089, vol. 63, No. 12—Abstract Only.
Y. Zhang et al., The basis of pod dehiscence: anatomical traits of the dehiscence zone and expression of eight pod shatter-related genes in four species of Brassicaceae, Biologia Plantarum, 2016, pp. 343-354, vol. 60 (2).
International Search Report and Written Opinion, PCT/US2015/040559, dated Jan. 5, 2016.

* cited by examiner

*Primary Examiner* — Brent T Page

(57) ABSTRACT

Markers associated with shatter resistance in *Brassica* are provided. Methods of identifying shatter resistant and susceptible plants, using the markers are provided. Methods for identifying and isolating QTLs are a feature of the invention, as are QTLs associated with shatter resistance in *Brassica*.

15 Claims, No Drawings
Specification includes a Sequence Listing.

SEQUENCE LISTING

```
<160> NUMBER OF SEQ ID NOS: 830

<210> SEQ ID NO 1
<211> LENGTH: 401
<212> TYPE: DNA
<213> ORGANISM: Brassica napus

<400> SEQUENCE: 1
aaggagagac taaggaagga gcatatgcac tgacctttgc atccgtccgg tgtatatgcg      60
tttcctgtgt gcaaccacaa tgtgcataac taatattaga aatggtggtt ttgtcgcaga     120
tgcacttcat ttgggattta gtcgaggaag tattacgtcg gtactcttt ctgttgtcgc      180 agggcaagga actcaggaat kaatgattct ttgtttgtat cacccatcct agagtaaggg     240
tagcatatcc cttaccaagt aactgtgttg gtcttgtcgc attggacaaa gtgtagactt     300
catccgtcat gaaggccact ctacaatgtt cttctcttgt tgttgttgtt gttgtcgagt     360
ttccaccatt gctctctcta tcatgatgcc aatagtttgt t                         401

<210> SEQ ID NO 2
<211> LENGTH: 151
<212> TYPE: DNA
<213> ORGANISM: Brassica napus
<220> FEATURE:
<221> NAME/KEY: misc_feature
```

<222> LOCATION: (98)..(98)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t

<400> SEQUENCE: 2
gcttgatctc ttcaattcgg ggattagagc tttccggtac tcatgcggcc ccaatccaga    60
atcgatctct cactasggac tacttccctt ggtacagncg tncccaaggt cgccanttcg   120
cttcgaaatc aaacggtact gatgaaagca g                                  151

<210> SEQ ID NO 3
<211> LENGTH: 121
<212> TYPE: DNA
<213> ORGANISM: Brassica napus
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t

<400> SEQUENCE: 3
ttttgtccnt agctattcat aattaatcaa aaaggtggtc caattttaca ccttagtgct    60
rtgantatct ttcatacatc tctagagtgg aacatatgat actgcnaatt gcagttatat   120
t                                                                   121

<210> SEQ ID NO 4
<211> LENGTH: 401
<212> TYPE: DNA
<213> ORGANISM: Brassica napus

<400> SEQUENCE: 4
ttatgatggt gacaggagtt aagtgtgcat gtgaatgtag atgactgaaa aagatagcca    60
actacttata accaacatac gacctttggg tctttcctct tctctctctc aacttatttt   120
gattatacaa aatgttatgt ttgcaaactg gcatttaact gggccgctta gctctcttcg   180 gttattttttt tcttgtgata raccacattc agatatatat atgtcatctc gtcatgtgct   240
gttgttgttt tctatatcgt ttcgattaat caagaagttg ggaacgtcgg aactccaaac   300
caaatgtcct acgattatta attatacatg tatcctgatc atatctatct aacatgaacg   360
aaaatttgaa tctactataa aagaaatatt agagacaatt c                       401

<210> SEQ ID NO 5
<211> LENGTH: 801
<212> TYPE: DNA
<213> ORGANISM: Brassica napus
<220> FEATURE:
<221> NAME/KEY: misc_feature
<222> LOCATION: (1)..(90)
<223> OTHER INFORMATION: n is a, c, g, or t
<220> FEATURE:
<221> NAME/KEY: misc_feature
<222> LOCATION: (214)..(214)

```
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (633)..(732)
<223> OTHER INFORMATION: n is a, c, g, or t

<400> SEQUENCE: 5
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn ataactcttt tattcaagtg gagtttcaac     120
tttttgtaaa cctcagaatg cttcttttgt tccttcaaat tcaaacaata atgaataata     180
taacatactc tttttatacg cgatattaca ttanattcaa attcgaatnt tcttggatca     240
aatgcttcag gcctcatgta tgtgggccaa ttttgaatgg aatcgttggg ttatacttag     300
aagtagattc atcaggttta gttatgtggg gctcatgact cgcgtccatt gatcaaacaa     360
caagccctct catgtacaat gtangattat gttttcttca yaatcaacta gttagatttg     420
atgcatagcg gtggttaaca cataaccgat ttgtttttca attagttgtg gacaagcaac     480
tctaatttct gaatatagat tttatttagt catatgatta gcgccaaaga ttaacacaaa     540
agttattgac catagtctac ngaaatcaca accaaacacg agatacggca ttgtcaaaca     600
caaagtctaa aagagaatat aaagtttgag acnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnaggtcagg agaaggttct acaagaactg ggcaaagtcc aagaagaagg     780
ctttcaccgg gtacgccaag c                                               801

<210> SEQ ID NO 6
<211> LENGTH: 801
<212> TYPE: DNA
<213> ORGANISM: Brassica napus
<220> FEATURE:
<221> NAME/KEY: misc_feature
<222> LOCATION: (14)..(113)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t

<400> SEQUENCE: 6
```

```
acaataaaaa tatnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnncactttg   120
atatccataa acctaatctt ttataaaccc cctcttgagg ttctatcctc tgcgctcggc   180
tgtactttag gagaaatcta caccgtttat tttccctgag attaaaattt aatcacccta   240
cgctcttatt gggccgggcc gggccgagtt tgtactgaga aattggtttg agtgaactaa   300
tcctctgtag aaagctatac cgtacacaaa atcagngcnt tttcttcacc gtacgatgaa   360
tcagacgaaa gtaggatttt tttttagtga acagagagat kaattgggcc aggcccatta   420
gtagcttcgt tctataattt attcgtttct tagaacagaa gagttttttga ttgtgcaaaa   480 atcagaaaga gacgatcacg aagatggcga cggagagctc ttcagctaag agatggcttc   540
ctcttgaagc taacccagag gttatgaatc aggtattcgt ctcactttcc cttcttcttc   600
ttctccgatc atcngctttt ttttcgaaat tgggaagatt gattctaggt cagttcagtg   660
attttttttt gtattggtgt gtattgtgta cagtttcttt ggggnctggg tcttgcacca   720
gatgcagcgg agtgcaatga tgtgtttgga ttcgacgacg aacttcttga gatggttccn   780
aagcctgttc ttgctgttct c                                             801
```

<210> SEQ ID NO 7  
<211> LENGTH: 801  
<212> TYPE: DNA  
<213> ORGANISM: Brassica napus  
<220> FEATURE:  
<221> NAME/KEY: misc_feature  
<222> LOCATION: (69)..(69)  
<223> OTHER INFORMATION: n is a, c, g, or t  
<220> FEATURE:  
<221> NAME/KEY: misc_feature  
<222> LOCATION: (423)..(423)  
<223> OTHER INFORMATION: n is a, c, g, or t  
<220> FEATURE:  
<221> NAME/KEY: misc_feature  
<222> LOCATION: (676)..(676)  
<223> OTHER INFORMATION: n is a, c, g, or t  
<220> FEATURE:  
<221> NAME/KEY: misc_feature  
<222> LOCATION: (748)..(801)  
<223> OTHER INFORMATION: n is a, c, g, or t

<400> SEQUENCE: 7

```
agcaccacca tcgacatgcg accccttagg taacaccata tccgaaacat tttagtagct    60 gttatttnt ttctgattaa gatttagcct tcatattctt cttggatcat aactctttat   120
ttgctatatt caatgcacag tcatgaattc atattccatc cattattttc gttaatcact   180
cgtaaaatgc atattatatt gaggaaaaat aacaactcca cttaattaga cttatatgag   240
ccgtttcaaa tgtttgaaaa atcaacacaa ctagatatat aatttctta ctgatattgt   300 ggaaattggc tggatgttca aatgaaataa ttaatccgca tgaattgatg atgcttccct   360
tcaaagaaag acatttctaa tatggatacc ttgtttttgt rcaacttcta atatggatac   420
cangcattca aaatatgta aatgtaatat aggctttgat tggtaacatg taaatacttt   480
tgagttagac atacaactaa caaatgttac caactttgaa ttttgaaat tgtctttgag   540 ttgtgatgga ttattgttga gttacaattt tgtgttataa cctttataaa attgaccact   600
caaatgttaa atcaagataa aaaaatctc atgtattaaa atttgaattg gaaaaatggg   660
tttcataata attgcncacg tccatatttt atttaacaa attaaacaat ttacaaaaca   720
tgatcatata gtttagtacg tttaggtnnn nnnnnnnnn nnnnnnnnnn nnnnnnnnnn   780
```
nnnnnnnnnn nnnnnnnnnn n                                                         801

<210> SEQ ID NO 8
<211> LENGTH: 598
<212> TYPE: DNA
<213> ORGANISM: Brassica napus
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t

<400> SEQUENCE: 8
aatctccgaa cagagagaca tccttgtnaa aagtnngaga cttngcgaac ccatcaaatg      60
aaaaggagga gttctcntgt gtagtagcca tggttccrta actcacgaag cacagagcaa    120
agaaaaagga tagagctttg agcaacatcg ccatagcttt gaacagggac aagctcttnt    180
tcttcttctt cttcttctag atggaatctt ttaggaatcg agaaagagtt ttacttttc    240 aagaagacaa gtaaagttgt tttctttgtt tttgtgtgga tttacgtgaa gaagaagatt    300
aaaatataat ctttgcagaa accagagacc acgattcgct ctcattctct ttcttgtagt    360
gcttgctgac taaaggttgt gaatgcattt aatgctgttt ctgatgtttt ttaattcaat    420
gttattatta cattctcttt tgtttagcct ttgagattat gaaacctatg cgcattttct    480
tcaaaacgtt tataacatac attaaaatgg ttgaagaggc tttgcttcac acttttgtt    540 ttacttacga tcagatggtt acatacatat atgtaaggac agcttgagtg aatagtac     598

<210> SEQ ID NO 9
<211> LENGTH: 801
<212> TYPE: DNA
<213> ORGANISM: Brassica napus
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (493)..(493)
<223> OTHER INFORMATION: n is a, c, g, or t
<220> FEATURE:
<221> NAME/KEY: misc_feature
<222> LOCATION: (615)..(714)
<223> OTHER INFORMATION: n is a, c, g, or t

<400> SEQUENCE: 9
tcgagctcgt tgcgcgcata gggaaacacg tgtacagcag aaatggagta ctcacggagg      60

```
tcaaatcctt cggcaaggtc gaattgggtt acggcattag aaagctcgac ggcagacact    120
atcaggtacc aatgagaatt gattcaattt ttgccttgtt gaatcggtga ttagtcgagt    180
ccgtagantt tgttttgatt aggttggcct tttggtaaaa gctttgcttt agcatctttc    240
tgatcgattc ctattgttaa agaaactagc ttttgagcct ttgagttgaa ttatcgaagc    300
agcanagttt tgaattttga attagtttat tcaaattagt cacaaggatt cttgattcac    360
ctctttgagc taacactagt cacaaagata tacagaacca mcatgggttt gcttggtagc    420
attttgtccc ttggatcttt cagtgtntat atataataac atagttatgt gtgggtgaat    480
ggcgcaggga canttgatgc agataacaat gatggcaaca ccaaacatga acaaggagct    540
tcactacctc aacaaggaag acaaactcct gcgctggctc ctcgttaaac accgcgacat    600
caagattgga gcttnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnacaatc    720 aaagctaatc gagaatggtt aaccaaatcg aataaagagt agtcgggatc gttacccata    780
acgacggaac tgatccctaa c                                              801
```

<210> SEQ ID NO 10
<211> LENGTH: 697
<212> TYPE: DNA
<213> ORGANISM: Brassica napus
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (574)..(574)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (592)..(592)
<223> OTHER INFORMATION: n is a, c, g, or t

<400> SEQUENCE: 10

```
aagagcaagg gtactagcat tcactgtgtg ttgctgcaga acnggtccaa agaccatggt      60
agggcaaatg ctgacgagac taatcccggt tcgttttgca aactcgaaag cttcactttc     120
tgcttgtgtc tttgacgcac aataccantt ctcagttctt ttgcaaaact ccaggtcaga     180
ccaacaagac tcatctatna ctcgatcctt tgaccaatta gggttcatca taagcgcagc     240
tgcagangaa acgtacayaa cacgcttaac atttgcttcg acacaagctt taagcacatt     300
caacgtgcca tccacagctg gtgccatcac ttccacctca gggtttggga ctgaagatga     360
tggaacaggg ctagcgacat ggaagacgcc gatgcaacct gcgatcgcag attgaagaga     420
ggcgtantca agcaaatcag ccttgacgag cttgagtttn tcaccngctt tctccagctt     480
cttcaaatga gaatactttt cgttatcagg gtctctgaca gtgccatgga cnaagtaatc     540
cttggagagg aggagatcga cgacccacga agcnagaaan cctccggcac cngtaacgca     600 aaccttcct ttcgccgcca ccgacatttt tttatttttt ttatctccga gatgcttctt     660
caatattctt ctaccttgtc tgaatgccag gtgtgtc                              697

<210> SEQ ID NO 11
<211> LENGTH: 151
<212> TYPE: DNA
<213> ORGANISM: Brassica napus
<220> FEATURE:
<221> NAME/KEY: misc_feature
<222> LOCATION: (101)..(101)
<223> OTHER INFORMATION: n is a, c, g, or t

<400> SEQUENCE: 11
tcccgtgtta atgattttac acgttattat cacaataaaa ccagagcttc caaattcttg      60
gttctgtgta atcatytgga aaagaaaaaa gagaaaaaaa ntgaatatgt aaatgatgtg     120
atttttggtt cgttgcggtt tgcatgctct a                                    151

<210> SEQ ID NO 12
<211> LENGTH: 401
<212> TYPE: DNA
<213> ORGANISM: Brassica napus

<400> SEQUENCE: 12
ccctaaaaac agtcatatta atcggggggcc tgaggcgaat accttttttca atacactgta    60 ggcacgcctc tgatgaaaac tacagaaaac tttttcatttt gccgtgttca tatcggctta   120
catatagaga acaattaaca catcacctga ccgaaagaaa cactagttaa gaaaatatag   180
tactaaagat aaaaattactg wtattagcaa tttagcatag ctaaatgaag aataattctt   240
acagaaagaa ttgtaaacct taattttctc aaaaaaaaaa gaactaggat aataaattat   300
ggtttagtat agcttataag gttttaaata taatgtgtat atcatataat tctttcagag   360
aaaaatcatt ttttctacgg taggaatgta gataagaaaa a                         401

<210> SEQ ID NO 13
<211> LENGTH: 151
<212> TYPE: DNA
<213> ORGANISM: Brassica napus
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t

<400> SEQUENCE: 13
```

```
atgagcagac ccntttttta tcttttgttg aatggggatt tttnngacag tggaggagct    60
tctccaactt ccaaaktatc aaatttagct gtcttttcct attttctttt gacgtatgta   120
actcttacat gctcaattct aagttggtaa c                                  151
```

<210> SEQ ID NO 14
<211> LENGTH: 626
<212> TYPE: DNA
<213> ORGANISM: Brassica napus
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (606)..(608)
<223> OTHER INFORMATION: n is a, c, g, or t

<400> SEQUENCE: 14

```
agaagcttgc taatattccg acgccggaag ccaccgtgga cgacgtagac ttcaaaggtg    60
tgactcgtca aggagttgat tatcacgcca aggtctccgt caagaatcct taccctcagg   120
ccatccctat ttgccagatc tcttacatcc tcaagagtga cacaaggatg atagcgtctg   180
gnacaatacc ngatccgggt tcgttgatcg cgaacgggtc gacggttctt gacgtaccgg   240
tcaaggtgcc ttatagcata gcggtgagtt tgatgaagga catgtgtttg gactgggaca   300
ttgactatca actcgatatt ggactgacca tcgatattcc tattgttggt gacattacta   360
ttcctgtctc nactcagggt gagatgaagc tcccttccct tcgcgacttc ttttaatcat   420
ctntataagt tataatctga tttttnaata agtacgatcc gtaaacgaca tagacgatcg   480
ttggatgttt cagttgtgga ytcttgtgtt tgttggttat atgtatttgt tgctttgaat   540
attttgttgg tgagagttaa aaactacaag atgtcatagt tcgaatacta acgaagtgat   600
ggagannnaa aaaaaaaaa aaaaaa                                         626
```

<210> SEQ ID NO 15
<211> LENGTH: 301
<212> TYPE: DNA
<213> ORGANISM: Brassica napus

<400> SEQUENCE: 15

```
agctggattt tgtttcttct acaaaaatgt tggatttaaa gagttttta ctgtgcttga    60 taatgggatt actgtggctt ttttggtagc aggaagcaga gagaaagagt gggaaagaaa   120
agagtaagaa gaaaggcttt gggaagctaa rgcgtggaga gagcagttca tttcttccca   180
tcttcagaga gcctagtagt attgaaaaga ttttggcaga agctgagaga gatcataatc   240
ttgttttcag gcctcctact cctcctgatc aatcaaatcc accctcagcc tctcctccac   300
``` c                                                                    301

<210> SEQ ID NO 16
<211> LENGTH: 401
<212> TYPE: DNA
<213> ORGANISM: Brassica napus
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (235)..(235)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t

<400> SEQUENCE: 16
ctacttgtat ttcaattcac attcattgtt ttgctaaaaa cagacaaagg cttttgatat    60
acacctactt ttcggcaatg aatacagttg cttgtgacca gtcaaagcga tgagtcaaag   120
caatgaacaa tctggccaca cagacggggt gaatatctgt ttctattcac atatgggaat   180
ggaacaagag aagaatcaac kagaagtanc agagaaagtc atgagttttt caagnttaaa   240
gaagtgaaaa ccttggcttt atgaataact ttaacagcaa cttcttcttg acccttcagg   300
ctgccttttt tacccttggc ngagcaagtg tcctcgaccc acctngccgt ccatctcata   360
ctccttgtct tcaggaatag agacctcgtt gggagcctaa a                       401

<210> SEQ ID NO 17
<211> LENGTH: 401
<212> TYPE: DNA
<213> ORGANISM: Brassica napus
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (220)..(220)
<223> OTHER INFORMATION: n is a, c, g, or t

<400> SEQUENCE: 17
aatagctata ctaccagtct ctgactacna caacaaatna caattttact caaaaaggac    60
catttcttca cctattaaca acaaatgact agtagaaaaa tggattgata acaaaggcna   120
atactgaaac aaacaanatt cgtttgaaaa aagcaatcga atttcagatg ttgatcaaca   180
actagcaaat caaaagtgac maagttttaa acttgtaatn ataagttcgt caaagaacac   240
tttattccac cattatcaac aaaaccaaaa gacactgctt caaagttcca aagcatcaaa   300
catctgatcc tctcaatcgg aagaatctcc ggcgagcctc tccgcctcga gccgctccag   360

```
ggccttctga tgagcccaag tctcgatcga gagatcaggc t                401
```

<210> SEQ ID NO 18
<211> LENGTH: 401
<212> TYPE: DNA
<213> ORGANISM: Brassica napus
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t

<400> SEQUENCE: 18

```
acacgagaag cgctcttcac cgaggngatg atgcccttta caggttaatg ggctttctct    60
tgttttttgc ttaatgggct ttctcttgtt ttttgcttaa tgggctttct cttgntaact   120
ctttaactaa ctgtgaacag tgttgtttgt tcttgttgtg ntagcaagaa acaagaatgt   180
aaaggagaag aagaagagca stcgaggagt tactggcgac caattggttg ggacaggctc   240
tctgagcttg ttcagacagt gaaggttgat ggtgagtggt cagtgcagaa cgttgatgta   300
gatcatgagg atgntgatac aacggttgct gagctggctg ctccttactg ggaccgacca   360
ctcgcgggtc ccacgtggtg gtgccacgtg gatgctagcc a                      401
```

<210> SEQ ID NO 19
<211> LENGTH: 401
<212> TYPE: DNA
<213> ORGANISM: Brassica napus
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t

<400> SEQUENCE: 19

```
atcaggagaa caataagaaa cttgtttnaa aggcaaaaca aaatgataaa agccgttttt    60
gctaactctt atggtaatgc aattagaaca atgataataa aaaggttcca tctaaggcct   120
aacaacatac tttgaatatg ttcctctaga aatatgataa catgttgtat agaagtaaca   180
gatcattcta actcattgcc rccaagttta acncaatgaa ctaaacacta atatatataa   240
ggggcggtgt agattacctc tgagctgagg aagttatgaa gcacaataat tcgagggggac   300
caactaacta cttcaggctt gacctgcact aaaccaaatc aacattaaga acagaccttg   360
aatttacaga atggatatga taagacttac atagccaagc c                      401
```

<210> SEQ ID NO 20
<211> LENGTH: 401
<212> TYPE: DNA
<213> ORGANISM: Brassica napus
<220> FEATURE:
<221> NAME/KEY: misc_feature
<222> LOCATION: (28)..(28)

<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t

<400> SEQUENCE: 20

```
taaactgaaa cccatattaa cgacaganga atatacgtaa catgtggtgt ttacttagtt      60
ttattttatt taacaattct tttgtcttgt agggttctga ttgtagtttc gttttgaagc     120
aagcataata ttgtattcat attttgtta tanaagtatt tcatgtttct gtcgtgaaaa     180
aataattttc tatatttcca wtttttttgg taatgtgaaa tttattgatt agtaaaagat     240
agttcattac aataaaatgg tactataaat gataaaagaa aatatgataa gcgaataaat     300
tttgaatatc gaagtcgcta taatacttta aaatgaatat agccagtaag tacggaatcc     360
ttctttgtta tatagcgact tgtataatcg ttttattcct t                         401
```

<210> SEQ ID NO 21
<211> LENGTH: 401
<212> TYPE: DNA
<213> ORGANISM: Brassica napus
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t

<400> SEQUENCE: 21

```
acggattcac cttctccctc tctctctgta tattcttcgc atcttctcaa gaagctcnag      60
cttgaggaga gagagagaga gagagcttta gattcttgag tgtctgtaaa attagatctc     120
attgaganag agagagtatc caattctaca aggttttggg cttgtgaatg cactngttga     180
gctgatctta caggtccatt raggttagtt tgatcgatct gntctctgtt ttcttcaccg     240
gagctgataa aaatgtnanc tttacaatgt ggccatgctt gattctgctc ccaagtttac     300
atttttatct tatgggtttt gagatctatc acggctactg agatctgatg gctctcgtga     360
cttgtcattt tgaatgctta tgttgttttc attgtgnagc g                         401
```

<210> SEQ ID NO 22
<211> LENGTH: 401
<212> TYPE: DNA
<213> ORGANISM: Brassica napus
<220> FEATURE:
<221> NAME/KEY: misc_feature
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (246)..(247)
<223> OTHER INFORMATION: n is a, c, g, or t

<400> SEQUENCE: 22
gacaaaaaag agacccaaca actcangtgt tctttttct gcttcttcgg ctcancaaat    60
cagcaccaca tttcacacta gtcttcacga cattcatgtt ctcnttgntc cntcatttcc   120
atcactatca tttatccatt taccacaanc ntactattcn tttatcattt taaagtttac   180
ttttatacat cacgagatta rtactaaaat tataactata tactagtttt ttaaagattt   240
ttatanntat atatcatttt gtttcaacag aaattaaaag aaactagttg aggaaaaaat   300
gaaacaatgg ctaacataac atcaaaaaac ttattaatat tttctgtaat cagaaaactt   360
tagaccaaac ctcaaactta tttatgagaa catatattca c                       401

<210> SEQ ID NO 23
<211> LENGTH: 401
<212> TYPE: DNA
<213> ORGANISM: Brassica napus
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (166)..(166)

```
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t

<400> SEQUENCE: 23
gngatgtgtt tcatcagaat gatttatggt ttcttntaga ggcatatatt tgtgagatga       60
gggatgtgga gagttacagg gcctcataat ttgatggttt attgaagagc atagaaactc      120
catcagaagc attangcngg aggagttnga gagacaaaca aattcngcta tgagataatt      180
caaggtgatt aagtgatatt rgataatatt agaattagng gtgggccaaa aaacccaaaa      240
acttttggaa atgggctggc ttttttatgg atccggatgg ttcaaggtcc atcagcttaa      300
tatacgctat gacgtggcta ataatagac ttagaatatt tcaggtgatg tggcatcnan       360
ataaaaccag agatttactt tcttttatat agttaaatga t                          401

<210> SEQ ID NO 24
<211> LENGTH: 401
<212> TYPE: DNA
<213> ORGANISM: Brassica napus
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (160)..(161)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t

<400> SEQUENCE: 24
tagtgtngat ataaagccct aatttacggc agctaccgaa taaatttnct ccggccggtg       60
gggtgttcga gagcagatca tcagcttctc tagtctccgg taagttaatt ttttttaatt      120
cttatatctc gtaggttttt ttttttttgt aatttgatcn ntttaattag cttcgaatcg      180
atcagaatct aaacggttat kagnaattnt gtttaaattg tgcttttaat atttcaaatt      240
gattaagtgc aaagtcaatt ttgatcagat ctcactttct ggtagaggag aagaagaaga      300
agaagttttt tttcagtgct tgaggaggat ctgccatatc catcagaggt tttcaaacaa      360
tggtaaattt tgatccttag ctatatgaat actctatata a                          401

<210> SEQ ID NO 25
<211> LENGTH: 401
<212> TYPE: DNA
<213> ORGANISM: Brassica napus
<220> FEATURE:
<221> NAME/KEY: misc_feature
```

<222> LOCATION: (80)..(80)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t

<400> SEQUENCE: 25

```
ttttcgaaaa aaaaaataaa aaaaaaaatg gatggcattt tcgtaaatta tatgaacttg    60
tggggtgaat agggcaaaan caattttcaa aaaaaaagga ggttagtttt gtgtttgact   120
ttaagttata ggtcaatttt gcaaaaatcc cattttttat acatgccaaa accaatatag   180
aaaaaaacaa aacactcttc rtatacnaga caagcactat aaatacattc cataaccgtt   240
aaagcttcca acaccaccac caccaccact acagcactac tccactctct ctccctcttt   300
aattatctct gaacaagtgt aagttagcga catacaatgg cttcacttct tttcctcttc   360
gtcttcttct tctccatctc ctcttgcttt gctcattcct a                       401
```

<210> SEQ ID NO 26
<211> LENGTH: 201
<212> TYPE: DNA
<213> ORGANISM: Brassica napus
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t

<400> SEQUENCE: 26

```
atgttcattg tagttaatta gtanagaact atcggggcag aaaaaaataa gtcaacgcgt    60
tgcccgaaaa attgtatacg aatgtacctg atttaaagaa rgaaaattcc ataaaaatac   120
ttcaactaaa ttttttcttaa gctttttaag antcatttttt ccgctatcca ctttagtact   180
tcaactaatt attttgccca g                                             201
```

<210> SEQ ID NO 27
<211> LENGTH: 401
<212> TYPE: DNA
<213> ORGANISM: Brassica napus
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (218)..(218)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t

<400> SEQUENCE: 27

```
ttgtatgaac tggtttttaat taagtaatgc aagtagttgg ttgacaaaaa aaaagtacta    60
caccgtggat cttcaatcgc ctgatcagca taattagtat attcaatcat atgcanaatt   120
aatctaggaa ctaattgata aactaattct tttacagtgt agctaaagct tttattttct   180
tctggataca gataagaata matactatat ggggacanat nctttttgtcg attttttctat   240
```

| tcagctttgc aatgaagtct gagcaaagat atgaccagac tgaaaaggna attaaaggat | 300 |
|---|---|
| gataacatgg aaaaaattaa aaacaaaatt catgcatctg ctagtgaggt tatttggatt | 360 |
| cattgcatgt atgttgatga ttcgttttcc tttcacctcc c | 401 |

<210> SEQ ID NO 28
<211> LENGTH: 401
<212> TYPE: DNA
<213> ORGANISM: Brassica napus
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t

<400> SEQUENCE: 28

| aattttaca ctttggccag agatataang aaaggttgta aactcataga cttaagagat | 60 |
|---|---|
| tttttggttt agtcngtang tgattttgta gaaataatag cgcatattga taaatatgca | 120 |
| acacttgctt tagcctttgt ttgtgaattg tggtgacata agtccatccc tacaagtcat | 180 |
| gtatttgtaa cgacttgaaa rtaaaatatt ttcggaagac atntcgatnt ataatctgca | 240 |
| tttcagtccg gactccgaat atccatatat atgatctaaa ttgggtttct gaaataaaaa | 300 |
| naaancacaa cttacgtcaa gtcaacggag gttaaatcca ccctgtcgct cttgtttgct | 360 |
| cctttggcaa aacaaaagtc aactactatt ttaggtgctt g | 401 |

<210> SEQ ID NO 29
<211> LENGTH: 401
<212> TYPE: DNA
<213> ORGANISM: Brassica napus
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (172)..(173)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature

```
<222> LOCATION: (396)..(396)
<223> OTHER INFORMATION: n is a, c, g, or t

<400> SEQUENCE: 29
ttgaattggt ctgaaagttt gttagctgtt actttgaata gatgcctcgg agaccatcag    60
gaggaagaag gttcataaag caccaacctt tagcattttc accgtttatg cggtcacttg   120
ctttagcttc aaggcgtaaa ctgcatcgtc atcaacaaga agangactct cnncgttctg   180
aagagctgat gtcttttggt kagtagtagt agtaatcatt aaaactgaga agtttctgtt   240
cagaaacatt gtaanaacga atcattcttg ttttgttaga tcaaaagctc ccaactttgt   300
cnaaaaagga gcaaaagaa cagctttctg actcctctga tgaagaagac tctcaggtaa   360
taagattatt cagactcctc tgttttgatc cttgantctc t                       401

<210> SEQ ID NO 30
<211> LENGTH: 401
<212> TYPE: DNA
<213> ORGANISM: Brassica napus
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t

<400> SEQUENCE: 30
aagtgtaaaa gttataaaac ngagacgttg tgtttggnca tgtcatgtaa ttgttgaatg    60
ttgtgnatat gacacagacg gtgatgaant caacaaggag acagctggag agagagctga   120
tgctggaaga cataatgcat cttgaagact tgccttccta cgccctcctc tctcaatagc   180
cttttaagag ttttctaacc wcaacactcc cgcttttaat aacacaaaag gttgctcgct   240
gctgcctctt ctttgatctt tttcttctac tgtttgttgg ttggctatat gaaaaacagc   300
tctaaaactg agttgttgtt gttatattaa nacaagnaag agggagatag agaaggaggt   360
tgtgggataa aatctcaatt tggttgtggg tttggaaagt g                       401

<210> SEQ ID NO 31
<211> LENGTH: 401
<212> TYPE: DNA
<213> ORGANISM: Brassica napus
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
```

```
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t

<400> SEQUENCE: 31
tattngaaat aatattgagg gctgtgacga aggatgcacg agaaatntca acagcttctt      60
ctctatcact gcattcactc acgaagntga ttagttcttg caccttctnc atccgtagag     120
cttgggtggc ctcgatacgc tgtggtgaga acagatgagt aactgatatt ttcctcaaca     180
gcctgaaaaa tataacataa ytattttttt aatnaaatac acaaatctat tggttcngtt     240
aaggtaacta tatgttatgt atacagcagt tatatatccg ggacagtcnt ctagtataat     300
gaggataata ttttggtaat gaccgggata gctcagttgg tagagcagat gacaaataaa     360
aagactacca ataggaaaaa aaaacttagc aacggttacc t                         401

<210> SEQ ID NO 32
<211> LENGTH: 401
<212> TYPE: DNA
<213> ORGANISM: Brassica napus
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t

<400> SEQUENCE: 32
ggcaacatat atcacagtat aaggaagtca atacaaaaac attataacat ttccaaatat      60
tgaaagattt ctttctcata atacnaatgc actgaatcaa aataaaaaat caataatttt     120
ccaaaaacaa aatctaataa ttctaaggat gatattaact agaaaatatt aatcctccat     180
tgttgcgtat gacaagctcg yacgttttag ccaatctctc acgaacgata ccggcgcgtt     240
tcntacactc gctcttctnt cctcctccct tatattactt accctcgaac tacttcgtat     300
caacctttaa cctttagaca aactcactcg tcacacattc tactcatcct tgaccttgtg     360
ttgtgtgtta tatatacact actacacacg cttattatat a                         401

<210> SEQ ID NO 33
<211> LENGTH: 401
<212> TYPE: DNA
<213> ORGANISM: Brassica napus
<220> FEATURE:
<221> NAME/KEY: misc_feature
<222> LOCATION: (31)..(31)
<223> OTHER INFORMATION: n is a, c, g, or t
```

```
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t

<400> SEQUENCE: 33
ctgctgctgt tgctgttgca cggatgaaga ngaagaagtc ggagacgcag cggatgatgt      60
ggagttggtc cgacccgccg gacccatgcc cggattccgn gcggggcctc cgccactgcc     120
tccagattgc attcaattct tcgatcaatc aaacctaatt caaatgcaca ataagacaaa     180
aattcaaaac aagaaaaaat raagctggga nttagcaata aacgtttgaa aacggaaatt     240
tacaaagcca cacacncact cactcactct ctgccacttt ccttcacttg atttgaatcg     300 atttctgag ggagggaggg agagagaaac gaaagtcgcg ggatgcaacg gaataaacca     360
gatcctntgn gggtggcttc tcgagaaacg naatccacgg a                        401

<210> SEQ ID NO 34
<211> LENGTH: 401
<212> TYPE: DNA
<213> ORGANISM: Brassica napus
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (286)..(286)
<223> OTHER INFORMATION: n is a, c, g, or t
<220> FEATURE:
<221> NAME/KEY: misc_feature
<222> LOCATION: (376)..(376)
<223> OTHER INFORMATION: n is a, c, g, or t

<400> SEQUENCE: 34
gtatccttcc ggctatcaat tcccacctat gaaccacata ccatagattc taaatcgtca      60
aatactatat tttatgtaaa tagcttttta aaataattta acttaaacaa tctgntgaat     120
aaataacttt caagtaaaat caanaaatag aagattagca tggccgttgc gcaaggatta     180
cacgcacaaa ttcgagaaat rgtccaattt tttttccagt caaaaangta aaatcaagaa     240
caaactggat cagcgagatc aggctgaaca tagtcattga cagctnggtt ccaataataa     300
```
gcaataaaat acataaaaac gaccgactta tgagataaat caaaagccat agtatattct    360
tttaaaaaaa tcagantaaa ctaaagatgg aaacagacaa a    401

<210> SEQ ID NO 35
<211> LENGTH: 401
<212> TYPE: DNA
<213> ORGANISM: Brassica napus
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t

<400> SEQUENCE: 35
tgagtatcat ctttgccttt gttgtacctt ttctgaggat ttagaacgag attggattga    60
ggattagtcc tctntatcct aagaaataca tgcaatttag tgtnttcctt actaanatct    120
gattttcaca aatggattgc tgcttctcat gactnatctt gaatctcaag acttggttca    180
ttttatttaa tggacctttg maacgttgtt gttttgttaa cacagtggtt cgtttacaag    240
aacatgatct tcaaaccaga caggtcaagc antctcccct caattacata atttggtttc    300
gtctagtgtt ttctttnaga aatatgaaac tcatattttt ctatcgtaac gtgtttcagg    360
gaggtgctgt ttcagaaggt caaggataca tacagagaca t    401

<210> SEQ ID NO 36
<211> LENGTH: 401
<212> TYPE: DNA
<213> ORGANISM: Brassica napus
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t

<400> SEQUENCE: 36
ttattatngt tttatttat tttttgccgg ccaatcatat caattagacc aagttctaat    60
ttgtcacaaa gagttgttcc gaataaaata tttgtctgac catgtctgat ctagatggaa    120
aaatacaatg cctctagtcc ttccatatgg tttacaanga gttagattaa aacttcccat    180

| | | |
|---|---|---|
| tatcattgtg caatttccga stgaggaaat aacaaattgt atctggagaa gcaagaaagg | 240 | |
| nggtacaaaa tcttagctta tcaaaatgtt cacttgtctt tggtctattg ggagtgtcac | 300 | |
| tttttgtctt agttgaagcc catagaaaag cccaaattat tagtcggtat ctgncccatt | 360 | |
| ttttaaaatt tgtgaaccgg tgtctgtctt cttcgcttgc t | 401 | |

<210> SEQ ID NO 37
<211> LENGTH: 401
<212> TYPE: DNA
<213> ORGANISM: Brassica napus
<220> FEATURE:
<221> NAME/KEY: misc_feature
<222> LOCATION: (336)..(336)
<223> OTHER INFORMATION: n is a, c, g, or t

<400> SEQUENCE: 37

| | | |
|---|---|---|
| tccgagtcaa ctcaatccga ctcgagatcc accaccagtg tgccacggac tctcatcgga | 60 | |
| gggctgttgc ttgtcgagat tggacctgaa gcatcgagac agggctttgg tggtctcgtt | 120 | |
| taacgaagaa gaaggagcga tgaacttgtt ggaagaataa cacagggaac cgcttaaggt | 180 | |
| ttgatcctca gttcgctcgt stcctaagat gatgaggatc ggaaggggat gatttaaaga | 240 | |
| gttcgtataa ttattcatct gatgggagcg ttaatatata tagattttga atttcaaatg | 300 | |
| aaacaaaaat attaccgtta ttcactcaag tcggtnaaaa aaagtaact tgtgcatcaa | 360 | |
| gcaagtaact tttgtgggct ggcctctctg tttctgatgt g | 401 | |

<210> SEQ ID NO 38
<211> LENGTH: 151
<212> TYPE: DNA
<213> ORGANISM: Brassica napus
<220> FEATURE:
<221> NAME/KEY: misc_feature
<222> LOCATION: (65)..(65)
<223> OTHER INFORMATION: n is a, c, g, or t

<400> SEQUENCE: 38

| | | |
|---|---|---|
| cttgttgcga agcttctctt attggttctt ccatcgtctc tcctgaatca gagttttgat | 60 | |
| attcnaagtc tcccasctat caaaacgatc agagaacttt ctttcgaata gattaaaacg | 120 | |
| atgatatcta aaatcgaaac actgaattgc a | 151 | |

<210> SEQ ID NO 39
<211> LENGTH: 801
<212> TYPE: DNA
<213> ORGANISM: Brassica napus
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (644)..(743)
<223> OTHER INFORMATION: n is a, c, g, or t

<400> SEQUENCE: 39

| | | |
|---|---|---|
| tccttcttct ctccttctga tattttggct ttttcttaga atcttccttt tttattttca | 60 | |
| ccaaaaaaaa gaaaaatcaa aaagtattaa tcatttaccg gtatcagtta cacctacact | 120 | |
| ttgcgccgct gaacaaatca ataaggataa taagaagaag ctcgtttgct tccattttca | 180 | |

-continued

```
gacattcttt gcctagagca aaaaaacaaa acaaaaagat tgagacttga tcttagcaaa    240
atgggtaatt gtttggattc atcagctaaa gtggatagta gcagccgcca tgctaactct    300
ggttcgtctc ctcctctcct tgctttctct tcctttaccc agtttcgttg cttccttaag    360
acttaaagac ctctccttac tctccaattc caagccaaag wcttaacctt taagctgttt    420
ggatcttcaa agatcaatcc ttttcaatta ccagctgtct gatttcanag attgtagata    480
tctctttggt actcaatgtt ggatcaagtt gatttaagat ggttgatatg cttaacgttg    540
agattaantt tatgagccaa agctaaaagt cttaaccttt ttaagcttct gttttgtctg    600
tgatcttcaa agatcaatcc ttttgaatta cccatctctg cagnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnntctataa gaacagcgag gagaaattaa acaaaacaac    780
atcacttcat atttacagtg t                                              801
```

<210> SEQ ID NO 40
<211> LENGTH: 151
<212> TYPE: DNA
<213> ORGANISM: Brassica napus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t

<400> SEQUENCE: 40

```
acntcggant tgtccttctc ctcggatgca ggctcgtctc cgttggtggt ggtngtggtt     60
tcaccgagac aggtckcctc cacgtggacg gagacttctt cctctgtttt gaaagggttg    120
ccgcagatcg gacactcgaa catgttcaga g                                   151
```

<210> SEQ ID NO 41
<211> LENGTH: 401
<212> TYPE: DNA
<213> ORGANISM: Brassica napus
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature

```
<222> LOCATION: (92)..(92)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (289)..(290)
<223> OTHER INFORMATION: n is a, c, g, or t
<220> FEATURE:
<221> NAME/KEY: misc_feature
<222> LOCATION: (301)..(302)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (338)..(339)
<223> OTHER INFORMATION: n is a, c, g, or t
<220> FEATURE:
<221> NAME/KEY: misc_feature
<222> LOCATION: (343)..(344)
<223> OTHER INFORMATION: n is a, c, g, or t

<400> SEQUENCE: 41
gtccggtgtt tctcctgtgc taagaaactc cantanagac caaaccgttt tatggaccan      60
ggtggttgtt gaacnaccat tgagttcntn tntaaccgac gataatctat ggttcacttt    120
gaaatccnca ggaaagttga atttgattcg ccntgtggtt gacgcaaacc ctttgatcaa    180
naaggtaact tgatcatcac raaactcgac tggncatagt gaaacntttt aagttagggg    240
ttgttgttga ggaatgantt ttctttcttt ctttctcagn taattgtgnn gggatgcacg    300
nngttagttc cagaaggaat cattgcatgt gntgaaannt tgnngaagaa caatcataag    360
ttggagacac ttcacatcaa tggcgtccct ggcttcacta a                       401

<210> SEQ ID NO 42
<211> LENGTH: 801
<212> TYPE: DNA
<213> ORGANISM: Brassica napus
<220> FEATURE:
<221> NAME/KEY: misc_feature
<222> LOCATION: (1)..(38)
<223> OTHER INFORMATION: n is a, c, g, or t
<220> FEATURE:
<221> NAME/KEY: misc_feature
<222> LOCATION: (152)..(152)
```

<223> OTHER INFORMATION: n is a, c, g, or t
<220> FEATURE:
<221> NAME/KEY: misc_feature
<222> LOCATION: (747)..(801)
<223> OTHER INFORMATION: n is a, c, g, or t

<400> SEQUENCE: 42

```
nnnnnnnnnn nnnnnnnnnn nnnnnnnnnn nnnnnnnntc tgtagtagct gctgggtgat      60
ggtcctgaaa cgttcttggc ctgctgtgtc ccactgtata cacggtcatt gccacgagtt     120
atagtagtat acacgcttgc caagttttaa angaatatat gttatcaaga acacttacaa     180
tctggagttt gattgtcttt ccgtcttgtt caactgtgcg gattttctga atcacatcta     240
acattagcca acactaatat ttttttgttt tccgagtact aacaagtgat gggaagagta     300
aacttacaaa gtcaacacca atggtactga tgtagctatc caggtaagaa tcatcctgta     360
cacacaaatt caagacatca aactataagc acacaaagag maacaacgat actatactgt     420
aacctgagaa ctaaacaagt attaaacttc aaagacccat agatttgtta ctcgtgttca     480
atgttaaaac gcaattaccg aagataatac actcatagta acaatgatag catagtgtaa     540
actattttgg agagacaagt aattgaactt gaaggacgca cagattgtta ttaaacggca     600
attaacacat gcaagtaaga aatctaaaac aattattcag ctggagaaag agttacttac     660
agcaaacctt agaagcaagc aagattttcc aacaccagag tcaccgataa gcaaaagctt     720
gaacaggtag tcactgcaaa ttaaaannnn nnnnnnnnnn nnnnnnnnnn nnnnnnnnnn     780
nnnnnnnnnn nnnnnnnnnn n                                              801
```

<210> SEQ ID NO 43
<211> LENGTH: 801
<212> TYPE: DNA
<213> ORGANISM: Brassica napus
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t

<400> SEQUENCE: 43

| | |
|---|---|
| tttcccatac cgtgtaagaa tatggacaat caaagaacaa gtgatctcga gtctcatcnc | 60 |
| tttctccaca cagtccacag ctttgtgtgn ttccccaagc cctatgtctc ctgtagcaag | 120 |
| cctgttgagc actgctagcc acgtaatgaa tgaataccta ggaatgcttt gcgtgaacca | 180 |
| aaccacctta ctccaancaa cctttgcttt cttgggtcta atctggttcc aagtgttagc | 240 |
| cgttggnaac atatccctga aaccatcctc cttatgcctc caaagtatca gatcagtccc | 300 |
| cctactagta tntggaagtg gctccgcgag aatttgagtg tttaaactct gaaaccttct | 360 |
| gctgcgcttg tttctaagac tccaaccgtc ccctgaaacc rcattgctca ctagtgcact | 420 |
| cctaggaaga cccaaatagg tcgtaccgat ggctccagta acatcaatca atcttccact | 480 |
| gcccatccaa ttatcgaacc aaaaatatgt ggtttctcca tttcgaanct ctactttcat | 540 |
| gaactcataa gccaaatcnc ttagctttag tagcttcctc caaatccatg aacntttgga | 600 |
| atcatctctc acgtcccaaa aagagctttg tctgagtaga tagtgcttta ttcacttcag | 660 |
| ttgagaattg tcaactantt gaaagttaaa aatgtgaagc cagaaatgat acatgttaac | 720 |
| agctgaagaa attaatatat aaccaaaaaa aaaattcatt ctataaggaa acttttaaaa | 780 |
| aaattataca taccaaagtt c | 801 |

<210> SEQ ID NO 44
<211> LENGTH: 496
<212> TYPE: DNA
<213> ORGANISM: Brassica napus
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (403)..(403)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t

<400> SEQUENCE: 44

| | |
|---|---|
| tgacctctca ttactgttac atcccgataa acatagacac cattttttgac ttcaccggct | 60 |
| ccaatcagag tcctcgtaaa atgctcctgc aaaatacaca aagtgtctgt gaatactgtc | 120 |
| aagcagccag tttttcgaag caatttcgct acagacaata gagtacaatt cagattagga | 180 |
| acaaatagaa catttgccaa caanaaactc gcagacaatc tcaaactgcc actcttggta | 240 |
| gccatcacgt kactaccgtc tgcaaagctc acatgacagg aatgatacta cgtacatcaa | 300 |
| ccagtaatag aacatccccc ttcctgtnan gtgatatctg gtgtctataa taacctcacc | 360 |
| agtttgtacc gtaccgttta accgatnagg agttggagaa ggnttttgac gctccagcag | 420 |

```
tgatgtcaag gacgcccatt gctctanagt gaactgtggc atagaattcc cttggtttgn      480
agacgaactt ccagtc                                                     496

<210> SEQ ID NO 45
<211> LENGTH: 801
<212> TYPE: DNA
<213> ORGANISM: Brassica napus
<220> FEATURE:
<221> NAME/KEY: misc_feature
<222> LOCATION: (34)..(133)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (634)..(634)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t

<400> SEQUENCE: 45
tgaccgatgt ctaaaacggt tcggggtgt tacnnnnnnn nnnnnnnnnn nnnnnnnnnn       60
nnnnnnnnnn nnnnnnnnnn nnnnnnnnnn nnnnnnnnnn nnnnnnnnnn nnnnnnnnnn      120
nnnnnnnnnn nnnattttac atagaaaact aaaaacgtca tataatttgg aacatacaaa     180
tttctctaaa acgacttata taagaaaacg gtgggagtat atattttcat atattaatta     240
atacaaatta acaataatgg actcttaaac ctaaagtaaa agtgtaaaag aaattangga     300
tcttgtgcat ttgcactctt ggcncatggc cagagccgat gctgcttgta atgcttctgg     360
ccattcacag ttaatacgtt ttctatgccc gcattcactc sgttcaattc gttggttcaa     420
cattgtaaga tagttggtgc tttaattttc aaaagtttng aatactttt tactaantga     480 cataaaggat anaatacatt tggaagagtc aaataatttt cttgaagaaa atctcaacat     540
atatcagaaa ttgagatatt gtaacttant tngcctaaaa tgcaaaaant gtcgtacaac     600
```
tgatggttat aagaaattta agttttcaag ttgntgaatt cagtaagcac ttctggaatc    660
taaccggtaa gattgttgtc agggagagtg gtaaagagat ttaaaatata aacatcagtt    720
aggaattttc cactnaacgg aaatcaagaa ttaacgaaaa tataaccggt aattgtgnac    780
gtatcatcac tgcccatcta c                                              801

<210> SEQ ID NO 46
<211> LENGTH: 801
<212> TYPE: DNA
<213> ORGANISM: Brassica napus
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t

<400> SEQUENCE: 46
ttggttagat cgtaatttta tgtataagag gtccacacag aatagaagag actgtttgag     60 attttttgt atgcttagaa gactaaaaga gattaaatcc tgatttggcc tagatttttt    120
ttttaactca caaaaggttc attaactaaa cnaacacaaa tccattactt cttacacaaa    180
agaacagacc cactagtttt tagaccatca aactaatcta ttaaaattca caaatcatca    240
attatcaagt tgaacctccc aaaaagcatt tccttcttcc atctcttctc aaataaatgt    300
tttgtatgta taggtacctt ccacaaacca agtttgacac aagccatgca acatggaagc    360
ctatctggaa gtttgagctt gctcattgaa gttgagctaa saatatagtt tttcatttgt    420
ttcatagatc tatgacggtg acatcttgtt gagaacattt tgacatttgt cactataact    480
agtgtaagag caggagtctc atcttttttc ttcaaacgat gtacataaat tttctttaaa    540
atatatcgaa tagaatcagc taaaatagaa caattttcgc acaatcaata tcttttgngt    600
gcatatctga aggcaacttt aggtttatca tataacggat aactttcacc acataaatac    660
atgtgattga gaagatactt gggattaaca tgtctgagtg cattggtgat gactcttggc    720
aatagatcat attcgttttg tacaagataa acaatgtttt gttgtagatc ccatttgatg    780
ttgatttatt agtataaaca a                                              801

<210> SEQ ID NO 47
<211> LENGTH: 801
<212> TYPE: DNA
<213> ORGANISM: Brassica napus
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (638)..(737)
<223> OTHER INFORMATION: n is a, c, g, or t

<400> SEQUENCE: 47
actgggtaac atcagataaa atttcanttc cacttcagtt ntggttacgt tctagtttta     60

```
ggataatttc ggataattca cgtgaaaatc agatttttta ttttttagtt tttcaaatca      120
aatatcaggt aatttgata aatttagata gtccagataa aaaaatattt ggataattca      180 attttttat agttcatata atattaaata ttttggacaa atattaaaa taattcagtt      240 tataagaagc attttagact ctttggtaat tttagaacta aaaattgttt ttaattatat    300
aaacggaatt ttagacgaat accgattcag ttttttgttc ggtttcagtt tttcagttta    360
agaaatatat aaaccgctta gatatttgtg catatcggtt yagtttactt ttcggttctn    420
ggtttatatg ctgaggtcta ccatgaacta tcgaggttct tatcaaattt ttgattatcg    480
tcattgccaa tatcctctag tcaaaaatca tggatcgtaa atacatgaat gctgattgct    540
agtataagaa agtaaatcat tgacttcaat attaacattg actttgaaca gtacacaaaa    600
tagttacatg actgggatag atatgcactt tgcagagnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnngat ttaaagtttt ttttactatt gactacccgt gggcttccag    780
ttcggtccaa tttggttttg g                                              801
```

<210> SEQ ID NO 48
<211> LENGTH: 801
<212> TYPE: DNA
<213> ORGANISM: Brassica napus
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t

<400> SEQUENCE: 48

```
cgtccagata tccaactact cggcaanctc acctgtaatg ggaagaaaga ggggtgagta     60
acatgggagt cactcatcaa ggtatgggat gctaaaaacg caaaccactg aatcagtaaa    120
tagaactctc actatgggag tttagctcta acatgaacaa acacgatgtc taaggatca    180 cacaaaacaa acaatgcgat gataacacat agctattaca cacaccctga attctcctca   240
taaggatata aaatatcaat tgcgccggta gtacaaaagt ctgtctctgt accccagcaa    300
tgtccgctnt gtgtctacat gcaaacncct ttgcaccccg caatctctgc tctgtgtcac    360
tatgcaaacc actgcacccc gtaatctctt gaacatctgc rtcgctagct cagacgtctc    420
tggtccccgc gatctccaca tagtacttat atttataact atatatcagt tcaatcaaca    480
gttgaatcct ctagacccct aattctgatt tacaatgaat gtacaaacta ccaagcaaga    540
ctcgaacaga ctcagttcaa acagacagat catgcttcaa aactaaatta ccatagaaag    600
agttctacac tagtttggga tttaacggat taacggaata taccctcacc ttagccaata    660
gtagaaacgg aaatgaatct gacaacaacc aagataactt gattaccaag aaacataggg    720
ttcaccttgg atcatgcaag caatgggttt gccaacttca ttggagattt aacacgatcc    780
aaagcacgat tgcataaggg c                                              801
```

<210> SEQ ID NO 49
<211> LENGTH: 401
<212> TYPE: DNA
<213> ORGANISM: Brassica napus

<400> SEQUENCE: 49

```
ttctctgata gtgctgtgtc tctcctttgc cctccggtga agaaaggaa ttcttacctt      60
cacacatatt tcattgattg tcgggcaatc atccgcgtgg tggatgatta ggttttggtt    120
tcttcatcaa tgggttttct tggtgcttac ggctccaagt tgcttttagt ttgggtcttt    180
cttgtttggg ccatttactc ygtttgataa tttatctttc tcaaggcttt tttttacgta    240
agtatagcct tgtttaata aactttcagt gaaaaaaaaa ttatgatagc tcatacaaaa     300
ttgaaacatg gttgccttgg cagtattatc tatattatct tattgaaagc tgggccaact    360
aacgagagag ttcgtgaagc tctccatgtt caaaaggtat t                        401
```

<210> SEQ ID NO 50
<211> LENGTH: 401
<212> TYPE: DNA
<213> ORGANISM: Brassica napus

<400> SEQUENCE: 50

```
gcacccaaat tgataacga tacacaagca gctaatggct tataaacact gctagaggaa     60
cttgaaggaa aaaaatatt gatggtgttg atgatgtttt ggtctggagc tgagtcctcc    120
ttacttgaga atttacccac taacataccg aatctcaaga tcttgttgac ttctcggttt    180
aactcgcttg atttcggtga mactttaaa ttggaacctt tgaaaaagga acatgccaag    240
acccttctca ttcaatatgc atcgcgtcct gatcacgcat ctgatgccga gtatgaacgt    300
cttttccaga aggtattctc tattgagcct ttccattggt gatctaacat tttgtaaatg    360
ttgtgggtat aatgtgtgat gtgcctcagt ccgaggaact c                        401
```

<210> SEQ ID NO 51
<211> LENGTH: 496
<212> TYPE: DNA
<213> ORGANISM: Brassica napus
<220> FEATURE:
<221> NAME/KEY: misc_feature
<222> LOCATION: (284)..(284)
<223> OTHER INFORMATION: n is a, c, g, or t

<400> SEQUENCE: 51

```
ctttgttgcc gcgagcgaca ggtttattgc tatcccatcc tcaaaaacct ctcctacagc     60
tttatcgcta tcgattccca acgttgctat catgcagaac aaaacaaacg accacaaaag    120
ccatttggga cctccatgga ggtaaaacta ctcggagcgg caaagttgaa gctaaaaatg    180
agaaacttaa aaagagtttt aaaataaacc tttttatata gagtagtcga gatggtttga    240
tttgcttatg ytattctctc attaaaattc agatgagtga taangtgtaa ttaggcttta    300
gaatttagat ccatctaact tcacagagtc aacgactgca aaagattgat ttgcgagtaa    360
gctaaaccct cgtgatatag tcaatcattc aattatacta ttatcggacg acgggatggt    420
gggtttacgt agaaacgcca aggcaagacg caaactcaca gtttccatgt aattttgcag    480
gaagtcaacg gctaca                                                    496
```

<210> SEQ ID NO 52
<211> LENGTH: 401
<212> TYPE: DNA
<213> ORGANISM: Brassica napus

<400> SEQUENCE: 52

```
cgcagatcaa gttctagttt cagtctagtt gtatacagct ttaattcatg tttatagtcc     60
```

```
tagtttaatt gtatctcagt tttggtatat gtcgtgagcc gctaaacatg tcaagcataa      120
cgtacaagat tttctctcct taaatctcat tccctcttaa aaatgttata ttttcgttta      180
attgtctgct ggttttgacc rtcgcaagtc accctgtgaa aaagcccacg ttttttttgt      240
tttctttctt tcaccttgcg ccgtgctggt ctcttggcct tgtctccttt agcggcattt      300
gtagggttga gtatttctta gcggtggtgg ttgcgtggtg gtccgatggt tttggctgag      360
gctatgatct cacgtattgg aactgaatgg ttggatgtgg t                         401
```

<210> SEQ ID NO 53
<211> LENGTH: 801
<212> TYPE: DNA
<213> ORGANISM: Brassica napus
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (250)..(251)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (577)..(577)
<223> OTHER INFORMATION: n is a, c, g, or t

```
<400> SEQUENCE: 53
ctggtggagt ccagggagaa gcacaagagg aaatcatggg acaaagtatn tgttaataaa       60
gagaaaagag gattggggtt caaagatatt actgatttca acacagcgat gattggtaaa      120
cagttatggc gtttgatagg gaagacgaac actttatttt ntcgagtttt caaangtcgg      180
tattacaana acgcatcacc cttggaactg atttgttcat attctccgtc atatggctgg      240
cggagtatcn natatgctag atctttggta agcaaaacac taatcaaaaa ggtngaatca      300
ggatcatcca tatctgtatg gaacgatntc tggctctcaa ccactcgccc gagactagct      360
aataaaacca acacaactat tacccaaacc tcaaagtgga sactctcatt gattctactc      420
catgttctaa aacgcggtca ccgcggccgc aaacgcggcg gttaagcgct ccacgactct      480
taagcgtctt gattttgcta tactcggcta attatacaga acaattagaa aagttaattn      540
ttttgttctt tttgagttca aaatcaattg ctatatnata gatctgtgag tttaatgtgt      600
aaacaacaaa aagtaagcac aagatttaag gactatgtat ttttttaatgg cggtcgcaga      660 aggtttacag taaacgtaaa cccttaaaag aggaagacga agctaaaaat tatgattatg      720
```

```
ccctcacat taaaaaaaga gagcaaaaag cgttgttgct gcgtttcgaa cacgagtccc      780
gacagtactt agggaaagcc g                                              801
```

<210> SEQ ID NO 54
<211> LENGTH: 801
<212> TYPE: DNA
<213> ORGANISM: Brassica napus
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (736)..(736)
<223> OTHER INFORMATION: n is a, c, g, or t

<400> SEQUENCE: 54

```
tcaattgctt gataaaataa ttcaaaatac aacagtataa ccccgcacgt acgcctccgt       60
agtaccctgt gaacatcttt agangcatta actagtacta attactttaa acattatata      120
tacaaaaata cattatcatg aattaatcat atacggccaa cncttaactt cnagaaaaaa      180
atagttgtgg atatactgcc gatgcatgta taggccatta gggatccaac acatacatat      240
tatgaccttt ctaaacgtta tatatcaaat ataagtttga catcctcaca gttttttttt      300
aatttaacca cagtgtctgg cgaccgagat taaccgacta ttctgtgnaa tccagaagta      360
caatgttaaa ttctggtggc caacaaaaat cgaactgcag rttcaccgta tcagggttat      420
tcctcaagtg ctactagcct aaggcccgtt ggttacatcc tcacagttac caacatattt      480
aacatgttta ccaaaaaaca cataattata aaaaaaatta aatatcacta gatgcatata      540
ttcctaaatt atgacatctt tgcagcaata tattagtttt atatttntaa tgtttagatg      600
atattctaaa tattttttata tcatcaaata ttattttaat atgtagtcag taaagtgacg      660
acaaaaaatg tagtcagtaa agtaaatgat caaaattaat gaaatagaac gtctccttcg      720
cgttgacgat tgcacnagtg aggcttgtgt gttgtgacca ataggcaata gcccatatga      780
agtggtagat tccttggggt g                                               801
```

<210> SEQ ID NO 55
<211> LENGTH: 401
<212> TYPE: DNA
<213> ORGANISM: Brassica napus

<400> SEQUENCE: 55

```
atcggggagg gaaagccagt gggagaagag ttcctcagcg ataagagggt ttgatttaac       60
ggacaaaccg ggaagctgca agagctctgg atccagtata tgaacttcct ctatatccat      120
cttatcccta aactctacct accgagtcaa ttttcgaaaa ctggatgatc gtttaccact      180
```
gaaaccctaa tttaggatat rtcccaccac ggaaaattca aaaggcagct atgaacaatc      240
gaggaggtca actaagtacg agaggtttgt attatactcg cgagaaaaag agaagaaaaa      300
acgaaaccta gattcgaatt tctataaaca aagagactat acaacttctt cttcttctac      360
ggtacgatat gtgcgatcga acgaagagag agtcggagaa a                          401

<210> SEQ ID NO 56
<211> LENGTH: 668
<212> TYPE: DNA
<213> ORGANISM: Brassica napus
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (212)..(213)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (494)..(494)
<223> OTHER INFORMATION: n is a, c, g, or t
<220> FEATURE:
<221> NAME/KEY: misc_feature
<222> LOCATION: (515)..(515)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t

<400> SEQUENCE: 56
gccaaattac cattcaaact ttgacggcta tcgctatgca caagattggg cctaagctag      60
agaaagctca taactaacta atttnccttg ccggtgagta tgatgacncc tacagagcta     120
tcgtctctgg cgtcnttaaa cgcacgcata agctccttca cagtctgagn ccggaacgcg     180
tttcttntct ccggacggtt tatagtgatc tnnataacca aaaactattc aactgaagaa     240

```
gaaagaaaca cacacaccag agagagatca tcgaacactt tacattaaca aancttggca    300
atatcttcac cgacggcttt ctcatatata atgtcaacna actctttygt ttctccgtcg    360
tcaccgacga gatcagcttt tctccaaacg acttggtgag tcggcacttc accgtgaacc    420
ttatggtant tgtcattcat cgacgangca gtagagagtt ccactgagtg aacgcgagtt    480
ggaattgttt ccanggggat gagatgattg gtgangacgg agatacggcg gctcgcggtg    540
ccgagttccn tggagtcngc cattggagag gaagacgcga gagacagaga aagatgagac    600
tgattgatga tgaagatgac aagagattct atcgcatgga ctttgacaat atttggataa    660
aatattt                                                              668
```

```
<210> SEQ ID NO 57
<211> LENGTH: 552
<212> TYPE: DNA
<213> ORGANISM: Brassica napus
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (211)..(212)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (422)..(423)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (479)..(479)
<223> OTHER INFORMATION: n is a, c, g, or t

<400> SEQUENCE: 57
gtatgacagt gatgatgagt ttattgctcc tcctaggcaa atcaggcagc cattcatcaa    60
ccgncaaccc gccctgtta cgggtgtccc tgttgctccn actttggacc aacgcccgag    120
ccgcagtgac ccttggagtg cacgtatgag ggagaagtat ggactngaca cgtctgagtt    180
cacatacaat ccctcacagt cacaccggtt nncagcaaat gccgacgcaa ccaaatgaag    240
aaaaaggacg atgcaccatc atgtgagtcc atgtctttaa aaaagttcag tcagttctcs    300
```

```
tttcctattt ttatttctgc ttgcgtataa caatcaagag tgtcagtgaa attagaggtg      360
tgtttcnggg tngttnttga tgatgattac tctagcactg gaggtatctc aaatcaacct      420
anncattttg ttgaaactcn ttttattgtg tctgtgtagt cttttgtaa gtacttnanc       480 atcatgaatg ttcatcttgg ttatctgatt cggtcctatc attcttatta tatataaaat     540
tcatctgttt ta                                                          552
```

<210> SEQ ID NO 58
<211> LENGTH: 401
<212> TYPE: DNA
<213> ORGANISM: Brassica napus

<400> SEQUENCE: 58

```
gagaagaact gtatagaagc ttcacttgat tccctaaaac tgttgttcga acaacatag       60 agtagttgaa aatgacgttg aaatacccaa atgaatttgg tttgagagcg attagaataa     120
actgtctctg gtggtgagat gatctccttt gtggtagagc tgaaagatga tgttctcttc     180
attaaagaga gaagttatct ygtcataccg aaggaccata gtggtaataa gcggttggct     240
tctaaaacat agcagtttcg tggagatgga gcagagccta ggaccgtgaa gtagcttatt     300
tggtggtgac ggaggatgct ggccggaaat atctgctgtg aacctattga aaacatctag     360
aaaaagggat tttgacgctg aagatcagat tggatgaaca a                         401
```

<210> SEQ ID NO 59
<211> LENGTH: 496
<212> TYPE: DNA
<213> ORGANISM: Brassica napus
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (409)..(409)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t

<400> SEQUENCE: 59

```
gtaatgaagg caaaacgagg cgacccttgg acgaaccata ccactttact ccgattctgc      60
ntctctctat gcggttgtat ctnctcccat gtttggaaag angagaacct gcacttatac     120
tcatccgacc ctgatttcca tagaaccatg tcctcctcnt taccaacaac tagtgctttg     180
aaacttctaa cactcgtgat tatttgctgt agagtttggt ctctgcatct tcgaatctgc     240
```

-continued

```
caaccagaag matttgcagc atcagcaacc ttggtatatc gcccaatatc aagccgttgt      300
ggaccactat cccccnctat gtcnataagt cggcccccag gaagccaggg gtccgaccaa      360
aatagagttc tctgcccatt tttaatttgc attctgatga attgagcanc cagcggcctc      420
agcctcagga gcttcctcca cacccacgat cccttagctg actccctaat gtcccanaat      480
gaatcattgc tccata                                                     496
```

<210> SEQ ID NO 60
<211> LENGTH: 801
<212> TYPE: DNA
<213> ORGANISM: Brassica napus
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t

<400> SEQUENCE: 60

```
agcgttcacc caatgttcac cgtaccactc cgttaacgag gagtggttgc tatatctcac       60
cggggccggg attgaaccgg naatatacta tgccttcaac ggatgaactc acaanccgag      120
ccaccgtctt tacaactcga tcacctagct tctctctcac tctacaatac atctgagtnc      180
tgatctaaca agatcctaat cagctcagct catncttatc ctagtctaac cgtcacacgt      240
gcgcacactt cacacgtgag atcaactaac tcgagagaga gagccggttc taattgatta      300
caagcttaac cgactaaacc aactttaatc ccnctataca attagaaacct aaaccaatgg      360 atagaaactt gactatatcc aacaaaagcc ttagggtgta rgttaattat cttgttcanc      420
aaaaccttag ctttttattt actgctttaa tcataatcat ctagttttag ttcgaaaact      480
acaaatttat tgtgtaaatc ctaaagtcta tgtcgattcg attcttaaat attgcaattg      540
aaacttttaa ttaaaagaat aaaatcactg tttagggcaa tttaaatgat atcacaccta      600
ctctccggta acaaaaataa atgtaatcat aatgttgatg gatggcacta caagatctaa      660
aantcaatca aatagatttt aaaacttcct ttctatatgg taatcaagca gtagagattt      720
atatgaaaaa atctaaaagg ttggttgtcc cataacaaga aaagtctaca gacttgttaa      780
gtcattatac aaactaaaac a                                                801
```

<210> SEQ ID NO 61
<211> LENGTH: 401
<212> TYPE: DNA

<213> ORGANISM: Brassica napus

<400> SEQUENCE: 61

```
gaggtaaaaa atcagtaact gtcatgttct tcgttagcaa cggaagccct aagtatctga    60
caggtatatt accagaagca aaagaaaatg attcatgatc tcttctttct tttgatctaa   120
aaaaccagcc ataaacaagg tagacttttc caagctaatc ttcagacaag acattctatt   180
aaactcctca atactttca rtatcccttc aactgatctt ctagtgcctt caataaacac    240
cattaagtca tctgcaaagc ataggtgagt gataccctatg ttttttgcatt ttgggtggaa   300
tccaattaga tttcttgagg ctgcttcatc cagcatcttt gatagcacat tcatgcagat   360
aacaaagaag tagggagata aagagaatcc ttgacgcaga c                       401
```

<210> SEQ ID NO 62
<211> LENGTH: 801
<212> TYPE: DNA
<213> ORGANISM: Brassica napus
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (184)..(184)
<223> OTHER INFORMATION: n is a, c, g, or t
<220> FEATURE:
<221> NAME/KEY: misc_feature
<222> LOCATION: (218)..(218)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t
<220> FEATURE:
<221> NAME/KEY: misc_feature
<222> LOCATION: (637)..(637)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t

<400> SEQUENCE: 62

```
aaattgatct gatacagttc tcaactggca tgcctatggg taccctgcct gtctgttatc    60
ttggtgtncc attgtgtact aaaaagctca cgctcttaaa ctgtgaaggt ttacttcagc   120
agattatcct cntggagtgc caaatcactc tctttcgctg gcaggctgct gcttatcaaa   180
acantcatca caggcataac cactttctgg tgtacaangt tcatccttcc gcaagcatgt   240
gtaaaacnca taaattcct atgtggtgtc ttcctctgga aaggtgatat tgaggagcac   300
tacgcagcac gagcctcttg gnaggttgtc acaaagccga agcaagaagg aggccttggg   360
attaagaatc tttcgatatg gaacaaagca tgctgcctta rgttgatctg gctacttttc   420
tttcaggcag gctcggtttg ggttgcttgg ttcaaggagg aagttctgga tggatatgtc   480
tcaacaatct ctggactatg gttccacata gacgctactc ttggcaggtt aataagcttc   540
```

```
ttaaactgag ctcctctatc ttcaattgag ttaagcttcg tgtccaaaat agtctctctt    600
gtcggttctg gagtgacaac tggtcccctt acggctntat gaggtcttat cttagcatcn    660
gctccaactc aactatgggg atcgcagcac aagcaacttt agcatcccct catcataaca    720
acaactggtg gattcctcct gcaagatcag aagctcttgt caatgtccat gccctattga    780
ccaccattga actaaacaat a                                              801
```

<210> SEQ ID NO 63
<211> LENGTH: 801
<212> TYPE: DNA
<213> ORGANISM: Brassica napus
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t

<400> SEQUENCE: 63

```
cttcttagac taaaaatagt aattaaaaat tctaagatgt ttgctaagag ttttcattga     60
taatgttgct cttaggatga tgcacaaaac tgtgactgtg gcatataata tatcaaagtt    120
atctgcagct tcaccacaca acaaaaaata cctataattt ctccattctt ctacaaggta    180
gcagactagc aatcaataat aatacactac taaatctctc ttcaagaata atcacgtgca    240
cgaacgattg ttctntatcg atatctgctt aacattacat gctctccctg aagttaatag    300
atcttgacat atctgcaggg tttgtttgaa ggtttagata cgtcttaggg acaaatctat    360
tgttgcagct ctttgtttca aacccattag aggaaaaact saattgatgt gncttctcgc    420
gtttcatcgg taccggatac aacacacgat tattcgtagn tacgtcaata cttcgagatt    480
gtgagtccaa tcttgctctt acaaaagtgt ctttgttttc tctaacactt tcatgtgttt    540
tagcacaaaa aacacttatc atgtaaagct tcgtctcttg tccttttccc tagacacgtg    600
gaagtctcta gagtatacca aaatggtacc atgcagcccc agtagacaag gatgtggtag    660
aatgtagggt aaagaggaca ctggtgaggg ccgtgaggcc atggaggcga aaaaggggat    720
gttacttgcg aaggaagaaa tccttgggag ttgttgaaat ctttgaaaac agagtcagaa    780
gttatcttca ctttgcttga t                                              801
```

<210> SEQ ID NO 64
<211> LENGTH: 401
<212> TYPE: DNA
<213> ORGANISM: Brassica napus

<400> SEQUENCE: 64

```
tgtacacttt cccttgcttg gccatccatg agttgaagat cagcatggcc tcagcgtcga     60
aaacgctgtc gctgtggctg ggaccagtgg ccacacggtg gccagaactg ccaacaacat    120
ggtggttata gtcgtatgaa acgacggaca tgtccatggc cgtggcacaa gatgcgatga    180
gcattgctag taagaagatc mgcatggctg atttagcact acccatcaaa actaatgaaa    240
ctttaattta tgtttgtttc aacaagttta aaaaagctca tagaaaaaga gaacaagatt    300
ttgtgctgat taattttgcc tactatatga gagtatttat agtattcaga gctcagatag    360
```

```
gtaacacttg tgttaagaat ctcacatcag aagaggtgat a                    401
```

<210> SEQ ID NO 65
<211> LENGTH: 401
<212> TYPE: DNA
<213> ORGANISM: Brassica napus

<400> SEQUENCE: 65

```
gcctctgtta ttccctccgg ctctctggtt ggtgttattc ctgctactgt tcagagctcc    60
gcctctgtta ttccctccgg ttctccggtt ggtagtcttt cctccggtcc tccgattggt   120
attcttcctg ctgcaattca gagctctgcc tctgtctctc catctggatc accggttggt   180 gctctccccct ctggctctct rgcgggcgtt gttcctcctg agacagtgac ggtgataagt   240
cctcgctctg ctcatgctcc tctagcttcc atagctccat cacaaaacta tgcttctctg   300
ttgaagaaat cttctcagtt gaaagagctg ggaacgccgg tggaacacgt ctctggtgta   360
ccgtttgtca tgatccctga taaaaacatt gagtcagcaa a                       401
```

<210> SEQ ID NO 66
<211> LENGTH: 151
<212> TYPE: DNA
<213> ORGANISM: Brassica napus
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t

<400> SEQUENCE: 66

```
cnaacgactc ccaaacgatc acactttgtt ttcaattatt catcgataac tatattcatc    60
gactcccaaa caacawaagt taccaccagt tcacaacaaa agtanaacat aaagatctac   120
cacgcagatg gtccaaatag catncggaca a                                 151
```

<210> SEQ ID NO 67
<211> LENGTH: 801
<212> TYPE: DNA
<213> ORGANISM: Brassica napus
<220> FEATURE:
<221> NAME/KEY: misc_feature
<222> LOCATION: (15)..(114)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (308)..(308)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (575)..(575)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t

<400> SEQUENCE: 67

```
gtttgcgaat tatannnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnntgtaaa     120
agaagcttat gtacccgtat tttgtggaag cacgcaaggg cgaatccaaa gattattttc     180
agtgggtgca caaattaaag tgtatnctta cgtatgatcg taggtgtata catcaaattt     240
gttaagaaat atactaaaaa atttaaaatt attatggggg caagtgcatc cataatcctn     300
tacctagntt cgtcagaaca tcgtagtcta ttgattaagg ttcaaaagct tatacactta     360
agtctttgaa tttcaaacta tgcatttttt ttgccgatta rgatgcgaag ctcatcagaa     420
gttttagagt attgtaagta gagctgtttg ttgtggtgat ggaaagagtt tgtctatcgc     480
ggatgtcgta catgctggac cgtctgtcga tccaaatgtt tcggaaagaa ctttatcnga     540
aaattcttat ccatcatcaa tattgcatat attgnaggta gttgagcagc acatttaaaa     600
agttaagtag aattttgatc gctgttttac ctacagaagc tggcgagaca ctagtgtaag     660
agagattgta ttgagtgaac atttgatatt gatantggat tttccaaaac taaccacctc     720
gtgagtatat gctgcaatca ttttgattag acactgaaac aagtaatctt gtatgtcttt     780
tcgatttcaa cttatgctta t                                               801
```

<210> SEQ ID NO 68
<211> LENGTH: 801
<212> TYPE: DNA
<213> ORGANISM: Brassica napus
<220> FEATURE:
<221> NAME/KEY: misc_feature
<222> LOCATION: (1)..(48)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (693)..(792)
<223> OTHER INFORMATION: n is a, c, g, or t

<400> SEQUENCE: 68

```
nnnnnnnnnn nnnnnnnnnn nnnnnnnnnn nnnnnnnnnn nnnnnnnnca atattttaaa      60
ttttttaga ggaagacacc tagtataatt tttaattaac taaaangggg attacataat      120
tggatcctac gttaccgaag ccggactcct tccgcctctg tcgatctgca gtcttgccgc     180
tcctccaaaa caccgccacg taaagccatt ccggtgagag acaaccaggt tcaaagtaag     240
atgcatatcg aacagaaaaa tcaacgatgg agagataggc aaaaagaaaa aagagtaacc     300
tccggcaccg cttattgctg gaccggaaaa aagatctttt gcgcttgaga gcttttaaag     360
agagatagtt ctgttagaga gagggtccac tgcatgcaat katatattct ttctcatcag     420
actttgattg gtatggtgct taaatgggct gaaagcctta tatagtattt atcgttcatg     480
ataatcaatt atataagttt cttaacaaat aaattaaaat aaagattttt tgaatgattg     540
aatctgaaaa atatatcgca aaagcggcag cctagggtta gatcaacttc tccatggaca     600
cgtacactag ccagattagg tcctcaaggg gccgataagg ttcgaaagtg aggctgctcg     660
ggaagccttc ctcgagagga acttaaggcc ccnnnnnnnn nnnnnnnnnn nnnnnnnnnn     720
```

```
nnnnnnnnnn nnnnnnnnnn nnnnnnnnnn nnnnnnnnnn nnnnnnnnnn nnnnnnnnnn    780
nnnnnnnnnn nntttggttt g                                               801
```

<210> SEQ ID NO 69
<211> LENGTH: 401
<212> TYPE: DNA
<213> ORGANISM: Brassica napus

<400> SEQUENCE: 69

```
atcacagagc tgcatataac agatacagaa atactagata ttggttcatg ggtcaaggaa     60
ctctctcatc taggccgact tgtactctac ggatgcaaga acctggtatc tctcccacag    120
cttccaggtt ccctactaga ccttgatgca tcaaactgtg agtccctgga gagactagat    180
agctcccttc acaacctgaa mtctactact ttcagattca ttaactgctt caaacttaat    240
caagaagcca tacatctcat cagccagact ccatgtcgcc tagttgcagt tttacccggt    300
ggagaagtgc ctgcctgctt tacttaccga gcttttggga atttcgtaac agtagagttg    360
gatgggaggt ctcttcctag atcgaaaaaa tttagggctt g                        401
```

<210> SEQ ID NO 70
<211> LENGTH: 668
<212> TYPE: DNA
<213> ORGANISM: Brassica napus
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (266)..(267)
<223> OTHER INFORMATION: n is a, c, g, or t
<220> FEATURE:
<221> NAME/KEY: misc_feature
<222> LOCATION: (287)..(288)
<223> OTHER INFORMATION: n is a, c, g, or t
<220> FEATURE:
<221> NAME/KEY: misc_feature
<222> LOCATION: (481)..(481)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t
<220> FEATURE:
<221> NAME/KEY: misc_feature
<222> LOCATION: (542)..(542)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t

```
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (620)..(620)
<223> OTHER INFORMATION: n is a, c, g, or t
<220> FEATURE:
<221> NAME/KEY: misc_feature
<222> LOCATION: (631)..(631)
<223> OTHER INFORMATION: n is a, c, g, or t

<400> SEQUENCE: 70
cttganccgc caatagatga gtctcctgaa ccgtttcctt catatttcca caggccagta      60
tcttgggatg cnaacttctt gactgcagaa acataatctg gcttgaagaa aaacatatta     120
tcctttccag cagattggta atggttccct gtttgttgca tatcatcscc accaaactgt     180
gcagggctta gggcaggaaa atccatgggn gtnagattag gagccggagc aggagcagga     240
atcttaggcc tcatgttctg attcannccca ttatccactt gtagctnnag tacaaacata     300
accaaatcac tcgaatgaac aaaacattca taaagtagca aaacaacatg attggagcaa     360
aaaaaaagga catcaacaca ttcaataact taaaaattac aattagcatc aacattgaac     420
catatgttca caaggaataa tgagtttcat aggaagagaa gcagaaagct agggagaata     480
nctcaagctg agtaagcatc tcaacngtca actgcaaatc acaccccatta gcaaaataaa     540 cntcngcaag actctcagca gcaaanccag ggaactgagn agcnagaaac tccacagggt     600
tcacctccat ttccctatn cttggattct nggaaaccat gaatcgacca aaagggtttc     660
ttctctcc                                                              668

<210> SEQ ID NO 71
<211> LENGTH: 801
<212> TYPE: DNA
<213> ORGANISM: Brassica napus
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (670)..(769)
<223> OTHER INFORMATION: n is a, c, g, or t

<400> SEQUENCE: 71
cttcataaat aattgacaca atatatttga atatatgata tatttaataa aaacctcaat      60
acataaaaat aattaatagt attaattta atatatatat ttatattcac tctattcatt     120
actattaaaa tttggatatt atataaatta aaaactatga ttatattttt attgatatat     180
gatattgtat tttttttaa agaaggnaag cgtgattcca aaacagaatc ataagcttcc     240
```

```
aacatgtttt taaagagaat attttgnaag cgttttggaa tcgagattcc gtaagcttcc    300
acaaggttcc gattccngtt ccaaagcggg aagcagatgt ccggatgaag nttccatgca    360
acgtaggaaa caagtatcaa aaggataaga gaaaggaaaa katagagaag ttcacacata    420
ccaaaacaat tcgacctcga ggtttagacc taatcttcgg ccaggttcct tctatcatcc    480
tttgttactt tccgttagat tgtaacccat attctctgta acctttcagt tactaatata    540
tanacatttc ttttcgtcaa tcttgatatg tatcttgcct agccaacaac tggatcgtga    600
gtgttaaacg tcttccgatc atatttattc aatttcgcat cacaattcgc taggcccaat    660
ccaaacgacn nnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnt acgtagccgc    780
ttccgtttcc atgtaaagta g                                              801

<210> SEQ ID NO 72
<211> LENGTH: 151
<212> TYPE: DNA
<213> ORGANISM: Brassica napus
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t

<400> SEQUENCE: 72
gccgccgagc gaagttccct tgccggcgtt cttcgcgaag agaagcgtct cctcgttcga    60
accagccgac gcaacsaccg atctgatcag aatcttgggg atagacgtcg atcgatctca    120
gatctccgat taataagaaa aagntatcnc t                                   151

<210> SEQ ID NO 73
<211> LENGTH: 401
<212> TYPE: DNA
<213> ORGANISM: Brassica napus

<400> SEQUENCE: 73
ataaaagttt ggatacttat ataataaagt aattatatac gaataaaagt gaaatatgat    60
aaaaatcatg atgaatagtt ggaaacaaac atgaccttgt ctcttttttc ctgaacaaca    120
catgaccttg tcctaagaaa tgaaaagata attaaataaa acgaaccaac aaacaacata    180
aaaaactaag aaatagccac raatgaaaat atagagggag gaaaatccta gtaataaatg    240
tttggatact taaataaagt gaaatgtgat atattcatga tgaatggttg gaaacaaaca    300
tgacattgtc ctaagaaacc aaaagataat taactaaaat gaaattaaaa aaactaagaa    360
aaagaccaca aatggaaaaa tatagggaga gaaactctag t                        401

<210> SEQ ID NO 74
<211> LENGTH: 301
<212> TYPE: DNA
<213> ORGANISM: Brassica napus
<220> FEATURE:
<221> NAME/KEY: misc_feature
<222> LOCATION: (42)..(42)
<223> OTHER INFORMATION: n is a, c, g, or t

<400> SEQUENCE: 74
gggtgacccg ggttcgatcc ccggcaacgg cgaatctttt tnttacattt taagaaattg    60
aaatgttttc atgaaaatga acaaaagatt ataatggctt cgcccggggtt cgaaccggag    120
```

```
accttcagtg tgttagactg acgtgataac maactacacc acggaacctt tgtgcttaca      180
ttgggaacaa agagctttga taattttgat gtctaagaaa tctttagatg tttggtccgt      240
agagtcatgt aagctgctct gtctattaag ccatctcgac tgctctgatc ttctgtaaaa      300
a                                                                     301
```

<210> SEQ ID NO 75
<211> LENGTH: 151
<212> TYPE: DNA
<213> ORGANISM: Brassica napus
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 75

```
cctcatgcat ngttcaagng gaagatcaga gacttcaaca actggttcat ctggaatagc       60
atctaccaca gacttrtctg tttctttgca tccatcttca ctggcgttta caccaccatt      120
ctcattattc tgagtggtct gagttgagtc c                                    151
```

<210> SEQ ID NO 76
<211> LENGTH: 801
<212> TYPE: DNA
<213> ORGANISM: Brassica napus
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (745)..(801)
<223> OTHER INFORMATION: n is a, c, g, or t

<400> SEQUENCE: 76

```
gctcaaattg ctacaacgat tgaatagaat ttcccgtaca naacactgta gttggccaga       60
tacgttgnag gtttaagaag tgtaatgtat cttgtattcc ttatttattt ttccttttt      120 ttgctaaaaa tatgctttat tttttacaat taatttctct tattttttac aattaatttc      180
tcttatttcc ttttacaatt aatttctctt atttcccgta cataattatt tgttttattt      240
taaatttatt atgtttgtat taatttattt cagtagtcag attgaaataa cagttaaaat      300
gaataaattt cattacttcc gatcatgtat tgttangttt agaactacaa gcttactgat      360
catgttagtt ggcagttttt tgtatctttt gagtatgcag rtatgtcaat attttcaaat      420
natatatttt tctaaatatc atattcaatt tctcttacaa acaatggctc tcattaatct      480
acattaattt attctaaaat aataataacc ctttgtaaat atcaatccta acatttaggg      540
aggtgtattc aattgggagt ttgaagtgat ttttattaaa atgataaatc tactgttctt      600
```

```
aaaacatgat tttttattaa aaaaactact ttgaaatcta gtagtattga acttgttatt    660
tcataaaaca ctcttaaatg cactattatt gaataaattt aagttagaaa ttttagagtg    720
atttatttct atagtgtttg aggannnnnn nnnnnnnnnn nnnnnnnnnn nnnnnnnnnn    780
nnnnnnnnnn nnnnnnnnnn n                                              801
```

```
<210> SEQ ID NO 77
<211> LENGTH: 1001
<212> TYPE: DNA
<213> ORGANISM: Brassica napus
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (405)..(406)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
```

```
<222> LOCATION: (604)..(604)
<223> OTHER INFORMATION: n is a, c, g, or t
<220> FEATURE:
<221> NAME/KEY: misc_feature
<222> LOCATION: (617)..(618)
<223> OTHER INFORMATION: n is a, c, g, or t
<220> FEATURE:
<221> NAME/KEY: misc_feature
<222> LOCATION: (701)..(702)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t
<220> FEATURE:
<221> NAME/KEY: misc_feature
<222> LOCATION: (931)..(931)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (970)..(970)
<223> OTHER INFORMATION: n is a, c, g, or t

<400> SEQUENCE: 77
tctttgactc ctgtttgaca tctcctangt gcattttgta ntgaaagagc tggtnagaaa      60
gtcnatttca gaaacagagg ngagaagacg ccttctgttg tgacaattcc tctttaactc     120
tttacgttct gtttcaaccc taaaatgcca tttttttatn aggagctgaa gcgattccca     180
actctagcna gcgatatagc agcngctgca aatgaagctc ttgaaagatt cagagacgaa     240
agcaggaaaa cngttctgcg tctggtggac atggaatcca gctacctcac tgttgagttc     300
ttcagnaaac ttcacatgga accngagaaa gagaaaccaa acccgaggaa tgccccacag     360
ccaaacgcag acatatactc cgacagtcac ttcagaaaga tcggnncgtc tctgcttacc     420
tcactatgaa tgaatgagac atatcaaatn tgtgttgact tttgaatata actcnggatc     480
caacgtgagt gcatacataa wcatggtctg cgacacattg agaatctctc ttccaaaagc     540
tgttgtctac tgccaagtna gagaagctaa gagatcgctc cntaacttct tctacgctca     600
agtnggcagg aaagagnnaa gtaattttct aaactagaga atatctgaat cattttaaag     660
agtgaagaac actttctaat gatcattaaa aaaaatgggt nnagaaggag aagctggggg     720
cgatgttgga cgaagaccca cagctgatgg aangaagagg aacattagcc aaacggctcg     780
agctttacaa acaagctaga gacgacatcg atgctgtggc ttggaagtaa ggtgtgatca     840
aaaagggttt cctaagaaaa tattctttat atcttttaat tgctttgctc gtgtgggcac     900
ttatgttgga agttctaacc tccnatccat ngctgcacac acatacagac gataactcgt     960
attttntttn gccgctaata tttgtttccc acttttttgg t                        1001

<210> SEQ ID NO 78
<211> LENGTH: 121
<212> TYPE: DNA
<213> ORGANISM: Brassica napus
<220> FEATURE:
<221> NAME/KEY: misc_feature
<222> LOCATION: (40)..(40)
<223> OTHER INFORMATION: n is a, c, g, or t

<400> SEQUENCE: 78
```

```
tgatttgcct agaccaattt ttagaacact ggtaataagn gacactgttt gtctttggtt      60
rtagttgata cttcagctta acggttcatg ttttaaccat ttcctaacta ttattgattc     120
t                                                                    121
```

<210> SEQ ID NO 79
<211> LENGTH: 151
<212> TYPE: DNA
<213> ORGANISM: Brassica napus
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t

<400> SEQUENCE: 79

```
agtttccttc tcctccgaga aagttagctc ntttctcttg ttctctntcn aaaanatctc      60
tcctttcaac gttaartcgt ttagttgttt gagtgatgtc tacggatacg gaggcgaatt     120
tacttgcgtt agcggctgtg ttccgcagga g                                   151
```

<210> SEQ ID NO 80
<211> LENGTH: 801
<212> TYPE: DNA
<213> ORGANISM: Brassica napus
<220> FEATURE:
<221> NAME/KEY: misc_feature
<222> LOCATION: (56)..(155)
<223> OTHER INFORMATION: n is a, c, g, or t

<400> SEQUENCE: 80

```
taattaacgt gatatattat ttccataatt atgcacaaat tatttgttaa cataannnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnngaaaa aaggtgtatt gcacaattat     180
gttaacaaat aatttgtgca taattatgga aatattacat cacgttaagc cttttagtct     240
tatgtttaga tcaatgttat aaaaattggt agacggtggt taagcgtctt gtaaaagatt     300
attgtttagt tggatatcta ggcgccgctt aaacagattt ttataacact aatttatata     360
gaaaatatgt aaaactttt ccatcatcca tttctaacat mgtggaaata aataaacaac     420
ttagacaata taaattaca aatagattat tagttttac aaaaaagta taaatagatt      480 attatggcac ccatcatata ttgcataggc tatattcttc tcgccttaag cgtaaaaaag     540
agacaaaata ttctttagtg aagatgggaa cagagacgtc gacgatgacg gcgaagttag     600
cattcttccc accaaatccg ccgacgtaca cggtggtgac ggatgaatcg acggggaaga     660
tcgatgagga tatcggcgga catgattcgt cgtcatagac gaggaaattg aagtggtgaa     720
gataatgact agaagaggga atgagatcgt ggggttgtat gtaaagaatc caacggctaa     780
actcaccggt gtgtattctc a                                              801
```

<210> SEQ ID NO 81
<211> LENGTH: 801

```
<212> TYPE: DNA
<213> ORGANISM: Brassica napus
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (359)..(359)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t

<400> SEQUENCE: 81
nnnnnnnnnn nnnnacaaca agctatcgtt tttatataat aagtctttgc atattcattt      60
taaattctga accgtttgtg tttgatctag gttgatactt ggtactgccc gagtgatatg     120
gacactccac actgaaagaa ttgtgaaaaa aaattagata ataaattata gttttttttt     180
gtaacttagt aaattataat gtttagaagc taaaaacata acacggagtt atggacagtc     240
gatactgact gaatcacact tcagacatat ccaaatatan tttgacttgc attcctattt     300
ttaaaaatt aacgttttga tgtgaaaata taagtttcac atcgagatcg aanattcant     360
tganacatga ataatatata aaagatttgg atcaatccac rtattaccaa tttatttta     420
tttgaaaact catgataaat ccaaacttaa catgatatta tagttcgaac acatgctagc     480
tgcccaaccg accgaaattg attaggctca tcgaaagagg ttcaattgat cctaaacctc     540
atggcctgaa tggtctggcg aactgaccga accaaatcct aaattgagat attgtcgagg     600
ttaatggtta taagaatcac tatnttgaag aggcgtgtga naatataaac tcacatattg     660
gaagtttaag tgggacatga ataatatata aatagttaaa gctaatccac ttatcatcaa     720
ttggttttaa gttaaaagcc tatgataaat ccaaatttaa catatttgct tattaatcag     780
tgttttagat aaaagtggat a                                               801

<210> SEQ ID NO 82
<211> LENGTH: 401
<212> TYPE: DNA
<213> ORGANISM: Brassica napus

<400> SEQUENCE: 82
ctagcttcct caccatgaaa tcaatacggt ccaatctcga aaggatgggt tcttccacta      60
tagccataat gttgataaca caccgttgtt ctgttgcaca cttcacagct ttggttgttg     120
ccgtggagta gttaaagcct taaagacaag acactatatg aaacgccaaa actggtcatc     180
ttggagattg aagacatgaa ytacgacacg tttaatatta cagagagagc tggttacggt     240
cttacgcgtg tcgttgatca cacgtactgg gtttagtttg tggacacctc ttctgtctca     300
```

```
cacgtccaac attattccat ccttccttat cttaatcgct gacgcctctc cgagattata    360
tcagacgcaa gataaaattt ctagtgttta ttgcaagtgt t                        401
```

<210> SEQ ID NO 83
<211> LENGTH: 801
<212> TYPE: DNA
<213> ORGANISM: Brassica napus
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (626)..(626)
<223> OTHER INFORMATION: n is a, c, g, or t

<400> SEQUENCE: 83

```
gttaaaactc gtgagtggta atcttgtaaa ttgatgaaga cttgggttct aagttggctg     60
aaaccaaatg gggtttctgc gcgcttcgcc gtcgaccgat gacacaggat gtgcatcgat    120
cgattattat ctctgaatgt cgaccgatgg tcttgctcga tggtcagctc ggatgctttc    180
tccaaatatt tccaaaatgc tccaaaatca tcactttctt tcaaatcact catgatcgta    240
taaatatact aaatagattt tataatataa taattagtta ttaaaacatc tataaaccgt    300
gggtaaaagt gggtaaaatc catggcattc caataccttc cgccaagttt taaacaaaat    360
caataaatca tattttctat aatagaagac tcgaatggtg sttgaaactt caaactaaac    420
cacaaagctt nacgttttta tatcgaaatt caaagataca ctatacaact attaactgca    480
canctaatct ctaagttact ataaatccag caaaacgaag ttgttgacat gttcgcgtca    540
gagtgtgaga ggtacaattt ttaagaatga tncgaaacta agaagatatg agtaacgnaa    600
ggtattaaaa acatatatga ggttgnagtg aagattcagt tttggtgaat aaaatgactg    660
atcagaatat tttgaacatg tacatatata agtgtgtatc agattcagat tgtagattat    720
agatttcttt aattgtgtga ggatatttat gaagatcgca ttactctggt tcgtatgtca    780
aaaacatagt tggtagcttc a                                              801
```

<210> SEQ ID NO 84
<211> LENGTH: 401
<212> TYPE: DNA
<213> ORGANISM: Brassica napus

<400> SEQUENCE: 84

```
taagaaaaga aactgagatt aatcgcggtc taagtgctag tttgaggtga cttttatgaa     60
agtataccat tacagtaaaa ctgactctta gtcatagcct cataggttta tcattcaacc    120
cataaactag aataatatta ctcagccaat tttaagtaaa tcattgaata ttgttagtgt    180
gagattaccc ctctctgagt waattgattc tataaacata aatacccata tccccatgca    240
atgatacaac acatactatt tcgaaatccc tccgtgattg aaaatatgca ttgttcacgc    300
ctcttctcta ttttatctct aattgtaacc atcgccggag ctttcgccgc cgctctagag    360
```

```
tgttcatgta atgatctggt ctgtttattt aatataaatc a                            401
```

<210> SEQ ID NO 85
<211> LENGTH: 801
<212> TYPE: DNA
<213> ORGANISM: Brassica napus
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (296)..(296)
<223> OTHER INFORMATION: n is a, c, g, or t
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (622)..(622)
<223> OTHER INFORMATION: n is a, c, g, or t

<400> SEQUENCE: 85

```
agtataagga agatgtttga aaacatggaa actcacatat tatttagaag nctgccttac         60
cattgccaat tgttagccac aacaaaaaat accaatctaa caaggtactt tcatgactcg        120
atctcaactt agcaacctaa ccatttcag cccacagctc ataggagtta tccaaattca        180
ctatcactga cctcatttaa gactaaaagt gcagtctcat cgagggagta tcgatcataa        240
gacacatgga ctcttaccta ttcaagtatc tgatcacaca tataatttta ctctgntttc        300
tttcctctct ctttctcatt tcctcattng atttctctat actctgtagg gtatcatttt        360
attttctat cgactgagtt tattagacaa gattccatga sacacaagca ctgatggtgg        420
taaccactaa gcacgcgatg cacttcttgt tgattttat cttttttctt tcattttttt        480
tgaagagaag agagagtaaa accatattca cacagactag tctttttaga cgtgagcaag        540
aagtccaacc caatgtatac caagatttaa gacaagagaa tcaaatagat taggtgagag        600
gtcagctttg gatccttcga angcccaaca aacatggatg gcagatcaat ccactttggc        660
aacaatgtct tttgttcagt attgctactt ggaaagcaaa acacaaaagc agcttatttg        720
ttttattttc ttctcatact tgtgtggttc aactggaagt agctcagttt ggaagggttc        780
catcatagtg ttctctgtag g                                                  801
```

<210> SEQ ID NO 86
<211> LENGTH: 801
<212> TYPE: DNA
<213> ORGANISM: Brassica napus
<220> FEATURE:
<221> NAME/KEY: misc_feature
<222> LOCATION: (1)..(85)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (704)..(704)

<223> OTHER INFORMATION: n is a, c, g, or t

<400> SEQUENCE: 86

```
nnnnnnnnnn nnnnnnnnnn nnnnnnnnnn nnnnnnnnnn nnnnnnnnnn nnnnnnnnnn        60
nnnnnnnnnn nnnnnnnnnn nnnnccttt  attacatgcc agttcatcgt cattcgtcac        120
tgtattgaca cgtgtcgtaa gaccattata tactttctgt aatcccatga acagtagtt         180
aattacactt ttaacttctg cacgtaagac taaagatgaa gggaagatga atgacatctt        240
atgcatgtgc actgcacgcg gccggcgact cccgccggtt tcgggtttaa gtgggtctct        300
cttctgcatg aatagtagta gctttctttt tttaaatgtg tatatagtag ctatatagtt        360
tatttatgnt tcctagtaat atataatgtg ttttattttc sagacttctc aattactcaa        420
ttctttataa taattaggta acactgttgt taatttttta ttttctttct taaaatggtt        480
ttagcaaaat taaataagct agatagatat agctaatata catctttcat tttaagtgtt        540
tgtgtgtatt tttgtaaatt tgaagttcaa aaacgagtat ttaaatgatt ggatccgctt        600
gcaagtggta tngacaatta gcacaaaatt ccactctaac tctcagtatc gtttacaaag        660
aaaagcgtat ggaaataaat naacctttac gtattagatt ttangaacga aaactcaaat        720
cctaatgat taattgtctt taattataaa aagttataaa taattacata ttactagcaa         780
cctccagtga ctcttaatta g                                                  801
```

<210> SEQ ID NO 87
<211> LENGTH: 401
<212> TYPE: DNA
<213> ORGANISM: Brassica napus

<400> SEQUENCE: 87

```
accagaacta gatattgatc cttatccctg aataatctgg tatattcgga aggctcgaaa        60
tgaaaaaact ctttaaggga tagacatgga tcctttggag ctagttcgct atgcagagag        120
tgagtgtcaa gtctgattca atgcaaacaa gatggtaacg ccaactacac aagagcataa        180
ttttgaagac cctcaagtct kaaacttggg taatatttgc attgtaactt ccacagcttc        240
gttcagcggg tgtggttggg tttgaaagga tatatagctc ggggaaggtt caacttatgg        300
ggacacgaaa ttatagacgg tgagagattg ctttgctttc agaagtggag gtcttacaat        360
gggcgatgga gagcatgctg cagaattcga catgccagag t                            401
```

<210> SEQ ID NO 88
<211> LENGTH: 401
<212> TYPE: DNA
<213> ORGANISM: Brassica napus

<400> SEQUENCE: 88

```
aatatatctt ttttgaaaa  atcgtgtatc tttaaaacag aagcgcacgt aatccacttt        60
tctctcagtt tcgagtctct cttttcctcg gagcttgtca ccaagagaga gagagagaca        120
tggaaagact tctgcaacca ccgtcttctt ccacaatctc tccttccaaa ttcacctcga        180
ggatcccccc tctccttcct ygtctccggt tcgtctcaac gtacagaccc gagtcacgcc        240
gagtgagctc catttcctgc agcaatctcc agagcccatt tgtgggatct aatcagacca        300
acatttcctt gaatggatct ccttcctcat ctcctgtagc aggagaatcg aaccctaatc        360
atgggttttt ccaacggatc gtcaccacgg ctgatgagca g                            401
```

<210> SEQ ID NO 89
<211> LENGTH: 401

```
<212> TYPE: DNA
<213> ORGANISM: Brassica napus

<400> SEQUENCE: 89
tcacaagggc tttaaagtaa actcccatca gacccatgac catatctact aacttcaaat      60
cagaccctga agtggtgtgc actgtttggt caactgtctt catgaatcat gatggcctct     120
cccctggtga ttcgttcttg gtatttcacc tctcatgttg ctataaggtt atctatcttc     180
agtcagatct catggcaatg ygagaagttg ttaagtttcc tttagttcaa tttgtgattg     240
cttcagaata ttgactcttt ggctatgact ttaatgtgtg attgattctg cggatttgaa     300
gggccagtcc tattactgga actatcagaa gcttcatcag ttacttcagt ttctgcttgt     360
attctctgtg tgttagtggt tttgtctagc tccttgctaa t                         401

<210> SEQ ID NO 90
<211> LENGTH: 801
<212> TYPE: DNA
<213> ORGANISM: Brassica napus
<220> FEATURE:
<221> NAME/KEY: misc_feature
<222> LOCATION: (583)..(583)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t

<400> SEQUENCE: 90
atttattgaa ttcttaacaa gcgtgaacat tttagaaaat ttaacttttg agaatagagg      60
gagtagtact gatattttta accagtatct actatctaca ttggttttag taatgtgtta     120
ttcatggccg tggttaagtt aatctggtta attaaaaata agaaacaaat taccgtggtg     180
tctgatagac acgggcttga gcgaatgagt aaaataagaa agcgtgggga gtggaaactc     240
gagcctcaca gaatcaatca cctagactaa atattctttg aacaatgaca gtcacatcct     300
cttattatag tgtatttata atttactaga ttaatttata gttcttttc tcacaaagat      360
catgtactca ttacttcttt tccatgatat ggacaatctt rtgttgcggt tggccatctc     420
ttttggcttg caagcttttt gactgaaaaa gttagatcct ctttctaggt ggtgactttt     480
gttgcaagtg atctggatta tgggttttca tcctgtatct gtagtttata aatatatctg     540
tgaggaaaaa agaagaagat catgtactcg taattcagta ttnttctgca gcacaattct     600
gaatttggaa agtttaaaat agacttctta attcanataa gtcagcaagg taagttacat     660
gattacatat ctacaattat ggaaaatcaa canatttcaa ttaattgttt gttncttaaa     720
ctcaataatt tttataataa aaacaaatat ttaaaaataa aataacgtgt ttactttta     780
ttatatatat gattatagtt t                                               801

<210> SEQ ID NO 91
<211> LENGTH: 801
<212> TYPE: DNA
<213> ORGANISM: Brassica napus
<220> FEATURE:
<221> NAME/KEY: misc_feature
<222> LOCATION: (65)..(65)
```

```
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (667)..(667)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t

<400> SEQUENCE: 91
aagagtatcc aaaaagaaag agagaagaat ggatgacgcg cgtctctgtt tttagtagca      60
gagangagag agaaatgaag aacaatggtc gctantttt tgacgtcagn ggcaacaccg     120
gaaatcttag ccttttttga cgctgcgttg cttgttaatg gccgctgcgg tcatcggtgt     180
tgtgtgttgc catgactccc gtttaaattt tggccgctgc cgctgcgtcc tgcagctaag     240
aaacgaacac ggctattgtt attttcgttg ttgacatggt caatgtaagc tgcatgtttc     300
tcttctgtat ttccatacat cttttctgat caaatgtttg cagccatggg taagaataat     360
ctcccctcct tctagagtct gggaatcgaa atttgcgtca wtaaaatttg taacanagaa     420
aataaagctt ttaatggggg tccaaatttt ctgcagagcc aacganaagt aatcaaacac     480
catatatatc taaactccaa atatcaatca tgatctaagt gttaaacagc tcaaaatttt     540
gctataattt tagacattaa tatatatata taaacccaaa aaaaactaac aatttaaaat     600
ataattttat attaattata ataatatgat ttataatatt tacataatat aaagtgttaa     660
tattgtncat ttattttaaa ctgatgtcaa ccggttataa ttatcccaca acataccaa      720 tttctaattg attgtaccag tcgtactaat cggttaataa cntttgaaac ngcatccgca     780
aactcgcatt tacaccagtt a                                                801

<210> SEQ ID NO 92
<211> LENGTH: 462
<212> TYPE: DNA
<213> ORGANISM: Brassica napus

<400> SEQUENCE: 92
ggaatttctg ggtcgacgat tccgtcccaa cgtcaccact tccctcccag atctactatc      60
accctgcaag ttcatctaca cttaatccga cacagcgccc tcgcctatca aagcamgtct     120
cagatggtca gatctgtgga atgaactcac ttagcagaag ctcgataact gaagagaggc     180
agggaactcc tttaagatgt gattcttctg agagtggacc atctgaaggt tggtcactgc     240
aggccttttc tgaaatgatg tcatcttctc gcagcaccga gcctttgtct tatgataacg     300
accactttgg gcttgaacgg gacatgatag gccatcacag caaccgaatg tccaatcatc     360
```

```
agcagcaaag ctgtggtgcg tgctctagac ccttgtcaga gaaatccttg tggagcagcc    420
aaaagatgtt tatgaccaac gagctctctg tgtctgcaat tc                       462

<210> SEQ ID NO 93
<211> LENGTH: 801
<212> TYPE: DNA
<213> ORGANISM: Brassica napus
<220> FEATURE:
<221> NAME/KEY: misc_feature
<222> LOCATION: (200)..(200)
<223> OTHER INFORMATION: n is a, c, g, or t

<400> SEQUENCE: 93
atagatagtt cataatcaag agattataat ttgtaatatt tccatttatt tatgacggtg     60
taatctttta tataaagaac ttctatgctt tgaataaaga taaattttct tattttttata   120 agaaaaatat aatttttgtta aaaaccgaca tacaatgaga cttgtgtcgc cgtctcatcg   180 tgttttctt ttcccttcan gactatttta taaatcttgc gttagacgtt aacgctccaa    240
ttgatttgtg cgagaaaatt ttacataaac cctagaaaac tctcttattg ttcgcgttta   300
attcttcagg tacgatttgc catcctctct ctctctctct tttcaaaagg tatctgcttt    360
tcatcgtcta cgatcgagag aaacttcgag actttgcctc ytttgttggg attgaaattg   420
gttaaaggtt taattgtttt tggtgttgat tgttttatcg gcgcgcagat atgccggtga    480
tgaatccgtc gtcgttgtgt attggtgcac aaccattggt cttcctccct cctcgcttta    540
atcatcgacc agctaatggt atctctctac ttttgggata tacacttctt cttgatttgc   600
ttcttgccac taatttatga ttgctcatga aaaaactgat gttcttgtag cattagatcc   660
ttgcttaatc agatttctca agcttttgat tttcgtattc tattgaatgt ttcaagtgtt   720
aataaaagct cttcttcttt ttgttctgtg gtaggacaat ttcgtgggcg ttactaccct    780
acaagagttt ctatgcaatt c                                              801

<210> SEQ ID NO 94
<211> LENGTH: 401
<212> TYPE: DNA
<213> ORGANISM: Brassica napus

<400> SEQUENCE: 94
atgtaaaaga acgtaaacag attaatagta tataaagtaa tttgtatata gaatatttat     60
tccactcaag gcgcggttaa gtagttatta ttcagcatgt atatatttgt taactattat    120
taaaatgcaa aaaatatgta tagtagaata cttaatgttt ataatcacga gatataattg    180
ttttcataaa ttcatcccca matgatgcgg ttatcaccct agtgtgatat tatacatggc    240
caccaggttg atccgatcca acagagtcca tcggtcctct tcaaaaagaa caaagcttta    300
ttgtacaaca gataaaacgt agcatatcgt gctgcttaga cttatcttct ccatatggtt    360
gcagagctct cggatacagt cgttgttttc tagcaggctg a                        401

<210> SEQ ID NO 95
<211> LENGTH: 151
<212> TYPE: DNA
<213> ORGANISM: Brassica napus

<400> SEQUENCE: 95
acgaccgagg aaagcacctg cggaatagag accaaggccc aacagcagga aggaatcgat     60
actctataga tccacmacta gcaacctaga atttgaagca gagatggagc ggagaaccgc    120
```
accacacaaa taagccacca ccaaaatacc t                                      151

<210> SEQ ID NO 96
<211> LENGTH: 801
<212> TYPE: DNA
<213> ORGANISM: Brassica napus
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (493)..(493)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (772)..(772)
<223> OTHER INFORMATION: n is a, c, g, or t

<400> SEQUENCE: 96
tactagcact tgtttgcaag atcggtggac tcacactttg atgatggagt ttctgtgtgt        60
tgtatagagt caatgaccta catgagtaac cctgtttgta gtccttatta tcacgtaatg       120
gaaggttccc cttctggtga tcaaggtcga tgttattgtg ctaacaanga aggcgagaat       180
acttggattt taaaataaat ttgaatagtt aaacaatttt gtatttatct ttgaagttta       240
catgtgttta taagaaatc tangccaaca taagccaaag ccctcatcat atttttcacta       300 tgaaagcaat acccttttgt ttaatcctac tctaacttgt tttactactt aaggatgtaa       360
actgagtaat tatagtattg tgccaacccct tttgttagac sgacttcttt gtccttctcc      420
ncttgcacaa gtcaaacaaa agcccctagg cccatcctca tggccttagc tcgtgatctt       480
tttatcggcc cangtgtaaa aagaaataga tctttaactt ggatgataga ctcattttg       540 cctgtgaaaa gcccatttng accatctttc tttaaaggtg gttctaggtt ctctttgact       600
tgtccatgat gttcatcgct tccaattagt caaaaatgtc cttacatagt catttccagc       660
tccgagtcat ctttctcatt cttattctca tttcacgacc ataacgcata gtcgacctca       720
tntcaggttg atcgaagatc gaatcgtcca ttnccagcta gtccatgttc angtgtcgca       780
tttcccgcct actcatggtt g                                                 801

<210> SEQ ID NO 97
<211> LENGTH: 401
<212> TYPE: DNA
<213> ORGANISM: Brassica napus

<400> SEQUENCE: 97
ttggtgattg aataataaga aaagaacttc ttattgatat tgtgattcta tagataacac         60

```
tcccatcatc cagcaggacg caactcagca gttcaatcct gaaggaactc ccacaccacc      120
cccaactggc agtgttacca acggcatcaa ccatcaatct gaatggtatg ttatcacaaa      180
tacgtgataa tttgcaaaaa kttctctgtt ttgatttaac atacaggtca gtaggatgcc      240
gtggcacagc aagcttttta acgcttcaag caactcaatc aggtctagac caaccagtag      300
gcgcaaatca attccttaag tgcatatcac caaagactcc acgccagccc taatcaccaa      360
agactccacg ccagccctag gtggacgtac aaactcaata g                         401
```

<210> SEQ ID NO 98
<211> LENGTH: 801
<212> TYPE: DNA
<213> ORGANISM: Brassica napus
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (587)..(686)
<223> OTHER INFORMATION: n is a, c, g, or t

<400> SEQUENCE: 98

```
tgagatttgg gccatgactc gaagataaag ctttatgacg atcatcacac tacaagaaga       60
gatctggaaa cttctccaaa ggccagcatc gatcgacacc gccaacccaa catcgatcga      120
ccccgcccac ctgataccga tcgacatcca cctaatgata tcgatcgaca cccatcgttg      180
gacgacctgc caaggtcaca gttgggctga aagtagttga ggagagaatg cacacgtcta      240
cgacctcaca ccttgctgtc cccgaacatc ngagaccacc tatatgcaca gaagaagctg      300
ctgggtttca caaagagtc aagaggatac atgaccatgt gaagtttgtg gtcccatgca       360
ttgtatttga agttgaatct cctattccaa caaatagaag ygtgcatcta ggttcttaca      420
ttgggaaatt tgatgatcat atgtatgcac tagtttttga gagagggttg agacatataa      480
gtgacgtcga cacagcccca acagaaacaa catcgatcga cactaccact tcatcgtcga      540
tcgacattgg acgtgtatca gatcagaagg agtttgaagt gtgtcgnnnn nnnnnnnnnn      600
nnnnnnnnnn nnnnnnnnnn nnnnnnnnnn nnnnnnnnnn nnnnnnnnnn nnnnnnnnnn      660
nnnnnnnnnn nnnnnnnnnn nnnnncggc gaagagtagt aactgttagc accatcagag       720
atttaagatt tgtgcacccg ggaaaagcca tattcaatta gtcttcttta tccggagatg      780
ctaggtctgc tggtaaaaaa a                                                801
```

<210> SEQ ID NO 99
<211> LENGTH: 801
<212> TYPE: DNA
<213> ORGANISM: Brassica napus
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:

```
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (784)..(784)
<223> OTHER INFORMATION: n is a, c, g, or t

<400> SEQUENCE: 99
tttaatacga aaagaaaat tcagttttta acaaataacg accataaaaa tactaaaata    60
aaaaacaaga aacattattt aacatttcac tttttgtcta tactttatta aatttgnaac   120
atgttctcat acatagagga aaaaacaaat tncaaataca tagttaattt taacgtgcaa   180
acatgtcatt atttttaanta tttcactctg cacagggcgc ggattattat tatgaatgag   240
ataagtatgt ttgatacgat cattcatatt tatgcaatta gtatattttt ggtatacggt   300
ttatattata tgcattcttt gtttgggata tgaatattaa ataactagcc agaaaacatt   360
atcataatgt catgactgcc tggttttaat taacatgata macatatggg atgtgtaaga   420
ccaatcnaat taacgatgtg tgtagttggt ttttaagant ggtntggtcc aatggtttta   480 atctttatt gaattagaaa tctaatttga ttggatttta ataataaagt aaagactatc   540
tgattagtaa ttaaaaatta ataattttaa tacgattaaa attagtttaa ttatttataa   600
ttcagttaaa atacataaaa gatttgtatt agttatattt atattttata ttatatataa   660
attttaaatg taaaattaaa ttagattaaa attgtttcct caattgattt caagtatttt   720
ttatgtttac acagtcttat caactatcaa agctcgtttc gttgtaagat ganttttggca   780 aagnaaggtg tcgttagtta c                                             801

<210> SEQ ID NO 100
<211> LENGTH: 801
<212> TYPE: DNA
<213> ORGANISM: Brassica napus
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t

<400> SEQUENCE: 100
aattaatttg tatagttaca ttttttagt tgtattacaa atctcataac gtaaatcat     60 taatgaatct ttagttaaat tattagacta gactcgctag atagatttcc acaaaccta   120 ttacattttc tttataataa cagtgaaaat tacatgaaaa tgtgaaaggc tactgcacat   180
tttcttatgt ggtataaaaa tattaaatta taaatttggt atatatgccg aaactatttta  240 tgttggttca tatacggtta catataaata cttttttatcg gtatattcca ctaaacacta  300
```

```
aaatattgaa gatattaaat atttaagata tcattgtccg tttagaattt caaagttaag    360
cgtgttcgac ctggaatatc ggaagaatag atgacttatc rgaaagtgat tcgcgatatc    420
gtgcaagtga atcnaaaaca cggagaaaag tcacgtggtn aacgggtgga tagtttggta    480
ggcggtcggg ccgttacatc taccacgtcc tgtaacacag gtgcagcctc tgtgaanaaa    540
aatgctggtt ccatacggac aggtgcagcc agtggtatgg acgggcaggg ccgggtctga    600
atagaagtnc atcgagcatg tgtttggagc ctgacgaata tatagatatt ttggggccaa    660
ttattttcca tacagaacat gcagctctat tggcttgggg tccaacgaaa atatagatgg    720
acctctgttc gcttctccgc aatcgcatct tatattatta tcactatttt ttagaaacaa    780
gggtcaaaaa tatttttta g                                               801
```

```
<210> SEQ ID NO 101
<211> LENGTH: 801
<212> TYPE: DNA
<213> ORGANISM: Brassica napus
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (782)..(782)
<223> OTHER INFORMATION: n is a, c, g, or t

<400> SEQUENCE: 101
cttgactatt tttatgtgaa tttaagaaaa aaaataaaag taaaaaatta ttattttta     60 ttgttttcag ttattgtcta atgagtgata actcctaact tcttaagaag tcttaaataa    120
gaataattat gaaagctagt tatttttttt gtcaaccgga tgtttattaa acaaggtcta    180
taatataaaa caggtccaag aagatgggca gtaaaactat tacaaaaang tccaactgaa    240
aggcaaataa acataaatg aaaggcctan catataaagc ccaatataca agcatcttg     300 aggccttaag cccacgagag aaagatctgt tggggaagag ggtcacacga cgccatatac    360
gatcacccaa cgatcaatgt acacgcgtca agacgcggtt ycaacattct tcctccggag    420
ccagcgaaga ggcgtgatgg aactccgacg tcgaccaagc ctattagatc gttgaacgaa    480
aacatcaatc gnctgtaatc gatcagaaat ccaatttct tgcatgcgca aaactccatc     540
tttgatgatt tatataagct tgaaaatggn gacaaccta accgagggga ggaaagagac    600
attgaacctt cagatcaaga ggtacggtgc tatagaagcc accacttccc gtaaacctaa    660
agccggcgaa gatggtgata agggatccac cgcttccaga ggcagaaacc cgaccattgg    720
gagactgagt ccaaagagat ccgacaaaca aaactcgacg ctctctcnct gaaagatagg    780
anagagataa gagagagcag a                                              801
```

<210> SEQ ID NO 102
<211> LENGTH: 801
<212> TYPE: DNA
<213> ORGANISM: Brassica napus
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t

<400> SEQUENCE: 102

```
agatctcttg tccgaagcag agcatttttt cgctgaaata tgctctaaga agttttttcg    60
ccctgatgtt ccaacgtatc gaacgatgat ggatgcatat gtgaagaagg gtagagtcag   120
cgatgctgtc aaaactgtga accaaacttt ggatgcctct ctaacctata ttgctaagaa   180
ggtcttagta atgtaacttc cgtttatgtg catcactatg caattcagat tcttagttgc   240
ataccaactg ttgtttatcc acaaatctgg tggaacttna ttagtagtgc ttaatcttga   300
ttgtttatct tttaagtcta gttaacaaga tcgttaatac tcctttctta aagctagcaa   360
taaaacaaaa acaataatct gacgcacata tttgaactta ycaaactatg aagcgggctt   420
ccagactttt aattggggct atcaatctga gactccgttt ggtcataatc tgcccaccat   480
taattgggcg tataatggct cttgagggag agtatagttt atattatnag cagtcacaat   540
gaaccttctg catattgagt caagctataa tgtggtttca tgtgttcata acgcagaagg   600
agctcgaaat gggtctatcc gaaagcaact gttgtaccta acttccatct cccagtgcgc   660
agctttgggn ttaatgtaga atattttgtt ttcaacgacg cgcgtgtttg gttctactat   720
atgaaacggc gcacatgttt gattatgttg atagaaacgg catggctttg ccgtcttcga   780
acggtcacgg catggccatg t                                             801
```

<210> SEQ ID NO 103
<211> LENGTH: 801
<212> TYPE: DNA
<213> ORGANISM: Brassica napus
<220> FEATURE:
<221> NAME/KEY: misc_feature
<222> LOCATION: (76)..(175)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (478)..(478)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (526)..(526)
<223> OTHER INFORMATION: n is a, c, g, or t
<220> FEATURE:
<221> NAME/KEY: misc_feature
<222> LOCATION: (631)..(631)
<223> OTHER INFORMATION: n is a, c, g, or t
<220> FEATURE:
<221> NAME/KEY: misc_feature

```
<222> LOCATION: (636)..(636)
<223> OTHER INFORMATION: n is a, c, g, or t

<400> SEQUENCE: 103
tctctggtaa aatcacatat atactataaa taaatagtaa tctctccgct tcataatata    60
tgatgtgtta gaagannnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnatcta   180
ttcttccctc cttagtcatg aaaataaact ttagaaatgt tagtttatag tatataaata   240 aactttgtt atcgtatatt aagattgtta gtgactatag taaatgttat tctgtaaaga    300
tttagtgttt attagaagaa atgagaccca cctgtgtttt tagagcctgg tgcgtatgta   360
tcataaaata ttgttggcac gaaacaactc taaaactgtg rtggtttaaa ctaataaact   420
agagatggtt attaatcatt actctatgca tctttcgatg tatattaaga tggttnangt   480
ccaaanaaag aggattctac gtaaaacgtt gagtgttgcg taaagnatgt aacctacaat   540
acagcattaa aatatgcatt cactagtgtt ggggtgtaat aatatgatta acacgtatta   600
taaggaaaaa gaaattaaaa atcttgcccc nagatntagg ttattcgata acaaaaagag   660
tatgcgttaa ctctgaacat tggtgtatca ggaaatcctt agacgaaatt ggtgttagtt   720 taggattta tgtaattttc tcaatgctta taaggcctct aagaatgcga aaggagata    780 atataaaatat tacattcgta t                                           801

<210> SEQ ID NO 104
<211> LENGTH: 496
<212> TYPE: DNA
<213> ORGANISM: Brassica napus
<220> FEATURE:
<221> NAME/KEY: misc_feature
<222> LOCATION: (1)..(57)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t

<400> SEQUENCE: 104
nnnnnnnnnn nnnnnnnnnn nnnnnnnnnn nnnnnnnnnn nnnnnnnnnn nnnnnncctt    60
gtcatgttat gatcaagcat ctggtcaaga gaagcgacca tatgaatgta cttctttctt   120
ggnaaacact ttaagaaact tttaacaagc tttggctctt ctatcatctg tcccaaagaa   180
gccgatttgg aggagatttc ggatagcttc ccggaaaagg tatcgattgt atcttcatat   240
ttcatcttga ktctattgaa ttctgtcttt agggtttgaa gcgtagccta ttttacccctc   300 tcagctccta catgtcttgt ntttatagca tcccatatcg cttttgttgt gtctaagtcg   360
ccaacttgca taatcaaacc ctccggtata gactggaaca aaagcacagt ggccatactg   420
tttttcttct cgtctttggt nccagggtct attgcttccc aaacttcgct aaccttgagt   480
gcaatcttca ttctca                                                  496

<210> SEQ ID NO 105
<211> LENGTH: 401
<212> TYPE: DNA
```

<213> ORGANISM: Brassica napus

<400> SEQUENCE: 105

```
ctttaagtag ttgtactatg acttcttaat agtagataaa ataggaccc taaactaata      60
gattagatat attgttattt ataataatga taaaaaagat aaaacattat tcgaaattta    120
gagatttaaa tgaatcatgg aaaatgcaag acctatttgg accaggatcg atttgagatg    180
aaagctaagg atatagctag rcaattcaat tgttgaatgt taccttttt gttcaaaagt     240
tgactgttga acaatctatt gattattcaa gccaagatta atacaaaaca aatcatcttt    300
ggcatcaaca gcttctagga ttttagatgc ttacatattt tgtgcaagga ccgccagtgt    360
ttttgataac agtgttgaaa cacaagtggt catcaaaaac g                        401
```

<210> SEQ ID NO 106
<211> LENGTH: 801
<212> TYPE: DNA
<213> ORGANISM: Brassica napus
<220> FEATURE:
<221> NAME/KEY: misc_feature
<222> LOCATION: (165)..(166)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (623)..(623)
<223> OTHER INFORMATION: n is a, c, g, or t

<400> SEQUENCE: 106

```
ctttaaagaa ttcaatttaa ggaatatctg aagaagaaaa tcaaaatgac tatggatact     60
agaaagaatt agagaagcaa agtgagaaaa ttcaaaattg taacgctta tggtctgaaa    120
atataaaatt tgacgctgaa atgatcaaag ttgactcaaa aggtnnataa aagtcttgaa    180
aattatgata taaatttg agaatagtta tgattgatgt gaataatgt ctacaaataa      240
aagagaatat gatgttttcg gtgaatgaat gtcatattta tatattttac cttgatgagg    300
ctgaactgaa ttcgagtcat gaaattatta ttctcattgg atttggagtt tcggtaaacc    360
agtacaaaat atccaaatgt ttttcatcta tcacttgtgc waatctcttg acaagccatt    420
atttatcttc aaactatttt aaatccgtac aactancaaa ttcgatgcta gaaagnttgg    480
aaaaaactct catacctat cttttgttat atttaattaa tccaatgctt ttatgtatca    540
catgcagaag ataancaata tctggtttaa tcaatntccc atgagcagaa gttttaaaaa    600
agtagtttag caatcgcggt gangagatat ataattacaa ttaacttttg tctttgacaa    660
aaaaatacta cgagtttcgt cccaattatt acaaaacaaa agttttaaaa agcattaaaa    720
tatatacata ttaaaaatca ttcttctgaa aataatgctt gcatccaaag tgaaaatgcg    780
acacttaatc tgaattttg a                                                801
```

```
<210> SEQ ID NO 107
<211> LENGTH: 151
<212> TYPE: DNA
<213> ORGANISM: Brassica napus

<400> SEQUENCE: 107
gtcttcagga cttcaaaatc actccccagt acccaatgct catctctttt gccaagaaat      60
gaagagaaac tgcctktgtt ttgtttgtct tttaagatga tgacagtgag acttggtgtg     120
tataaccgac ggtttaatgt ttcggttcga t                                    151

<210> SEQ ID NO 108
<211> LENGTH: 401
<212> TYPE: DNA
<213> ORGANISM: Brassica napus

<400> SEQUENCE: 108
gaggaattat atacgcgaaa gcaataagca accagacaga caccttacca ccacagggtg      60
tatttattca tttaatctat tttttagtt aaaccttgca aggtttaacg aaacttctgg      120
tgtctatctg gcttgaccgg caggggccca agcggttatt tccatgcttt gcctaagaga     180
ttgcttcatg tgcagctaat yttcgttcaa ccatagtcag atgactacaa gcacaagcac     240
agtgcggaag agtgtgacgc cgctgtccct gcaaagaat tgcaatcaaa ctataattat     300
gttaagatag tattggttat agaggaaatt aaataaaaag taccaaaaag ggtatgagac     360
aagtccttgg agatcggttt cagcatgaaa aaacatgggt a                         401

<210> SEQ ID NO 109
<211> LENGTH: 801
<212> TYPE: DNA
<213> ORGANISM: Brassica napus
<220> FEATURE:
<221> NAME/KEY: misc_feature
<222> LOCATION: (396)..(396)
<223> OTHER INFORMATION: n is a, c, g, or t

<400> SEQUENCE: 109
ttctttccct ctagtacttg tctcctgaac ctaatcgtat gtatctttga ccaggtgaaa      60
ggtgttaaga gtggtatggt ttagtaaggt ctactaaacc aaaccgagac tcgggttgtt     120
aaggttgttg agataagtac aatgtattag aagataaaga tgcacggtag atgtagataa     180
agtagaatct ccttgtaaag atacgaaggt cgagtatatg tatccaacgt gatcaatgag     240
atccacacac agtttactaa atacagtttc tctctgagtt tacatggtat caaagcgggc     300
ccaacatttc catattcatc tcctcaggaa acatcttgat catgatcaga agaaaagctt     360
cggggaggat ttgttatacc attgcatcaa gcaatnagcc wttgagaagt gtgctaccgt     420
tgtccaacga ccctctgttt cctcggagat cagtaaagga aatgcttttg cagtcttaaa     480
atgttaatgg caatcaaagt tgcctcctca tgaaatatt atacgaggcc taagtaggtc     540
catatctttc agttaacaag tttgaagttc accttttgc atatggagtc tgaatgatca     600
acaccaaaat ttcatgtggt ttcagattta tagcgtaatc cttgataaac aatatcaaca     660
agaatcattt ttaagcaagt tttcaaaact ctgcttcctg ctttctgatc taatcagtgc     720
taagatcatc acttgttaag tagttcaaca tcaagctttt ctgaaaatga gaaacatctc     780
acatgttctg cctgctttca g                                               801

<210> SEQ ID NO 110
<211> LENGTH: 801
<212> TYPE: DNA
```

<213> ORGANISM: Brassica napus
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (308)..(308)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (752)..(752)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t

<400> SEQUENCE: 110

```
tgtatcgatc gacggcactg gatgtgcatc gatcgattgc gtcttcttcg tatcgacctc    60
taatggtcag ctcggatgaa atctatttta agctcctaaa tgctccatag tcatcacttt   120
actccaaaat actcctgaac ctgaaaacat acctaatatg atagaatata taatatatag   180
atagtaaaac acttatatac catggatgaa aatgggtcaa atccatggta tatcaagcat   240
cccaaatact tcgtcaaatc caacctcant ggtattgggg aatacactca gtgctgcttt   300
gtatgtcntg tatttcaatg taatacatct aagaattttc ttcactagtt tctttccttg   360
tacttccttc caggaataag agcctattct gacaaggaac waagtttaga gtgtgggaac   420
cgaaatncgc actgtcaatt tccgataaaa ataggaaagc taagtaatcc taactttccc   480
agaggtcccg gatatctgct aaaccacacg ccaagcgatc aaacaatgag aacaaacnaa   540
ataaaaaata gtagaaaacg aaaagagagc agagaagatc ttattccgaa ttgantgaac   600
gagcattaca acagataaag cctcggcggt tagagatgtc ggngagttcc tagttctaac   660
cttgtgagac ttgattaacc tagttgagtc gcagctcgaa aacagaaaac ggaaatatgc   720
ctaagtttcc ctaagtgcta tgctttgttc tnaataaaaa atgcntccct tcagcatctg   780
caacctcgac atccttatat a                                             801
```

<210> SEQ ID NO 111
<211> LENGTH: 401
<212> TYPE: DNA
<213> ORGANISM: Brassica napus

<400> SEQUENCE: 111

```
tttattgatg aaattcccaa gaatcattaa gcttttgtta atgtacttcc cttccgtcaa    60
gcgtactcca ccagcaccag ttttggcaat tctttcagat ccagccaaat caaccagatt   120
ctagaatcca ttaaaagaag gcacataaga gaataaacag ctttctacac ccgtagagaa   180
aatgatcact caccaagact ragacacgga taggatccat agaattgttt cctttccccc   240
```

```
tgctctcaat caccttatcc caccagagat attgtatcag aacaaatact tcaaaaaaaa    300
aaacagttga aggtttcatt cataggtttc gaaaacccca ccattctgaa gatggtgtgg    360
gacgtgctac tgtgaacgtt catgtttgtc tcaccaaagt g                       401
```

<210> SEQ ID NO 112
<211> LENGTH: 401
<212> TYPE: DNA
<213> ORGANISM: Brassica napus

<400> SEQUENCE: 112

```
ggctcccaac cactcacccg agaccagcaa acatcaatca agaaaaatct ctacccaaat    60
atcacggtgg attctcttat cgattcaaca tcccacacgt ggaattccaa ggttattcgg   120
tcattggtgg aaccagagga cgcaaagatc atagaaagca tacctggcat cgtctggttg   180
atcaagatgc atgacatttt rccattaatg gaaaatatac gataaaatcg ggttatcaag   240
tggaatgggt atacccagat agggagaaat cgttgccggt atttggacct acaataaacc   300
ttttaaaagc atactcttgg aaaatacgtt gtccaccaaa aataaaacat tttttatggc   360
agttagtgtc gggctgtata tcagtaaaga aaaatttacg g                       401
```

<210> SEQ ID NO 113
<211> LENGTH: 401
<212> TYPE: DNA
<213> ORGANISM: Brassica napus

<400> SEQUENCE: 113

```
gactatttta agagcttcta aaggatgtca catgggcaga atattctca ccaatcattt     60 tgccatgtcg ttacgggctg ggtttcaaac taatttaaat aattccagcc caaccttgcc   120
ccattccgat ccaacctagt taataaagtt acattttatt tcttcataga cctccacatc   180
accaagaaaa agggagacac rtgtcattaa aaaatattca ccaaaacttt attgtgtttg   240 ggttttttgct ttacacttac gcatgggctt cagacccatc gtaaaattaa gtttccttgc   300
cttctcgcct aaggacagga ttatcgggg ttttagtgag gttttagtgg gttttttaag    360
agaggaggga cctacaggaa ggaaaaaccg gtggcagaaa g                       401
```

<210> SEQ ID NO 114
<211> LENGTH: 801
<212> TYPE: DNA
<213> ORGANISM: Brassica napus
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t

<400> SEQUENCE: 114

```
gtatgatcaa gggtcgacta aataaaaatg ttggcttgaa gagcttcagc tgggatccgg    60
ttaacgttcg gaatgatcct ataggatcgg agtttgttct gtttccaatt gagttgttga   120
ttgttttacg aagctgacga gctcgagtaa aacatgatgt gtgcgttatg accttcgaat   180
cttcgtcgca atcaattaat atcagtttct cttgagttcc ataacttcaa cttcaatgtt   240
```

```
tttattctct gcttcttatt ctttcattta aataatcgag acacgttact taaccaaaag    300
tatggctcgt tatactgcac tactgacaaa ttgctaagag taaagcacac aaaggtttct    360
taggaagatt attattagac tctcatgaga attaggtctg sgcattcggg tttctgccna    420
gtccgggtct ttcgtgtcct aaacatttga acctgactag gtatttaaaa attttggttc    480
gggttcggat cattcttgtg ggtccgaatc ggttctaatt catatacccg taaaacccta    540
attttcgggt aattttgagt tccgttcggt ttgggtattt aggacccgaa gtaaagtatc    600
cgaactggat ttgaaaaccc gaaatacctt aaaccaac aaaaaaaatc cggaaaatac     660 ccaattttttt ttaccattaa tctaacacaa agatctaaaa ataccaaatt ttttattcaa    720
atacacgaat tatatttctg aaaattttaa attttnacct gaaacctgaa actatacacg    780
aaaacctgaa cccaaaactn a                                              801
```

<210> SEQ ID NO 115
<211> LENGTH: 801
<212> TYPE: DNA
<213> ORGANISM: Brassica napus
<220> FEATURE:
<221> NAME/KEY: misc_feature
<222> LOCATION: (1)..(76)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (627)..(726)
<223> OTHER INFORMATION: n is a, c, g, or t

<400> SEQUENCE: 115

```
nnnnnnnnnn nnnnnnnnnn nnnnnnnnnn nnnnnnnnnn nnnnnnnnnn nnnnnnnnnn     60
nnnnnnnnnn nnnnnngcag aaaaaaagaa accgtttcta aatacacctc tctctctctc    120
tctccggatt tgcttacttg aagtttttga atcgcgtctc gttgaagtta tggatgattt    180
tgcagtcccc cttgaaaagc aattttgacc aaatatagta taatatataa ttcctatttt    240
acaatattct aatatacacc gttattttttt tttcagtaaa ttgatgaaga aggattatcc    300
atattgcatt tcaagatttt tagatatcct taagactcat aaaaatctaa cataaattac    360
atctattccc agagaatacg ttttttcgaa atcaattcct sgtctctgaa ctaatcgggt    420
tttatatngt gttacctcat tcttttcact agggcattg ctggacagag ttcttgtttc    480
atcttaatat ttgctaangt tattgtagtt gtgaattttg cgttttgagt tgttttttcaa    540 gtttttttta ttgttatggg attagagttg tgatgatgat ctgtgtatgc tttgttctcc    600
acttatgaag gactaaactg tgttagnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnaaaa gtttcttcat tttttctttt cttgatgatt tctgggaaga ggaagaggta    780
gttgaacttg ttgggcttga t                                              801
```

<210> SEQ ID NO 116
<211> LENGTH: 801
<212> TYPE: DNA
<213> ORGANISM: Brassica napus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t

<400> SEQUENCE: 116

```
tgnatatgtt gatgtggtcg tgttcaagtt tcgaagtttc gaactcatta tctagattgt    60
tgtttctgga catatttttt tttgtaaccg attgntgtgt tgataatgag taatcaatct   120
acctacatta cattttnaaa ggatgataac atgatcattg atcactaaca tacgtgtgta   180
gtttgatgat tggttatgtc atgttacatt gagtntttac ttgttacaaa tgttctcgaa   240
tggtgtacaa aaacgagctt cgactcatca atatgaaaac tntatccaag gattatgttc   300
atgaaataac agatccgaac taactctaat cgtgatcaat gtattaaaat cggataatgc   360
ttacccacct ccattcatca ttcccaatcc caacaccaag wtcttacttt cagtgtgatt   420
cttagccgag caggctctcg gctaataaaa tgcacaaatc actaataaaa tctgtaaact   480
aataaaattc caaaattgaa aaaaaattta acctatccaa aattgcatta tttataatac   540
aacactaaat ttaaaagtta ttaattgtat tgaagattta tcattttaat caaagttatt   600
aatctacaac actcaaatat ttttttaaat acacataaac gtaaaattca attaaaagta   660
tttaatgttt tagaaacttt tcttgtaaac aacacatttt gttttctatt gtgatcgcaa   720
tactaagtga aaattgtagg tgccacattt taaaagaaa ccttgttttt ggccgaggaa   780
taaacatcat aagtattaaa a                                              801
```

<210> SEQ ID NO 117
<211> LENGTH: 801
<212> TYPE: DNA
<213> ORGANISM: Brassica napus
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (478)..(478)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:

<221> NAME/KEY: misc_feature
<222> LOCATION: (730)..(730)
<223> OTHER INFORMATION: n is a, c, g, or t

<400> SEQUENCE: 117

| | |
|---|---|
| ttccatgttt ggctcataag ccacctatgt gtgtttagtg gttttccatt ttgtattttc | 60 |
| aacaggtaga acaaacttaa ccaagtataa tctattctac tttagttta cttttacaac | 120 |
| aagtccattt actcattcag tcagtgacgg tcctaaaaaa atttgggctg gacgcaaatt | 180 |
| ataaattgtg tgacctataa atttataata aaacaaaaat atgctaatta tatcccacaa | 240 |
| aaggttcgaa cctctccata cttttnaaa aatatcacg attaaccaac aacgctacta | 300 |
| aaggtttggt gcaaaacacg gccaaaatat tacatactgt aaaccgggcn ggaagcacat | 360 |
| gnttctgccg cttttgccca tggccgatat tgcattcagt wgttgaataa taaatttaaa | 420 |
| atccaagtgt attcttaacg ttggtagtat aatgctttat cttttctctc tttaaatntt | 480 |
| attgaaaatg agttatttta aaagtacttc taagtgtctt acaaaattgt ttaggttttt | 540 |
| ctggagcaag gtgacgagta tggtggcttc catatgtgaa cacaatattc ttttgnattt | 600 |
| tgttctcttt tgatgttat cacttcttgg taatagatta accggcttca tctcnttct | 660 |
| gttttgctat gccatcattt cttttctgga ctgtttgtat atagtcccaa ccgatccctg | 720 |
| cacaacgaan atcatgaatt ttcttttctg aaaatcaact tgttggatct gtaaaatgat | 780 |
| gataagaata gacaaaggaa a | 801 |

<210> SEQ ID NO 118
<211> LENGTH: 801
<212> TYPE: DNA
<213> ORGANISM: Brassica napus
<220> FEATURE:
<221> NAME/KEY: misc_feature
<222> LOCATION: (1)..(63)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (694)..(793)
<223> OTHER INFORMATION: n is a, c, g, or t

<400> SEQUENCE: 118

| | |
|---|---|
| nnnnnnnnnn nnnnnnnnnn nnnnnnnnnn nnnnnnnnnn nnnnnnnnnn nnnnnnnnnn | 60 |
| nnncaagttt ctagtttctt gtttaattct gaaaagggat aaagatttct tgtcgactga | 120 |
| gaaagaagag tcgaagacaa cgntagagtt ctgtttcttt tttttcta atgttttac | 180 |
| tttgtatttc attatagttt aaagtaaaat gttaatttta ttaactgtat tttaaagaaa | 240 |
| atgacaaaac tggattatta ttattattta tactaaagga acatgatttt tggttttagt | 300 |

```
tctaagatga taagagtnta gttgttttgt tacttttttac caaatttcct tttataatac    360
attgaacaac agtttgccat ttccttacta ttttactttc sctttttacgg aaaggtcgng    420 tcaacataaa catccaagaa attgataggt aatggatgcc ttttntaatg aactggaccn    480
ctccttgagg catttgtcta cttttgacaa aatattcaca tggttttgtt tatggtttta    540
agagcatgat taaccctaga attccattag agtctcttaa tgatttttta agtattaaat    600
gttagttaag aacctagtt aagagacatc tagtttttgt tgctccaatg ctattctttt     660
taattaaggg ttcttaaaac acaactagat tttnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnaagtggg g                                              801

<210> SEQ ID NO 119
<211> LENGTH: 401
<212> TYPE: DNA
<213> ORGANISM: Brassica napus

<400> SEQUENCE: 119
atttgacact ctaactaaaa caactaagtt tttttgtcat tgttggatt aataatcaaa      60 atagaaatga gagttacacc aagccggcaa aggtacacaa catttacaga gccataagct    120
aacatttata tatgatttaa aagcgaaaag attcacttt gtttctttga aatatttcaa     180
cgatcttgtt ttggttttc kggtttatga tttggcaatg aaactagagt atactaaggc     240
tgaaaagatt gtgtatgata ctttagcttt taatatttca agatcttgtt ttcgtttttc    300
gagtttatga atttcatccc aattaaattt tggattttg ggttttttga atttcggcct     360
catgaaaata ctataaaatt tttattcaaa tttagttcgg g                        401

<210> SEQ ID NO 120
<211> LENGTH: 401
<212> TYPE: DNA
<213> ORGANISM: Brassica napus

<400> SEQUENCE: 120
tccatggtat atttttgattt aggattgatt tatcttagaa tatagaatttt ggtatggtcg    60 attttttgcag atataagata tttatagtaa agatcagtcg caaaccggat atgttttat    120 tattggtgga accacaatta atagagttcc caaaaataaa ctccagttgc aacttcttca    180
aatcatacgg aaacaatagc rtttcattaa acatgtatag aatgtatatg ctttggtct    240 atgggtcatc acatataaga agcaagcaaa atagttacaa aaaagagcca acaaaattgt    300
ttgaagataa ttggcttgtg acgttcaact caaagaaagt tatgttaaga atgatagaac    360
aaagcatatt cctaaatatg agatatcaag aaaaataaga a                        401

<210> SEQ ID NO 121
<211> LENGTH: 401
<212> TYPE: DNA
<213> ORGANISM: Brassica napus

<400> SEQUENCE: 121
tcttgagaag tgcgtgtatg cgcttggtat gctaaaccct ccacagattc aggaacacct     60
aacatttctt gcttcgaatt caaatcgcac cctgtaacag aatcctagtg gagatacaag    120
acatcagtca tatacgttac taatctacca atggaaggat tcagtcaaat gactaacctg    180
cgcaagtggc ggcccggttg rttcgacaca gatatctact ttcccactcc cttgactagt    240
```

```
aacagagaac acagtagtcg aacacgaacc attatcaaca agaagaagtg aataatcttc      300
ttccgcattg ttgctttcac gaaaatcctg ctctttctca tcgagatact gcaatgtagg      360
agaggcaaca agcggagttt ccaatatcga atcgctatct a                         401
```

<210> SEQ ID NO 122
<211> LENGTH: 401
<212> TYPE: DNA
<213> ORGANISM: Brassica napus

<400> SEQUENCE: 122

```
tttcggaaga catctcttcg taaaggtgaa ttcaaagcta tgattagtct cagtggtcaa       60
caatcaaagt tttatacaag taaacatttg tttcaatata cccaacccttt acaccatttt     120 ctttgtacca aaactatcaa taatgatcgg gaaaaataca cttaccagga aggaggtcaa     180
gatcttaaat tatttgttaa yggagcatta gtataaatga taaatataaa aagagaacat     240
aatgtagaaa gtcgatgcta gagcatgatt atcggttcag gtgggttttt agtagtaatt     300
agaaattaaa aaaaaaaaaa acgggaaaat aacttaagcg acgtattcta attaaggcac     360
aagaaccctc tcttgtaaga cacgcgtcac gtgggaggag a                          401
```

<210> SEQ ID NO 123
<211> LENGTH: 496
<212> TYPE: DNA
<213> ORGANISM: Brassica napus
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t

<400> SEQUENCE: 123

```
atgatcgacc gcttattttg tgcataactt agagagagtt ttttaatga aattatttga       60 tgatatttcn caatggggt acacacatat ttataagcaa ggataaggcg ctgacataag       120
cgcttacctc agcgattaca tcatcgctta catcacgctt acataagctt atagcgatta     180
catcatcgct tacatcatta ttcattttt agacacactt attttatatg atattttaca     240
taattaaaca ycgataatgg tgtgcttaat gatccatctc gaantcgang atgtgcttgt     300
cgcaactacc gtagtgatct tctggacata tgtagtcttc ctctggatat tcattttggg     360
tntttttttt tgacttcaat gttgaacatt tttctgattt catcaatatt cattgagtca     420
ctgggagctg cgagtcatgg aagtattctg gtgggcattc ttgggacaga gattcgtgcn     480
ttactatctt ctgana                                                     496
```

```
<210> SEQ ID NO 124
<211> LENGTH: 401
<212> TYPE: DNA
<213> ORGANISM: Brassica napus

<400> SEQUENCE: 124
tgtccgtgta ataaaaaacg ggttttaaga acaataaacg gccaagccca tttaagacct      60
ctttttttga aaatacaaga attattagtt tgatgttcta ggttaaacaa atataatcat     120
ctcaaatcgt cagccctaga aactgacaag acccttttgc tccactgtct cttcagaaac     180
ggagagacgg aggtggaatc yagcgaatcc gagtccaggt ttcagttaag gatttgagat     240
taggttatga ttactgcacc aagcttattc tgttaaaatt ttaagctttg tggatttgag     300
cttatttctc tctctagaaa taggtgatta ctgatctggc agaggtgtct tccaaaacta     360
gggcagacaa cgaggtatca tcagaaccac tgtctccgat t                         401

<210> SEQ ID NO 125
<211> LENGTH: 801
<212> TYPE: DNA
<213> ORGANISM: Brassica napus
<220> FEATURE:
<221> NAME/KEY: misc_feature
<222> LOCATION: (119)..(218)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (533)..(533)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t

<400> SEQUENCE: 125
ggaaaaagcc tctgtaactc ctcgagaaca tcgcctgaga gcgttttaca ttttttttcct    60 tttggtattt tagtcaaaag aaaattaacc aaatcttttta aatattttttt aaaatcctnn  120 nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnta ttgaaaacgt gttttaacag     240
atatggcaat gtttctcatt ttaatttcca gagtttcttg ctcctcgttc tctctcttat    300
ttctctctgt atcgagcttt gcttcaggtt tgggtgaagg agaaggttgt agagagngat    360
gaccagagtt gatccaggaa tgtaagagac actgagctca waggccagaa acggagtctt   420
ctgatgtgtc caagatcacc gtgcctgttg aacctcctaa agctatctgc aagacacaac    480
agagaaagag ttggagttta dacggtctag aatggttgga agtagttcaa canaagcctg    540
ctaatgattc tattaccttg cgtggcatca ttcctagaag ctccatcatc aaaggcaagt   600
gctcctgtta gacgcaacaa gtgaagtgaa ttagctcaca agcaacagcc tatagctaca    660
ataatgtttc atgacagaat caagaaacca aaccacagtt acctcatctc tatcatagtt   720
gtctccncta tggggatcga acagtacatc tccagtggca agttcaanac atatacacgt    780
aaacgaccag aatcagccga t                                              801

<210> SEQ ID NO 126
```

<211> LENGTH: 801
<212> TYPE: DNA
<213> ORGANISM: Brassica napus
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (325)..(325)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t

<400> SEQUENCE: 126

```
tcaaaattaa tatgacctag ttgtgaatgt tatcttcttg actcattctc agttgatgct      60
tggagacatg tggttggctt tataaccata tgaactttat acaatctgtt tcgtgatctt     120
cnagctttga cgagcaattt tctgtactga tcttgcatca ttaattcttc ccctctcatc     180
ctgatgtgac accctgcttt tgtagcttac cccaagctta taatattact ctttaggtta     240
gnaatgaaat acacgtcagt catctttctc gagtcnctgt tcatgtcggt gaagtatatt     300
gtgccttttc ttttaatgtc tctangagaa ncgtcaccaa accgtacttt ccctatgatg     360
gtactatcaa tcngtgagaa gtaccttcga tctcctgtca watgattact agctccattg     420
tcgagatacc atatgttctc ccctctagta tttgtctcat atttctcaag agaacattc      480
ttttcgttca aaatacttct tcatacatca aagttcatc agcttcttgc atctcagtgt      540
ttcggtctct tgagcctcct gtaacttaag cttganctcc ggacattgag ccacgaagtg     600
tccaatttta tcacactgat agcaagttat tctcattgcn tttcgtccan cattaaaacg     660
tcttngacct cttcctctgt aatagtttga tcgaccgcct ctgcctcgac tctgtatgt      720
atctccattg taatctaggt ttgcttgttc ttgataagat cagtttggtt gatcttgaga     780
agaacgattt tggttgactt g                                              801
```

<210> SEQ ID NO 127
<211> LENGTH: 801
<212> TYPE: DNA
<213> ORGANISM: Brassica napus
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (409)..(409)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (487)..(487)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t

<400> SEQUENCE: 127

```
atcgttattt ccttttttc attatgacgt attatnatat cctttcctt attnggtttg      60
tccaatcgaa gggatatata acagagctt tgtttcttgt ttgaagatac gtttgattta    120
atagaaagag ctttgctta taccttgtt agattngatt aaattcatca aaacagaagt    180
tggtctcaag aagctatcga aagaaantt tgatcgatcc aagaacacgt ctcgaagaac    240
cctaaattct tatatcgagc gttcacccat tcgtacgctg cgccattatg agatgcttac    300
tcttatccat gccggtcagt ctagtacgtc tcgttttcat caatttctct gttccagagt    360
acctgcattg gcaggtttta aatctcagat ttgtgcataa wgacacccna gtaagaaaca    420
caaagattgt ttgtgcgtta tgttnatcta cagtaacact tccattggtt ttgagcaagg    480
ccaagtnata cttatcagtt ntctcttcag aactggaaaa atctttgtcg ctactattag    540
acaccagaat gggaccgata cgtaagttag atgactcaga gaaaaccact tagacgacaa    600
gttgcatata agaaagccga ataataagaa tgcattttca agggatgtac taaaaatgaa    660
tggaggtcaa ttttgggagt tgaatgtctt tctaaagcaa aacaagactt ataatattct    720
acagctttgc ataccatttc agatatagaa cagccaaatt cagtcaggtc gtacaaagcg    780
atcaaaccaa tagaattcaa a                                              801
```

<210> SEQ ID NO 128
<211> LENGTH: 801
<212> TYPE: DNA
<213> ORGANISM: Brassica napus
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (254)..(254)

```
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (443)..(443)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t
<220> FEATURE:
<221> NAME/KEY: misc_feature
<222> LOCATION: (603)..(702)
<223> OTHER INFORMATION: n is a, c, g, or t

<400> SEQUENCE: 128
attcgtccaa gacttcaggc aagatattta aattagtctc acacctttag ttgcttcagt     60
tttcctgtcc atgatttctt gtccatgatt ttctgtccat gatcaatcag gttcttcatg    120
tttttagtct tgctctttat tctcttcacg tcaacagaaa ccagctactt aggcagttaa    180
tcaatgtatt gaacatgnag agatcatttc gaatccntac agcttccatc tttttccaca    240
gagagatgac gacntcgtac ttcttcagtt tganaatggc gttcaacagt ttattgagat    300
cgatgattga agggaagggg cgagatttgg ccatgtcgtt gaacaaatcg atagcgtcat    360
ctagtttgat atcacgacga cggtttctgc tcagtctctc wcggagatca atcacgctgg    420
agaaagctcg tacccagcaa ccnagagaag ggagagcgct tttgcgttta ctattttcga    480
aaagattccg atgaagcaat gtcttcgccg tcatcgcaat ngatctctgc atcgttttgc    540
gatngtctct ctgattccga atcctaaaac gagacatgtt tatggagaga gagagagaga    600
gannnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnattctcag gggtaaactc    720
tttgccgctt ggaataatta aactgttcct tgcgttgcaa gtaatcatgt tatgaaagtt    780
aattcacgca aatccaaagt c                                              801

<210> SEQ ID NO 129
<211> LENGTH: 801
<212> TYPE: DNA
<213> ORGANISM: Brassica napus
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t

<400> SEQUENCE: 129
tgtgcaggat agaacgttat atggggagtt ggaatacttt catttgtttg aagctgccaa     60
tgaaggagga tggttgggac actactgttt atagatgntc tgctttcttt ctacaacgga    120
ataccctgc gttactgcct tgacaatgag tctgacctca agacctatcc cgacattagc     180
caagctgcgt ctgataccag cagacgtatc tttgtttcgg taaagggatg tctatcgtta    240
```

```
attattatct tatatataat actattggta attctatttg gctatgaatg ttttcgttgc      300
tttatcaacc acaaaacgaa cctgaattct gcaaatgaat aaatatctta tataagtatt      360
tgaaatccta cacgatttta agcatgtcaa tttttaagcc wggggtgtat cgcgagacgg      420
aatgagggtg atgcgcctgt tctcaaacga aaggagtat gtgttagcca agaagaaggt      480
gacacgcatc cattgggaca acgtcgcaac agatcacatc actgatagtt ctgtccaaca      540
gagaatggga ctttgcaacg acgtgatgta cgaatatctg tctgtttatt cagncacacc      600
agtttgtaag gtgttgggtg tggttcggca ataaggcaa gcttggccac agcttcttcn      660
gagataacat tggtgcagct accgaaatcg atcacgaaac gacaaacctt tccccggatg      720
gtgcaagagg agcgcgattc gtcaatcacc tgaggagtca gcatatttcg acgaataacc      780
aatagttgtc caatatctcc a                                                801

<210> SEQ ID NO 130
<211> LENGTH: 801
<212> TYPE: DNA
<213> ORGANISM: Brassica napus
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t

<400> SEQUENCE: 130
atcgaaccat cgacgaaacc gagcttcttc cttgctttaa gcgccatacg caagttagta       60
gcccattcat tgtagttagg tcctttgagn aatngctggg aaatcaccga gcctggattg      120
tcantagaag ataagtcata cggagatatc ctccttcgtt ggacttcaac acgagattgt      180
gaagaagcag atttcgtagc cgaagcgtta gtcaaatcgt caccatcatt actacccata      240
ttggcaaact tagagaagaa caaaagagga tgaaaaccc caagaacaaa gaaattttt       300 tgtgtttaat gctctgatac catgtcaaga aaccagagaa agcatagaag agtttcttgt      360
attcatctag gtcaacgacc ataagtatat atacatgcta sgttacctaa taccgtaaga      420
tatgtacatc gagataaaag gaatattaac ataatagatt acanccaaat atatggcaag      480
atatgcatgt atatcctcaa tattgccgct cttccagctg aagtatagct gcattgacct      540
catcaatagt cgtgtaacgg gtcatattgg tctcaaattg gcaaatagat cctgcgttga      600
gacagaagtt gacacattaa tttgttacag atatgcggaa ccnaagtgaa aactgaataa      660
acaaatgttt taagaactaa cctgcaagtc aaattcaata tccagaggaa gatgacccct      720
gctcagtatg tatctctgga aatgtatcaa aaaattgatc aatcctttc tttgaagaac      780 cttatatgat gttgaagtta a                                                801

<210> SEQ ID NO 131
```

```
<211> LENGTH: 801
<212> TYPE: DNA
<213> ORGANISM: Brassica napus
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (509)..(509)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (791)..(801)
<223> OTHER INFORMATION: n is a, c, g, or t

<400> SEQUENCE: 131
actcaagaag tatcttctca gcgcaggttt tcatanctct cttgctgata cgtctctatt    60
cattctccgc catgaaggac agtatgtcta cttnctggtt tatgtggacg atattctcgt   120
tactggtact gatagcactc tggttcaacg aggnatcnaa cgtctggctg caaagatctc   180
tatcaaggat atgggtcatc tcagttattt tctcggaatc gaggtgatac gaacgaaaca   240
aggactccat ctaatgcagc gganatatgt tacagacttn ctgcagaaga caaacatgct   300
tcatgcaaaa ccggttgcta cgcctctccc ttcctcacca agctaactc tgcactctgg    360 tcctctnttg tatgatcctt ntgactatcg acgtgtagta sgcagtctac aatacctgc    420 cttaactcgt cctgatgttt catatgatgt taaccgactc tcgcagttta tgcacaagcc   480
atcggtggac cattggaatg cagtcaagng tatgctatgc taccttgccg gaactctaag   540
ccatgggatc ttccttcgca aacaatcatc tcctcagctc catgcattat ctgacgccga   600
cttggccggn gacacagatg attatggggg tgattggttg gctgtaact gtagtaaatt    660 tactttagaa tttagtctgt aggattttg atttaccttt aanggatgta gctttaaaat   720
ttcctacacc taaaagatg gggctttaga aaataagata tttacaacca ttttttgttt   780
```

```
gttttttgttg nnnnnnnnnn n                                              801

<210> SEQ ID NO 132
<211> LENGTH: 496
<212> TYPE: DNA
<213> ORGANISM: Brassica napus
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (459)..(496)
<223> OTHER INFORMATION: n is a, c, g, or t

<400> SEQUENCE: 132
caagttgata tggatcttgt tatttcatcc ataaagggtc aattgataac tattattgga      60
ctaccaaagc aagtgtatcc ttctcatgcc tcgctaacaa actactaaag ctcaaggaca     120
tagtctttcc tctcattaag caaaggctgg aaaatggcct ctcagctagg ttctggttca     180
ataattggac atcttttggg accttagcat cttnccttga ctcctctact actaggctag     240
ggattcttct yattgagttg cttctatttg taggaatgga acttggctaa tcccaccttc     300
aagaacagac aactagcttc aaattcaggc tttttgacca ctatcaactt tttttnacca     360
ctatcaactt cttgcaaaac tagggtgtggg cgttcggttc ttcggttcag ttcgggtcgg    420
ttctttcggt tctcggttct cggttctttc ggttcctgnn nnnnnnnnnn nnnnnnnnnn     480
nnnnnnnnnn nnnnnn                                                    496

<210> SEQ ID NO 133
<211> LENGTH: 801
<212> TYPE: DNA
<213> ORGANISM: Brassica napus
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (719)..(719)
<223> OTHER INFORMATION: n is a, c, g, or t

<400> SEQUENCE: 133
acttccgtgt ggcaataagc gctcggaaaa agtttgcttt tancaacgga tctataccaa      60
aacctgcacg actcacccga ccttgaagat tggatagcta acaatcacct actggtgaat     120
tggatcaaac taacaatcga accaaaactt cgatcgaata tctctcacaa agaaatcact     180
cgagacctct gggaccacat caaaaagcga tttnctctta aaagtggagc tcgttaccaa     240
caactacgag cttccctggc aacttgtcga catgtgggat ctacggtcga agactacttt     300
ggacgcttga caagaatctg ggattctatg gctaaatgta tgtcaaccaa gacatgtgac     360
tgcggaaagt gtgaatgcaa cttggtcagc actcatgaaa yagagcgcga gatcattcgt     420
```

```
gctcatgatt tcctatatgg tgttcaattt caattaattt agaggacact tccaaaattc    480
tgagcttccc cggagtttgg ctgtgatccc tacatctgga aaccaaagca tacttagtct    540
caacaatcta acacanaatg aaaaatgtat taaagtaaat gcactttgta agaaacaggg    600
gactgttata tatttaagtg aatgggtgca atattatata tgaaccattg caattgttta    660
tatgaacaat tgcaactata taatgaaacc ttgcaaccat taatgattgc aacatttgnt    720
aattaaccat attgataatt gcaacccttg gtgattaacc attgcaactt ttggtttaac    780
cattgcaact attggttgca a                                              801

<210> SEQ ID NO 134
<211> LENGTH: 801
<212> TYPE: DNA
<213> ORGANISM: Brassica napus
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t

<400> SEQUENCE: 134
tgaatttgtt caccagaaat atattaaacn agattactga accaggttta accaggtcaa    60
accatattga accgtgaccc aaaaattatc cggttcagct nccggtccgg ttttaaaaac    120
actgtccaaa actgattaat aacgagtttc agattgttat taataacgat atctaatgtt    180
tgccagcaga ggacttctgt atatcacggt gatctttatt tattttttaag aatattttca    240 tgcgactgct tacttagtta tataaaatat cgaagtcgaa gaccatataa gatttttttt    300
ttggccaaca ataactaatc tgctacgaaa tactcaccga ttcggaatga tcatataaga    360
tcaaacttca aagtatggtg atatgttaat gtctgcacta watctatccg cttatttttat    420 taacgnttta acctaaaata tttaaaaact ataaagtctt gcatccgtaa ttacccagct    480
aaattcatga aattgaattt gattaaagtc tttaattatt tgaatagtct taaaagatgg    540
tacatagctg atgtaaaaaa gcgcgttctt gaagagaaca ggaagtcgta caagctttta    600
gtcaaaaaaa aaaagtcgta caagcttaat acttcaatgt tttttttattc ncgagacggt    660 tgattatgtc tgcttaaaac tatatatata ctcactgctg gtcaagacaa gaacaacaac    720
gaaacaatga caaagattct tctaagcttg ctccatatac ttttatgtgt gtctttacat    780
ggtgtggcag aggctagttt c                                              801

<210> SEQ ID NO 135
<211> LENGTH: 801
<212> TYPE: DNA
<213> ORGANISM: Brassica napus
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (96)..(195)
<223> OTHER INFORMATION: n is a, c, g, or t
```

```
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (295)..(295)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t

<400> SEQUENCE: 135
gactngtaaa agcctgcccg gagaatgttt ttgacattga agacatgggc aatggtaaaa      60
gtaaaatcct tcctttaaac aataggagag gatgcnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnngaatg tctgtaacaa gcttgggttt attgatggaa cggtgattca     240
accggcgtct acttaccgtg antatggtgc ttggtctcgt tgcaatgata tggtngcaat     300
atggctgatg aactctgtat ccaagaaaat tggtcagagc ttgttattca tcaataccgc     360
tgaaggtata tcgaagaatc tcttggctcg tttcaaaccg ratgatgcac cganggnttt     420
tgatattaaa caaaagctga gtaagactga acaaggttca atggatgtat caacatatta     480
tactgaactt gtgactttgt gggaagagca ccgacccgcg aacgagtcgg tcgctaccta     540
gcgaccgacc aaacctttcg ttcggtcgat acgtagcgac cgatccagcg cggaccaggt     600
cgctacgtag cgaccgaact atctcggaca tcgatcaacg ggtacgaccc aaatctgtgc     660
attctcgttt attcatcaat gctatctccc atgtaccgca tccatatcat ttctcagatc     720
attccgatca aagttaccgt tgaaacttta cgataaaaac cgcgagaact gttttttgtc     780
gaaaagaaaa tcgtaacaaa c                                               801

<210> SEQ ID NO 136
<211> LENGTH: 401
<212> TYPE: DNA
<213> ORGANISM: Brassica napus

<400> SEQUENCE: 136
ttactatttt ggtttattga tactttgatt caaaatttta gtagttcggt ttaattttt      60
tttaattaga attgaaataa ttagggtttt gtgcctttag ttaacaatct atcgacagcc    120
cctctggaag gaaaaaagca accaaagaag tgtttgatat aacttatttt tattcgtact    180
ttttgttttt taacttgaac watatggacg atatgatttt aagtcttccc atggattgat    240
ggaggagatt ctctcaaggg ttccggtgaa atctattgga gcagtacgat caacttgtag    300
aaactggaac gctttatcta aagatcaaag ttttgtcaat aagcatattg acaaagcagc    360
agcatcatca agagaaacgg aggttcatgt gatcacggtg a                        401

<210> SEQ ID NO 137
<211> LENGTH: 401
<212> TYPE: DNA
<213> ORGANISM: Brassica napus
```

<400> SEQUENCE: 137

```
tttggtggtt gtttggaatt gaatcgtgtg taataaatgg ttaggttagt gttagattat    60
ggttggtgtt agtaataaat agaagtgatg aatgagttag ataaaggtct agtatatttg   120
ttgggttatg aattcactcg atggttgtta gatatatgtc tagtcctaag tatatttatt   180
atcatatatt caacgttcac matctctact cggttaaaca caaagtctt cctcttgttc    240
ttctcttcca tcaaaacacc ttcgttcatc ttcttcttct cttttctca tatttcacac    300
actagaatat ggattataat ccataaacga gtggggaaaa ttttgttgct cttttcaaa    360
gtcaacaaca aagtgtcttc ggttcatcac aagttccttt t                       401
```

<210> SEQ ID NO 138
<211> LENGTH: 801
<212> TYPE: DNA
<213> ORGANISM: Brassica napus
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (563)..(563)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t

<400> SEQUENCE: 138

```
aaagtttcac cgccanacga atgagtttga atggccagga gccccgatac gggatggccc    60
ctagtaccag ccagattcga ccaatcacga gccagaggtg gtgccggtta agcggggaca   120
gggtcgtccc aggaaggata agccggcgcc cggcatagag tgggtccctg agccacctgt   180
ataggagcca cccaagaaga aaaggggggcg tccgcgcaag gccgctgccc ccaaggaaga   240
cgcttcaaaa aagagtttgg aatcgtgtgg gagtgatgtc acggtcccaa agtcttgctc   300
agtgggtgaa tacttggagg ggttcctgaa tacgactaag gggtgcgcac ccaagctcgt   360
ataagtgtgg tgccaattgt ttaaggcagg gatccgcaag racattcggg gggagccgga   420
gagcgccaag gatcccctgg agttcttgct gatgaaaagg atagtcgggc aaacaataac   480
cgcaggggag tggatcgtgg ggttgggcga agaggatcga agatncgcac ttcgtcagac   540
agaggagaac ccagagccga ganatgatga cctaggacct acacctcgcg atgcngggat   600
ggttggttta ggaccggagg ccgaccgtgt atttccacat ccttgtggct agttgaggct   660
ttatgatcac ttcgtaggag taggacgtga gcttttctat tggatttatt ctaactattg   720
agtggttgct ttggtgttgt ttctccattt ctaaaggcat tttgtgtntg tacatatgcc   780
ttganctttt caaattattg t                                             801
```

<210> SEQ ID NO 139
<211> LENGTH: 401

```
<212> TYPE: DNA
<213> ORGANISM: Brassica napus

<400> SEQUENCE: 139
aaaccggagt tccaaacata gacaacagaa gctcggctcc agcgtaaaat ccaaactaca      60
gaggccatgg gagatcttct tacagaggca gaggaggcta cacctccaga ggaagaggct     120
ttattcaaca tcagtcacaa ccaacatcct ctggagagcg tcttgtttgc caaatctgtg     180
gtcgcactgg ttatacagct mtgaagtgct acaacagatt caacaacaac taccaaagta     240
atgaagctta tacggttgtt cgtgttgctg atgaacacgg aagagaatgg taccctgatt     300
ctggttcctc agttcatgtc acctcgtcga ctcagaatct acaaacctcc caccccctacg    360 aagctcatga tgctgtcatg gtgggagatg gagctttcct t                         401

<210> SEQ ID NO 140
<211> LENGTH: 401
<212> TYPE: DNA
<213> ORGANISM: Brassica napus

<400> SEQUENCE: 140
acgaacttat catacaagat gattcggaaa tagtatcaca ctcacgaggg tcatggaaat      60
caaaaatata atggtcgaga tccgagaact acatataatt aacgtggatg agttgctcaa     120
aagcatatgt acagcttgca acgaacaaaa taaaagatgg agatgtaaca ttttatagag     180
ataaaataaa aggctgaatc mgttttttcag aaattggaag ggcttaaaag aaagtacaga    240
cagatcgaga ctggttttctt tatgtgcggc agatccaaac actgtggtcg ccattaaaca    300
atctttgtaa taatcgcaag ttcacaacat ttacacataa atttccacat tatcaaagaa     360
ttaattagat gttgagaaaa gaaaatcaaa gtactaatta a                         401

<210> SEQ ID NO 141
<211> LENGTH: 151
<212> TYPE: DNA
<213> ORGANISM: Brassica napus
<220> FEATURE:
<221> NAME/KEY: misc_feature
<222> LOCATION: (98)..(98)
<223> OTHER INFORMATION: n is a, c, g, or t

<400> SEQUENCE: 141
tacctcaaac ttgaagaatc catcaagaac atcaagaagg agtggtttgc tacctccgtt      60
tctgttgagc tcatakccac tgttgctact aaagtcgngt aactcagact tccatgaatc     120
ttttgccttt tgcataggtt tccagaatgt t                                    151

<210> SEQ ID NO 142
<211> LENGTH: 496
<212> TYPE: DNA
<213> ORGANISM: Brassica napus
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t

<400> SEQUENCE: 142
cacattaatg gagtcatgcc ggaagccttg atttcactcc acagccaaat acttcctctt      60
ctccaacatg aaatcatgtt tcttgatgaa ctagaatgca atatcgacat ctactggagg     120
```

```
gtgtgtttgc atatgttgat cctgttcgta cagtgttcan tggcagaaca acaatttctt    180
tgtggcgatg ttgttggacg gctcatgttg gatcgtgggg ttttgatagc ttttctttcn    240
acgaaaaagg saaaacaaaa tatttgtggc gaccatgggt ttatgaattc ttcatggttc    300
ttcttcaaac attctcagtt gagtggcagt tcatactttt ctattggaga gttggagacg    360
ttgctcaaga gttggattgt tatagtaatg gtgcttgcga atctaacaac gtgttgtgca    420
ttctggtttc gaatattgta ccaaaacctg tttggaagtg catgtctttg agtacagctg    480
gcaagaaggt cgtgat                                                    496
```

<210> SEQ ID NO 143
<211> LENGTH: 801
<212> TYPE: DNA
<213> ORGANISM: Brassica napus
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (518)..(518)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t

<400> SEQUENCE: 143

```
tctgtgagct cttcattgtc aacnacccag acataggtgt cctcaattgt tgatagagag     60
ggtagttgca gataagtcaa atatataagg agttcctcag ccgcctctga tcgagcacca    120
gggaatatcc aaccagctct gttgcaagcg tcagagactg ttgctgtgtt tgggatttga    180
agttcccttg gggccaagat ccccaaacct gtgaaagagc ggtcctagcg gtgtccaaca    240
atcatgccag aagcttatga cnctgccatt tcccagattt ccatgttgag gaggaagcgt    300
tgttttcatc aacagcccat agattttcac ccttcagtct gtattcncga gtccantctg    360
cccaaagtga atcagtattc aaaaatagtt tccataaaag sttcaggcag agagttctgt    420
gacatatcct cttgcacaaa tttaggcccct gtgcaagcta attccttacg tttggaagaa    480
gcaagaaagt ggttcagccc aggattgaaa tgcctaanta ataaaaattt gagaagagag    540
acttcactat gacatatcct cttgtgtaaa caggggggat tgcaagagca gatttgaagc    600
gagaaagatt tgttgctagg aatagccaag aatctgcttc agaaaacaat agattgaaca    660
aaatcatttt gaatctgaga tcaaatgaaa tttaagaaa aaacataagt cacattagac    720
tcaactgaag ctctctaggc aggtatatat agtcatgaaa tatattactt tttgtctntt    780
aatatatagn cttcgaaagt g                                              801
```

<210> SEQ ID NO 144
<211> LENGTH: 801
<212> TYPE: DNA
<213> ORGANISM: Brassica napus
<220> FEATURE:
<221> NAME/KEY: misc_feature
<222> LOCATION: (549)..(549)
<223> OTHER INFORMATION: n is a, c, g, or t

<400> SEQUENCE: 144

```
taaacacaac aaagatcaca aaaatatgct gaaaaacaga atataattaa atcacatcgt    60
aaactggtag caaatataaa tatgcaattt caaaaccatt tgctataaat tagaaatgta   120
aataaagctt aaataaacat aacaatatca gataaagcat tttctaatta gagtactaaa   180
atccatttaa tcaaattact ttcacaggga gataattaga taagaagata acaaacttgt   240
gaccaaaact agacgcgaga caagatttct tagaatctac tgtcaatacc attcaatagc   300
gatcctacag ctgcaaatac aaatcgtcta attaactaga acaaaacaaa agaaggtttg   360
aatcgagcat taatgactta ccatccttca atcaaaccag sgttactact ctgcttctga   420
tgttcctgag gctgtgggta ttgcggtgca tacggaggtg gatagccttg ctgaggatat   480
ccctgcggtg gtggataaca ttgttgagga tagggttgtt gttgtgccgg aggattttct   540
ggaggcgtng gagaagcgtc cttagggtta gggtgtccat ctgacggatt acctgttcaa   600
ccataatatg aaataaacta atcagaagaa aaaacgatta gaagttagga tggaacattt   660
aaattgaccc cctcccccc ccccccaaa agagttatta tatgatatat agatgtcatg   720
acacctaatt atcaaaaaaa ttaatttata taagcctaaa aatgtttatg atctatgaca   780
acaatactta tatctgtctt g                                             801
```

<210> SEQ ID NO 145
<211> LENGTH: 801
<212> TYPE: DNA
<213> ORGANISM: Brassica napus
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t

<400> SEQUENCE: 145

```
ttaaattaan aattaacctt tcttttatgg aaaaactgtc ctggtcgaac ttgggagact    60
ttttgagttc gcctagaatg ggtgagaggt aaagaacatg attggtttgt aacgaatgaa   120
aataattgat ttngaaagaa aaaaacatag ttatatatga tctttgggaa ttttaaatgt   180
tagactgtgg cctaccaata tgtagtatta aagtttaatt ggttaaagat gctttaggta   240
cattatgcat cctctgtata aaatgtttat cagttgcacc taagccggac gtatgtggat   300
tttcgttcac attaacaagt aaantgaata agccattact tgtatcgacc gtgttaagct   360
```

| | |
|---|---|
| gtaaatcgat aacaaactaa aacgtttttt ttattatgaa rgtcatgcaa gtgagataca | 420 |
| tttcttcact actagttact tattttaaga gaccagtttc aaacattcca ccaagctttt | 480 |
| ccattagtna tatatattgt ccaaaaacac taacaatcac ccaccaaaat aattttatat | 540 |
| ttccatctaa atctacccttt actatataca ttcatggacg aattagtttg gagttaaaat | 600 |
| cctaatcgta ccaccacatt tcccaagca taaataaaca acgaacgaag ttgatgctac | 660 |
| tttgtggtaa accagtggta agagttgatt tgaattaaag cgaaaatcca tcgattctgt | 720 |
| attnaagttt tggtaaaacg aaattactgt caatcagacg aagatgggat tatactttag | 780 |
| acctcgttaa aaatctgtac c | 801 |

```
<210> SEQ ID NO 146
<211> LENGTH: 723
<212> TYPE: DNA
<213> ORGANISM: Brassica napus
<220> FEATURE:
<221> NAME/KEY: misc_feature
<222> LOCATION: (308)..(308)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (335)..(335)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t

<400> SEQUENCE: 146
```

| | |
|---|---|
| tttttttttt tttttttttt ttttttttttg aaaattaatt attcgtgacc attttatttt | 60 |
| gaaacaaaag aacgacagag acataacgag attacattta ttacaagcga aaatactact | 120 |
| agtctactac tacaaaacat ctataacaac aatataacat gggaataaca aaatggtagt | 180 |
| aaaaagaata ataagccgag ccaccaagta aaccaagctt ctstcgctta cacaagaatc | 240 |
| tcaacacgcc atctgaacat ttcctccctc gtcacaggta ggttcaacgt cacaagccca | 300 |
| acctccgngt cgtagttgaa ctcagtctcg gtncnatcaa cagcgcatct nagnggacgc | 360 |
| tgagaagagt aagccccaaa acgaccacaa cctctaacac ctagagatat cagagctgtt | 420 |
| ggagaacggn tttcgctgac cactgaagaa gaagagagct caggtttctc gtctgtcacg | 480 |
| gtattgatct ccatggactg gatagctcca cttgagttga acatgtccag gagtccaata | 540 |
| ggtgcgaatg agatgcttgc agtgattcc tttagaggag agatgtggaa gagttcatat | 600 |
| tcaagaacct tgagagtgag tgggattgat gcacccttg gtagtctaac cagctcccct | 660 |
| gatttgtaag cgtagactat tgaatctcca ctccagtctt caccagccac ttcagagatg | 720 |
| aga | 723 |

```
<210> SEQ ID NO 147
<211> LENGTH: 801
<212> TYPE: DNA
<213> ORGANISM: Brassica napus
```

<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (497)..(497)
<223> OTHER INFORMATION: n is a, c, g, or t
<220> FEATURE:
<221> NAME/KEY: misc_feature
<222> LOCATION: (560)..(560)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t

<400> SEQUENCE: 147 gcttttgtg aaatgaatgg ttggctggtt tttgcaagtc atgcttctga agataacctt      60
gctttcatta ggtagccgcg aatcaccct cttggacatt gtggcatatg caggctatgc     120
tttcactggt ctcttcttgg caagatcatt tggggatatt cttactatgt tttgattccg    180
tggacttgct tatgcaccgg agttctcttg gtgaagacaa tgaagcgagt tctctttgca    240
gaagctagga gttatgactc aagcagaaaa tcattacctc ttgattttt agcattagca    300 cagtttcctc ttttgatctg gcttggtaac attagtgtcg attggctctt tgagattca    360 ttagttgtga atnaaaagaa cacttatgat gttatgagat stacgatact cctgatgaag    420
tagtacacct ctctctttc ataacttctt tttaatgtca attttttttg catagactac     480
atttccaaca tgatttnaaa ccaaacaagg acatgaactt tggtcatata gtattattat    540
ctatactcca agccctcctn ttgcattgca ttggtgcatt gtgatactcc ttggcagatg    600
gttcntttta aacctgaatg aaagacatgg aacccttctn tttaaagata gtattcttat    660
acaaagaaaa agaagaagna ggtcgtcgtg ttgaacctaa ttaggatcta atatgcttcc    720
catctttgta gcgttgttga taagttacat caaancaaat attgaccgac ctcaaaaact    780
agttttaaat cattttcact t                                              801

<210> SEQ ID NO 148
<211> LENGTH: 656
<212> TYPE: DNA
<213> ORGANISM: Brassica napus
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (189)..(189)

```
<223> OTHER INFORMATION: n is a, c, g, or t
<220> FEATURE:
<221> NAME/KEY: misc_feature
<222> LOCATION: (216)..(217)
<223> OTHER INFORMATION: n is a, c, g, or t
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (407)..(407)
<223> OTHER INFORMATION: n is a, c, g, or t
<220> FEATURE:
<221> NAME/KEY: misc_feature
<222> LOCATION: (409)..(409)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (467)..(467)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (626)..(626)
<223> OTHER INFORMATION: n is a, c, g, or t
<220> FEATURE:
<221> NAME/KEY: misc_feature
```

<222> LOCATION: (635)..(635)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (653)..(653)
<223> OTHER INFORMATION: n is a, c, g, or t

<400> SEQUENCE: 148

```
cgctgtaact tctcaagagt ttctcgctaa catcaccgtt gctttctcct ttagccactc    60
tcctaagctt caagagagac tcngcnagag aaccctccan tgcatttcct ccaagtttca   120
aactttgctc ggttttaacc tcgttgttct tcgctktatc acctttcctc tgaatcaacc   180
cccaaagant ccatccttc ccccatttct ttccanncctt cttcaaacca aaaccatcct   240
gcttcacctc nccacnacca gcaacacaaa ctacgccttt ggaagctaac tctaagctct   300
ccggtttgta gttttgatg gaataccaat tcgaatcnct cagttcnctc tcngtaacaa    360
gcaacttagc tccatgaaac aaaccaacac cttcaggtga caacttngnt ttnacatcca   420
ccaatccatg cntngatgac cgatcaaagc ttcttctccg ccgtgantcc aagtantaat   480
ccctcgtctg agctgtcccn cctggcttct tctccggcga ggctttanca tcttcggtca   540
cggatganaa aggtancagc tttggatacg tcttcccgat caagcatccg tcccatgacg   600
ctctangctc ctcgaaagag actcgncaca acctnggatc nacatcacat gancga       656
```

<210> SEQ ID NO 149
<211> LENGTH: 801
<212> TYPE: DNA
<213> ORGANISM: Brassica napus
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t

<400> SEQUENCE: 149

```
atatttaatt attatatata tggagtaaaa gtataagagt ctttttcctc ttaatgaagt    60
agatattttt gaaatatttt atttagtgat gataaacatg aataatgata cgagcaaagt   120
```

```
gttaaacatg aaaattcccc ttaaatattc tctttgtttt acaaagtatt attattattt       180
tgacatattt ttttgttaca caaagaatat cattttagaa tttaagtgtg atttatattt       240
attttaaact taatctttat ttctaaatgc attgatttta taaantattt tacttatctc       300
aaatatgatt tgttagataa atatgattaa taaaaatata attttttgt ttgaataacc        360 tgaaggtttc ctcgtggaat gactccgatt aatccctaag magagaagta acccaaaaat      420
aaactattnc ttcgtgtatt taaatagacc gcaaggaccc atatctatat aggtgtctag       480
gataatgtaa cttaatttca cacataagat atatcgaatt tgaaatgtgt tggcattcta      540 attcattnt cctcgtcact cgaccacaca aaaacataaa tattcaaatc atatntttaa       600
ccggtgtgag aattaaaatt gagaaattgc cacaaatacc acattcatag taccacttt       660 natgtntaca ctaatcactt ttatcctcaa ttttaataaa gggtaaaaga cattatacc       720 nctatggtta actaatctaa acttagggtt tagagttgag aganggtagg ttttttggca     780
tctgaaattt aggattctaa t                                                 801

<210> SEQ ID NO 150
<211> LENGTH: 121
<212> TYPE: DNA
<213> ORGANISM: Brassica napus
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t

<400> SEQUENCE: 150
aatacgtcta caatttcatt agtctcaaga aaaacaatat aaaaacaaaa taaatagcca       60
rattacatcc caaattcatc aagtagnctt gagtggngcc ccaatccaat tatccagaag      120
c                                                                      121

<210> SEQ ID NO 151
<211> LENGTH: 801
<212> TYPE: DNA
<213> ORGANISM: Brassica napus
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (487)..(487)
<223> OTHER INFORMATION: n is a, c, g, or t
<220> FEATURE:
<221> NAME/KEY: misc_feature
<222> LOCATION: (602)..(603)
<223> OTHER INFORMATION: n is a, c, g, or t
```

<220> FEATURE:
<221> NAME/KEY: misc_feature
<222> LOCATION: (632)..(632)
<223> OTHER INFORMATION: n is a, c, g, or t

<400> SEQUENCE: 151

```
tgtgttttgc ttgtgcaaat gtgcancttt gagtctgtgt gatggacctt tagggtttga      60
taagggaag ggaaagatgg tagatgcagg ggtgttgcag gacagccaag gagcaagggc     120
ttatgaaggt tcttcccaac ttcatggcag gtttgcgcat gggggaaaac tgaccatcgc    180
agaatgtacg gccatgnata atttgtgaaa tttcatgcat cttcagtcaa taaattcccg    240
taactgtcat tacaacttac tgtactggga catcagttgg ccntcttcta ctcggcttca    300
tgagtataag tatgagtttg ttgagatctc gtcagaatac gctgaagagt tgccaataac    360
gattgcgttt ttgcgtgaag tcaaaggctt tgcaagtgtc wttcatgact ggtggtggtg    420
gtagatcaaa cacgtttcag tatgagttgc ttagattctc tcncagcatc ccttcaacta    480
aattganagg gaaagaaagg aactgtgttc ctgttggttc ttatgagctt gatacagctg    540
cgttaccaca aatgatagaa gatggtgaag aggaagactg gtgatatttg ggcaatgtac    600
annaactgga ggaatgaaat cagggtaggg ancttgaaga agtgtgctta cgaggttgtt    660
gatgttggag tgggtggacg ggtttgtata ttgtgcaaag tctctagctt ttaatgtttt    720
agattcagac attaacttgc atcggatctg tcttttgact ctagttttag tcaatctggt    780
gaaatgttct tttacctctt c                                              801
```

<210> SEQ ID NO 152
<211> LENGTH: 688
<212> TYPE: DNA
<213> ORGANISM: Brassica napus
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (265)..(265)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t

<400> SEQUENCE: 152

```
gaccgacggc gttcttcaag agcttaggng gacaggtgga catcgtcaaa gacgggaagc      60
cttacgtgat gttcggagac gggaagctnt gcgcttgcaa gcccatcagc gaggaggatt     120
tagcttcgtt catagcggac tgtgtcttgg aagaggataa gatcaataag gttttgccta     180
tcggtggacc ggggaaggcc ttgacgccnt tggagcaagg ngagattctg tttaggatac     240
ttgggagaga gcctaagttt ctganagtnc ctattgagat tatggacttt gtgattgggg     300
tkcttgatgg tgtggcgaag gtgtttccta gtgttgcgga ggctgctgag tttgggaaga     360
ttgggaggta ttatgctgcg gagagtatgt tgattcttga tccngagact ggggagtata     420
gtgaggagaa gactccgagc tatgggaagg atactcttga ggacttcttt gagaaagtgg     480
ttagagaagg gatggctggt caagagcttg gtgaacagtt cttctagtgg ggagaagttt     540
ttatgctaat gagtttgagc tgtgttgagt gttgttagct gttgagatta taaaaactgt     600
gaatttgaga gatttgttga tccaaaaaaa acagttataa aacacatatt tcacangtnc     660
aaaaaaaaaa aaaaaaaaaa aaaaaaa                                         688

<210> SEQ ID NO 153
<211> LENGTH: 706
<212> TYPE: DNA
<213> ORGANISM: Brassica napus
<220> FEATURE:
<221> NAME/KEY: misc_feature
<222> LOCATION: (247)..(248)
<223> OTHER INFORMATION: n is a, c, g, or t
<220> FEATURE:
<221> NAME/KEY: misc_feature
<222> LOCATION: (334)..(334)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t
<220> FEATURE:
<221> NAME/KEY: misc_feature
<222> LOCATION: (581)..(581)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t

<400> SEQUENCE: 153
gaaacaatat gttcatctac atttacactt ccatttgttt tgagatagta atctcttcaa      60
aactggaaaa gcattgtcgc tactgttaga caccagaatg ggaccgatat ataagttaga     120
```

```
tgactcaaag aaacaacact tagacgacaa gttgcacaac aaagacctat aataagaatg    180
cattttcgag gggtgttcta aaaatgtgaa ccaagaagcg tgatctgata taagtagaca    240
taaattnnac ctcaagcgtc gaccgagatg aggaggaggt tgatgaagaa agcttatcgg    300
caccagatat agcgctgatt atgatgatgc tganggcaaa gcgtaaaacn cttntggagg    360 atcccttga tangcaaagt ccatatacag aatctctaac ttggagtgaa gcgattgagc     420
atctctcaac tcnanatctc gaattagaga catanccaag tgccagtgat tccatcacca    480
ctgaaacaga tgtgttccca rgacaaaacc caagcataac atcatagtgg aaatgcaaaa    540
cccacagtaa tagttacaag agagaaacag cnttttttgca nccccggat ggtgcatagc    600 cacggctcaa catttctttg ataagctcgg ccgataagnt tatatcacca tctctaagac    660
atagcgtgcc atcattcagc ataagcccat ctcctttcat ctttgt                   706

<210> SEQ ID NO 154
<211> LENGTH: 801
<212> TYPE: DNA
<213> ORGANISM: Brassica napus
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (761)..(801)
<223> OTHER INFORMATION: n is a, c, g, or t

<400> SEQUENCE: 154
tagacgtaat aaatgtagat ctgttgaggt tcttttata tatattttcc gtatttggtc     60
ggtctttgag atgagtttgt ttaagaaaaa cgtaaaatga agttgcttgg ggtctangtg    120
attncctgat tggcacgaag agcgacgcat ccccgaagcg cggcactctc cacgtgctct    180
tgtgatccac taaacaagcc catactaata taaagtcatc ttaaaaccga cgctgcataa    240
tctttaggtt catgcacatt cttgaataga tttcgaggaa catactgtag ttaatatttn    300
agcctggacc agaaataata tactcggatt gcatctcaat aaagagtatt aaaaaacaaa    360
aacaaaaaca aaatcattct gagactttga aacgaaaaag yaattagttt attgagcgcg    420
gggaagagta tatacattat taaacataca tctctcactt nctttctat acggcgagtt     480 catcttcaag ataactgtat tcaaacgtga actcgttttt gatcctttga acctacaca    540 gagttttcat aaagaaaaaa gattaggatc atcacctcga acgacaaaga gaacaagnag    600
acgagaaatc gatagatcat accatcctcc ttcttggctc tcatctttgg gggtttggaa    660
atcaaagtaa acataggctc cttgttcata ctcatcagtt gcaatctttg gctccttgtg    720
tctctgaaac catgtgttga actttctgtg gtatctccac nnnnnnnnnn nnnnnnnnnn    780
```
nnnnnnnnnn nnnnnnnnnn n           801

<210> SEQ ID NO 155
<211> LENGTH: 496
<212> TYPE: DNA
<213> ORGANISM: Brassica napus
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (466)..(466)
<223> OTHER INFORMATION: n is a, c, g, or t

<400> SEQUENCE: 155
cttgttctcg ctgagactgt ctttcttttc taggaagaag acgctaatac cgcggagccg      60
ccacctcctc ttccttgccg atacaggtct ctgcggagcc tgtttaaaac ttgtcctcta     120
ctcggctgtt tcctgaaagt tgagcaaaat cgcagccact gctgctacgg ccattttcag     180
ttggcacgag aatttgccca acgagctgtg gcttttcatt acttcgacgg attccttgat     240
ggagaacatc raaagagggt ttgtatcttg gctctgctga acagtgtccg aggcttacaa     300
acaggtgttc caaatctgga tcacgttgct ggattattca ccacacttcc ttggcagcta     360
aagatcatac cagaaaatgc agnaaattgg ctatttttca agacacccc actacgctac     420 acatcgatga gctacacanc gacgaactgt ggcantaagc cgncgnccat ctggtggaaa     480
aaaaatccat tcctaa                                                     496

<210> SEQ ID NO 156
<211> LENGTH: 801
<212> TYPE: DNA
<213> ORGANISM: Brassica napus
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t

<400> SEQUENCE: 156

```
ttctntgcaa tatgggaagt tgtatctctc tctcgctatc atgtgatcag tgtacgaatc      60
aagtctttca gtggttatgc atcagaaggg gttatattca caatctcgag gagaatctca     120
aggctttgga gacaaccatg gaggagcttc aggcaaatcg ggatgatttg tcaaaaaggg     180
nggagagaga ggagggtaaa ggactaaaaa ggctntccca aatccaggta tggcttacga     240
gagtcgacac aatcaaaaca cangtgaatg ctatatttng tgcaatacct gttggaagtc     300
aaaggttgtc tctctgtggg ttttgctcta ngaatttaaa atctagatat cgttacggga     360
aaagggtttt tctgatgttg aaggaggttg agaatctaaa ytctggtgga gactttgaag     420
tcnttgccga gcaagctcaa gcatcngagg tagaggagcg gnctatccaa ccgggaattg     480
ttggtcggga cacgatgctc aaaaaggcat gggtgtagaa gaatttagct taggttactt     540
aggtttcaag ttagccttag aacagtaaat acataatcaa tttaacgagt tcccggccct     600
cggcacggta cgtctcgtgg gagaacttct gctcccaaac ttgactagat caaaagagtc     660
accagccaca ccaaataagt gtgctagtta gtttacaatg aaccaaatac tccaagctag     720
agaatacaac aagcccttag ataatagact taagcctaag ctagttatct tgtatgttgt     780
cttctttctc ttgctaatct c                                               801
```

<210> SEQ ID NO 157
<211> LENGTH: 24
<212> TYPE: DNA
<213> ORGANISM: Artificial sequence
<220> FEATURE:
<223> OTHER INFORMATION: primer

<400> SEQUENCE: 157

```
acgtcggtac tcttttctgt tgtc                                             24
```

<210> SEQ ID NO 158
<211> LENGTH: 25
<212> TYPE: DNA
<213> ORGANISM: Artificial sequence
<220> FEATURE:
<223> OTHER INFORMATION: primer

<400> SEQUENCE: 158

```
cccttactct aggatgggtg ataca                                            25
```

<210> SEQ ID NO 159
<211> LENGTH: 18
<212> TYPE: DNA
<213> ORGANISM: Artificial sequence
<220> FEATURE:
<223> OTHER INFORMATION: probe

<400> SEQUENCE: 159

```
aactcaggaa ttaatgat                                                    18
```

<210> SEQ ID NO 160

```
<211> LENGTH: 17
<212> TYPE: DNA
<213> ORGANISM: Artificial sequence
<220> FEATURE:
<223> OTHER INFORMATION: probe

<400> SEQUENCE: 160
actcaggaat gaatgat                                                    17

<210> SEQ ID NO 161
<211> LENGTH: 20
<212> TYPE: DNA
<213> ORGANISM: Artificial sequence
<220> FEATURE:
<223> OTHER INFORMATION: primer

<400> SEQUENCE: 161
ttcggggatt agagctttcc                                                 20

<210> SEQ ID NO 162
<211> LENGTH: 22
<212> TYPE: DNA
<213> ORGANISM: Artificial sequence
<220> FEATURE:
<223> OTHER INFORMATION: primer

<400> SEQUENCE: 162
tcatcagtac cgtttgattt cg                                              22

<210> SEQ ID NO 163
<211> LENGTH: 17
<212> TYPE: DNA
<213> ORGANISM: Artificial sequence
<220> FEATURE:
<223> OTHER INFORMATION: probe

<400> SEQUENCE: 163
tcgatctctc actacgg                                                    17

<210> SEQ ID NO 164
<211> LENGTH: 18
<212> TYPE: DNA
<213> ORGANISM: Artificial sequence
<220> FEATURE:
<223> OTHER INFORMATION: probe

<400> SEQUENCE: 164
tctctcacta gggactac                                                   18

<210> SEQ ID NO 165
<211> LENGTH: 32
<212> TYPE: DNA
<213> ORGANISM: Artificial sequence
<220> FEATURE:
<223> OTHER INFORMATION: primer

<400> SEQUENCE: 165
tagctattca taattaatca aaaaggtggt cc                                   32

<210> SEQ ID NO 166
<211> LENGTH: 29
<212> TYPE: DNA
<213> ORGANISM: Artificial sequence
<220> FEATURE:
<223> OTHER INFORMATION: primer

<400> SEQUENCE: 166
```

```
gcagtatcat atgttccact ctagagatg                                              29

<210> SEQ ID NO 167
<211> LENGTH: 22
<212> TYPE: DNA
<213> ORGANISM: Artificial sequence
<220> FEATURE:
<223> OTHER INFORMATION: probe

<400> SEQUENCE: 167
attttacacc ttagtgctgt ga                                                     22

<210> SEQ ID NO 168
<211> LENGTH: 23
<212> TYPE: DNA
<213> ORGANISM: Artificial sequence
<220> FEATURE:
<223> OTHER INFORMATION: probe

<400> SEQUENCE: 168
aattttacac cttagtgcta tga                                                    23

<210> SEQ ID NO 169
<211> LENGTH: 25
<212> TYPE: DNA
<213> ORGANISM: Artificial sequence
<220> FEATURE:
<223> OTHER INFORMATION: primer

<400> SEQUENCE: 169
ccgcttagct ctcttcggtt atttt                                                  25

<210> SEQ ID NO 170
<211> LENGTH: 25
<212> TYPE: DNA
<213> ORGANISM: Artificial sequence
<220> FEATURE:
<223> OTHER INFORMATION: primer

<400> SEQUENCE: 170
aacagcacat gacgagatga catat                                                  25

<210> SEQ ID NO 171
<211> LENGTH: 18
<212> TYPE: DNA
<213> ORGANISM: Artificial sequence
<220> FEATURE:
<223> OTHER INFORMATION: probe

<400> SEQUENCE: 171
ctgaatgtgg tctatcac                                                          18

<210> SEQ ID NO 172
<211> LENGTH: 18
<212> TYPE: DNA
<213> ORGANISM: Artificial sequence
<220> FEATURE:
<223> OTHER INFORMATION: probe

<400> SEQUENCE: 172
ctgaatgtgg tttatcac                                                          18

<210> SEQ ID NO 173
<211> LENGTH: 24
<212> TYPE: DNA
```

```
<213> ORGANISM: Artificial sequence
<220> FEATURE:
<223> OTHER INFORMATION: primer

<400> SEQUENCE: 173
aacaagccct ctcatgtaca atgt                                          24

<210> SEQ ID NO 174
<211> LENGTH: 22
<212> TYPE: DNA
<213> ORGANISM: Artificial sequence
<220> FEATURE:
<223> OTHER INFORMATION: primer

<400> SEQUENCE: 174
accaccgcta tgcatcaaat ct                                            22

<210> SEQ ID NO 175
<211> LENGTH: 20
<212> TYPE: DNA
<213> ORGANISM: Artificial sequence
<220> FEATURE:
<223> OTHER INFORMATION: probe

<400> SEQUENCE: 175
actagttgat tatgaagaaa                                               20

<210> SEQ ID NO 176
<211> LENGTH: 19
<212> TYPE: DNA
<213> ORGANISM: Artificial sequence
<220> FEATURE:
<223> OTHER INFORMATION: probe

<400> SEQUENCE: 176
ctagttgatt gtgaagaaa                                                19

<210> SEQ ID NO 177
<211> LENGTH: 25
<212> TYPE: DNA
<213> ORGANISM: Artificial sequence
<220> FEATURE:
<223> OTHER INFORMATION: primer

<400> SEQUENCE: 177
ccgtacgatg aatcagacga aagta                                         25

<210> SEQ ID NO 178
<211> LENGTH: 35
<212> TYPE: DNA
<213> ORGANISM: Artificial sequence
<220> FEATURE:
<223> OTHER INFORMATION: primer

<400> SEQUENCE: 178
gaaacgaata aattatagaa cgaagctact aatgg                              35

<210> SEQ ID NO 179
<211> LENGTH: 18
<212> TYPE: DNA
<213> ORGANISM: Artificial sequence
<220> FEATURE:
<223> OTHER INFORMATION: probe

<400> SEQUENCE: 179
aacagagaga ttaattgg                                                 18
```

<210> SEQ ID NO 180
<211> LENGTH: 17
<212> TYPE: DNA
<213> ORGANISM: Artificial sequence
<220> FEATURE:
<223> OTHER INFORMATION: probe

<400> SEQUENCE: 180
acagagagat gaattgg                                                    17

<210> SEQ ID NO 181
<211> LENGTH: 25
<212> TYPE: DNA
<213> ORGANISM: Artificial sequence
<220> FEATURE:
<223> OTHER INFORMATION: primer

<400> SEQUENCE: 181
tgatgcttcc cttcaaagaa agaca                                           25

<210> SEQ ID NO 182
<211> LENGTH: 35
<212> TYPE: DNA
<213> ORGANISM: Artificial sequence
<220> FEATURE:
<223> OTHER INFORMATION: primer

<400> SEQUENCE: 182
acatgttacc aatcaaagcc tatattacat ttaca                                35

<210> SEQ ID NO 183
<211> LENGTH: 15
<212> TYPE: DNA
<213> ORGANISM: Artificial sequence
<220> FEATURE:
<223> OTHER INFORMATION: probe

<400> SEQUENCE: 183
tttttgtgca acttc                                                      15

<210> SEQ ID NO 184
<211> LENGTH: 19
<212> TYPE: DNA
<213> ORGANISM: Artificial sequence
<220> FEATURE:
<223> OTHER INFORMATION: probe

<400> SEQUENCE: 184
cttgtttttg tacaacttc                                                  19

<210> SEQ ID NO 185
<211> LENGTH: 21
<212> TYPE: DNA
<213> ORGANISM: Artificial sequence
<220> FEATURE:
<223> OTHER INFORMATION: primer

<400> SEQUENCE: 185
cccatcaaat gaaaaggagg a                                               21

<210> SEQ ID NO 186
<211> LENGTH: 20
<212> TYPE: DNA
<213> ORGANISM: Artificial sequence
<220> FEATURE:

<223> OTHER INFORMATION: primer

<400> SEQUENCE: 186
ctatggcgat gttgctcaaa                                           20

<210> SEQ ID NO 187
<211> LENGTH: 15
<212> TYPE: DNA
<213> ORGANISM: Artificial sequence
<220> FEATURE:
<223> OTHER INFORMATION: probe

<400> SEQUENCE: 187
atggttccat aactc                                                15

<210> SEQ ID NO 188
<211> LENGTH: 15
<212> TYPE: DNA
<213> ORGANISM: Artificial sequence
<220> FEATURE:
<223> OTHER INFORMATION: probe

<400> SEQUENCE: 188
catggttccg taact                                                15

<210> SEQ ID NO 189
<211> LENGTH: 25
<212> TYPE: DNA
<213> ORGANISM: Artificial sequence
<220> FEATURE:
<223> OTHER INFORMATION: primer

<400> SEQUENCE: 189
cctctttgag ctaacactag tcaca                                     25

<210> SEQ ID NO 190
<211> LENGTH: 24
<212> TYPE: DNA
<213> ORGANISM: Artificial sequence
<220> FEATURE:
<223> OTHER INFORMATION: primer

<400> SEQUENCE: 190
atccaaggga caaaatgcta ccaa                                      24

<210> SEQ ID NO 191
<211> LENGTH: 15
<212> TYPE: DNA
<213> ORGANISM: Artificial sequence
<220> FEATURE:
<223> OTHER INFORMATION: probe

<400> SEQUENCE: 191
acccatggtg gttct                                                15

<210> SEQ ID NO 192
<211> LENGTH: 18
<212> TYPE: DNA
<213> ORGANISM: Artificial sequence
<220> FEATURE:
<223> OTHER INFORMATION: probe

<400> SEQUENCE: 192
caaacccatg ttggttct                                             18

```
<210> SEQ ID NO 193
<211> LENGTH: 20
<212> TYPE: DNA
<213> ORGANISM: Artificial sequence
<220> FEATURE:
<223> OTHER INFORMATION: primer

<400> SEQUENCE: 193
ttgcaaaact ccaggtcaga                                               20

<210> SEQ ID NO 194
<211> LENGTH: 21
<212> TYPE: DNA
<213> ORGANISM: Artificial sequence
<220> FEATURE:
<223> OTHER INFORMATION: primer

<400> SEQUENCE: 194
aaagcttgtg tcgaagcaaa t                                             21

<210> SEQ ID NO 195
<211> LENGTH: 17
<212> TYPE: DNA
<213> ORGANISM: Artificial sequence
<220> FEATURE:
<223> OTHER INFORMATION: probe

<400> SEQUENCE: 195
acgtacataa cacgctt                                                  17

<210> SEQ ID NO 196
<211> LENGTH: 15
<212> TYPE: DNA
<213> ORGANISM: Artificial sequence
<220> FEATURE:
<223> OTHER INFORMATION: probe

<400> SEQUENCE: 196
aacgtacaca acacg                                                    15

<210> SEQ ID NO 197
<211> LENGTH: 22
<212> TYPE: DNA
<213> ORGANISM: Artificial sequence
<220> FEATURE:
<223> OTHER INFORMATION: primer

<400> SEQUENCE: 197
cacaataaaa ccagagcttc ca                                            22

<210> SEQ ID NO 198
<211> LENGTH: 20
<212> TYPE: DNA
<213> ORGANISM: Artificial sequence
<220> FEATURE:
<223> OTHER INFORMATION: primer

<400> SEQUENCE: 198
gcaacgaacc aaaaatcaca                                               20

<210> SEQ ID NO 199
<211> LENGTH: 19
<212> TYPE: DNA
<213> ORGANISM: Artificial sequence
<220> FEATURE:
<223> OTHER INFORMATION: probe
```

```
<400> SEQUENCE: 199
cttttccaaa tgattacac                                              19

<210> SEQ ID NO 200
<211>LENGTH: 17
<212> TYPE: DNA
<213> ORGANISM: Artificial sequence
<220> FEATURE:
<223> OTHER INFORMATION: probe

<400> SEQUENCE: 200
cttttccaga tgattac                                                17

<210> SEQ ID NO 201
<211> LENGTH: 25
<212> TYPE: DNA
<213> ORGANISM: Artificial sequence
<220> FEATURE:
<223> OTHER INFORMATION: primer

<400> SEQUENCE: 201
cacctgaccg aaagaaacac tagtt                                       25

<210> SEQ ID NO 202
<211> LENGTH: 36
<212> TYPE: DNA
<213> ORGANISM: Artificial sequence
<220> FEATURE:
<223> OTHER INFORMATION: primer

<400> SEQUENCE: 202
tctttctgta agaattattc ttcatttagc tatgct                           36

<210> SEQ ID NO 203
<211> LENGTH: 23
<212> TYPE: DNA
<213> ORGANISM: Artificial sequence
<220> FEATURE:
<223> OTHER INFORMATION: probe

<400> SEQUENCE: 203
aagataaaat tactgttatt agc                                         23

<210> SEQ ID NO 204
<211> LENGTH: 23
<212> TYPE: DNA
<213> ORGANISM: Artificial sequence
<220> FEATURE:
<223> OTHER INFORMATION: probe

<400> SEQUENCE: 204
aagataaaat tactgatatt agc                                         23

<210> SEQ ID NO 205
<211> LENGTH: 22
<212> TYPE: DNA
<213> ORGANISM: Artificial sequence
<220> FEATURE:
<223> OTHER INFORMATION: primer

<400> SEQUENCE: 205
tcttttgttg aatggggatt tt                                          22

<210> SEQ ID NO 206
<211> LENGTH: 26
```

```
<212> TYPE: DNA
<213> ORGANISM: Artificial sequence
<220> FEATURE:
<223> OTHER INFORMATION: primer

<400> SEQUENCE: 206
cgtcaaaaga aaatagaaaa agacag                                    26

<210> SEQ ID NO 207
<211> LENGTH: 16
<212> TYPE: DNA
<213> ORGANISM: Artificial sequence
<220> FEATURE:
<223> OTHER INFORMATION: probe

<400> SEQUENCE: 207
tccaacttcc aaatta                                               16

<210> SEQ ID NO 208
<211> LENGTH: 17
<212> TYPE: DNA
<213> ORGANISM: Artificial sequence
<220> FEATURE:
<223> OTHER INFORMATION: probe

<400> SEQUENCE: 208
tccaacttcc aaagtat                                              17

<210> SEQ ID NO 209
<211> LENGTH: 21
<212> TYPE: DNA
<213> ORGANISM: Artificial sequence
<220> FEATURE:
<223> OTHER INFORMATION: primer

<400> SEQUENCE: 209
aacgacatag acgatcgttg g                                         21

<210> SEQ ID NO 210
<211> LENGTH: 24
<212> TYPE: DNA
<213> ORGANISM: Artificial sequence
<220> FEATURE:
<223> OTHER INFORMATION: primer

<400> SEQUENCE: 210
tctccatcac ttcgttagta ttcg                                      24

<210> SEQ ID NO 211
<211> LENGTH: 17
<212> TYPE: DNA
<213> ORGANISM: Artificial sequence
<220> FEATURE:
<223> OTHER INFORMATION: probe

<400> SEQUENCE: 211
cacaagaatc cacaact                                              17

<210> SEQ ID NO 212
<211> LENGTH: 17
<212> TYPE: DNA
<213> ORGANISM: Artificial sequence
<220> FEATURE:
<223> OTHER INFORMATION: probe

<400> SEQUENCE: 212
```

```
acacaagagt ccacaac                                               17

<210> SEQ ID NO 213
<211> LENGTH: 27
<212> TYPE: DNA
<213> ORGANISM: Artificial sequence
<220> FEATURE:
<223> OTHER INFORMATION: primer

<400> SEQUENCE: 213
gagagaaaga gtgggaaaga aaagagt                                    27

<210> SEQ ID NO 214
<211> LENGTH: 25
<212> TYPE: DNA
<213> ORGANISM: Artificial sequence
<220> FEATURE:
<223> OTHER INFORMATION: primer

<400> SEQUENCE: 214
gctctctgaa gatgggaaga aatga                                      25

<210> SEQ ID NO 215
<211> LENGTH: 15
<212> TYPE: DNA
<213> ORGANISM: Artificial sequence
<220> FEATURE:
<223> OTHER INFORMATION: probe

<400> SEQUENCE: 215
ctccacgcct tagct                                                 15

<210> SEQ ID NO 216
<211> LENGTH: 16
<212> TYPE: DNA
<213> ORGANISM: Artificial sequence
<220> FEATURE:
<223> OTHER INFORMATION: probe

<400> SEQUENCE: 216
tctccacgct ttagct                                                16

<210> SEQ ID NO 217
<211> LENGTH: 20
<212> TYPE: DNA
<213> ORGANISM: Artificial sequence
<220> FEATURE:
<223> OTHER INFORMATION: primer

<400> SEQUENCE: 217
acaatctggc cacacagacg                                            20

<210> SEQ ID NO 218
<211> LENGTH: 30
<212> TYPE: DNA
<213> ORGANISM: Artificial sequence
<220> FEATURE:
<223> OTHER INFORMATION: primer

<400> SEQUENCE: 218
gttattcata aagccaaggt tttcacttct                                 30

<210> SEQ ID NO 219
<211> LENGTH: 22
<212> TYPE: DNA
<213> ORGANISM: Artificial sequence
```

```
<220> FEATURE:
<223> OTHER INFORMATION: probe

<400> SEQUENCE: 219
agagaagaat caactagaag ta                                              22

<210> SEQ ID NO 220
<211> LENGTH: 20
<212> TYPE: DNA
<213> ORGANISM: Artificial sequence
<220> FEATURE:
<223> OTHER INFORMATION: probe

<400> SEQUENCE: 220
agaagaatca acgagaagta                                                 20

<210> SEQ ID NO 221
<211> LENGTH: 47
<212> TYPE: DNA
<213> ORGANISM: Artificial sequence
<220> FEATURE:
<223> OTHER INFORMATION: primer

<400> SEQUENCE: 221
gaaggtgacc aagttcatgc tcaacaacta gcaaatcaaa agtgacc                   47

<210> SEQ ID NO 222
<211> LENGTH: 50
<212> TYPE: DNA
<213> ORGANISM: Artificial sequence
<220> FEATURE:
<223> OTHER INFORMATION: primer

<400> SEQUENCE: 222
gaaggtcgga gtcaacggat tgatcaacaa ctagcaaatc aaaagtgaca               50

<210> SEQ ID NO 223
<211> LENGTH: 29
<212> TYPE: DNA
<213> ORGANISM: Artificial sequence
<220> FEATURE:
<223> OTHER INFORMATION: primer

<400> SEQUENCE: 223
ggtggaataa agtgttcttt gacgaactt                                       29

<210> SEQ ID NO 224
<211> LENGTH: 47
<212> TYPE: DNA
<213> ORGANISM: Artificial sequence
<220> FEATURE:
<223> OTHER INFORMATION: primer

<400> SEQUENCE: 224
gaaggtgacc aagttcatgc taatgtaaag gagaagaaga agagcac                   47

<210> SEQ ID NO 225
<211> LENGTH: 47
<212> TYPE: DNA
<213> ORGANISM: Artificial sequence
<220> FEATURE:
<223> OTHER INFORMATION: primer

<400> SEQUENCE: 225
gaaggtcgga gtcaacggat taatgtaaag gagaagaaga agagcag                   47
```

<210> SEQ ID NO 226
<211> LENGTH: 24
<212> TYPE: DNA
<213> ORGANISM: Artificial sequence
<220> FEATURE:
<223> OTHER INFORMATION: primer

<400> SEQUENCE: 226
tcccaaccaa ttggtcgcca gtaa                                          24

<210> SEQ ID NO 227
<211> LENGTH: 46
<212> TYPE: DNA
<213> ORGANISM: Artificial sequence
<220> FEATURE:
<223> OTHER INFORMATION: primer

<400> SEQUENCE: 227
gaaggtgacc aagttcatgc taacagatca ttctaactca ttgccg                  46

<210> SEQ ID NO 228
<211> LENGTH: 48
<212> TYPE: DNA
<213> ORGANISM: Artificial sequence
<220> FEATURE:
<223> OTHER INFORMATION: primer

<400> SEQUENCE: 228
gaaggtcgga gtcaacggat tgtaacagat cattctaact cattgcca               48

<210> SEQ ID NO 229
<211> LENGTH: 25
<212> TYPE: DNA
<213> ORGANISM: Artificial sequence
<220> FEATURE:
<223> OTHER INFORMATION: primer

<400> SEQUENCE: 229
gaggtaatct acaccgcccc ttata                                         25

<210> SEQ ID NO 230
<211> LENGTH: 52
<212> TYPE: DNA
<213> ORGANISM: Artificial sequence
<220> FEATURE:
<223> OTHER INFORMATION: primer

<400> SEQUENCE: 230
gaaggtgacc aagttcatgc tgtcgtgaaa aataattttt ctatatttcc aa           52

<210> SEQ ID NO 231
<211> LENGTH: 54
<212> TYPE: DNA
<213> ORGANISM: Artificial sequence
<220> FEATURE:
<223> OTHER INFORMATION: primer

<400> SEQUENCE: 231
gaaggtcgga gtcaacggat tctgtcgtga aaaataatt ttctatattt ccat          54

<210> SEQ ID NO 232
<211> LENGTH: 30
<212> TYPE: DNA
<213> ORGANISM: Artificial sequence
<220> FEATURE:
<223> OTHER INFORMATION: primer

```
<400> SEQUENCE: 232
gtaccatttt attgtaatga actatctttt                                    30

<210> SEQ ID NO 233
<211> LENGTH: 47
<212> TYPE: DNA
<213> ORGANISM: Artificial sequence
<220> FEATURE:
<223> OTHER INFORMATION: primer

<400> SEQUENCE: 233
gaaggtgacc aagttcatgc tgttgagctg atcttacagg tccatta                 47

<210> SEQ ID NO 234
<211> LENGTH: 44
<212> TYPE: DNA
<213> ORGANISM: Artificial sequence
<220> FEATURE:
<223> OTHER INFORMATION: primer

<400> SEQUENCE: 234
gaaggtcgga gtcaacggat tgagctgatc ttacaggtcc attg                    44

<210> SEQ ID NO 235
<211> LENGTH: 25
<212> TYPE: DNA
<213> ORGANISM: Artificial sequence
<220> FEATURE:
<223> OTHER INFORMATION: primer

<400> SEQUENCE: 235
tcagctccgg tgaagaaaac agaga                                         25

<210> SEQ ID NO 236
<211> LENGTH: 53
<212> TYPE: DNA
<213> ORGANISM: Artificial sequence
<220> FEATURE:
<223> OTHER INFORMATION: primer

<400> SEQUENCE: 236
gaaggtgacc aagttcatgc tttaaagttt acttttatac atcacgagat taa          53

<210> SEQ ID NO 237
<211> LENGTH: 44
<212> TYPE: DNA
<213> ORGANISM: Artificial sequence
<220> FEATURE:
<223> OTHER INFORMATION: primer

<400> SEQUENCE: 237
gaaggtcgga gtcaacggat tgagctgatc ttacaggtcc attg                    44

<210> SEQ ID NO 238
<211> LENGTH: 30
<212> TYPE: DNA
<213> ORGANISM: Artificial sequence
<220> FEATURE:
<223> OTHER INFORMATION: primer

<400> SEQUENCE: 238
ctcaactagt ttcttttaat ttctgttgaa                                    30

<210> SEQ ID NO 239
```

```
<211> LENGTH: 51
<212> TYPE: DNA
<213> ORGANISM: Artificial sequence
<220> FEATURE:
<223> OTHER INFORMATION: primer

<400> SEQUENCE: 239
gaaggtgacc aagttcatgc tgagataatt caaggtgatt aagtgatatt g          51

<210> SEQ ID NO 240
<211> LENGTH: 53
<212> TYPE: DNA
<213> ORGANISM: Artificial sequence
<220> FEATURE:
<223> OTHER INFORMATION: primer

<400> SEQUENCE: 240
gaaggtcgga gtcaacggat tatgagataa ttcaaggtga ttaagtgata tta        53

<210> SEQ ID NO 241
<211> LENGTH: 29
<212> TYPE: DNA
<213> ORGANISM: Artificial sequence
<220> FEATURE:
<223> OTHER INFORMATION: primer

<400> SEQUENCE: 241
cagcccattt ccaaaagttt ttgggtttt                                   29

<210> SEQ ID NO 242
<211> LENGTH: 48
<212> TYPE: DNA
<213> ORGANISM: Artificial sequence
<220> FEATURE:
<223> OTHER INFORMATION: primer

<400> SEQUENCE: 242
gaaggtgacc aagttcatgc tgaatcgatc agaatctaaa cggttatg              48

<210> SEQ ID NO 243
<211> LENGTH: 49
<212> TYPE: DNA
<213> ORGANISM: Artificial sequence
<220> FEATURE:
<223> OTHER INFORMATION: primer

<400> SEQUENCE: 243
gaaggtcgga gtcaacggat tcgaatcgat cagaatctaa acggttatt             49

<210> SEQ ID NO 244
<211> LENGTH: 30
<212> TYPE: DNA
<213> ORGANISM: Artificial sequence
<220> FEATURE:
<223> OTHER INFORMATION: primer

<400> SEQUENCE: 244
gagatctgat caaaattgac tttgcactta                                  30

<210> SEQ ID NO 245
<211> LENGTH: 51
<212> TYPE: DNA
<213> ORGANISM: Artificial sequence
<220> FEATURE:
<223> OTHER INFORMATION: primer

<400> SEQUENCE: 245
```

-continued gaaggtgacc aagttcatgc tccaatatag aaaaaaacaa aacactcttc g    51

<210> SEQ ID NO 246
<211> LENGTH: 54
<212> TYPE: DNA
<213> ORGANISM: Artificial sequence
<220> FEATURE:
<223> OTHER INFORMATION: primer

<400> SEQUENCE: 246
gaaggtcgga gtcaacggat taaaccaata tagaaaaaaa caaaacactc ttca    54

<210> SEQ ID NO 247
<211> LENGTH: 29
<212> TYPE: DNA
<213> ORGANISM: Artificial sequence
<220> FEATURE:
<223> OTHER INFORMATION: primer

<400> SEQUENCE: 247
gttggaagct ttaacggtta tggaatgta    29

<210> SEQ ID NO 248
<211> LENGTH: 18
<212> TYPE: DNA
<213> ORGANISM: Artificial sequence
<220> FEATURE:
<223> OTHER INFORMATION: primer

<400> SEQUENCE: 248
caacgcgttg cccgaaaa    18

<210> SEQ ID NO 249
<211> LENGTH: 28
<212> TYPE: DNA
<213> ORGANISM: Artificial sequence
<220> FEATURE:
<223> OTHER INFORMATION: primer

<400> SEQUENCE: 249
ttgaagtact aaagtggata gcggaaaa    28

<210> SEQ ID NO 250
<211> LENGTH: 18
<212> TYPE: DNA
<213> ORGANISM: Artificial sequence
<220> FEATURE:
<223> OTHER INFORMATION: probe

<400> SEQUENCE: 250
tttaaagaag gaaaattc    18

<210> SEQ ID NO 251
<211> LENGTH: 21
<212> TYPE: DNA
<213> ORGANISM: Artificial sequence
<220> FEATURE:
<223> OTHER INFORMATION: probe

<400> SEQUENCE: 251
tgatttaaag aaagaaaatt c    21

<210> SEQ ID NO 252
<211> LENGTH: 52
<212> TYPE: DNA

```
<213> ORGANISM: Artificial sequence
<220> FEATURE:
<223> OTHER INFORMATION: primer

<400> SEQUENCE: 252
gaaggtgacc aagttcatgc ttttattttc ttctggatac agataagaat aa        52

<210> SEQ ID NO 253
<211> LENGTH: 51
<212> TYPE: DNA
<213> ORGANISM: Artificial sequence
<220> FEATURE:
<223> OTHER INFORMATION: primer

<400> SEQUENCE: 253
gaaggtcgga gtcaacggat tttatttct tctggataca gataagaata c           51

<210> SEQ ID NO 254
<211> LENGTH: 29
<212> TYPE: DNA
<213> ORGANISM: Artificial sequence
<220> FEATURE:
<223> OTHER INFORMATION: primer

<400> SEQUENCE: 254
ctcagacttc attgcaaagc tgaatagaa                                    29

<210> SEQ ID NO 255
<211> LENGTH: 51
<212> TYPE: DNA
<213> ORGANISM: Artificial sequence
<220> FEATURE:
<223> OTHER INFORMATION: primer

<400> SEQUENCE: 255
gaaggtgacc aagttcatgc tacaagtcat gtatttgtaa cgacttgaaa a           51

<210> SEQ ID NO 256
<211> LENGTH: 50
<212> TYPE: DNA
<213> ORGANISM: Artificial sequence
<220> FEATURE:
<223> OTHER INFORMATION: primer

<400> SEQUENCE: 256
gaaggtcgga gtcaacggat tcaagtcatg tatttgtaac gacttgaaag             50

<210> SEQ ID NO 257
<211> LENGTH: 25
<212> TYPE: DNA
<213> ORGANISM: Artificial sequence
<220> FEATURE:
<223> OTHER INFORMATION: primer

<400> SEQUENCE: 257
ggagtccgga ctgaaatgca gatta                                        25

<210> SEQ ID NO 258
<211> LENGTH: 45
<212> TYPE: DNA
<213> ORGANISM: Artificial sequence
<220> FEATURE:
<223> OTHER INFORMATION: primer

<400> SEQUENCE: 258
gaaggtgacc aagttcatgc tctgaagagc tgatgtcttt tggtg                  45
```

<210> SEQ ID NO 259
<211> LENGTH: 45
<212> TYPE: DNA
<213> ORGANISM: Artificial sequence
<220> FEATURE:
<223> OTHER INFORMATION: primer

<400> SEQUENCE: 259
gaaggtcgga gtcaacggat tctgaagagc tgatgtcttt tggtt    45

<210> SEQ ID NO 260
<211> LENGTH: 30
<212> TYPE: DNA
<213> ORGANISM: Artificial sequence
<220> FEATURE:
<223> OTHER INFORMATION: primer

<400> SEQUENCE: 260
caatgtttct gaacagaaac ttctcagttt    30

<210> SEQ ID NO 261
<211> LENGTH: 49
<212> TYPE: DNA
<213> ORGANISM: Artificial sequence
<220> FEATURE:
<223> OTHER INFORMATION: primer

<400> SEQUENCE: 261
gaaggtgacc aagttcatgc tcaatagcct tttaagagtt ttctaacca    49

<210> SEQ ID NO 262
<211> LENGTH: 49
<212> TYPE: DNA
<213> ORGANISM: Artificial sequence
<220> FEATURE:
<223> OTHER INFORMATION: primer

<400> SEQUENCE: 262
gaaggtcgga gtcaacggat tcaatagcct tttaagagtt ttctaacct    49

<210> SEQ ID NO 263
<211> LENGTH: 29
<212> TYPE: DNA
<213> ORGANISM: Artificial sequence
<220> FEATURE:
<223> OTHER INFORMATION: primer

<400> SEQUENCE: 263
cctttTgtgt tattaaaagc gggagtgtt    29

<210> SEQ ID NO 264
<211> LENGTH: 50
<212> TYPE: DNA
<213> ORGANISM: Artificial sequence
<220> FEATURE:
<223> OTHER INFORMATION: primer

<400> SEQUENCE: 264
gaaggtgacc aagttcatgc tcctcaacag cctgaaaaat ataacataat    50

<210> SEQ ID NO 265
<211> LENGTH: 50
<212> TYPE: DNA
<213> ORGANISM: Artificial sequence
<220> FEATURE:

<223> OTHER INFORMATION: primer

<400> SEQUENCE: 265
gaaggtcgga gtcaacggat tcctcaacag cctgaaaaat ataacataac            50

<210> SEQ ID NO 266
<211> LENGTH: 29
<212> TYPE: DNA
<213> ORGANISM: Artificial sequence
<220> FEATURE:
<223> OTHER INFORMATION: primer

<400> SEQUENCE: 266
gtcccggata taactgct gtatacata                                     29

<210> SEQ ID NO 267
<211> LENGTH: 45
<212> TYPE: DNA
<213> ORGANISM: Artificial sequence
<220> FEATURE:
<223> OTHER INFORMATION: primer

<400> SEQUENCE: 267
gaaggtgacc aagttcatgc tcattgttgc gtatgacaag ctcgt                 45

<210> SEQ ID NO 268
<211> LENGTH: 41
<212> TYPE: DNA
<213> ORGANISM: Artificial sequence
<220> FEATURE:
<223> OTHER INFORMATION: primer

<400> SEQUENCE: 268
gaaggtcgga gtcaacggat tgttgcgtat gacaagctcg c                     41

<210> SEQ ID NO 269
<211> LENGTH: 25
<212> TYPE: DNA
<213> ORGANISM: Artificial sequence
<220> FEATURE:
<223> OTHER INFORMATION: primer

<400> SEQUENCE: 269
ggtatcgttc gtgagagatt ggcta                                       25

<210> SEQ ID NO 270
<211> LENGTH: 54
<212> TYPE: DNA
<213> ORGANISM: Artificial sequence
<220> FEATURE:
<223> OTHER INFORMATION: primer

<400> SEQUENCE: 270
gaaggtgacc aagttcatgc tcaataagac aaaaattcaa aacaagaaaa aatg       54

<210> SEQ ID NO 271
<211> LENGTH: 54
<212> TYPE: DNA
<213> ORGANISM: Artificial sequence
<220> FEATURE:
<223> OTHER INFORMATION: primer

<400> SEQUENCE: 271
gaaggtcgga gtcaacggat tcaataagac aaaaattcaa aacaagaaaa aata       54

<210> SEQ ID NO 272
<211> LENGTH: 30
<212> TYPE: DNA
<213> ORGANISM: Artificial sequence
<220> FEATURE:
<223> OTHER INFORMATION: primer

<400> SEQUENCE: 272
ggctttgtaa atttccgttt tcaaacgttt                              30

<210> SEQ ID NO 273
<211> LENGTH: 47
<212> TYPE: DNA
<213> ORGANISM: Artificial sequence
<220> FEATURE:
<223> OTHER INFORMATION: primer

<400> SEQUENCE: 273
gaaggtgacc aagttcatgc tgattacacg cacaaattcg agaaatg            47

<210> SEQ ID NO 274
<211> LENGTH: 43
<212> TYPE: DNA
<213> ORGANISM: Artificial sequence
<220> FEATURE:
<223> OTHER INFORMATION: primer

<400> SEQUENCE: 274
gaaggtcgga gtcaacggat tacacgcaca aattcgagaa ata               43

<210> SEQ ID NO 275
<211> LENGTH: 29
<212> TYPE: DNA
<213> ORGANISM: Artificial sequence
<220> FEATURE:
<223> OTHER INFORMATION: primer

<400> SEQUENCE: 275
atctcgctga tccagtttgt tcttgattt                               29

<210> SEQ ID NO 276
<211> LENGTH: 49
<212> TYPE: DNA
<213> ORGANISM: Artificial sequence
<220> FEATURE:
<223> OTHER INFORMATION: primer

<400> SEQUENCE: 276
gaaggtgacc aagttcatgc ttggttcatt ttatttaatg gacctttgc           49

<210> SEQ ID NO 277
<211> LENGTH: 51
<212> TYPE: DNA
<213> ORGANISM: Artificial sequence
<220> FEATURE:
<223> OTHER INFORMATION: primer

<400> SEQUENCE: 277
gaaggtcgga gtcaacggat tcttggttca ttttatttaa tggacctttg a         51

<210> SEQ ID NO 278
<211> LENGTH: 30
<212> TYPE: DNA
<213> ORGANISM: Artificial sequence
<220> FEATURE:
<223> OTHER INFORMATION: primer

```
<400> SEQUENCE: 278
gaaccactgt gttaacaaaa caacaacgtt                              30

<210> SEQ ID NO 279
<211> LENGTH: 47
<212> TYPE: DNA
<213> ORGANISM: Artificial sequence
<220> FEATURE:
<223> OTHER INFORMATION: primer

<400> SEQUENCE: 279
gaaggtgacc aagttcatgc tcccattatc attgtgcaat ttccgag           47

<210> SEQ ID NO 280
<211> LENGTH: 47
<212> TYPE: DNA
<213> ORGANISM: Artificial sequence
<220> FEATURE:
<223> OTHER INFORMATION: primer

<400> SEQUENCE: 280
gaaggtcgga gtcaacggat tcccattatc attgtgcaat ttccgac           47

<210> SEQ ID NO 281
<211> LENGTH: 30
<212> TYPE: DNA
<213> ORGANISM: Artificial sequence
<220> FEATURE:
<223> OTHER INFORMATION: primer

<400> SEQUENCE: 281
cctttcttgc ttctccagat acaatttgtt                              30

<210> SEQ ID NO 282
<211> LENGTH: 44
<212> TYPE: DNA
<213> ORGANISM: Artificial sequence
<220> FEATURE:
<223> OTHER INFORMATION: primer

<400> SEQUENCE: 282
gaaggtgacc aagttcatgc tgtttgatcc tcagttcgct cgtc              44

<210> SEQ ID NO 283
<211> LENGTH: 44
<212> TYPE: DNA
<213> ORGANISM: Artificial sequence
<220> FEATURE:
<223> OTHER INFORMATION: primer

<400> SEQUENCE: 283
gaaggtcgga gtcaacggat tgtttgatcc tcagttcgct cgtg              44

<210> SEQ ID NO 284
<211> LENGTH: 25
<212> TYPE: DNA
<213> ORGANISM: Artificial sequence
<220> FEATURE:
<223> OTHER INFORMATION: primer

<400> SEQUENCE: 284
tccccttccg atcctcatca tctta                                   25

<210> SEQ ID NO 285
<211> LENGTH: 21
```

```
<212> TYPE: DNA
<213> ORGANISM: Artificial sequence
<220> FEATURE:
<223> OTHER INFORMATION: primer

<400> SEQUENCE: 285
ttcttccatc gtctctcctg a                                              21

<210> SEQ ID NO 286
<211> LENGTH: 22
<212> TYPE: DNA
<213> ORGANISM: Artificial sequence
<220> FEATURE:
<223> OTHER INFORMATION: primer

<400> SEQUENCE: 286
tgcaattcag tgtttcgatt tt                                             22

<210> SEQ ID NO 287
<211> LENGTH: 15
<212> TYPE: DNA
<213> ORGANISM: Artificial sequence
<220> FEATURE:
<223> OTHER INFORMATION: probe

<400> SEQUENCE: 287
ctcccaccta tcaaa                                                     15

<210> SEQ ID NO 288
<211> LENGTH: 15
<212> TYPE: DNA
<213> ORGANISM: Artificial sequence
<220> FEATURE:
<223> OTHER INFORMATION: probe

<400> SEQUENCE: 288
ctcccagcta tcaaa                                                     15

<210> SEQ ID NO 289
<211> LENGTH: 27
<212> TYPE: DNA
<213> ORGANISM: Artificial sequence
<220> FEATURE:
<223> OTHER INFORMATION: primer

<400> SEQUENCE: 289
acttaaagac ctctccttac tctccaa                                        27

<210> SEQ ID NO 290
<211> LENGTH: 29
<212> TYPE: DNA
<213> ORGANISM: Artificial sequence
<220> FEATURE:
<223> OTHER INFORMATION: primer

<400> SEQUENCE: 290
gctggtaatt gaaaaggatt gatctttga                                      29

<210> SEQ ID NO 291
<211> LENGTH: 17
<212> TYPE: DNA
<213> ORGANISM: Artificial sequence
<220> FEATURE:
<223> OTHER INFORMATION: probe

<400> SEQUENCE: 291
```

```
caagccaaag tcttaac                                               17

<210> SEQ ID NO 292
<211> LENGTH: 17
<212> TYPE: DNA
<213> ORGANISM: Artificial sequence
<220> FEATURE:
<223> OTHER INFORMATION: probe

<400> SEQUENCE: 292
caagccaaag acttaac                                               17

<210> SEQ ID NO 293
<211> LENGTH: 18
<212> TYPE: DNA
<213> ORGANISM: Artificial sequence
<220> FEATURE:
<223> OTHER INFORMATION: primer

<400> SEQUENCE: 293
ctcgtctccg ttggtggt                                              18

<210> SEQ ID NO 294
<211> LENGTH: 20
<212> TYPE: DNA
<213> ORGANISM: Artificial sequence
<220> FEATURE:
<223> OTHER INFORMATION: primer

<400> SEQUENCE: 294
ggcaaccctt tcaaaacaga                                            20

<210> SEQ ID NO 295
<211> LENGTH: 15
<212> TYPE: DNA
<213> ORGANISM: Artificial sequence
<220> FEATURE:
<223> OTHER INFORMATION: probe

<400> SEQUENCE: 295
acaggtctcc tccac                                                 15

<210> SEQ ID NO 296
<211> LENGTH: 13
<212> TYPE: DNA
<213> ORGANISM: Artificial sequence
<220> FEATURE:
<223> OTHER INFORMATION: probe

<400> SEQUENCE: 296
acaggtcgcc tcc                                                   13

<210> SEQ ID NO 297
<211> LENGTH: 22
<212> TYPE: DNA
<213> ORGANISM: Artificial sequence
<220> FEATURE:
<223> OTHER INFORMATION: primer

<400> SEQUENCE: 297
ggaaagttga atttgattcg cc                                         22

<210> SEQ ID NO 298
<211> LENGTH: 23
<212> TYPE: DNA
<213> ORGANISM: Artificial sequence
```

```
<220> FEATURE:
<223> OTHER INFORMATION: primer

<400> SEQUENCE: 298
cattcctcaa caacaacccc taa                                              23

<210> SEQ ID NO 299
<211> LENGTH: 17
<212> TYPE: DNA
<213> ORGANISM: Artificial sequence
<220> FEATURE:
<223> OTHER INFORMATION: probe

<400> SEQUENCE: 299
cttgatcatc acaaaac                                                     17

<210> SEQ ID NO 300
<211> LENGTH: 17
<212> TYPE: DNA
<213> ORGANISM: Artificial sequence
<220> FEATURE:
<223> OTHER INFORMATION: probe

<400> SEQUENCE: 300
tcacgaaact cgactgg                                                     17

<210> SEQ ID NO 301
<211> LENGTH: 27
<212> TYPE: DNA
<213> ORGANISM: Artificial sequence
<220> FEATURE:
<223> OTHER INFORMATION: primer

<400> SEQUENCE: 301
tcctgtacac acaaattcaa gacatca                                          27

<210> SEQ ID NO 302
<211> LENGTH: 33
<212> TYPE: DNA
<213> ORGANISM: Artificial sequence
<220> FEATURE:
<223> OTHER INFORMATION: primer

<400> SEQUENCE: 302
gggtctttga agtttaatac ttgtttagtt ctc                                   33

<210> SEQ ID NO 303
<211> LENGTH: 15
<212> TYPE: DNA
<213> ORGANISM: Artificial sequence
<220> FEATURE:
<223> OTHER INFORMATION: probe

<400> SEQUENCE: 303
caaagagcaa caacg                                                       15

<210> SEQ ID NO 304
<211> LENGTH: 17
<212> TYPE: DNA
<213> ORGANISM: Artificial sequence
<220> FEATURE:
<223> OTHER INFORMATION: probe

<400> SEQUENCE: 304
cacaaagaga aacaacg                                                     17
```

<210> SEQ ID NO 305
<211> LENGTH: 23
<212> TYPE: DNA
<213> ORGANISM: Artificial sequence
<220> FEATURE:
<223> OTHER INFORMATION: primer

<400> SEQUENCE: 305
tgcgcttgtt tctaagactc caa                                         23

<210> SEQ ID NO 306
<211> LENGTH: 22
<212> TYPE: DNA
<213> ORGANISM: Artificial sequence
<220> FEATURE:
<223> OTHER INFORMATION: primer

<400> SEQUENCE: 306
gggtcttcct aggagtgcac ta                                          22

<210> SEQ ID NO 307
<211> LENGTH: 16
<212> TYPE: DNA
<213> ORGANISM: Artificial sequence
<220> FEATURE:
<223> OTHER INFORMATION: probe

<400> SEQUENCE: 307
cctgaaaccg cattgc                                                 16

<210> SEQ ID NO 308
<211> LENGTH: 16
<212> TYPE: DNA
<213> ORGANISM: Artificial sequence
<220> FEATURE:
<223> OTHER INFORMATION: probe

<400> SEQUENCE: 308 cctgaaaacca cattgc                                                16

<210> SEQ ID NO 309
<211> LENGTH: 25
<212> TYPE: DNA
<213> ORGANISM: Artificial sequence
<220> FEATURE:
<223> OTHER INFORMATION: primer

<400> SEQUENCE: 309
caatctcaaa ctgccactct tggta                                       25

<210> SEQ ID NO 310
<211> LENGTH: 21
<212> TYPE: DNA
<213> ORGANISM: Artificial sequence
<220> FEATURE:
<223> OTHER INFORMATION: primer

<400> SEQUENCE: 310
tcctgtcatg tgagctttgc a                                           21

<210> SEQ ID NO 311
<211> LENGTH: 17
<212> TYPE: DNA
<213> ORGANISM: Artificial sequence
<220> FEATURE:
<223> OTHER INFORMATION: probe

<400> SEQUENCE: 311
ccatcacgtt actaccg                                                  17

<210> SEQ ID NO 312
<211> LENGTH: 16
<212> TYPE: DNA
<213> ORGANISM: Artificial sequence
<220> FEATURE:
<223> OTHER INFORMATION: probe

<400> SEQUENCE: 312
catcacgtga ctaccg                                                   16

<210> SEQ ID NO 313
<211> LENGTH: 25
<212> TYPE: DNA
<213> ORGANISM: Artificial sequence
<220> FEATURE:
<223> OTHER INFORMATION: primer

<400> SEQUENCE: 313
ttctggccat tcacagttaa tacgt                                         25

<210> SEQ ID NO 314
<211> LENGTH: 33
<212> TYPE: DNA
<213> ORGANISM: Artificial sequence
<220> FEATURE:
<223> OTHER INFORMATION: primer

<400> SEQUENCE: 314
aattaaagca ccaactatct tacaatgttg aac                                33

<210> SEQ ID NO 315
<211> LENGTH: 20
<212> TYPE: DNA
<213> ORGANISM: Artificial sequence
<220> FEATURE:
<223> OTHER INFORMATION: probe

<400> SEQUENCE: 315
caacgaattg aaccgagtga                                               20

<210> SEQ ID NO 316
<211> LENGTH: 20
<212> TYPE: DNA
<213> ORGANISM: Artificial sequence
<220> FEATURE:
<223> OTHER INFORMATION: probe

<400> SEQUENCE: 316
caacgaattg aacggagtga                                               20

<210> SEQ ID NO 317
<211> LENGTH: 24
<212> TYPE: DNA
<213> ORGANISM: Artificial sequence
<220> FEATURE:
<223> OTHER INFORMATION: primer

<400> SEQUENCE: 317
cctatctgga agtttgagct tgct                                          24

<210> SEQ ID NO 318

```
<211> LENGTH: 25
<212> TYPE: DNA
<213> ORGANISM: Artificial sequence
<220> FEATURE:
<223> OTHER INFORMATION: primer

<400> SEQUENCE: 318
ctcaacaaga tgtcaccgtc ataga                                25

<210> SEQ ID NO 319
<211> LENGTH: 19
<212> TYPE: DNA
<213> ORGANISM: Artificial sequence
<220> FEATURE:
<223> OTHER INFORMATION: primer

<400> SEQUENCE: 319
aagttgagct aagaatata                                       19

<210> SEQ ID NO 320
<211> LENGTH: 19
<212> TYPE: DNA
<213> ORGANISM: Artificial sequence
<220> FEATURE:
<223> OTHER INFORMATION: primer

<400> SEQUENCE: 320
aagttgagct aacaatata                                       19

<210> SEQ ID NO 321
<211> LENGTH: 38
<212> TYPE: DNA
<213> ORGANISM: Artificial sequence
<220> FEATURE:
<223> OTHER INFORMATION: primer

<400> SEQUENCE: 321
cagtttttca gtttaagaaa tatataaacc gcttagat                  38

<210> SEQ ID NO 322
<211> LENGTH: 25
<212> TYPE: DNA
<213> ORGANISM: Artificial sequence
<220> FEATURE:
<223> OTHER INFORMATION: primer

<400> SEQUENCE: 322
gatagttcat ggtagacctc agcat                                25

<210> SEQ ID NO 323
<211> LENGTH: 20
<212> TYPE: DNA
<213> ORGANISM: Artificial sequence
<220> FEATURE:
<223> OTHER INFORMATION: probe

<400> SEQUENCE: 323
cgaaaagtaa actaaaccga                                      20

<210> SEQ ID NO 324
<211> LENGTH: 20
<212> TYPE: DNA
<213> ORGANISM: Artificial sequence
<220> FEATURE:
<223> OTHER INFORMATION: probe

<400> SEQUENCE: 324
```
cgaaaagtaa actgaaccga    20

<210> SEQ ID NO 325
<211> LENGTH: 19
<212> TYPE: DNA
<213> ORGANISM: Artificial sequence
<220> FEATURE:
<223> OTHER INFORMATION: primer

<400> SEQUENCE: 325
ccactgcacc ccgtaatct    19

<210> SEQ ID NO 326
<211> LENGTH: 19
<212> TYPE: DNA
<213> ORGANISM: Artificial sequence
<220> FEATURE:
<223> OTHER INFORMATION: primer

<400> SEQUENCE: 326
gggaccagag acgtctgag    19

<210> SEQ ID NO 327
<211> LENGTH: 17
<212> TYPE: DNA
<213> ORGANISM: Artificial sequence
<220> FEATURE:
<223> OTHER INFORMATION: probe

<400> SEQUENCE: 327
aacatctgcg tcgctag    17

<210> SEQ ID NO 328
<211> LENGTH: 20
<212> TYPE: DNA
<213> ORGANISM: Artificial sequence
<220> FEATURE:
<223> OTHER INFORMATION: probe

<400> SEQUENCE: 328
ttgaacatct gcatcgctag    20

<210> SEQ ID NO 329
<211> LENGTH: 24
<212> TYPE: DNA
<213> ORGANISM: Artificial sequence
<220> FEATURE:
<223> OTHER INFORMATION: primer

<400> SEQUENCE: 329
cggctccaag ttgcttttag tttg    24

<210> SEQ ID NO 330
<211> LENGTH: 30
<212> TYPE: DNA
<213> ORGANISM: Artificial sequence
<220> FEATURE:
<223> OTHER INFORMATION: primer

<400> SEQUENCE: 330
gctatactta cgtaaaaaaa agccttgaga    30

<210> SEQ ID NO 331
<211> LENGTH: 19
<212> TYPE: DNA

```
<213> ORGANISM: Artificial sequence
<220> FEATURE:
<223> OTHER INFORMATION: probe

<400> SEQUENCE: 331
ttatcaaaca gagtaaatg                                                        19

<210> SEQ ID NO 332
<211> LENGTH: 17
<212> TYPE: DNA
<213> ORGANISM: Artificial sequence
<220> FEATURE:
<223> OTHER INFORMATION: probe

<400> SEQUENCE: 332
atcaaacgga gtaaatg                                                          17

<210> SEQ ID NO 333
<211> LENGTH: 28
<212> TYPE: DNA
<213> ORGANISM: Artificial sequence
<220> FEATURE:
<223> OTHER INFORMATION: primer

<400> SEQUENCE: 333
agatcttgtt gacttctcgg tttaactc                                              28

<210> SEQ ID NO 334
<211> LENGTH: 22
<212> TYPE: DNA
<213> ORGANISM: Artificial sequence
<220> FEATURE:
<223> OTHER INFORMATION: primer

<400> SEQUENCE: 334
agggtcttgg catgttcctt tt                                                    22

<210> SEQ ID NO 335
<211> LENGTH: 15
<212> TYPE: DNA
<213> ORGANISM: Artificial sequence
<220> FEATURE:
<223> OTHER INFORMATION: probe

<400> SEQUENCE: 335
tcggtgacac tttta                                                            15

<210> SEQ ID NO 336
<211> LENGTH: 18
<212> TYPE: DNA
<213> ORGANISM: Artificial sequence
<220> FEATURE:
<223> OTHER INFORMATION: probe

<400> SEQUENCE: 336
atttcggtga aactttta                                                         18

<210> SEQ ID NO 337
<211> LENGTH: 33
<212> TYPE: DNA
<213> ORGANISM: Artificial sequence
<220> FEATURE:
<223> OTHER INFORMATION: primer

<400> SEQUENCE: 337
acctttttat atagagtagt cgagatggtt tga                                        33
```

<210> SEQ ID NO 338
<211> LENGTH: 30
<212> TYPE: DNA
<213> ORGANISM: Artificial sequence
<220> FEATURE:
<223> OTHER INFORMATION: primer

<400> SEQUENCE: 338
gttgactctg tgaagttaga tggatctaaa                                    30

<210> SEQ ID NO 339
<211> LENGTH: 18
<212> TYPE: DNA
<213> ORGANISM: Artificial sequence
<220> FEATURE:
<223> OTHER INFORMATION: probe

<400> SEQUENCE: 339
tttgcttatg ttattctc                                                 18

<210> SEQ ID NO 340
<211> LENGTH: 17
<212> TYPE: DNA
<213> ORGANISM: Artificial sequence
<220> FEATURE:
<223> OTHER INFORMATION: probe

<400> SEQUENCE: 340
ttgcttatgc tattctc                                                  17

<210> SEQ ID NO 341
<211> LENGTH: 34
<212> TYPE: DNA
<213> ORGANISM: Artificial sequence
<220> FEATURE:
<223> OTHER INFORMATION: primer

<400> SEQUENCE: 341
aaatgttata ttttcgttta attgtctgct ggtt                               34

<210> SEQ ID NO 342
<211> LENGTH: 22
<212> TYPE: DNA
<213> ORGANISM: Artificial sequence
<220> FEATURE:
<223> OTHER INFORMATION: primer

<400> SEQUENCE: 342
aaaacgtggg ctttttcaca gg                                            22

<210> SEQ ID NO 343
<211> LENGTH: 15
<212> TYPE: DNA
<213> ORGANISM: Artificial sequence
<220> FEATURE:
<223> OTHER INFORMATION: probe

<400> SEQUENCE: 343
acttgcgacg gtcaa                                                    15

<210> SEQ ID NO 344
<211> LENGTH: 17
<212> TYPE: DNA
<213> ORGANISM: Artificial sequence
<220> FEATURE:

```
<223> OTHER INFORMATION: probe

<400> SEQUENCE: 344
tgacttgcga tggtcaa                                          17

<210> SEQ ID NO 345
<211> LENGTH: 26
<212> TYPE: DNA
<213> ORGANISM: Artificial sequence
<220> FEATURE:
<223> OTHER INFORMATION: primer

<400> SEQUENCE: 345
aaccaacaca actattaccc aaacct                                26

<210> SEQ ID NO 346
<211> LENGTH: 25
<212> TYPE: DNA
<213> ORGANISM: Artificial sequence
<220> FEATURE:
<223> OTHER INFORMATION: primer

<400> SEQUENCE: 346
ccgcgtttta gaacatggag tagaa                                 25

<210> SEQ ID NO 347
<211> LENGTH: 19
<212> TYPE: DNA
<213> ORGANISM: Artificial sequence
<220> FEATURE:
<223> OTHER INFORMATION: probe

<400> SEQUENCE: 347
caatgagagt ctccacttt                                        19

<210> SEQ ID NO 348
<211> LENGTH: 19
<212> TYPE: DNA
<213> ORGANISM: Artificial sequence
<220> FEATURE:
<223> OTHER INFORMATION: probe

<400> SEQUENCE: 348
caatgagagt gtccacttt                                        19

<210> SEQ ID NO 349
<211> LENGTH: 25
<212> TYPE: DNA
<213> ORGANISM: Artificial sequence
<220> FEATURE:
<223> OTHER INFORMATION: primer

<400> SEQUENCE: 349
caatgttaaa ttctggtggc caaca                                 25

<210> SEQ ID NO 350
<211> LENGTH: 25
<212> TYPE: DNA
<213> ORGANISM: Artificial sequence
<220> FEATURE:
<223> OTHER INFORMATION: primer

<400> SEQUENCE: 350
gtagcacttg aggaataacc ctgat                                 25
```

```
<210> SEQ ID NO 351
<211> LENGTH: 15
<212> TYPE: DNA
<213> ORGANISM: Artificial sequence
<220> FEATURE:
<223> OTHER INFORMATION: probe

<400> SEQUENCE: 351
actgcaggtt caccg                                                    15

<210> SEQ ID NO 352
<211> LENGTH: 16
<212> TYPE: DNA
<213> ORGANISM: Artificial sequence
<220> FEATURE:
<223> OTHER INFORMATION: probe

<400> SEQUENCE: 352
aactgcagat tcaccg                                                   16

<210> SEQ ID NO 353
<211> LENGTH: 26
<212> TYPE: DNA
<213> ORGANISM: Artificial sequence
<220> FEATURE:
<223> OTHER INFORMATION: primer

<400> SEQUENCE: 353
aactggatga tcgtttacca ctgaaa                                        26

<210> SEQ ID NO 354
<211> LENGTH: 25
<212> TYPE: DNA
<213> ORGANISM: Artificial sequence
<220> FEATURE:
<223> OTHER INFORMATION: primer

<400> SEQUENCE: 354
tcgattgttc atagctgcct tttga                                         25

<210> SEQ ID NO 355
<211> LENGTH: 22
<212> TYPE: DNA
<213> ORGANISM: Artificial sequence
<220> FEATURE:
<223> OTHER INFORMATION: probe

<400> SEQUENCE: 355
cctaatttag gatatgtccc ac                                            22

<210> SEQ ID NO 356
<211> LENGTH: 23
<212> TYPE: DNA
<213> ORGANISM: Artificial sequence
<220> FEATURE:
<223> OTHER INFORMATION: probe

<400> SEQUENCE: 356
ccctaattta ggatatatcc cac                                           23

<210> SEQ ID NO 357
<211> LENGTH: 20
<212> TYPE: DNA
<213> ORGANISM: Artificial sequence
<220> FEATURE:
<223> OTHER INFORMATION: primer
```

<400> SEQUENCE: 357
tatcttcacc gacggctttc				20

<210> SEQ ID NO 358
<211> LENGTH: 20
<212> TYPE: DNA
<213> ORGANISM: Artificial sequence
<220> FEATURE:
<223> OTHER INFORMATION: primer

<400> SEQUENCE: 358
gaagtgccga ctcaccaagt				20

<210> SEQ ID NO 359
<211> LENGTH: 15
<212> TYPE: DNA
<213> ORGANISM: Artificial sequence
<220> FEATURE:
<223> OTHER INFORMATION: probe

<400> SEQUENCE: 359
ctcttttgtt tctcc				15

<210> SEQ ID NO 360
<211> LENGTH: 15
<212> TYPE: DNA
<213> ORGANISM: Artificial sequence
<220> FEATURE:
<223> OTHER INFORMATION: probe

<400> SEQUENCE: 360
actctttcgt ttctc				15

<210> SEQ ID NO 361
<211> LENGTH: 19
<212> TYPE: DNA
<213> ORGANISM: Artificial sequence
<220> FEATURE:
<223> OTHER INFORMATION: primer

<400> SEQUENCE: 361
cgatgcacca tcatgtgag				19

<210> SEQ ID NO 362
<211> LENGTH: 25
<212> TYPE: DNA
<213> ORGANISM: Artificial sequence
<220> FEATURE:
<223> OTHER INFORMATION: primer

<400> SEQUENCE: 362
cctctaattt cactgacact cttga				25

<210> SEQ ID NO 363
<211> LENGTH: 18
<212> TYPE: DNA
<213> ORGANISM: Artificial sequence
<220> FEATURE:
<223> OTHER INFORMATION: probe

<400> SEQUENCE: 363
cagttctcct ttcctatt				18

<210> SEQ ID NO 364
<211> LENGTH: 15

```
<212> TYPE: DNA
<213> ORGANISM: Artificial sequence
<220> FEATURE:
<223> OTHER INFORMATION: probe

<400> SEQUENCE: 364
cagttctcgt ttcct                                                    15

<210> SEQ ID NO 365
<211> LENGTH: 26
<212> TYPE: DNA
<213> ORGANISM: Artificial sequence
<220> FEATURE:
<223> OTHER INFORMATION: primer

<400> SEQUENCE: 365
tggtagagct gaaagatgat gttctc                                        26

<210> SEQ ID NO 366
<211> LENGTH: 24
<212> TYPE: DNA
<213> ORGANISM: Artificial sequence
<220> FEATURE:
<223> OTHER INFORMATION: primer

<400> SEQUENCE: 366
agccaaccgc ttattaccac tatg                                          24

<210> SEQ ID NO 367
<211> LENGTH: 18
<212> TYPE: DNA
<213> ORGANISM: Artificial sequence
<220> FEATURE:
<223> OTHER INFORMATION: probe

<400> SEQUENCE: 367
ttcggtatga caagataa                                                 18

<210> SEQ ID NO 368
<211> LENGTH: 19
<212> TYPE: DNA
<213> ORGANISM: Artificial sequence
<220> FEATURE:
<223> OTHER INFORMATION: probe

<400> SEQUENCE: 368
cttcggtatg acgagataa                                                19

<210> SEQ ID NO 369
<211> LENGTH: 23
<212> TYPE: DNA
<213> ORGANISM: Artificial sequence
<220> FEATURE:
<223> OTHER INFORMATION: primer

<400> SEQUENCE: 369
tggtctctgc atcttcgaat ctg                                           23

<210> SEQ ID NO 370
<211> LENGTH: 24
<212> TYPE: DNA
<213> ORGANISM: Artificial sequence
<220> FEATURE:
<223> OTHER INFORMATION: primer

<400> SEQUENCE: 370
```

```
cgatatacca aggttgctga tgct                                          24

<210> SEQ ID NO 371
<211> LENGTH: 14
<212> TYPE: DNA
<213> ORGANISM: Artificial sequence
<220> FEATURE:
<223> OTHER INFORMATION: probe

<400> SEQUENCE: 371
ccagaagcat ttgc                                                     14

<210> SEQ ID NO 372
<211> LENGTH: 16
<212> TYPE: DNA
<213> ORGANISM: Artificial sequence
<220> FEATURE:
<223> OTHER INFORMATION: probe

<400> SEQUENCE: 372
aaccagaaga atttgc                                                   16

<210> SEQ ID NO 373
<211> LENGTH: 30
<212> TYPE: DNA
<213> ORGANISM: Artificial sequence
<220> FEATURE:
<223> OTHER INFORMATION: primer

<400> SEQUENCE: 373
gaacctaaac caatggatag aaacttgact                                    30

<210> SEQ ID NO 374
<211> LENGTH: 38
<212> TYPE: DNA
<213> ORGANISM: Artificial sequence
<220> FEATURE:
<223> OTHER INFORMATION: primer

<400> SEQUENCE: 374
tcgaactaaa actagatgat tatgattaaa gcagtaaa                           38

<210> SEQ ID NO 375
<211> LENGTH: 18
<212> TYPE: DNA
<213> ORGANISM: Artificial sequence
<220> FEATURE:
<223> OTHER INFORMATION: probe

<400> SEQUENCE: 375
cttagggtgt aggttaat                                                 18

<210> SEQ ID NO 376
<211> LENGTH: 19
<212> TYPE: DNA
<213> ORGANISM: Artificial sequence
<220> FEATURE:
<223> OTHER INFORMATION: probe

<400> SEQUENCE: 376
ccttagggtg taagttaat                                                19

<210> SEQ ID NO 377
<211> LENGTH: 30
<212> TYPE: DNA
<213> ORGANISM: Artificial sequence
```

```
<220> FEATURE:
<223> OTHER INFORMATION: primer

<400> SEQUENCE: 377
gtagactttt ccaagctaat cttcagacaa                                    30

<210> SEQ ID NO 378
<211> LENGTH: 28
<212> TYPE: DNA
<213> ORGANISM: Artificial sequence
<220> FEATURE:
<223> OTHER INFORMATION: primer

<400> SEQUENCE: 378
ggtgtttatt gaaggcacta gaagatca                                      28

<210> SEQ ID NO 379
<211> LENGTH: 19
<212> TYPE: DNA
<213> ORGANISM: Artificial sequence
<220> FEATURE:
<223> OTHER INFORMATION: probe

<400> SEQUENCE: 379
caaatacttt cagtatccc                                                19

<210> SEQ ID NO 380
<211> LENGTH: 19
<212> TYPE: DNA
<213> ORGANISM: Artificial sequence
<220> FEATURE:
<223> OTHER INFORMATION: probe

<400> SEQUENCE: 380
caaatacttt caatatccc                                                19

<210> SEQ ID NO 381
<211> LENGTH: 25
<212> TYPE: DNA
<213> ORGANISM: Artificial sequence
<220> FEATURE:
<223> OTHER INFORMATION: primer

<400> SEQUENCE: 381
ggccttggga ttaagaatct ttcga                                         25

<210> SEQ ID NO 382
<211> LENGTH: 23
<212> TYPE: DNA
<213> ORGANISM: Artificial sequence
<220> FEATURE:
<223> OTHER INFORMATION: primer

<400> SEQUENCE: 382
cgagcctgcc tgaaagaaaa gta                                           23

<210> SEQ ID NO 383
<211> LENGTH: 17
<212> TYPE: DNA
<213> ORGANISM: Artificial sequence
<220> FEATURE:
<223> OTHER INFORMATION: probe

<400> SEQUENCE: 383
cagatcaacc taaggca                                                  17
```

```
<210> SEQ ID NO 384
<211> LENGTH: 18
<212> TYPE: DNA
<213> ORGANISM: Artificial sequence
<220> FEATURE:
<223> OTHER INFORMATION: probe

<400> SEQUENCE: 384
ccagatcaac ttaaggca                                                 18

<210> SEQ ID NO 385
<211> LENGTH: 25
<212> TYPE: DNA
<213> ORGANISM: Artificial sequence
<220> FEATURE:
<223> OTHER INFORMATION: primer

<400> SEQUENCE: 385
gcagctcttt gtttcaaacc catta                                         25

<210> SEQ ID NO 386
<211> LENGTH: 21
<212> TYPE: DNA
<213> ORGANISM: Artificial sequence
<220> FEATURE:
<223> OTHER INFORMATION: primer

<400> SEQUENCE: 386
gtaccgatga aacgcgagaa g                                             21

<210> SEQ ID NO 387
<211> LENGTH: 18
<212> TYPE: DNA
<213> ORGANISM: Artificial sequence
<220> FEATURE:
<223> OTHER INFORMATION: probe

<400> SEQUENCE: 387
cacatcaatt cagttttt                                                 18

<210> SEQ ID NO 388
<211> LENGTH: 18
<212> TYPE: DNA
<213> ORGANISM: Artificial sequence
<220> FEATURE:
<223> OTHER INFORMATION: probe

<400> SEQUENCE: 388
cacatcaatt gagtttt                                                  18

<210> SEQ ID NO 389
<211> LENGTH: 20
<212> TYPE: DNA
<213> ORGANISM: Artificial sequence
<220> FEATURE:
<223> OTHER INFORMATION: primer

<400> SEQUENCE: 389
gtggcacaag atgcgatgag                                               20

<210> SEQ ID NO 390
<211> LENGTH: 30
<212> TYPE: DNA
<213> ORGANISM: Artificial sequence
<220> FEATURE:
<223> OTHER INFORMATION: primer
```

```
<400> SEQUENCE: 390
aagtttcatt agttttgatg ggtagtgcta                                        30

<210> SEQ ID NO 391
<211> LENGTH: 15
<212> TYPE: DNA
<213> ORGANISM: Artificial sequence
<220> FEATURE:
<223> OTHER INFORMATION: probe

<400> SEQUENCE: 391
aagatccgca tggct                                                        15

<210> SEQ ID NO 392
<211> LENGTH: 18
<212> TYPE: DNA
<213> ORGANISM: Artificial sequence
<220> FEATURE:
<223> OTHER INFORMATION: probe

<400> SEQUENCE: 392
aagaagatca gcatggct                                                     18

<210> SEQ ID NO 393
<211> LENGTH: 20
<212> TYPE: DNA
<213> ORGANISM: Artificial sequence
<220> FEATURE:
<223> OTHER INFORMATION: primer

<400> SEQUENCE: 393
catctggatc accggttggt                                                   20

<210> SEQ ID NO 394
<211> LENGTH: 21
<212> TYPE: DNA
<213> ORGANISM: Artificial sequence
<220> FEATURE:
<223> OTHER INFORMATION: primer

<400> SEQUENCE: 394
ccgtcactgt ctcaggagga a                                                 21

<210> SEQ ID NO 395
<211> LENGTH: 15
<212> TYPE: DNA
<213> ORGANISM: Artificial sequence
<220> FEATURE:
<223> OTHER INFORMATION: probe

<400> SEQUENCE: 395
aacgcccgcc agaga                                                        15

<210> SEQ ID NO 396
<211> LENGTH: 16
<212> TYPE: DNA
<213> ORGANISM: Artificial sequence
<220> FEATURE:
<223> OTHER INFORMATION: probe

<400> SEQUENCE: 396
caacgcccgc tagaga                                                       16

<210> SEQ ID NO 397
```

```
<211> LENGTH: 27
<212> TYPE: DNA
<213> ORGANISM: Artificial sequence
<220> FEATURE:
<223> OTHER INFORMATION: primer

<400> SEQUENCE: 397
gataactata ttcatcgact cccaaac                                              27

<210> SEQ ID NO 398
<211> LENGTH: 19
<212> TYPE: DNA
<213> ORGANISM: Artificial sequence
<220> FEATURE:
<223> OTHER INFORMATION: primer

<400> SEQUENCE: 398
ggaccatctg cgtggtaga                                                       19

<210> SEQ ID NO 399
<211> LENGTH: 19
<212> TYPE: DNA
<213> ORGANISM: Artificial sequence
<220> FEATURE:
<223> OTHER INFORMATION: probe

<400> SEQUENCE: 399
acataagtta ccaccagtt                                                       19

<210> SEQ ID NO 400
<211> LENGTH: 19
<212> TYPE: DNA
<213> ORGANISM: Artificial sequence
<220> FEATURE:
<223> OTHER INFORMATION: probe

<400> SEQUENCE: 400
acaaaagtta ccaccagtt                                                       19

<210> SEQ ID NO 401
<211> LENGTH: 36
<212> TYPE: DNA
<213> ORGANISM: Artificial sequence
<220> FEATURE:
<223> OTHER INFORMATION: primer

<400> SEQUENCE: 401
cttatacact taagtctttg aatttcaaac tatgca                                    36

<210> SEQ ID NO 402
<211> LENGTH: 28
<212> TYPE: DNA
<213> ORGANISM: Artificial sequence
<220> FEATURE:
<223> OTHER INFORMATION: primer

<400> SEQUENCE: 402
ccacaacaaa cagctctact tacaatac                                             28

<210> SEQ ID NO 403
<211> LENGTH: 16
<212> TYPE: DNA
<213> ORGANISM: Artificial sequence
<220> FEATURE:
<223> OTHER INFORMATION: probe

<400> SEQUENCE: 403
```
cttcgcatcc taatcg                                               16

<210> SEQ ID NO 404
<211> LENGTH: 16
<212> TYPE: DNA
<213> ORGANISM: Artificial sequence
<220> FEATURE:
<223> OTHER INFORMATION: probe

<400> SEQUENCE: 404
cttcgcatct taatcg                                               16

<210> SEQ ID NO 405
<211> LENGTH: 28
<212> TYPE: DNA
<213> ORGANISM: Artificial sequence
<220> FEATURE:
<223> OTHER INFORMATION: primer

<400> SEQUENCE: 405
cgcttgagag cttttaaaga gagatagt                                  28

<210> SEQ ID NO 406
<211> LENGTH: 24
<212> TYPE: DNA
<213> ORGANISM: Artificial sequence
<220> FEATURE:
<223> OTHER INFORMATION: primer

<400> SEQUENCE: 406
gcccatttaa gcaccatacc aatc                                      24

<210> SEQ ID NO 407
<211> LENGTH: 19
<212> TYPE: DNA
<213> ORGANISM: Artificial sequence
<220> FEATURE:
<223> OTHER INFORMATION: probe

<400> SEQUENCE: 407
actgcatgca attatatat                                            19

<210> SEQ ID NO 408
<211> LENGTH: 18
<212> TYPE: DNA
<213> ORGANISM: Artificial sequence
<220> FEATURE:
<223> OTHER INFORMATION: probe

<400> SEQUENCE: 408
ctgcatgcaa tgatatat                                             18

<210> SEQ ID NO 409
<211> LENGTH: 22
<212> TYPE: DNA
<213> ORGANISM: Artificial sequence
<220> FEATURE:
<223> OTHER INFORMATION: primer

<400> SEQUENCE: 409
aaactgtgag tccctggaga ga                                        22

<210> SEQ ID NO 410
<211> LENGTH: 28
<212> TYPE: DNA

```
<213> ORGANISM: Artificial sequence
<220> FEATURE:
<223> OTHER INFORMATION: primer

<400> SEQUENCE: 410
gtatggcttc ttgattaagt ttgaagca                                              28

<210> SEQ ID NO 411
<211> LENGTH: 18
<212> TYPE: DNA
<213> ORGANISM: Artificial sequence
<220> FEATURE:
<223> OTHER INFORMATION: probe

<400> SEQUENCE: 411
cacaacctga actctact                                                         18

<210> SEQ ID NO 412
<211> LENGTH: 18
<212> TYPE: DNA
<213> ORGANISM: Artificial sequence
<220> FEATURE:
<223> OTHER INFORMATION: probe

<400> SEQUENCE: 412
cacaacctga aatctact                                                         18

<210> SEQ ID NO 413
<211> LENGTH: 22
<212> TYPE: DNA
<213> ORGANISM: Artificial sequence
<220> FEATURE:
<223> OTHER INFORMATION: primer

<400> SEQUENCE: 413
cagattggta atggttccct gt                                                    22

<210> SEQ ID NO 414
<211> LENGTH: 20
<212> TYPE: DNA
<213> ORGANISM: Artificial sequence
<220> FEATURE:
<223> OTHER INFORMATION: primer

<400> SEQUENCE: 414
catggatttt cctgccctaa                                                       20

<210> SEQ ID NO 415
<211> LENGTH: 16
<212> TYPE: DNA
<213> ORGANISM: Artificial sequence
<220> FEATURE:
<223> OTHER INFORMATION: probe

<400> SEQUENCE: 415
ttgcatatca tcccca                                                           16

<210> SEQ ID NO 416
<211> LENGTH: 15
<212> TYPE: DNA
<213> ORGANISM: Artificial sequence
<220> FEATURE:
<223> OTHER INFORMATION: probe

<400> SEQUENCE: 416
ttgcatatca tcgcc                                                            15
```

<210> SEQ ID NO 417
<211> LENGTH: 25
<212> TYPE: DNA
<213> ORGANISM: Artificial sequence
<220> FEATURE:
<223> OTHER INFORMATION: primer

<400> SEQUENCE: 417
ccatgcaacg taggaaacaa gtatc                                             25

<210> SEQ ID NO 418
<211> LENGTH: 25
<212> TYPE: DNA
<213> ORGANISM: Artificial sequence
<220> FEATURE:
<223> OTHER INFORMATION: primer

<400> SEQUENCE: 418
cgaggtcgaa ttgttttggt atgtg                                             25

<210> SEQ ID NO 419
<211> LENGTH: 18
<212> TYPE: DNA
<213> ORGANISM: Artificial sequence
<220> FEATURE:
<223> OTHER INFORMATION: probe

<400> SEQUENCE: 419
aacttctcta tattttcc                                                     18

<210> SEQ ID NO 420
<211> LENGTH: 20
<212> TYPE: DNA
<213> ORGANISM: Artificial sequence
<220> FEATURE:
<223> OTHER INFORMATION: probe

<400> SEQUENCE: 420
tgaacttctc tatcttttcc                                                   20

<210> SEQ ID NO 421
<211> LENGTH: 21
<212> TYPE: DNA
<213> ORGANISM: Artificial sequence
<220> FEATURE:
<223> OTHER INFORMATION: primer

<400> SEQUENCE: 421
aagagaagcg tctcctcgtt c                                                 21

<210> SEQ ID NO 422
<211> LENGTH: 20
<212> TYPE: DNA
<213> ORGANISM: Artificial sequence
<220> FEATURE:
<223> OTHER INFORMATION: primer

<400> SEQUENCE: 422
tcgacgtcta tccccaagat                                                   20

<210> SEQ ID NO 423
<211> LENGTH: 14
<212> TYPE: DNA
<213> ORGANISM: Artificial sequence
<220> FEATURE:

<223> OTHER INFORMATION: probe

<400> SEQUENCE: 423
acgcaaccac cgat                                                      14

<210> SEQ ID NO 424
<211> LENGTH: 14
<212> TYPE: DNA
<213> ORGANISM: Artificial sequence
<220> FEATURE:
<223> OTHER INFORMATION: probe

<400> SEQUENCE: 424
acgcaacgac cgat                                                      14

<210> SEQ ID NO 425
<211> LENGTH: 37
<212> TYPE: DNA
<213> ORGANISM: Artificial sequence
<220> FEATURE:
<223> OTHER INFORMATION: primer

<400> SEQUENCE: 425
gaaaagataa ttaaataaaa cgaaccaaca aacaaca                             37

<210> SEQ ID NO 426
<211> LENGTH: 31
<212> TYPE: DNA
<213> ORGANISM: Artificial sequence
<220> FEATURE:
<223> OTHER INFORMATION: primer

<400> SEQUENCE: 426
ccaaacattt attactagga ttttcctccc t                                   31

<210> SEQ ID NO 427
<211> LENGTH: 16
<212> TYPE: DNA
<213> ORGANISM: Artificial sequence
<220> FEATURE:
<223> OTHER INFORMATION: probe

<400> SEQUENCE: 427
aatagccacg aatgaa                                                    16

<210> SEQ ID NO 428
<211> LENGTH: 19
<212> TYPE: DNA
<213> ORGANISM: Artificial sequence
<220> FEATURE:
<223> OTHER INFORMATION: probe

<400> SEQUENCE: 428
agaaatagcc acaaatgaa                                                 19

<210> SEQ ID NO 429
<211> LENGTH: 23
<212> TYPE: DNA
<213> ORGANISM: Artificial sequence
<220> FEATURE:
<223> OTHER INFORMATION: primer

<400> SEQUENCE: 429
cggagacctt cagtgtgtta gac                                            23

```
<210> SEQ ID NO 430
<211> LENGTH: 24
<212> TYPE: DNA
<213> ORGANISM: Artificial sequence
<220> FEATURE:
<223> OTHER INFORMATION: primer

<400> SEQUENCE: 430
gttcccaatg taagcacaaa ggtt                                          24

<210> SEQ ID NO 431
<211> LENGTH: 17
<212> TYPE: DNA
<213> ORGANISM: Artificial sequence
<220> FEATURE:
<223> OTHER INFORMATION: probe

<400> SEQUENCE: 431
acgtgataac caactac                                                  17

<210> SEQ ID NO 432
<211> LENGTH: 17
<212> TYPE: DNA
<213> ORGANISM: Artificial sequence
<220> FEATURE:
<223> OTHER INFORMATION: probe

<400> SEQUENCE: 432
acgtgataac aaactac                                                  17

<210> SEQ ID NO 433
<211> LENGTH: 22
<212> TYPE: DNA
<213> ORGANISM: Artificial sequence
<220> FEATURE:
<223> OTHER INFORMATION: primer

<400> SEQUENCE: 433
tcaacaactg gttcatctgg aa                                            22

<210> SEQ ID NO 434
<211> LENGTH: 21
<212> TYPE: DNA
<213> ORGANISM: Artificial sequence
<220> FEATURE:
<223> OTHER INFORMATION: primer

<400> SEQUENCE: 434
ccagtgaaga tggatgcaaa g                                             21

<210> SEQ ID NO 435
<211> LENGTH: 16
<212> TYPE: DNA
<213> ORGANISM: Artificial sequence
<220> FEATURE:
<223> OTHER INFORMATION: probe

<400> SEQUENCE: 435
ctaccacaga cttatc                                                   16

<210> SEQ ID NO 436
<211> LENGTH: 17
<212> TYPE: DNA
<213> ORGANISM: Artificial sequence
<220> FEATURE:
<223> OTHER INFORMATION: probe
```

```
<400> SEQUENCE: 436
tctaccacag acttgtc                                                 17

<210> SEQ ID NO 437
<211> LENGTH: 28
<212> TYPE: DNA
<213> ORGANISM: Artificial sequence
<220> FEATURE:
<223> OTHER INFORMATION: primer

<400> SEQUENCE: 437
cttactgatc atgttagttg gcagtttt                                     28

<210> SEQ ID NO 438
<211> LENGTH: 32
<212> TYPE: DNA
<213> ORGANISM: Artificial sequence
<220> FEATURE:
<223> OTHER INFORMATION: primer

<400> SEQUENCE: 438
gagccattgt ttgtaagaga aattgaatat ga                                32

<210> SEQ ID NO 439
<211> LENGTH: 19
<212> TYPE: DNA
<213> ORGANISM: Artificial sequence
<220> FEATURE:
<223> OTHER INFORMATION: probe

<400> SEQUENCE: 439
ttgagtatgc aggtatgtc                                               19

<210> SEQ ID NO 440
<211> LENGTH: 19
<212> TYPE: DNA
<213> ORGANISM: Artificial sequence
<220> FEATURE:
<223> OTHER INFORMATION: probe

<400> SEQUENCE: 440
ttgagtatgc agatatgtc                                               19

<210> SEQ ID NO 441
<211> LENGTH: 24
<212> TYPE: DNA
<213> ORGANISM: Artificial sequence
<220> FEATURE:
<223> OTHER INFORMATION: primer

<400> SEQUENCE: 441
cgtctctgct tacctcacta tgaa                                         24

<210> SEQ ID NO 442
<211> LENGTH: 23
<212> TYPE: DNA
<213> ORGANISM: Artificial sequence
<220> FEATURE:
<223> OTHER INFORMATION: primer

<400> SEQUENCE: 442
gcagtagaca acagcttttg gaa                                          23

<210> SEQ ID NO 443
<211> LENGTH: 17
```

```
<212> TYPE: DNA
<213> ORGANISM: Artificial sequence
<220> FEATURE:
<223> OTHER INFORMATION: probe

<400> SEQUENCE: 443
acataaacat ggtctgc                                                 17

<210> SEQ ID NO 444
<211> LENGTH: 17
<212> TYPE: DNA
<213> ORGANISM: Artificial sequence
<220> FEATURE:
<223> OTHER INFORMATION: probe

<400> SEQUENCE: 444
acataatcat ggtctgc                                                 17

<210> SEQ ID NO 445
<211> LENGTH: 29
<212> TYPE: DNA
<213> ORGANISM: Artificial sequence
<220> FEATURE:
<223> OTHER INFORMATION: primer

<400> SEQUENCE: 445
tgatttgcct agaccaattt ttagaacac                                    29

<210> SEQ ID NO 446
<211> LENGTH: 27
<212> TYPE: DNA
<213> ORGANISM: Artificial sequence
<220> FEATURE:
<223> OTHER INFORMATION: primer

<400> SEQUENCE: 446
ggttaaaaca tgaaccgtta agctgaa                                      27

<210> SEQ ID NO 447
<211> LENGTH: 20
<212> TYPE: DNA
<213> ORGANISM: Artificial sequence
<220> FEATURE:
<223> OTHER INFORMATION: probe

<400> SEQUENCE: 447
tttgtctttg gttgtagttg                                              20

<210> SEQ ID NO 448
<211> LENGTH: 22
<212> TYPE: DNA
<213> ORGANISM: Artificial sequence
<220> FEATURE:
<223> OTHER INFORMATION: probe

<400> SEQUENCE: 448
tgtttgtctt tggttatagt tg                                           22

<210> SEQ ID NO 449
<211> LENGTH: 21
<212> TYPE: DNA
<213> ORGANISM: Artificial sequence
<220> FEATURE:
<223> OTHER INFORMATION: primer

<400> SEQUENCE: 449
```

```
tccttctcct ccgagaaagt t                                               21

<210> SEQ ID NO 450
<211> LENGTH: 21
<212> TYPE: DNA
<213> ORGANISM: Artificial sequence
<220> FEATURE:
<223> OTHER INFORMATION: primer

<400> SEQUENCE: 450
cctccgtatc cgtagacatc a                                               21

<210> SEQ ID NO 451
<211> LENGTH: 19
<212> TYPE: DNA
<213> ORGANISM: Artificial sequence
<220> FEATURE:
<223> OTHER INFORMATION: probe

<400> SEQUENCE: 451
acgttaaatc gtttagttg                                                  19

<210> SEQ ID NO 452
<211> LENGTH: 18
<212> TYPE: DNA
<213> ORGANISM: Artificial sequence
<220> FEATURE:
<223> OTHER INFORMATION: probe

<400> SEQUENCE: 452
caacgttaag tcgtttag                                                   18

<210> SEQ ID NO 453
<211> LENGTH: 40
<212> TYPE: DNA
<213> ORGANISM: Artificial sequence
<220> FEATURE:
<223> OTHER INFORMATION: primer

<400> SEQUENCE: 453
cactaattta tatagaaaat atgtaaaact ttttccatca                           40

<210> SEQ ID NO 454
<211> LENGTH: 37
<212> TYPE: DNA
<213> ORGANISM: Artificial sequence
<220> FEATURE:
<223> OTHER INFORMATION: primer

<400> SEQUENCE: 454
gatgggtgcc ataataatct atttatactt tttttgt                              37

<210> SEQ ID NO 455
<211> LENGTH: 19
<212> TYPE: DNA
<213> ORGANISM: Artificial sequence
<220> FEATURE:
<223> OTHER INFORMATION: probe

<400> SEQUENCE: 455
tttctaacat cgtggaaat                                                  19

<210> SEQ ID NO 456
<211> LENGTH: 22
<212> TYPE: DNA
<213> ORGANISM: Artificial sequence
```

```
<220> FEATURE:
<223> OTHER INFORMATION: probe

<400> SEQUENCE: 456
ccatttctaa catagtggaa at                                              22

<210> SEQ ID NO 457
<211> LENGTH: 31
<212> TYPE: DNA
<213> ORGANISM: Artificial sequence
<220> FEATURE:
<223> OTHER INFORMATION: primer

<400> SEQUENCE: 457
tgtgaaaata taagtttcac atcgagatcg a                                    31

<210> SEQ ID NO 458
<211> LENGTH: 37
<212> TYPE: DNA
<213> ORGANISM: Artificial sequence
<220> FEATURE:
<223> OTHER INFORMATION: primer

<400> SEQUENCE: 458
tcatgttaag tttggattta tcatgagttt tcaaatt                              37

<210> SEQ ID NO 459
<211> LENGTH: 17
<212> TYPE: DNA
<213> ORGANISM: Artificial sequence
<220> FEATURE:
<223> OTHER INFORMATION: probe

<400> SEQUENCE: 459
tcaatccacg tattacc                                                    17

<210> SEQ ID NO 460
<211> LENGTH: 18
<212> TYPE: DNA
<213> ORGANISM: Artificial sequence
<220> FEATURE:
<223> OTHER INFORMATION: probe

<400> SEQUENCE: 460
atcaatccac atattacc                                                   18

<210> SEQ ID NO 461
<211> LENGTH: 23
<212> TYPE: DNA
<213> ORGANISM: Artificial sequence
<220> FEATURE:
<223> OTHER INFORMATION: primer

<400> SEQUENCE: 461
aaacgccaaa actggtcatc ttg                                             23

<210> SEQ ID NO 462
<211> LENGTH: 25
<212> TYPE: DNA
<213> ORGANISM: Artificial sequence
<220> FEATURE:
<223> OTHER INFORMATION: primer

<400> SEQUENCE: 462
accgtaacca gctctctctg taata                                           25
```

<210> SEQ ID NO 463
<211> LENGTH: 18
<212> TYPE: DNA
<213> ORGANISM: Artificial sequence
<220> FEATURE:
<223> OTHER INFORMATION: probe

<400> SEQUENCE: 463
acgtgtcgta attcatgt                                                 18

<210> SEQ ID NO 464
<211> LENGTH: 18
<212> TYPE: DNA
<213> ORGANISM: Artificial sequence
<220> FEATURE:
<223> OTHER INFORMATION: probe

<400> SEQUENCE: 464
acgtgtcgta gttcatgt                                                 18

<210> SEQ ID NO 465
<211> LENGTH: 35
<212> TYPE: DNA
<213> ORGANISM: Artificial sequence
<220> FEATURE:
<223> OTHER INFORMATION: primer

<400> SEQUENCE: 465
ccgccaagtt ttaaacaaaa tcaataaatc atatt                              35

<210> SEQ ID NO 466
<211> LENGTH: 32
<212> TYPE: DNA
<213> ORGANISM: Artificial sequence
<220> FEATURE:
<223> OTHER INFORMATION: primer

<400> SEQUENCE: 466
tgtgcagtta atagttgtat agtgtatctt tg                                 32

<210> SEQ ID NO 467
<211> LENGTH: 19
<212> TYPE: DNA
<213> ORGANISM: Artificial sequence
<220> FEATURE:
<223> OTHER INFORMATION: probe

<400> SEQUENCE: 467
tgaagtttca accaccatt                                                19

<210> SEQ ID NO 468
<211> LENGTH: 19
<212> TYPE: DNA
<213> ORGANISM: Artificial sequence
<220> FEATURE:
<223> OTHER INFORMATION: probe

<400> SEQUENCE: 468
tgaagtttca agcaccatt                                                19

<210> SEQ ID NO 469
<211> LENGTH: 37
<212> TYPE: DNA
<213> ORGANISM: Artificial sequence
<220> FEATURE:
<223> OTHER INFORMATION: primer

```
<400> SEQUENCE: 469
agccaatttt aagtaaatca ttgaatattg ttagtgt                              37

<210> SEQ ID NO 470
<211> LENGTH: 26
<212> TYPE: DNA
<213> ORGANISM: Artificial sequence
<220> FEATURE:
<223> OTHER INFORMATION: primer

<400> SEQUENCE: 470
cggagggatt tcgaaatagt atgtgt                                          26

<210> SEQ ID NO 471
<211> LENGTH: 18
<212> TYPE: DNA
<213> ORGANISM: Artificial sequence
<220> FEATURE:
<223> OTHER INFORMATION: probe

<400> SEQUENCE: 471
cctctctgag ttaattga                                                   18

<210> SEQ ID NO 472
<211> LENGTH: 18
<212> TYPE: DNA
<213> ORGANISM: Artificial sequence
<220> FEATURE:
<223> OTHER INFORMATION: probe

<400> SEQUENCE: 472
cctctctgag taaattga                                                   18

<210> SEQ ID NO 473
<211> LENGTH: 34
<212> TYPE: DNA
<213> ORGANISM: Artificial sequence
<220> FEATURE:
<223> OTHER INFORMATION: primer

<400> SEQUENCE: 473
gtagggtatc attttatttt tctatcgact gagt                                 34

<210> SEQ ID NO 474
<211> LENGTH: 20
<212> TYPE: DNA
<213> ORGANISM: Artificial sequence
<220> FEATURE:
<223> OTHER INFORMATION: primer

<400> SEQUENCE: 474
cgcgtgctta gtggttacca                                                 20

<210> SEQ ID NO 475
<211> LENGTH: 17
<212> TYPE: DNA
<213> ORGANISM: Artificial sequence
<220> FEATURE:
<223> OTHER INFORMATION: probe

<400> SEQUENCE: 475
agtgcttgtg tctcatg                                                    17

<210> SEQ ID NO 476
```

```
<211> LENGTH: 18
<212> TYPE: DNA
<213> ORGANISM: Artificial sequence
<220> FEATURE:
<223> OTHER INFORMATION: probe

<400> SEQUENCE: 476
cagtgcttgt gtgtcatg                                                    18

<210> SEQ ID NO 477
<211> LENGTH: 39
<212> TYPE: DNA
<213> ORGANISM: Artificial sequence
<220> FEATURE:
<223> OTHER INFORMATION: primer

<400> SEQUENCE: 477
gcatgaatag tagtagcttt cttttttaa atgtgtata                              39

<210> SEQ ID NO 478
<211> LENGTH: 40
<212> TYPE: DNA
<213> ORGANISM: Artificial sequence
<220> FEATURE:
<223> OTHER INFORMATION: primer

<400> SEQUENCE: 478
aaattaacaa cagtgttacc taattattat aaagaattga                            40

<210> SEQ ID NO 479
<211> LENGTH: 18
<212> TYPE: DNA
<213> ORGANISM: Artificial sequence
<220> FEATURE:
<223> OTHER INFORMATION: probe

<400> SEQUENCE: 479
ttgagaagtc tcgaaaat                                                    18

<210> SEQ ID NO 480
<211> LENGTH: 18
<212> TYPE: DNA
<213> ORGANISM: Artificial sequence
<220> FEATURE:
<223> OTHER INFORMATION: probe

<400> SEQUENCE: 480
ttgagaagtc tggaaaat                                                    18

<210> SEQ ID NO 481
<211> LENGTH: 25
<212> TYPE: DNA
<213> ORGANISM: Artificial sequence
<220> FEATURE:
<223> OTHER INFORMATION: primer

<400> SEQUENCE: 481
cgccaactac acaagagcat aattt                                            25

<210> SEQ ID NO 482
<211> LENGTH: 25
<212> TYPE: DNA
<213> ORGANISM: Artificial sequence
<220> FEATURE:
<223> OTHER INFORMATION: primer

<400> SEQUENCE: 482
```

```
gaagctgtgg aagttacaat gcaaa                                          25

<210> SEQ ID NO 483
<211> LENGTH: 17
<212> TYPE: DNA
<213> ORGANISM: Artificial sequence
<220> FEATURE:
<223> OTHER INFORMATION: probe

<400> SEQUENCE: 483
cctcaagtct taaactt                                                   17

<210> SEQ ID NO 484
<211> LENGTH: 16
<212> TYPE: DNA
<213> ORGANISM: Artificial sequence
<220> FEATURE:
<223> OTHER INFORMATION: probe

<400> SEQUENCE: 484
ctcaagtctg aaactt                                                    16

<210> SEQ ID NO 485
<211> LENGTH: 26
<212> TYPE: DNA
<213> ORGANISM: Artificial sequence
<220> FEATURE:
<223> OTHER INFORMATION: primer

<400> SEQUENCE: 485
tccacaatct ctccttccaa attcac                                         26

<210> SEQ ID NO 486
<211> LENGTH: 21
<212> TYPE: DNA
<213> ORGANISM: Artificial sequence
<220> FEATURE:
<223> OTHER INFORMATION: primer

<400> SEQUENCE: 486
actcgggtct gtacgttgag a                                              21

<210> SEQ ID NO 487
<211> LENGTH: 14
<212> TYPE: DNA
<213> ORGANISM: Artificial sequence
<220> FEATURE:
<223> OTHER INFORMATION: probe

<400> SEQUENCE: 487
cggagacaag gaag                                                      14

<210> SEQ ID NO 488
<211> LENGTH: 16
<212> TYPE: DNA
<213> ORGANISM: Artificial sequence
<220> FEATURE:
<223> OTHER INFORMATION: probe

<400> SEQUENCE: 488
accggagacg aggaag                                                    16

<210> SEQ ID NO 489
<211> LENGTH: 29
<212> TYPE: DNA
```

```
<213> ORGANISM: Artificial sequence
<220> FEATURE:
<223> OTHER INFORMATION: primer

<400> SEQUENCE: 489
tcacctctca tgttgctata aggttatct                              29

<210> SEQ ID NO 490
<211> LENGTH: 29
<212> TYPE: DNA
<213> ORGANISM: Artificial sequence
<220> FEATURE:
<223> OTHER INFORMATION: primer

<400> SEQUENCE: 490
ctgaagcaat cacaaattga actaaagga                              29

<210> SEQ ID NO 491
<211> LENGTH: 16
<212> TYPE: DNA
<213> ORGANISM: Artificial sequence
<220> FEATURE:
<223> OTHER INFORMATION: probe

<400> SEQUENCE: 491
aacttctcac attgcc                                            16

<210> SEQ ID NO 492
<211> LENGTH: 16
<212> TYPE: DNA
<213> ORGANISM: Artificial sequence
<220> FEATURE:
<223> OTHER INFORMATION: probe

<400> SEQUENCE: 492
aacttctcgc attgcc                                            16

<210> SEQ ID NO 493
<211> LENGTH: 34
<212> TYPE: DNA
<213> ORGANISM: Artificial sequence
<220> FEATURE:
<223> OTHER INFORMATION: primer

<400> SEQUENCE: 493
ttttctcaca aagatcatgt actcattact tctt                        34

<210> SEQ ID NO 494
<211> LENGTH: 23
<212> TYPE: DNA
<213> ORGANISM: Artificial sequence
<220> FEATURE:
<223> OTHER INFORMATION: primer

<400> SEQUENCE: 494
aagcttgcaa gccaaaagag atg                                    23

<210> SEQ ID NO 495
<211> LENGTH: 14
<212> TYPE: DNA
<213> ORGANISM: Artificial sequence
<220> FEATURE:
<223> OTHER INFORMATION: probe

<400> SEQUENCE: 495
cgcaacacaa gatt                                              14
```

<210> SEQ ID NO 496
<211> LENGTH: 16
<212> TYPE: DNA
<213> ORGANISM: Artificial sequence
<220> FEATURE:
<223> OTHER INFORMATION: probe

<400> SEQUENCE: 496
accgcaacat aagatt                                                     16

<210> SEQ ID NO 497
<211> LENGTH: 25
<212> TYPE: DNA
<213> ORGANISM: Artificial sequence
<220> FEATURE:
<223> OTHER INFORMATION: primer

<400> SEQUENCE: 497
ctccttctag agtctgggaa tcgaa                                           25

<210> SEQ ID NO 498
<211> LENGTH: 25
<212> TYPE: DNA
<213> ORGANISM: Artificial sequence
<220> FEATURE:
<223> OTHER INFORMATION: primer

<400> SEQUENCE: 498
gcagaaaatt tggaccccca ttaaa                                           25

<210> SEQ ID NO 499
<211> LENGTH: 16
<212> TYPE: DNA
<213> ORGANISM: Artificial sequence
<220> FEATURE:
<223> OTHER INFORMATION: probe

<400> SEQUENCE: 499
tttgcgtcat taaaat                                                     16

<210> SEQ ID NO 500
<211> LENGTH: 16
<212> TYPE: DNA
<213> ORGANISM: Artificial sequence
<220> FEATURE:
<223> OTHER INFORMATION: probe

<400> SEQUENCE: 500
tttgcgtcaa taaaat                                                     16

<210> SEQ ID NO 501
<211> LENGTH: 27
<212> TYPE: DNA
<213> ORGANISM: Artificial sequence
<220> FEATURE:
<223> OTHER INFORMATION: primer

<400> SEQUENCE: 501
aagttcatct acacttaatc cgacaca                                         27

<210> SEQ ID NO 502
<211> LENGTH: 25
<212> TYPE: DNA
<213> ORGANISM: Artificial sequence
<220> FEATURE:

```
<223> OTHER INFORMATION: primer

<400> SEQUENCE: 502
gagttcattc cacagatctg accat                                          25

<210> SEQ ID NO 503
<211> LENGTH: 17
<212> TYPE: DNA
<213> ORGANISM: Artificial sequence
<220> FEATURE:
<223> OTHER INFORMATION: probe

<400> SEQUENCE: 503
cctatcaaag cacgtct                                                   17

<210> SEQ ID NO 504
<211> LENGTH: 16
<212> TYPE: DNA
<213> ORGANISM: Artificial sequence
<220> FEATURE:
<223> OTHER INFORMATION: probe

<400> SEQUENCE: 504
ctatcaaagc aagtct                                                    16

<210> SEQ ID NO 505
<211> LENGTH: 24
<212> TYPE: DNA
<213> ORGANISM: Artificial sequence
<220> FEATURE:
<223> OTHER INFORMATION: primer

<400> SEQUENCE: 505
cgatcgagag aaacttcgag actt                                           24

<210> SEQ ID NO 506
<211> LENGTH: 32
<212> TYPE: DNA
<213> ORGANISM: Artificial sequence
<220> FEATURE:
<223> OTHER INFORMATION: primer

<400> SEQUENCE: 506
ccgataaaac aatcaacacc aaaaacaatt aa                                  32

<210> SEQ ID NO 507
<211> LENGTH: 16
<212> TYPE: DNA
<213> ORGANISM: Artificial sequence
<220> FEATURE:
<223> OTHER INFORMATION: probe

<400> SEQUENCE: 507
cccaacaaaa gaggca                                                    16

<210> SEQ ID NO 508
<211> LENGTH: 16
<212> TYPE: DNA
<213> ORGANISM: Artificial sequence
<220> FEATURE:
<223> OTHER INFORMATION: probe

<400> SEQUENCE: 508
cccaacaaag gaggca                                                    16
```

```
<210> SEQ ID NO 509
<211> LENGTH: 45
<212> TYPE: DNA
<213> ORGANISM: Artificial sequence
<220> FEATURE:
<223> OTHER INFORMATION: primer

<400> SEQUENCE: 509
agtagaatac ttaatgttta taatcacgag atataattgt tttca          45

<210> SEQ ID NO 510
<211> LENGTH: 25
<212> TYPE: DNA
<213> ORGANISM: Artificial sequence
<220> FEATURE:
<223> OTHER INFORMATION: primer

<400> SEQUENCE: 510
cctggtggcc atgtataata tcaca                                25

<210> SEQ ID NO 511
<211> LENGTH: 15
<212> TYPE: DNA
<213> ORGANISM: Artificial sequence
<220> FEATURE:
<223> OTHER INFORMATION: probe

<400> SEQUENCE: 511
atccccacat gatgc                                           15

<210> SEQ ID NO 512
<211> LENGTH: 16
<212> TYPE: DNA
<213> ORGANISM: Artificial sequence
<220> FEATURE:
<223> OTHER INFORMATION: probe

<400> SEQUENCE: 512
catccccaaa tgatgc                                          16

<210> SEQ ID NO 513
<211> LENGTH: 20
<212> TYPE: DNA
<213> ORGANISM: Artificial sequence
<220> FEATURE:
<223> OTHER INFORMATION: primer

<400> SEQUENCE: 513
tagagaccaa ggcccaacag                                      20

<210> SEQ ID NO 514
<211> LENGTH: 20
<212> TYPE: DNA
<213> ORGANISM: Artificial sequence
<220> FEATURE:
<223> OTHER INFORMATION: primer

<400> SEQUENCE: 514
ttatttgtgt ggtgcggttc                                      20

<210> SEQ ID NO 515
<211> LENGTH: 16
<212> TYPE: DNA
<213> ORGANISM: Artificial sequence
<220> FEATURE:
<223> OTHER INFORMATION: probe
```

```
<400> SEQUENCE: 515
tccacaacta gcaacc                                              16

<210> SEQ ID NO 516
<211> LENGTH: 14
<212> TYPE: DNA
<213> ORGANISM: Artificial sequence
<220> FEATURE:
<223> OTHER INFORMATION: probe

<400> SEQUENCE: 516
ccaccactag caac                                                14

<210> SEQ ID NO 517
<211> LENGTH: 29
<212> TYPE: DNA
<213> ORGANISM: Artificial sequence
<220> FEATURE:
<223> OTHER INFORMATION: primer

<400> SEQUENCE: 517
ctgagtaatt atagtattgt gccaaccct                                29

<210> SEQ ID NO 518
<211> LENGTH: 23
<212> TYPE: DNA
<213> ORGANISM: Artificial sequence
<220> FEATURE:
<223> OTHER INFORMATION: primer

<400> SEQUENCE: 518
gggcttttgt ttgacttgtg caa                                      23

<210> SEQ ID NO 519
<211> LENGTH: 18
<212> TYPE: DNA
<213> ORGANISM: Artificial sequence
<220> FEATURE:
<223> OTHER INFORMATION: probe

<400> SEQUENCE: 519
caaagaagtc cgtctaac                                            18

<210> SEQ ID NO 520
<211> LENGTH: 18
<212> TYPE: DNA
<213> ORGANISM: Artificial sequence
<220> FEATURE:
<223> OTHER INFORMATION: probe

<400> SEQUENCE: 520
caaagaagtc ggtctaac                                            18

<210> SEQ ID NO 521
<211> LENGTH: 27
<212> TYPE: DNA
<213> ORGANISM: Artificial sequence
<220> FEATURE:
<223> OTHER INFORMATION: primer

<400> SEQUENCE: 521
gcatcaacca tcaatctgaa tggtatg                                  27

<210> SEQ ID NO 522
<211> LENGTH: 25
```

```
<212> TYPE: DNA
<213> ORGANISM: Artificial sequence
<220> FEATURE:
<223> OTHER INFORMATION: primer

<400> SEQUENCE: 522
ggcatcctac tgacctgtat gttaa                                      25

<210> SEQ ID NO 523
<211> LENGTH: 18
<212> TYPE: DNA
<213> ORGANISM: Artificial sequence
<220> FEATURE:
<223> OTHER INFORMATION: probe

<400> SEQUENCE: 523
atttgcaaaa atttctct                                              18

<210> SEQ ID NO 524
<211> LENGTH: 19
<212> TYPE: DNA
<213> ORGANISM: Artificial sequence
<220> FEATURE:
<223> OTHER INFORMATION: probe

<400> SEQUENCE: 524
aatttgcaaa aagttctct                                             19

<210> SEQ ID NO 525
<211> LENGTH: 26
<212> TYPE: DNA
<213> ORGANISM: Artificial sequence
<220> FEATURE:
<223> OTHER INFORMATION: primer

<400> SEQUENCE: 525
gtcccatgca ttgtatttga agttga                                     26

<210> SEQ ID NO 526
<211> LENGTH: 31
<212> TYPE: DNA
<213> ORGANISM: Artificial sequence
<220> FEATURE:
<223> OTHER INFORMATION: primer

<400> SEQUENCE: 526
tgcatacata tgatcatcaa atttcccaat g                               31

<210> SEQ ID NO 527
<211> LENGTH: 17
<212> TYPE: DNA
<213> ORGANISM: Artificial sequence
<220> FEATURE:
<223> OTHER INFORMATION: probe

<400> SEQUENCE: 527
ctagatgcac acttcta                                               17

<210> SEQ ID NO 528
<211> LENGTH: 17
<212> TYPE: DNA
<213> ORGANISM: Artificial sequence
<220> FEATURE:
<223> OTHER INFORMATION: probe

<400> SEQUENCE: 528
```
ctagatgcac gcttcta                             17

<210> SEQ ID NO 529
<211> LENGTH: 26
<212> TYPE: DNA
<213> ORGANISM: Artificial sequence
<220> FEATURE:
<223> OTHER INFORMATION: primer

<400> SEQUENCE: 529
atcataatgt catgactgcc tggttt                   26

<210> SEQ ID NO 530
<211> LENGTH: 27
<212> TYPE: DNA
<213> ORGANISM: Artificial sequence
<220> FEATURE:
<223> OTHER INFORMATION: primer

<400> SEQUENCE: 530
tcttaaaaac caactacaca catcgtt                  27

<210> SEQ ID NO 531
<211> LENGTH: 18
<212> TYPE: DNA
<213> ORGANISM: Artificial sequence
<220> FEATURE:
<223> OTHER INFORMATION: probe

<400> SEQUENCE: 531
tcccatatgt gtatcatg                            18

<210> SEQ ID NO 532
<211> LENGTH: 20
<212> TYPE: DNA
<213> ORGANISM: Artificial sequence
<220> FEATURE:
<223> OTHER INFORMATION: probe

<400> SEQUENCE: 532
catcccatat gtttatcatg                          20

<210> SEQ ID NO 533
<211> LENGTH: 23
<212> TYPE: DNA
<213> ORGANISM: Artificial sequence
<220> FEATURE:
<223> OTHER INFORMATION: primer

<400> SEQUENCE: 533
gttcgacctg gaatatcgga aga                      23

<210> SEQ ID NO 534
<211> LENGTH: 22
<212> TYPE: DNA
<213> ORGANISM: Artificial sequence
<220> FEATURE:
<223> OTHER INFORMATION: primer

<400> SEQUENCE: 534
cacttgcacg atatcgcgaa tc                       22

<210> SEQ ID NO 535
<211> LENGTH: 20
<212> TYPE: DNA
<213> ORGANISM: Artificial sequence

```
<220> FEATURE:
<223> OTHER INFORMATION: probe

<400> SEQUENCE: 535
tagatgactt atcggaaagt                                               20

<210> SEQ ID NO 536
<211> LENGTH: 21
<212> TYPE: DNA
<213> ORGANISM: Artificial sequence
<220> FEATURE:
<223> OTHER INFORMATION: probe

<400> SEQUENCE: 536
atagatgact tatcagaaag t                                             21

<210> SEQ ID NO 537
<211> LENGTH: 23
<212> TYPE: DNA
<213> ORGANISM: Artificial sequence
<220> FEATURE:
<223> OTHER INFORMATION: primer

<400> SEQUENCE: 537
gatcaatgta cacgcgtcaa gac                                           23

<210> SEQ ID NO 538
<211> LENGTH: 21
<212> TYPE: DNA
<213> ORGANISM: Artificial sequence
<220> FEATURE:
<223> OTHER INFORMATION: primer

<400> SEQUENCE: 538
ggagttccat cacgcctctt c                                             21

<210> SEQ ID NO 539
<211> LENGTH: 17
<212> TYPE: DNA
<213> ORGANISM: Artificial sequence
<220> FEATURE:
<223> OTHER INFORMATION: probe

<400> SEQUENCE: 539
aagaatgttg aaaccgc                                                  17

<210> SEQ ID NO 540
<211> LENGTH: 17
<212> TYPE: DNA
<213> ORGANISM: Artificial sequence
<220> FEATURE:
<223> OTHER INFORMATION: probe

<400> SEQUENCE: 540
aagaatgttg gaaccgc                                                  17

<210> SEQ ID NO 541
<211> LENGTH: 32
<212> TYPE: DNA
<213> ORGANISM: Artificial sequence
<220> FEATURE:
<223> OTHER INFORMATION: primer

<400> SEQUENCE: 541
caataaaaca aaaacaataa tctgacgcac at                                 32
```

<210> SEQ ID NO 542
<211> LENGTH: 25
<212> TYPE: DNA
<213> ORGANISM: Artificial sequence
<220> FEATURE:
<223> OTHER INFORMATION: primer

<400> SEQUENCE: 542
gagtctcaga ttgatagccc caatt                                          25

<210> SEQ ID NO 543
<211> LENGTH: 20
<212> TYPE: DNA
<213> ORGANISM: Artificial sequence
<220> FEATURE:
<223> OTHER INFORMATION: probe

<400> SEQUENCE: 543
cttcatagtt tgataagttc                                                20

<210> SEQ ID NO 544
<211> LENGTH: 19
<212> TYPE: DNA
<213> ORGANISM: Artificial sequence
<220> FEATURE:
<223> OTHER INFORMATION: probe

<400> SEQUENCE: 544
ttcatagttt ggtaagttc                                                 19

<210> SEQ ID NO 545
<211> LENGTH: 25
<212> TYPE: DNA
<213> ORGANISM: Artificial sequence
<220> FEATURE:
<223> OTHER INFORMATION: primer

<400> SEQUENCE: 545
agcctggtgc gtatgtatca taaaa                                          25

<210> SEQ ID NO 546
<211> LENGTH: 34
<212> TYPE: DNA
<213> ORGANISM: Artificial sequence
<220> FEATURE:
<223> OTHER INFORMATION: primer

<400> SEQUENCE: 546
atcgaaagat gcatagagta atgattaata acca                                34

<210> SEQ ID NO 547
<211> LENGTH: 19
<212> TYPE: DNA
<213> ORGANISM: Artificial sequence
<220> FEATURE:
<223> OTHER INFORMATION: probe

<400> SEQUENCE: 547
ctaaaactgt ggtggttta                                                 19

<210> SEQ ID NO 548
<211> LENGTH: 21
<212> TYPE: DNA
<213> ORGANISM: Artificial sequence
<220> FEATURE:
<223> OTHER INFORMATION: probe

```
<400> SEQUENCE: 548
ctctaaaact gtgatggttt a                                          21

<210> SEQ ID NO 549
<211> LENGTH: 25
<212> TYPE: DNA
<213> ORGANISM: Artificial sequence
<220> FEATURE:
<223> OTHER INFORMATION: primer

<400> SEQUENCE: 549
cttcccggaa aaggtatcga ttgta                                      25

<210> SEQ ID NO 550
<211> LENGTH: 25
<212> TYPE: DNA
<213> ORGANISM: Artificial sequence
<220> FEATURE:
<223> OTHER INFORMATION: primer

<400> SEQUENCE: 550
acgcttcaaa ccctaaagac agaat                                      25

<210> SEQ ID NO 551
<211> LENGTH: 20
<212> TYPE: DNA
<213> ORGANISM: Artificial sequence
<220> FEATURE:
<223> OTHER INFORMATION: probe

<400> SEQUENCE: 551
atttcatctt gattctattg                                            20

<210> SEQ ID NO 552
<211> LENGTH: 20
<212> TYPE: DNA
<213> ORGANISM: Artificial sequence
<220> FEATURE:
<223> OTHER INFORMATION: probe

<400> SEQUENCE: 552
atttcatctt gagtctattg                                            20

<210> SEQ ID NO 553
<211> LENGTH: 25
<212> TYPE: DNA
<213> ORGANISM: Artificial sequence
<220> FEATURE:
<223> OTHER INFORMATION: primer

<400> SEQUENCE: 553
ccaggatcga tttgagatga aagct                                      25

<210> SEQ ID NO 554
<211> LENGTH: 29
<212> TYPE: DNA
<213> ORGANISM: Artificial sequence
<220> FEATURE:
<223> OTHER INFORMATION: primer

<400> SEQUENCE: 554
tcaacagtca acttttgaac aaaaaaggt                                  29

<210> SEQ ID NO 555
```

```
<211> LENGTH: 18
<212> TYPE: DNA
<213> ORGANISM: Artificial sequence
<220> FEATURE:
<223> OTHER INFORMATION: probe

<400> SEQUENCE: 555
atatagctag gcaattca                                                       18

<210> SEQ ID NO 556
<211> LENGTH: 21
<212> TYPE: DNA
<213> ORGANISM: Artificial sequence
<220> FEATURE:
<223> OTHER INFORMATION: probe

<400> SEQUENCE: 556
aggatatagc tagacaattc a                                                   21

<210> SEQ ID NO 557
<211> LENGTH: 30
<212> TYPE: DNA
<213> ORGANISM: Artificial sequence
<220> FEATURE:
<223> OTHER INFORMATION: primer

<400> SEQUENCE: 557
cggtaaacca gtacaaaata tccaaatgtt                                          30

<210> SEQ ID NO 558
<211> LENGTH: 37
<212> TYPE: DNA
<213> ORGANISM: Artificial sequence
<220> FEATURE:
<223> OTHER INFORMATION: primer

<400> SEQUENCE: 558
cggatttaaa atagtttgaa gataaataat ggcttgt                                  37

<210> SEQ ID NO 559
<211> LENGTH: 16
<212> TYPE: DNA
<213> ORGANISM: Artificial sequence
<220> FEATURE:
<223> OTHER INFORMATION: probe

<400> SEQUENCE: 559
acttgtgcta atctct                                                         16

<210> SEQ ID NO 560
<211> LENGTH: 15
<212> TYPE: DNA
<213> ORGANISM: Artificial sequence
<220> FEATURE:
<223> OTHER INFORMATION: probe

<400> SEQUENCE: 560
cttgtgcaaa tctct                                                          15

<210> SEQ ID NO 561
<211> LENGTH: 20
<212> TYPE: DNA
<213> ORGANISM: Artificial sequence
<220> FEATURE:
<223> OTHER INFORMATION: primer

<400> SEQUENCE: 561
```
cccagtaccc aatgctcatc                                           20

<210> SEQ ID NO 562
<211> LENGTH: 21
<212> TYPE: DNA
<213> ORGANISM: Artificial sequence
<220> FEATURE:
<223> OTHER INFORMATION: primer

<400> SEQUENCE: 562
ccgtcggtta tacacaccaa g                                         21

<210> SEQ ID NO 563
<211> LENGTH: 17
<212> TYPE: DNA
<213> ORGANISM: Artificial sequence
<220> FEATURE:
<223> OTHER INFORMATION: probe

<400> SEQUENCE: 563
aactgccttt gttttgt                                              17

<210> SEQ ID NO 564
<211> LENGTH: 15
<212> TYPE: DNA
<213> ORGANISM: Artificial sequence
<220> FEATURE:
<223> OTHER INFORMATION: probe

<400> SEQUENCE: 564
ctgcctgtgt tttgt                                                15

<210> SEQ ID NO 565
<211> LENGTH: 25
<212> TYPE: DNA
<213> ORGANISM: Artificial sequence
<220> FEATURE:
<223> OTHER INFORMATION: primer

<400> SEQUENCE: 565
gctttgccta agagattgct tcatg                                     25

<210> SEQ ID NO 566
<211> LENGTH: 23
<212> TYPE: DNA
<213> ORGANISM: Artificial sequence
<220> FEATURE:
<223> OTHER INFORMATION: primer

<400> SEQUENCE: 566
tgcttgtgct tgtagtcatc tga                                       23

<210> SEQ ID NO 567
<211> LENGTH: 16
<212> TYPE: DNA
<213> ORGANISM: Artificial sequence
<220> FEATURE:
<223> OTHER INFORMATION: probe

<400> SEQUENCE: 567
ttgaacgaaa attagc                                               16

<210> SEQ ID NO 568
<211> LENGTH: 16
<212> TYPE: DNA

```
<213> ORGANISM: Artificial sequence
<220> FEATURE:
<223> OTHER INFORMATION: probe

<400> SEQUENCE: 568
ttgaacgaag attagc                                                        16

<210> SEQ ID NO 569
<211> LENGTH: 27
<212> TYPE: DNA
<213> ORGANISM: Artificial sequence
<220> FEATURE:
<223> OTHER INFORMATION: primer

<400> SEQUENCE: 569
ggatttgtta taccattgca tcaagca                                             27

<210> SEQ ID NO 570
<211> LENGTH: 20
<212> TYPE: DNA
<213> ORGANISM: Artificial sequence
<220> FEATURE:
<223> OTHER INFORMATION: primer

<400> SEQUENCE: 570
acagagggtc gttggacaac                                                    20

<210> SEQ ID NO 571
<211> LENGTH: 16
<212> TYPE: DNA
<213> ORGANISM: Artificial sequence
<220> FEATURE:
<223> OTHER INFORMATION: probe

<400> SEQUENCE: 571
acacttctca aaggct                                                        16

<210> SEQ ID NO 572
<211> LENGTH: 17
<212> TYPE: DNA
<213> ORGANISM: Artificial sequence
<220> FEATURE:
<223> OTHER INFORMATION: probe

<400> SEQUENCE: 572
cacacttctc aatggct                                                       17

<210> SEQ ID NO 573
<211> LENGTH: 28
<212> TYPE: DNA
<213> ORGANISM: Artificial sequence
<220> FEATURE:
<223> OTHER INFORMATION: primer

<400> SEQUENCE: 573
ctagtttctt tccttgtact tccttcca                                           28

<210> SEQ ID NO 574
<211> LENGTH: 30
<212> TYPE: DNA
<213> ORGANISM: Artificial sequence
<220> FEATURE:
<223> OTHER INFORMATION: primer

<400> SEQUENCE: 574
gctttcctat ttttatcgga aattgacagt                                         30
```

<210> SEQ ID NO 575
<211> LENGTH: 19
<212> TYPE: DNA
<213> ORGANISM: Artificial sequence
<220> FEATURE:
<223> OTHER INFORMATION: probe

<400> SEQUENCE: 575
tgacaaggaa ctaagttta                                        19

<210> SEQ ID NO 576
<211> LENGTH: 19
<212> TYPE: DNA
<213> ORGANISM: Artificial sequence
<220> FEATURE:
<223> OTHER INFORMATION: probe

<400> SEQUENCE: 576
tgacaaggaa caaagttta                                        19

<210> SEQ ID NO 577
<211> LENGTH: 27
<212> TYPE: DNA
<213> ORGANISM: Artificial sequence
<220> FEATURE:
<223> OTHER INFORMATION: primer

<400> SEQUENCE: 577
agaataaaca gctttctaca cccgtag                               27

<210> SEQ ID NO 578
<211> LENGTH: 24
<212> TYPE: DNA
<213> ORGANISM: Artificial sequence
<220> FEATURE:
<223> OTHER INFORMATION: primer

<400> SEQUENCE: 578
tctggtggga taaggtgatt gaga                                  24

<210> SEQ ID NO 579
<211> LENGTH: 17
<212> TYPE: DNA
<213> ORGANISM: Artificial sequence
<220> FEATURE:
<223> OTHER INFORMATION: probe

<400> SEQUENCE: 579
caccaagact gagacac                                          17

<210> SEQ ID NO 580
<211> LENGTH: 18
<212> TYPE: DNA
<213> ORGANISM: Artificial sequence
<220> FEATURE:
<223> OTHER INFORMATION: probe

<400> SEQUENCE: 580
tcaccaagac taagacac                                         18

<210> SEQ ID NO 581
<211> LENGTH: 22
<212> TYPE: DNA
<213> ORGANISM: Artificial sequence
<220> FEATURE:

<223> OTHER INFORMATION: primer

<400> SEQUENCE: 581
ggcatcgtct ggttgatcaa ga                                    22

<210> SEQ ID NO 582
<211> LENGTH: 25
<212> TYPE: DNA
<213> ORGANISM: Artificial sequence
<220> FEATURE:
<223> OTHER INFORMATION: primer

<400> SEQUENCE: 582
cccattccac ttgataaccc gattt                                 25

<210> SEQ ID NO 583
<211> LENGTH: 19
<212> TYPE: DNA
<213> ORGANISM: Artificial sequence
<220> FEATURE:
<223> OTHER INFORMATION: probe

<400> SEQUENCE: 583
catgacattt tgccattaa                                        19

<210> SEQ ID NO 584
<211> LENGTH: 21
<212> TYPE: DNA
<213> ORGANISM: Artificial sequence
<220> FEATURE:
<223> OTHER INFORMATION: probe

<400> SEQUENCE: 584
tgcatgacat tttaccatta a                                     21

<210> SEQ ID NO 585
<211> LENGTH: 25
<212> TYPE: DNA
<213> ORGANISM: Artificial sequence
<220> FEATURE:
<223> OTHER INFORMATION: primer

<400> SEQUENCE: 585
catagacctc cacatcacca agaaa                                 25

<210> SEQ ID NO 586
<211> LENGTH: 30
<212> TYPE: DNA
<213> ORGANISM: Artificial sequence
<220> FEATURE:
<223> OTHER INFORMATION: primer

<400> SEQUENCE: 586
tgtaaagcaa aaacccaaac acaataaagt                            30

<210> SEQ ID NO 587
<211> LENGTH: 17
<212> TYPE: DNA
<213> ORGANISM: Artificial sequence
<220> FEATURE:
<223> OTHER INFORMATION: probe

<400> SEQUENCE: 587
agggagacac gtgtcat                                          17

```
<210> SEQ ID NO 588
<211> LENGTH: 18
<212> TYPE: DNA
<213> ORGANISM: Artificial sequence
<220> FEATURE:
<223> OTHER INFORMATION: probe

<400> SEQUENCE: 588
aagggagaca catgtcat                                            18

<210> SEQ ID NO 589
<211> LENGTH: 30
<212> TYPE: DNA
<213> ORGANISM: Artificial sequence
<220> FEATURE:
<223> OTHER INFORMATION: primer

<400> SEQUENCE: 589
agcacacaaa ggtttcttag gaagattatt                               30

<210> SEQ ID NO 590
<211> LENGTH: 27
<212> TYPE: DNA
<213> ORGANISM: Artificial sequence
<220> FEATURE:
<223> OTHER INFORMATION: primer

<400> SEQUENCE: 590
ggttcaaatg tttaggacac gaaagac                                  27

<210> SEQ ID NO 591
<211> LENGTH: 16
<212> TYPE: DNA
<213> ORGANISM: Artificial sequence
<220> FEATURE:
<223> OTHER INFORMATION: probe

<400> SEQUENCE: 591
cccgaatgcc cagacc                                              16

<210> SEQ ID NO 592
<211> LENGTH: 15
<212> TYPE: DNA
<213> ORGANISM: Artificial sequence
<220> FEATURE:
<223> OTHER INFORMATION: probe

<400> SEQUENCE: 592
ccgaatgcgc agacc                                               15

<210> SEQ ID NO 593
<211> LENGTH: 29
<212> TYPE: DNA
<213> ORGANISM: Artificial sequence
<220> FEATURE:
<223> OTHER INFORMATION: primer

<400> SEQUENCE: 593
atctattccc agagaatacg tttttttcga                               29

<210> SEQ ID NO 594
<211> LENGTH: 25
<212> TYPE: DNA
<213> ORGANISM: Artificial sequence
<220> FEATURE:
<223> OTHER INFORMATION: primer
```

```
<400> SEQUENCE: 594 gccctagtg aaagaatga ggtaa                                         25

<210> SEQ ID NO 595
<211> LENGTH: 16
<212> TYPE: DNA
<213> ORGANISM: Artificial sequence
<220> FEATURE:
<223> OTHER INFORMATION: probe

<400> SEQUENCE: 595
tcagagacca ggaatt                                                 16

<210> SEQ ID NO 596
<211> LENGTH: 16
<212> TYPE: DNA
<213> ORGANISM: Artificial sequence
<220> FEATURE:
<223> OTHER INFORMATION: probe

<400> SEQUENCE: 596
tcagagacga ggaatt                                                 16

<210> SEQ ID NO 597
<211> LENGTH: 24
<212> TYPE: DNA
<213> ORGANISM: Artificial sequence
<220> FEATURE:
<223> OTHER INFORMATION: primer

<400> SEQUENCE: 597
acctccattc atcattccca atcc                                        24

<210> SEQ ID NO 598
<211> LENGTH: 24
<212> TYPE: DNA
<213> ORGANISM: Artificial sequence
<220> FEATURE:
<223> OTHER INFORMATION: primer

<400> SEQUENCE: 598
gctcggctaa gaatcacact gaaa                                        24

<210> SEQ ID NO 599
<211> LENGTH: 17
<212> TYPE: DNA
<213> ORGANISM: Artificial sequence
<220> FEATURE:
<223> OTHER INFORMATION: probe

<400> SEQUENCE: 599
caacaccaag ttcttac                                                17

<210> SEQ ID NO 600
<211> LENGTH: 17
<212> TYPE: DNA
<213> ORGANISM: Artificial sequence
<220> FEATURE:
<223> OTHER INFORMATION: probe

<400> SEQUENCE: 600
caacaccaag atcttac                                                17

<210> SEQ ID NO 601
<211> LENGTH: 17
```

```
<212> TYPE: DNA
<213> ORGANISM: Artificial sequence
<220> FEATURE:
<223> OTHER INFORMATION: primer

<400> SEQUENCE: 601
ccgcttttgc ccatggc                                               17

<210> SEQ ID NO 602
<211> LENGTH: 30
<212> TYPE: DNA
<213> ORGANISM: Artificial sequence
<220> FEATURE:
<223> OTHER INFORMATION: primer

<400> SEQUENCE: 602
actaccaacg ttaagaatac acttggattt                                 30

<210> SEQ ID NO 603
<211> LENGTH: 19
<212> TYPE: DNA
<213> ORGANISM: Artificial sequence
<220> FEATURE:
<223> OTHER INFORMATION: probe

<400> SEQUENCE: 603
attgcattca gttgttgaa                                             19

<210> SEQ ID NO 604
<211> LENGTH: 19
<212> TYPE: DNA
<213> ORGANISM: Artificial sequence
<220> FEATURE:
<223> OTHER INFORMATION: probe

<400> SEQUENCE: 604
attgcattca gtagttgaa                                             19

<210> SEQ ID NO 605
<211> LENGTH: 26
<212> TYPE: DNA
<213> ORGANISM: Artificial sequence
<220> FEATURE:
<223> OTHER INFORMATION: primer

<400> SEQUENCE: 605
gaacaacagt ttgccatttc cttact                                     26

<210> SEQ ID NO 606
<211> LENGTH: 28
<212> TYPE: DNA
<213> ORGANISM: Artificial sequence
<220> FEATURE:
<223> OTHER INFORMATION: primer

<400> SEQUENCE: 606
ggcatccatt acctatcaat ttcttgga                                   28

<210> SEQ ID NO 607
<211> LENGTH: 16
<212> TYPE: DNA
<213> ORGANISM: Artificial sequence
<220> FEATURE:
<223> OTHER INFORMATION: probe

<400> SEQUENCE: 607
```
cgtaaaagcg aaagta                                                  16

<210> SEQ ID NO 608
<211> LENGTH: 17
<212> TYPE: DNA
<213> ORGANISM: Artificial sequence
<220> FEATURE:
<223> OTHER INFORMATION: probe

<400> SEQUENCE: 608
ccgtaaaagg gaaagta                                                 17

<210> SEQ ID NO 609
<211> LENGTH: 30
<212> TYPE: DNA
<213> ORGANISM: Artificial sequence
<220> FEATURE:
<223> OTHER INFORMATION: primer

<400> SEQUENCE: 609
agcgaaaaga ttacactttg tttctttgaa                                   30

<210> SEQ ID NO 610
<211> LENGTH: 30
<212> TYPE: DNA
<213> ORGANISM: Artificial sequence
<220> FEATURE:
<223> OTHER INFORMATION: primer

<400> SEQUENCE: 610
gccttagtat actctagttt cattgccaaa                                   30

<210> SEQ ID NO 611
<211> LENGTH: 20
<212> TYPE: DNA
<213> ORGANISM: Artificial sequence
<220> FEATURE:
<223> OTHER INFORMATION: probe

<400> SEQUENCE: 611
ttttggtttt tctggtttat                                              20

<210> SEQ ID NO 612
<211> LENGTH: 18
<212> TYPE: DNA
<213> ORGANISM: Artificial sequence
<220> FEATURE:
<223> OTHER INFORMATION: probe

<400> SEQUENCE: 612
ttggtttttc gggtttat                                                18

<210> SEQ ID NO 613
<211> LENGTH: 26
<212> TYPE: DNA
<213> ORGANISM: Artificial sequence
<220> FEATURE:
<223> OTHER INFORMATION: primer

<400> SEQUENCE: 613
ctccagttgc aacttcttca aatcat                                       26

<210> SEQ ID NO 614
<211> LENGTH: 25
<212> TYPE: DNA
<213> ORGANISM: Artificial sequence

```
<220> FEATURE:
<223> OTHER INFORMATION: primer

<400> SEQUENCE: 614
gatgacccat agaccaaagc catat                                           25

<210> SEQ ID NO 615
<211> LENGTH: 20
<212> TYPE: DNA
<213> ORGANISM: Artificial sequence
<220> FEATURE:
<223> OTHER INFORMATION: probe

<400> SEQUENCE: 615
tgtttaatga aacgctattg                                                 20

<210> SEQ ID NO 616
<211> LENGTH: 22
<212> TYPE: DNA
<213> ORGANISM: Artificial sequence
<220> FEATURE:
<223> OTHER INFORMATION: probe

<400> SEQUENCE: 616
catgtttaat gaaatgctat tg                                              22

<210> SEQ ID NO 617
<211> LENGTH: 23
<212> TYPE: DNA
<213> ORGANISM: Artificial sequence
<220> FEATURE:
<223> OTHER INFORMATION: primer

<400> SEQUENCE: 617
caaatgacta acctgcgcaa gtg                                             23

<210> SEQ ID NO 618
<211> LENGTH: 24
<212> TYPE: DNA
<213> ORGANISM: Artificial sequence
<220> FEATURE:
<223> OTHER INFORMATION: primer

<400> SEQUENCE: 618
agtcaaggga gtgggaaagt agat                                            24

<210> SEQ ID NO 619
<211> LENGTH: 15
<212> TYPE: DNA
<213> ORGANISM: Artificial sequence
<220> FEATURE:
<223> OTHER INFORMATION: probe

<400> SEQUENCE: 619
ccggttggtt cgaca                                                      15

<210> SEQ ID NO 620
<211> LENGTH: 16
<212> TYPE: DNA
<213> ORGANISM: Artificial sequence
<220> FEATURE:
<223> OTHER INFORMATION: probe

<400> SEQUENCE: 620
cccggttgat tcgaca                                                     16
```

<210> SEQ ID NO 621
<211> LENGTH: 25
<212> TYPE: DNA
<213> ORGANISM: Artificial sequence
<220> FEATURE:
<223> OTHER INFORMATION: primer

<400> SEQUENCE: 621
accaggaagg aggtcaagat cttaa                                    25

<210> SEQ ID NO 622
<211> LENGTH: 31
<212> TYPE: DNA
<213> ORGANISM: Artificial sequence
<220> FEATURE:
<223> OTHER INFORMATION: primer

<400> SEQUENCE: 622
agcatcgact ttctacatta tgttctcttt t                             31

<210> SEQ ID NO 623
<211> LENGTH: 17
<212> TYPE: DNA
<213> ORGANISM: Artificial sequence
<220> FEATURE:
<223> OTHER INFORMATION: probe

<400> SEQUENCE: 623
aatgctccat taacaaa                                             17

<210> SEQ ID NO 624
<211> LENGTH: 16
<212> TYPE: DNA
<213> ORGANISM: Artificial sequence
<220> FEATURE:
<223> OTHER INFORMATION: probe

<400> SEQUENCE: 624
atgctccgtt aacaaa                                              16

<210> SEQ ID NO 625
<211> LENGTH: 33
<212> TYPE: DNA
<213> ORGANISM: Artificial sequence
<220> FEATURE:
<223> OTHER INFORMATION: primer

<400> SEQUENCE: 625
cgcttacatc attattcatt ttttagacac act                           33

<210> SEQ ID NO 626
<211> LENGTH: 21
<212> TYPE: DNA
<213> ORGANISM: Artificial sequence
<220> FEATURE:
<223> OTHER INFORMATION: primer

<400> SEQUENCE: 626
ggtagttgcg acaagcacat c                                        21

<210> SEQ ID NO 627
<211> LENGTH: 19
<212> TYPE: DNA
<213> ORGANISM: Artificial sequence
<220> FEATURE:
<223> OTHER INFORMATION: probe

```
<400> SEQUENCE: 627
caccattatc gatgtttaa                                                  19

<210> SEQ ID NO 628
<211> LENGTH: 18
<212> TYPE: DNA
<213> ORGANISM: Artificial sequence
<220> FEATURE:
<223> OTHER INFORMATION: probe

<400> SEQUENCE: 628
accattatcg gtgtttaa                                                   18

<210> SEQ ID NO 629
<211> LENGTH: 23
<212> TYPE: DNA
<213> ORGANISM: Artificial sequence
<220> FEATURE:
<223> OTHER INFORMATION: primer

<400> SEQUENCE: 629
tgctccactg tctcttcaga aac                                             23

<210> SEQ ID NO 630
<211> LENGTH: 25
<212> TYPE: DNA
<213> ORGANISM: Artificial sequence
<220> FEATURE:
<223> OTHER INFORMATION: primer

<400> SEQUENCE: 630
aatccttaac tgaaacctgg actcg                                           25

<210> SEQ ID NO 631
<211> LENGTH: 15
<212> TYPE: DNA
<213> ORGANISM: Artificial sequence
<220> FEATURE:
<223> OTHER INFORMATION: probe

<400> SEQUENCE: 631
attcgctaga ttcca                                                      15

<210> SEQ ID NO 632
<211> LENGTH: 15
<212> TYPE: DNA
<213> ORGANISM: Artificial sequence
<220> FEATURE:
<223> OTHER INFORMATION: probe

<400> SEQUENCE: 632
attcgctgga ttcca                                                      15

<210> SEQ ID NO 633
<211> LENGTH: 25
<212> TYPE: DNA
<213> ORGANISM: Artificial sequence
<220> FEATURE:
<223> OTHER INFORMATION: primer

<400> SEQUENCE: 633
gaccagagtt gatccaggaa tgtaa                                           25

<210> SEQ ID NO 634
```

```
<211> LENGTH: 21
<212> TYPE: DNA
<213> ORGANISM: Artificial sequence
<220> FEATURE:
<223> OTHER INFORMATION: primer

<400> SEQUENCE: 634
gcacggtgat cttggacaca t                                             21

<210> SEQ ID NO 635
<211> LENGTH: 19
<212> TYPE: DNA
<213> ORGANISM: Artificial sequence
<220> FEATURE:
<223> OTHER INFORMATION: probe

<400> SEQUENCE: 635
tttctggcct atgagctca                                                19

<210> SEQ ID NO 636
<211> LENGTH: 19
<212> TYPE: DNA
<213> ORGANISM: Artificial sequence
<220> FEATURE:
<223> OTHER INFORMATION: probe

<400> SEQUENCE: 636
tttctggcct ttgagctca                                                19

<210> SEQ ID NO 637
<211> LENGTH: 25
<212> TYPE: DNA
<213> ORGANISM: Artificial sequence
<220> FEATURE:
<223> OTHER INFORMATION: primer

<400> SEQUENCE: 637
caaaccgtac tttccctatg atggt                                         25

<210> SEQ ID NO 638
<211> LENGTH: 24
<212> TYPE: DNA
<213> ORGANISM: Artificial sequence
<220> FEATURE:
<223> OTHER INFORMATION: primer

<400> SEQUENCE: 638
tggtatctcg acaatggagc tagt                                          24

<210> SEQ ID NO 639
<211> LENGTH: 18
<212> TYPE: DNA
<213> ORGANISM: Artificial sequence
<220> FEATURE:
<223> OTHER INFORMATION: probe

<400> SEQUENCE: 639
atctcctgtc atatgatt                                                 18

<210> SEQ ID NO 640
<211> LENGTH: 17
<212> TYPE: DNA
<213> ORGANISM: Artificial sequence
<220> FEATURE:
<223> OTHER INFORMATION: probe

<400> SEQUENCE: 640
```
tctcctgtca aatgatt                                                    17

<210> SEQ ID NO 641
<211> LENGTH: 25
<212> TYPE: DNA
<213> ORGANISM: Artificial sequence
<220> FEATURE:
<223> OTHER INFORMATION: primer

<400> SEQUENCE: 641
gcattggcag gttttaaatc tcaga                                           25

<210> SEQ ID NO 642
<211> LENGTH: 26
<212> TYPE: DNA
<213> ORGANISM: Artificial sequence
<220> FEATURE:
<223> OTHER INFORMATION: primer

<400> SEQUENCE: 642
ctcaaaacca atggaagtgt tactgt                                          26

<210> SEQ ID NO 643
<211> LENGTH: 18
<212> TYPE: DNA
<213> ORGANISM: Artificial sequence
<220> FEATURE:
<223> OTHER INFORMATION: probe

<400> SEQUENCE: 643
ttgtgcataa tgacaccc                                                   18

<210> SEQ ID NO 644
<211> LENGTH: 17
<212> TYPE: DNA
<213> ORGANISM: Artificial sequence
<220> FEATURE:
<223> OTHER INFORMATION: probe

<400> SEQUENCE: 644
tgtgcataaa gacaccc                                                    17

<210> SEQ ID NO 645
<211> LENGTH: 23
<212> TYPE: DNA
<213> ORGANISM: Artificial sequence
<220> FEATURE:
<223> OTHER INFORMATION: primer

<400> SEQUENCE: 645
tgatatcacg acgacggttt ctg                                             23

<210> SEQ ID NO 646
<211> LENGTH: 21
<212> TYPE: DNA
<213> ORGANISM: Artificial sequence
<220> FEATURE:
<223> OTHER INFORMATION: primer

<400> SEQUENCE: 646
gagctttctc cagcgtgatt g                                               21

<210> SEQ ID NO 647
<211> LENGTH: 19
<212> TYPE: DNA

```
<213> ORGANISM: Artificial sequence
<220> FEATURE:
<223> OTHER INFORMATION: probe

<400> SEQUENCE: 647
ctcagtctct ctcggagat                                              19

<210> SEQ ID NO 648
<211> LENGTH: 19
<212> TYPE: DNA
<213> ORGANISM: Artificial sequence
<220> FEATURE:
<223> OTHER INFORMATION: probe

<400> SEQUENCE: 648
ctcagtctct cacggagat                                              19

<210> SEQ ID NO 649
<211> LENGTH: 29
<212> TYPE: DNA
<213> ORGANISM: Artificial sequence
<220> FEATURE:
<223> OTHER INFORMATION: primer

<400> SEQUENCE: 649
gaaatcctac acgattttaa gcatgtcaa                                   29

<210> SEQ ID NO 650
<211> LENGTH: 18
<212> TYPE: DNA
<213> ORGANISM: Artificial sequence
<220> FEATURE:
<223> OTHER INFORMATION: primer

<400> SEQUENCE: 650
gcgcatcacc ctcattcc                                               18

<210> SEQ ID NO 651
<211> LENGTH: 16
<212> TYPE: DNA
<213> ORGANISM: Artificial sequence
<220> FEATURE:
<223> OTHER INFORMATION: probe

<400> SEQUENCE: 651
tacaccccag gcttaa                                                 16

<210> SEQ ID NO 652
<211> LENGTH: 15
<212> TYPE: DNA
<213> ORGANISM: Artificial sequence
<220> FEATURE:
<223> OTHER INFORMATION: probe

<400> SEQUENCE: 652
acacccctgg cttaa                                                  15

<210> SEQ ID NO 653
<211> LENGTH: 29
<212> TYPE: DNA
<213> ORGANISM: Artificial sequence
<220> FEATURE:
<223> OTHER INFORMATION: primer

<400> SEQUENCE: 653
gagtttcttg tattcatcta ggtcaacga                                   29
```

```
<210> SEQ ID NO 654
<211> LENGTH: 34
<212> TYPE: DNA
<213> ORGANISM: Artificial sequence
<220> FEATURE:
<223> OTHER INFORMATION: primer

<400> SEQUENCE: 654
tgaggatata catgcatatc ttgccatata tttg                          34

<210> SEQ ID NO 655
<211> LENGTH: 21
<212> TYPE: DNA
<213> ORGANISM: Artificial sequence
<220> FEATURE:
<223> OTHER INFORMATION: probe

<400> SEQUENCE: 655
cggtattagg taacctagca t                                        21

<210> SEQ ID NO 656
<211> LENGTH: 21
<212> TYPE: DNA
<213> ORGANISM: Artificial sequence
<220> FEATURE:
<223> OTHER INFORMATION: probe

<400> SEQUENCE: 656
cggtattagg taacgtagca t                                        21

<210> SEQ ID NO 657
<211> LENGTH: 23
<212> TYPE: DNA
<213> ORGANISM: Artificial sequence
<220> FEATURE:
<223> OTHER INFORMATION: primer

<400> SEQUENCE: 657
caccaaagct aactctgcac tct                                      23

<210> SEQ ID NO 658
<211> LENGTH: 21
<212> TYPE: DNA
<213> ORGANISM: Artificial sequence
<220> FEATURE:
<223> OTHER INFORMATION: primer

<400> SEQUENCE: 658
caggacgagt taaggcaagg t                                        21

<210> SEQ ID NO 659
<211> LENGTH: 19
<212> TYPE: DNA
<213> ORGANISM: Artificial sequence
<220> FEATURE:
<223> OTHER INFORMATION: probe

<400> SEQUENCE: 659
attgtagact gcctactac                                           19

<210> SEQ ID NO 660
<211> LENGTH: 19
<212> TYPE: DNA
<213> ORGANISM: Artificial sequence
<220> FEATURE:
```

<223> OTHER INFORMATION: probe

<400> SEQUENCE: 660
attgtagact gcgtactac                                            19

<210> SEQ ID NO 661
<211> LENGTH: 25
<212> TYPE: DNA
<213> ORGANISM: Artificial sequence
<220> FEATURE:
<223> OTHER INFORMATION: primer

<400> SEQUENCE: 661
gacatctttt gggaccttag catct                                     25

<210> SEQ ID NO 662
<211> LENGTH: 25
<212> TYPE: DNA
<213> ORGANISM: Artificial sequence
<220> FEATURE:
<223> OTHER INFORMATION: primer

<400> SEQUENCE: 662
ggattagcca agttccattc ctaca                                     25

<210> SEQ ID NO 663
<211> LENGTH: 19
<212> TYPE: DNA
<213> ORGANISM: Artificial sequence
<220> FEATURE:
<223> OTHER INFORMATION: probe

<400> SEQUENCE: 663
aagcaactca ataagaaga                                            19

<210> SEQ ID NO 664
<211> LENGTH: 19
<212> TYPE: DNA
<213> ORGANISM: Artificial sequence
<220> FEATURE:
<223> OTHER INFORMATION: probe

<400> SEQUENCE: 664
aagcaactca atgagaaga                                            19

<210> SEQ ID NO 665
<211> LENGTH: 20
<212> TYPE: DNA
<213> ORGANISM: Artificial sequence
<220> FEATURE:
<223> OTHER INFORMATION: primer

<400> SEQUENCE: 665
tgcaacttgg tcagcactca                                           20

<210> SEQ ID NO 666
<211> LENGTH: 27
<212> TYPE: DNA
<213> ORGANISM: Artificial sequence
<220> FEATURE:
<223> OTHER INFORMATION: primer

<400> SEQUENCE: 666
caccatatag gaaatcatga gcacgaa                                   27

```
<210> SEQ ID NO 667
<211> LENGTH: 15
<212> TYPE: DNA
<213> ORGANISM: Artificial sequence
<220> FEATURE:
<223> OTHER INFORMATION: probe

<400> SEQUENCE: 667
tcgcgctcta tttca                                                      15

<210> SEQ ID NO 668
<211> LENGTH: 15
<212> TYPE: DNA
<213> ORGANISM: Artificial sequence
<220> FEATURE:
<223> OTHER INFORMATION: probe

<400> SEQUENCE: 668
tcgcgctctg tttca                                                      15

<210> SEQ ID NO 669
<211> LENGTH: 32
<212> TYPE: DNA
<213> ORGANISM: Artificial sequence
<220> FEATURE:
<223> OTHER INFORMATION: primer

<400> SEQUENCE: 669
cgattcggaa tgatcatata agatcaaact tc                                   32

<210> SEQ ID NO 670
<211> LENGTH: 30
<212> TYPE: DNA
<213> ORGANISM: Artificial sequence
<220> FEATURE:
<223> OTHER INFORMATION: primer

<400> SEQUENCE: 670
gggtaattac ggatgcaaga ctttatagtt                                      30

<210> SEQ ID NO 671
<211> LENGTH: 19
<212> TYPE: DNA
<213> ORGANISM: Artificial sequence
<220> FEATURE:
<223> OTHER INFORMATION: probe

<400> SEQUENCE: 671
atgtctgcac tatatctat                                                  19

<210> SEQ ID NO 672
<211> LENGTH: 18
<212> TYPE: DNA
<213> ORGANISM: Artificial sequence
<220> FEATURE:
<223> OTHER INFORMATION: probe

<400> SEQUENCE: 672
tgtctgcact aaatctat                                                   18

<210> SEQ ID NO 673
<211> LENGTH: 25
<212> TYPE: DNA
<213> ORGANISM: Artificial sequence
<220> FEATURE:
<223> OTHER INFORMATION: primer
```

```
<400> SEQUENCE: 673
ccgctgaagg tatatcgaag aatct                                    25

<210> SEQ ID NO 674
<211> LENGTH: 26
<212> TYPE: DNA
<213> ORGANISM: Artificial sequence
<220> FEATURE:
<223> OTHER INFORMATION: primer

<400> SEQUENCE: 674
ccttgttcag tcttactcag cttttg                                   26

<210> SEQ ID NO 675
<211> LENGTH: 15
<212> TYPE: DNA
<213> ORGANISM: Artificial sequence
<220> FEATURE:
<223> OTHER INFORMATION: probe

<400> SEQUENCE: 675
caaaccggat gatgc                                               15

<210> SEQ ID NO 676
<211> LENGTH: 17
<212> TYPE: DNA
<213> ORGANISM: Artificial sequence
<220> FEATURE:
<223> OTHER INFORMATION: probe

<400> SEQUENCE: 676
ttcaaaccga atgatgc                                             17

<210> SEQ ID NO 677
<211> LENGTH: 38
<212> TYPE: DNA
<213> ORGANISM: Artificial sequence
<220> FEATURE:
<223> OTHER INFORMATION: primer

<400> SEQUENCE: 677
aaagcaacca agaagtgtt tgatataact tattttta                       38

<210> SEQ ID NO 678
<211> LENGTH: 25
<212> TYPE: DNA
<213> ORGANISM: Artificial sequence
<220> FEATURE:
<223> OTHER INFORMATION: primer

<400> SEQUENCE: 678
ctccatcaat ccatgggaag actta                                    25

<210> SEQ ID NO 679
<211> LENGTH: 18
<212> TYPE: DNA
<213> ORGANISM: Artificial sequence
<220> FEATURE:
<223> OTHER INFORMATION: probe

<400> SEQUENCE: 679
tcgtccatat agttcaag                                            18

<210> SEQ ID NO 680
<211> LENGTH: 19
```

```
<212> TYPE: DNA
<213> ORGANISM: Artificial sequence
<220> FEATURE:
<223> OTHER INFORMATION: probe

<400> SEQUENCE: 680
atcgtccata ttgttcaag                                               19

<210> SEQ ID NO 681
<211> LENGTH: 33
<212> TYPE: DNA
<213> ORGANISM: Artificial sequence
<220> FEATURE:
<223> OTHER INFORMATION: primer

<400> SEQUENCE: 681
cgatggttgt tagatatatg tctagtccta agt                               33

<210> SEQ ID NO 682
<211> LENGTH: 27
<212> TYPE: DNA
<213> ORGANISM: Artificial sequence
<220> FEATURE:
<223> OTHER INFORMATION: primer

<400> SEQUENCE: 682
ggaagagaag aacaagagga agacttt                                      27

<210> SEQ ID NO 683
<211> LENGTH: 16
<212> TYPE: DNA
<213> ORGANISM: Artificial sequence
<220> FEATURE:
<223> OTHER INFORMATION: probe

<400> SEQUENCE: 683
aacgttcacc atctct                                                  16

<210> SEQ ID NO 684
<211> LENGTH: 16
<212> TYPE: DNA
<213> ORGANISM: Artificial sequence
<220> FEATURE:
<223> OTHER INFORMATION: probe

<400> SEQUENCE: 684
aacgttcaca atctct                                                  16

<210> SEQ ID NO 685
<211> LENGTH: 25
<212> TYPE: DNA
<213> ORGANISM: Artificial sequence
<220> FEATURE:
<223> OTHER INFORMATION: primer

<400> SEQUENCE: 685
cgtataagtg tggtgccaat tgttt                                        25

<210> SEQ ID NO 686
<211> LENGTH: 18
<212> TYPE: DNA
<213> ORGANISM: Artificial sequence
<220> FEATURE:
<223> OTHER INFORMATION: primer

<400> SEQUENCE: 686
```

```
ggatccttgg cgctctcc                                                    18
```

<210> SEQ ID NO 687
<211> LENGTH: 13
<212> TYPE: DNA
<213> ORGANISM: Artificial sequence
<220> FEATURE:
<223> OTHER INFORMATION: probe

<400> SEQUENCE: 687

```
cgcaaggaca ttc                                                         13
```

<210> SEQ ID NO 688
<211> LENGTH: 14
<212> TYPE: DNA
<213> ORGANISM: Artificial sequence
<220> FEATURE:
<223> OTHER INFORMATION: probe

<400> SEQUENCE: 688

```
ccgcaagaac attc                                                        14
```

<210> SEQ ID NO 689
<211> LENGTH: 22
<212> TYPE: DNA
<213> ORGANISM: Artificial sequence
<220> FEATURE:
<223> OTHER INFORMATION: primer

<400> SEQUENCE: 689

```
gcgtcttgtt tgccaaatct gt                                               22
```

<210> SEQ ID NO 690
<211> LENGTH: 28
<212> TYPE: DNA
<213> ORGANISM: Artificial sequence
<220> FEATURE:
<223> OTHER INFORMATION: primer

<400> SEQUENCE: 690

```
ctttggtagt tgttgttgaa tctgttgt                                         28
```

<210> SEQ ID NO 691
<211> LENGTH: 21
<212> TYPE: DNA
<213> ORGANISM: Artificial sequence
<220> FEATURE:
<223> OTHER INFORMATION: probe

<400> SEQUENCE: 691

```
ctggttatac agctctgaag t                                                21
```

<210> SEQ ID NO 692
<211> LENGTH: 21
<212> TYPE: DNA
<213> ORGANISM: Artificial sequence
<220> FEATURE:
<223> OTHER INFORMATION: probe

<400> SEQUENCE: 692

```
ctggttatac agctatgaag t                                                21
```

<210> SEQ ID NO 693
<211> LENGTH: 31
<212> TYPE: DNA
<213> ORGANISM: Artificial sequence
<220> FEATURE:
<223> OTHER INFORMATION: primer

<400> SEQUENCE: 693
gcaacgaaca aaataaaaga tggagatgta a                          31

<210> SEQ ID NO 694
<211> LENGTH: 27
<212> TYPE: DNA
<213> ORGANISM: Artificial sequence
<220> FEATURE:
<223> OTHER INFORMATION: primer

<400> SEQUENCE: 694
tctgtacttt cttttaagcc cttccaa                               27

<210> SEQ ID NO 695
<211> LENGTH: 18
<212> TYPE: DNA
<213> ORGANISM: Artificial sequence
<220> FEATURE:
<223> OTHER INFORMATION: probe

<400> SEQUENCE: 695
aaaggctgaa tccgtttt                                         18

<210> SEQ ID NO 696
<211> LENGTH: 17
<212> TYPE: DNA
<213> ORGANISM: Artificial sequence
<220> FEATURE:
<223> OTHER INFORMATION: probe

<400> SEQUENCE: 696
aaggctgaat cagtttt                                          17

<210> SEQ ID NO 697
<211> LENGTH: 20
<212> TYPE: DNA
<213> ORGANISM: Artificial sequence
<220> FEATURE:
<223> OTHER INFORMATION: primer

<400> SEQUENCE: 697
tggtttgcta cctccgtttc                                       20

<210> SEQ ID NO 698
<211> LENGTH: 20
<212> TYPE: DNA
<213> ORGANISM: Artificial sequence
<220> FEATURE:
<223> OTHER INFORMATION: primer

<400> SEQUENCE: 698
tgcaaaaggc aaaagattca                                       20

<210> SEQ ID NO 699
<211> LENGTH: 17
<212> TYPE: DNA
<213> ORGANISM: Artificial sequence
<220> FEATURE:
<223> OTHER INFORMATION: probe

<400> SEQUENCE: 699
ctcatatcca ctgttgc                                          17

```
<210> SEQ ID NO 700
<211> LENGTH: 16
<212> TYPE: DNA
<213> ORGANISM: Artificial sequence
<220> FEATURE:
<223> OTHER INFORMATION: probe

<400> SEQUENCE: 700
ctcatagcca ctgttg                                               16

<210> SEQ ID NO 701
<211> LENGTH: 19
<212> TYPE: DNA
<213> ORGANISM: Artificial sequence
<220> FEATURE:
<223> OTHER INFORMATION: primer

<400> SEQUENCE: 701
acggctcatg ttggatcgt                                            19

<210> SEQ ID NO 702
<211> LENGTH: 19
<212> TYPE: DNA
<213> ORGANISM: Artificial sequence
<220> FEATURE:
<223> OTHER INFORMATION: primer

<400> SEQUENCE: 702
acccatggtc gccacaaat                                            19

<210> SEQ ID NO 703
<211> LENGTH: 19
<212> TYPE: DNA
<213> ORGANISM: Artificial sequence
<220> FEATURE:
<223> OTHER INFORMATION: probe

<400> SEQUENCE: 703
attttgtttt ccctttttc                                            19

<210> SEQ ID NO 704
<211> LENGTH: 18
<212> TYPE: DNA
<213> ORGANISM: Artificial sequence
<220> FEATURE:
<223> OTHER INFORMATION: probe

<400> SEQUENCE: 704
ttttgttttg ccttttc                                              18

<210> SEQ ID NO 705
<211> LENGTH: 25
<212> TYPE: DNA
<213> ORGANISM: Artificial sequence
<220> FEATURE:
<223> OTHER INFORMATION: primer

<400> SEQUENCE: 705
tctgcccaaa gtgaatcagt attca                                     25

<210> SEQ ID NO 706
<211> LENGTH: 25
<212> TYPE: DNA
<213> ORGANISM: Artificial sequence
<220> FEATURE:
<223> OTHER INFORMATION: primer
```

```
<400> SEQUENCE: 706
tgcaagagga tatgtcacag aactc                                    25

<210> SEQ ID NO 707
<211> LENGTH: 16
<212> TYPE: DNA
<213> ORGANISM: Artificial sequence
<220> FEATURE:
<223> OTHER INFORMATION: probe

<400> SEQUENCE: 707
ctgcctgaac ctttta                                              16

<210> SEQ ID NO 708
<211> LENGTH: 16
<212> TYPE: DNA
<213> ORGANISM: Artificial sequence
<220> FEATURE:
<223> OTHER INFORMATION: probe

<400> SEQUENCE: 708
ctgcctgaag ctttta                                              16

<210> SEQ ID NO 709
<211> LENGTH: 27
<212> TYPE: DNA
<213> ORGANISM: Artificial sequence
<220> FEATURE:
<223> OTHER INFORMATION: primer

<400> SEQUENCE: 709
cgagcattaa tgacttacca tccttca                                  27

<210> SEQ ID NO 710
<211> LENGTH: 22
<212> TYPE: DNA
<213> ORGANISM: Artificial sequence
<220> FEATURE:
<223> OTHER INFORMATION: primer

<400> SEQUENCE: 710
acagcctcag gaacatcaga ag                                       22

<210> SEQ ID NO 711
<211> LENGTH: 20
<212> TYPE: DNA
<213> ORGANISM: Artificial sequence
<220> FEATURE:
<223> OTHER INFORMATION: probe

<400> SEQUENCE: 711
cagagtagta accctggttt                                          20

<210> SEQ ID NO 712
<211> LENGTH: 20
<212> TYPE: DNA
<213> ORGANISM: Artificial sequence
<220> FEATURE:
<223> OTHER INFORMATION: probe

<400> SEQUENCE: 712
cagagtagta acgctggttt                                          20

<210> SEQ ID NO 713
```

```
<211> LENGTH: 27
<212> TYPE: DNA
<213> ORGANISM: Artificial sequence
<220> FEATURE:
<223> OTHER INFORMATION: primer

<400> SEQUENCE: 713
gaccgtgtta agctgtaaat cgataac                                         27

<210> SEQ ID NO 714
<211> LENGTH: 37
<212> TYPE: DNA
<213> ORGANISM: Artificial sequence
<220> FEATURE:
<223> OTHER INFORMATION: primer

<400> SEQUENCE: 714
ggtctcttaa ataagtaac tagtagtgaa gaaatgt                               37

<210> SEQ ID NO 715
<211> LENGTH: 18
<212> TYPE: DNA
<213> ORGANISM: Artificial sequence
<220> FEATURE:
<223> OTHER INFORMATION: probe

<400> SEQUENCE: 715
acttgcatga ccttcata                                                   18

<210> SEQ ID NO 716
<211> LENGTH: 19
<212> TYPE: DNA
<213> ORGANISM: Artificial sequence
<220> FEATURE:
<223> OTHER INFORMATION: probe

<400> SEQUENCE: 716
cacttgcatg actttcata                                                  19

<210> SEQ ID NO 717
<211> LENGTH: 20
<212> TYPE: DNA
<213> ORGANISM: Artificial sequence
<220> FEATURE:
<223> OTHER INFORMATION: primer

<400> SEQUENCE: 717
taataagccg agccaccaag                                                 20

<210> SEQ ID NO 718
<211> LENGTH: 20
<212> TYPE: DNA
<213> ORGANISM: Artificial sequence
<220> FEATURE:
<223> OTHER INFORMATION: primer

<400> SEQUENCE: 718
gacgagggag gaaatgttca                                                 20

<210> SEQ ID NO 719
<211> LENGTH: 14
<212> TYPE: DNA
<213> ORGANISM: Artificial sequence
<220> FEATURE:
<223> OTHER INFORMATION: probe

<400> SEQUENCE: 719
```

```
accaagcttc tctc                                                    14

<210> SEQ ID NO 720
<211> LENGTH: 15
<212> TYPE: DNA
<213> ORGANISM: Artificial sequence
<220> FEATURE:
<223> OTHER INFORMATION: probe

<400> SEQUENCE: 720
ccaagcttct gtcgc                                                   15

<210> SEQ ID NO 721
<211> LENGTH: 25
<212> TYPE: DNA
<213> ORGANISM: Artificial sequence
<220> FEATURE:
<223> OTHER INFORMATION: primer

<400> SEQUENCE: 721
tgtcgattgg ctcttttgag attca                                        25

<210> SEQ ID NO 722
<211> LENGTH: 31
<212> TYPE: DNA
<213> ORGANISM: Artificial sequence
<220> FEATURE:
<223> OTHER INFORMATION: primer

<400> SEQUENCE: 722
agaagttatg aaaagagaga ggtgtactac t                                 31

<210> SEQ ID NO 723
<211> LENGTH: 19
<212> TYPE: DNA
<213> ORGANISM: Artificial sequence
<220> FEATURE:
<223> OTHER INFORMATION: probe

<400> SEQUENCE: 723
aggagtatcg tacatctca                                               19

<210> SEQ ID NO 724
<211> LENGTH: 19
<212> TYPE: DNA
<213> ORGANISM: Artificial sequence
<220> FEATURE:
<223> OTHER INFORMATION: probe

<400> SEQUENCE: 724
aggagtatcg tagatctca                                               19

<210> SEQ ID NO 725
<211> LENGTH: 20
<212> TYPE: DNA
<213> ORGANISM: Artificial sequence
<220> FEATURE:
<223> OTHER INFORMATION: primer

<400> SEQUENCE: 725
ttgctcggtt ttaacctcgt                                              20

<210> SEQ ID NO 726
<211> LENGTH: 20
<212> TYPE: DNA
```

```
<213> ORGANISM: Artificial sequence
<220> FEATURE:
<223> OTHER INFORMATION: primer

<400> SEQUENCE: 726
aagaaatggg ggaaaggatg                                               20

<210> SEQ ID NO 727
<211> LENGTH: 16
<212> TYPE: DNA
<213> ORGANISM: Artificial sequence
<220> FEATURE:
<223> OTHER INFORMATION: probe

<400> SEQUENCE: 727
tcttcgcttt atcacc                                                   16

<210> SEQ ID NO 728
<211> LENGTH: 15
<212> TYPE: DNA
<213> ORGANISM: Artificial sequence
<220> FEATURE:
<223> OTHER INFORMATION: probe

<400> SEQUENCE: 728
cttcgctgta tcacc                                                    15

<210> SEQ ID NO 729
<211> LENGTH: 23
<212> TYPE: DNA
<213> ORGANISM: Artificial sequence
<220> FEATURE:
<223> OTHER INFORMATION: primer

<400> SEQUENCE: 729
gaaggtttcc tcgtggaatg act                                           23

<210> SEQ ID NO 730
<211> LENGTH: 24
<212> TYPE: DNA
<213> ORGANISM: Artificial sequence
<220> FEATURE:
<223> OTHER INFORMATION: primer

<400> SEQUENCE: 730
gatatgggtc cttgcggtct attt                                          24

<210> SEQ ID NO 731
<211> LENGTH: 16
<212> TYPE: DNA
<213> ORGANISM: Artificial sequence
<220> FEATURE:
<223> OTHER INFORMATION: probe

<400> SEQUENCE: 731
tccctaagca gagaag                                                   16

<210> SEQ ID NO 732
<211> LENGTH: 21
<212> TYPE: DNA
<213> ORGANISM: Artificial sequence
<220> FEATURE:
<223> OTHER INFORMATION: probe

<400> SEQUENCE: 732
attaatccct aagaagagaa g                                             21
```

<210> SEQ ID NO 733
<211> LENGTH: 32
<212> TYPE: DNA
<213> ORGANISM: Artificial sequence
<220> FEATURE:
<223> OTHER INFORMATION: primer

<400> SEQUENCE: 733
cgtctacaat ttcattagtc tcaagaaaaa ca                          32

<210> SEQ ID NO 734
<211> LENGTH: 22
<212> TYPE: DNA
<213> ORGANISM: Artificial sequence
<220> FEATURE:
<223> OTHER INFORMATION: primer

<400> SEQUENCE: 734
gcttctggat aattggattg gg                                     22

<210> SEQ ID NO 735
<211> LENGTH: 19
<212> TYPE: DNA
<213> ORGANISM: Artificial sequence
<220> FEATURE:
<223> OTHER INFORMATION: probe

<400> SEQUENCE: 735
tgggatgtaa tctggctat                                         19

<210> SEQ ID NO 736
<211> LENGTH: 21
<212> TYPE: DNA
<213> ORGANISM: Artificial sequence
<220> FEATURE:
<223> OTHER INFORMATION: probe

<400> SEQUENCE: 736
tttgggatgt aatttggcta t                                      21

<210> SEQ ID NO 737
<211> LENGTH: 22
<212> TYPE: DNA
<213> ORGANISM: Artificial sequence
<220> FEATURE:
<223> OTHER INFORMATION: primer

<400> SEQUENCE: 737
gattgcgttt ttgcgtgaag tc                                     22

<210> SEQ ID NO 738
<211> LENGTH: 25
<212> TYPE: DNA
<213> ORGANISM: Artificial sequence
<220> FEATURE:
<223> OTHER INFORMATION: primer

<400> SEQUENCE: 738
gcaactcata ctgaaacgtg tttga                                  25

<210> SEQ ID NO 739
<211> LENGTH: 18
<212> TYPE: DNA
<213> ORGANISM: Artificial sequence
<220> FEATURE:

<223> OTHER INFORMATION: probe

<400> SEQUENCE: 739
ttgcaagtgt ctttcatg                                              18

<210> SEQ ID NO 740
<211> LENGTH: 17
<212> TYPE: DNA
<213> ORGANISM: Artificial sequence
<220> FEATURE:
<223> OTHER INFORMATION: probe

<400> SEQUENCE: 740
tgcaagtgtc attcatg                                               17

<210> SEQ ID NO 741
<211> LENGTH: 22
<212> TYPE: DNA
<213> ORGANISM: Artificial sequence
<220> FEATURE:
<223> OTHER INFORMATION: primer

<400> SEQUENCE: 741
tgggagagag cctaagtttc tg                                         22

<210> SEQ ID NO 742
<211> LENGTH: 21
<212> TYPE: DNA
<213> ORGANISM: Artificial sequence
<220> FEATURE:
<223> OTHER INFORMATION: primer

<400> SEQUENCE: 742
cgcaacacta ggaaacacct t                                          21

<210> SEQ ID NO 743
<211> LENGTH: 14
<212> TYPE: DNA
<213> ORGANISM: Artificial sequence
<220> FEATURE:
<223> OTHER INFORMATION: probe

<400> SEQUENCE: 743
acaccatcaa gaac                                                  14

<210> SEQ ID NO 744
<211> LENGTH: 14
<212> TYPE: DNA
<213> ORGANISM: Artificial sequence
<220> FEATURE:
<223> OTHER INFORMATION: probe

<400> SEQUENCE: 744
acaccatcaa gcac                                                  14

<210> SEQ ID NO 745
<211> LENGTH: 21
<212> TYPE: DNA
<213> ORGANISM: Artificial sequence
<220> FEATURE:
<223> OTHER INFORMATION: primer

<400> SEQUENCE: 745
ttccatcacc actgaaacag a                                          21

```
<210> SEQ ID NO 746
<211> LENGTH: 18
<212> TYPE: DNA
<213> ORGANISM: Artificial sequence
<220> FEATURE:
<223> OTHER INFORMATION: primer

<400> SEQUENCE: 746
cgtggctatg caccatcc                                                 18

<210> SEQ ID NO 747
<211> LENGTH: 15
<212> TYPE: DNA
<213> ORGANISM: Artificial sequence
<220> FEATURE:
<223> OTHER INFORMATION: probe

<400> SEQUENCE: 747
ttcccaagac aaaac                                                    15

<210> SEQ ID NO 748
<211> LENGTH: 13
<212> TYPE: DNA
<213> ORGANISM: Artificial sequence
<220> FEATURE:
<223> OTHER INFORMATION: probe

<400> SEQUENCE: 748
cccaggacaa aac                                                      13

<210> SEQ ID NO 749
<211> LENGTH: 34
<212> TYPE: DNA
<213> ORGANISM: Artificial sequence
<220> FEATURE:
<223> OTHER INFORMATION: primer

<400> SEQUENCE: 749
aaacaaaaac aaaatcattc tgagactttg aaac                               34

<210> SEQ ID NO 750
<211> LENGTH: 27
<212> TYPE: DNA
<213> ORGANISM: Artificial sequence
<220> FEATURE:
<223> OTHER INFORMATION: primer

<400> SEQUENCE: 750
tgaagatgaa ctcgccgtat agaaaag                                       27

<210> SEQ ID NO 751
<211> LENGTH: 22
<212> TYPE: DNA
<213> ORGANISM: Artificial sequence
<220> FEATURE:
<223> OTHER INFORMATION: probe

<400> SEQUENCE: 751
tcaataaact aattactttt tc                                            22

<210> SEQ ID NO 752
<211> LENGTH: 21
<212> TYPE: DNA
<213> ORGANISM: Artificial sequence
<220> FEATURE:
<223> OTHER INFORMATION: probe
```

```
<400> SEQUENCE: 752
caataaacta attgctttt c                                              21

<210> SEQ ID NO 753
<211> LENGTH: 22
<212> TYPE: DNA
<213> ORGANISM: Artificial sequence
<220> FEATURE:
<223> OTHER INFORMATION: primer

<400> SEQUENCE: 753
cttcgacgga ttccttgatg ga                                            22

<210> SEQ ID NO 754
<211> LENGTH: 23
<212> TYPE: DNA
<213> ORGANISM: Artificial sequence
<220> FEATURE:
<223> OTHER INFORMATION: primer

<400> SEQUENCE: 754
ctgttcagca gagccaagat aca                                           23

<210> SEQ ID NO 755
<211> LENGTH: 16
<212> TYPE: DNA
<213> ORGANISM: Artificial sequence
<220> FEATURE:
<223> OTHER INFORMATION: probe

<400> SEQUENCE: 755
ccctctttcg atgttc                                                   16

<210> SEQ ID NO 756
<211> LENGTH: 18
<212> TYPE: DNA
<213> ORGANISM: Artificial sequence
<220> FEATURE:
<223> OTHER INFORMATION: probe

<400> SEQUENCE: 756
aaccctcttt tgatgttc                                                 18

<210> SEQ ID NO 757
<211> LENGTH: 26
<212> TYPE: DNA
<213> ORGANISM: Artificial sequence
<220> FEATURE:
<223> OTHER INFORMATION: primer

<400> SEQUENCE: 757
gtttttctga tgttgaagga ggttga                                        26

<210> SEQ ID NO 758
<211> LENGTH: 20
<212> TYPE: DNA
<213> ORGANISM: Artificial sequence
<220> FEATURE:
<223> OTHER INFORMATION: primer

<400> SEQUENCE: 758
gtgtcccgac caacaattcc                                               20

<210> SEQ ID NO 759
<211> LENGTH: 16
```

```
<212> TYPE: DNA
<213> ORGANISM: Artificial sequence
<220> FEATURE:
<223> OTHER INFORMATION: probe

<400> SEQUENCE: 759
tccaccagaa tttaga                                              16

<210> SEQ ID NO 760
<211> LENGTH: 17
<212> TYPE: DNA
<213> ORGANISM: Artificial sequence
<220> FEATURE:
<223> OTHER INFORMATION: probe

<400> SEQUENCE: 760
ctccaccaga gtttaga                                             17

<210> SEQ ID NO 761
<211> LENGTH: 151
<212> TYPE: DNA
<213> ORGANISM: Brassica napus

<400> SEQUENCE: 761
agtgtcaata tcaaaygagy cctgattcaa gaagtcgcag agtttctgtg aatayccaac    60
sgagttctta gtttcrtctg tattcttccc atttgcatat cccttgtcta gcttgagctt   120
gggaatgtag gtggtggatc ttatcggaat c                                  151

<210> SEQ ID NO 762
<211> LENGTH: 801
<212> TYPE: DNA
<213> ORGANISM: Brassica napus

<400> SEQUENCE: 762
ctaagcatga tacaagagtc tgcctttcgg tccttttctt tcaagtgggc cactttttt     60 tcccgaacgc agtccgaata tgaagcgcat ggatacaagt tatgacttgg aatgaaagac   120 aattcctta gctttgattt ggtttgtttc ttacgaatat tttatattat tatttgattg   180 tttttacaa ttacgaatat ccatattttt ttattcgaat cgaaatggat aatgaatcaa   240
atcaaaawwt ttgaatattc cgcctagtcc tagtttggag cctagtgaaa attaaaatag   300
cttgacatta gttctcaaca tttacggtaa tgattattaa ggacaatcga acttttcaat   360
atagacgatt accaatttac catataggga tatatagagc mgaagactca aaacctttag   420
ttggacaaat ggttaagtca cgagtgcaat aacatatttt atatacaaat gtcaacaatt   480
ctgttagtag tcgttcgtgc cacataatta tatatctttg tgattttctg tttcgattaa   540
tctgtctcat agttgcagtc gttagctagt attaagatca acaaattttc gggtgcatat   600
ttttttaagt ttcttaatta aggatataaa gtacgcgcgc tcaactattt gtaaattaaa   660
acatcactgc aagagttcag tcaaacaggg gcagaccccc actatggtcc aagggagtca   720
cttgacaccc ctaaaatagt taaataaatg aattgcatag aatatccaat ggattttgt    780 agcagaaata gttactttgw a                                             801

<210> SEQ ID NO 763
<211> LENGTH: 527
<212> TYPE: DNA
<213> ORGANISM: Brassica napus
<220> FEATURE:
<221> NAME/KEY: misc_feature
<222> LOCATION: (80)..(80)
```

<223> OTHER INFORMATION: n is a, c, g, or t

<400> SEQUENCE: 763

```
aaactatggt tctgttacac ttgtgtgttc tttaacttga agcatacgag tctccaacga      60
gttaggagca ggaaatccan aagtggcaaa actggctgta tatgtcattg taggcatagc     120
agttgcccaa ggtatcgtgg tggtaacggt tttgttgtcg gttcgaaagg tcctaggccg     180
agcttttagc agtgacccga aaatcatctc ttatgctgca tcgatgatac ctattgtcgc     240
atgtggaaac ttccttgatg gtctccaatg cgttctctca ggttcttatt gcttgcasac     300
tcgaccatat gtttctggaa caagaaaata ttggtttagg ctcctcctag cttatatata     360
tatatgtccg gttaatcctg gtttggtatg gtttaggggt tgctagagga tgtggatggc     420
agaaaattgg agcgtgtgta aatcttggtt catattatct cgttggagtt ccgttagggc     480
tattacttgg tttccatttc cacatcggtg gtcgggtaat aatctttt                  527
```

<210> SEQ ID NO 764
<211> LENGTH: 801
<212> TYPE: DNA
<213> ORGANISM: Brassica napus
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t

<400> SEQUENCE: 764

```
aaattcatat tatttacttt gttatttatt tttattttc tacaattttt atgtattntg      60
gaacaagtat aattttaata aaatatgacg atataagttt gataatacga naagtttgtc     120
aaccataata aaattattgt tattcagata ctccggtaat tttattttt gactgaaaat      180
tccagtaagg ttccaatccc agattagata atttttattg cattaatctg tatatcaaac     240
attactttg ctaatctata ccttgtataa tatgtcanaa ttgctttat cttttcaata       300
tctatagatt aaaatttata atcttttata gtctattcaa cttgcgcagc atcatctcgt     360
aggtgttaaa ccctctgggt tttctgaact ttgttaaacc stctttatac gatagactag     420
tagtgcgcac caaaatcttg aacattattt tataaaatca aaacaaaat aaccaccacc     480
ttatctcggt cttgtatctg cagatgaccc ggtttaagtg cagaggatta gctttcggcc     540
tgagctgggc caacatcatg ggagattcnt tctctttatt ctatgccttc aacttatggg     600
ttaaggtcct ttcaggagaa aaaatctatg ccccggaaac ttctatnata gacagaaggt     660
ttcagaatcc aaatccaacg gtgaaagacc cggaatcaat aaaacaggtt gacccggttg     720
gagatctatg gatcactcca agcaacaaga aaatggtgag ttactgtttc aacctcaccg     780
```

-continued tcnccgacca gatgtcaccg c                                                    801

<210> SEQ ID NO 765
<211> LENGTH: 801
<212> TYPE: DNA
<213> ORGANISM: Brassica napus
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t

<400> SEQUENCE: 765
gggtaagctc aagcaactag agactgaggc aaaagctaaa aaggagaggg tcaaagagct      60
cgaggattct aaatatggta tccgagcttg catcaatgtc gtaaggaggg ctctatcaga     120
ccaaggttgc agctgagaat tttgacaccg atgtcataaa ggatctagca gacactcaga     180
gggaaagtaa gaagctcgtt aaccggctta aactggcgca aagagctcat aaggaggagt     240
tccagaggct gaatgaatca agatccagaa ggtttagaaa aanggcttgt caagctgcag     300
nggtgaaata ccagtcgcat tttgatcaga tatgtgagct ttggccgatt ctaagatcgt     360
aaaggagaat gccttgttga tgtctcaggc ggctagtcag wcaggtttga tcgataagat     420
gacacaaagg ggactcgtgg gtcatgtggc agatcaggag atatgggtgc agtctctcaa     480
gaatttctaa gtgaagatcg acgagataga catcgtccaa ctagatccat aaaaggatct     540
aagngtctca cccgtttctg atgtctccag ctgaaatagc ctcccttttgg ggccaattcc     600 tgagctaaat cctatcgatg attaagaggt caggaattag acngtcatgt cagaaactgt     660
gaccattcca ggatggtcga gttgaggatc ctcctgctga ccagaagaag accgatgcaa     720
caacngctga ggagcctctg gatatagatc agtttgactc gaaactcgtc tgtaactccg     780
ttgtggatgt ttcgggcgct g                                                801

<210> SEQ ID NO 766
<211> LENGTH: 801
<212> TYPE: DNA
<213> ORGANISM: Brassica napus
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t
<220> FEATURE:
<221> NAME/KEY: misc_feature
<222> LOCATION: (801)..(801)

<223> OTHER INFORMATION: n is a, c, g, or t

<400> SEQUENCE: 766

```
cacttatgca gtttgcgatc tttgtggaga cagggcagtc tctagactca gacnacactt      60
tgcccacaag agctcttacc tcttcattgt ggcgtaatct cctatcgtag cagaaactat     120
acggtcgttt cttccctgta gcagtgaagg acgagataag aggcctgtga tcagagcctt     180
caaaagggag atagacacng tttcctttcg ggaaacagtc agaccaggag atattggcta     240
gagcttgatc cagtctgcag tgcactcgat gagtatgtct cgttcctctc caggagagaa     300
aatttccacg gtgtctcaga tcaaagagat cattcgttgc gaggaaagtc ctaaagttac     360
tgaaggagct ttccggtcta tctctgcctc cagttttctc sgagttgtca gtgatttcgt     420
tgaaatctcc agtcattaac caaggatcgc ttctcgaacc acctagctgt gtaagttggt     480
cccatacttc ttgtctatgg gatacttcaa gagctccata aacgaaggaa ctgaagaagt     540
ttgaatttt gtaggagata tgggtatnta tgtagttagg agtcgccgtc agcacctgga     600
cctttacgtc agacttccag agcaggcaga gccccctga gcttggactg ttcggtgaaa     660
caaggaagtg aaactcaaga agtaaaggtt ccaggtcttt aaggacaaag gcatctggat     720
tctttgtttc ctggataaag atgatatctg gagagaattt tttgttgaga gcaatgagcc     780
tttggactgt tctgggattc n                                               801
```

<210> SEQ ID NO 767
<211> LENGTH: 474
<212> TYPE: DNA
<213> ORGANISM: Brassica napus
<220> FEATURE:
<221> NAME/KEY: misc_feature
<222> LOCATION: (363)..(363)
<223> OTHER INFORMATION: n is a, c, g, or t

<400> SEQUENCE: 767

```
aaaaaaatgg agaataacga ctaaaatgtc cgtgagtaaa catcaaatca acatactatt      60
tagatgtttt aacgtgcggt tggatttggc cttacctccg cccagatccc cccttttgt      120
aactgtgatt gcccatcaac acctttctga cctgacccga catattaaca taactttwat     180
ttgggggtaa actaaaattg ggttttgatc cgtttatttc tcagttacag acatgacgaa     240
gaacataaga agagagagag agagaggacg tacaacagag aagacgatga cgaagagtcg     300
aagaccagta acagagagag agagacgatg acgacgacca gtaacagaga gagacgacgt     360
agnagagaga gagaaagacg acttagaaca gacagagaga gacgcaaacc aagaacaaag     420
agagagatga caatgaacga cgaaacgtgg agagcgagac gaagccagag agag           474
```

<210> SEQ ID NO 768
<211> LENGTH: 401
<212> TYPE: DNA
<213> ORGANISM: Brassica napus

<400> SEQUENCE: 768

```
tggaaaattc tataggtttt attgtaatct tttgtttgaa aatcatttgt gtgtccataa      60
ttgctctttg agagaattgt tttcttgaat gctttgatgg aacactttgc cgcatatgaa     120
aagggatgta gagaggatat gtggccggag taccgtttgc aaaacaacca tggcaaggca     180
caaacaccat gtaagtacac wtctttgtca atacctaacg agccttcaaa ctgatatctc     240
attgaatttc gtattaggct tgcctagaat caggaaggg aaggactcaa tctatgtagt     300
cgtacataaa atgacacatt ttattccttg ttaaaacgcc aacgaataat tgaatcgcac     360
```

```
gcgagaacac tttctttaaa aagtattttg actctattcc a                    401
```

<210> SEQ ID NO 769
<211> LENGTH: 801
<212> TYPE: DNA
<213> ORGANISM: Brassica napus

<400> SEQUENCE: 769

```
cctaatttcc ctaattttta ctatgtaata caccaaacta taaaaagttt tatcaaacgg    60
acaatgttga gatttattat tctaaataga tgtttgtctc cctacatttt catattttgt   120
accgaaacat ttatttaaaa gatatgcaaa gtagtgtgta gccaaatgct atcatgttta   180
aatttgccaa gagcatatcc acctatacag tgcagataat tgtttacttt tgttaagcta   240
caaaaagatg ttaagctgta agagtgattc gcatgaaaaa tctattacaa taaaagagag   300
ttacctctct ctayatgyca ccacgtcatc aggaaatata agacgttttt ggacacttgg   360
cacttcacca aaccagcccg cgtctgattt gattttgtat matccggttt wtctcatgcc   420
tctatcctgg actgggccat tattacaact tttccttggg cctttraaaa cactatgaca   480
agctcactag aattttatgt ttcttcttct tctttgcggt tgcgacagtg gacaattttt   540
ttttcagaac taagggacg ttccaatctc tcccgtaacg tatcaatact tcattaatct   600
gttcttaact ctgaggtttt gcgtgattag ccmactcctc ccactggaaa gcattcaatc   660
gacatcttta atctaacttt aagatgatat ygtttatttt tcttcktgac ctttgtgatt   720
tctccatctt cttccactca cttcatctgt tattgacatc ataattcctc ttcaacccyc   780
attctctcta tagaaagcca g                                              801
```

<210> SEQ ID NO 770
<211> LENGTH: 801
<212> TYPE: DNA
<213> ORGANISM: Brassica napus
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t

<400> SEQUENCE: 770

```
gcatcttggc attactagtt tgtatttta ttttgcaaag agaaccaaan cttagttatt    60
acaatatgat tatcttgcaa cagtatttcc aacagcgtta ttttagagta ctaatactca   120
tggctgcttt ttggagtgtc tctctgcaaa gttatttagc tggaaaatca gtttatgatg   180
aggtcagtat caaccgcaaa ggtgatacat aaccagttct taagcaacag ctcgacctgc   240
```

```
caaaccacca tctgttattt taaatgtcaa acaaagctcg ttagcaagac acaaatatan     300
ttaccgggta gaatgattac ggcaactnta agcctgcagc aaaccaacac gaagtctcat     360
tgttcacatt aatgaagaac acgccgcctt ttctgctgaa sttgtacttc catttgtctt     420
caaagaaatt ggtatgaaga caataagcaa agatgtgatg gagtcgtgct ttagaaacaa     480
ttgtcaaagc ccaaaaacta agaacaacaa atgccaaaat tgtgaaagaa caacgaactg     540
gttttgcnag ccaggaaatc tgatcatgac agttgtccaa cacagctgac gccaaccgct     600
tgcattgtgt gttttgagaa acagccgcnt cgtcaaacat tgtccatgag aagagacatc     660
aatgtgtatg aatgtggtgg agcaatgaaa taattaccaa gtgataaact cccagtggat     720
atgctgataa ttattatgaa antcaaattg agaaccagct ttctcaaacc catgctctca     780
gtttcttgcc accaaacatt a                                              801
```

```
<210> SEQ ID NO 771
<211> LENGTH: 801
<212> TYPE: DNA
<213> ORGANISM: Brassica napus
<220> FEATURE:
<221> NAME/KEY: misc_feature
<222> LOCATION: (241)..(241)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t

<400> SEQUENCE: 771
```

```
tagattgtta tgttttgata tcatcacaac caaataacat gccatgtatt tccatcatca      60
ttatcgttat cattattttg ccaacattat tatcaattta tcactgtttt gttaaataac     120
gtatttccat tatacggttc ctttgttgtt gatattatat aatataaaag gtcacatgta     180
ttactattat cgaacatgac ataatataag gattattaga gcggaagcta aataaaattt     240
ngctngatat tgtaatggtg ctgcatcatg ttttcttttt tggtaaaatt ttaattgatt     300
acaccaaaat gttcgtatgt tacaacttac aaggttggga ctgaaatggc tcgttgcttc     360
tctttccaaa gaggcatctt agctctccta aaatcgctat wcttgggcag atgatcatca     420
tgaggatggt ttcacttttg atttcctcct gctctgtttt atgcttttg cccacttgtt      480 ttgggttatt attgnctatt ggcatttgtt tttgcttgaa ctacctctag tcgttttgac     540
tagaatactt tatgattttt aatcaatgan aaaaaaaaca gttacaaaag gatattaata     600
gcagaaaact ggatgaaact aaacaacaga gctactcaac cacatcttaa ctttgaacaa     660
agactagaag gtagacagta gagagggaaa ccaacgaaac aagcttagac caaggaattg     720
gtaaggaccg caagaacaaa tgggtcgcag cgagaaagag agagntggat gccctcaaac     780
catgttgcaa caccttccta c                                              801
```

```
<210> SEQ ID NO 772
<211> LENGTH: 618
```

```
<212> TYPE: DNA
<213> ORGANISM: Brassica napus

<400> SEQUENCE: 772
taagacattg ttttataatt tattcaaaca attatttcca ttttaaccaa agttgagcaa      60
ttattgtgga agtttgaaaa attggtagat ttgtcagtaa tgtactatct aaacccatca     120
atagagtgat ggttgaagag agtattggtt tccacccgca atgcaaggaa atcaacttat     180
ctcatttgag ttttgccgat gatattgtgg tttttacrga tggttctcca atgtcgcttc     240
agggtactct aaaggtcttt gaagacttca ctgctatgtc tggtttgcag ataaacatag     300
caaagtccac ggtcttaact gctggtagag gaaagcatgt actagaggat gcagcagctg     360
atgcgggtct ctccgtttct gccctgccta ttaggtatct tggactaccg cttaccacca     420
agataatgtg cagggatgat tatgagccgc ttattactaa gatcaggaac yggttcctct     480
cttggacgag caaagctctc tcatatgcag gtcgattaca acttataaaa tcagttattg     540
ctagtatcac aaacttttgg tgtgctgcgt tctgtcttcc gcaaaactgt atagcggaaa     600
tcgagagtat gtgctctg                                                   618

<210> SEQ ID NO 773
<211> LENGTH: 790
<212> TYPE: DNA
<213> ORGANISM: Brassica napus

<400> SEQUENCE: 773
ccattaacat taggacatta catcttttct tttttgttgc ttttgtccg tacgttatcg       60 tcgtccgttt gaaacttttt aatcttatcc ctaattttt atcatcgtaa gcaaatctag     120
ttttatgttc gagatatgat ggttattgaa atatatatgg gttgtgcttt caataatctt     180
gtccatagtt tttttgtcaa aaaaacccat ccataatcac cagctaccgc cacaaaatct     240
ttatacgtta gcttgttgca gtgaacttta aaaaaaatat tgttgttatt tcaataaaca     300
cggacatggg ccattatgct taatagactt tagtctacag ctttatctct caaaacccat     360
agtaaaacac aagtctaatg atacaagcty agagcctaag catttacaaa tagaaattta     420
aggttaactt ttataattgt tatcaaacat ttcataggca aaagatagaa aatggacaaa     480
ttaacaggta gtatacgatt tctacatttt agcagtattt tatattaatc atgctattaa     540
tttagctgat taaatcattt tatgtagttt atcttctttt tatcaactta tagttttatct    600 ttgttggcaa ataatttgtt ttcttttttaa atcaaaatcg ttgattttat ccatggtaaa     660 cttttgagtat ctaacgcatt ataattttt aaggtctggg aaaataaatc gaatccaaaa    720
atccaagccg aacccgatcc aataaaaatg aatatcaaat ggatcttatt ttatgatatt     780
ttggattatg                                                            790

<210> SEQ ID NO 774
<211> LENGTH: 801
<212> TYPE: DNA
<213> ORGANISM: Brassica napus

<400> SEQUENCE: 774
cttgtctttc ttttttgata gagagaatat tgctctgctt tctkattaga ggctttgatw      60
acatacttta ggtggtaaag ggtctgatcc agattttctg aagaggtaac ttgtattgat     120
tacatacttt agatccaggg tgcgtttata actgataccet ttgcttgtgg tggattttct     180
tttgccagcg aagagctgta agttttgtac tttagtcaat tttgcagctc tacagaacct     240
```

```
tctaagaagc tacctcacta gacaggtgat tytaaagatt ctcttgygtc tgctactgtt    300
cactcttaga tctcagtctt tcctgtttct gaagttacct ttgccaactc tacttattct    360
cgtctttctc gctttctcac ttttttttgtt cttagctttg yagacgggtt aggttagtaa    420
aagccagtgg taaaaaatat gactctgtag aaaggagtat tatatcagta acaaggagat    480
gccttttcat tctgaggacg acaaragtga agactacctc ttcaagattc tgcagctcgg    540
aaatcaaatt ttgctcgcaa gatttgctag ggattagtta tacccagtt aaaagtcgac      600 gactagagtg gagtttcaga cggagatcaa ataacagata tgggacacag aggtgctgtt    660
ggagctcttc tggttcacaa catcagcaga cagaaaactt ttcagagcat tggtagatgg    720
ctttaactag ctgcatagta agaaaactac tcgtgggtaa caagtcggat ctaaagtaca    780
taagcactaa acatcggaag g                                              801
```

<210> SEQ ID NO 775
<211> LENGTH: 21
<212> TYPE: DNA
<213> ORGANISM: Artificial sequence
<220> FEATURE:
<223> OTHER INFORMATION: primer

<400> SEQUENCE: 775
cctgattcaa gaagtcgcag a                                               21

<210> SEQ ID NO 776
<211> LENGTH: 21
<212> TYPE: DNA
<213> ORGANISM: Artificial sequence
<220> FEATURE:
<223> OTHER INFORMATION: primer

<400> SEQUENCE: 776
tcccaagctc aagctagaca a                                               21

<210> SEQ ID NO 777
<211> LENGTH: 19
<212> TYPE: DNA
<213> ORGANISM: Artificial sequence
<220> FEATURE:
<223> OTHER INFORMATION: probe

<400> SEQUENCE: 777
cttagtttca tctgtattc                                                  19

<210> SEQ ID NO 778
<211> LENGTH: 19
<212> TYPE: DNA
<213> ORGANISM: Artificial sequence
<220> FEATURE:
<223> OTHER INFORMATION: probe

<400> SEQUENCE: 778
cttagtttcg tctgtattc                                                  19

<210> SEQ ID NO 779
<211> LENGTH: 31
<212> TYPE: DNA
<213> ORGANISM: Artificial sequence
<220> FEATURE:
<223> OTHER INFORMATION: primer

<400> SEQUENCE: 779
aggacaatcg aacttttcaa tatagacgat t                                    31

<210> SEQ ID NO 780
<211> LENGTH: 25
<212> TYPE: DNA
<213> ORGANISM: Artificial sequence
<220> FEATURE:
<223> OTHER INFORMATION: primer

<400> SEQUENCE: 780
tcgtgactta accatttgtc caact                                         25

<210> SEQ ID NO 781
<211> LENGTH: 15
<212> TYPE: DNA
<213> ORGANISM: Artificial sequence
<220> FEATURE:
<223> OTHER INFORMATION: probe

<400> SEQUENCE: 781
tagagccgaa gactc                                                    15

<210> SEQ ID NO 782
<211> LENGTH: 20
<212> TYPE: DNA
<213> ORGANISM: Artificial sequence
<220> FEATURE:
<223> OTHER INFORMATION: probe

<400> SEQUENCE: 782
atatatagag cagaagactc                                               20

<210> SEQ ID NO 783
<211> LENGTH: 25
<212> TYPE: DNA
<213> ORGANISM: Artificial sequence
<220> FEATURE:
<223> OTHER INFORMATION: primer

<400> SEQUENCE: 783
ccaatgcgtt ctctcaggtt cttat                                         25

<210> SEQ ID NO 784
<211> LENGTH: 25
<212> TYPE: DNA
<213> ORGANISM: Artificial sequence
<220> FEATURE:
<223> OTHER INFORMATION: primer

<400> SEQUENCE: 784
agctaggagg agcctaaacc aatat                                         25

<210> SEQ ID NO 785
<211> LENGTH: 17
<212> TYPE: DNA
<213> ORGANISM: Artificial sequence
<220> FEATURE:
<223> OTHER INFORMATION: probe

<400> SEQUENCE: 785
atggtcgagt ctgcaag                                                  17

<210> SEQ ID NO 786
<211> LENGTH: 17
<212> TYPE: DNA
<213> ORGANISM: Artificial sequence
<220> FEATURE:

<223> OTHER INFORMATION: probe

<400> SEQUENCE: 786
atggtcgagt gtgcaag                                                   17

<210> SEQ ID NO 787
<211> LENGTH: 24
<212> TYPE: DNA
<213> ORGANISM: Artificial sequence
<220> FEATURE:
<223> OTHER INFORMATION: primer

<400> SEQUENCE: 787
accctctggg ttttctgaac tttg                                           24

<210> SEQ ID NO 788
<211> LENGTH: 24
<212> TYPE: DNA
<213> ORGANISM: Artificial sequence
<220> FEATURE:
<223> OTHER INFORMATION: primer

<400> SEQUENCE: 788
aagattttgg tgcgcactac tagt                                           24

<210> SEQ ID NO 789
<211> LENGTH: 19
<212> TYPE: DNA
<213> ORGANISM: Artificial sequence
<220> FEATURE:
<223> OTHER INFORMATION: probe

<400> SEQUENCE: 789
tcgtataaag acggtttaa                                                 19

<210> SEQ ID NO 790
<211> LENGTH: 22
<212> TYPE: DNA
<213> ORGANISM: Artificial sequence
<220> FEATURE:
<223> OTHER INFORMATION: probe

<400> SEQUENCE: 790
ctatcgtata aagagggttt aa                                             22

<210> SEQ ID NO 791
<211> LENGTH: 24
<212> TYPE: DNA
<213> ORGANISM: Artificial sequence
<220> FEATURE:
<223> OTHER INFORMATION: primer

<400> SEQUENCE: 791
ggagaatgcc ttgttgatgt ctca                                           24

<210> SEQ ID NO 792
<211> LENGTH: 25
<212> TYPE: DNA
<213> ORGANISM: Artificial sequence
<220> FEATURE:
<223> OTHER INFORMATION: primer

<400> SEQUENCE: 792
gtcccctttg tgtcatctta tcgat                                          25

<210> SEQ ID NO 793
<211> LENGTH: 17
<212> TYPE: DNA
<213> ORGANISM: Artificial sequence
<220> FEATURE:
<223> OTHER INFORMATION: probe

<400> SEQUENCE: 793
ctagtcagtc aggtttg                                                       17

<210> SEQ ID NO 794
<211> LENGTH: 17
<212> TYPE: DNA
<213> ORGANISM: Artificial sequence
<220> FEATURE:
<223> OTHER INFORMATION: probe

<400> SEQUENCE: 794
ctagtcagac aggtttg                                                       17

<210> SEQ ID NO 795
<211> LENGTH: 23
<212> TYPE: DNA
<213> ORGANISM: Artificial sequence
<220> FEATURE:
<223> OTHER INFORMATION: primer

<400> SEQUENCE: 795
aaggagcttt ccggtctatc tct                                                23

<210> SEQ ID NO 796
<211> LENGTH: 25
<212> TYPE: DNA
<213> ORGANISM: Artificial sequence
<220> FEATURE:
<223> OTHER INFORMATION: primer

<400> SEQUENCE: 796
cgatccttgg ttaatgactg gagat                                              25

<210> SEQ ID NO 797
<211> LENGTH: 18
<212> TYPE: DNA
<213> ORGANISM: Artificial sequence
<220> FEATURE:
<223> OTHER INFORMATION: probe

<400> SEQUENCE: 797
cagttttctc ggagttgt                                                      18

<210> SEQ ID NO 798
<211> LENGTH: 19
<212> TYPE: DNA
<213> ORGANISM: Artificial sequence
<220> FEATURE:
<223> OTHER INFORMATION: probe

<400> SEQUENCE: 798
ccagttttct ccgagttgt                                                     19

<210> SEQ ID NO 799
<211> LENGTH: 22
<212> TYPE: DNA
<213> ORGANISM: Artificial sequence
<220> FEATURE:
<223> OTHER INFORMATION: primer

```
<400> SEQUENCE: 799
ttgcccatca acacctttct ga                                              22

<210> SEQ ID NO 800
<211> LENGTH: 28
<212> TYPE: DNA
<213> ORGANISM: Artificial sequence
<220> FEATURE:
<223> OTHER INFORMATION: primer

<400> SEQUENCE: 800
ctgagaaata aacggatcaa aacccaat                                        28

<210> SEQ ID NO 801
<211> LENGTH: 24
<212> TYPE: DNA
<213> ORGANISM: Artificial sequence
<220> FEATURE:
<223> OTHER INFORMATION: probe

<400> SEQUENCE: 801
catattaaca taactttat ttgg                                             24

<210> SEQ ID NO 802
<211> LENGTH: 24
<212> TYPE: DNA
<213> ORGANISM: Artificial sequence
<220> FEATURE:
<223> OTHER INFORMATION: probe

<400> SEQUENCE: 802
catattaaca taacttaat ttgg                                             24

<210> SEQ ID NO 803
<211> LENGTH: 20
<212> TYPE: DNA
<213> ORGANISM: Artificial sequence
<220> FEATURE:
<223> OTHER INFORMATION: primer

<400> SEQUENCE: 803
ccatggcaag gcacaaacac                                                 20

<210> SEQ ID NO 804
<211> LENGTH: 26
<212> TYPE: DNA
<213> ORGANISM: Artificial sequence
<220> FEATURE:
<223> OTHER INFORMATION: primer

<400> SEQUENCE: 804
cagtttgaag gctcgttagg tattga                                          26

<210> SEQ ID NO 805
<211> LENGTH: 19
<212> TYPE: DNA
<213> ORGANISM: Artificial sequence
<220> FEATURE:
<223> OTHER INFORMATION: probe

<400> SEQUENCE: 805
atgtaagtac acttctttg                                                  19

<210> SEQ ID NO 806
<211> LENGTH: 19
```

```
<212> TYPE: DNA
<213> ORGANISM: Artificial sequence
<220> FEATURE:
<223> OTHER INFORMATION: probe

<400> SEQUENCE: 806
atgtaagtac acatctttg                                          19

<210> SEQ ID NO 807
<211> LENGTH: 21
<212> TYPE: DNA
<213> ORGANISM: Artificial sequence
<220> FEATURE:
<223> OTHER INFORMATION: primer

<400> SEQUENCE: 807
acttggcact tcaccaaacc a                                       21

<210> SEQ ID NO 808
<211> LENGTH: 23
<212> TYPE: DNA
<213> ORGANISM: Artificial sequence
<220> FEATURE:
<223> OTHER INFORMATION: primer

<400> SEQUENCE: 808
cagtccagga tagaggcatg aga                                     23

<210> SEQ ID NO 809
<211> LENGTH: 20
<212> TYPE: DNA
<213> ORGANISM: Artificial sequence
<220> FEATURE:
<223> OTHER INFORMATION: probe

<400> SEQUENCE: 809
atttgatttt gtatcatccg                                         20

<210> SEQ ID NO 810
<211> LENGTH: 20
<212> TYPE: DNA
<213> ORGANISM: Artificial sequence
<220> FEATURE:
<223> OTHER INFORMATION: probe

<400> SEQUENCE: 810
atttgatttt gtataatccg                                         20

<210> SEQ ID NO 811
<211> LENGTH: 20
<212> TYPE: DNA
<213> ORGANISM: Artificial sequence
<220> FEATURE:
<223> OTHER INFORMATION: primer

<400> SEQUENCE: 811
gaagaacacg ccgccttttc                                         20

<210> SEQ ID NO 812
<211> LENGTH: 29
<212> TYPE: DNA
<213> ORGANISM: Artificial sequence
<220> FEATURE:
<223> OTHER INFORMATION: primer

<400> SEQUENCE: 812
```
tcacatcttt gcttattgtc ttcatacca                                       29

<210> SEQ ID NO 813
<211> LENGTH: 19
<212> TYPE: DNA
<213> ORGANISM: Artificial sequence
<220> FEATURE:
<223> OTHER INFORMATION: probe

<400> SEQUENCE: 813
atggaagtac aacttcagc                                                  19

<210> SEQ ID NO 814
<211> LENGTH: 19
<212> TYPE: DNA
<213> ORGANISM: Artificial sequence
<220> FEATURE:
<223> OTHER INFORMATION: probe

<400> SEQUENCE: 814
atggaagtac aagttcagc                                                  19

<210> SEQ ID NO 815
<211> LENGTH: 23
<212> TYPE: DNA
<213> ORGANISM: Artificial sequence
<220> FEATURE:
<223> OTHER INFORMATION: primer

<400> SEQUENCE: 815
gctcgttgct tctctttcca aag                                             23

<210> SEQ ID NO 816
<211> LENGTH: 25
<212> TYPE: DNA
<213> ORGANISM: Artificial sequence
<220> FEATURE:
<223> OTHER INFORMATION: primer

<400> SEQUENCE: 816
caggaggaaa tcaaaagtga aacca                                           25

<210> SEQ ID NO 817
<211> LENGTH: 19
<212> TYPE: DNA
<213> ORGANISM: Artificial sequence
<220> FEATURE:
<223> OTHER INFORMATION: probe

<400> SEQUENCE: 817
ctaaaatcgc tattcttgg                                                  19

<210> SEQ ID NO 818
<211> LENGTH: 20
<212> TYPE: DNA
<213> ORGANISM: Artificial sequence
<220> FEATURE:
<223> OTHER INFORMATION: probe

<400> SEQUENCE: 818
cctaaaatcg ctatacttgg                                                 20

<210> SEQ ID NO 819
<211> LENGTH: 28
<212> TYPE: DNA
<213> ORGANISM: Artificial sequence

```
<220> FEATURE:
<223> OTHER INFORMATION: primer

<400> SEQUENCE: 819
acttatctca tttgagtttt gccgatga                                          28

<210> SEQ ID NO 820
<211> LENGTH: 21
<212> TYPE: DNA
<213> ORGANISM: Artificial sequence
<220> FEATURE:
<223> OTHER INFORMATION: primer

<400> SEQUENCE: 820
gtaccctgaa gcgacattgg a                                                 21

<210> SEQ ID NO 821
<211> LENGTH: 18
<212> TYPE: DNA
<213> ORGANISM: Artificial sequence
<220> FEATURE:
<223> OTHER INFORMATION: probe

<400> SEQUENCE: 821
tggtttttac ggatggtt                                                     18

<210> SEQ ID NO 822
<211> LENGTH: 20
<212> TYPE: DNA
<213> ORGANISM: Artificial sequence
<220> FEATURE:
<223> OTHER INFORMATION: probe

<400> SEQUENCE: 822
tgtggttttt acagatggtt                                                   20

<210> SEQ ID NO 823
<211> LENGTH: 29
<212> TYPE: DNA
<213> ORGANISM: Artificial sequence
<220> FEATURE:
<223> OTHER INFORMATION: primer

<400> SEQUENCE: 823
tctcaaaacc catagtaaaa cacaagtct                                         29

<210> SEQ ID NO 824
<211> LENGTH: 39
<212> TYPE: DNA
<213> ORGANISM: Artificial sequence
<220> FEATURE:
<223> OTHER INFORMATION: primer

<400> SEQUENCE: 824
tgcctatgaa atgtttgata acaattataa aagttaacc                              39

<210> SEQ ID NO 825
<211> LENGTH: 16
<212> TYPE: DNA
<213> ORGANISM: Artificial sequence
<220> FEATURE:
<223> OTHER INFORMATION: probe

<400> SEQUENCE: 825
ttaggctcta agcttg                                                       16
```

```
<210> SEQ ID NO 826
<211> LENGTH: 17
<212> TYPE: DNA
<213> ORGANISM: Artificial sequence
<220> FEATURE:
<223> OTHER INFORMATION: probe

<400> SEQUENCE: 826
cttaggctct gagcttg                                                17

<210> SEQ ID NO 827
<211> LENGTH: 25
<212> TYPE: DNA
<213> ORGANISM: Artificial sequence
<220> FEATURE:
<223> OTHER INFORMATION: primer

<400> SEQUENCE: 827
tcgtctttct cgctttctca ctttt                                       25

<210> SEQ ID NO 828
<211> LENGTH: 29
<212> TYPE: DNA
<213> ORGANISM: Artificial sequence
<220> FEATURE:
<223> OTHER INFORMATION: primer

<400> SEQUENCE: 828
cagagtcata tttttttacca ctggctttt                                  29

<210> SEQ ID NO 829
<211> LENGTH: 14
<212> TYPE: DNA
<213> ORGANISM: Artificial sequence
<220> FEATURE:
<223> OTHER INFORMATION: probe

<400> SEQUENCE: 829
cccgtctaca aagc                                                   14

<210> SEQ ID NO 830
<211> LENGTH: 15
<212> TYPE: DNA
<213> ORGANISM: Artificial sequence
<220> FEATURE:
<223> OTHER INFORMATION: probe

<400> SEQUENCE: 830
acccgtctgc aaagc                                                  15
```

QTLS ASSOCIATED WITH AND METHODS FOR IDENTIFYING SHATTER RESISTANCE IN CANOLA

CROSS-REFERENCE TO RELATED APPLICATIONS

This application claims the benefit of U.S. Application No. 62/162,301, filed May 15, 2015 and U.S. Application No. 62/024,686, filed Jul. 15, 2014, the entire contents of which are herein incorporated by reference.

FIELD OF THE INVENTION

The present invention relates generally to plant molecular biology. More specifically, it relates to quantitative trait loci (QTLs) associated with resistance or tolerance to pod shatter in *Brassica*, and use of those QTLs to identify such resistance or tolerance in *Brassica*.

BACKGROUND OF THE INVENTION

*Brassica napus* (commonly referred to as canola or oilseed rape), which is grown in temperate climates of the northern and southern hemispheres, is an important cultivated oilseed crop species. While herbicide resistance has provided enhanced crop value, *B. napus* remains vulnerable to siliqua or pod shatter, resulting in significant seed loss, especially under adverse weather and harvest conditions. In crops with dry, dehiscent fruits, such as *B. napus*, the siliques or pods naturally release their seeds through a process called fruit dehiscence. When this process occurs prematurely, such as during adverse weather conditions (i.e., wind storm), seed recovery is reduced. This is especially problematic in crops where the oil from the seeds is desired. *B. napus* yield losses due to shatter fall within the range of 10%-25%, with increased losses observed as much as 50% when adverse climate conditions delay harvesting. Shatter can also result in the growth of volunteer plants or weeds.

Many plant species, including *B. napus*, disperse seed through the natural process of fruit dehiscence. In these species, siliques or pods are formed by two carpels that are separated by a thin replum. The dehiscence zone (DZ) is where the valve (fruit wall) margin connects to the replum. As the pod matures late in fruit development, the valve margin detaches from the replum, leading to seed dispersal. The DZ demarcates the precise location where the valves detach.

Several factors have been described to contribute to siliqua shatter resistance, including the morphology, anatomy and biochemistry of siliqua development and physiology, as well as environmental factors. Assessment of *B. napus* accessions for shatter resistance identified two resistant lines (Wen et al, 2008, *Acta Agronomic Sinica* 34: 163-166). Other studies of *B. napus* indicated limited genetic variation. *Brassica rapa* vars Yellow Sarson and Brown Sarson showed genetic variation in increased siliqua strength resulting in shatter resistance. Improved resistance to shatter was seen upon introgression of the trait from these *Brassica* types and *B. juncea*.

Several genes have been identified with putative roles in shatter resistance, including genes involved in dehiscence zone differentiation and their regulatory genes (see review by Hossain et al., 2012, in Plant Breeding, Dr. Ibrokhim Abdurakhmonov (Ed), ISBN: 978-953-307-932-5, InTech at URL intechopen.com/books/plant-breeding/breeding-*brassica-napus*-for-shatter-resistance). WO 2012/084742 A1 discloses *Brassica* plants comprising mutant ALCATRAZ (ALC) genes, ALC nucleic acid sequences and proteins that confer increased pod shatter resistance and reduction or delay of seed shatter, as well as methods for generating and identifying the resistant plants and alleles. US 2012/0023603 A1 discloses plants that comprise at least two IND genes, whereby the plants comprise in their genome either two partial knock-out mutant IND alleles or two partial and two full knock-out mutant IND alleles, and confer reduced shattering while simultaneously maintaining an agronomically acceptable pod threshability. Many other genes with numerous putative functions are described in WO 2012/084742 and US 2012/0023603. It is evident from these disclosures that shatter is controlled by numerous and diverse genetic factors, which are additive and/or interrelated in their effect.

Early methods for evaluating shatter resistance were based on imprecise, subjective visual measurements and manual testing, using field observations, crude mechanical tests and anatomical tests (Hossain et al., 2012, supra). Subsequent mechanical testing methods were developed that demonstrated greater accuracy. Means of measuring the level of resistance to pod shatter tendency are known in the art and include, but are not limited to, the pendulum-based test, cantilever test, manual bending test, microfracture test (MFT), siliqua twisting, 'Ripping' method and Random Impact Test (RIT) (See Hossain, 2012, supra for review). U.S. Pat. No. 7,412,880 B2 describes a device and method for screening crop plants, including *Brassica*, for stalk strength, root lodging, and/or other wind damage resistance traits by selectively applying wind forces to stands of plants in an agricultural environment. Current methods employed to reduce shattering include windrowing (swathing) and spraying desiccants, resulting in increased costs and less flexible farming practices (see Hossain, 2012, supra, for review)

What is needed in the art and industry is a means to identify genes or germplasm conferring resistance to shatter using molecular markers. These markers can then be used to tag the favorable alleles of these genes in segregating populations and then employed to make selection for resistance more effective, and to combine several resistance sources in a single genotype that has a high level of shattering resistance. The present invention provides these and other advantages.

SUMMARY OF THE INVENTION

The present invention provides methods and markers for identifying Quantitative Trait Loci ("QTLs") associated with resistance to shatter in *Brassica*.

One aspect of the invention features a method of identifying a *Brassica* plant or germplasm that exhibits resistance to shatter. The method comprises detecting in the plant or germplasm at least one allele of at least one quantitative trait locus (QTL) that is associated with the shatter resistance, wherein the QTL is localized to a linkage group selected from N1, N3, N4, N6, N7, N9, N13, N14, N15, N18 or N19, wherein each said linkage group comprises at least one marker that is associated with the resistance to shatter with a statistical significance of p≤0.01, wherein the QTL is localized to a chromosomal interval selected from the group consisting of: (a) an interval flanked by and including markers N20003-001-Q001 and N23426-001-Q001 on linkage group N1; (b) an interval flanked by and including markers N05671-1-Q1 and N12643-001-Q001 on linkage group N3; (c) an interval flanked by and including markers N05943-1-Q1 and N88537-001-K001 on linkage group N4; (d) an interval flanked by and including markers N07541-1-Q1 and N14649-001-Q001 on linkage group N6; (e) one or more intervals flanked by and including: (i) markers N23310-001-Q001 and N23409-001-Q001 on linkage group N7, or (ii) markers N07278-1-Q1 and N23417-001-Q001 on linkage group N7; (f) one or more intervals flanked by and including: (i) markers N23119-001-Q001 and N20380-001-Q001 on linkage group N9, or (ii) markers NO5490-1-Q1 and N20834-001-Q001 on linkage group N9; (g) one or more intervals flanked by and including: (i) markers N21144-001-Q001 and N09862-001-Q001 on linkage group N13, or (ii) markers N22903-001-Q001 and N12902-001-Q001 on linkage group N13; (h) one or more intervals flanked by and including: (i) markers N23033-001-Q001 and N22724-001-Q001 on linkage group N14, or (ii) markers N23033-001-Q001 and N22802-001-Q001 on linkage group N14; (i) an interval flanked by and including markers N12785-001-Q001 and N19296-001-Q001 on linkage group N15; (j) one or more intervals flanked by and including: (i) markers N05205-1-Q1 and N22925-001-Q001 on linkage group N18, or (ii) markers N22803-001-Q001 and N18401-001-Q001 on linkage group N18; and (k) an interval flanked by and including markers N05656-1-Q1 and N16006-001-Q001 on linkage group N19; wherein each said linkage group comprises at least one marker that is associated with the shatter resistance with a statistical significance of $p \leq 0.01$, thereby identifying the *Brassica* plant or germplasm that will exhibit shatter resistance. More particularly, the QTL is localized to a chromosomal interval selected from the group consisting of: (a) an interval flanked by and including markers N10336-001-Q001 and N23426-001-Q001 on linkage group N1; (b) one or more intervals flanked by and including (i) markers N88514-001-K001 and N88537-001-K001 on linkage group N4, or (ii) markers N05943-1-Q1 and N06675-1-Q1 on linkage group N4; and (c) one or more intervals flanked by and including (i) markers N001RWT-001-Q001 and N20834-001-Q001 on linkage group N9, or (ii) markers N04807-1-Q1 and N17314-001-Q001 on linkage group N9.

In the method, the marker comprises a polymorphism that identifies the at least one allele of the at least one quantitative trait locus (QTL) as being associated with the shatter resistance, and the detecting comprises identifying the polymorphism. In certain embodiments, the polymorphism is a single nucleotide polymorphism (SNP) or a simple sequence repeat (SSR).

In certain embodiments, the detecting comprises detecting at least one marker selected from the group consisting of: N20003-001-Q001 (SEQ ID NO: 1); N03491-1-Q1 (SEQ ID NO:2); N0017NR-001-Q001 (SEQ ID NO:3); N10336-001-Q001 (SEQ ID NO:4); N23133-001-Q001 (SEQ ID NO:5); N16487-001-Q001 (SEQ ID NO:6); N23426-001-Q001 (SEQ ID NO:7); N05671-1-Q1 (SEQ ID NO:8); N12643-001-Q001 (SEQ ID NO:9); N05943-1-Q1 (SEQ ID NO:10); N06007-1-Q1 (SEQ ID NO: 11); N10105-001-Q001 (SEQ ID NO:12); N08181-1-Q1 (SEQ ID NO:13); N06675-1-Q1 (SEQ ID NO:14); N001KH2-001-Q001 (SEQ ID NO:15); N29313-001-Q001 (SEQ ID NO:16); N88512-001-K001 (SEQ ID NO:17); N88514-001-K001 (SEQ ID NO:18); N88515-001-K001 (SEQ ID NO:19); N88516-001-K001 (SEQ ID NO:20); N88517-001-K001 (SEQ ID NO:21); N88518-001-K001 (SEQ ID NO:22); N88519-001-K001 (SEQ ID NO:23); N88520-001-K001 (SEQ ID NO:24); N88521-001-K001 (SEQ ID NO:25); N001KFE-001-Q001 (SEQ ID NO:26); N88522-001-K001 (SEQ ID NO:27); N88523-001-K001 (SEQ ID NO:28); N88524-001-K001 (SEQ ID NO:29); N88525-001-K001 (SEQ ID NO:30); N88529-001-K001 (SEQ ID NO:31); N88530-001-K001 (SEQ ID NO:32); N88531-001-K001 (SEQ ID NO:33); N88533-001-K001 (SEQ ID NO:34); N88535-001-K001 (SEQ ID NO:35); N88536-001-K001 (SEQ ID NO:36); N88537-001-K001 (SEQ ID NO:37); N07541-1-Q1 (SEQ ID NO:38); N23413-001-Q001 (SEQ ID NO:39); N08344-1-Q1 (SEQ ID NO:40); N23533-001-Q011 (SEQ ID NO:41); N14649-001-Q001 (SEQ ID NO:42); N23310-001-Q001 (SEQ ID NO:43); N10526-001-Q001 (SEQ ID NO:44); N23373-001-Q001 (SEQ ID NO:45); N23353-001-Q001 (SEQ ID NO:46); N23206-001-Q001 (SEQ ID NO:47); N11025-001-Q001 (SEQ ID NO:48); N09969-001-Q001 (SEQ ID NO:49); N09882-001-Q001 (SEQ ID NO:50); N10389-001-Q001 (SEQ ID NO:51); N09940-001-Q001 (SEQ ID NO:52); N23409-001-Q001 (SEQ ID NO:53); N23119-001-Q001 (SEQ ID NO:54); N09861-001-Q001 (SEQ ID NO:55); N04807-1-Q1 (SEQ ID NO:56); N06778-1-Q1 (SEQ ID NO:57); N09897-001-Q001 (SEQ ID NO:58); N10499-001-Q001 (SEQ ID NO:59); N23447-001-Q001 (SEQ ID NO:60); N19834-001-Q001 (SEQ ID NO:61); N23362-001-Q001 (SEQ ID NO:62); N23266-001-Q001 (SEQ ID NO:63); N19862-001-Q001 (SEQ ID NO:64); N22187-001-Q001 (SEQ ID NO:65); N08651-1-Q1 (SEQ ID NO:66); N23296-001-Q001 (SEQ ID NO:67); N17314-001-Q001 (SEQ ID NO:68); N20380-001-Q001 (SEQ ID NO:69); N05490-1-Q1 (SEQ ID NO:70); N18849-001-Q001 (SEQ ID NO:71); N08200-1-Q1 (SEQ ID NO:72); N19827-001-Q001 (SEQ ID NO:73); N001R9W-001-Q001 (SEQ ID NO:74); N08264-1-Q1 (SEQ ID NO:75); N23132-001-Q001 (SEQ ID NO:76); N03615-1-Q1 (SEQ ID NO:77); N001RWT-001-Q001 (SEQ ID NO:78); N08465-1-Q1 (SEQ ID NO:79); N10774-001-Q001 (SEQ ID NO:80); N17035-001-Q001 (SEQ ID NO:81); N20834-001-Q001 (SEQ ID NO:82); N22903-001-Q001 (SEQ ID NO:83); N09920-001-Q001 (SEQ ID NO:84); N22822-001-Q001 (SEQ ID NO:85); N22688-001-Q001 (SEQ ID NO:86); N10074-001-Q001 (SEQ ID NO:87); N10057-001-Q001 (SEQ ID NO:88); N10086-001-Q001 (SEQ ID NO:89); N11084-001-Q001 (SEQ ID NO:90); N22814-001-Q001 (SEQ ID NO:91); N01564-2-Q1 (SEQ ID NO:92); N12902-001-Q001 (SEQ ID NO:93); N21144-001-Q001 (SEQ ID NO:94); N07534-1-Q1 (SEQ ID NO:95); N22993-001-Q001 (SEQ ID NO:96); N09963-001-Q001 (SEQ ID NO:97); N11542-001-Q001 (SEQ ID NO:98); N14681-001-Q001 (SEQ ID NO:99); N11636-001-Q001 (SEQ ID NO:100); N13732-001-Q001 (SEQ ID NO: 101); N11255-001-Q001 (SEQ ID NO: 102); N15511-001-Q001 (SEQ ID NO: 103); N10536-001-Q001 (SEQ ID NO:104); N09862-001-Q001 (SEQ ID NO:105); N23033-001-Q001 (SEQ ID NO:106); N06039-1-Q1 (SEQ ID NO:107); N10016-001-Q001 (SEQ ID NO:108); N22743-001-Q001 (SEQ ID NO:109); N22953-001-Q001 (SEQ ID NO: 110); N09987-001-Q001 (SEQ ID NO:111); N10092-001-Q001 (SEQ ID NO: 112); N10096-001-Q001 (SEQ ID NO: 113); N22728-001-Q001 (SEQ ID NO: 114); N22747-001-Q001 (SEQ ID NO:115); N22840-001-Q001 (SEQ ID NO:116); N23027-001-Q001 (SEQ ID NO:117); N22777-001-Q001 (SEQ ID NO:118); N09636-001-Q001 (SEQ ID NO: 119); N09879-001-Q001 (SEQ ID NO: 120); N10123-001-Q001 (SEQ ID NO:121); N10316-001-Q001 (SEQ ID NO: 122); N10507-001-Q001 (SEQ ID NO: 123); N09834-001-Q001 (SEQ ID NO: 124); N22934-001-Q001 (SEQ ID NO:125); N22700-001-Q001 (SEQ ID NO: 126); N22725-001-Q001 (SEQ ID NO: 127); N22881-001-Q001 (SEQ ID NO: 128); N23032-001-Q001 (SEQ ID NO:129); N22786-001-Q001 (SEQ ID NO:130); N23014-001-Q001 (SEQ ID NO:131); N10471-001-Q001 (SEQ ID NO:132); N11419-001-Q001 (SEQ ID NO: 133); N22724-001-Q001 (SEQ ID NO: 134); N12785-001-Q001 (SEQ ID NO: 135); N09910-001-Q001 (SEQ ID NO:136); N21146-001-Q001 (SEQ ID NO:137); N17618-001-Q001 (SEQ ID NO:138); N09776-001-Q001 (SEQ ID NO:139); N19296-001-Q001 (SEQ ID NO:140); N05205-1-Q1 (SEQ ID NO:141); N10406-001-Q001 (SEQ ID NO:142); N22941-001-Q001 (SEQ ID NO:143); N22875-001-Q001 (SEQ ID NO:144); N13286-001-Q001 (SEQ ID NO:145); N04503-1-Q1 (SEQ ID NO:146); N22925-001-Q001 (SEQ ID NO: 147); N05656-1-Q1 (SEQ ID NO: 148); N17581-001-Q001 (SEQ ID NO: 149); N001NVH-001-Q001 (SEQ ID NO: 150); N22928-001-Q001 (SEQ ID NO: 151); N08219-1-Q001 (SEQ ID NO:152); N05710-1-Q1 (SEQ ID NO: 153); N15338-001-Q001 (SEQ ID NO: 154); N10424-001-Q001 (SEQ ID NO: 155); N16006-001-Q001 (SEQ ID NO: 156), N07278-1-Q1 (SEQ ID NO: 761); N16343-001-Q001 (SEQ ID NO: 762); N23417-001-Q001 (SEQ ID NO: 763); N22902-001-Q001 (SEQ ID NO: 764); N23063-001-Q001 (SEQ ID NO: 765); N22723-001-Q001 (SEQ ID NO: 766); N23049-001-Q001 (SEQ ID NO: 767); N10321-001-Q001 (SEQ ID NO: 768); N15374-001-Q001 (SEQ ID NO: 769); N22802-001-Q001 (SEQ ID NO: 770), N22803-001-Q001 (SEQ ID NO: 771), N18929-001-Q001 (SEQ ID NO: 772); N16041-001-Q001 (SEQ ID NO: 773); and N18401-001-Q001 (SEQ ID NO: 774).

More particularly, the detecting comprises detecting at least one marker selected from the group consisting of: N88514-001-K001 (SEQ ID NO:18); N88515-001-K001 (SEQ ID NO: 19); N88516-001-K001 (SEQ ID NO:20); N88517-001-K001 (SEQ ID NO:21); N88518-001-K001 (SEQ ID NO:22); N88519-001-K001 (SEQ ID NO:23); N88520-001-K001 (SEQ ID NO:24); N88521-001-K001 (SEQ ID NO:25); N001KFE-001-Q001 (SEQ ID NO:26); N88522-001-K001 (SEQ ID NO:27); N88523-001-K001 (SEQ ID NO:28); N88524-001-K001 (SEQ ID NO:29); N88525-001-K001 (SEQ ID NO:30); N88529-001-K001 (SEQ ID NO:31); N88530-001-K001 (SEQ ID NO:32); N88531-001-K001 (SEQ ID NO:33); N88533-001-K001 (SEQ ID NO:34); N88535-001-K001 (SEQ ID NO:35); N88536-001-K001 (SEQ ID NO:36); and N88537-001-K001 (SEQ ID NO:37).

In certain embodiments, the method comprises detecting two or more markers located in two or more different linkage groups. The detecting can involve amplifying the marker from genomic DNA of the plant or germplasm and determining if the marker comprises the polymorphism associated with the shatter resistance.

The Brassica plant to which the method is applied can be Brassica napus; Brassica juncea; Brassica rapa; Brassica oleracea; or Brassica carinata. In particular, the plant is Brassica napus (canola), and can be spring canola, winter canola or semi-winter canola.

Another aspect of the invention features a method of introgressing shatter resistance in a second plant by cross pollinating the identified plant or a progeny thereof of claim 1 with a second plant, wherein the second plant lacks the at least one allele of the at least one QTL detected in the identified plant.

Yet another aspect of the invention features a method of producing an F1 hybrid seed, wherein the F1 hybrid plant derived from the F1 hybrid seed exhibits shatter resistance, the method comprising cross pollinating the identified plant or progeny thereof of claim 1 with a second plant, wherein the second plant lacks the at least one allele of the at least one QTL detected in the identified plant.

Still another aspect of the invention features a method of positional cloning of a nucleic acid comprising a quantitative trait locus (QTL) associated with shatter resistance. The method comprises: (a) providing a nucleic acid from a plant comprising a marker that is associated with shatter resistance with a statistical significance of $p \leq 0.01$, wherein the QTL is localized to a linkage group selected from N1, N3, N4, N6, N7, N9, N13, N14, N15, N18 or N19 and intervals therein as set forth in the method described above, and wherein the linkage group comprises the marker; and (b) cloning the nucleic acid comprising a quantitative trait locus (QTL) associated with shatter resistance.

Yet another aspect of the invention features a method of making a transgenic dicot comprising a quantitative trait locus (QTL) associated with shatter resistance. The method comprises the steps of: (a) introducing a nucleic acid cloned according to the above-described cloning method into a dicot cell; and (b) growing the cell under cell growth conditions.

Still another aspect of the invention features a method of identifying a candidate nucleic acid comprising a QTL associated with shatter resistance from a dicot. This method comprises: (a) providing a nucleic acid cloned according to the above-described method; and (b) identifying a homolog of the nucleic acid in a dicot.

Another aspect of the invention features a method of marker assisted selection (MAS) of a quantitative trait locus (QTL) associated with shatter resistance in Brassica. This method comprises the steps of: (a) obtaining a first Brassica plant having at least one allele of a marker locus associated with the shatter resistance with a statistical significance of $p \leq 0.01$ as described above; (b) crossing the first Brassica plant with a second Brassica plant; (c) evaluating the progeny for the allele associated with the shatter resistance; and (d) selecting progeny plants that possess the allele. In one embodiment, the plant is a member of a segregating population. In certain embodiments, the marker assisted selection is performed using high throughput screening.

Another aspect of the invention features a Brassica plant identified by the marker assisted breeding method described above. Progeny of that Brassica plant are also provided, particularly F1, F2, and/or F3 progeny.

Another aspect of the invention features an isolated or recombinant nucleic acid comprising a polynucleotide selected from: (a) a sequence selected from any one of marker sequences: N20003-001-Q001 (SEQ ID NO: 1); N03491-1-Q1 (SEQ ID NO:2); N10336-001-Q001 (SEQ ID NO:4); N23133-001-Q001 (SEQ ID NO:5); N16487-001-Q001 (SEQ ID NO:6); N23426-001-Q001 (SEQ ID NO:7); N05671-1-Q1 (SEQ ID NO:8); N12643-001-Q001 (SEQ ID NO:9); N05943-1-Q1 (SEQ ID NO:10); N06007-1-Q1 (SEQ ID NO: 11); N10105-001-Q001 (SEQ ID NO:12); N08181-1-Q1 (SEQ ID NO:13); N06675-1-Q1 (SEQ ID NO:14); N29313-001-Q001 (SEQ ID NO:16); N88512-001-K001 (SEQ ID NO: 17); N88514-001-K001 (SEQ ID NO: 18); N88515-001-K001 (SEQ ID NO: 19); N88516-001-K001 (SEQ ID NO:20); N88517-001-K001 (SEQ ID NO:21); N88518-001-K001 (SEQ ID NO:22); N88519-001-K001 (SEQ ID NO:23); N88520-001-K001 (SEQ ID NO:24); N88521-001-K001 (SEQ ID NO:25); N88522-001-K001 (SEQ ID NO:27); N88523-001-K001 (SEQ ID NO:28); N88524-001-K001 (SEQ ID NO:29); N88525-001-K001 (SEQ ID NO:30); N88529-001-K001 (SEQ ID NO:31); N88530-001-K001 (SEQ ID NO:32); N88531-001-K001 (SEQ ID NO:33); N88533-001-K001 (SEQ ID NO:34); N88535-001-K001 (SEQ ID NO:35); N88536-001-K001 (SEQ ID NO:36); N88537-001-K001 (SEQ ID NO:37); N07541-1-Q1 (SEQ ID NO:38); N23413-001-Q001 (SEQ ID NO:39); N08344-1-Q1 (SEQ ID NO:40); N23533-001-Q011 (SEQ ID NO:41); N14649-001-Q001 (SEQ ID NO:42); N23310-001-Q001 (SEQ ID NO:43); N10526-001-Q001 (SEQ ID NO:44); N23373-001-Q001 (SEQ ID NO:45); N23353-001-Q001 (SEQ ID NO:46); N23206-001-Q001 (SEQ ID NO:47); N11025-001-Q001 (SEQ ID NO:48); N09969-001-Q001 (SEQ ID NO:49); N09882-001-Q001 (SEQ ID NO:50); N10389-001-Q001 (SEQ ID NO:51); N09940-001-Q001 (SEQ ID NO:52); N23409-001-Q001 (SEQ ID NO:53); N23119-001-Q001 (SEQ ID NO:54); N09861-001-Q001 (SEQ ID NO:55); N04807-1-Q1 (SEQ ID NO:56); N06778-1-Q1 (SEQ ID NO:57); N09897-001-Q001 (SEQ ID NO:58); N10499-001-Q001 (SEQ ID NO:59); N23447-001-Q001 (SEQ ID NO:60); N19834-001-Q001 (SEQ ID NO:61); N23362-001-Q001 (SEQ ID NO:62); N23266-001-Q001 (SEQ ID NO:63); N19862-001-Q001 (SEQ ID NO:64); N22187-001-Q001 (SEQ ID NO:65); N08651-1-Q1 (SEQ ID NO:66); N23296-001-Q001 (SEQ ID NO:67); N17314-001-Q001 (SEQ ID NO:68); N20380-001-Q001 (SEQ ID NO:69); N05490-1-Q1 (SEQ ID NO:70); N18849-001-Q001 (SEQ ID NO:71); N08200-1-Q1 (SEQ ID NO:72); N19827-001-Q001 (SEQ ID NO:73); N08264-1-Q1 (SEQ ID NO:75); N23132-001-Q001 (SEQ ID NO:76); N03615-1-Q1 (SEQ ID NO:77); N08465-1-Q1 (SEQ ID NO:79); N10774-001-Q001 (SEQ ID NO:80); N17035-001-Q001 (SEQ ID NO:81); N20834-001-Q001 (SEQ ID NO:82); N22903-001-Q001 (SEQ ID NO:83); N09920-001-Q001 (SEQ ID NO:84); N22822-001-Q001 (SEQ ID NO:85); N22688-001-Q001 (SEQ ID NO:86); N10074-001-Q001 (SEQ ID NO:87); N10057-001-Q001 (SEQ ID NO:88); N10086-001-Q001 (SEQ ID NO:89); N11084-001-Q001 (SEQ ID NO:90); N22814-001-Q001 (SEQ ID NO:91); N01564-2-Q1 (SEQ ID NO:92); N12902-001-Q001 (SEQ ID NO:93); N21144-001-Q001 (SEQ ID NO:94); N07534-1-Q1 (SEQ ID NO:95); N22993-001-Q001 (SEQ ID NO:96); N09963-001-Q001 (SEQ ID NO:97); N11542-001-Q001 (SEQ ID NO:98); N14681-001-Q001 (SEQ ID NO:99); N11636-001-Q001 (SEQ ID NO: 100); N13732-001-Q001 (SEQ ID NO: 101); N11255-001-Q001 (SEQ ID NO: 102); N15511-001-Q001 (SEQ ID NO: 103); N10536-001-Q001 (SEQ ID NO: 104); N09862-001-Q001 (SEQ ID NO:105); N23033-001-Q001 (SEQ ID NO:106); N06039-1-Q1 (SEQ ID NO:107); N10016-001-Q001 (SEQ ID NO:108); N22743-001-Q001 (SEQ ID NO: 109); N22953-001-Q001 (SEQ ID NO: 110); N09987-001-Q001 (SEQ ID NO: 111); N10092-001-Q001 (SEQ ID NO: 112); N10096-001-Q001 (SEQ ID NO: 113); N22728-001-Q001 (SEQ ID NO: 114); N22747-001-Q001 (SEQ ID NO: 115); N22840-001-Q001 (SEQ ID NO: 116); N23027-001-Q001 (SEQ ID NO: 117); N22777-001-Q001 (SEQ ID NO: 118); N09636-001-Q001 (SEQ ID NO:119); N09879-001-Q001 (SEQ ID NO:120); N10123-001-Q001 (SEQ ID NO:121); N10316-001-Q001 (SEQ ID NO:122); N10507-001-Q001 (SEQ ID NO:123); N09834-001-Q001 (SEQ ID NO:124); N22934-001-Q001 (SEQ ID NO: 125); N22700-001-Q001 (SEQ ID NO:126); N22725-001-Q001 (SEQ ID NO:127); N22881-001-Q001 (SEQ ID NO:128); N23032-001-Q001 (SEQ ID NO:129); N22786-001-Q001 (SEQ ID NO:130); N23014-001-Q001 (SEQ ID NO:131); N10471-001-Q001 (SEQ ID NO: 132); N11419-001-Q001 (SEQ ID NO:133); N22724-001-Q001 (SEQ ID NO:134); N12785-001-Q001 (SEQ ID NO:135); N09910-001-Q001 (SEQ ID NO:136); N21146-001-Q001 (SEQ ID NO:137); N17618-001-Q001 (SEQ ID NO:138); N09776-001-Q001 (SEQ ID NO:139); N19296-001-Q001 (SEQ ID NO: 140); N05205-1-Q1 (SEQ ID NO:141); N10406-001-Q001 (SEQ ID NO:142); N22941-001-Q001 (SEQ ID NO:143); N22875-001-Q001 (SEQ ID NO:144); N13286-001-Q001 (SEQ ID NO:145); N04503-1-Q1 (SEQ ID NO: 146); N22925-001-Q001 (SEQ ID NO: 147); N05656-1-Q1 (SEQ ID NO: 148); N17581-001-Q001 (SEQ ID NO: 149); N22928-001-Q001 (SEQ ID NO:151); N08219-1-Q001 (SEQ ID NO:152); N05710-1-Q1 (SEQ ID NO: 153); N15338-001-Q001 (SEQ ID NO: 154); N10424-001-Q001 (SEQ ID NO: 155); N16006-001-Q001 (SEQ ID NO: 156); N07278-1-Q1 (SEQ ID NO: 761); N16343-001-Q001 (SEQ ID NO: 762); N23417-001-Q001 (SEQ ID NO: 763); N22902-001-Q001 (SEQ ID NO: 764); N23063-001-Q001 (SEQ ID NO: 765); N22723-001-Q001 (SEQ ID NO: 766); N23049-001-Q001 (SEQ ID NO: 767); N10321-001-Q001 (SEQ ID NO: 768); N15374-001-Q001 (SEQ ID NO: 769); N22802-001-Q001 (SEQ ID NO: 770), N22803-001-Q001 (SEQ ID NO: 771), N18929-001-Q001 (SEQ ID NO: 772); N16041-001-Q001 (SEQ ID NO: 773); and N18401-001-Q001 (SEQ ID NO: 774), (b) a polynucleotide sequence with at least 70% sequence identity to the polynucleotide of (a); and (c) a polynucleotide sequence complementary to the sequence of (a) or (b). In particular, the isolated or recombinant nucleic acid comprises a polynucleotide selected from: (a) a sequence selected from any one of marker sequences: N88514-001-K001 (SEQ ID NO:18); N88515-001-K001 (SEQ ID NO:19); N88516-001-K001 (SEQ ID NO:20); N88517-001-K001 (SEQ ID NO:21); N88518-001-K001 (SEQ ID NO:22); N88519-001-K001 (SEQ ID NO:23); N88520-001-K001 (SEQ ID NO:24); N88521-001-K001 (SEQ ID NO:25); N88522-001-K001 (SEQ ID NO:27); N88523-001-K001 (SEQ ID NO:28); N88524-001-K001 (SEQ ID NO:29); N88525-001-K001 (SEQ ID NO:30); N88529-001-K001 (SEQ ID NO:31); N88530-001-K001 (SEQ ID NO:32); N88531-001-K001 (SEQ ID NO:33); N88533-001-K001 (SEQ ID NO:34); N88535-001-K001 (SEQ ID NO:35); N88536-001-K001 (SEQ ID NO:36); and N88537-001-K001 (SEQ ID NO:37); (b) a polynucleotide sequence with at least 70% sequence identity to the polynucleotide of (a); and (c) a polynucleotide sequence complementary to the sequence of (a) or (b). In certain embodiments, the above-described isolated or recombinant nucleic acid is associated with shatter resistance in *Brassica*.

Another aspect of the invention features a synthetic and/or chemically modified nucleic acid molecule that detects a polymorphism in a *Brassica* plant DNA associated with shatter resistance, wherein the nucleic acid molecule comprises at least 10 nucleotides and is identical to a sequence of the same number of consecutive nucleotides in either strand of the plant DNA where the polymorphism is located, wherein the nucleic acid molecule comprises a sequence that is at least 70% identical to a marker sequence or a fragment of a marker sequence selected from the group consisting of: N20003-001-Q001 (SEQ ID NO: 1); N03491-1-Q1 (SEQ ID NO:2); N0017NR-001-Q001 (SEQ ID NO:3); N10336-001-Q001 (SEQ ID NO:4); N23133-001-Q001 (SEQ ID NO:5); N16487-001-Q001 (SEQ ID NO:6); N23426-001-Q001 (SEQ ID NO:7); N05671-1-Q1 (SEQ ID NO:8); N12643-001-Q001 (SEQ ID NO:9); N05943-1-Q1 (SEQ ID NO:10); N06007-1-Q1 (SEQ ID NO: 11); N10105-001-Q001 (SEQ ID NO:12); N08181-1-Q1 (SEQ ID NO:13); N06675-1-Q1 (SEQ ID NO:14); N001KH2-001-Q001 (SEQ ID NO:15); N29313-001-Q001 (SEQ ID NO:16); N88512-001-K001 (SEQ ID NO: 17); N88514-001-K001 (SEQ ID NO: 18); N88515-001-K001 (SEQ ID NO:19); N88516-001-K001 (SEQ ID NO:20); N88517-001-K001 (SEQ ID NO:21); N88518-001-K001 (SEQ ID NO:22); N88519-001-K001

(SEQ ID NO:23); N88520-001-K001 (SEQ ID NO:24); N88521-001-K001 (SEQ ID NO:25); N001KFE-001-Q001 (SEQ ID NO:26); N88522-001-K001 (SEQ ID NO:27); N88523-001-K001 (SEQ ID NO:28); N88524-001-K001 (SEQ ID NO:29); N88525-001-K001 (SEQ ID NO:30); N88529-001-K001 (SEQ ID NO:31); N88530-001-K001 (SEQ ID NO:32); N88531-001-K001 (SEQ ID NO:33); N88533-001-K001 (SEQ ID NO:34); N88535-001-K001 (SEQ ID NO:35); N88536-001-K001 (SEQ ID NO:36); N88537-001-K001 (SEQ ID NO:37); N07541-1-Q1 (SEQ ID NO:38); N23413-001-Q001 (SEQ ID NO:39); N08344-1-Q1 (SEQ ID NO:40); N23533-001-Q011 (SEQ ID NO:41); N14649-001-Q001 (SEQ ID NO:42); N23310-001-Q001 (SEQ ID NO:43); N10526-001-Q001 (SEQ ID NO:44); N23373-001-Q001 (SEQ ID NO:45); N23353-001-Q001 (SEQ ID NO:46); N23206-001-Q001 (SEQ ID NO:47); N11025-001-Q001 (SEQ ID NO:48); N09969-001-Q001 (SEQ ID NO:49); N09882-001-Q001 (SEQ ID NO:50); N10389-001-Q001 (SEQ ID NO:51); N09940-001-Q001 (SEQ ID NO:52); N23409-001-Q001 (SEQ ID NO:53); N23119-001-Q001 (SEQ ID NO:54); N09861-001-Q001 (SEQ ID NO:55); N04807-1-Q1 (SEQ ID NO:56); N06778-1-Q1 (SEQ ID NO:57); N09897-001-Q001 (SEQ ID NO:58); N10499-001-Q001 (SEQ ID NO:59); N23447-001-Q001 (SEQ ID NO:60); N19834-001-Q001 (SEQ ID NO:61); N23362-001-Q001 (SEQ ID NO:62); N23266-001-Q001 (SEQ ID NO:63); N19862-001-Q001 (SEQ ID NO:64); N22187-001-Q001 (SEQ ID NO:65); N08651-1-Q1 (SEQ ID NO:66); N23296-001-Q001 (SEQ ID NO:67); N17314-001-Q001 (SEQ ID NO:68); N20380-001-Q001 (SEQ ID NO:69); N05490-1-Q1 (SEQ ID NO:70); N18849-001-Q001 (SEQ ID NO:71); N08200-1-Q1 (SEQ ID NO:72); N19827-001-Q001 (SEQ ID NO:73); N001R9W-001-Q001 (SEQ ID NO:74); N08264-1-Q1 (SEQ ID NO:75); N23132-001-Q001 (SEQ ID NO:76); N03615-1-Q1 (SEQ ID NO:77); N001RWT-001-Q001 (SEQ ID NO:78); N08465-1-Q1 (SEQ ID NO:79); N10774-001-Q001 (SEQ ID NO:80); N17035-001-Q001 (SEQ ID NO:81); N20834-001-Q001 (SEQ ID NO:82); N22903-001-Q001 (SEQ ID NO:83); N09920-001-Q001 (SEQ ID NO:84); N22822-001-Q001 (SEQ ID NO:85); N22688-001-Q001 (SEQ ID NO:86); N10074-001-Q001 (SEQ ID NO:87); N10057-001-Q001 (SEQ ID NO:88); N10086-001-Q001 (SEQ ID NO:89); N11084-001-Q001 (SEQ ID NO:90); N22814-001-Q001 (SEQ ID NO:91); N01564-2-Q1 (SEQ ID NO:92); N12902-001-Q001 (SEQ ID NO:93); N21144-001-Q001 (SEQ ID NO:94); N07534-1-Q1 (SEQ ID NO:95); N22993-001-Q001 (SEQ ID NO:96); N09963-001-Q001 (SEQ ID NO:97); N11542-001-Q001 (SEQ ID NO:98); N14681-001-Q001 (SEQ ID NO:99); N11636-001-Q001 (SEQ ID NO:100); N13732-001-Q001 (SEQ ID NO:101); N11255-001-Q001 (SEQ ID NO: 102); N15511-001-Q001 (SEQ ID NO: 103); N10536-001-Q001 (SEQ ID NO: 104); N09862-001-Q001 (SEQ ID NO:105); N23033-001-Q001 (SEQ ID NO:106); N06039-1-Q1 (SEQ ID NO:107); N10016-001-Q001 (SEQ ID NO:108); N22743-001-Q001 (SEQ ID NO:109); N22953-001-Q001 (SEQ ID NO: 110); N09987-001-Q001 (SEQ ID NO: 111); N10092-001-Q001 (SEQ ID NO: 112); N10096-001-Q001 (SEQ ID NO: 113); N22728-001-Q001 (SEQ ID NO: 114); N22747-001-Q001 (SEQ ID NO:115); N22840-001-Q001 (SEQ ID NO:116); N23027-001-Q001 (SEQ ID NO:117); N22777-001-Q001 (SEQ ID NO:118); N09636-001-Q001 (SEQ ID NO: 119); N09879-001-Q001 (SEQ ID NO: 120); N10123-001-Q001 (SEQ ID NO:121); N10316-001-Q001 (SEQ ID NO:122); N10507-001-Q001 (SEQ ID NO: 123); N09834-001-Q001 (SEQ ID NO: 124); N22934-001-Q001 (SEQ ID NO: 125); N22700-001-Q001 (SEQ ID NO:126); N22725-001-Q001 (SEQ ID NO:127); N22881-001-Q001 (SEQ ID NO:128); N23032-001-Q001 (SEQ ID NO:129); N22786-001-Q001 (SEQ ID NO:130); N23014-001-Q001 (SEQ ID NO:131); N10471-001-Q001 (SEQ ID NO:132); N11419-001-Q001 (SEQ ID NO: 133); N22724-001-Q001 (SEQ ID NO: 134); N12785-001-Q001 (SEQ ID NO:135); N09910-001-Q001 (SEQ ID NO:136); N21146-001-Q001 (SEQ ID NO:137); N17618-001-Q001 (SEQ ID NO:138); N09776-001-Q001 (SEQ ID NO:139); N19296-001-Q001 (SEQ ID NO: 140); N05205-1-Q1 (SEQ ID NO: 141); N10406-001-Q001 (SEQ ID NO:142); N22941-001-Q001 (SEQ ID NO:143); N22875-001-Q001 (SEQ ID NO: 144); N13286-001-Q001 (SEQ ID NO: 145); N04503-1-Q1 (SEQ ID NO: 146); N22925-001-Q001 (SEQ ID NO:147); N05656-1-Q1 (SEQ ID NO:148); N17581-001-Q001 (SEQ ID NO: 149); N001NVH-001-Q001 (SEQ ID NO: 150); N22928-001-Q001 (SEQ ID NO: 151); N08219-1-Q001 (SEQ ID NO: 152); N05710-1-Q1 (SEQ ID NO: 153); N15338-001-Q001 (SEQ ID NO:154); N10424-001-Q001 (SEQ ID NO:155); N16006-001-Q001 (SEQ ID NO:156); N07278-1-Q1 (SEQ ID NO: 761); N16343-001-Q001 (SEQ ID NO: 762); N23417-001-Q001 (SEQ ID NO: 763); N22902-001-Q001 (SEQ ID NO: 764); N23063-001-Q001 (SEQ ID NO: 765); N22723-001-Q001 (SEQ ID NO: 766); N23049-001-Q001 (SEQ ID NO: 767); N10321-001-Q001 (SEQ ID NO: 768); N15374-001-Q001 (SEQ ID NO: 769); N22802-001-Q001 (SEQ ID NO: 770), N22803-001-Q001 (SEQ ID NO: 771), N18929-001-Q001 (SEQ ID NO: 772); N16041-001-Q001 (SEQ ID NO: 773); and N18401-001-Q001 (SEQ ID NO: 774).

In particular embodiments, the synthetic nucleic acid molecule is selected from any one of SEQ ID NOs: 157-760 and SEQ ID NOs: 775-830.

In certain embodiments, the synthetic nucleic acid molecule is associated with a marker sequence selected from any one of: N88514-001-K001 (SEQ ID NO:18); N88515-001-K001 (SEQ ID NO: 19); N88516-001-K001 (SEQ ID NO:20); N88517-001-K001 (SEQ ID NO:21); N88518-001-K001 (SEQ ID NO:22); N88519-001-K001 (SEQ ID NO:23); N88520-001-K001 (SEQ ID NO:24); N88521-001-K001 (SEQ ID NO:25); N001KFE-001-Q001 (SEQ ID NO:26); N88522-001-K001 (SEQ ID NO:27); N88523-001-K001 (SEQ ID NO:28); N88524-001-K001 (SEQ ID NO:29); N88525-001-K001 (SEQ ID NO:30); N88529-001-K001 (SEQ ID NO:31); N88530-001-K001 (SEQ ID NO:32); N88531-001-K001 (SEQ ID NO:33); N88533-001-K001 (SEQ ID NO:34); N88535-001-K001 (SEQ ID NO:35); N88536-001-K001 (SEQ ID NO:36); and N88537-001-K001 (SEQ ID NO:37). In particular embodiments, the synthetic nucleic acid molecule is selected from any one of SEQ ID NOs: 236-285.

Another aspect of the invention features a kit for screening a plant or germplasm for a QTL associated with shatter resistance. The kit includes a container in which is contained: (a) a plurality of synthetic and/or chemically modified nucleic acid molecules that detect polymorphism in *Brassica* plant DNA associated with shatter resistance, wherein each nucleic acid molecule comprises at least 10 nucleotides and is identical to a sequence of the same number of consecutive nucleotides in either strand of the plant DNA where the polymorphism is located, wherein the nucleic acid molecule comprises a sequence that is at least 70% identical to a marker sequence or a fragment of a marker sequence selected from SEQ ID NOs: 1-156 and SEQ ID Ns: 761-774; and (b) instructions for screening a *Brassica* plant for the QTL associated with shatter resistance.

In certain kits, the marker sequence or fragment of marker sequence is selected from SEQ ID NOs: 18-37. In certain embodiments, the kits contain at least one component for high throughput screening the plant or germplasm for the QTL.

Kits in some embodiments may include synthetic and/or chemically modified nucleic acids for detecting ten or more polymorphisms in *Brassica* plant DNA associated with shatter resistance. In other embodiments, the kits may include synthetic and/or chemically modified nucleic acids for detecting 20 or more polymorphisms in *Brassica* plant DNA associated with shatter resistance. In still other embodiments, the kits may include synthetic and/or chemically modified nucleic acids for detecting 30 or more polymorphisms in *Brassica* plant DNA associated with shatter resistance.

Another aspect of the invention features a *Brassica* plant that exhibits shatter resistance, comprising alleles favorable for shatter resistance in at least one QTL localized to a linkage group selected from N1, N3, N4, N6, N7, N9, N13, N14, N15, N18 or N19, wherein each said linkage group comprises at least one marker that is associated with the resistance to shatter with a statistical significance of $p \leq 0.01$, wherein the QTL is localized to a chromosomal interval selected from the group consisting of: (a) an interval flanked by and including markers N20003-001-Q001 and N23426-001-Q001 on linkage group N1; (b) an interval flanked by and including markers N05671-1-Q1 and N12643-001-Q001 on linkage group N3; (c) an interval flanked by and including markers N05943-1-Q1 and N88537-001-K001 on linkage group N4; (d) an interval flanked by and including markers N07541-1-Q1 and N14649-001-Q001 on linkage group N6; (e) one or more intervals flanked by and including: (i) markers N23310-001-Q001 and N23409-001-Q001 on linkage group N7, or (ii) markers N07278-1-Q1 and N23417-001-Q001 on linkage group N7; (f) one or more intervals flanked by and including: (i) markers N23119-001-Q001 and N20380-001-Q001; or (ii) NO5490-1-Q1 and N20834-001-Q001 on linkage group N9; (g) one or more intervals flanked by and including (i) markers N21144-001-Q001 and N09862-001-Q001 on linkage group N13, or (ii) markers N22903-001-Q001 and N12902-001-Q001 on linkage group N13; (h) one or more intervals flanked by and including: (i) markers N23033-001-Q001 and N22724-001-Q001 on linkage group N14, or (ii) markers N23033-001-Q001 and N22802-001-Q001 on linkage group N14; (i) an interval flanked by and including markers N12785-001-Q001 and N19296-001-Q001 on linkage group N15; (j) one or more intervals flanked by and including (i) markers N05205-1-Q1 and N22925-001-Q001 on linkage group N18, or (ii) markers N22803-001-Q001 and N18401-001-Q001 on linkage group N18; and (k) an interval flanked by and including markers N05656-1-Q1 and N16006-001-Q001 on linkage group N19; wherein each said linkage group comprises at least one marker that is associated with the shatter resistance with a statistical significance of $p \leq 0.01$. In particular embodiments, the QTL is localized to a chromosomal interval selected from the group consisting of: (a) an interval flanked by and including markers N10336-001-Q001 and N23426-001-Q001 on linkage group N1; (b) one or more intervals flanked by and including (i) markers N88514-001-K001 and N88537-001-K001, or (ii) markers N05943-1-Q1 and N06675-1-Q1 on linkage group N4; and (c) one or more intervals flanked by and including (i) markers N001RWT-001-Q001 and N20834-001-Q001, or (ii) markers N04807-1-Q1 and N17314-001-Q001 on linkage group N9.

In certain embodiments, the marker comprises a polymorphism that identifies the favorable allele. The polymorphism can be a single nucleotide polymorphism (SNP) or a simple sequence repeat (SSR).

In certain embodiments of the *Brassica* plant, the favorable allele is associated with a marker selected from the group consisting of: N20003-001-Q001 (SEQ ID NO: 1); N03491-1-Q1 (SEQ ID NO:2); N0017NR-001-Q001 (SEQ ID NO:3); N10336-001-Q001 (SEQ ID NO:4); N23133-001-Q001 (SEQ ID NO:5); N16487-001-Q001 (SEQ ID NO:6); N23426-001-Q001 (SEQ ID NO:7); N05671-1-Q1 (SEQ ID NO:8); N12643-001-Q001 (SEQ ID NO:9); N05943-1-Q1 (SEQ ID NO:10); N06007-1-Q1 (SEQ ID NO: 11); N10105-001-Q001 (SEQ ID NO:12); N08181-1-Q1 (SEQ ID NO:13); N06675-1-Q1 (SEQ ID NO:14); N001KH2-001-Q001 (SEQ ID NO:15); N29313-001-Q001 (SEQ ID NO:16); N88512-001-K001 (SEQ ID NO:17); N88514-001-K001 (SEQ ID NO:18); N88515-001-K001 (SEQ ID NO:19); N88516-001-K001 (SEQ ID NO:20); N88517-001-K001 (SEQ ID NO:21); N88518-001-K001 (SEQ ID NO:22); N88519-001-K001 (SEQ ID NO:23); N88520-001-K001 (SEQ ID NO:24); N88521-001-K001 (SEQ ID NO:25); N001KFE-001-Q001 (SEQ ID NO:26); N88522-001-K001 (SEQ ID NO:27); N88523-001-K001 (SEQ ID NO:28); N88524-001-K001 (SEQ ID NO:29); N88525-001-K001 (SEQ ID NO:30); N88529-001-K001 (SEQ ID NO:31); N88530-001-K001 (SEQ ID NO:32); N88531-001-K001 (SEQ ID NO:33); N88533-001-K001 (SEQ ID NO:34); N88535-001-K001 (SEQ ID NO:35); N88536-001-K001 (SEQ ID NO:36); N88537-001-K001 (SEQ ID NO:37); N07541-1-Q1 (SEQ ID NO:38); N23413-001-Q001 (SEQ ID NO:39); N08344-1-Q1 (SEQ ID NO:40); N23533-001-Q011 (SEQ ID NO:41); N14649-001-Q001 (SEQ ID NO:42); N23310-001-Q001 (SEQ ID NO:43); N10526-001-Q001 (SEQ ID NO:44); N23373-001-Q001 (SEQ ID NO:45); N23353-001-Q001 (SEQ ID NO:46); N23206-001-Q001 (SEQ ID NO:47); N11025-001-Q001 (SEQ ID NO:48); N09969-001-Q001 (SEQ ID NO:49); N09882-001-Q001 (SEQ ID NO:50); N10389-001-Q001 (SEQ ID NO:51); N09940-001-Q001 (SEQ ID NO:52); N23409-001-Q001 (SEQ ID NO:53); N23119-001-Q001 (SEQ ID NO:54); N09861-001-Q001 (SEQ ID NO:55); N04807-1-Q1 (SEQ ID NO:56); N06778-1-Q1 (SEQ ID NO:57); N09897-001-Q001 (SEQ ID NO:58); N10499-001-Q001 (SEQ ID NO:59); N23447-001-Q001 (SEQ ID NO:60); N19834-001-Q001 (SEQ ID NO:61); N23362-001-Q001 (SEQ ID NO:62); N23266-001-Q001 (SEQ ID NO:63); N19862-001-Q001 (SEQ ID NO:64); N22187-001-Q001 (SEQ ID NO:65); N08651-1-Q1 (SEQ ID NO:66); N23296-001-Q001 (SEQ ID NO:67); N17314-001-Q001 (SEQ ID NO:68); N20380-001-Q001 (SEQ ID NO:69); N05490-1-Q1 (SEQ ID NO:70); N18849-001-Q001 (SEQ ID NO:71); N08200-1-Q1 (SEQ ID NO:72); N19827-001-Q001 (SEQ ID NO:73); N001R9W-001-Q001 (SEQ ID NO:74); N08264-1-Q1 (SEQ ID NO:75); N23132-001-Q001 (SEQ ID NO:76); N03615-1-Q1 (SEQ ID NO:77); N001RWT-001-Q001 (SEQ ID NO:78); N08465-1-Q1 (SEQ ID NO:79); N10774-001-Q001 (SEQ ID NO:80); N17035-001-Q001 (SEQ ID NO:81); N20834-001-Q001 (SEQ ID NO:82); N22903-001-Q001 (SEQ ID NO:83); N09920-001-Q001 (SEQ ID NO:84); N22822-001-Q001 (SEQ ID NO:85); N22688-001-Q001 (SEQ ID NO:86); N10074-001-Q001 (SEQ ID NO:87); N10057-001-Q001 (SEQ ID NO:88); N10086-001-Q001 (SEQ ID NO:89); N11084-001-Q001 (SEQ ID NO:90); N22814-001-Q001 (SEQ ID NO:91); N01564-2-Q1 (SEQ ID NO:92); N12902-001-Q001 (SEQ ID NO:93); N21144-001-Q001 (SEQ ID NO:94); N07534-1-Q1 (SEQ ID NO:95); N22993-001-Q001 (SEQ ID NO:96); N09963-001-Q001 (SEQ ID NO:97); N11542-001-Q001 (SEQ ID NO:98); N14681-001-Q001 (SEQ ID NO:99); N11636-001-Q001 (SEQ ID NO:100); N13732-001-Q001 (SEQ ID NO: 101); N11255-001-Q001 (SEQ ID NO: 102); N15511-001-Q001 (SEQ ID NO: 103); N10536-001-Q001 (SEQ ID NO:104); N09862-001-Q001 (SEQ ID NO:105); N23033-001-Q001 (SEQ ID NO:106); N06039-1-Q1 (SEQ ID NO:107); N10016-001-Q001 (SEQ ID NO:108); N22743-001-Q001 (SEQ ID NO:109); N22953-001-Q001 (SEQ ID NO: 110); N09987-001-Q001 (SEQ ID NO:111); N10092-001-Q001 (SEQ ID NO:112); N10096-001-Q001 (SEQ ID NO:113); N22728-001-Q001 (SEQ ID NO:114); N22747-001-Q001 (SEQ ID NO:115); N22840-001-Q001 (SEQ ID NO:116); N23027-001-Q001 (SEQ ID NO: 117); N22777-001-Q001 (SEQ ID NO:118); N09636-001-Q001 (SEQ ID NO: 119); N09879-001-Q001 (SEQ ID NO: 120); N10123-001-Q001 (SEQ ID NO:121); N10316-001-Q001 (SEQ ID NO: 122); N10507-001-Q001 (SEQ ID NO: 123); N09834-001-Q001 (SEQ ID NO: 124); N22934-001-Q001 (SEQ ID NO:125); N22700-001-Q001 (SEQ ID NO: 126); N22725-001-Q001 (SEQ ID NO: 127); N22881-001-Q001 (SEQ ID NO: 128); N23032-001-Q001 (SEQ ID NO:129); N22786-001-Q001 (SEQ ID NO:130); N23014-001-Q001 (SEQ ID NO:131); N10471-001-Q001 (SEQ ID NO:132); N11419-001-Q001 (SEQ ID NO: 133); N22724-001-Q001 (SEQ ID NO: 134); N12785-001-Q001 (SEQ ID NO: 135); N09910-001-Q001 (SEQ ID NO:136); N21146-001-Q001 (SEQ ID NO:137); N17618-001-Q001 (SEQ ID NO:138); N09776-001-Q001 (SEQ ID NO:139); N19296-001-Q001 (SEQ ID NO:140); N05205-1-Q1 (SEQ ID NO:141); N10406-001-Q001 (SEQ ID NO:142); N22941-001-Q001 (SEQ ID NO:143); N22875-001-Q001 (SEQ ID NO:144); N13286-001-Q001 (SEQ ID NO:145); N04503-1-Q1 (SEQ ID NO:146); N22925-001-Q001 (SEQ ID NO: 147); N05656-1-Q1 (SEQ ID NO: 148); N17581-001-Q001 (SEQ ID NO: 149); N001NVH-001-Q001 (SEQ ID NO: 150); N22928-001-Q001 (SEQ ID NO: 151); N08219-1-Q001 (SEQ ID NO:152); N05710-1-Q1 (SEQ ID NO: 153); N15338-001-Q001 (SEQ ID NO: 154); N10424-001-Q001 (SEQ ID NO: 155); N16006-001-Q001 (SEQ ID NO: 156); N07278-1-Q1 (SEQ ID NO: 761); N16343-001-Q001 (SEQ ID NO: 762); N23417-001-Q001 (SEQ ID NO: 763); N22902-001-Q001 (SEQ ID NO: 764); N23063-001-Q001 (SEQ ID NO: 765); N22723-001-Q001 (SEQ ID NO: 766); N23049-001-Q001 (SEQ ID NO: 767); N10321-001-Q001 (SEQ ID NO: 768); N15374-001-Q001 (SEQ ID NO: 769); N22802-001-Q001 (SEQ ID NO: 770), N22803-001-Q001 (SEQ ID NO: 771), N18929-001-Q001 (SEQ ID NO: 772); N16041-001-Q001 (SEQ ID NO: 773); and N18401-001-Q001 (SEQ ID NO: 774).

More particularly, the favorable allele is associated with a marker selected from the group consisting of: N88514-001-K001 (SEQ ID NO:18); N88515-001-K001 (SEQ ID NO:19); N88516-001-K001 (SEQ ID NO:20); N88517-001-K001 (SEQ ID NO:21); N88518-001-K001 (SEQ ID NO:22); N88519-001-K001 (SEQ ID NO:23); N88520-001-K001 (SEQ ID NO:24); N88521-001-K001 (SEQ ID NO:25); N001KFE-001-Q001 (SEQ ID NO:26); N88522-001-K001 (SEQ ID NO:27); N88523-001-K001 (SEQ ID NO:28); N88524-001-K001 (SEQ ID NO:29); N88525-001-K001 (SEQ ID NO:30); N88529-001-K001 (SEQ ID NO:31); N88530-001-K001 (SEQ ID NO:32); N88531-001-K001 (SEQ ID NO:33); N88533-001-K001 (SEQ ID NO:34); N88535-001-K001 (SEQ ID NO:35); N88536-001-K001 (SEQ ID NO:36); and N88537-001-K001 (SEQ ID NO:37).

In certain embodiments, the *Brassica* plant contains a plurality of favorable alleles for resistance to shatter. For instance, the plant may contain 5, 10, 15, 20, 25, 30, 35, 40, 45 or 50 favorable alleles for resistance to shatter. In certain embodiments, the plurality of alleles are associated with two or more different linkage groups.

The aforementioned *Brassica* plant is selected from *Brassica napus*; *Brassica juncea*; *Brassica rapa*; *Brassica oleracea*; and *Brassica carina*. In one embodiment, the plant is *Brassica napus* (canola), which can be spring canola, winter canola or semi-winter canola.

Other features and advantages of the invention will be understood from the detailed description and examples that follow.

DETAILED DESCRIPTION

Overview

The present invention relates to the identification of genetic markers, e.g., marker loci and nucleic acids corresponding to (or derived from) these marker loci, such as probes and amplification products useful for genotyping plants, correlated with resistance or improved resistance to shatter. The markers of the invention are used to identify plants, particularly plants of the species *Brassica napus* (*B. napus*) (canola), that are resistant or exhibit improved resistance to shatter (sometimes referred to herein simply as "shatter resistance"). Accordingly, these markers are useful for marker-assisted selection (MAS) and breeding of shatter resistant plants, and for identification of susceptible plants. The markers of the invention are also used to identify and define nucleic acids that are proximal to and/or chromosome intervals corresponding to, or including, quantitative trait loci associated with shatter resistance. Quantitative Trait Loci (QTLs) associated with shatter resistance are isolated by positional cloning, e.g., nucleic acids proximal to or of genetic intervals defined by a pair of markers described herein, or subsequences of an interval defined by and including such markers. Such isolated QTL nucleic acids can be used for the production of transgenic cells and plants exhibiting shatter resistance. In addition, QTL nucleic acids isolated from one organism, e.g., canola, can, in turn, serve to isolate homologs of QTLs for shatter resistance from other plants, including a variety of commercially and/or scientifically important dicots, such as soybean, alfalfa, sunflower, flax, beans, (for example, white beans), potatoes, peas, peanuts and *Arabidopsis*.

Definitions

Units, prefixes, and symbols are denoted in their International System of Units (SI) accepted form. Unless otherwise indicated, nucleic acids are written left to right in 5' to 3' orientation; and amino acid sequences are written left to right in amino to carboxy orientation. Numeric ranges recited within the specification are inclusive of the numbers defining the range and include each integer within the defined range. Nucleotides may be referred to herein by their one-letter symbols recommended by the IUPAC-IUBMB Nomenclature Commission. The terms defined below are more fully defined by reference to the specification as a whole. Section headings provided throughout the specification are provided for convenience and are not limitations to the various objects and embodiments of the present invention.

"Resistance or improved resistance to shatter in *Brassica*", or simply "shatter resistance," refers to the resistance of a plant against pod shatter tendency, under field conditions and/or under extreme weather conditions such as a wind storm. Means of measuring the level of resistance to pod shatter tendency are known in the art and include, but are not limited to, the following: pendulum-based test (Kadkol et al., 1991; Liu et al. 1994), cantilever test (Kadkol et al., 1984), manual bending test (Roy 1982), microfracture test (MFT) (Child et al., 2003), siliqua twisting (Tys et al., 2007), 'Ripping' method (Tan et al., 2007), Random Impact Test (RIT) (Bruce et al., 2002; Morgan et al., 1998, 2003; Squires et al., 2003) and the device and method described in U.S. Pat. No. 7,412,880 B2. In one embodiment, a plant with field resistance to pod shatter has a rating of 5.0 or greater, based on the "shatter score" (SHTSC) rating scale. In other embodiments, a plant with resistance to pod shatter has a rating of 5.5, 6.0, 6.5, 7.0, 7.5, 8.0, 8.5 or 9.0, based on the SHTSC rating scale. Shatter scores are sometimes expressed in ranges; for instance in a range of 5-6, 6-7, 7-8, 8-9 or in a range of 5-7, 7-9 and so on, or by a number range within integers, such as 5.5-6.5, 5.5-7.5, 6-7.5, 7-8.5, for example. In those instances, a plant with resistance to shatter has a rating in the range of at least 5-6, or 6-7, or 7-8, or 8-9, based on the SHTSC rating scale.

It will be understood by the skilled artisan that the greater the number (or percentage) of favorable alleles for shatter resistance a plant possesses, the greater will be the level of resistance exhibited. In certain embodiments, a plant with shatter resistance has a genome containing at least about 50% favorable alleles. In more particular embodiments, a plant with shatter resistance has a genome containing at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% or more favorable alleles. The percentage of favorable alleles can also be expressed as a number value. For instance, if a total number of 15 favorable alleles are possible in a certain mapping population, a plant having 12 of those alleles would have 80% favorable alleles. In certain embodiments, the number or percent of favorable alleles in a plant can serve as a rough predictor of the expected level of shatter resistance a plant will exhibit.

It will also be understood by the skilled artisan that the QTLs described herein represent regions of the genome comprising genes that contribute to the shatter resistance of a plant. Further, each QTL can contribute differently to that resistance level. Thus, breeding efforts are directed to increasing the number of those QTLs, particularly quantitatively significant QTLs, present in the germplasm. Early in a breeding program, fewer QTLs may be present in a particular germplasm, but that number will increase as the breeding program progresses. Thus, in certain embodiments, a plant exhibiting shatter resistance may contain at least 2 of the QTLs described herein. More particularly, the plant may contain at least 3, 4, 5 or 6 of the QTLs described herein. Yet more particularly, the plant may contain all of the QTLs described herein.

As mentioned above, the term "shatter" refers to a process by which the silique or pod, on maturation late in fruit development, releases and disperses the seeds contained within it. The siliques or pods are formed by two carpels that are separated by a thin replum. The dehiscence zone (DZ) is where the valve (fruit wall) margin connects to the replum, and extends throughout the entire length of the fruit between the valve and replum. As the pod matures late in fruit development, the valve margin detaches from the replum, leading to seed dispersal. The DZ demarcates the precise location where the valves detach.

The term "quantitative trait locus" or "QTL" refers to a polymorphic genetic locus with at least two alleles that differentially affect the expression of a continuously distributed phenotypic trait, for example, resistance to shatter. For example, the QTL may have a favorable allele that confers, or contributes to, shatter resistance.

The term "favorable allele" is an allele at a particular locus that confers, or contributes to, a desirable phenotype, e.g., resistance to shatter, or alternatively is an allele that allows the identification of plants with decreased resistance that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants. Alleles that are favorable for resistance to shatter are provided, for example, in Table 6.

The term "associated with" or "associated" in the context of this invention refers to, e.g., a nucleic acid and a phenotypic trait or a second nucleic acid, that are in linkage disequilibrium, i.e., the nucleic acid and the trait/second nucleic acid are found together in progeny plants more often than if the nucleic acid and phenotype/second nucleic acid segregated separately.

The term "linkage" is used to describe the degree with which one marker locus is associated with another marker locus or some other locus (for example, a QTL). The linkage relationship between a molecular marker and a phenotype is given as a "probability" or "adjusted probability". Linkage can be expressed as a desired limit or range. For example, in some embodiments, any marker is linked (genetically and/or physically) to any other marker when the markers are separated by less than 50, 40, 30, 25, 20, or 15 map units (or cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" or "in proximity of each other. Since one cM is the distance between two markers that show a 1% recombination frequency, any marker is closely linked (genetically and/or physically) to any other marker that is in close proximity, e.g., at or less than 10 cM distance. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci. This implies that such loci are in sufficient physical proximity along a length of a chromosome that they tend to segregate together with greater than random frequency.

The term "genetically linked" refers to genetic loci that are in linkage disequilibrium and statistically determined not to assort independently. Genetically linked loci assort dependently from 51% to 99% of the time or any whole number value there between, preferably at least 60%, 70%, 80%, 90%, 95% or 99%. Loci or alleles that are inherited in this way are said to be linked, and are referred to as "linkage groups".

The "probability value" or "p-value" is the statistical likelihood that the particular combination of a phenotype and the presence or absence of a particular marker is random. The lower the probability value, the greater the likelihood that a phenotype and a particular marker will co-segregate. In some aspects, the probability value is considered "significant" or "non-significant". In some embodiments, a probability value of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.2, less than 0.15, less than 0.1, less than 0.05, less than 0.01 or less than 0.001.

The term "marker locus" is a specific chromosome location in the genome of a species where a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

The term "marker" is a nucleotide sequence or encoded product thereof (e.g., a protein) used as a point of reference. For markers to be useful at detecting recombinations, they need to detect differences, or polymorphisms, within the population being monitored.

For molecular markers, this means differences at the DNA level due to polynucleotide sequence differences (e.g., SSRs, RFLPs, FLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can refer also to nucleic acids used as probes or primer pairs capable of amplifying sequence fragments via the use of PCR-based methods. A large number of Brassica molecular markers are known in the art, and are published or available from various sources.

Examples of markers associated with shatter-resistance are provided, in SEQ ID NOS: 1-156 and SEQ ID NOS: 761-774. It will be understood by one skilled in the art that a marker of the present invention may comprise the entire sequence of any one of the sequences set out in SEQ ID NOS: 1-156 and SEQ ID NOS: 761-774, or a fragment of such a sequence. The fragment can be, for example, the SNPs (as highlighted, for example, in Table 7, or sequences that flank and includes the SNPs. It will also be understood by one skilled in the art that the sequences of markers such as those set out in any of SEQ ID NOS: 1-156 and SEQ ID NOS: 761-774 or a fragment of such a sequence will have some variation. Therefore, the markers of the present invention include sequences that have 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a sequence as provided in any of SEQ ID NOS: 1-156 and SEQ ID NOS: 761-774 or a fragment thereof.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

The term "molecular marker" may be used to refer to any type of nucleic acid based marker, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a molecular marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Any suitable marker detection technology may be used to identify such a hybridization marker, e.g., SNP technology is predominantly used in the examples provided herein. A "marker allele", alternatively an "allele of a marker locus", can refer to one of a plurality of polymorphic nucleotide sequences found at a marker locus in a population that is polymorphic for the marker locus.

The term "interval" refers to a continuous linear span of chromosomal DNA with termini that are typically defined by and including molecular markers.

The terms "nucleic acid," "nucleotide", "polynucleotide," "polynucleotide sequence" and "nucleic acid sequence" refer to single-stranded or double-stranded deoxyribonucleotide or ribonucleotide polymers, or chimeras thereof. As used herein, the term can additionally or alternatively include analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention optionally encompasses complementary sequences, in addition to the sequence explicitly indicated.

The term "gene" is used to refer to, e.g., a cDNA and an mRNA encoded by the genomic sequence, as well as to that genomic sequence.

The term "homologous" refers to nucleic acid sequences that are derived from a common ancestral gene through natural or artificial processes (e.g., are members of the same gene family), and thus, typically, share sequence similarity. Typically, homologous nucleic acids have sufficient sequence identity that one of the sequences or its complement is able to selectively hybridize to the other under selective hybridization conditions. The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences have about at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with each other. A nucleic acid that exhibits at least some degree of homology to a reference nucleic acid can be unique or identical to the reference nucleic acid or its complementary sequence.

The term "isolated" refers to material, such as a nucleic acid or a protein, which is substantially free from components that normally accompany or interact with it in its naturally occurring environment. The isolated material optionally comprises material not found with the material in its natural environment, e.g., a cell. In addition, if the material is in its natural environment, such as a cell, the material has been placed at a location in the cell (e.g., genome or subcellular organelle) not native to a material found in that environment. For example, a naturally occurring nucleic acid (e.g., a promoter) is considered to be isolated if it is introduced by non-naturally occurring means to a locus of the genome not native to that nucleic acid. Nucleic acids that are "isolated" as defined herein, are also referred to as "heterologous" nucleic acids. In certain embodiments, the isolated nucleic acids described herein are operably linked to or inserted within a heterologous sequence. Such a heterologous sequence may be a sequence within a different plant genome, or it may be a sequence within a vector, as explained below.

The term "recombinant" indicates that the material (e.g., a nucleic acid or protein) has been synthetically (non-naturally) altered by human intervention. The alteration to yield the synthetic material can be performed on the material within or removed from its natural environment or state. For example, a naturally occurring nucleic acid is considered a recombinant nucleic acid if it is altered, or if it is transcribed from DNA that has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such nucleic acid introduction means as "transfection," "transformation" and "transduction.

The terms "SSR" or "simple sequence repeat" refers to a polymorphic locus present in nuclear and organellar DNA that consist of repeating units of 1-6 base pairs in length. Different alleles can have different numbers of the repeating SSR, resulting in different lengths of the alleles, as detectable, for example, by gel electrophoresis after amplification of the allele. For example, a di-nucleotide repeat would be GAGAGAGA. It is believed that when DNA is being replicated, errors occur in the process and extra sets of these repeated sequences are added to the strand. Over time, these repeated sequences vary in length between one cultivar and another. An example of an allelic variation in SSRs would be: Allele A: 4 repeats of the GA sequence and Allele B: 6 repeats of the GA sequence. These variations in length are easy to trace in the lab and allow tracking of genotypic variation in breeding programs.

The term "microsatellite" is an alternative term for SSR.

The term "single nucleotide polymorphism" or "SNP" is a DNA sequence variation occurring when a single nucleotide—A, T, C, or G—in the genome (or other shared sequence) differs between members of a species (or between paired chromosomes in an individual). For example, two sequenced DNA fragments from different individuals, AAGCCTA to AAGCTTA, contain a difference in a single nucleotide. In this case we say that there are two alleles: C and T. Almost all common SNPs have only two alleles.

The term "host cell" means a cell that contains a heterologous nucleic acid, such as a vector, and supports the replication and/or expression of the nucleic acid. Host cells may be prokaryotic cells such as E. coli, or eukaryotic cells such as yeast, insect, amphibian, or mammalian cells. The host cells can be monocotyledonous or dicotyledonous plant cells. The dicotyledonous host cell can be, for example, a canola host cell.

The term "transgenic plant" refers to a plant that comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (i.e., crosses) or by naturally occurring events such as random cross-fertilization, non-recombinant viral infection, non-recombinant bacterial transformation, non-recombinant transposition, or spontaneous mutation.

The term "dicot" refers to the subclass of angiosperm plants also knows as "dicotyledoneae" and includes reference to whole plants, plant organs (e.g., leaves, stems, roots, etc.), seeds, plant cells, and progeny of the same. Plant cell, as used herein includes, without limitation, seeds, suspension cultures, embryos, meristematic regions, callus tissue, leaves, roots, shoots, gametophytes, sporophytes, pollen, and microspores.

The term "crossed" or "cross" in the context of this invention means the fusion of gametes via pollination to produce progeny (i.e., cells, seeds, or plants). The term encompasses both sexual crosses (the pollination of one plant by another) and selfing (self-pollination, i.e., when the pollen and ovule are from the same plant).

The term "introgression" refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene or a selected allele of a marker or QTL.

Markers

The present invention provides molecular markers genetically linked to quantitative trait loci ("QTLs") associated with resistance to shatter in *Brassica*. Such molecular markers are useful for identifying and producing dicotyledonous plants, in particular, such commercially important dicot crops as sunflower, canola, alfalfa, and soybean, displaying resistance to shatter.

Genetic mapping of several hundred molecular markers has developed a genetic linkage map covering approximately 1700 cM (centiMorgans) corresponding to 19 canola chromosomes. Additional details regarding the nature and use of molecular markers are provided below in the section entitled "Marker Assisted Selection and Breeding of Plants," and in the Examples.

Exemplary marker loci associated with resistance to shatter are localized to the following linkage groups in *Brassica napus*: N1, N3, N4, N6, N7, N9, N13, N14, N15, N18 and N19. These exemplary marker loci delineate chromosomal intervals including quantitative trait loci (QTL's) associated with phenotypic measures of shatter resistance. For example, Tables 4 and 5 list markers that localize to those linkage groups and set out the intervals on the linkage groups that define the QTLs associated with shatter resistance; for instance: (a) an interval flanked by and including markers N20003-001-Q001 and N23426-001-Q001 on linkage group N1; (b) an interval flanked by and including markers N05671-1-Q1 and N12643-001-Q001 on linkage group N3; (c) an interval flanked by and including markers N05943-1-Q1 and N88537-001-K001 on linkage group N4; (d) an interval flanked by and including markers N07541-1-Q1 and N14649-001-Q001 on linkage group N6; (e) one or more intervals flanked by and including: (i) markers N23310-001-Q001 and N23409-001-Q001 on linkage group N7, or (ii) markers N07278-1-Q1 and N23417-001-Q001 on linkage group N7; (f) one or more intervals flanked by and including: (i) markers N23119-001-Q001 and N20380-001-Q001 on linkage group N9, or (ii) markers NO5490-1-Q1 and N20834-001-Q001 on linkage group N9; (g) one or more intervals flanked by and including: (i) markers N21144-001-Q001 and N09862-001-Q001 on linkage group N13, or (ii) markers N22903-001-Q001 and N12902-001-Q001 on linkage group N13; (h) one or more intervals flanked by and including: (i) markers N23033-001-Q001 and N22724-001-Q001 on linkage group N14, or (ii) markers N23033-001-Q001 and N22802-001-Q001 on linkage group N14; (i) an interval flanked by and including markers N12785-001-Q001 and N19296-001-Q001 on linkage group N15; (j) one or more intervals flanked by and including: (i) markers N05205-1-Q1 and N22925-001-Q001 on linkage group N18, or (ii) markers N22803-001-Q001 and N18401-001-Q001 on linkage group N18; and (k) an interval flanked by and including markers N05656-1-Q1 and N16006-001-Q001 on linkage group N19. As described in detail herein, primers and probes corresponding to these markers or fragments of these markers can be designed based on the sequence information provided herein.

The following markers (sometimes referred to as "the markers exemplified by SEQ ID NOs: 1-156 and SEQ ID NOS: 761-774") contain single nucleotide polymorphisms (SNPs) or simple sequence repeats (SSRs) that identify QTLs contributing to shatter resistance and can be used as markers thereof: N20003-001-Q001 (SEQ ID NO: 1); N03491-1-Q1 (SEQ ID NO:2); N0017NR-001-Q001 (SEQ ID NO:3); N10336-001-Q001 (SEQ ID NO:4); N23133-001-Q001 (SEQ ID NO:5); N16487-001-Q001 (SEQ ID NO:6); N23426-001-Q001 (SEQ ID NO:7); N05671-1-Q1 (SEQ ID NO:8); N12643-001-Q001 (SEQ ID NO:9); N05943-1-Q1 (SEQ ID NO:10); N06007-1-Q1 (SEQ ID NO: 11); N10105-001-Q001 (SEQ ID NO:12); N08181-1-Q1 (SEQ ID NO:13); N06675-1-Q1 (SEQ ID NO:14); N001KH2-001-Q001 (SEQ ID NO:15); N29313-001-Q001 (SEQ ID NO:16); N88512-001-K001 (SEQ ID NO:17); N88514-001-K001 (SEQ ID NO:18); N88515-001-K001 (SEQ ID NO:19); N88516-001-K001 (SEQ ID NO:20); N88517-001-K001 (SEQ ID NO:21); N88518-001-K001 (SEQ ID NO:22); N88519-001-K001 (SEQ ID NO:23); N88520-001-K001 (SEQ ID NO:24); N88521-001-K001 (SEQ ID NO:25); N001KFE-001-Q001 (SEQ ID NO:26); N88522-001-K001 (SEQ ID NO:27); N88523-001-K001 (SEQ ID NO:28); N88524-001-K001 (SEQ ID NO:29); N88525-001-K001 (SEQ ID NO:30); N88529-001-K001 (SEQ ID NO:31); N88530-001-K001 (SEQ ID NO:32); N88531-001-K001 (SEQ ID NO:33); N88533-001-K001 (SEQ ID NO:34); N88535-001-K001 (SEQ ID NO:35); N88536-001-K001 (SEQ ID NO:36); N88537-001-K001 (SEQ ID NO:37); N07541-1-Q1 (SEQ ID NO:38); N23413-001-Q001 (SEQ ID NO:39); N08344-1-Q1 (SEQ ID NO:40); N23533-001-Q011 (SEQ ID NO:41); N14649-001-Q001 (SEQ ID NO:42); N23310-001-Q001 (SEQ ID NO:43); N10526-001-Q001 (SEQ ID NO:44); N23373-001-Q001 (SEQ ID NO:45); N23353-001-Q001 (SEQ ID NO:46); N23206-001-Q001 (SEQ ID NO:47); N11025-001-Q001 (SEQ ID NO:48); N09969-001-Q001 (SEQ ID NO:49); N09882-001-Q001 (SEQ ID NO:50); N10389-001-Q001 (SEQ ID NO:51); N09940-001-Q001 (SEQ ID NO:52); N23409-001-Q001 (SEQ ID NO:53); N23119-001-Q001 (SEQ ID NO:54); N09861-001-Q001 (SEQ ID NO:55); N04807-1-Q1 (SEQ ID NO:56); N06778-1-Q1 (SEQ ID NO:57); N09897-001-Q001 (SEQ ID NO:58); N10499-001-Q001 (SEQ ID NO:59); N23447-001-Q001 (SEQ ID NO:60); N19834-001-Q001 (SEQ ID NO:61); N23362-001-Q001 (SEQ ID NO:62); N23266-001-Q001 (SEQ ID NO:63); N19862-001-Q001 (SEQ ID NO:64); N22187-001-Q001 (SEQ ID NO:65); N08651-1-Q1 (SEQ ID NO:66); N23296-001-Q001 (SEQ ID NO:67); N17314-001-Q001 (SEQ ID NO:68); N20380-001-Q001 (SEQ ID NO:69); N05490-1-Q1 (SEQ ID NO:70); N18849-001-Q001 (SEQ ID NO:71); N08200-1-Q1 (SEQ ID NO:72); N19827-001-Q001 (SEQ ID NO:73); N001R9W-001-Q001 (SEQ ID NO:74); N08264-1-Q1 (SEQ ID NO:75); N23132-001-Q001 (SEQ ID NO:76); N03615-1-Q1 (SEQ ID NO:77); N001RWT-001-Q001 (SEQ ID NO:78); N08465-1-Q1 (SEQ ID NO:79); N10774-001-Q001 (SEQ ID NO:80); N17035-001-Q001 (SEQ ID NO:81); N20834-001-Q001 (SEQ ID NO:82); N22903-001-Q001 (SEQ ID NO:83); N09920-001-Q001 (SEQ ID NO:84); N22822-001-Q001 (SEQ ID NO:85); N22688-001-Q001 (SEQ ID NO:86); N10074-001-Q001 (SEQ ID NO:87); N10057-001-Q001 (SEQ ID NO:88); N10086-001-Q001 (SEQ ID NO:89); N11084-001-Q001 (SEQ ID NO:90); N22814-001-Q001 (SEQ ID NO:91); N01564-2-Q1 (SEQ ID NO:92); N12902-001-Q001 (SEQ ID NO:93); N21144-001-Q001 (SEQ ID NO:94); N07534-1-Q1 (SEQ ID NO:95); N22993-001-Q001 (SEQ ID NO:96); N09963-001-Q001 (SEQ ID NO:97); N11542-001-Q001 (SEQ ID NO:98); N14681-001-Q001 (SEQ ID NO:99); N11636-001-Q001 (SEQ ID NO:100); N13732-001-Q001 (SEQ ID NO: 101); N11255-

001-Q001 (SEQ ID NO: 102); N15511-001-Q001 (SEQ ID NO: 103); N10536-001-Q001 (SEQ ID NO:104); N09862-001-Q001 (SEQ ID NO:105); N23033-001-Q001 (SEQ ID NO:106); N06039-1-Q1 (SEQ ID NO:107); N10016-001-Q001 (SEQ ID NO: 108); N22743-001-Q001 (SEQ ID NO: 109); N22953-001-Q001 (SEQ ID NO: 110); N09987-001-Q001 (SEQ ID NO:111); N10092-001-Q001 (SEQ ID NO: 112); N10096-001-Q001 (SEQ ID NO: 113); N22728-001-Q001 (SEQ ID NO: 114); N22747-001-Q001 (SEQ ID NO:115); N22840-001-Q001 (SEQ ID NO:116); N23027-001-Q001 (SEQ ID NO: 117); N22777-001-Q001 (SEQ ID NO: 118); N09636-001-Q001 (SEQ ID NO: 119); N09879-001-Q001 (SEQ ID NO: 120); N10123-001-Q001 (SEQ ID NO:121); N10316-001-Q001 (SEQ ID NO: 122); N10507-001-Q001 (SEQ ID NO: 123); N09834-001-Q001 (SEQ ID NO:124); N22934-001-Q001 (SEQ ID NO:125); N22700-001-Q001 (SEQ ID NO: 126); N22725-001-Q001 (SEQ ID NO: 127); N22881-001-Q001 (SEQ ID NO: 128); N23032-001-Q001 (SEQ ID NO:129); N22786-001-Q001 (SEQ ID NO:130); N23014-001-Q001 (SEQ ID NO:131); N10471-001-Q001 (SEQ ID NO:132); N11419-001-Q001 (SEQ ID NO: 133); N22724-001-Q001 (SEQ ID NO: 134); N12785-001-Q001 (SEQ ID NO: 135); N09910-001-Q001 (SEQ ID NO:136); N21146-001-Q001 (SEQ ID NO:137); N17618-001-Q001 (SEQ ID NO:138); N09776-001-Q001 (SEQ ID NO:139); N19296-001-Q001 (SEQ ID NO:140); N05205-1-Q1 (SEQ ID NO:141); N10406-001-Q001 (SEQ ID NO:142); N22941-001-Q001 (SEQ ID NO:143); N22875-001-Q001 (SEQ ID NO:144); N13286-001-Q001 (SEQ ID NO:145); N04503-1-Q1 (SEQ ID NO:146); N22925-001-Q001 (SEQ ID NO: 147); N05656-1-Q1 (SEQ ID NO: 148); N17581-001-Q001 (SEQ ID NO: 149); N001NVH-001-Q001 (SEQ ID NO: 150); N22928-001-Q001 (SEQ ID NO: 151); N08219-1-Q001 (SEQ ID NO:152); N05710-1-Q1 (SEQ ID NO:153); N15338-001-Q001 (SEQ ID NO:154); N10424-001-Q001 (SEQ ID NO:155); N16006-001-Q001 (SEQ ID NO:156); N07278-1-Q1 (SEQ ID NO: 761); N16343-001-Q001 (SEQ ID NO: 762); N23417-001-Q001 (SEQ ID NO: 763); N22902-001-Q001 (SEQ ID NO: 764); N23063-001-Q001 (SEQ ID NO: 765); N22723-001-Q001 (SEQ ID NO: 766); N23049-001-Q001 (SEQ ID NO: 767); N10321-001-Q001 (SEQ ID NO: 768); N15374-001-Q001 (SEQ ID NO: 769); N22802-001-Q001 (SEQ ID NO: 770), N22803-001-Q001 (SEQ ID NO: 771); N18929-001-Q001 (SEQ ID NO: 772); N16041-001-Q001 (SEQ ID NO: 773); and N18401-001-Q001 (SEQ ID NO: 774). It will be appreciated that the number of repeats in any SSR can vary. Favorable alleles that contribute to shatter resistance are provided, for example, in Table 6.

It will be noted that, regardless of their molecular nature, e.g., whether the marker is a SNP, SSR, AFLP, RFLP, etc., markers are typically strain specific. That is, a particular polymorphic marker, such as the exemplary markers of the invention described above, is defined relative to the parental lines of interest. For each marker locus, resistance-associated, and conversely, susceptibility-associated alleles are identified for each pair of parental lines. Following correlation of specific alleles with susceptibility and resistance in parents of a cross, the marker can be utilized to identify progeny with genotypes that correspond to the desired resistance phenotype. In some circumstance, i.e., in some crosses of parental lines, the exemplary markers described herein will not be optimally informative.

In such cases, additional informative markers, e.g., certain linked markers and/or homologous markers are evaluated and substituted for genotyping, e.g., for marker-assisted selection, etc. In the case where a marker corresponds to a QTL, following identification of resistance- and susceptibility-associated alleles, it is possible to directly screen a population of samples, e.g., samples obtained from a seed bank, without first correlating the parental phenotype with an allele.

Linked Markers

Those of skill in the art will recognize that additional molecular markers can be identified within the intervals defined by the above-described pairs of markers. Such markers are also genetically linked to the QTLs identified herein as associated with shatter resistance, and are within the scope of the present invention. Markers can be identified by any of a variety of genetic or physical mapping techniques. Methods of determining whether markers are genetically linked to a QTL (or to a specified marker) associated with shatter resistance are known to those of skill in the art and include, e.g., interval mapping (Lander and Botstein (1989) *Genetics* 121:185), regression mapping (Haley and Knott (1992) *Heredity* 69:315) or MQM mapping (Jansen (1994) *Genetics* 138:871). In addition, such physical mapping techniques as chromosome walking, contig mapping and assembly, and the like, can be employed to identify and isolate additional sequences useful as markers in the context of the present invention.

Homologous Nucleotide Sequences

In addition, the markers exemplified by SEQ ID NOs: 1-156 and SEQ ID NOS: 761-774 are useful for the identification of homologous nucleotide sequences with utility in identifying QTLs associated with shatter resistance in different lines, varieties, or species of dicots. Such homologous markers are a feature of the invention.

Such homologous sequences can be identified by selective hybridization to a reference sequence. The reference sequence is typically a unique sequence, such as a unique oligonucleotide primer sequence, EST, amplified fragment (e.g., corresponding to AFLP markers) and the like, derived from any of the marker loci listed herein or its complement.

Two single-stranded nucleic acids "hybridize" when they form a double-stranded duplex. The double stranded region can include the full-length of one or both of the single-stranded nucleic acids, or all of one single stranded nucleic acid and a subsequence of the other single-stranded nucleic acid, or the double stranded region can include a subsequence of each nucleic acid. Selective hybridization conditions distinguish between nucleic acids that are related, e.g., share significant sequence identity with the reference sequence (or its complement) and those that associate with the reference sequence in a non-specific manner. Generally, selective hybridization conditions are those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Selective hybridization conditions may also be achieved with the addition of destabilizing agents such as formamide. Selectivity can be achieved by varying the stringency of the hybridization and/or wash conditions. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C.

Exemplary high stringency conditions include hybridization in 50% formamide, 1 M NaCl, 1% SDS at 37° C., and a wash in 0.1×SSC at 60 to 65° C.

Specificity is typically a function of post-hybridization washes, with the critical factors being ionic strength and temperature of the final wash solution. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$).

The $T_m$, is the temperature (under defined ionic strength and pH) at which 50% of a complementary target sequence hybridizes to a perfectly matched probe. For DNA-DNA hybrids, the $T_m$, can be approximated from the equation of Meinkoth and Wahl ((1984) *Anal. Biochem.* 138:267-284): $T_m$, =81.5° C.+16.6 (log M)+0.41 (% GC)−0.61 (% form) 500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$, is reduced by about 1° C. for each 1% of mismatching; thus, $T_m$, hybridization and/or wash conditions can be adjusted to hybridize to sequences of the desired identity. For example, if sequences with >90% identity are sought, the $T_m$, can be decreased 10° C.

Using the equation, hybridization and wash compositions, and desired $T_m$, those of ordinary skill will understand that variations in the stringency of hybridization and/or wash solutions are inherently described. If the desired degree of mismatching results in a $T_m$, of less than 45° C. (aqueous solution) or 32° C. (formamide solution) it is preferred to increase the SSC concentration so that a higher temperature can be used. Hybridization and/or wash conditions can be applied for at least 10, 30, 60, 90, 120, or 240 minutes. An extensive guide to the hybridization of nucleic acids is found in Tijssen (1993) *Laboratory Techniques in Biochemistry and Molecular Biology—Hybridization with Nucleic Acid Probes* Part I, Chapter 2 "Overview of principles of hybridization and the strategy of nucleic acid probe assays" Elsevier, New York. General Texts that discuss considerations relevant to nucleic acid hybridization, the selection of probes, and buffer and incubation conditions, and the like, as well as numerous other topics of interest in the context of the present invention (e.g., cloning of nucleic acids that correspond to markers and QTLs, sequencing of cloned markers/QTLs, the use of promoters, vectors, etc.) can be found in Berger and Kimmel (1987) *Guide to Molecular Cloning Techniques, Methods in Enzymology* vol. 152, Academic Press, Inc., San Diego ("Berger"); Sambrook et al., (2001) *Molecular Cloning—A Laboratory Manual,* 3$^{rd}$ ed. Vols. 1-3, Cold Spring Harbor Laboratory, Cold Spring Harbor ("Sambrook"); and Ausubel et al., (eds) (supplemented through 2001) *Current Protocols in Molecular Biology,* John Wiley and Sons, Inc., ("Ausubel").

In addition to hybridization methods described above, homologs of the markers of the invention can be identified in silico using any of a variety of sequence alignment and comparison protocols. For the purposes of the ensuing discussion, the following terms are used to describe the sequence relationships between a marker nucleotide sequence and a reference polynucleotide sequence.

A "reference sequence" is a defined sequence used as a basis for sequence comparison with a test sequence, e.g., a candidate marker homolog, of the present invention. A reference sequence may be a subsequence or the entirety of a specified sequence; for example, a segment of a full-length cDNA or gene sequence, or the complete cDNA or gene sequence.

As used herein, a "comparison window" is a contiguous and specified segment, (e.g., a subsequence) of a polynucleotide/polypeptide sequence to be compared to a reference sequence. The segment of the polynucleotide/polypeptide sequence in the comparison window can include one or more additions or deletions (i.e., gaps) with respect to the reference sequence, which (by definition) does not comprise addition(s) or deletion(s), for optimal alignment of the two sequences. An optimal alignment of two sequences yields the fewest number of unlike nucleotide/amino acid residues in a comparison window. Generally, the comparison window is at least 20 contiguous nucleotide/amino acid residues in length, and optionally can be 30, 40, 50, 100, or longer. Those of skill in the art understand that to avoid a falsely high similarity between two sequences, due to inclusion of gaps in the polynucleotide/polypeptide sequence, a gap penalty is typically assessed and is subtracted from the number of matches.

"Sequence identity" or "identity" in the context of two nucleic acid or polypeptide sequences refers to residues that are the same in both sequences when aligned for maximum correspondence over a specified comparison window.

"Percentage sequence identity" refers to the value determined by comparing two optimally aligned sequences over a comparison window. The percentage is calculated by determining the number of positions at which both sequences have the same nucleotide or amino acid residue, determining the number of matched positions, dividing the number of matched positions by the total number of positions in the comparison window, and multiplying the result by 100 to yield the percentage of sequence identity.

When percentage of sequence identity is used in reference to proteins it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ by conservative substitutions, the percent sequence identity may be adjusted upwards to correct for the conservative nature of the substitution. Sequences that differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller (1988) *Computer Applic. Biol. Sci.* 4:11-17, e.g., as implemented in the program PC/GENE (Intelligenetics, Mountain View, Calif., USA).

Methods of alignment of sequences for comparison are well-known in the art. Optimal alignment of sequences for comparison may be conducted by the local homology algorithm of Smith and Waterman ((1981) *Adv. Appl. Math.*

2:482); by the homology alignment algorithm of Needleman and Wunsch ((1970) *J. Mol. Biol.* 48:443); by the search for similarity method of Pearson and Lipman ((1988) *Proc. Natl. Acad. Sci. USA* 85:2444); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), Madison, Wis., USA; the CLUSTAL program is well described by Higgins and Sharp ((1988) *Gene* 73:237-244); Higgins and Sharp ((1989) *CABIOS* 5:151-153); Corpet et al. ((1988) *Nucleic Acids Research* 16:10881-90); Huang et al. ((1992) *Computer Applications in the Biosciences* 8: 155-65), and Pearson et al. ((1994) *Methods in Molecular Biology* 24:307-331).

The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, e.g., *Current Protocols in Molecular Biology*, Chapter 19, Ausubel et al., Eds., (1995) Greene Publishing and Wiley-Interscience, New York; Altschul et al. (1990) *J. Mol. Biol.* 215:403-410; and, Altschul et al. (1997) *Nucleic Acids Res.* 25:3389-3402.

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, e.g., Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-5877). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences that may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen (1993) *Comput. Chem.* 17:149-163) and XNU (Claverie and States (1993) *Comput. Chem.* 17:191-201) low-complexity filters can be employed alone or in combination.

Unless otherwise stated, nucleotide and protein identity/similarity values provided herein are calculated using GAP (CGC Version 10) under default values.

GAP (Global Alignment Program) can also be used to compare a polynucleotide or polypeptide of the present invention with a reference sequence. GAP uses the algorithm of Needleman and Wunsch ((1970) *J. Mol. Biol.* 48: 443-453), to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, e.g., Henikoff & Henikoff (1989) *Proc. Natl. Acad. Sci. USA* 89:10915).

Multiple alignment of the sequences can be performed using the CLUSTAL method of alignment (Higgins and Sharp (1989) *CABIOS.* 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

The percentage sequence identity of a homologous marker to its reference marker (e.g., any one of the markers described herein) is typically at least 70% and, rounded upwards to the nearest integer, can be expressed as an integer selected from the group of integers between 70 and 99. Thus, for example, the percentage sequence identity to a reference sequence can be at least 70%, 75%, 80%, 85%, 90%, 95%, 97%, or 99%. Sequence identity can be calculated using, for example, the BLAST, CLUSTALW, or GAP algorithms under default conditions.

Detection of Marker Loci

Markers corresponding to genetic polymorphisms between members of a population can be detected by numerous methods, well-established in the art (e.g., restriction fragment length polymorphisms, isozyme markers, allele specific hybridization (ASH), amplified variable sequences of the plant genome, self-sustained sequence replication, simple sequence repeat (SSR), single nucleotide polymorphism (SNP), or amplified fragment length polymorphisms (AFLP)).

The majority of genetic markers rely on one or more properties of nucleic acids for their detection. For example, some techniques for detecting genetic markers utilize hybridization of a probe nucleic acid to nucleic acids corresponding to the genetic marker. Hybridization formats include but are not limited to, solution phase, solid phase, mixed phase, or in situ hybridization assays. Markers that are restriction fragment length polymorphisms (RFLP), are detected by hybridizing a probe, which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals, and will often vary from line to line. Determining a (one or more) restriction enzyme that produces informative fragments for each cross is a simple procedure, well known in the art. After separation by length in an appropriate matrix (e.g., agarose) and transfer to a membrane (e.g., nitrocellulose, nylon), the labeled probe is hybridized under conditions that result in equilibrium binding of the probe to the target followed by removal of excess probe by washing.

Nucleic acid probes to the marker loci can be cloned and/or synthesized. Detectable labels suitable for use with nucleic acid probes include any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands that bind to antibodies labeled with fluorophores, chemiluminescent agents, and enzymes. Labeling markers is readily achieved such as by the use of labeled PCR primers to marker loci.

The hybridized probe is then detected using, most typically by autoradiography or other similar detection technique (e.g., fluorography, liquid scintillation counter, etc.). Examples of specific hybridization protocols are widely available in the art, see, e.g., Berger, Sambrook, Ausubel, all supra.

Amplified variable sequences refer to amplified sequences of the plant genome that exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Preferably, DNA from the plant serves as a template for amplification with primers that flank a variable sequence of DNA. The variable sequence is amplified and then sequenced.

In vitro amplification techniques are well known in the art. Examples of techniques sufficient to direct persons of skill through such in vitro methods, including the polymerase chain reaction (PCR), the ligase chain reaction (LCR), Q13-replicase amplification and other RNA polymerase mediated techniques (e.g., NASBA), are found in Berger, Sambrook and Ausubel (all supra) as well as Mullis et al. ((1987) U.S. Pat. No. 4,683,202); *PCR Protocols, A Guide to Methods and Applications* ((Innis et al., eds.) Academic Press Inc., San Diego Academic Press Inc. San Diego, Calif. (1990) (Innis)); Arnheim & Levinson ((Oct. 1, 1990) *C&EN* 36-47); *The Journal Of NIH Research* (1991) 3, 81-94; Kwoh et al. ((1989) *Proc. Natl. Acad. Sci. USA* 86, 1173); Guatelli et al. ((1990) *Proc. Natl. Acad. Sci. USA* 87, 1874); Lomell et al. ((1989) *J. Clin. Chem.* 35, 1826); Landegren et al. ((1988) *Science* 241, 1077-1080); Van Brunt ((1990) *Biotechnology* 8, 291-294); Wu and Wallace ((1989) *Gene* 4, 560); Barringer et al. ((1990) *Gene* 89, 117), and Sooknanan and Malek ((1995) *Biotechnology* 13: 563-564). Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684, and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra. Oligonucleotides for use as primers, e.g., in amplification reactions and for use as nucleic acid sequence probes are typically synthesized chemically according to the solid phase phosphoramidite triester method described by Beaucage and Caruthers ((1981) *Tetrahedron Lett.* 22:1859), or can simply be ordered commercially.

Alternatively, self-sustained sequence replication can be used to identify genetic markers. Self-sustained sequence replication refers to a method of nucleic acid amplification using target nucleic acid sequences that are replicated exponentially in vitro under substantially isothermal conditions by using three enzymatic activities involved in retroviral replication: (1) reverse transcriptase, (2) Rnase H, and (3) a DNA-dependent RNA polymerase (Guatelli et al. (1990) *Proc. Natl. Acad. Sci. USA* 87:1874). By mimicking the retroviral strategy of RNA replication by means of cDNA intermediates, this reaction accumulates cDNA and RNA copies of the original target.

Amplified fragment length polymorphisms (AFLP) can also be used as genetic markers (Vos et al. (1995) *Nucl. Acids Res.* 23:4407. The phrase "amplified fragment length polymorphism" refers to selected restriction fragments that are amplified before or after cleavage by a restriction endonuclease. The amplification step allows easier detection of specific restriction fragments. AFLP allows the detection large numbers of polymorphic markers and has been used for genetic mapping of plants (Becker et al. (1995) *Mol. Gen. Genet.* 249:65; and Meksem et al. (1995) *Mol. Gen. Genet.* 249:74.

Allele-specific hybridization (ASH) can be used to identify the genetic markers of the invention. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one embodiment, ASH data are obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on e.g., an acrylamide gel. However, alternative modes of detection, such as hybridization, e.g., ASH, or RFLP analysis are not excluded.

In yet another basis for providing a genetic linkage map, Simple sequence repeats (SSR), take advantage of high levels of di-, tri-, tetra-, penta- or hexa-nucleotide tandem repeats within a genome. Dinucleotide repeats have been reported to occur in the human genome as many as 50,000 times with n varying from 10 to 60 or more (Jacob et al. (1991) Cell 67:213. Dinucleotide repeats have also been found in higher plants (Condit and Hubbell (1991) *Genome* 34:66).

Briefly, SSR data are generated by hybridizing primers to conserved regions of the plant genome that flank the SSR sequence. PCR is then used to amplify the nucleotide repeats between the primers. The amplified sequences are then electrophoresed to determine the size and therefore the number of di-, tri-, and tetra-nucleotide repeats. The number of repeats distinguishes the favorable allele from an unfavorable allele.

Alternatively, isozyme markers are employed as genetic markers. Isozymes are multiple forms of enzymes that differ from one another in their amino acid, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes that differ at the nucleic acid level can be determined. In such cases, any of the nucleic acid based methods described herein can be used to analyze isozyme markers.

In alternative embodiments, in silico methods can be used to detect the marker loci. For example, the sequence of a nucleic acid comprising the marker can be stored in a computer. The desired marker locus sequence or its homolog can be identified using an appropriate nucleic acid search algorithm as provided by, for example, in such readily available programs as BLAST.

QTL Mapping

Multiple experimental paradigms have been developed to identify and analyze QTLs. In general, these paradigms involve crossing one or more parental pairs, which can be, for example, a single pair derived from two inbred strains, or multiple related or unrelated parents of different inbred strains or lines, which each exhibit different characteristics relative to the phenotypic trait of interest. The parents and a population of progeny are genotyped, typically for multiple marker loci, and evaluated for the trait of interest. In the context of the present invention, the parental and progeny plants are genotyped for any one or more of the molecular markers exemplified herein, or homologs, or alternative markers linked to any one or more of the markers exemplified herein, and evaluated for shatter resistance. QTLs associated with shatter resistance are identified based on the significant statistical correlations between the marker genotype(s) and the resistance phenotype of the evaluated progeny plants. Numerous methods for determining whether markers are genetically linked to a QTL (or to another marker) associated with shatter resistance are known to those of skill in the art and include, e.g., interval mapping (Lander and Botstein (1989) Genetics 121:185), regression mapping (Haley and Knott (1992) Heredity 69:315) or MQM mapping (Jansen (1994) Genetics 138:871). In addition, the following patent publications provide additional details regarding alternative statistical methods applicable to complex breeding populations that can be used to identify and localize QTLs associated with shatter resistance: U.S. Ser. No. 09/216,089 by Beavis et al. "QTL MAPPING IN PLANT BREEDING POPULATIONS" and PCT/US00/34971 by Jansen et al. "MQM MAPPING USING HAPLOTYPED PUTATIVE QTLS ALLELES: A SIMPLE APPROACH FOR MAPPING QTLS IN PLANT BREEDING POPULATIONS."

Marker Assisted Selection and Breeding of Plants

A primary motivation for development of molecular markers in crop species is the potential for increased efficiency in plant breeding through marker assisted selection (MAS). Genetic marker alleles, or alternatively, identified QTL alleles, are used to identify plants that contain a desired genotype at one or more loci, and that are expected to transfer the desired genotype, along with a desired phenotype to their progeny. Genetic marker alleles (or QTL alleles) can be used to identify plants that contain a desired genotype at one locus, or at several unlinked or linked loci (e.g., a haplotype), and that would be expected to transfer the desired genotype, along with a desired phenotype to their progeny. The present invention provides the means to identify plants, particularly dicots, e.g., *Brassica*, that have resistance to shatter by identifying plants having a specified allele, e.g., at one or more of the markers exemplified herein, or other markers within the intervals set forth herein. Similarly, by identifying plants lacking a desired allele of the marker, susceptible plants can be identified, and eliminated from subsequent crosses, if desired. It will be appreciated that, for the purposes of MAS, the term marker can encompass both marker and QTL loci as both can be used to identify plants that display shatter resistance.

After a desired phenotype, e.g., shatter resistance, and a polymorphic chromosomal locus, e.g., a marker locus or QTL, are determined to segregate together, it is possible to use those polymorphic loci to select for alleles corresponding to the desired phenotype—a process called marker-assisted selection (MAS). In brief, a nucleic acid corresponding to the marker nucleic acid is detected in a biological sample from a plant to be selected. This detection can take the form of hybridization of a probe nucleic acid to a marker, e.g., using allele-specific hybridization, southern blot analysis, northern blot analysis, in situ hybridization, hybridization of primers followed by PCR amplification of a region of the marker or the like. A variety of procedures for detecting markers are described herein, e.g., in the section entitled "DETECTION OF MARKER LOCI." After the presence (or absence) of a particular marker in the biological sample is verified, the plant is selected, i.e., used to make progeny plants by selective breeding.

Plant breeders need to combine stress tolerant loci with genes for high yield and other desirable traits to develop improved plant varieties. Screening for large numbers of samples can be expensive, time consuming, and unreliable. Use of the polymorphic loci described herein, and genetically-linked nucleic acids, as genetic markers for shatter resistance loci is an effective method for selecting tolerant varieties in breeding programs. For example, one advantage of marker-assisted selection over field evaluations for shatter resistance is that MAS can be done at any time of year regardless of the growing season. Moreover, environmental effects are irrelevant to marker-assisted selection. When a population is segregating for multiple loci affecting one or multiple traits, e.g., multiple loci involved in resistance to a single stress, or multiple loci each involved in resistance to different stresses, the efficiency of MAS compared to phenotypic screening becomes even greater because all the loci can be processed in the lab together from a single sample of DNA. In the present instance, this means that multiple markers selected from among the markers exemplified by SEQ ID NOs: 1-156 and SEQ ID NOS: 761-774 or markers homologous or linked thereto can be assayed simultaneously or sequentially in a single sample or population of samples. Thus, any one or more of these markers, e.g., two or more, up to and including all of the established markers, can be assayed simultaneously. In some instances, it is desirable to evaluate a marker corresponding to each of the linkage groups associated with shatter resistance.

Another use of MAS in plant breeding is to assist the recovery of the recurrent parent genotype by backcross breeding. Backcross breeding is the process of crossing a progeny back to one of its parents. Backcrossing is usually done for the purpose of introgressing one or a few loci from a donor parent into an otherwise desirable genetic background from the recurrent parent. The more cycles of backcrossing that are done, the greater the genetic contribution of the recurrent parent to the resulting variety. This is often necessary, because tolerant plants may be otherwise undesirable, i.e., due to low yield, low fecundity, or the like. In contrast, strains that are the result of intensive breeding programs may have excellent yield, fecundity or the like, merely being deficient in one desired trait such as resistance to a particular stress (e.g., resistance to shatter).

The presence and/or absence of a particular genetic marker allele, or a homolog thereof, in the genome of a plant exhibiting a preferred phenotypic trait is determined by any method listed above, e.g., RFLP, AFLP, SSR, etc. If the nucleic acids from the plant are positive for a desired genetic marker, the plant can be selfed to create a true breeding line with the same genotype, or it can be crossed with a plant with the same marker or with other desired characteristics to create a sexually crossed hybrid generation.

As mentioned above, the skilled artisan will understand that the QTLs described herein represent regions of the genome comprising genes that contribute to the shatter resistance of a plant. Further, each QTL can contribute differently to that resistance level. Thus, breeding efforts are directed to increasing the number of those QTLs, particularly quantitatively significant QTLs, present in the germplasm. Early in a breeding program, fewer QTLs may be present in a particular germplasm, but that number will increase as the breeding program progresses. Thus, in certain embodiments, a plant exhibiting shatter resistance may contain at least 6 of the QTLs described herein. More particularly, the plant may contain at least 2 or 3 of the QTLs described herein. Yet more particularly, the plant may contain 4, 5, 6 or all of the QTLs described herein.

Positional Cloning

The molecular markers of the present invention and nucleic acids homologous thereto, can be used, as indicated previously, to identify additional linked marker loci, which can be cloned by well established procedures, e.g., as described in detail in Ausubel, Berger and Sambrook, supra. Similarly, the exemplified markers, as well as any additionally identified linked molecular markers can be used to physically isolate, e.g., by cloning, nucleic acids associated with QTLs contributing to shatter resistance. Such nucleic acids, i.e., linked to QTLs, have a variety of uses, including as genetic markers for identification of additional QTLs in subsequent applications of marker assisted selection (MAS).

These nucleic acids are first identified by their genetic linkage to markers of the present invention. Isolation of the nucleic acid of interest is achieved by any number of methods as discussed in detail in such references as Ausubel, Berger and Sambrook, supra, and Clark, Ed. (1997) *Plant Molecular Biology: A Laboratory Manual* Springer-Verlag, Berlin.

For example, positional gene cloning uses the proximity of a genetic marker to physically define an isolated chromosomal fragment that is linked to a QTL. The isolated chromosomal fragment can be produced by such well known methods as digesting chromosomal DNA with one or more restriction enzymes, or by amplifying a chromosomal region in a polymerase chain reaction (PCR), or alternative amplification reaction. The digested or amplified fragment is typically ligated into a vector suitable for replication, e.g., a plasmid, a cosmid, a phage, an artificial chromosome, or the like, and, optionally, expression of the inserted fragment. Markers that are adjacent to an open reading frame (ORF) associated with a phenotypic trait can hybridize to a DNA clone, thereby identifying a clone on which an ORF is located. If the marker is more distant, a fragment containing the open reading frame is identified by successive rounds of screening and isolation of clones, which together comprise a contiguous sequence of DNA, a "contig." Protocols sufficient to guide one of skill through the isolation of clones associated with linked markers are found in, e.g., Berger, Sambrook and Ausubel, all supra.

Nucleic Acids in Proximity to Markers/Isolated Chromosome Intervals

The present invention provides isolated nucleic acids comprising a QTL associated with resistance to shatter. The QTL is in proximity to a marker described herein and/or is localized within an interval defined by two markers of the present invention wherein each marker flanks the QTL. Such nucleic acids and/or intervals can be utilized to identify homologous nucleic acids and/or can be used in the production of transgenic plants displaying improved shatter resistance conferred by the introduced QTL. The nucleic acid and/or chromosome interval comprising a QTL is isolated, e.g., cloned via positional cloning methods outlined above. A chromosome interval can contain one or more ORFs associated with resistance, and can be cloned on one or more individual vectors, e.g., depending on the size of the chromosome interval.

It will be appreciated that numerous vectors are available in the art for the isolation and replication of the nucleic acids of the invention. For example, plasmids, cosmids and phage vectors are well known in the art, and are sufficient for many applications (e.g., in applications involving insertion of nucleic acids ranging from less than 1 to about 20 kilobases (kb). In certain applications, it is advantageous to make or clone large nucleic acids to identify nucleic acids more distantly linked to a given marker, or to isolate nucleic acids in excess of 10-20 kb, e.g., up to several hundred kilobases or more, such as the entire interval between two linked markers, i.e., up to and including one or more centiMorgans (cM), linked to QTLs as identified herein. In such cases, a number of vectors capable of accommodating large nucleic acids are available in the art, these include, yeast artificial chromosomes (YACs), bacterial artificial chromosomes (BACs), plant artificial chromosomes (PACs) and the like. For a general introduction to YACs, BACs, PACs and MACs as artificial chromosomes, see, e.g., Monaco and Larin (1994) *Trends Biotechnol.* 12:280. In addition, methods for the in vitro amplification of large nucleic acids linked to genetic markers are widely available (e.g., Cheng et al. (1994) *Nature* 369:684, and references therein). Cloning systems can be created or obtained from commercially; see, for example, Stratagene Cloning Systems, Catalogs 2000 (La Jolla, Calif.).

Generation of Transgenic Plants and Cells

The present invention also relates to host cells and organisms that are transformed with nucleic acids corresponding to QTLs and other genes identified according to the invention. For example, such nucleic acids include chromosome intervals, ORFs, and/or cDNAs or corresponding to a sequence or subsequence included within the identified chromosome interval or ORF. Additionally, the invention provides for the production of polypeptides corresponding to QTLs by recombinant techniques. Host cells are genetically engineered (i.e., transduced, transfected or transformed) with the vectors of this invention (i.e., vectors that comprise QTLs or other nucleic acids identified according to the methods of the invention and as described above) that include, for example, a cloning vector or an expression vector. Such vectors include, in addition to those described above, e.g., an *Agrobacterium*, a virus (such as a plant virus), a naked polynucleotide, or a conjugated polynucleotide. The vectors are introduced into plant tissues, cultured plant cells or plant protoplasts by a variety of standard methods including electroporation (From et al. (1985) *Proc. Natl. Acad. Sci. USA* 82; 5824), infection by viral vectors such as cauliflower mosaic virus (CaMV) (Hohn et al. (1982) *Molecular Biology of Plant Tumors* (Academic Press, New York, pp. 549-560); Howell U.S. Pat. No. 4,407,956), high velocity ballistic penetration by small particles with the nucleic acid either within the matrix of small beads or particles, or on the surface (Klein et al. (1987) *Nature* 327; 70), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233; 496; Fraley et al. (1983) *Proc. Natl. Acad. Sci. USA* 80; 4803). The method of introducing a nucleic acid of the present invention into a host cell is not critical to the instant invention. Thus, any method, e.g., including but not limited to the above examples, which provides for effective introduction of a nucleic acid into a cell or protoplast can be employed.

The engineered host cells can be cultured in conventional nutrient media modified as appropriate for such activities as, for example, activating promoters or selecting transformants. These cells can optionally be cultured into transgenic plants. Plant regeneration from cultured protoplasts is described in Evans et al. ((1983) "Protoplast Isolation and Culture," *Handbook of Plant Cell Cultures* 1, 124-176 (MacMillan Publishing Co., New York); Davey ((1983) "Recent Developments in the Culture and Regeneration of Plant Protoplasts," *Protoplasts*, pp. 12-29, (Birkhauser, Basel)); Dale ((1983) "Protoplast Culture and Plant Regeneration of Cereals and Other Recalcitrant Crops," *Protoplasts*, pp. 31-41, (Birkhauser, Basel)); and Binding ((1985) "Regeneration of Plants," *Plant Protoplasts*, pp. 21-73, (CRC Press, Boca Raton)).

The present invention also relates to the production of transgenic organisms, which may be bacteria, yeast, fungi, or plants, transduced with the nucleic acids, e.g., cloned QTLs of the invention. A thorough discussion of techniques relevant to bacteria, unicellular eukaryotes and cell culture may be found in references enumerated above and are briefly outlined as follows. Several well-known methods of introducing target nucleic acids into bacterial cells are available, any of which may be used in the present invention. These include: fusion of the recipient cells with bacterial protoplasts containing the DNA, treatment of the cells with liposomes containing the DNA, electroporation, projectile bombardment (biolistics), carbon fiber delivery, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QJAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith ((1979) *Gene* 8:81); Roberts et al. ((1987) *Nature* 328:731); (Schneider et al. (1995) *Protein Expr. Purif* 6435:10); Ausubel, Sambrook, Berger (all supra). A catalogue of Bacteria and Bacteriophages useful for cloning is provided, e.g., by the ATCC, e.g., The ATCC Catalogue of Bacteria and Bateriophage (1992) Gherna et al. (eds) published by the ATCC. Additional basic procedures for sequencing, cloning and other aspects of molecular biology and underlying theoretical considerations are also found in Watson et al. (1992) *Recombinant DNA* Second Edition, Scientific American Books, NY.

Transforming Nucleic Acids into Plants

Embodiments of the present invention pertain to the production of transgenic plants comprising the cloned nucleic acids, e.g., chromosome intervals, isolated ORFs, and cDNAs associated with QTLs, of the invention. Techniques for transforming plant cells with nucleic acids are generally available and can be adapted to the invention by the use of nucleic acids encoding or corresponding to QTLs, QTL homologs, isolated chromosome intervals, and the like. In addition to Berger, Ausubel and Sambrook, useful general references for plant cell cloning, culture and regeneration include Jones (ed.) ((1995) *Plant Gene Transfer and Expression Protocols—Methods in Molecular Biology, Volume* 49 Humana Press Towata N.J.); Payne et al. ((1992) *Plant Cell and Tissue Culture in Liquid Systems* John Wiley & Sons, Inc. New York, N.Y. (Payne)); and Gamborg and Phillips (eds) ((1995) *Plant Cell, Tissue and Organ Culture; Fundamental Methods* Springer Lab Manual, Springer-Verlag (Berlin Heidelberg New York) (Gamborg)). A variety of cell culture media are described in Atlas and Parks (eds.) (*The Handbook of Microbiological Media* (1993) CRC Press, Boca Raton, Fla. (Atlas)). Additional information for plant cell culture is found in available commercial literature such as the *Life Science Research Cell Culture Catalogue* (1998) from Sigma-Aldrich, Inc. (St Louis, Mo.) (Sigma-LSRCCC) and, e.g., the *Plant Culture Catalogue* and supplement (1997) also from Sigma-Aldrich, Inc. (St Louis, Mo.) (Sigma-PCCS). Additional details regarding plant cell culture are found in Croy, (ed.) ((1993) *Plant Molecular Biology* Bios Scientific Publishers, Oxford, U.K.).

The nucleic acid constructs of the invention, e.g., plasmids, cosmids, artificial chromosomes, DNA and RNA polynucleotides, are introduced into plant cells, either in culture or in the organs of a plant by a variety of conventional techniques. Where the sequence is expressed, the sequence is optionally combined with transcriptional and translational initiation regulatory sequences that direct the transcription or translation of the sequence from the exogenous DNA in the intended tissues of the transformed plant.

Isolated nucleic acids of the present invention can be introduced into plants according to any of a variety of techniques known in the art. Techniques for transforming a wide variety of higher plant species are well known and described in the technical, scientific, and patent literature. See, for example, Weising et al. (1988) *Ann. Rev. Genet.* 22:421-477. The DNA constructs of the invention, for example, plasmids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of the plant cell using techniques such as electroporation and microinjection of plant cell protoplasts, or the DNA constructs can be introduced directly to plant cells using ballistic methods, such as DNA particle bombardment.

Microinjection techniques for injecting e.g., cells, embryos, callus and protoplasts, are known in the art and well described in the scientific and patent literature. For example, a number of methods are described in Jones (ed.) ((1995) *Plant Gene Transfer and Expression Protocols— Methods in Molecular Biology*, Volume 49 Humana Press Towata N.J.), as well as in the other references noted herein and available in the literature.

For example, the introduction of DNA constructs using polyethylene glycol precipitation is described in Paszkowski, et al. (*EMBO J.* 3:2717 (1984)). Electroporation techniques are described in Fromm, et al. (*Proc. Nat'l. Acad. Sci. USA* 82:5824 (1985)). Ballistic transformation techniques are described in Klein, et al. (*Nature* 327:70-73 (1987)). Additional details are found in Jones (1995) and Gamborg and Phillips (1995), supra, and in U.S. Pat. No. 5,990,387.

Alternatively, *Agrobacterium*-mediated transformation is employed to generate transgenic plants. *Agrobacterium*-mediated transformation techniques, including disarming and use of binary vectors, are also well described in the scientific literature. See, for example, Horsch, et al. (1984) *Science* 233:496; and Fraley et al. (1984) *Proc. Nat'l. Acad. Sci. USA* 80:4803 and reviewed in Hansen and Chilton (1998) *Current Topics in Microbiology* 240:22 and Das (1998) *Subcellular Biochemistry* 29: *Plant Microbe Interactions* pp. 343-363.

The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318. Other methods of transfection or transformation include (1) *Agrobacterium rhizogenes*-mediated transformation (see, e.g., Lichtenstein and Fuller (1987) In: *Genetic Engineering*, vol. 6, PWJ Rigby, Ed., London, Academic Press; and Lichtenstein; C. P., and Draper (1985) In: *DNA Cloning*, Vol. II, D. M. Glover, Ed., Oxford, IRI Press); WO 88/02405, published Apr. 7, 1988, describes the use of *A. rhizogenes* strain A4 and its Ri plasmid along with *A. tumefaciens* vectors pARC8 or pARC16 (2) liposome-mediated DNA uptake (see, e.g., Freeman et al. (1984) *Plant Cell Physiol.* 25:1353), (3) the vortexing method (see, e.g., Kindle (1990) *Proc. Natl. Acad. Sci.*, (USA) 87:1228).

DNA can also be introduced into plants by direct DNA transfer into pollen as described by Zhou et al. ((1983) *Methods in Enzymology*, 101:433); Hess ((1987) *Intern Rev. Cytol.* 107:367); and Luo et al. ((1988) *Plant Mol. Biol. Reporter* 6:165). Expression of polypeptide coding genes can be obtained by injection of the DNA into reproductive organs of a plant as described by Pena et al. ((1987) *Nature* 325:274). DNA can also be injected directly into the cells of immature embryos and the desiccated embryos rehydrated as described by Neuhaus et al. ((1987) *Theor. Appl. Genet.* 75:30); and Benbrook et al. ((1986) in *Proceedings Bio Expo* Butterworth, Stoneham, Mass., pp. 27-54). A variety of plant viruses that can be employed as vectors are known in the art and include cauliflower mosaic virus (CaMV), geminivirus, brome mosaic virus, and tobacco mosaic virus.

Regeneration of Transgenic Plants

Transformed plant cells that are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al. ((1983) *Protoplasts Isolation and Culture, Handbook of Plant Cell Culture* pp. 124-176, Macmillian Publishing Company, New York); and Binding ((1985) *Regeneration of Plants, Plant Protoplasts* pp. 21-73, CRC Press, Boca Raton). Regeneration can also be obtained from plant callus, explants, somatic embryos (Dandekar et al. (1989) *J. Tissue Cult. Meth.* 12:145; McGranahan, et al. (1990) *Plant Cell Rep.* 8:512) organs, or parts thereof. Such regeneration techniques are described generally in Klee et al. ((1987)., *Ann. Rev. of Plant Phys.* 38:467-486). Additional details are found in Payne (1992) and Jones (1995), both supra, and Weissbach and Weissbach, eds. ((1988) *Methods for Plant Molecular Biology* Academic Press, Inc., San Diego, Calif.). This regeneration and growth process includes the steps of selection of transformant cells and shoots, rooting the transformant shoots and growth of the plantlets in soil. These methods are adapted to the invention to produce transgenic plants bearing QTLs and other genes isolated according to the methods of the 10 invention.

In addition, the regeneration of plants containing the polynucleotide of the present invention and introduced by *Agrobacterium* into cells of leaf explants can be achieved as described by Horsch et al. ((1985) *Science* 227:1229-1231). In this procedure, transformants are grown in the presence of a selection agent and in a medium that induces the regeneration of shoots in the plant species being transformed as described by Fraley et al. ((1983) *Proc. Natl. Acad. Sci.* (*U.S.A.*) 80:4803). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Plants for the transformation and expression of QTLs associated with shatter resistance and other nucleic acids identified and cloned according to the present invention include, but are not limited to, agronomically and horticulturally important species. Such species include primarily dicots, e.g., of the families: Brassicaceae, Leguminosae (including pea, beans, lentil, peanut, yam bean, cowpeas, velvet beans, soybean, clover, alfalfa, lupine, vetch, lotus, sweet clover, wisteria, and sweetpea); and, Compositae (the largest family of vascular plants, including at least 1,000 genera, including important commercial crops such as sunflower).

Additionally, targets for modification with the nucleic acids of the invention, as well as those specified above, plants from the genera: *Allium, Apium, Arachis, Brassica, Capsicum, Cicer, Cucumis, Curcubita, Daucus, Fagopyrum, Glycine, Helianthus, Lactuca, Lens, Lycopersicon, Medicago, Pisum, Phaseolus, Solanurn, Trifolium, Vigna*, and many others.

Common crop plants that are targets of the present invention include soybean, sunflower, canola, peas, beans, lentils, peanuts, yam beans, cowpeas, velvet beans, clover, alfalfa, lupine, vetch, sweet clover, sweetpea, field pea, fava bean, broccoli, brussel sprouts, cabbage, cauliflower, kale, kohlrabi, celery, lettuce, carrot, onion, pepper, potato, eggplant, and tomato.

In construction of recombinant expression cassettes of the invention, which include, for example, helper plasmids comprising virulence functions, and plasmids or viruses comprising exogenous DNA sequences such as structural genes, a plant promoter fragment is optionally employed to direct expression of a nucleic acid in any or all tissues of a regenerated plant. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers.

Any of a number of promoters that direct transcription in plant cells can be suitable. The promoter can be either constitutive or inducible. In addition to the promoters noted above, promoters of bacterial origin that operate in plants include the octopine synthase promoter, the nopaline synthase promoter and other promoters derived from native Ti plasmids. See, Herrara-Estrella et al. ((1983), *Nature* 303: 209). Viral promoters include the 35S and 19S RNA promoters of cauliflower mosaic virus. See, Odell et al. ((1985) *Nature* 313:810). Other plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer ((1988) *EMBO J.* 7:3315). Many other promoters are in current use and can be coupled to an exogenous DNA sequence to direct expression of the nucleic acid.

If expression of a polypeptide, including those encoded by QTLs or other nucleic acids correlating with phenotypic traits of the present invention, is desired, a polyadenylation region at the 3'-end of the coding region is typically included. The polyadenylation region can be derived from the natural gene, from a variety of other plant genes, or from, e.g., T-DNA.

The vector comprising the sequences (e.g., promoters or coding regions) from genes encoding expression products and transgenes of the invention will typically include a nucleic acid subsequence, a marker gene that confers a selectable, or alternatively, a screenable, phenotype on plant cells. For example, the marker may encode biocide resistance, particularly antibiotic resistance, such as resistance to kanamycin, G418, bleomycin, hygromycin, or herbicide resistance, such as resistance to chlorosluforon, or phosphinothricin (the active ingredient in the herbicides bialaphos or Basta). See, e.g., Padgette et al. (1996) In: *Herbicide-Resistant Crops* (Duke, ed.), pp 53-84, CRC Lewis Publishers, Boca Raton ("Padgette, 1996"). For example, crop selectivity to specific herbicides can be conferred by engineering genes into crops that encode appropriate herbicide metabolizing enzymes from other organisms, such as microbes. See, Vasil (1996) In: *Herbicide-Resistant Crops* (Duke, ed.), pp 85-91, CRC Lewis Publishers, Boca Raton) ("Vasil", 1996).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self-crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a polynucleotide of the present invention can be screened for transmission of the nucleic acid of the present invention by, for example, standard immunoblot and DNA detection techniques. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

One embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

High Throughput Screening

In one aspect of the invention, the determination of genetic marker alleles is performed by high throughput screening. High throughput screening involves providing a library of genetic markers, e.g., RFLPs, AFLPs, isozymes, specific alleles and variable sequences, including SSR. Such libraries are then screened against plant genomes to generate a "fingerprint" for each plant under consideration. In some cases a partial fingerprint comprising a sub-portion of the markers is generated in an area of interest. Once the genetic marker alleles of a plant have been identified, the correspondence between one or several of the marker alleles and a desired phenotypic trait is determined through statistical associations based on the methods of this invention.

High throughput screening can be performed in many different formats. Hybridization can take place in a 96-, 324-, or a 1524-well format or in a matrix on a silicon chip or other format.

In one commonly used format, a dot blot apparatus is used to deposit samples of fragmented and denatured genomic DNA on a nylon or nitrocellulose membrane. After cross-linking the nucleic acid to the membrane, either through exposure to ultra-violet light or by heat, the membrane is incubated with a labeled hybridization probe. The labels are incorporated into the nucleic acid probes by any of a number of means well-known in the art. The membranes are washed to remove non-hybridized probes and the association of the label with the target nucleic acid sequence is determined.

A number of well-known robotic systems have been developed for high throughput screening, particularly in a 96 well format. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; ORCA™, Beckman Coulter, Fullerton Calif.). Any of the above devices are suitable for use with the present invention. The nature and implementation of modifications to these devices (if any) so that they can operate as discussed herein will be apparent to persons skilled in the relevant art.

In addition, high throughput screening systems themselves are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate or membrane in detector(s) appropriate for the assay. These configurable systems provide high throughput and rapid start up as well as a high degree of flexibility and customization. The manufacturers of such systems provide detailed protocols for the use of their products in high throughput applications.

In one variation of the invention, solid phase arrays are adapted for the rapid and specific detection of multiple polymorphic nucleotides. Typically, a nucleic acid probe is linked to a solid support and a target nucleic acid is hybridized to the probe. Either the probe, or the target, or both, can be labeled, typically with a fluorophore. If the target is labeled, hybridization is evaluated by detecting bound fluorescence. If the probe is labeled, hybridization is typically detected by quenching of the label by the bound nucleic acid. If both the probe and the target are labeled, detection of hybridization is typically performed by monitoring a color shift resulting from proximity of the two bound labels.

In one embodiment, an array of probes is synthesized on a solid support. Using chip masking technologies and photoprotective chemistry, it is possible to generate ordered arrays of nucleic acid probes. These arrays, which are known, e.g., as "DNA chips" or as very large scale immobilized polymer arrays (VLSIPS™ arrays) can include millions of defined probe regions on a substrate having an area of about 1 $cm^2$ to several $cm^2$.

In another embodiment, capillary electrophoresis is used to analyze a polymorphism. This technique works best when the polymorphism is based on size, for example, AFLP and SSR. This technique is described in detail in U.S. Pat. Nos. 5,534,123 and 5,728,282. Briefly, capillary electrophoresis tubes are filled with the separation matrix. The separation matrix contains hydroxyethyl cellulose, urea and optionally formamide. The AFLP or SSR samples are loaded onto the capillary tube and electrophoresed. Because of the small amount of sample and separation matrix required by capillary electrophoresis, the run times are very short. The molecular sizes and therefore, the number of nucleotides present in the nucleic acid sample are determined by techniques described herein. In a high throughput format, many capillary tubes are placed in a capillary electrophoresis apparatus. The samples are loaded onto the tubes and electrophoresis of the samples is run simultaneously. See, Mathies and Huang (1992) Nature 359:167.

Integrated Systems

Because of the great number of possible combinations present in one array, in one aspect of the invention, an integrated system such as a computer, software corresponding to the statistical models of the invention, and data sets corresponding to genetic markers and phenotypic values, facilitates mapping of phenotypic traits, including QTLs. The phrase "integrated system" in the context of this invention refers to a system in which data entering a computer corresponds to physical objects or processes external to the computer, e.g., nucleic acid sequence hybridization, and a process that, within a computer, causes a physical transformation of the input signals to different output signals. In other words, the input data, e.g., hybridization on a specific region of an array is transformed to output data, e.g., the identification of the sequence hybridized. The process within the computer is a set of instructions, or "program," by which positive hybridization signals are recognized by the integrated system and attributed to individual samples as a genotype. Additional programs correlate the genotype, and more particularly in the methods of the invention, the haplotype, of individual samples with phenotypic values, e.g., using the HAPLO-IM$^+$, HAPLO-MQM, and/or HAPLO-MQM$^+$ models of the invention. For example, the programs JoinMap® and MapQTL® are particularly suited to this type of analysis and can be extended to include the HAPLO-IM$^+$, HAPLO-MQM, and/or HAPLO-MQM$^+$ models of the invention. In addition there are numerous e.g., C/C++ programs for computing, Delphi and/or Java programs for GUI interfaces, and Active X applications (e.g., Olectra Chart and True WevChart) for charting tools. Other useful software tools in the context of the integrated systems of the invention include statistical packages such as SAS, Genstat, and S-Plus. Furthermore additional programming languages such as Fortran and the like are also suitably employed in the integrated systems of the invention.

In one aspect, the invention provides an integrated system comprising a computer or computer readable medium comprising a database with at least one data set that corresponds to genotypes for genetic markers. The system also includes a user interface allowing a user to selectively view one or more databases. In addition, standard text manipulation software such as word processing software (e.g., Microsoft Word™ or Corel Wordperfect™) and database or spreadsheet software (e.g., spreadsheet software such as Microsoft Excel™ Corel Quattro Pro™, or database programs such as Microsoft Access™ or Paradox™) can be used in conjunction with a user interface (e.g., a GUI in a standard operating system such as a Windows, Macintosh or Linux system) to manipulate strings of characters.

The invention also provides integrated systems for sample manipulation incorporating robotic devices as previously described. A robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system.

Integrated systems for genetic marker analysis of the present invention typically include a digital computer with one or more of high-throughput liquid control software, image analysis software, data interpretation software, a robotic liquid control armature for transferring solutions from a source to a destination operably linked to the digital computed, an input device (e.g., a computer keyboard) for entering data to the digital computer to control high throughput liquid transfer by the robotic liquid control armature and, optionally, an image scanner for digitizing label signals from labeled probes hybridized, e.g., to expression products on a solid support operably linked to the digital computer. The image scanner interfaces with the image analysis software to provide a measurement of, e.g., differentiating nucleic acid probe label intensity upon hybridization to an arrayed sample nucleic acid population, where the probe label intensity measurement is interpreted by the data interpretation software to show whether, and to what degree, the labeled probe hybridizes to a label. The data so derived is then correlated with phenotypic values using the statistical models of the present invention, to determine the correspondence between phenotype and genotype(s) for genetic markers, thereby, assigning chromosomal locations.

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or optical image, e.g., using PC (Intel x86 or pentium chip-compatible DOS™, OS2™ WINDOWS™, WINDOWS NT™ or WINDOWS95™ based machines), MACINTOSH™ LINUX, or UNIX based (e.g., SUN™ work station) computers.

Kits

Kits are also provided to facilitate the screening of germplasm for the markers of the present invention. The kits comprise the polynucleotides of the present invention, fragments or complements thereof, for use as probes or primers to detect the markers for shatter resistance. Examples of suitable primers and probes for use in the present invention are set forth in Table 8. The skilled artisan will understand that such primers and probes typically are made by nucleotide synthesis, and can be chemically modified, for instance, to improve stability or to detectably label the probe or primer. Primers and probes also can be affixed to solid supports, such as the arrays described above, and/or other solid supports as is well known in the art. Instructions for using the polynucleotides, as well as buffers and/or other solutions may also be provided to facilitate the use of the polynucleotides. The kit is useful for high throughput screening and in particular, high throughput screening with integrated systems. In certain embodiments, the kits contain a plurality of polynucleotides, e.g., to detect a plurality of the markers and/or polymorphisms associated with shatter resistance.

EXAMPLES

The following experimental methods and results provide additional details regarding specific aspects of protocols and procedures relevant to the practice of the present invention. The examples, which are provided without limitation to illustrate the claimed invention, involve the application of protocols well known to those of skill in the art, and detailed in the references cited herein.

Example 1: Description of Mapping Populations

Three mapping populations were examined. Parental lines were susceptible or resistant to shatter, as determined by one of two tests. In one test (Stirks), mature plants were challenged manually by dragging a wooden bar over the crop at the approximate height of the pods. In another test, a wind machine was used to simulate natural wind conditions.

Shatter resistance or susceptibility was ranked by way of a shatter score (SHTSC) from 1 to 9 (1=highly susceptible, 9=highly resistant). Table 1 below shows details of the ranking, along with the SHTSC of five parental lines used in the mapping populations. Table 2 shows details pertaining to the three mapping populations.

TABLE 1

Rating scale under high shatter pressure in the field

| Rating scale | Percent shatter | Category | Relative response of mapping parents |
|---|---|---|---|
| 1 | 80-100 | Highly susceptible | NS5902 |
| 2 | 70 | Susceptible | 06DSB13911 |
| 3 | 60 | Susceptible | |
| 4 | 50 | Moderately susceptible | |
| 5 | 40 | Moderately resistant | |
| 6 | 30 | Moderately resistant | AV Jade, 09DSB12654 |
| 7 | 20 | Resistant | NS6184 |
| 8 | 10 | Resistant | |
| 9 | 0 | Highly resistant | |

The parents used for the mapping population #1 (SH-Pop 1) are double haploid lines. 09DSB 12564 is a shatter resistant parent, whereas 06DSB 13911 is a susceptible parent. The lines were used to develop a double haploid mapping population consisting of 188 progeny. The progeny were phenotyped with three replicates in Year 1 and two replicates at each of two locations in Year 2. The progeny were mapped with 494 SNPs.

The parents used for the mapping population #2 (SH-Pop 2) were AV Jade (a shatter resistant variety) and 06DSB 13911 (a susceptible parent). The lines were used to develop a double haploid mapping population consisting of 180 progeny. The progeny were phenotyped with two replicates in Year 2 and mapped with 415 SNPs.

The parents used for the mapping population #3 (SH-Pop 3) were NS6184 contributing shatter resistance and NS5902 (a susceptible parent). The lines were used to develop a double haploid mapping population consisting of 180 progeny. The progeny were phenotyped with two replicates in Year 2 and mapped with 389 SNPs.

Example 2. Genetic Mapping and QTL Analysis

Genetic mapping and QTL analysis were performed using JoinMap v3.0 (Van Ooijen, J. W. and R. E. Voorrips, 2001 JoinMap® 3.0, Software for the calculation of genetic linkage maps. Plant Research International, Wageningen, the Netherlands). The Kosambi centiMorgan function was used. A QTL was declared if its LOD score exceeded the threshold of 2.0. LOD stands for logarithm of the odds (to the base 10).

Genetic Mapping

Genetic mapping of the three above-described mapping populations has placed 389-494 molecular markers in 19 linkage groups (LG) that correspond to 19 canola chromosomes and public linkage group nomenclature. The linkage map covers ~1600-1700 cM.

TABLE 2

Three shattering sources, population size, marker number and phenotypic data in three mapping populations

| Population | Population number | Shatter source | QTL nomenclature | Pop size | Marker No. | Shatter field data |
|---|---|---|---|---|---|---|
| 06DSB13911/ 09DSB12564 | SH-Pop 1 | 09DSB12564 | SH-564 | 188 | 494 | Year 1-3 reps; Year 2-2 locations, 2 reps |
| 06DSB13911/ AV Jade | SH-Pop 2 | AV Jade | SH-Jade | 180 | 415 | Year 2-2 reps |
| NS5902/ NS6184 | SH-Pop 3 | NS6184 | SH-6184 | 180 | 389 | Year 2-2 reps |

TABLE 3

Breakdown of Genetic Mapping.

| | Pop1 (06DSB13911/ 09DSB12564) Number of markers | cM on PHD | Pop2 (06DSB13911/ AV Jade) Number of markers | cM on PHD | Pop3 (NS5902/ NS6184) Number of markers | cM on PHD |
|---|---|---|---|---|---|---|
| N01 | 26 | 106.3 | 17 | 106.3 | 13 | 86.8 |
| N02 | 7 | 93.3 | 11 | 51.2 | 8 | 71.4 |
| N03 | 19 | 135.8 | 27 | 131.9 | 26 | 135.8 |
| N04 | 81 | 69.3 | 23 | 54.2 | 25 | 69.3 |
| N05 | 10 | 94.5 | 5 | 94.5 | 9 | 88.5 |
| N06 | 13 | 77.3 | 27 | 78.9 | 20 | 78.9 |
| N07 | 27 | 55.1 | 31 | 66.5 | 28 | 60.2 |
| N08 | 7 | 80.7 | 19 | 80.7 | 3 | 64.3 |
| N09 | 31 | 126.0 | 16 | 126.0 | 20 | 73.7 |
| N10 | 14 | 67.1 | 20 | 64.1 | 20 | 67.1 |
| N11 | 11 | 106.7 | 28 | 82.0 | 33 | 106.4 |
| N12 | 37 | 79.4 | 15 | 129.1 | 17 | 97.7 |
| N13 | 37 | 113.0 | 51 | 108.4 | 33 | 113.0 |
| N14 | 27 | 94.8 | 44 | 82.1 | 46 | 108.0 |
| N15 | 13 | 109.6 | 16 | 90.3 | 12 | 109.6 |
| N16 | 14 | 68.3 | 23 | 68.3 | 17 | 68.1 |
| N17 | 27 | 93.7 | 25 | 93.1 | 25 | 87.9 |
| N18 | 30 | 92.5 | 17 | 92.8 | 28 | 94.1 |
| N19 | 63 | 49.0 | 0 | 0.0 | 6 | 49.0 |
| Total | 494 | 1712.5 | 415 | 1600.3 | 389 | 1629.9 |

QTL Analysis

QTL analysis using simple interval mapping and composite interval mapping (CIM) (Zeng, 1994, Genetics 136: 1457) identified 11 linkage groups (N1, N3, N4, N6, N7, N9, N13, N14, N15, N18 and N19) contributing to shatter resistance. In addition, regions identified by interval mapping as being associated with shatter resistance were confirmed by single-factor analysis of variance (PROC GLM, SAS Enterprise Guide 4.2) on shatter parameters (using the above-described Shatter Score) at the P≤0.01 significance level. These QTLs and the markers associated therewith are identified in Tables 4-7 below. As shown by the "Phenotypic Variation Explained" values in Table 5, some QTLs had a larger effect on shatter resistance than others. With respect to marker designations, nomenclature is as follows: (1) the locus designation is indicated first; for instance, N20003-001; (2) the amplification chemistry is designated second; for instance, -Q001. Markers amplified using TaqMan chemistry (Life Technologies, Inc., Grand Island N.Y.) are designated with a Q, while markers amplified using KASPr chemistry (LGC Genomics, Boston Mass.) are designated with a K.

TABLE 4

Markers significantly associated with shatter resistance at P ≤ 0.01.

| Linkage Group | SNP marker | Genetic Position | Year for Pop1 | Year for Pop2 | Year for Pop3 |
|---|---|---|---|---|---|
| N1 | N20003-001-Q001 | 34.7 | Year 1 (rep1) | | |
| | N03491-1-Q1 | 37.9 | Year 1 (rep1) | | |
| | N0017NR-001-Q001 | 38.6 | Year 1 (rep1) | | |
| | N10336-001-Q001 | 43.3 | Year 1 (rep1) | Year 2 (rep2) | |
| | N23133-001-Q001 | 43.3 | Year 1 (rep1) | Year 2 (rep2) | |
| | N16487-001-Q001 | 46.2 | Year 1 (rep1) | Year 2 (rep2) | |
| | N23426-001-Q001 | 48.8 | | Year 2 (rep2) | |
| N3 | N05671-1-Q1 | 76.3 | | | Year 2 (rep1) |
| | N12643-001-Q001 | 90.8 | | | Year 2 (rep1) |
| N4 | N05943-1-Q1 | 42.9 | | | Year 2 |
| | N06007-1-Q1 | 45.2 | | | Year 2 |
| | N10105-001-Q001 | 54.2 | | | Year 2 |
| | N08181-1-Q1 | 55.3 | | | Years 2 and 3 |
| | N06675-1-Q1 | 69.3 | Years 1 and 2 | | Years 2 and 3 |
| | N001KH2-001-Q001 | 64.6 | Years 1 and 2 | | |
| | N29313-001-Q001 | 64.6 | Years 1 and 2 | | |
| | N88512-001-K001 | 64.3 | Years 1 and 2 | | |
| | N88514-001-K001 | 66.4 | Years 1 and 2 | | |
| | N88515-001-K001 | 66.4 | Years 1 and 2 | | |
| | N88516-001-K001 | 66.4 | Years 1 and 2 | | |
| | N88517-001-K001 | 66.4 | Years 1 and 2 | | |
| | N88518-001-K001 | 67.0 | Years 1 and 2 | | |
| | N88519-001-K001 | 65.9 | Years 1 and 2 | | |
| | N88520-001-K001 | 64.9 | Years 1 and 2 | | |

TABLE 4-continued

Markers significantly associated with shatter resistance at P ≤ 0.01.

| Linkage Group | SNP marker | Genetic Position | Year for Pop1 | Year for Pop2 | Year for Pop3 |
|---|---|---|---|---|---|
| | N88521-001-K001 | 65.1 | Years 1 and 2 | | |
| | N001KFE-001-Q001 | 66.4 | Years 1 and 2 | | |
| | N88522-001-K001 | 66.4 | Years 1 and 2 | | |
| | N88523-001-K001 | 67.1 | Years 1 and 2 | | |
| | N88524-001-K001 | 66.8 | Years 1 and 2 | | |
| | N88525-001-K001 | 67.5 | Years 1 and 2 | | |
| | N88529-001-K001 | 67.3 | Years 1 and 2 | | |
| | N88530-001-K001 | 68.2 | Years 1 and 2 | | |
| | N88531-001-K001 | 69.0 | Years 1 and 2 | | |
| | N88533-001-K001 | 69.2 | Years 1 and 2 | | |
| | N88535-001-K001 | 69.1 | Years 1 and 2 | | |
| | N88536-001-K001 | 69.1 | Years 1 and 2 | | |
| | N88537-001-K001 | 69.1 | Years 1 and 2 | | |
| N6 | N07541-1-Q1 | 39.6 | | | Years 2 and 3 |
| | N23413-001-Q001 | 56.6 | | | Years 2 and 3 |
| | N08344-1-Q1 | 58.9 | | | Years 2 and 3 |
| | N23533-001-Q011 | 59.7 | | | Years 2 and 3 |
| | N14649-001-Q001 | 65.6 | | | Years 2 and 3 |
| N7 | N23310-001-Q001 | 27.9 | | Year 2 | |
| | N10526-001-Q001 | 28.6 | | Year 2 | |
| | N23373-001-Q001 | 29.2 | | Year 2 | |
| | N23353-001-Q001 | 30.9 | | Year 2 | |
| | N23206-001-Q001 | 33.1 | | Year 2 | |
| | N11025-001-Q001 | 36.1 | | Year 2 | |
| | N09969-001-Q001 | 40.0 | | Year 2 | |
| | N09882-001-Q001 | 41.6 | | Year 2 | |
| | N10389-001-Q001 | 41.6 | | Year 2 | |
| | N09940-001-Q001 | 41.8 | | Year 2 | |
| | N23409-001-Q001 | 46.0 | | Year 2 | |
| N7 | N07278-1-Q1 | 55.1 | | Year 3 | |
| | N16343-001-Q001 | 58.6 | | Year 3 | |
| | N23417-001-Q001 | 64.5 | | Year 3 | |
| N9 | N23119-001-Q001 | 45.4 | | Years 2 and 3 | |
| | N09861-001-Q001 | 53.3 | | Years 2 and 3 | |
| | N04807-1-Q1 | 55.7 | | Years 2 and 3 | Year 2 |
| | N06778-1-Q1 | 60.0 | | Years 2 and 3 | Year 2 |
| | N09897-001-Q001 | 60.1 | | Years 2 and 3 | Year 2 |
| | N10499-001-Q001 | 60.1 | | Years 2 and 3 | Year 2 |
| | N23447-001-Q001 | 60.1 | | Years 2 and 3 | Year 2 |
| | N19834-001-Q001 | 60.1 | | Years 2 and 3 | Year 2 |
| | N23362-001-Q001 | 64.1 | | Years 2 and 3 | Year 2 |
| | N23266-001-Q001 | 70.0 | | Years 2 and 3 | Year 2 |
| | N19862-001-Q001 | 70.7 | | Years 2 and 3 | Year 2 |
| | N22187-001-Q001 | 70.7 | | Years 2 and 3 | Year 2 |
| | N08651-1-Q1 | 71.9 | | Years 2 and 3 | Year 2 |
| | N23296-001-Q001 | 73.1 | | Years 2 and 3 | Year 2 |
| | N17314-001-Q001 | 73.7 | | Years 2 and 3 | Year 2 |
| | N20380-001-Q001 | 74.2 | | Years 2 and 3 | |
| N9 | N05490-1-Q1 | 104.5 | Year 1 | | |
| | N18849-001-Q001 | 104.8 | Year 1 | | |
| | N08200-1-Q1 | 105.4 | Year 1 | | |
| | N19827-001-Q001 | 105.4 | Year 1 | | |
| | N001R9W-001-Q001 | 105.4 | Year 1 | | |
| | N08264-1-Q1 | 112.4 | Year 1 | | |
| | N23132-001-Q001 | 113.6 | Year 1 | | |
| | N03615-1-Q1 | 118.4 | Year 1 | | |
| | N001RWT-001-Q001 | 118.4 | Year 1 | | |
| | N08465-1-Q1 | 119.0 | Year 1 | | |
| | N10774-001-Q001 | 119.3 | Year 1 | | |
| | N17035-001-Q001 | 122.1 | Year 1 | | |
| | N20834-001-Q001 | 122.7 | Year 1 | | |
| N13 | N22903-001-Q001 | −22.6 | | | Years 2 and 3 |
| | N09920-001-Q001 | −15.5 | | | Years 2 and 3 |
| | N22822-001-Q001 | −13.0 | | | Years 2 and 3 |
| | N22688-001-Q001 | −9.8 | | | Years 2 and 3 |
| | N10074-001-Q001 | −9.7 | | | Years 2 and 3 |
| | N10057-001-Q001 | −8.5 | | | Years 2 and 3 |
| | N10086-001-Q001 | −8.5 | | | Years 2 and 3 |
| | N11084-001-Q001 | −8.4 | | | Years 2 and 3 |
| | N22814-001-Q001 | 2.5 | | | Years 2 and 3 |
| | N01564-2-Q1 | 3.2 | | | Years 2 and 3 |
| | N12902-001-Q001 | 3.5 | | | Years 2 and 3 |

TABLE 4-continued

Markers significantly associated with shatter resistance at P ≤ 0.01.

| Linkage Group | SNP marker | Genetic Position | Year for Pop1 | Year for Pop2 | Year for Pop3 |
|---|---|---|---|---|---|
| N13 | N21144-001-Q001 | 59.8 | | Years 2 and 3 | |
| | N07534-1-Q1 | 62.5 | | Years 2 and 3 | |
| | N22993-001-Q001 | 62.5 | | Years 2 and 3 | |
| | N09963-001-Q001 | 62.8 | | Years 2 and 3 | |
| | N11542-001-Q001 | 63.2 | | Years 2 and 3 | |
| | N14681-001-Q001 | 63.9 | | Years 2 and 3 | |
| | N11636-001-Q001 | 64.3 | | Years 2 and 3 | |
| | N13732-001-Q001 | 65.1 | | Years 2 and 3 | |
| | N11255-001-Q001 | 67.4 | | Years 2 and 3 | |
| | N15511-001-Q001 | 67.6 | | Years 2 and 3 | |
| | N10536-001-Q001 | 69.5 | | Years 2 and 3 | |
| | N09862-001-Q001 | 71.8 | | Years 2 and 3 | |
| N14 | N23033-001-Q001 | 14.1 | | | Year 2 |
| | N06039-1-Q1 | 31.7 | | | Year 2 |
| | N10016-001-Q001 | 31.7 | | | Years 2 and 3 |
| | N22743-001-Q001 | 32.4 | | | Years 2 and 3 |
| | N22953-001-Q001 | 32.5 | | | Years 2 and 3 |
| | N09987-001-Q001 | 33.4 | | | Years 2 and 3 |
| | N10092-001-Q001 | 33.4 | | | Years 2 and 3 |
| | N10096-001-Q001 | 33.4 | | | Years 2 and 3 |
| | N22728-001-Q001 | 33.4 | | | Years 2 and 3 |
| | N22747-001-Q001 | 33.4 | | | Years 2 and 3 |
| | N22840-001-Q001 | 33.4 | | | Years 2 and 3 |
| | N23027-001-Q001 | 33.4 | | | Years 2 and 3 |
| | N22777-001-Q001 | 33.9 | | | Years 2 and 3 |
| | N09636-001-Q001 | 34.2 | | | Years 2 and 3 |
| | N09879-001-Q001 | 35.6 | | | Years 2 and 3 |
| | N10123-001-Q001 | 35.6 | | | Years 2 and 3 |
| | N10316-001-Q001 | 35.6 | | | Years 2 and 3 |
| | N10507-001-Q001 | 35.6 | | | Years 2 and 3 |
| | N09834-001-Q001 | 36.8 | | | Years 2 and 3 |
| | N22934-001-Q001 | 37.2 | | | Years 2 and 3 |
| | N22700-001-Q001 | 37.8 | | | Years 2 and 3 |
| | N22725-001-Q001 | 37.8 | | | Years 2 and 3 |
| | N22881-001-Q001 | 37.8 | | | Years 2 and 3 |
| | N23032-001-Q001 | 37.8 | | | Years 2 and 3 |
| | N22786-001-Q001 | 37.9 | | | Years 2 and 3 |
| | N23014-001-Q001 | 37.9 | | | Years 2 and 3 |
| | N10471-001-Q001 | 38.2 | | | Years 2 and 3 |
| | N11419-001-Q001 | 39.5 | | | Years 2 and 3 |
| | N22724-001-Q001 | 43.4 | | | Years 2 and 3 |
| | N22902-001-Q001 | 43.0 | | | Years 2 and 3 |
| | N23063-001-Q001 | 43.3 | | | Years 2 and 3 |
| | N22723-001-Q001 | 43.4 | | | Years 2 and 3 |
| | N23049-001-Q001 | 43.5 | | | Years 2 and 3 |
| | N10321-001-Q001 | 47.1 | | | Years 2 and 3 |
| | N15374-001-Q001 | 48.3 | | | Years 2 and 3 |
| | N22802-001-Q001 | 49.4 | | | Years 2 and 3 |
| N15 | N12785-001-Q001 | 40.5 | | | Year 2 |
| | N09910-001-Q001 | 56.5 | | | Years 2 and 3 |
| | N21146-001-Q001 | 60.0 | | | Years 2 and 3 |
| | N17618-001-Q001 | 63.1 | | | Years 2 and 3 |
| | N09776-001-Q001 | 64.2 | | | Years 2 and 3 |
| | N19296-001-Q001 | 64.2 | | | Years 2 and 3 |
| N18 | N22803-001-Q001 | 43.8 | | | Year 3 |
| | N05205-1-Q1 | 57.2 | | | Years 2 and 3 |
| | N10406-001-Q001 | 58.0 | Year3 | | Years 2 and 3 |
| | N22941-001-Q001 | 58.6 | Year3 | | Years 2 and 3 |
| | N22875-001-Q001 | 63.9 | Year3 | | Years 2 and 3 |
| | N13286-001-Q001 | 63.9 | Year3 | | Years 2 and 3 |
| | N04503-1-Q1 | 64.6 | Year3 | | Years 2 and 3 |
| | N22925-001-Q001 | 65.0 | Year3 | | Years 2 and 3 |
| | N18929-001-Q001 | 74.8 | Year3 | | |
| | N16041-001-Q001 | 76.9 | Year3 | | |
| | N18401-001-Q001 | 84.6 | Year3 | | |
| N19 | N05656-1-Q1 | 27.7 | Year 1 | | |
| | N17581-001-Q001 | 30.7 | Year 1 | | |
| | N001NVH-001-Q001 | 38.4 | Year 1 | | |
| | N22928-001-Q001 | 38.9 | Year 1 | | |
| | N08219-1-Q001 | 40.1 | Year 1 | | |
| | N05710-1-Q1 | 40.2 | Year 1 | | |
| | N15338-001-Q001 | 41.6 | Year 1 | | |

TABLE 4-continued

Markers significantly associated with shatter resistance at P ≤ 0.01.

| Linkage Group | SNP marker | Genetic Position | Year for Pop1 | Year for Pop2 | Year for Pop3 |
|---|---|---|---|---|---|
| | N10424-001-Q001 | 41.7 | Year 1 | | |
| | N16006-001-Q001 | 44.4 | Year 1 | | |

TABLE 5

QTLs associated with shatter resistance.

| QTL | LG | Flanking Markers | QTL interval length (PHD v1.3) (cM) | Year | LOD score | Phenotypic variation explained (%) |
|---|---|---|---|---|---|---|
| a. Six SH-QTLs identified from 09DSB12564 in 06DSB13911/09DSB12564 (Pop1) | | | | | | |
| SH-564-N1.1 | N1 | N20003-001-Q001-N23426-001-Q001 | 13.3 (34.7-48.0) | 1 (rep1) | 3.4 | 4.7 |
| SH-564-N4.1 | N4 | N88514-001-K001-N88537-001-K001 | 6 (64.0-70.0) | 1 | 23.6 | 36.3 |
| | N4 | N88514-001-K001-N88537-001-K001 | 6 (64.0-70.0) | 2 | 16.3 | 23.1 |
| | N4 | N88514-001-K001-N88537-001-K001 | 6 (64.0-70.0) | 3 | 10.6 | 15.5 |
| SH-564-N7.1 | N7 | N23310-001-Q001 - N23409-001-Q001 | 18.1 (27.9-46.0) | 2 | 6.5 | 7.9 |
| SH-564-N9.1 | N9 | N05490-1-Q1 - N20834-001-Q001 | 18.2 (104.5-122.7) | 1 | 4.4 | 5.9 |
| | N9 | N001RWT-001-Q001 - N20834-001-Q001 | 4.5 (118.4-122.7) | 2 (one rep) | 2.8 | 4.9 |
| SH-564-N19.1 | N18 | N10406-001-Q001 - N18401-001-Q001 | 26.6 (58.0-84.6) | 3 | 8.2 | 12.8 |
| SH-564-N19.1 | N19 | N05656-1-Q1 - N87555-001-Q001 | 18 (28.0-46.0) | 1 | 6.1 | 7.6 |
| b. Four SH-QTLs identified from AV Jade in 06DSB13911/AV Jade (Pop2) | | | | | | |
| SH-Jade-N1.1 | N1 | N10336-001-Q001-N23426-001-Q001 | 5.5 (43.3-48.8) | 2 (Rep2) | 3.6 | 10.4 |
| SH-Jade-N7.1 | N7 | N07278-1-Q1-N23417-001-Q001 | 9.4 (55.1-64.5) | 3 | 6.2 | 10.4 |
| SH-Jade-N9.1 | N9 | N23119-001-Q001 - N20380-001-Q001 | 28.8 (45.4-74.2) | 2 | 4.8 | 9.8 |
| | N9 | N23119-001-Q001 - N20380-001-Q001 | 28.8 (45.4-74.2) | 3 | 9.9 | 20.2 |
| SH-Jade-N13.1 | N13 | N21144-001-Q001 - N09862-001-Q001 | 12 (59.8-71.8) | 2 | 6.6 | 12.3 |
| | N13 | N21144-001-Q001 - N09862-001-Q001 | 12 (59.8-71.8) | 3 | 5.3 | 8.5 |
| c. Eight SH-QTLs identified from NS6184 in NS5902/NS6184 (Pop3) | | | | | | |
| SH-6184-N3.1 | N3 | N05671-1-Q1-N12643-001-Q001 | 14.5 (76.3-90.8) | 2 (Rep1) | 4.2 | 9.0 |
| SH-6184-N4.1 | N4 | N05943-1-Q1 - N06675-1-Q1 | 26.5 (42.9-69.4) | 2 | 6.0 | 12.1 |
| | N4 | N08181-1-Q1-N06675-1-Q1 | 14.1 (55.3-69.4) | 3 (Rep2) | 3.4 | 6.9 |
| SH-6184-N6.1 | N6 | N07541-1-Q1 - N14649-001-Q001 | 26.0 (39.6-65.6) | 2 | 4.9 | 9.4 |
| | N6 | N07541-1-Q1 - N14649-001-Q001 | 26.0 (39.6-65.6) | 3 | 3.9 | 7.9 |
| SH-6184-N9.1 | N9 | N04807-1-Q1 - N17314-001-Q001 | 18.0 (55.7-73.7) | 2 | 4.2 | 7.5 |
| SH-6184-N13.1 | N13 | N22903-001-Q001 - N12902-001-Q001 | 26.1 (−22.6-3.5) | 2 | 4.3 | 8.4 |
| | N13 | N22903-001-Q001 - N12902-001-Q001 | 26.1 (−22.6-3.5) | 3 (Rep2) | 2.3 | 4.2 |
| SH-6184-N14.1 | N14 | N23033-001-Q001 - N22724-001-Q001 | 29.3 (14.1-43.4) | 2 | 6.4 | 12.8 |
| | N14 | N10016-001-Q001 - N22802-001-Q001 | 17.1 (31.7-49.4) | 3 (Rep2) | 2.7 | 5.1 |
| SH-6184-N15.1 | N15 | N12785-001-Q001 - N19296-001-Q001 | 23.7 (40.5-64.2) | 2 | 5.6 | 9.6 |
| | N15 | N09910-001-Q001 - N19296-001-Q001 | 7.7 (56.5-64.2) | 3 | 6.7 | 14.0 |

TABLE 5-continued

QTLs associated with shatter resistance.

| QTL | LG | Flanking Markers (cM) | QTL interval length (PHD v1.3) | Year | LOD score | Phenotypic variation explained (%) |
|---|---|---|---|---|---|---|
| SH-6184-N18.1 | N18 | N05205-1-Q1 - N22925-001-Q001 | 7.8 (57.2-65.0) | 2 | 3.9 | 6.6 |
| | N18 | N22803-001-Q001 - N22925-001-Q001 | 21.2 (43.8-65.0) | 3 | 2.6 | 7.9 |

Additional information about the alleles of each SNP marker flanking the QTLs associated with resistance to shatter is provided in Table 6.

TABLE 6

SNP marker alleles for Shatter QTLs:

| SNP marker | LG | SNP Type | Pop1 -QTL | Favorable allele from 09DSB-12564 | Pop2-QTL | Favorable allele from JADE | Pop3-QTL | Favorable allele from NS61-84BR |
|---|---|---|---|---|---|---|---|---|
| N20003-001-Q001 | N1 | G/T | SH-564-N1.1 | T | | | | |
| N03491-1-Q1 | N1 | C/G | SH-564-N1.1 | G | | | | |
| N0017NR-001-Q001 | N1 | A/G | SH-564-N1.1 | G | | | | |
| N10336-001-Q001 | N1 | A/G | SH-564-N1.1 | A | SH-Jade-N1.1 | A | | |
| N23133-001-Q001 | N1 | C/T | SH-564-N1.1 | C | SH-Jade-N1.1 | T | | |
| N16487-001-Q001 | N1 | G/T | SH-564-N1.1 | G | SH-Jade-N1.1 | T | | |
| N23426-001-Q001 | N1 | A/G | | | SH-Jade-N1.1 | A | | |
| N05671-1-Q1 | N3 | C/T | | | | | SH-6184-N3.1 | C |
| N12643-001-Q001 | N3 | A/C | | | | | SH-6184-N3.1 | A |
| N05943-1-Q1 | N4 | A/G | | | | | SH-6184-N4.1 | G |
| N06007-1-Q1 | N4 | C/T | | | | | SH-6184-N4.1 | T |
| N10105-001-Q001 | N4 | A/T | | | | | SH-6184-N4.1 | A |
| N08181-1-Q1 | N4 | G/T | | | | | SH-6184-N4.1 | G |
| N06675-1-Q1 | N4 | C/T | SH-564-N4.1 | T | | | SH-6184-N4.1 | T |
| N001KH2-001-Q001 | N4 | A/G | SH-564-N4.1 | G | | | | |
| N29313-001-Q001 | N4 | G/T | SH-564-N4.1 | T | | | | |
| N88512-001-K001 | N4 | A/C | SH-564-N4.1 | C | | | | |
| N88514-001-K001 | N4 | C/G | SH-564-N4.1 | G | | | | |
| N88515-001-K001 | N4 | A/G | SH-564-N4.1 | A | | | | |
| N88516-001-K001 | N4 | A/T | SH-564-N4.1 | T | | | | |
| N88517-001-K001 | N4 | A/G | SH-564-N4.1 | G | | | | |
| N88518-001-K001 | N4 | A/G | SH-564-N4.1 | A | | | | |
| N88519-001-K001 | N4 | A/G | SH-564-N4.1 | A | | | | |
| N88520-001-K001 | N4 | G/T | SH-564-N4.1 | G | | | | |
| N88521-001-K001 | N4 | A/G | SH-564-N4.1 | A | | | | |
| N001KFE-001-Q001 | N4 | A/G | SH-564-N4.1 | A | | | | |
| N88522-001-K001 | N4 | A/C | SH-564-N4.1 | A | | | | |
| N88523-001-K001 | N4 | A/G | SH-564-N4.1 | A | | | | |
| N88524-001-K001 | N4 | G/T | SH-564-N4.1 | G | | | | |
| N88525-001-K001 | N4 | A/T | SH-564-N4.1 | A | | | | |
| N88529-001-K001 | N4 | C/T | SH-564-N4.1 | C | | | | |
| N88530-001-K001 | N4 | C/T | SH-564-N4.1 | C | | | | |
| N88531-001-K001 | N4 | A/G | SH-564-N4.1 | A | | | | |
| N88533-001-K001 | N4 | A/G | SH-564-N4.1 | A | | | | |
| N88535-001-K001 | N4 | A/C | SH-564-N4.1 | C | | | | |
| N88536-001-K001 | N4 | C/G | SH-564-N4.1 | G | | | | |
| N88537-001-K001 | N4 | C/G | SH-564-N4.1 | G | | | | |
| N07541-1-Q1 | N6 | C/G | | | | | SH-6184-N6.1 | C |
| N23413-001-Q001 | N6 | A/T | | | | | SH-6184-N6.1 | T |
| N08344-1-Q1 | N6 | A/C | | | | | SH-6184-N6.1 | C |
| N23533-001-Q011 | N6 | C/T | | | | | SH-6184-N6.1 | T |
| N14649-001-Q001 | N6 | A/C | | | | | SH-6184-N6.1 | A |
| N23310-001-Q001 | N7 | A/G | SH-564-N7.1 | A | | | | |
| N10526-001-Q001 | N7 | G/T | SH-564-N7.1 | T | | | | |
| N23373-001-Q001 | N7 | C/G | SH-564-N7.1 | G | | | | |
| N23353-001-Q001 | N7 | C/G | SH-564-N7.1 | C | | | | |
| N23206-001-Q001 | N7 | C/T | SH-564-N7.1 | T | | | | |
| N11025-001-Q001 | N7 | A/G | SH-564-N7.1 | A | | | | |
| N09969-001-Q001 | N7 | C/T | SH-564-N7.1 | C | | | | |
| N09882-001-Q001 | N7 | A/C | SH-564-N7.1 | C | | | | |
| N10389-001-Q001 | N7 | C/T | SH-564-N7.1 | C | | | | |

TABLE 6-continued

SNP marker alleles for Shatter QTLs:

| SNP marker | LG | SNP Type | Pop1 -QTL | Favorable allele from 09DSB - 12564 | Pop2-QTL | Favorable allele from JADE | Pop3-QTL | Favorable allele from NS61- 84BR |
|---|---|---|---|---|---|---|---|---|
| N09940-001-Q001 | N7 | A/G | SH-564-N7.1 | A | | | | |
| N23409-001-Q001 | N7 | C/G | SH-564-N7.1 | G | | | | |
| N07278-1-Q1 | N7 | A/G | | | SH-Jade-N7.1 | G | | |
| N16343-001-Q001 | N7 | A/C | | | SH-Jade-N7.1 | C | | |
| N23417-001-Q001 | N7 | C/G | | | SH-Jade-N7.1 | C | | |
| N23119-001-Q001 | N9 | A/G | | | SH-Jade-N9.1 | A | | |
| N09861-001-Q001 | N9 | A/G | | | SH-Jade-N9.1 | A | | |
| N04807-1-Q1 | N9 | A/G | | | SH-Jade-N9.1 | G | SH-6184-N9.1 | G |
| N06778-1-Q1 | N9 | C/G | | | SH-Jade-N9.1 | G | SH-6184-N9.1 | C |
| N09897-001-Q001 | N9 | C/T | | | SH-Jade-N9.1 | C | SH-6184-N9.1 | T |
| N10499-001-Q001 | N9 | A/C | | | SH-Jade-N9.1 | A | SH-6184-N9.1 | C |
| N23447-001-Q001 | N9 | A/G | | | SH-Jade-N9.1 | A | SH-6184-N9.1 | G |
| N19834-001-Q001 | N9 | A/G | | | SH-Jade-N9.1 | A | SH-6184-N9.1 | G |
| N23362-001-Q001 | N9 | A/G | | | SH-Jade-N9.1 | A | SH-6184-N9.1 | G |
| N23266-001-Q001 | N9 | C/G | | | SH-Jade-N9.1 | G | SH-6184-N9.1 | G |
| N19862-001-Q001 | N9 | A/C | | | SH-Jade-N9.1 | A | SH-6184-N9.1 | A |
| N22187-001-Q001 | N9 | A/G | | | SH-Jade-N9.1 | G | SH-6184-N9.1 | G |
| N08651-1-Q1 | N9 | A/T | | | SH-Jade-N9.1 | A | SH-6184-N9.1 | T |
| N23296-001-Q001 | N9 | A/G | | | SH-Jade-N9.1 | A | SH-6184-N9.1 | A |
| N17314-001-Q001 | N9 | G/T | | | SH-Jade-N9.1 | T | SH-6184-N9.1 | G |
| N20380-001-Q001 | N9 | A/C | | | SH-Jade-N9.1 | C | | |
| N05490-1-Q1 | N9 | C/G | SH-564-N9.1 | G | | | | |
| N18849-001-Q001 | N9 | G/T | SH-564-N9.1 | T | | | | |
| N08200-1-Q1 | N9 | C/G | SH-564-N9.1 | G | | | | |
| N19827-001-Q001 | N9 | A/G | SH-564-N9.1 | G | | | | |
| N001R9W-001-Q001 | N9 | A/C | SH-564-N9.1 | C | | | | |
| N08264-1-Q1 | N9 | C/T | SH-564-N9.1 | C | | | | |
| N23132-001-Q001 | N9 | A/G | SH-564-N9.1 | G | | | | |
| N03615-1-Q1 | N9 | A/T | SH-564-N9.1 | A | | | | |
| N001RWT-001-Q001 | N9 | A/G | SH-564-N9.1 | A | | | | |
| N08465-1-Q1 | N9 | A/G | SH-564-N9.1 | A | | | | |
| N10774-001-Q001 | N9 | A/C | SH-564-N9.1 | A | | | | |
| N17035-001-Q001 | N9 | A/G | SH-564-N9.1 | A | | | | |
| N20834-001-Q001 | N9 | C/T | SH-564-N9.1 | T | | | | |
| N22903-001-Q001 | N13 | C/G | | | | | SH-6184-N13.1 | C |
| N09920-001-Q001 | N13 | A/T | | | | | SH-6184-N13.1 | T |
| N22822-001-Q001 | N13 | C/G | | | | | SH-6184-N13.1 | G |
| N22688-001-Q001 | N13 | C/G | | | | | SH-6184-N13.1 | C |
| N10074-001-Q001 | N13 | G/T | | | | | SH-6184-N13.1 | G |
| N10057-001-Q001 | N13 | C/T | | | | | SH-6184-N13.1 | T |
| N10086-001-Q001 | N13 | C/T | | | | | SH-6184-N13.1 | C |
| N11084-001-Q001 | N13 | A/G | | | | | SH-6184-N13.1 | A |
| N22814-001-Q001 | N13 | A/T | | | | | SH-6184-N13.1 | T |
| N01564-2-Q1 | N13 | A/C | | | | | SH-6184-N13.1 | C |
| N12902-001-Q001 | N13 | C/T | | | | | SH-6184-N13.1 | C |
| N21144-001-Q001 | N13 | A/C | | | SH-Jade-N13.1 | A | | |
| N07534-1-Q1 | N13 | G/T | | | SH-Jade-N13.1 | G | | |
| N22993-001-Q001 | N13 | C/G | | | SH-Jade-N13.1 | C | | |
| N09963-001-Q001 | N13 | G/T | | | SH-Jade-N13.1 | G | | |
| N11542-001-Q001 | N13 | C/T | | | SH-Jade-N13.1 | T | | |
| N14681-001-Q001 | N13 | A/C | | | SH-Jade-N13.1 | C | | |
| N11636-001-Q001 | N13 | A/G | | | SH-Jade-N13.1 | G | | |
| N13732-001-Q001 | N13 | C/T | | | SH-Jade-N13.1 | T | | |
| N11255-001-Q001 | N13 | C/T | | | SH-Jade-N13.1 | T | | |
| N15511-001-Q001 | N13 | A/G | | | SH-Jade-N13.1 | A | | |
| N10536-001-Q001 | N13 | G/T | | | SH-Jade-N13.1 | G | | |
| N09862-001-Q001 | N13 | A/G | | | SH-Jade-N13.1 | A | | |
| N23033-001-Q001 | N14 | A/T | | | | | SH-6184-N14.1 | T |
| N06039-1-Q1 | N14 | G/T | | | | | SH-6184-N14.1 | G |
| N10016-001-Q001 | N14 | C/T | | | | | SH-6184-N14.1 | T |
| N22743-001-Q001 | N14 | A/T | | | | | SH-6184-N14.1 | T |
| N22953-001-Q001 | N14 | A/T | | | | | SH-6184-N14.1 | A |
| N09987-001-Q001 | N14 | A/G | | | | | SH-6184-N14.1 | G |
| N10092-001-Q001 | N14 | A/G | | | | | SH-6184-N14.1 | A |
| N10096-001-Q001 | N14 | A/G | | | | | SH-6184-N14.1 | A |
| N22728-001-Q001 | N14 | C/G | | | | | SH-6184-N14.1 | G |
| N22747-001-Q001 | N14 | C/G | | | | | SH-6184-N14.1 | C |
| N22840-001-Q001 | N14 | A/T | | | | | SH-6184-N14.1 | T |
| N23027-001-Q001 | N14 | A/T | | | | | SH-6184-N14.1 | T |
| N22777-001-Q001 | N14 | C/G | | | | | SH-6184-N14.1 | C |
| N09636-001-Q001 | N14 | G/T | | | | | SH-6184-N14.1 | T |
| N09879-001-Q001 | N14 | A/G | | | | | SH-6184-N14.1 | G |

TABLE 6-continued

SNP marker alleles for Shatter QTLs:

| SNP marker | LG | SNP Type | Pop1-QTL | Favorable allele from 09DSB-12564 | Pop2-QTL | Favorable allele from JADE | Pop3-QTL | Favorable allele from NS61-84BR |
|---|---|---|---|---|---|---|---|---|
| N10123-001-Q001 | N14 | A/G | | | | | SH-6184-N14.1 | A |
| N10316-001-Q001 | N14 | C/T | | | | | SH-6184-N14.1 | T |
| N10507-001-Q001 | N14 | C/T | | | | | SH-6184-N14.1 | T |
| N09834-001-Q001 | N14 | C/T | | | | | SH-6184-N14.1 | C |
| N22934-001-Q001 | N14 | A/T | | | | | SH-6184-N14.1 | A |
| N22700-001-Q001 | N14 | A/T | | | | | SH-6184-N14.1 | A |
| N22725-001-Q001 | N14 | A/T | | | | | SH-6184-N14.1 | A |
| N22881-001-Q001 | N14 | A/T | | | | | SH-6184-N14.1 | A |
| N23032-001-Q001 | N14 | A/T | | | | | SH-6184-N14.1 | T |
| N22786-001-Q001 | N14 | C/G | | | | | SH-6184-N14.1 | C |
| N23014-001-Q001 | N14 | C/G | | | | | SH-6184-N14.1 | G |
| N10471-001-Q001 | N14 | C/T | | | | | SH-6184-N14.1 | T |
| N11419-001-Q001 | N14 | C/T | | | | | SH-6184-N14.1 | T |
| N22724-001-Q001 | N14 | A/T | | | | | SH-6184-N14.1 | T |
| N22902-001-Q001 | N14 | C/G | | | | | SH-6184-N14.1 | G |
| N23063-001-Q001 | N14 | A/T | | | | | SH-6184-N14.1 | A |
| N22723-001-Q001 | N14 | C/G | | | | | SH-6184-N14.1 | C |
| N23049-001-Q001 | N14 | A/T | | | | | SH-6184-N14.1 | A |
| N10321-001-Q001 | N14 | A/T | | | | | SH-6184-N14.1 | A |
| N15374-001-Q001 | N14 | A/C | | | | | SH-6184-N14.1 | A |
| N22802-001-Q001 | N14 | C/G | | | | | SH-6184-N14.1 | C |
| N12785-001-Q001 | N15 | A/G | | | | | SH-6184-N15.1 | G |
| N09910-001-Q001 | N15 | A/T | | | | | SH-6184-N15.1 | T |
| N21146-001-Q001 | N15 | A/C | | | | | SH-6184-N15.1 | A |
| N17618-001-Q001 | N15 | A/G | | | | | SH-6184-N15.1 | G |
| N09776-001-Q001 | N15 | A/C | | | | | SH-6184-N15.1 | A |
| N19296-001-Q001 | N15 | A/C | | | | | SH-6184-N15.1 | C |
| N22803-001-Q001 | N18 | A/T | | | | | SH-6184-N18.1 | A |
| N05205-1-Q1 | N18 | G/T | | | | | SH-6184-N18.1 | T |
| N10406-001-Q001 | N18 | C/G | SH-564-N18.1 | G | | | SH-6184-N18.1 | G |
| N22941-001-Q001 | N18 | C/G | SH-564-N18.1 | C | | | SH-6184-N18.1 | G |
| N22875-001-Q001 | N18 | C/G | SH-564-N18.1 | G | | | SH-6184-N18.1 | C |
| N13286-001-Q001 | N18 | A/G | SH-564-N18.1 | A | | | SH-6184-N18.1 | G |
| N04503-1-Q1 | N18 | C/G | SH-564-N18.1 | G | | | SH-6184-N18.1 | G |
| N22925-001-Q001 | N18 | C/G | SH-564-N18.1 | G | | | SH-6184-N18.1 | C |
| N18929-001-Q001 | N18 | A/G | SH-564-N18.1 | G | | | | |
| N16041-001-Q001 | N18 | C/T | SH-564-N18.1 | C | | | | |
| N18401-001-Q001 | N18 | C/T | SH-564-N18.1 | T | | | | |
| N05656-1-Q1 | N19 | G/T | SH-564-N19.1 | G | | | | |
| N17581-001-Q001 | N19 | A/C | SH-564-N19.1 | C | | | | |
| N001NVH-001-Q001 | N19 | A/G | SH-564-N19.1 | A | | | | |
| N22928-001-Q001 | N19 | A/T | SH-564-N19.1 | T | | | | |
| N08219-1-Q001 | N19 | G/T | SH-564-N19.1 | T | | | | |
| N05710-1-Q1 | N19 | A/G | SH-564-N19.1 | G | | | | |
| N15338-001-Q001 | N19 | C/T | SH-564-N19.1 | T | | | | |
| N10424-001-Q001 | N19 | A/G | SH-564-N19.1 | A | | | | |
| N16006-001-Q001 | N19 | C/T | SH-564-N19.1 | T | | | | |

Example 3: Marker Sequences Containing Polymorphisms, and Exemplary Primers

Set forth below in Table 7 is sequence information for markers of QTLs significantly associated with shatter resistance at P≤0.01, as set forth in the foregoing examples. In the sequences, n=an unknown nucleotide; underlined sequences indicate the primer sequences from Table 8 that follows, and sequences in brackets indicate polymorphic regions (SNPs). Publicly available markers are indicated with an asterisk (*).

TABLE 7

Markers of QTLs significantly associated with shatter resistance (P ≤ 0.01)

| SEQ ID NO: | Marker Name and Sequence |
|---|---|
| 1 | N20003-001-Q001<br>AAGGAGAGACTAAGGAAGGAGCATATGCACTGACCTTTGC<br>ATCCGTCCGGTGTATATGCGTTTCCTGTGTGCAACCACAA<br>TGTGCATAACTAATATTAGAAATGGTGGTTTTGTCGCAGA<br>TGCACTTCATTTGGGATTTAGTCGAGGAAGTATTACGTCG<br>GTACTCTTTTCTGTTGTCGCAGGGCAAGGAACTCAGGAAT<br>[G/T]AATGATTCTTTGTTTGTATCACCCATCCTAGAGTA<br>AGGGTAGCATATCCCTTACCAAGTAACTGTGTTGGTCTTG<br>TCGCATTGGACAAAGTGTAGACTTCATCCGTCATGAAGGC<br>CACTCTACAATGTTCTTCTCTTGTTGTTGTTGTTGTTGTC<br>GAGTTTCCACCATTGCTCTCTATCATGATGCCAATAGT<br>TTGTT |
| 2 | N03491-1-Q1*<br>GCTTGATCTCTTCAATTCGGGGATTAGAGCTTTCCGGTAC<br>TCATGCGGCCCCAATCCAGAATCGATCTCTCACTA[C/G]<br>GGACTACTTCCCTTGGTACAGNCGTNCCCAAGGTCGCCAN<br>TTCGCTTCGAAATCAAACGGTACTGATGAAAGCAG |
| 3 | N0017NR-001-Q001<br>TTTTGTCCNTAGCTATTCATAATTAATCAAAAAGGTGGTC<br>CAATTTTACACCTTAGTGCT[A/G]TGANTATCTTTCATA<br>CATCTCTAGAGTGGAACATATGATACTGCNAATTGCAGTT<br>ATATT |
| 4 | N10336-001-Q001<br>TTATGATGGTGACAGGAGTTAAGTGTGCATGTGAATGTAG<br>ATGACTGAAAAAGATAGCCAACTACTTATAACCAACATAC<br>GACCTTTTGGTCTTTCCTCTTCTCTCTCAACTTATTTT<br>GATTATACAAAATGTTATGTTTGCAAACTGGCATTTAACT<br>GGGCCGCTTAGCTCTCTTCGGTTATTTTTTTTCTTTGTGATA<br>[A/G]ACCACATTCAGATATATATATGTCATCTCGTCATG<br>TGCTGTTGTTGTTTTCTATATCGTTTCGATTAATCAAGAA<br>GTTGGGAACGTCGGAACTCCAAACCAAATGTCCTACGATT<br>ATTAATTATACATGTATCCTGATCATATCTATCTAACATG<br>AACGAAAATTTGAATCTACTATAAAAGAAATATTAGAGAC<br>AATTC |
| 5 | N23133-001-Q001<br>NNNNNNNNNNNNNNNNNNNNNNNNNNNNNNNNNNNNNNNN<br>NNNNNNNNNNNNNNNNNNNNNNNNNNNNNNNNNNNNNNNN<br>NNNNNNNNNNNATAACTCTTTTATTCAAGTGGAGTTTCAAC<br>TTTTTGTAAACCTCAGAATGCTTTTGGTTTCCTTCAAAT<br>TCAAACAATAATGAATAATATAACATACTCTTTTTATACG<br>CGATATTACATTANATTCAAATTCGAATNTTCTTGGATCA<br>AATGCTTCAGGCCTCATGTATGTGGGCCAATTTTGAATGG<br>AATCGTTGGGTTATACTTAGAAGTAGATTCATCAGGTTTA<br>GTTATGTGGGGCTCATGACTCGCGTCCATTGATCAAACAA<br>CAAGCCCTCTCATGTACAATGTANGATTATGTTTTCTTCA<br>[C/T]AATCAACTAGTTAGATTTGATGCATAGCGGTGGTT<br>AACACATAACCGATTTGTTTTTCAATTAGTTGTGGACAAG<br>CAACTCTAATTTCTGAATATAGATTTTATTTAGTCATATG<br>ATTAGCGCCAAAGATTAACACAAAAGTTATTGACCATAGT<br>CTACNGAAATCACAACCAAACACGAGATACGGCATTGTCA<br>AACACAAAGTCTAAAAGAGAATATAAAGTTTGAGACNNNN<br>NNNNNNNNNNNNNNNNNNNNNNNNNNNNNNNNNNNNNNNN<br>NNNNNNNNNNNNNNNNNNNNNNNNNNNNNNNNNNNNNNNN<br>NNNNNNNNNNNNNAGGTCAGGAGAAGGTTCTACAAGA<br>ACTGGGCAAAGTCCAAGAAGAAGGCTTTCACCGGGTACGC<br>CAAGC |
| 6 | N16487-001-Q001<br>ACAATAAAAATATNNNNNNNNNNNNNNNNNNNNNNNNNNN<br>NNNNNNNNNNNNNNNNNNNNNNNNNNNNNNNNNNNNNNNN<br>NNNNNNNNNNNNNNNNNNNNNNNNNNNNNNNCACTTTG<br>ATATCCATAAACCTAATCTTTTATAAACCCCCTCTTGAGG<br>TTCTATCCTCTGCGCTCGGCTGTACTTTAGGAGAAATCTA<br>CACCGTTTATTTTCCCTGAGATTAAAATTTAATCACCCTA<br>CGCTCTTATTGGGCCGGGCCGGGCCGAGTTTGTACTGAGA<br>AATTGGTTTGAGTGAACTAATCCTCTGTAGAAAGCTATAC<br>CGTACACAAAATCAGNGCNTTTTCTTCACCGTACGATGAA<br>TCAGACGAAAGTAGGATTTTTTTTAGTGAACAGAGAGAT<br>[G/T]AATTGGGCCAGGCCCATTAGTAGCTTCGTTCTATA<br>ATTTATTCGTTTCTTAGAACAGAAGAGTTTTTGATTGTGC<br>AAAAATCAGAAAGAGACGATCACGAAGATGGCGACGGAGA<br>GCTCTTCAGCTAAGAGATGGCTTCCTCTTGAAGCTAACCC<br>AGAGGGTTATGAATCAGGTATTCGTCTCACTTTCCCTTCTT<br>CTTCTTCTCCGATCATCNGCTTTTTTTTCGAAATTGGGAA<br>GATTGATTCTAGGTCAGTTCAGTGATTTTTTTTTGTATTG<br>GTGTGTATTGTGTACAGTTTCTTTGGGGNCTGGGTCTTGC<br>ACCAGATGCAGCGGAGTGCAATGATGTGTTTGGATTCGAC<br>GACGAACTTCTTGAGATGGTTCCNAAGCCTGTTCTTGCTG<br>TTCTC |
| 7 | N23426-001-Q001<br>AGCACCACCATCGACATGCGACCCCTTAGGTAACACCATA<br>TCCGAAACATTTTAGTAGCTGTTATTTTNTTTCTGATTAA<br>GATTTAGCCTTCATATTCTTCTTGGATCATAACTCTTTAT<br>TTGCTATATTCAATGCACAGTCATGAATTCATATTCCATC<br>CATTATTTTCGTTAATCACTCGTAAAATGCATATTATATT<br>GAGGAAAAATAACAACTCCACTTAATTAGACTTATATGAG<br>CCGTTTCAAATGTTTGAAAAATCAACACAACTAGATATAT<br>AATTTTCTTACTGATATTGTGGAAATTGGCTGGATGTTCA<br>AATGAAATAATTAATCCGCATGAATTGATGATGCTTCCCT<br>TCAAAGAAAGACATTTCTAATATGGATACCTTGTTTTTGT<br>[A/G]CAACTTCTAATATGGATACCANGCATTCAAAAATA<br>TGTAAATGTAATATAGGCTTTGATTGGTAACATGTAAATA<br>CTTTTGAGTTAGACATACAACTAACAAATGTTACCAACTT<br>TGAATTTTTGAAATTGTCTTTGAGTTGTGATGGATTATTG<br>TTGAGTTACAATTTTGTGTTATAACCTTTATAAAATTGAC<br>CACTCAAATGTTAAATCAAGATAAAAAAAATCTCATGTAT<br>TAAAATTTGAATTGGAAAAATGGGTTTCATAATAATTGCN<br>CACGTCCATATTTTATTTTAACAAATTAAACAATTTACAA<br>AACATGATCATATAGTTTAGTACGTTTAGGTNNNNNNNNN<br>NNNNNNNNNNNNNNNNNNNNNNNNNNNNNNNNNNNNNNNN<br>NNNNN |
| 8 | N05671-1-Q1<br>AATCTCCGAACAGAGAGACATCCTTGTNAAAAGTNNGAGA<br>CTTNGCGAACCCATCAAATGAAAAGGAGGAGTTCTCNTGT<br>GTAGTAGCCATGGTTCC[A/G]TAACTCACGAAGCACAGA<br>GCAAAGAAAAAGGATAGAGCTTTGAGCAACATCGCCATAG<br>CTTTGAACAGGGACAAGCTCTTNTTCTTCTTCTTCTTCTT<br>CTAGATGGAATCTTTTAGGAATCGAGAAAGAGTTTTACTT<br>TTTCAAGAAGCAAGTAAAGTTGTTTTCTTTGTTTTGTG<br>TGGATTTACGTGAAGAAGAAGATTAAAATATAATCTTTGC<br>AGAAACCAGAGACCCACGATTCGCTCTCATTCTCTTTCTTG<br>TAGTGCTTGCTGACTAAAGGTTGTGAATGCATTTAATGCT<br>GTTTCTGATGTTTTTAATTCAATGTTATTATTACATTCT<br>CTTTTGTTTAGCCTTTGAGATTATGAAACCTATGCGCATT<br>TTCTTCAAAACGTTTATAACATCATTAAAATGGTTGAAG<br>AGGCTTTGCTTCACACTTTTTGTTTTACTTACGATCAGAT<br>GGTTACATACATATATGTAAGGACAGCTTGAGTGAATAGT<br>AC |
| 9 | N12643-001-Q001<br>TCGAGCTCGTTGCGCGCATAGGGAAACACGTGTACAGCAG<br>AAATGGAGTACTCACGGAGGTCAAATCCTTCGGCAAGGTC<br>GAATTGGGTTACGGCATTAGAAAGCTCGACGGCAGACACT<br>ATCAGGTACCAATGAGAATTGATTCAATTTTTGCCTTGTT<br>GAATCGGTGATTAGTCGAGTCCGTAGANTTTGTTTTGATT<br>AGGTTGGCCTTTTGGTAAAAGCTTTGCTTTAGCATCTTTC<br>TGATCGATTCCTATTGTTAAAGAAACTAGCTTTTGAGCCT<br>TTGAGTTGAATTATCGAAGCAGCANAGTTTTGAATTTTGA |

TABLE 7-continued

Markers of QTLs significantly associated with shatter resistance (P ≤ 0.01)

| SEQ ID NO: | Marker Name and Sequence |
|---|---|
|  | ATTAGTTTATTCAAATTAGTCACAAGGATTCTTGATTCAC CTCTTTGAGCTAACACTAGTCACAAAGATATACAGAACCA [A/C]CATGGGTTTGCTTGGTAGCATTTTGTCCCTTGGAT CTTTCAGTGTNTATATATAATAACATAGTTATGTGTGGGT GAATGGCGCAGGGACANTTGATGCAGATAACAATGATGGC AACACCAAACATGAACAAGGAGCTTCACTACCTCAACAAG GAAGACAAACTCCTGCGCTGGCTCCTCGTTAAACACCGCG ACATCAAGATTGGAGCTTNNNNNNNNNNNNNNNNNNNNNN NNNNNNNNNNNNNNNNNNNNNNNNNNNNNNNNNNNNNNNN NNNNNNNNNNNNNNNNNNNNNNNNNNNNNNNNNNNNNNAC AATCAAAGCTAATCTGAGAATGGTTAACCAAATCGAATAAA GAGTAGTCGGGATCGTTACCCATAACGACGGAACTGATCC CTAAC |
| 10 | N05943-1-Q1 AAGAGCAAGGGTACTAGCATTCACTGTGTGTTGCTGCAGA ACNGGTCCAAAGACCATGGTAGGGCAAATGCTGACGAGAC TAATCCCGGTTCGTTTTGCAAACTCGAAAGCTTCACTTTC TGCTTGTGTCTTTGACGCACAATACCANTTCTCAGTTCTT TTGCAAAACTCCAGGTCAGACCAACAAGACTCATCTATNA CTCGATCCTTTGACCAATTAGGGTTCATCATAAGCGCAGC TGCAGANGAAACGTACA[C/T]AACACGCTTAACATTTGC TTCGACACAAGCTTTAAGCACATTCAACGTGCCATCCACA GCTGGTGCCATCACTTCCACCTCAGGGTTTGGGACTGAAG ATGATGGAACAGGGCTAGCGACATGGAAGACGCCGATGCA ACCTGCGATCGCAGATTGAAGAGAGGCGTANTCAAGCAAA TCAGCCTTGACGAGCTTGAGTTTNTCACCNGCTTTCTCCA GCTTCTTCAAATGAGAATACTTTTCGTTATCAGGGTCTCT GACAGTGCCATGGACNAAGTAATCCTTGGAGAGGAGGAGA TCGACGACCCACGAAGCNAGAAACCTCCGGCACCNGTAA CGCAAACCTTTCCTTTCGCCGCCACCGACATTTTTTTATT TTTTTTATCTCCGAGATGCTTCTTCAATATTCTTCTACCT TGTCTGAATGCCAGGTGTGTC |
| 11 | N06007-1-Q1 TCCCGTGTTAATGATTTTACACGTTATTATCACAATAAAA CCAGAGCTTCCAAATTCTTGGTTCTGTGTAATCAT[C/T] TGGAAAAGAAAAAGAGAAAAAAANTGAATATGTAAATGA TGTGATTTTTGGTTCGTTGCGGTTTGCATGCTCTA |
| 12 | N10105-001-Q001 CCCTAAAACAGTCATATTAATCGGGGGCCTGAGGCGAAT ACCTTTTTCAATACACTGTAGGCACGCCTCTGATGAAAAC TACAGAAAACTTTTCATTTTGCCGTGTTACATATCGGCTTA CATATAGAGAACAATTAACACATCACCTGACCGAAAGAAA CACTAGTTAAGAAAATATAGTACTAAAGATAAAATTACTG [A/T]TATTAGCAATTTAGCATAGCTAAATGAAGAATAAT TCTTACAGAAAGAATTGTAAACTTTAATTTTCTCAAAAAA AAAAGAACTAGGATAATAAATTATGGTTTAGTATAGCTTA TAAGGTTTTAAATATAATGTGTATATCATATAATTCTTTC AGAGAAAAATCATTTTTTCTACGGTAGGAATGTAGATAAG AAAAA |
| 13 | N08181-1-Q1 ATGAGCAGACCCNTTTTTTATCTTTTGTTGAATGGGGATT TTTNNGACAGTGGAGGAGCTTCTCCAACTTCCAAA[G/T] TATCAAATTTAGCTGTCTTTTTTCTATTTTCTTTTGACGTA TGTAACTCTTACATGCTCAATTCTAAGTTGGTAAC |
| 14 | N06675-1-Q1 AGAAGCTTGCTAATATTCCGACGCCGGAAGCCACCGTGGA CGACGTAGACTTCAAAGGTGTGACTCGTCAAGGAGTTGAT TATCACGCCAAGGTCTCCGTCAAGAATCCTTACCCTCAGG CCATCCCTATTTGCCAGATCTCTTACATCCTCAAGAGTGA CACAAGGATGATAGCGTCTGGNACAATACCNGATCCGGGT TCGTTGATCGCGAACGGGTCGACGGTTCTTGACGTACCGG TCAAGGTGCCTTATAGCATAGCGGTGAGTTTGATGAAGGA CATGTGTTTGGACTGGGACATTGACTATCAACTCGATATT GGACTGACCATCGATATTCCTATTGTTGGTGACTACTA TTCCTGTCTCNACTCAGGGTGAGATGAAGCTCCCTTCCCT TCGCGACTTCTTTTAATCATCTNTATAAGTTATAATCTGA TTTTTNAATAAGTACGATCCGTAAACGACATAGACGATCG TTGGATGTTTCAGTTGTGGA[C/T]CTTGTGTTTGTTGG TTATATGTATTTGTTGCTTTGAATATTTTGTTGGTGAGAG |

TABLE 7-continued

Markers of QTLs significantly associated with shatter resistance (P ≤ 0.01)

| SEQ ID NO: | Marker Name and Sequence |
|---|---|
|  | TTAAAAACTACAAGATGTCATAGTTCGAATACTAACGAAG TGATGGAGANNNAAAAAAAAAAAAAAAAAAA |
| 15 | N001KH2-001-Q001* AGCTGGATTTTGTTTCTTCTACAAAAATGTTGGATTTAAA GAGTTTTTTACTGTGCTTGATAATGGGATTACTGTGGCTT TTTTGGTAGCAGGAAGCAGAGAGAAAGAGTGGGAAAGAAA AGAGTAAGAAGAAAGGCTTTGGGAAGCTAA[A/G]GCGTG GAGAGAGCAGTTCATTTCTTCCCATCTTCAGAGAGCCTAG TAGTATTGAAAAGATTTTGGCAGAAGCTGAGAGAGATCAT AATCTTGTTTTCAGGCCTCCTACTCCTCCTGATCAATCAA ATCCACCCTCAGCCTCTCCTCCACC |
| 16 | N29313-001-Q001 CTACTTGTATTTCAATTCACATTCATTGTTTTGCTAAAAA CAGACAAAGGCTTTTGATATACACCTACTTTTCGGCAATG AATACAGTTGCTTGTGACCAGTCAAAGCGATGAGTCAAAG CAATGAACAATCTGGCCACACAGACGGGGTGAATATCTGT TTCTATTCACATATGGGAATGGAACAAGAGAAGAATCAAC [G/T]AGAAGTANCAGAGAAAGTCATGAGTTTTTCAAGNT TAAAGAAGTGAAAACCTTGGCTTTATGAATAACTTTAACA GCAACTTCTTCTTGACCCTTCAGGCTGCCTTTTTTACCCT TGGCNGAGCAAGTGTCCTCGACCCACCTTGCCGTCCATCT CATACTCCTTGTCTTCAGGAATAGAGACCTCGTTGGGAGC CTAAA |
| 17 | N88512-001-K001 AATAGCTATACTACCAGTCTCTGACTACNACAACAAATNA CAATTTTACTCAAAAAGGACCATTTCTTCACCTATTAACA ACAAATGACTAGTAGAAAAATGGATTGATAACAAAGGCNA ATACTGAAACAAACAANATTCGTTTGAAAAAAGCAATCGA ATTTCAGATGTTGATCAACAACTAGCAAATCAAAAGTGAC [A/C]AAGTTTTAAACTTGTAATNATAAGTTCGTCAAAGA ACACTTTATTCCACCATTATCAACAAAACCAAAAGACACT GCTTCAAAGTTCCAAAGCATCAAACATCTGATCCTCTCAA TCGGAAGAATCTCCGGCGAGCCTCTCCGCCTCGAGCCGCT CCAGGGCCTTCTGATGAGCCCAAGTCTCGATCGAGAGATC AGGCT |
| 18 | N88514-001-K001 ACACGAGAAGCGCTCTTCACCGAGGNGATGATGCCCTTTA CAGGTTAATGGGCTTTCTCTTGTTTTTTGCTTAATGGGCT TTCTCTTGTTTTTTGCTTAATGGGCTTTCTCTTGNTAACT CTTTAACTAACTGTGAACAGTGTTGTTTGTTCTTGTTGTG NTAGCAAGAAACAAGAATGTAAAGGAGAAGAAGAAGAGCA [C/G]TCGAGGAGTTACTGGCGACCAATTGGTTGGGACAG GCTCTCTGAGCTTGTTCAGACAGTGAAGGTTGATGGTGAG TGGTCAGTGCAGAACGTTGATGATCATGAGGATGNTG ATACAACGGTTGCTGAGCTGGCTGGCTCCTTACTGGGACCG ACCACTCGCGGGTCCCACGTGGTGGTGCCACGTGGATGCT AGCCA |
| 19 | N88515-001-K001 ATCAGGAGAACAATAAGAAACTTGTTTNAAAGGCAAAACA AAATGATAAAAGCCGTTTTTGCTAACTCTTATGGTAATGC AATTAGAACAATGATAATAAAAAGGTTCCATCTAAGGCCT AACAACATACTTTGAATATGTTCCTCTAGAAATATGATAA CATGTTGTATAGAAGTAACAGATCATTCTAACTCATTGCC [A/G]CCAAGTTTAACNCAATGAACTAAACACTAATATAT ATAAGGGGCGGTGTAGATTACCTCTGAGCTGAGGAAGTTA TGAAGCACAATAATTCGAGGGGACCAACTAACTACTTCAG GCTTGACCTGCACTAAACCAAATCAACATTAAGAACAGAC CTTGAATTTACAGAATGGATATGATAAGACTTACATAGCC AAGCC |
| 20 | N88516-001-K001 TAAACTGAAACCCATATTAACGACAGANGAATATACGTAA CATGTGGTGTTTACTTAGTTTTATTTTATTTAACAATTCT TTTGCTCTTGTAGGTTTCTGATTGTAGTTTCGTTTTGAAGC AAGCATAATATTGTATTCATATTTTTGTTATANAAGTATT TCATGTTTCTGTCGTGAAAAAATAATTTTCTATATTTCCA [A/T]TTTTTTTGGTAATGTGAAATTTATTGATTAGTAAA AGATAGTTCATTACAATAAAATGGTACTATAAATGATAAA AGAAAATATGATAAGCGAATAAATTTTGAATATCGAAGTC |

TABLE 7-continued

Markers of QTLs significantly associated with shatter resistance (P ≤ 0.01)

| SEQ ID NO: | Marker Name and Sequence |
|---|---|
| | GCTATAATACTTTAAAATGAATATAGCCAGTAAGTACGGA ATCCTTCTTTGTTATATAGCGACTTGTATAATCGTTTTAT TCCTT |
| 21 | N88517-001-K001 ACGGATTCACCTTCTCCCTCTCTCTCTGTATATTCTTCGC ATCTTCTCAAGAAGCTCNAGCTTGAGGAGAGAGAGAGAGA GAGAGCTTTAGATTCTTGAGTGTCTGTAAAATTAGATCTC ATTGAGANAGAGAGAGTATCCAATTCTACAAGGTTTTGGG CTTGTGAATGCACTNGTTGAGCTGATCTTACAGGTCCATT [A/G]AGGTTAGTTTGATCGATCTGNTCTCTGTTTTCTTC ACCGGAGCTGATAAAAATGTNANCTTTACAATGTGGCCAT GCTTGATTCTGCTCCCAAGTTTACATTTTTATCTTATGGG TTTTGAGATCTATCACGGCTACTGAGATCTGATGGCTCTC GTGACTTGTCATTTTGAATGCTATGTTGTTTTCATTGTG NAGCG |
| 22 | N88518-001-K001 GACAAAAAAGAGACCCAACAACTCANGTGTTTCTTTTTCT GCTTCTTCGGCTCANCAAATCAGCACCACATTTCACACTA GTCTTCACGACATTCATGTTCTCNTTGNTCCNTCATTTCC ATCACTATCATTTATCCATTTACCACAANCNTACTATTCN TTTATCATTTTAAAGTTTACTTTTATACATCACGAGATTA [A/G]TACTAAAATTATAACTATATACTAGTTTTTTAAAG ATTTTTATANNTATATATCATTTTGTTTCAACAGAAATTA AAAGAAACTAGTTGAGGAAAAAATGAAACAATGGCTAACA TAACATCAAAAAACTTATTAATATTTTCTGTAATCAGAAA ACTTTAGACCAAACCTCAAACTTATTTATGAGAACATATA TTCAC |
| 23 | N88519-001-K001 GNGATGTGTTTCATCAGAATGATTTATGGTTTCTTNTAGA GGCATATATTTGTGAGATGAGGGATGTGGAGAGTTACAGG GCCTCATAATTTGATGGTTTATTGAAGAGCATAGAAACTC CATCAGAAGCATTANGCNGGAGGAGTTNGAGAGACAAACA AATTCNGCTATGAGATAATTCAAGGTGATTAAGTGATATT [A/G]GATAATATTAGAATTAGNGGTGGGCCAAAAAAACCC AAAAACTTTTGGAAATGGGCTGGCTTTTTTATGGATCCGG ATGGTTCAAGGTCCATCAGCTTAATATACGCTATGACGTG GCTAAATAATAGACTTAGAATATTTCAGGTGATGTGGCAT CNANATAAAACCAGAGATTTACTTTCTTTTATATAGTTAA ATGAT |
| 24 | N88520-001-K001 TAGTGTNGATATAAAGCCCTAATTTACGGCAGCTACCGAA TAAATTTNCTCCGGCCGGTGGGGTGTTCGAGAGCAGATCA TCAGCTTCTCTAGTCTCCGGTAAGTTAATTTTTTTTAATT CTTATATCTCGTAGGTTTTTTTTTTTTGTAATTTGATCN NTTTAATTAGCTTCGAATCGATCAGAATCTAAACGGTTAT [G/T]AGNAATTNTGTTTAAATTGTGCTTTTAATATTTCA AATTGATTAAGTGCAAAGTCAATTTTGATCAGATCTCACT TTCGGTAGAGGAGAAGAAGAAGAAGAAGTTTTTTTTCAG TGCTTGAGGAGGATCTGCCATATCCATCAGAGGTTTTCAA ACAATGGTAAATTTTGATCCTTAGCTATATGAATACTCTA TATAA |
| 25 | N88521-001-K001 TTTTCGAAAAAAAAATAAAAAAAAAAATGGATGGCATTT TCGTAAATTATATGAACTTGTGGGGTGAATAGGGCAAAAN CAATTTTCAAAAAAAAGGAGGTTAGTTTTGTGTTTGACT TTAAGTTATAGGTACTTTTAGTTCTGCAAAAATCCCATTTTTTAT ACATGCCAAAACCAATATAGAAAAAACAAAACACTCTTC [A/G]TATACNAGACAAGCACTATAAATACATTCCATAAC CGTTAAAGCTTCCAACACCACCACCACCACCACTACAGCA CTACTCCACTCTCTCCCTCTTTAATTATCTCTGAACAA GTGTAAGTTAGCGACATACAATGGCTTCACTTCTTTTCCT CTTCGTCTTCTTCTTCTCCATCCCTCTTGCTTTGCTCAT TCCTA |
| 26 | N001KFE-001-Q001* ATGTTCATTGTAGTTAATTAGTANAGAACTATCGGGGCAG AAAAAAATAAGTCAACGCGTTGCCCGAAAATTGTATACG AATGTACCTGATTTAAAGAA[A/G]GAAAATTCCATAAAA ATACTTCAACTAAATTTTTCTTAAGCTTTTTAAGANTCAT |

TABLE 7-continued

Markers of QTLs significantly associated with shatter resistance (P ≤ 0.01)

| SEQ ID NO: | Marker Name and Sequence |
|---|---|
| | TTTTCCGCTATCCACTTTAGTACTTCAACTAATTATTTTG CCCAG |
| 27 | N88522-001-K001 TTGTATGAACTGGTTTTAATTAAGTAATGCAAGTAGTTGG TTGACAAAAAAAAGTACTACACCGTGGATCTTCAATCGC CTGATCAGCATAATTAGTATATTCAATCATATGCANAATT AATCTAGGAACTAATTGATAAACTAATTCTTTTACAGTGT AGCTAAAGCTTTTATTTTCTTCTGGATACAGATAAGAATA [A/C]ATACTATATGGGGACANATNCTTTTGTCGATTTTT CTATTCAGCTTTGCAATGAAGTCTGAGCAAAGATATGACC AGACTGAAAAGGNAATTAAAGGATGATAACATGGAAAAAA TTAAAAACAAAATTCATGCATCTGCTAGTGAGGTTATTTG GATTCATTGCATGTATGTTGATGATTCGTTTTCCTTTCAC CTCCC |
| 28 | N88523-001-K001 AATTTTTCACTTTGGCCAGAGATATAANGAAAGGTTGTA AACTCATAGACTTAAGAGATTTTTTGGTTTAGTCNGTANG TGATTTTGTAGAAATAATAGCGCATATTGATAAATATGCA ACACTTGCTTTAGCCTTTGTTTGTGAATTGTGGTGACATA AGTCCATCCCTACAAGTCATGTATTTGTAACGACTTGAAA [A/G]TAAAATATTTTCGGAAGACATNTCGATNTATAATC TGCATTTCAGTCCGGACTCCGAATATCCATATATATGATC TAAATTGGGTTTCTGAAATAAAAANAAAANCACAACTTACG TCAAGTCAACGGAGGTTAAATCCACCCTGTCGCTCTTGTT TGCTCCTTTGGCAAAACAAAAGTCAACTACTATTTTAGGT GCTTG |
| 29 | N88524-001-K001 TTGAATTGGTCTGAAAGTTTGTTAGCTGTTACTTTGAATA GATGCCTCGGAGACCATCAGGAGGAAGAAGGTTCATAAAG CACCAACCTTTAGCATTTTCACCGTTTATGCGGTCACTTG CTTTAGCTTCAAGGCGTAAACTGCATCGTCATCAACAAGA AGANGACTCTCNNCGTTCTGAAGAGCTGATGTCTTTTGGT [G/T]AGTAGTAGTAGTAACATCATAAAACTGAGAAGTTTC TGTTCAGAAACATTGTAAANAACGAATCATTCTTGTTTTGT TAGATCAAAAGCTCCCAACTTTGTCNAAAAAGGAGCAAAA AGAACAGCTTTCTGACTCCTCTGATGAAGAAGACTCTCAG GTAATAAGATTATTCAGACTCCTCTGTTTTGATCCTTGAN TCTCT |
| 30 | N88525-001-K001 AAGTGTAAAAGTTATAAAACNGAGACGTTGTGTTTGGNCA TGTCATGTAATTGTTGAATGTTGTGNATATGACACAGACG GTGATGAANTCAACAAGGAGACAGCTGGAGAGAGAGCTGA TGCTGGAAGACATAATGCATCTTGAAGACTTGCCTTCCTA CGCCCTCCTCTCTCCAATAGCCTTTTAAGAGTTTTCTAACC [A/T]CAACACTCCCGCTTTTAATAACACAAAAGGTTGCT CGCTGCTGCCTCTTCTTTGATCTTTTTCTTCTACTGTTTG TTGGTTGGCTATATGAAAACAGCTCTAAAACTGAGTTGT TGTTGTTATATTAANACAAGNAAGAGGGAGATAGAGAAGG AGGTTGTGGGATAAAATCTCAATTTGGTTGTGGGTTTGGA AAGTG |
| 31 | N88529-001-K001 TATTNGAAATAATATTGAGGGCTGTGACGAAGGATGCACG AGAAATNTCAACAGCTTCTTCTCTATCACTGCATTCACTC ACGAAGNTGATTAGTTCTTGCACCTTCTNCATCCGTAGAG CTTGGGTGGCCTCGATACGCTGTGGTGAGAACAGATGAGT AACTGATATTTTCCTCAACAGCCTGAAAAATATAACATAA [C/T]TATTTTTTTAATNAAATACACAAATCTATTGGTTC NGTTAAGGTAACTATATGTTATGTATACAGCAGTTATATA TCCGGGACAGTCNTCTAGTATAATGAGGATAATATTTTGG TAATGACCGGGATAGCTCAGTTGGTAGAGCAGATGACAAA TAAAAGACTACCAATAGGAAAAAAAAACTTAGCAACGGT TACCT |
| 32 | N88530-001-K001 GGCAACATATATCACAGTATAAGGAAGTCAATACAAAAAC ATTATAACATTTCCAAATATTGAAAGATTTCTTTCTCATA ATACNAATGCACTGAATCAAAATAAAAAATCAATAATTTT CCAAAAACAAAATCTAATAATTCTAAGGATGATATTAACT AGAAAATATTAATCCTCCATTGTTGCGTATGACAAGCTCG |

TABLE 7-continued

Markers of QTLs significantly associated with shatter resistance (P ≤ 0.01)

| SEQ ID NO: | Marker Name and Sequence |
|---|---|
|  | [C/T]ACGTTTT<u>TAGCCAATCTCTCACGAACGATACCGGCG</u>CGTTTCNTACACTCGCTCTTCNTCCTCCTCCCTTATATTACTTACCCTCGAACTACTTCGTATCAACCTTTAACCTTTAGACAAACTCACTCGTCACACATTCTACTCATCCTTGACCTTGTGTTGTGTGTTATATATACACTACTACACACGCTTATTATATA |
| 33 | N88531-001-K001<br>CTGCTGCTGTTGCTGTTGCACGGATGAAGANGAAGAAGTCGGAGACGCAGCGGATGATGTGGAGTTGGTCCGACCCGCCGGACCCATGCCCGGATTCCGNGCGGGGCCTCCGCCACTGCCTCCAGATTGCATTCAATTCTTCGATCAATCAAACCTAATTCAAATGCA<u>CAATAAGACAAAAATTCAAACAAGAAAAAAT</u>[A/G]AAGCTGGGANTTAGCAAT<u>AAACGTTTGAAAACGGAAATTTACAAAGCCACACACNCACTCACTCACTCTCTGCCA</u>CTTTCCTTCACTTGATTTGAATCGATTTTCTGAGGGAGGGAGGGAGAGAGAAACGAAAGTCGCGGGATGCAACGGAATAAACCAGATCCTNTGNGGGTGGCTTCTCGAGAAACGNAATCCACGGA |
| 34 | N88533-001-K001<br>GTATCCTTCCGGCTATCAATTCCCACCTATGAACCACATACCATAGATTCTAAATCGTCAAATACTATATTTTATGTAAATAGCTTTTTAAAATAATTTAACTTAAACAATCTGNTGAATAAATAACTTTCAAGTAAAATCAANAAATAGAAGATTAGCATGGCCGTTGCGCAAG<u>GATTACACGCACAAATTCGAGAAAT</u>[A/G]GTCCAATTTTTTTTTCCAGTCAAAAAANGTA<u>AAATCAAGAACAAACTGGATCAGCGAGAT</u>CAGGCTGAACATAGTCATTGACAGCTNGGTTCCAATAATAAGCAATAAAATACATAAAAACGACCGACTTATGAGATAAATCAAAAGCCATAGTATATTCTTTTAAAAAAATCAGANTAAACTAAAGATGGAAACAGACAAA |
| 35 | N88535-001-K001<br>TGAGTATCATCTTTGCCTTTGTTGTACCTTTTCTGAGGATTTAGAACGAGATTGGATTGAGGATTAGTCCTTATGATCCTAAGAAATACATGCAATTTAGTGTNTTCCTTACTAANATCTGATTTTCACAAATGGATTGCTGCTTCTCATGACTNATCTTGAATCTCAAGA<u>CTTGGTTCATTTTATTTAATGGACCTTTG</u>[A/C]<u>AACGTTGTTGTTTGTTAACACAGTGGTTCGTTTA</u>CAAGAACATGATCTTCAAACCAGACAGGTCAAGCANTCTCCCCTCAATTACATAATTTGGTTTCGTCTAGTGTTTTCTTTNAGAAATATGAAACTCATATTTTTCTATCGTAACGTGTTTCAGGGAGGTGCTGTTTCAGAAGGTCAAGGATACATACAGAGACAT |
| 36 | N88536-001-K001<br>TTATTATNGTTTTTATTTATTTTTTGCCGGCCAATCATATCAATTAGACCAAGTTCTAATTTGTCACAAAGAGTTGTTCCGAATAAAATATTTGTCTGACCATGTCTGATCTAGATGGAAAAATACAATGCCTCTAGTCCTTCCATATGGTTTACAANGAGTTAGATTAAAACTT<u>CCCATTATCATTTCGA</u>[C/G]TGAGGAAAT<u>AACAAATTGTATCTGGAGAAGCAAGAAAGGN</u>GGTACAAAATCTTAGCTTATCAAAATGTTCACTTGTCTTTGGTCTATTGGGAGTGTCACTTTTTGTCTTAGTTGAAGCCCATAGAAAAGCCCAAATTATTAGTCGGTATCTGNCCCATTTTTTAAAATTTGTGAACCGGTGTCTGTCTTCTTCGCTTGCT |
| 37 | N88537-001-K001<br>TCCGAGTCAACTCAATCCGACTCGAGATCCACCACCAGTGTGCCACGGACTCTCATCGGAGGGCTGTTGCTTGTCGAGATTGGACCTGAAGCATCGAGACAGGGCTTTGGTGGTCTCGTTTAACGAAGAAGAAGGAGCGATGAACTTGTTGGAAGAATAACACAGGGAACCGCTTAAGGTTTGATCTGCAATTTCGT[C/G]TCC<u>TAAGATGATGAGGATCGGAAGGGGATGATTTA</u>AAGAGTTCGTATAATTATTCATCTGATGGGAGCGTTAATATATATAGATTTTGAATTTCAAATGAAACAAAAATATTACCGTTATTCACTCCAAGTCGGTNAAAAAAAGTAACTTGCATCAAGCAAGTAACTTTTGTGGGCTGGCCTCTCTGTTTCTGATGTG |
| 38 | N07541-1-Q1<br>CTTGTTGCGAAGCTTCTCTTATTGG<u>TTCTTCCATCGTCTC</u><u>TCCTGAATCAGAGTTTTGATATTCNAAGTCTCCCA</u>[C/G]CTATCAAAACGATCAGAGAACTTTCTTTCGAATAGATTAAAACGATGATATCT<u>AAAATCGAAACACTGAATTGCA</u> |
| 39 | N23413-001-Q001<br>TCCTTCTTCTCTCCTTCTGATATTTTGGCTTTTTCTTAGAATCTTCCTTTTTTATTTTCACCAAAAAAAAGAAAAATCAAAAAGTATTAATCATTTACCGGTATCAGTTACACCTACACTTTGCGCCGCTGAACAAATCAATAAGGATAATAAGAAGAGCTCGTTTGCTTCCATTTTCAGACATTCTTTGCCTAGAGCAAAAAAACAAAACAAAAAGATTGAGACTTTGATCTTAGCAAAATGGGTAATTGTTTGGATTCATCAGCTAAAGTGGATAGTAGCAGCCGCCATGCTAACTCTGGTTCGTCCTCCTCTCCTTGCTTTCTCTTCCTTTACCCAGTTTCGTTGCTTCCTTAAG<u>ACTTAAAGACCTCTCCTTACTCTCCAATTCCAAGCCAAG</u>[A/T]CTTAACCTTTAAGCTGTTTGGATCT<u>TCAAAGATCAATCCTTTTCAATTACCAGCTGTCTGATTTTCANAGATTGTA</u>GATATCTCTTTGGTACTCAATGTTGGATCAAGTTGATTTAAGATGGTTGATATGCTTAACGTTGAGATTAANTTTTATGAGCCAAAGCTAAAAGTCTTAACCTTTTTAAGCTTCTGTTTTGTCTGTGATCTTCAAAGATCAATCCTTTTGAATTACCCATCTCTGCAGNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNTCTATAAGAACAGCGAGGAGAAATAAACAAAACAACATCACTTCATATTTACAGTGT |
| 40 | N08344-1-Q1<br>ACNTCGGANTTGTCCTTCTCCTCGGATGCAGG<u>CTCGTCTC</u><u>CGTTGGTGGT</u>GGTNGTGGTTTCACCGAGACAGGTC[G/T]CCTCCACGTGGACGGAGACTTCTTCCT<u>CTGTTTTGAAAGG</u><u>GTTGCC</u>GCAGATCGGACACTCGAACATGTTCAGAG |
| 41 | N23533-001-Q011<br>GTCCGGTGTTTCTCCTGTGCTAAGAAACTCCANTANAGACCAAACCGTTTTATGGACCANGGTGGTTGTTGAACNACCATTGAGTTCNTNTNTAACCGACGATAATCTATGGTTCACTTTGAAATCCN<u>CAGGAAAGTTGAATTTGATTCGCC</u>NTGTGGTTGACGCAAACCCTTTGATCAANAAGGTAACTTGATCATCAC[A/G]AAACTCGACTGGNCATAGTGAAACNTTTTAAG<u>TTA</u><u>GGGGTTGTTGTTGAGGAATGAN</u>TTTTCTTTCTTTCTCAGNTAATTGTGNNGGGATGCACGNNGTTAGTTCCAGAAGGAATCATTGCATGTGNTGAAANNTTGNNGAAGAACAATCATAAGTTGGAGACACTTCACATCAATGGCGTCCCTGGCTTCACTAA |
| 42 | N14649-001-Q001<br>NNNNNNNNNNNNNNNNNNNNNNNNNNNNNNNNNNNNNTCTGTAGTAGCTGCTGGGTGATGGTCCTGAAACGTTCTTGGCCTGCTGTGTCCCACTGTATACACGGTCATTGCCACGAGTTATAGTAGTATACACGCTTGCCAAGTTTTAAANGAATATATGTTATCAAGAACACTTACAATCTGGAGTTTGATTGTCTATTCCGTCTTGTTCAACTGTGCGGATTTTCTGAATCACATCTAACATTAGCCAACACTAATATTTTTTGTTTTCCGAGTACTAACAAGTGATGGGAAGAGTAAACTTACAAAGTCAACACCAATGGTACTGATGTAGCTATCCAGGTAAGAATCA<u>TCCTGTA</u><u>CACACAAATTCAAGACAT</u>CAAACTATAAGCACACAAAGAG[A/C]AACAACGATACTATACTGTAACCT<u>GAGAACTAAAC</u><u>AAGTATTAAACTTCAAAGACCC</u>CATAGATTTGTTACTCGTGTTCAATGTTAAAACGCAATTACCGAAGATAATACACTCATAGTAACAATGATAGCATAGTGTAAACTATTTTGGAGAGACAAGTAATTGAACTTGAAGGACGCACAGATTGTTATTAAACGGCAATTAACACATGCAAGTAAGAAATCTAAACAATTATTCAGCTGGAGAAAGAGTTACTTACAGCAAACCTTAGAAGCAAGCAAGTTTCCAACGACTGGNCACGGTCACCGATAAGCAAAGCTTGAACAGGTAGTCACTGCAAATTAAAANNNNNNNNNNNNNNNNNNNNNNNNNNNNNNNNNNNNNNNNNNNNNN |
| 43 | N23310-001-Q001<br>TTTCCCATACCGTGTAAGAATATGGACAATCAAAGAACAAGTGATCTCGAGTCTCATCNCTTTCTCCACACAGTCCACAGCTTTGTGTGNTTCCCCAAGCCCTATGTCTCCTGTAGCAAGCCTGTTGAGCACTGCTAGCCACGTAATGAATGAATCCTA |

TABLE 7-continued

Markers of QTLs significantly associated with shatter resistance (P ≤ 0.01)

| SEQ ID NO: | Marker Name and Sequence |
|---|---|
|  | GGAATGCTTTGCGTGAACCAAACCACCTTACTCCAANCAA CCTTTGCTTTCTTGGGTCTAATCTGGTTCCAAGTGTTAGC CGTTGGNAACATATCCCTGAAACCATCCTTCCTTATGCCTC CAAAGTATCAGATCAGTCCCCCTACTAGTATNTGGAAGTG GCTCCGCGAGAATTTGAGTGTTTAAACTCTGAAACCTTCT GCT<u>TGCGCTTGTTTCTAAGACTCCAAC</u>CGTCCCCTGAAACC [A/G]CATTGCTCAC<u>TAGTGCACTCCTAGGAAGACCC</u>AAA TAGGTCGTACCCGATGGCTCCAGTAACATCAATCAATCTTC CACTGCCCATCCAATTATCGAACCAAAAATATGTGGTTTC TCCATTTCGAANCTCTACTTTCATGAACTCATAAGCCAAA TCNCTTAGCTTTAGTAGCTTCCTCCAAATCCATGAACNTT TGGAATCATCTCTCACGTCCCAAAAAGAGCTTTGTCTGAG TAGATAGTGCTTTATTCACTTCAGTTGAGAATTGTCAACT ANTTGAAAGTTAAAAATGTGAAGCCAGAAATGATACATGT TAACAGCTGAAGAAATTAATATATAACCAAAAAAAAAATT CATTCTATAAGGAAACTTTTAAAAAAATTATACATACCAA AGTTC |
| 44 | N10526-001-Q001 TGACCTCTCATTACTGTTACATCCCGATAAACATAGACAC CATTTTTGACTTCACCGGCTCCAATCAGAGTCCTCGTAAA ATGCTCCTGCAAAATACACAAAGTGTCTGTGAATACTGTC AAGCAGCCAGTTTTTCGAAGCAATTTCGCTACAGACAATA GAGTACAATTCAGATTAGGAACAAATAGAACATTTGCCAA CAANAAACTCGCAGA<u>CAATCTCAAACTGCCACTCTTGGTA GCCATCACGT</u>[G/T]ACTACCGTC<u>TGCAAAGCTCACATGA CAGGA</u>ATGATACTACGTACATCAACCAGTAATAGAACATC CCCCTTCCTGTNAGTGTATATCTGGTGTCTATAATAACCT CACCAGTTTGTACCGTACCGTTTAACCGATNAGGAGTTGG AGAAGGNTTTTGACGCTCCAGCAGTGATGTCAAGGACGCC CATTGCTCTANAGTGAACTGTGGCATAGAATTCCCTTGGT TTGNAGACGAACTTCCAGTC |
| 45 | N23373-001-Q001 TGACCGATGTCTAAAACGGTTCGGGGGTGTTACNNNNNNN NNNNNNNNNNNNNNNNNNNNNNNNNNNNNNNNNNNNNNN NNNNNNNNNNNNNNNNNNNNNNNNNNNNNNNNNNNNNNN NNNNNNNNNNNNATTTTACATAGAAAACTAAAAACGTCA TATAATTTGGAACATACAAATTTCTCTAAAACGACTTATA TAAGAAAACGGTGGGAGTATATATTTTCATAATATTAATTA ATACAAATTAACAATAATGGACTCTTAAACCTAAAGTAAA AGTGTAAAAGAAATTAAGGGATCTTGTGCATTTGCACTCTT GGCNCATGGCCAGAGCCGATGCTGCTTGTAATG<u>CTTCTGG CCATTCACAGTTAATAC</u>GTTTTCTATGCCCGCATTCACTC [C/G]GTTCAATTCGTT<u>GGTTCAACATTGTAAGATAGTTG GTGCTTTAATTTTC</u>AAAAGTTTNGAATACTTTTTTACTAA NTGACATAAAGGATANAATACATTTGGAAGAGTCAAATAA TTTTCTTGAAGAAAATCTCAACATATATCAGAAATTGAGA TATTGTAACTTANTTNGCCTAAAATGCAAAAANTGTCGTA CAACTGATGGTTATAAGAAATTTAAGTTTTCAAGTTGNTG AATTCAGTAAGCACTTCTGGAATCTAACCGGTAAGATTGT TGTCAGGGAGAGTGGTAAAGAGATTTAAAATATAAACATC AGTTAGGAATTTTCCACTNAACGGAAATCAAGAATTAACG AAAATATAACCGGTAATTGTGNACGTATCATCACTGCCCA TCTAC |
| 46 | N23353-001-Q001 TTGGTTAGATCGTAATTTTATGTATAAGAGGTCCACACAG AATAGAAGAGACTGTTTGAGATTTTTTGTATGCTTAGAA GACTAAAAGAGATTAAATCCTGATTTGGCCTAGATTTTTT TTTTAACTCACAAAAGGTTCATTAACTAAACNAACACAAA TCCATTACTTCTTACACAAAAGAACAGACCCACTAGTTTT TAGACCATCAAACTAATCTATTAAAATTCACAAATCATCA ATTATCAAGTTGAACCTCCCAAAAAGCATTTCCTTCTTCC ATCTCTTCTCAAATAAATGTTTTGTATGTATAGGTACCTT CCACAAACCAAGTTTGACACAAGCCATGCAACATGGAAG<u>C CTATCTGGAAGTTTGAGCTTGCTC</u>ATTGAAGTTGAGCTAA [C/G]AATATAGTTTTTCATTTGTTTCATGA<u>TCTATGAC GGTGACATCTTGTT</u>GAGAACATTTTGACATTTGTCACTTA AACTAGTGTAAGAGCAGGAGTCTCATCTTTTTTCTTCAAA CGATGTACATAAATTTTCTTTAAAATATATCGAATAGAAT CAGCTAAAATAGAACAATTTTCGCACAATCAATATCTTTT GNGTGCATATCTGAAGGCAACTTTAGGTTTATCATATAAC GGATAACTTTCACCACATAAATACATGTGATTGAGAAGAT ACTTGGGATTAACATGTCTGAGTGCATTGGTGATGACTCT TGGCAATAGATCATATTCGTTTTGTACAAGATAAACAATG TTTTGTTGTAGATCCCATTTGATGTTGATTTATTAGTATA AACAA |
| 47 | N23206-001-Q001 ACTGGGTAACATCAGATAAAATTTCANTTCCACTTCAGTT NTGGTTACGTTCTAGTTTTAGGATAATTTCGGATAATTCA CGTGAAAATCAGATTTTTTATTTTTAGTTTTTCAAATCA AATATCAGGTAATTTTGATAAATTTAGATAGTCCAGATAA AAAAATATTTGGTAATTTCAATTTTTTTATAGTTCATATA ATATTAAATATTTGGACAAAATATTAAAATAATTCAGTT TATAAGAAGCATTTTAGACTCTTTGGTAATTTTAGAACTA AAAATTGTTTTTAATTATATAAACGGAATTTTAGACGAAT ACCGATTCAGTTTTTTGTTCGGTTTC<u>AGTTTTTCAGTTTA AGAAATATATAAACCGCTTAGATAT</u>TTGTGCATATCGGTT [C/T]AGTTTACTTTTCGGTTCTNGGTTTATA<u>TGCTGAGG TCTACCATGAACTATC</u>GAGGTTCTTATCAAATTTTTGATT ATCGTCATTGCCAATATCCTCTAGTCAAAATCATGGATC GTAAATACATGAATGCTGATTGCTAGTATAAGAAAGTAAA TCATTGACTTCAATATTAACATTGACTTTGAACAGTACAC AAAATAGTTACATGACTGGGATAGATATGCACTTTGCAGA GNNNNNNNNNNNNNNNNNNNNNNNNNNNNNNNNNNNNNN NNNNNNNNNNNNNNNNNNNNNNNNNNNNNNNNNNNNNNN NNNNNNNNNNNNNNNNNNNNGATTTAAAGTTTTTTTTAC TATTGACTACCCGTGGGCTTCCAGTTCGGTCCAATTTGGT TTTGG |
| 48 | N11025-001-Q001 CGTCCAGATATCCAACTACTCGGCAANCTCACCTGTAATG GGAAGAAAGAGGGGTGAGTAACATGGAGTCACTCATCAA GGTATGGGATGCTAAAAACGCAAACCACTGAATCAGTAAA TAGAACTCTCACTATGGGAGTTTAGCTCTAACATGAACAA ACACGATGTCTAAAGGATCACACAAAACAAACAATGCGAT GATAACACATAGCTATTACACACACCCTGAATTCTCCTCA TAAGGATATAAAATATCAATTGCGCCGGTAGTACAAAAGT CTGTCTCTGTACCCCAGCAATGTCCGATCTNTGTGTCTACAT GCAAACNCCTTTGCACCCCGCAATCTCTGCTCTGTGTCAC TATGCAAA<u>CCACTGCACCCCGTAATC</u>TCTTGAACATCTGC [A/G]TCGCTAGC<u>TCAGACGTCTCTGGTCCC</u>CGCGATCTC CACATAGTACTTATATTTATAACTATATATCAGTTCAATC AACAGTTGAATCCTCTAGACCCCTAATTCTGATTTACAAT GAATGTACAAACTACCAAGCAAGACTCGAACAGACTCAGT TCAAACAGACAGATCATGCTTCAAAACTAAATTACCATAG AAAGAGTTCTACACTAGTTTGGGATTTAACGGATTAACGG AATATACCCTCACCTTAGCCAATAGTAGAAACGGAAATGA ATCTGACAACAACCAAGATAACTTGATTACCAAGAAACAT AGGGTTCACCTTGGATCATGCAAGCAATGGGTTTGCCAAC TTCATTGGAGATTTAACACGATCCAAAGCACGATTGCATA AGGGC |
| 49 | N09969-001-Q001 TTCTCTGATAGTGCTGTGTCTCTCCTTTGCCCTCCGGTGA AGAAAGGAATTCTTACCTTCACACATATTTCATTGATTG TCGGGCAATCATCCGCGTGGTGGATGATTAGGTTTTGGTT TCTTCATCAATGGGTTTCTTGGTGCTTA<u>CGGCTCCAAGT TGCTTTTAGTT</u>TGGGTCTTTCTTGTTTGGGCCATTTACTC [C/T]GTTTGATAATTTATCTTT<u>CTCAAGGCTTTTTTTA CGTAAGTATAGC</u>CTTTGTTTAATAAACTTTCAGTGAAAAA AAAATTATGATAGCTCATACAAAATTGAAACATGGTTGCC TTGGCGTATTATCTATATTATCTTATTGAAAGCTGGGCC AACTAACGAGAGAGTTCGTGAAGCTCTCCATGTTCAAAAG GTATT |
| 50 | N09882-001-Q001 GCACCCAAATTTGATAACGATACACAAGCAGCTAATGGCT TATAAACACTGCTAGAGGAACTTGAAGGAAAAAAATATT GATGGTGTTGGATGATGTTTGGTCGGAGCTGAGTCCTCC TTACTTGAGAATTTACCCACTAACATACCGAATCT<u>CAAGA TCTTGTTGACTTCTCCGGTTTAACT</u>CGCTTGATTTCGGTGA [A/C]ACTTTTAAATTGGAACCTTTGAAAAAGGAACATGC CAAGACCCTTCTCATTCAATATGCATCGCGTCCTGATCAC GCATCTGATGCCGAGTATGAACGTCTTTTCCAGAAGGTAT TCTCTATTGAGCCTTTCCATTGGTGATCTAACATTTTGTA |

TABLE 7-continued

Markers of QTLs significantly associated with shatter resistance (P ≤ 0.01)

| SEQ ID NO: | Marker Name and Sequence |
|---|---|
|  | AATGTTGTGGGTATAATGTGTGATGTGCCTCAGTCCGAGG AACTC |
| 51 | N10389-001-Q001<br>CTTTGTTGCCGCGAGCGACAGGTTTATTGCTATCCCATCC TCAAAAACCTCTCCTACAGCTTTATCGCTATCGATTCCCA ACGTTGCTATCATGCAGAACAAAACAAACGACCACAAAAG CCATTTGGGACCTCCATGGAGGTAAAACTACTCGGAGCGG CAAAGTTGAAGCTAAAAATGAGAAACTTAAAAGAGTTTT AAAATAAACCTTTTTATATAGAGTAGTCGAGATGGTTTGA TTTGCTTATG[C/T]TATTCTCTCATTAAAATTCAGATGA GTGATAAGTGTAATTAGGCTTTAGAATTTAGATCCATCT AACTTCACAGAGTCAACGACTGCAAAAGATTGATTTGCGA GTAAGCTAAACCCTCGTGATATAGTCAATCATTCAATTAT ACTATTATCGGACGACGGGATGGTGGGTTTACGTAGAAAC GCCAAGGCAAGACGCAAACTCACAGTTTCCATGTAATTTT GCAGGAAGTCAACGGCTACA |
| 52 | N09940-001-Q001<br>CGCAGATCAAGTTCTAGTTTCAGTCTAGTTGTATACAGCT TTAATTCATGTTTATAGTCCTAGTTTAATTGTATCTCAGT TTTGGTATATGTCGTGAGCCGCTAAACATGTCAAGCATAA CGTACAAGATTTTCTCTCCTTAAATCTCATTCCCTCTTAA AAATGTTATATTTTCGTTTAATTGTCTGCTGGTTTTGACC [A/G]TCGCAAGTCACCCTGTGAAAAAGCCCACGTTTTTT TTGTTTTCTTTCTTTCACCTTGCGCCGTGCTGGTCTCTTG GCCTTGTCTCCTTTAGCGGCATTTGTAGGGTTGAGTATTT CTTAGCGGTGGTGGTTGCGTGGTGGTCCGATGGTTTTGGC TGAGGCTATGATCTCACGTATTGGAACTGAATGGTTGGAT GTGGT |
| 53 | N23409-001-Q001<br>CTGGTGGAGTCCAGGGAGAAGCACAAGAGGAAATCATGGG ACAAAGTATNTGTTAATAAAGAGAAAAGAGGATTGGGGTT CAAAGATATTACTGATTTCAACACAGCGATGATTGGTAAA CAGTTATGGCGTTTGATAGGGAAGACGAACACTTTATTTT NTCGAGTTTTCAAANGTCGGTATTACAANAACGCATCACC CTTGGAACTGATTTGTTCATATTCTCCGTCATATGGCTGG CGGAGTATCNNATATGCTAGATCTTTGGTAAGCAAAACAC TAATCAAAAAGGTNGAATCAGGATCATCCATATCTGTATG GAACGATNTCTGGCTCTCAACCACTCGCCCGAGACTAGCT AATAAAACCAACACAACTATTACCCAAACCTCAAAGTGGA [C/G]ACTCTCATTGATTCTACTCCATGTTCTAAAACGCG GTCACCGCGGCCGCAAACGCGGCGGTTAAGCGCTCCACGA CTCTTAAGCGTCTTGATTTTGCTATACTCGGCTAATTATA CAGAACAATTAGAAAAGTTAATTNTTTTGTTCTTTTTGAG TTCAAAATCAATTGCTATATNATAGATCTGTGAGTTTAAT GTGTAAACAACAAAAAGTAAGCACAAGATTTAAGGACTAT GTATTTTTTAATGGCGGTCGCAGAAGGTTTACAGTAAACG TAAACCCTTAAAAGAGGAAGACGAAGCTAAAAATTATGAT TATGCCCTTCACATTAAAAAAAGAGAGCAAAAAGCGTTGT TGCTGCGTTTCGAACACGAGTCCCGACAGTACTTAGGGAA AGCCG |
| 54 | N23119-001-Q001<br>TCAATTGCTTGATAAATAATTCAAAATACAACAGTATAA CCCCGCACGTACGCCTCCGTAGTACCCTGTGAACATCTTT AGANGCATTAACTAGTACTAATTACTTTAAACATTATATA TACAAAAATACATTATCATGAATTAATCATATACGGCCAA CNCTTAACTTCNAGAAAAAAATAGTTGTGGATATACTGCC GATGCATGTATAGGCCATTAGGGATCCAACACATACATAT TATGACCTTTCTAAACGTTATATATCAAATATAAGTTTGA CATCCTCACAGTTTTTTTTAATTTAACCACAGTGTCTGG CGACCGAGATTAACCGACTATTCTGTGNAATCCAGAAGTA CAATGTTAAATTCTGGTGGCCAACAAAAATCGAACTGCAG [A/G]TTCACCGTATCAGGGTTATTCCTCAAGTGCTACTA GCCTAAGGCCCGTTGGTTACATCCTCACAGTTACCAACAT ATTTAACATGTTTACCAAAAAACACATAATTATAAAAAAA ATTAAATATCCATAGAGATCTTTAAACAAGATTTATAAAA TCTTTGCAGCAATATATTAGTTTTATATTTNTAATGTTTA GATGATATTCTAAATATTTTTATATCATCAAATATTATTT TAATATGTAGTCAGTAAAGTGACGACAAAAAATGTAGTCA GTAAAGTAAATGATCAAAATTAATGAAATAGAACGTCTC TTCGCGTTGACGATTGCACNAGTGAGGCTTGTGTGTTGTG |
| 55 | N09861-001-Q001<br>ATCGGGGAGGGAAAGCCAGTGGGAGAAGAGTTCCTCAGCG ATAAGAGGGTTTGATTTAACGGACAAACCGGGAAGCTGCA AGAGCTCTGGATCCAGTATATGAACTTCCTCTATATCCAT CTTATCCCTAAACTCTACCTACCGAGTCAATTTTCGAAAA CTGGATGATCGTTTACCACTGAAACCCTAATTTAGGATAT [A/G]TCCCACCACGGAAAATTCAAAAGGCAGCTATGAAC AATCGAGGAGGTCAACTAAGTACGAGAGGTTTGTATTATA CTCGCGAGAAAAGAGAAGAAAACGAAACCTAGATTCG AATTTCTATAAACAAAGAGACTATACAACTTCTTCTTCTT CTACGGTACGATATGTGCGATCGAACGAAGAGAGAGTCGG AGAAA |
| 56 | N04807-1-Q1<br>GCCAAATTACCATTCAAACTTTGACGGCTATCGCTATGCA CAAGATTGGGCCTAAGCTAGAGAAAGCTCATAACTAACTA ATTTNCCTTGCCGGTGAGTATGATGACNCCTACAGAGCTA TCGTCTCTGGCGTCNTTAAACGCACGCATAAGCTCCTTCA CAGTCTGAGNCCGGAACGCGTTTCTTNTCTCCGGACGGTT TATAGTGATCTNNATAACCAAAAACTATTCAACTGAAGAA GAAAGAAACACACACACCAGAGAGAGATCATCGAACACTT TACATTAACAAANCTTGGCAATATCTTCACCGACGGCTTT CTCATATATAATGTCAACNAACTCTTT[C/T]GTTTCTCC GTCGTCACCGACGAGATCAGCTTTTCTCCAAACGACTTGG TGAGTCGGCACTTCACCGTGAACCTTATGGTANTTGTCAT TCATCGACGANGCAGTAGAGAGTTCCACTGAGTGAACGCG AGTTGGAATTGTTTCCANGGGGATGAGATGATTGGTGANG ACGGAGATACGGCGGCTCGCGGTGCCGAGTTCCNTGGAGT CNGCCATTGGAGAGGAAGACGCGCAGAGACAGAGAAAGATG AGACTGATTGATGATGAAGATGACAAGAGATTCTATCGCA TGGACTTTGACAATATTTGGATAAAATATTTT |
| 57 | N06778-1-Q1<br>GTATGACAGTGATGATGAGTTTATTGCTCCTCCTAGGCAA ATCAGGCAGCCATTCATCAACCGNCAACCCGCCCCTGTTA CGGGTGTCCCTGTTGCTCCNACTTTGGACCAACGCCCGAG CCGCAGTGACCCTTGCGGTGCACGTATGAGGGAGAAGTAT GGACTNGACACGTCTGAGTTCACATACAATCCCTCACAGT CACACCGGTTNNCAGCAAATGCCGACGCAACCAAATGAAG AAAAAGGACGATGCACCATCATGTGAGTCCATGTCTTTAA AAAAGTTCAGTCAGTTCTC[C/G]TTTCCTATTTTTATTT CTGCTTGCGTATAACAATCAAGAGTGTCAGTGAAATTAGA GGTGTGTTTCNGGGTNGTTNTTGATGATGATTACTCTAGC ACTGGAGGTATCTCAAATCAACCTANNCATTTTGTTGAAA CTCNTTTTATTGTGCTGTGTAGTCTTTTTGTAAGTACTT NANCATCATGAATGTTCATCTTGGTTATCTGATTCGGTCC TATCATTCTTATTATATATAAAATTCATCTGTTTTA |
| 58 | N09897-001-Q001<br>GAGAAGAACTGTATAGAAGCTTCACTTGATTCCCTAAAAC TGTTGTTCGAAACAACATAGAGTAGTTGAAAATGACGTTG AAATACCCAAATGAATTTGGTTTGAGAGCGATTAGAATAA ACTGTCTCTGGTGGTGGAGATGATCTCCTTTGTGGTAGAGC TGAAAGATGATGTTCTCTTCATTAAAGAGAGAAGTTATCT [C/T]GTCATACCGAAGGACCATAGTGGTAATAAGCGGTT GGCTTCTAAAACATAGCAGTTTCGTGGAGATGGAGCAGAG CCTAGGACCGTGAAGTAGCTTATTGGTGGTGACGGAGGA TGCTGGCCGGAAATATCTGCTGTGAACCTATTGAAAACAT CTAGAAAAAGGGATTTTGACGCTGAAGATCAGATTGGATG AACAA |
| 59 | N10499-001-Q001<br>GTAATGAAGGCAAAACGAGGCGACCCTTGGACGAACCATA CCACTTTACTCCGATTCTGCNTCTCTCTATGCGGTTGTAT CTNCTCCCATGTTTGGAAAGANGAGAACCTGCACTTATAC TCATCCGACCCTGATTTCCATAGAACCATGTCCTCCTCNT TACCAACAACTAGTGCTTTGAAACTTCTAACACTCGTGAT TATTTGCTGTAGAGTTTGGTCTCTGCATCTTCGAATCTGC CAACCAGAAG[A/C]ATTTGCAGCATCAGCAACCTTGGTA TATCGCCCAATATCAAGCCGTTGTGGACCACTATCCCCCN CTATGTCNATAAGTCGGCCCCCAGGAAGCCAGGGGTCCGA |

TABLE 7-continued

Markers of QTLs significantly associated with shatter resistance (P ≤ 0.01)

| SEQ ID NO: | Marker Name and Sequence |
|---|---|
| | CCAAAATAGAGTTCTCTGCCCATTTTTAATTTGCATTCTG ATGAATTGAGCANCCAGCGGCCTCAGCCTCAGGAGCTTCC TCCACACCCACGATCCCTTAGCTGACTCCCTAATGTCCCA NAATGAATCATTGCTCCATA |
| 60 | N23447-001-Q001<br>AGCGTTCACCCAATGTTCACCGTACCACTCCGTTAACGAG GAGTGGTTGCTATATCTCACCGGGGCCGGGATTGAACCGG NAATATACTATGCCTTCAACGGATGAACTCACAANCCGAG CCACCGTCTTTACAACTCGATCACCTAGCTTCTCTCTCAC TCTACAATACATCTGAGTNCTGATCTAACAAGATCCTAAT CAGCTCAGCTCATNCTTATCCTAGTCTAACCGTCACACGT GCGCACACTTCACACGTGAGATCAACTAACTCGAGAGAGA GAGCCGGTTCTAATTGATTACAAGCTTAACCGACTAAACC AACTTTAATCCCNCTATACAATT<u>AGAACCTAAACCAATGG ATAGAAACTTGACT</u>ATATCCAACAAAAGCCTTAGGGTGTA [A/G]GTTAATTATCTTGTTCNCAAAACCTTAGCTTTTT <u>ATTTACTGCTTTAATCATAATCATCTAGTTTTAGTTCGAA</u> AACTACAAATTTATTGTGTAAATCCTAAAGTCTATGTCGA TTCGATTCTTAAATATTGCAATTGAAACTTTTAATTAAAA GAATAAAATCACTGTTTAGGGCAATTTAAATGATATCACA CCTACTCTCCGGTAACAAAAATAAATGTAATCATAATGTT GATGGATGGCACTACAAGATCTAAAANTCAATCAAATAGA TTTTAAAACTTCCTTTCTATATGGTAATCAAGCAGTAGAG ATTTATATGAAAAAATCTAAAAGGTTGGTTGTCCCATAAC AAGAAAAGTCTACAGACTTGTTAAGTCATTATACAAACTA AACA |
| 61 | N19834-001-Q001<br>GAGGTAAAAAATCAGTAACTGTCATGTTCTTCGTTAGCAA CGGAAGCCCTAAGTATCTGACAGGTATATTACCAGAAGCA AAAGAAAATGATTCATGATCTCTTCTTTCTTTTGATCTAA AAAACCAGCCATAAACAAGG<u>TAGACTTTTCCAAGCTAATC TTCAGACAAG</u>ACATTCTATTAAACTCCTCAAATACTTTCA [A/G]TATCCCTTCAACT<u>GATCTTCTAGTGCCTTCAATAA ACACC</u>ATTAAGTCATCTGCAAAGCATAGGTGAGTGATACC TATGTTTTTGCATTTTGGGTGGAATCCAATTAGATTTCTT GAGGCTGCTTCATCCAGCATCTTTGATAGCACATTCATGC AGATAACAAAGAAGTAGGGAGATAAAGAGAATCCTTGACG CAGAC |
| 62 | N23362-001-Q001<br>AAAATTGATCTGATACAGTTCTCAACTGGCATGCCTATGG TACCCTGCCTGTCTGTTATCTTGGTGTNCCATTGTGTACT AAAAAAGCTCACGCTCTTAAACTGTGAAGGTTTACTTCAG AGATTATCCTCNTGGAGTGCCAAATCACTCTCTTTCGCTG GCAGGCTGCTGCTTATCAAAACANTCATCACAGGCATAAC CACTTTCTGGTGTACAANGTTCATCCTTCCGCAAGCATGT GTAAAACNCATAAATTCNCTATGTGGTGTCTTCCTCTGGA AAGGTGATATTGAGGAGCACTACGCAGCACGAGCCTCTTG GNAGGTTGTCACAAAGCCGAAGCAAGAAGG<u>AGGCCTTGGG ATTAAGAATCTTTC</u>GATATGGAACAAAGCATGCTGCCTTA [A/G]GTTGATCTGGC<u>TACTTTTCTTTCAGGCAGGCTCGG</u> TTTGGGTTGCTTGGTTCAAGGAGGAAGTTCTGGATGGATA TGTCTCAACAATCTCTGGACTATGGTTCCACATAGACGCT ACTCTTGGCAGGTTAATAAGCTTCTTAAACTGAGCTCCTC TATCTTCAATTGAGTTAAGCTTCGTGTCCAAAATAGTCTC TCTTGTCGGTTCTGGAGTGACACTGGTCCCCTTACGGCT NTATGAGGTCTTATCTTAGCATCNGCTCCAACTCAACTAT GGGGATCGCAGCACAAGCAACTTTAGCATCCCTTCATCAT AACAACAACTGGTGGATTCCTCCTGCAAGATCAGAAGCTC TTGTCAATGTCCATGCCCTATTGACCACCATTGAACTAAA CAATA |
| 63 | N23266-001-Q001<br>CTTCTTAGACTAAAAATAGTAATTAAAAATTCTAAGATGT TTGCTAAGAGTTTTCATTGATAATGTTGCTCTTAGGATGA TGCACAAAACTGTGACTGTGGCATATAATATATCAAAGTT ATCTGCAGCTTCACCACACAAACAAAAATACCTATAATTT CTCCATTCTTCTACAAGGTAGCAGACTAGCAATCAATAAT AATACACTACTAAATCTCTCTTCAAGAATAATCACGTGCA CGAACGATTGTTCTNTATCGATATCTGCTTAACATTACAT GCTCTCCCTGAAGTTAATAGATCTTGACATATCTGCAGGG TTTGTTTGAAGGTTTAGATACGTCTTAGGGACAAATCTAT |
| | TGTT<u>GCAGCTCTTTGTTTCAAACCCATTAGAGGAAAAACT</u> [C/G]AATTGATGTGN<u>CTTCTCGCGTTTCATCGGTACCGG</u> ATACAACACACGATTATTCGTAGNTACGTCAATACTTCGA GATTGTGAGTCCAATCTTGCTCTTACAAAAGTGTCTTTGT TTTCTCTAACACTTTCATGTGTTTTAGCACAAAAAACACT TATCATGTAAAGCTTCGTCTCTTGTCCTTTTCCCTAGACA CGTTGGAAGTCTCTAGAGTATACCAAAATGGTACCATGCA CCCCAGTAGACAAGGATGTGGTAGAATGTAGGGTAAAGAG GACACTGGTGAGGGCCGTGAGGCCATGGAGGCGAAAAAGG GGATGTTACTTGCGAAGGAAGAAATCCTTGGGAGTTGTTG AAATCTTTGAAAACAGAGTCAGAAGTTATCTTCACTTTGC TTGAT |
| 64 | N19862-001-Q001<br>TGTACACTTTCCCTTGCTTGGCCATCCATGAGTTGAAGAT CAGCATGGCCTCAGCGTCGAAAACGCTGTCGCTGTGGCTG GGACCAGTGGCCACACGGTGGCCAGAACTGCCAACAACAT GGTGGTTATAGTCGTATGAAACGACGGACATGTCCATGGC <u>CGTGGCACAAGATGCGATGAG</u>CATTGCTAGTAAGAAGATC [A/C]GCATGGCTGATT<u>AGCACTACCCATCAAAACTAAT GAAACTT</u>TAATTTATGTTTGTTTCAACAAGTTTAAAAAAG CTCATAGAAAAGAGAACAAGATTTTGTGCTGATTAATTT TGCCTACTATATGAGAGTATTTATAGTATTCAGAGCTCAG ATAGGTAACACTTGTGTTAAGAATCTCACATCAGAAGAGG TGATA |
| 65 | N22187-001-Q001<br>GCCTCTGTTATTCCCTCCGGCTCTCTGGTTGGTGTTATTC CTGCTACTGTTCAGAGCTCCGCCTCTGTTATTCCCTCCGG TTCTCCGGTTGGTAGTCTTTCCTCCGGTCCTCCGATTGGT ATTCTTCCTGCTGCAATTCAGAGCTCTGCCTCTGTCTCTC <u>CATCTGGATCACCGTTGGT</u>GCTCTCCCCTCTGGCTCTCT [A/G]GCGGGCGTTGTTCCTCCTGAGACAGTGACGGTGAT AAGTCCTCGCTCTGCTCATGCTCCTCTAGCTTCCATAGCT CCATCACAAAACTATGCTTCTCTGTTGAAGAAATCTTCTC AGTTGAAAGAGCTGGGAACGCCGGTGGAACACGTCTCTGG TGTACCGTTTGTCATGATCCCTGATAAAAACATTGAGTCA GCAAA |
| 66 | N08651-1-Q1<br>CNAACGACTCCCAAACGATCACACTTTGTTTTCAATTATT CATC<u>GATAACTATATTCATCGACTCCCAAACAACA</u>[A/T] AAGTTACCACCAGTTCACAACAAAAGTANAACATAAAGA<u>T CTACCACGCAGATGGTCC</u>AAATAGCATNCGGACAA |
| 67 | N23296-001-Q001<br>GTTTGCGAATTATANNNNNNNNNNNNNNNNNNNNNNNNN NNNNNNNNNNNNNNNNNNNNNNNNNNNNNNNNNNNNNNNN NNNNNNNNNNNNNNNNNNNNNNNNNNNNNNNNNNTGTAAA AGAAGCTTATGTACCCGTATTTTGTGGAAGCACGCAAGGG CGAATCCAAAGATTATTTTCAGTGGGTGCACAAATTAAAG TGTATNCTTACGTATGATCGTAGGTGTATACATCAAATTT GTTAAGAAATATACTAAAAAATTTAAAATTATTATGGGGG CAAGTGCATCCATAATCCTNTACCTAGNTTCGTCAGAACA TCGTAGTCTATTGATTAAGGTTCAAAAG<u>CTTATACACTTA AGTCTTTGAATTTCAAACTATGCATTTTTTTTGCCGATTA</u> [A/G]GATGCGAAGCTCATCAGAAGTTTTAG<u>AGTATTGTA AGTAGAGCTGTTTGTTGTGGTGATGGAAAGAGTTTGTCTA</u> TCGCGGATGTCGTACATGCTGGACCGTCTGTCGATCCAAA TGTTTCGGAAAGAACTTTATCNGAAAATTCTTATCCATCA TCAATATTGCATATATTGNAGGTAGTTGAGCAGCACATTT AAAAAGTTAAGTAGAATTTTGATCGCTGTTTTACCTACAG AAGCTGGCGAGACACTAGTGTAAGAGAGATTGTATTGAGT GAACATTTGATATTGATANTGGATTTCCAAAACTAACCA CCTCGTGAGTATATGCTGCAATCATTTTGATTAGACACTG AAACAATAATCTTGTATGTCTTTTCGATTTCAACTTATG CTTAT |
| 68 | N17314-001-Q001<br>NNNNNNNNNNNNNNNNNNNNNNNNNNNNNNNNNNNNNNNN NNNNNNNNCAATATTTAAATTTTTTAGAGGAAGACACC TAGTATAATTTTTAATTAACTAAAANGGGGATTACATAAT TGGATCCTACGTTACCGAAGCCGGACTCCTTCCGCCTCTG TCGATCTGCAGTCTTGCCGCTCCTCCAAAACACCGCCACG |

TABLE 7-continued

Markers of QTLs significantly associated with shatter resistance (P ≤ 0.01)

| SEQ ID NO: | Marker Name and Sequence |
|---|---|
|  | TAAAGCCATTCCGGTGAGAGACAACCAGGTTCAAAGTAAG ATGCATATCGAACAGAAAAATCAACGATGGAGAGATAGGC AAAAAGAAAAAAGAGTAACCTCCGGCACCGCTTATTGCTG GACCGGAAAAAAGATCTTTTGCGCTTGAGAGCTTTTAAAG AGAGATAGTTCTGTTAGAGAGAGGGTCCACTGCATGCAAT [G/T]ATATATTCTTTCTCATCAGACTTTTGATTGGTATGG TGCTTAAATGGGCTGAAAGCCTTATATAGTATTTATCGTT CATGATAATCAATTATATAAGTTTCTTAACAAATAAATTA AAATAAAGATTTTTTGAATGATTGAATCTGAAAAATATAT CGCAAAAGCGGCAGCCTAGGGTTAGATCAACTTCTCCATG GACACGTACACTAGCCAGATTAGGTCCTCAAGGGGCCGAT AAGGTTCGAAAGTGAGGCTGCTCGGGAAGCCTTCCTCGAG AGGAACTTAAGGCCCCNNNNNNNNNNNNNNNNNNNNNNNNN NNNNNNNNNNNNNNNNNNNNNNNNNNNNNNNNNNNNNNNN NNNNNNNNNNNNNNNNNNNNNNNNNNNNNNNNNNNTTTG GTTTG |
| 69 | N20380-001-Q001 ATCACAGAGCTGCATATAACAGATACAGAAATACTAGATA TTGGTTCATGGGTCAAGGAACTCTCTCATCTAGGCCGACT TGTACTCTACGGATGCAAGAACCTGGTATCTCTCCCACAG CTTCCAGGTTCCCTACTAGACCTTGATGCATCAAACTGTG AGTCCCTGGAGAGACTAGATAGCTCCCTTCCACAACCTGAA [A/C]TCTACTACTTTCAGATTCATTAACTGCTTCAAACT TAATCAAGAAGCCATACATCTCATCAGCCAGACTCCATGT CGCCTAGTTGCAGTTTTACCCGGTGGAGAAGTGCCTGCCT GCTTACTTACCGAGCTTTTGGGAATTTCGTAACAGTAGA GTTGGATGGGAGGTCTCTTCCTAGATCGAAAAAATTTAGG GCTTG |
| 70 | N05490-1-Q1 CTTGANCCGCCAATAGATGAGTCTCCTGAACCGTTTCCTT CATATTTCCACAGGCCAGTATCTTGGGATGCNAACTTCTT GACTGCAGAAACATAATCTGGCTTGAAGAAAACATATTA TCCTTTCCAGCAGATTGGTAATGGTTCCCTGTTTGTTGCA TATCATC[C/G]CCACCAAACTGTGCAGGGCTTAGGGCAG GAAAATCCATGGGNGTNAGATTAGGACGCGGAGCAGGAGC AGGAATCTTAGGCCTCATGTTCTGATTCANNCCATTATCC ACTTGTAGCTNNAGTACAAACATAACCAAATCACTCGAAT GAACAAACATTCATAAAGTAGCAAACAACATGATTGGA GCAAAAAAAAGGACATCAACACATTCAATAACTTAAAA TTACAATTAGCATCAACATTGAACCATATGTTCACAAGGA ATAATGAGTTTCATAGGAAGAGAAGCAGAAAGCTAGGGAG AATANCTCAAGCTGAGTAAGCATCTCAACNGTCAACTGCA AATCACACCCATTAGCAAAATAAACNTCNGCAAGACTCTC AGCAGCAAANCCAGGGAACTGAGNAGCNAGAAACTCCACA GGGTTCACCTCCATTTCCCTATNCTTGGATTCTNGGAAA CCATGAATCGACCAAAAGGGTTCTTCTCTCC |
| 71 | N18849-001-Q001 CTTCATAAATAATTGACACAATATATTTGAATATATGATA TATTTAATAAAAACCTCAATACATAAAAATAATTAATAGT ATTAATTTTAATATATATATTTATATTCACTCTATTCATT ACTATTAAAATTTGGATATTATATAAATTAAAACTATGA TTATATTTTTATTGATATATGATATTGTATTTTTTTAA AGAAGGNAAGCGTGATTCCAAAACAGAATCATAAGCTTCC AACATGTTTTTAAAGAGAATATTTTGNAAGCGTTTTGGAA TCGAGATTCCGTAAGCTTCCACAAGGTTCCGATTCCNGTT CCAAAGCGGGAAGCAGATGTCCGGATGAAGNTTCCATGCA ACGTAGGAAACAAGTATCAAAAGGATAAGAGAAAGGAAAA [G/T]ATAGAGAAGTTCACACATACCAAAACATTCGACC TCGAGGTTTAGACCTAATCTTCGGCCAGGTTCCTTCTATC ATCCTTTGTTACTTTCCGTTAGATTGTAACCCATATTCTC TGTAACCTTTCAGTTACTAATATATANACATTTCTTTTCG TCAATCTTGATATGTATCTTGCCTAGCCAACAACTGGATC GTGAGTGTTAAACGTCTTCCGATCATATTTATTCAATTTC GCATCACAATTCGCTAGGCCCAATCCAAACGACNNNNNNN NNNNNNNNNNNNNNNNNNNNNNNNNNNNNNNNNNNNNNNN NNNNNNNNNNNNNNNNNNNNNNNNNNNNNNNTACGTAGCCGCTTCCGTTTCCATGTAA AGTAG |
| 72 | N08200-1-Q1 GCCGCCGAGCGAAGTTCCCTTGCCGGCGTTCTTCGCGAAG |
| | AGAAGCGTCTCCTCGTTCGAACCAGCCGACGCAAC[C/G] ACCGATCTGATCAGAATCTTGGGGATAGACGTCGATCGAT CTCAGATCTCCGATTAATAAGAAAAAGNTATCNCT |
| 73 | N19827-001-Q001 ATAAAAGTTTGGATACTTATATAATAAAGTAATTATATAC GAATAAAAGTGAAATATGATAAAAATCATGATGAATAGTT GGAAACAAACATGACCTTGTCTCTTTTTTCCTGAACAACA CATGACCTTGTCCTAAGAAATGAAAAGATAATTAAATAAA ACGAACCAACAAACAACATAAAAAACTAAGAAATAGCCAC [A/G]AATGAAAATATAGAGGGAGGAAAATCCTAGTAATA AATGTTTGGATACTTAAATAAAGTGAAATGTGATATATTC ATGATGAATGGTTGGAAACAAACATGACATTGTCCTAAGA AACCAAAAGATAATTAACTAAAATGAAATTAAAAAAACTA AGAAAAAGACCACAAATGGAAAATATAGGGAGAGAAACT CTAGT |
| 74 | N001R9W-001-Q001* GGGTGACCCGGGTTCGATCCCCGGCAACGGCGAATCTTTT TNTTACATTTTAAGAAATTGAAATGTTTTCATGAAAATGA ACAAAAGATTATAATGGCTTCGCCCGGGTTCGAACCGGAG ACCTTCAGTGTGTTAGACTGACGTGATAAC[A/C]AACTA CACCACGGAACCTTTGTGCTTACATTGGGAACAAAGAGCT TTGATAATTTTGATGTCTAAGAAATCTTTAGATGTTTGGT CCGTAGAGTCATGTAAGCTGCTCTGTCTATTAAGCCATCT CGACTGCTCTGATCTTCTGTAAAAA |
| 75 | N08264-1-Q1 CCTCATGCATNGTTCAAGNGGAAGATCAGAGACTTCAACA ACTGGTTCATCTGGAATAGCATCTACCACAGAGTT[A/G] TCTGTTTCTTTGCATCCATCTTCACTGGCGTTTACACCAC CATTCTCATTATTCTGAGTGGTCTGAGTTGAGTCC |
| 76 | N23132-001-Q001 GCTCAAATTGCTACAACGATTGAATAGAATTTCCCGTACA NAACACTGTAGTTGGCCAGATACGTTGNAGGTTTAAGAAG TGTAATGTATCTTGTATTCCTTATTTATTTTCCTTTTTTT TTGCTAAAAATATGCTTTATTTTTACAATTAATTTCTCT TATTTTTTACAATTAATTTCTCTTATTTCCTTTTACAATT AATTTCTCTTATTTCCCGTACATAATTATTTGTTTTTATTT TAAATTTATTATGTTTGTATTAATTTATTTCAGTAGTCAG ATTGAAATAACAGTTAAAATGAATAAATTTCATTACTTCC GATCATGTATTGTTANGTTTAGAACTACAAGCTTACTGAT CATGTTAGTTGGCAGTTTTTTGTATCTTTTGAGTATGCAG [A/G]TATGTCAATATTTTCAAATNATATATTTTTCTAAA TATCATATTCAATTTCTCTTACAAACAATGGCTCTCATTA ATCTACATTAATTTATTCTAAAATAATAATAACCCTTTGT AAATATCAATCCTAACATTTAGGGAGGTGTATTCAATTGG GAGTTTGAAGTGATTTTTATTAAAATGATAAATCTACTGT TCTTAAAACATGATTTTTTATTAAAAAACTACTTTGAAA TCTAGTAGTATTGAACTTGTTATTTCATAAAACACTCTTA AATGCACTATTATTGAATAAATTTAAGTTAGAAATTTTAG AGTGATTTATTTCTATAGTGTTTGAGGANNNNNNNNNNNN NNNNNNNNNNNNNNNNNNNNNNNNNNNNNNNNNNNNNNNN NNNNN |
| 77 | N03615-1-Q1 TCTTTGACTCCTGTTTGACATCTCCTANGTGCATTTTGTA NTGAAAGAGCTGGTNAGAAAGTCNATTTCAGAAACAGAGG NGAGAAGACGCCTTCTGTTGTGACAATTCCTCTTTAACTC TTTACGTTCTGTTTCAACCCTAAAATGCCATTTTTTTATN AGGAGCTGAAGCGATTCCCAACTCTAGCNAGCCGATATAGC AGCNGCTGCAAATGAAGCTCTTGAAAGATTCAGAGACGAA AGCAGGAAAACNGTTCTGCGTCTGGTGGACATGGAATCCA GCTACCTCACTGTTGGTCTTCAGNAACTTCACATGGA ACCNGAGAGAGAAACCAAACCCGAGGAATGCCCCACAG CCAAACGCAGACATATACTCCGACAGTCACTTCAGAAAGA TCGGNNCGTCTCTGCTTACCTCACTATGAATGAATGAGAC ATATCAAATNTGTGTTGACTTTGAATATAACTCNGGATC CAACGTGAGTGCATACATAA[A/T]CATGGTCTGCGACAC ATTGAGAATCTCTCTTCCAAAAGCTGTTGTCTACTGCCAA GTNAGAGAAGCTAAGAGATCGCTCCNTAACTTCTTCTACG CTCAAGTNGGCAGGAAAGAGNNAAGTAATTTTCTAAACTA GAGAATATCTGAATCATTTTAAAGAGTGAAGAACACTTTC |

TABLE 7-continued

Markers of QTLs significantly associated with shatter resistance (P ≤ 0.01)

| SEQ ID NO: | Marker Name and Sequence |
|---|---|
| | TAATGATCATTAAAAAAAATGGGTNNAGAAGGAGAAGCTG GGGGCGATGTTGGACGAAGACCCACAGCTGATGGAANGAA GAGGAACATTAGCCAAACGGCTCGAGCTTTACAAACAAGC TAGAGACGACATCGATGCTGTGGCTTGGAAGTAAGGTGTG ATCAAAAAGGGTTTCCTAAGAAAATATTCTTTATATCTTT TAATTGCTTTGCTCGTGTGGGCACTTATGTTGGAAGTTCT AACCTCCNATCCATNGCTGCACACACATACAGACGATAAC TCGTATTTTNTTTNGCCGCTAATATTTGTTTCCCACTTTT TTGGT |
| 78 | N001RWT-001-Q001* TGATTTGCCTAGACCAATTTTTAGAACACTGGTAATAAGN GACACTGTTTGTCTTTGGTT[A/G]TAGTTGATACTTCAG CTTAACGGTTCATGTTTTAACCATTTCCTAACTATTATTG ATTCT |
| 79 | N08465-1-Q1 AGTTTCCTTCTCCTCCGAGAAAGTTAGCTCNTTTCTCTTG TTCTCTNTCNAAAANATCTCTCCTTTCAACGTTAA[A/G] TCGTTTAGTTGTTTGAGTGATGTCTACGGATACGGAGGCG AATTTACTTGCGTTAGCGGCTGTGTTCCGCAGGAG |
| 80 | N10774-001-Q001 TAATTAACGTGATATATTATTTCCATAATTATGCACAAAT TATTTGTTAACATAANNNNNNNNNNNNNNNNNNNNNNNN NNNNNNNNNNNNNNNNNNNNNNNNNNNNNNNNNNNNNNNN NNNNNNNNNNNNNNNNNNNNNNNNNNNNNNNNNGAAAA AAGGTGTATTGCACAATTATGTTAACAAATAATTTGTGCA TAATTATGGAAATATTACATCACGTTAAGCCTTTTAGTCT TATGTTTAGATCAATGTTATAAAAATTGGTAGACGGTGGT TAAGCGTCTTGTAAAAGATTATTGTTTAGTTGGATATCTA GGCGCCGCTTAAACAGATTTTTATAACACTAATTTATATA GAAAATATGTAAAACTTTTTCCATCATCCATTTCTAACAT [A/C]GTGGAAATAAATAAACAACTTAGACAATATAAAT TACAAATAGATTATTAGTTTTTACAAAAAAGTATAAATA GATTATTATGGCACCCATCATATATTGCATAGGCTATATT CTTCTCGCCTTAAGCGTAAAAAAGAGACAAAATATTCTTT AGTGAAGATGGGAACAGAGACGTCGACGATGACGGCGAAG TTAGCATTCTTCCCACCAAATCCGCCGACGTACACGGTGG TGACGGATGAATCGACGGGGAAGATCGATGAGGATCATCGG CGGACATGATTCGTCGTCATAGACGGGAAATTGAAGTGG TGAAGATAATGACTAGAAGAGGGAATGAGATCGTGGGGTT GTATGTAAAGAATCCAACGGCTAAACTCACCGGTGTGTAT TCTCA |
| 81 | N17035-001-Q001 NNNNNNNNNNNNNNACAACAAGCTATCGTTTTTATATAAT AAGTCTTTGCATATTCATTTTAAATTCTGAACCGTTTGTG TTTGATCTAGGTTGATACTTGGTACTGCCCGAGTGATATG GACACTCCACACTGAAAGAATTGTGAAAAAAAATTAGATA ATAAATTATAGTTTTTTTTTGTAACTTAGTAAATTATAAT GTTTAGAAGCTAAAAACATAACACGGAGTTATGGACAGTC GATACTGACTGAATCACACTTCAGACATATCCAAATATAN TTTGACTTGCATTCCTATTTTAAAAAATTAACGTTTTGA TGTGAAAATATAAGTTTCACATCGAGATCGAANATTCANT TGANACATGAATAATATATAAAAGATTTGGATCAATCCAC [A/G]TATTACCAATTTATTTTAATTTGAAAACTCATGAT AAATCCAAACTTAACATGATATTATAGTTCGAACACATGC TAGCTGCCCAACCGACCGAATTGATTAGGCTCATCGAAA GAGGTTCAATTGATCCTAAACCTCATGGCCTGAATGGTCT GGCGAACTGACCGAACCATCATCTAAATTGAGATATTGTC GAGGTTAATGGTTATAAGAATCACTATNTTGAAGAGGCGT GTGANAATATAAACTCACATATTGGAAGTTTAAGTGGGAC ATGAATAATATATAAATAGTTAAAGCTAATCCACTTATCA TCAATTGGTTTTAAGTTAAAAGCCTATGATAAATCCAAAT TTAACATATTTGCTTATTAATCAGTGTTTTAGATAAAAGT GGATA |
| 82 | N20834-001-Q001 CTAGCTTCCTCACCATGAAATCAATACGGTCCAATCTCGA AAGGATGGGTTCTTCCACTATAGCCATAATGTTGATAACA CACCGTTGTTCTGTTGCACACTTCACAGCTTTGGTTGTTG CCGTGGGAGTAGTTAAAGCCTTAAAGACAAGCACTATATG AAACGCCAAAACTGGTCATCTTGGAGATTGAAGACATGAA |
| | [C/T]TACGACACGTTTAATATTACAGAGAGAGCTGGTTA CGGTCTTACGCTGTCGTTGATCACACGTACTGGGTTTAG TTTGTGGACACCTCTTCTGTCTCACACGTCCAACATTATT CCATCCTTCCTTATCTTAATCGCTGACGCCTCTCCGAGAT TATATCAGACGCAAGATAAAATTTCTAGTGTTTATTGCAA GTGTT |
| 83 | N22903-001-Q001 GTTAAAACTCGTGAGTGGTAATCTTGTAAATTGATGAAGA CTTGGGTTCTAAGTTGGCTGAAACCAAATGGGGTTTCTGC GCGCTTCGCCGTCGACCGATGACACAGGATGTGCATCGAT CGATTATTATCTCTGAATGTCGACCGATGGTCTTGCTCGA TGGTCAGCTCGGATGCTTTCTCCAAATATTTCCAAAATGC TCCAAAATCATCACTTTCTTTCAAATCACTCATGATCGTA TAAATATACTAAATAGATTTTATAATATAATAATTAGTTA TTAAAACATCTATAAACCGTGGGTAAAAGTGGGTAAAATC CATGGCATTCCAATACCTTCCGCCAAGTTTTAAACAAAAT CAATAAATCATATTTTCTATAATAGAAGACTCGAATGGTG [C/G]TTGAAACTTCAAACTAAACCACAAAGCTTNACGTT TTTATATCGAAATTCAAAGATACACTATACAACTATTAAC TGCACANCTAATCTCTAAGTTACTATAAATCCAGCAAAAC GAAGTTGTTGACATGTTCGCGTCAGAGTGTGAGAGGTACA ATTTTTAAGAATGATNCGAAACTAAGAAGATATGAGTAAC GNAAGGTATTAAAAACATATATGAGGTTGNAGTGAAGATT CAGTTTTGGTGAATAAATGACTGATCAGAATATTTTGAA CATGTACATATATAAGTGTGTATCAGATTCAGATTGTAGA TTATAGATTCTTTAATTGTGTGAGGATATTTATGAAGAT CGCATTACTCTGGTTCGTATGTCAAAAACATAGTTGGTAG CTTCA |
| 84 | N09920-001-Q001 TAAGAAAAGAAACTGAGATTAATCGCGGTCTAAGTGCTAG TTTGAGGTGACTTTTATGAAAGTATACCATTACAGTAAAA CTGACTCTTAGTCATAGCCTCATAGGTTTATCATTCAACC CATAAACTAGAATAATATTACTCAGCCAATTTTAAGTAAA TCATTGAATATTGTTAGTGTGAGATTACCCCTCTCTGAGT [A/T]AATTGATTCTATAAACATAAATACCCCATATCCCCA TGCAATGATACAACACATACTATTTCGAAATCCCTCCGTG ATTGAAAATATGCATTGTTCACGCCTCTTCTCTATTTTAT CTCTAATTGTAACCATCGCCGGAGCTTTCGCCGCCGCTCT AGAGTGTTCATGTAATGATCTGGTCTGTTTATTTAATATA AATCA |
| 85 | N22822-001-Q001 AGTATAAGGAAGATGTTTGAAACATGGAAACTCACATAT TATTTAGAAGNCTGCCTTACCATTGCCAATTGTTAGCCAC AACAAAAATACCAATCTAACAAGGTACTTTCATGACTCG ATCTCAACTTAGCAACCTAACCATTTTCAGCCCACAGCTC ATAGGAGTTATCCAAATTCACTATCACTGACCTCATTTAA GACTAAAGTGCAGTCTCATCGAGGGAGTATCGATCATAA GACACATGGACTCTTACCTATTCAAGTATCTGATCACACA TATAATTTTACTCGTNTTTCTTTCCTCTCTCTTTCTCATT TCCTCATTNGATTTCTCTATACTTCTGTAGGGTATCATTTT ATTTTTCTATCGACTGAGTTTATTAGACAAGATTCCATGA [C/G]ACACAAGCACTGATGGTGGTAACCACTAAGCACGC GATGCACTTCTTGTTGATTTTTATCTTTTTTCTTTCATTT TTTTTGAAGAAGAGAGAGTAAAACCATATTCACACAGA CTAGTCTTTTTAGACGTGAGCAAGAAGTCCAACCCAATGT ATACCAAGATTTAAGACAAGAGAATCAAATAGATTAGGTG AGAGGTCAGCTTTGGATCCTTCGAANGCCCAACAAACATG GATGGCAGATCATCCACTTTGGCAACAATGTCTTTTGTT CAGTATTGCTACTTGGAAAGCAAAACACAAAAGCAGCTTA TTTGTTTATTTTCTTCTCATACTTGTGTGGTTCAACTGG AAGTAGCTCAGTTTGGAAGGGTTCCATCATAGTGTTCTCT GTAGG |
| 86 | N22688-001-Q001 NNNNNNNNNNNNNNNNNNNNNNNNNNNNNNNNNNNNNNNN NNNNNNNNNNNNNNNNNNNNNNNNNNNNNNNNNNNNNNNN NNNNNCCTTTATTACATGCCAGTTCATCGTCATTCGTCAC TGTATTGACACGTGTCGTAAGACCATTATATACTTTCTGT AATCCCATGAAACAGTAGTTAATTACACTTTTAACTTCTG CACGTAAGACTAAAGATGAAGGGAAGATGAATGACATCTT ATGCATGTGCACTGCACGCGGCCGGCGACTCCCGCCGGTT |

TABLE 7-continued

Markers of QTLs significantly associated with shatter resistance (P ≤ 0.01)

| SEQ ID NO: | Marker Name and Sequence |
|---|---|
| | TCGGGTTTAAGTGGGTCTCTCTTCT<u>GCATGAATAGTAGTA<br>GCTTTCTTTTTTTAAATGTGTATATAGTAGCTATATAGTT</u><br>TATTTATGNTTCCTAGTAATAATAATGTGTTTTATTTTC<br>[C/G]AGACTTCTCAATTACT<u>CAATTCTTTATAATAATTA<br>GGTAACACTGTTGTTAATT</u>TTTTATTTTCTTTCTTAAAAT<br>GGTTTTAGCAAAATTAAATAAGCTAGATAGATATAGCTAA<br>TATACATCTTTCATTTTAAGTGTTTGTGTGTATTTTGTA<br>AATTTGAAGTTCAAAAACGAGTATTTAAATGATTGGATCC<br>GCTTGCAAGTGGTATNGACAATTAGCACAAAATTCCACTC<br>TAACTCTCAGTATCGTTTACAAAGAAAAGCGTATGGAAAT<br>AAATNAACCTTTACGTATTAGATTTTANGAACGAAAACTC<br>AAATCCTAATATGATAATTGTCTTTAATTATAAAAGTTA<br>TAAATAATTACATATTACTAGCAACCTCCAGTGACTCTTA<br>ATTAG |
| 87 | N10074-001-Q001<br>ACCAGAACTAGATATTGATCCTTATCCCTGAATAATCTGG<br>TATATTCGGAAGGCTCGAAATGAAAAAACTCTTTAAGGGA<br>TAGACATGGATCCTTTGGAGCTAGTTCGCTATGCAGAGAG<br>TGAGTGTCAAGTCTGATTCAATGCAAACAAGATGGTAAC<u>G<br>CCAACTACACAAGAGCATAATTTTGAAGACCCTCAAGTCT</u><br>[G/T]<u>AAACTTGGGTAATATTTGCATTGTAACTTCCACAG<br>CTTC</u>GTTCAGCGGGTGTGGTTGGGTTTGGAAGGATATATA<br>GCTCGGGGAAGGTTCAACTTATGGGGACACGAAATTATAG<br>ACGGTGAGAGATTGCTTTGCTTTCAGAAGTGGAGGTCTTA<br>CAATGGGCGATGGAGAGCATGCTGCAGAATTCGACATGCC<br>AGAGT |
| 88 | N10057-001-Q001<br>AATATATCTTTTTTGAAAAATCGTGTATCTTTAAAACAG<br>AAGCGCACGTAATCCACTTTTCTCTCAGTTTCGAGTCTCT<br>CTTTTCCTCGGAGCTTGTCACCAAGAGAGAGAGAGACA<br>TGGAAAGACTTCTGCAACCACCGTCTTCTT<u>CCACAATCTC<br>TCCTTCCAAATTCACC</u>TCGAGGAATCCCCCTCTCCTTCCT<br>[C/T]GTCTCCGGTTCG<u>TCTCAACGTACAGACCCGAGT</u>CA<br>CGCCGAGTGAGCTCCATTTCCTGCAGCAATCTCAGAGCC<br>CATTTGTGGGATCTAATCAGACCAACATTTCCTTGAATGG<br>ATCTCCTTCCTCATCTCCTGTAGCAGGAGAATCGAACCCT<br>AATCATGGGTTTTTCCAACGGATCGTCACCACGGCTGATG<br>AGCAG |
| 89 | N10086-001-Q001<br>TCACAAGGGCTTTAAAGTAAACTCCCATCAGACCCATGAC<br>CATATCTACTAACTTCAAATCAGACCCTGAAGTGGTGTGC<br>ACTGTTTGGTCAACTGTCTTCATGAATCATGATGGCCTCT<br>CCCCTGGTGATTCGTTCTTGGTATT<u>TCACCTCTCATGTTG<br>CTATAAGGTTATC</u>TATCTTCAGTCAGATCTCATGGCAATG<br>[C/T]GAGAAGTTGTTAAGTT<u>TCCTTTAGTTCAATTTGTG<br>ATTGCTT</u>CAGAATATTGACTCTTTGGCTATGACTTTAATG<br>TGTGATTGATTCTGCGGATTTGAAGGGCCAGTCCTATTAC<br>TGGAACTATCAGAAGCTTCATCAGTTACTTCAGTTTCTGC<br>TTGTATTCTCTGTGTGTTAGTGGTTTTGTCTAGCTCCTTG<br>CTAAT |
| 90 | N11084-001-Q001<br>ATTTATTGAATTCTTAACAAGCGTGAACATTTTAGAAAAT<br>TTAACTTTTGAGAATAGAGGGAGTAGTACTGATATTTTA<br>ACCAGTATCTACTATCTACATTGGTTTTAGTAATGTGTTA<br>TTCATGGCCGTGGTTAAGTTAATCTGGTTAATTAAAAATA<br>AGAAACAAATTACCGTGGTGTCTGATAGACACGGGCTTGA<br>GCGAATGAGTAAAATAAGAACGTGGGGAGTGGAAACTC<br>GAGCCTCACAGAATCAATCACCTAGACTAAATATTCTTTG<br>AACAATGACAGTCACATCCTCTTATTATAGTGTATTTATA<br>ATTTACTAGATTAATTTATAGTTCT<u>TTTTTCTCACAAAGAT<br>CATGTACTCATTACTTCTTTTC</u>CATGATATGGACAATCTT<br>[A/G]TGTTGCGGTTGGC<u>CATCTCTTTTGGCTTGCAAGCT<br>TTTT</u>GACTGAAAAGTTAGATCCTCTTTCTAGGTGGTGAC<br>TTTTGTTGCAAGTGATCTGGATTATGGGTTTTCATCCTGT<br>ATCTGTAGTTTATAAATATACTGTGAGGAAAAGAAGA<br>AGATCATGTACTCGTAATTCAGTATTNTTCTGCAGCACAA<br>TTCTGAATTTGGAAAGTTTAAAATAGACTTCTTAATTCAN<br>ATAAGTCAGCAAGGTAAGTTACATGATTACATATCTACAA<br>TTATGGAAAATCAACANATTTCAATTAATTGTTTGTTNCT<br>TAAACTCAATAATTTTTATAATAAAACAAATATTTAAAA |

TABLE 7-continued

Markers of QTLs significantly associated with shatter resistance (P ≤ 0.01)

| SEQ ID NO: | Marker Name and Sequence |
|---|---|
| | ATAAAATAACGTGTTTACTTTTTATTATATATATGATTAT<br>AGTTT |
| 91 | N22814-001-Q001<br>AAGAGTATCCAAAAGAAAGAGAGAAGAATGGATGACGCG<br>CGTCTCTGTTTTTAGTAGCAGAGANGAGAGAGAAATGAAG<br>AACAATGGTCGCTANTTTTTTGACGTCAGNGGCAACACCG<br>GAAATCTTAGCCTTTTTTGACGCTGCGTTGCTTGTTAATG<br>GCCGCTGCGGTCATCGGTGTTGTGTGTTGCCATGACTCCC<br>GTTTAAATTTTGGCCGCTGCCGCTGCGTCCTGCAGCTAAG<br>AAACGAACACGGCTATTGTTATTTTCGTTGTTGACATGGT<br>CAATGTAAGCTGCATGTTTCTCTTCTGTATTTCCATACAT<br>CTTTCTCGATCAAATGTTTGCAGCCATGGGTAAGAATAAT<br>CTCCC<u>CTCCTTCTAGAGTCTGGGAATCGAAATTTGCGTCA</u><br>[A/T]TAAAATTTGTAACANAGAAAATAAAGCT<u>TTTTAATG<br>GGGGTCCAAATTTTCTGCAGAGCCAACGANAAGTAATCAA</u><br>ACACCATATATATCTAAACTCCAAATATCAATCATGATCT<br>AAGTGTTAAACAGCTCAAAATTTTGCTATAATTTTAGACA<br>TTAATATATATATAAACACAAAAAACTAACAATTTA<br>AAATATAATTTTATATTAATTATAATAATATGATTTATAA<br>TATTTACATAATATAAAGTGTTAATATTGTNCATTTATTT<br>TAAACTGATGTCAACCGGTTATAATTATCCCACAAACATA<br>CCAATTTCTAATTGATTGTACCAGTCGTACTAATCGGTTA<br>ATAACNTTTGAAACNGCATCCGCAAACTCGCATTTACACC<br>AGTTA |
| 92 | N01564-2-Q1<br>GGAATTTCTGGGTCGACGATTCCGTCCCAACGTCACCACT<br>TCCCTCCCAGATCTACTATCACCCTGC<u>AAGTTCATCTACA<br>CTTAATCCGACAC</u>AGCGCCCTCGCCTATCAAAGCA[A/C]<br>GTCTCAG<u>ATGGTCAGATCTGTGGAATGAACT</u>CACTTAGCA<br>GAAGCTCGATAACTGAAGGAGAGGCAGGGAACTCCTTTAAG<br>ATGTGATTCTTCTGAGAGTGGACCATCTGAAGGTTGGTCA<br>CTGCAGGCCTTTTCTGAAATGATGTCATCTTCTCGCAGCA<br>CCGAGCCTTTGTCTTATGATAACGACCACTTTGGGCTTGA<br>ACGGGACATGATAGGCCATCACAGCAACCGAATGTCCAAT<br>CATCAGCAGCAAAGCTGTGGTGCGTGCTCTAGACCCTTGT<br>CAGAGAAATCCTTGTGGAGCAGCCAAAAGATGTTTATGAC<br>CAACGAGCTCTCTGTGTCTGCAATTC |
| 93 | N12902-001-Q001<br>ATAGATAGTTCATAATCAAGAGATTATAATTTGTAATATT<br>TCCATTTATTTTATGACGGTGTAATCTTTTATATAAAGAAC<br>TTCTATGCTTTCAAAAGATAAATTTCTTATTTTTATA<br>AGAAAAATATAATTTTGTTAAAAACCGACATACAATGAGA<br>CTTGTGTCGCCGTCTCATCGTGTTTTTCTTTTCCCTTCAN<br>GACTATTTTATAAATCTTGCGTTAGACGTTAACGCTCCAA<br>TTGATTTGTGCGAGAAATTTTTACATAAACCCTAGAAAAC<br>TCTCTTATTGTTCGCGTTTAATTCTTCAGGTACGATTTGC<br>CATCCTCTCTCTCTCTCTTTTCAAAAGGTATCTGCTTTT<br>TCATCGTCT<u>ACGATCGAGAGAAACTTCGAGACTTT</u>GCCTC<br>[C/T]TTTGTTGGGATTGAAATTGGTTAAAGGTT<u>TAATTG<br>TTTTT</u>GGTGTTGATTGTTTTATCGGCGCGCAGATATGCCG<br>GTGATGAATCCGTCGTCGTTGTGTATTGGTGCACAACCAT<br>TGGTCTTCCTCCCTCCTCGCTTTAATCATCGACCAGCTAA<br>TGGTATCTCTCTACTTTTGGGATATACACTTCTTCTTGAT<br>TTGCTTCTTGCCACTAATTTATGATTGCTCATGAAAAAAC<br>TGATGTTCTTGTAGCATTAGATCCTTGCTTAATCAGATTT<br>CTCAAGCTTTTGATTTCGTATTCTATTGAATGTTTCAAG<br>TGTTAATAAAAGCTCTTCTTCTTTTGTTCTGTGGTAGGA<br>CAATTTCGTGGGCGTTACTACCCTACAAGAGTTTCTATGC<br>AATTC |
| 94 | N21144-001-Q001<br>ATGTAAAGAACGTAAACAGATTAATAGTATATAAAGTAA<br>TTTGTATATAGAATATTTATTCCACTCAAGGCGCGGTTAA<br>GTAGTTATTATTCAGCATGTATATATTTGTTAACTATTAT<br>TAAAATGCAAAAAATGTATA<u>AGTAGAATACTTAATGTTT<br>ATAATCACGAGATATAATTGTTTTCATAAATTCATCCCCA</u><br>[A/C]ATGATGCGGTTATCACCTAGT<u>GTGATATTATACA<br>TGGCCACC</u>AGGTTGATCCGATCCAACAGAGTCCATCGGTC<br>CTCTTCAAAAAGAACAAAGCTTTATTGTACAACAGATAAA<br>ACGTAGCATATCGTGCTGCTTAGACTTATCTTCTCCATAT |

TABLE 7-continued

Markers of QTLs significantly associated with shatter resistance (P ≤ 0.01)

| SEQ ID NO: | Marker Name and Sequence |
|---|---|
| | GGTTGCAGAGCTCTCGGATACAGTCGTTGTTTTCTAGCAGGCTGA |
| 95 | N07534-1-Q1<br>ACGACCGAGGAAAGCACCTGCGGAA<u>TAGAGACCAAGGCCC<br>AACAGC</u>AGGAAGGAATCGATACTCTATAGATCCAC[A/C]<br>ACTAGCAACCTAGAATTTGAAGCAGAGATGGAGCGGA<u>GAA<br>CCGCACCACACAAATAAG</u>CCACCACCAAAATACCT |
| 96 | N22993-001-Q001<br>TACTAGCACTTGTTTGCAAGATCGGTGGACTCACACTTTG<br>ATGATGGAGTTTCTGTGTGTTGTATAGAGTCAATGACCTA<br>CATGAGTAACCCTGTTTGTAGTCCTTATTATCACGTAATG<br>GAAGGTTCCCCTTCTGGTGATCAAGGTCGATGTTATTGTG<br>CTAACAANGAAGGCGAGAATACTTGGATTTTAAAATAAAT<br>TTGAATAGTTAAACAATTTTGTATTTATCTTTGAAGTTTA<br>CATGTGTTTATAAAGAAATCTANGCCAACATAAGCCAAAG<br>CCCTCATCATATTTTCACTATGAAAGCAATACCCTTTTGT<br>TTAATCCTACTCTAACTTGTTTTACTACTTAAGGATGTAA<br><u>A</u>CTGAGTAATTATAGTATTGTGCCAACCC<u>TTTTGTTAGAC</u><br>[C/G]GACTTCTTTGTCCTTCTCCN<u>TTGCACAAGTCAAA</u><br><u>CAAAAGCCCC</u>TAGGCCCATCCTCATGGCCTTAGCTCGTGA<br>TCTTTTTATCGGCCCANGTGTAAAAAGAAATAGATCTTTA<br>ACTTGGATGATAGACTCATTTTTGCCTGTGAAAAGCCCAT<br>TTNGACCATCTTCTTTAAAGGTGGTTCTAGGTTCTCTTT<br>GACTTGTCCATGATGTTCATCGCTTCCAATTAGTCAAAAA<br>TGTCCTTACATAGTCATTTCCAGCTCCGAGTCATCTTTCT<br>CATTCTTATTCTCATTTCACGACCATAACGCATAGTCGAC<br>CTCATNTCAGGTTGATCGAAGATCGAATCGTCCATTNCCA<br>GCTAGTCCATGTTCANGTGTCGCATTTCCCGCCTACTCAT<br>GGTTG |
| 97 | N09963-001-Q001<br>TTGGTGATTGAATAATAAGAAAAGAACTTCTTATTGATAT<br>TGTGATTCTATAGATAACACTCCCATCATCCAGCAGGACG<br>CAACTCAGCAGTTCAATCCTGAAGGAACTCCCACACCAAC<br>CCCAACTGGCAGTGTTACCAACG<u>GCATCAACCATCAATCT<br>GAATGGTATG</u>TTATCACAAATACGTGATAATTTGCAAAAA<br>[G/T]TTCTCTGTTTTGAT<u>TTAACATACAGGTCAGTAGGA<br>TGCC</u>GTGGCACACGAAGCTTTTTAACGCTTCAAGCAACTC<br>AATCAGGTCTAGACCAACCAGTAGGCGCAAATCAATTCCT<br>TAAGTGCATATCACCAAAGACTCCACGCCAGCCCTAATCA<br>CCAAAGACTCCACGCCAGCCCTAGGTGGACGTACAAACTC<br>AATAG |
| 98 | N11542-001-Q001<br>TGAGATTTGGGCCATGACTCGAAGATAAAGCTTTATGACG<br>ATCATCACACTACAAGGAGAGATCTGGAAACTTCTCCAAA<br>GGCCAGCATCGATCGACACCGCCAACCCAACATCGATCGA<br>CCCCGCCCACCTGATACCGATCGACATCCACCTAATGATA<br>TCGATCGACACCCATCGTTGGACGACCTGCCAAGGTCACA<br>GTTGGGCTGAAAGTAGTTGAGGAGGAGACGCACACGTCTA<br>CGACCTCACACCTTGCTGTCCCCGAACATCN<u>GA</u>GACCACC<br>TATATGCACAGAAGAAGCTGCTGGGTTTCACAAAAGAGTC<br>AAGAGGATACATGACCATGTGAAGTTTGT<u>GGTCCCATGCA<br>TTGTATTT</u>GAAGTTGAATCTCCTATTCCAACAAATAGAAG<br>[C/T]GTGCATCTAGGTTCTTA<u>CATTGGGAAATTTGATGA<br>TCATATGTATGC</u>ACTAGTTTTTGAGAGAGGGTTGAGACAT<br>ATAAGTGACGTCGACACAGCCCCAACAGAAACAACATCGA<br>TCGACACTACCACTTCATCGTCGATCGACATTGGACGTGT<br>ATCAGATCAGAAGGAGTTTGAAGTGTGTCGNNNNNNNNNNN<br>NNNNNNNNNNNNNNNNNNNNNNNNNNNNNNNNNNNNNNNN<br>NNNNNNNNNNNNNNNNNNNNNNNNNNNNNNNNNNNNNNNN<br>NNNNNNNNNNCGGCGAAGAGTAGTAACTGTTAGCACCATC<br>AGAGATTTAAGATTTGTGCACCCGGGAAAAGCCATATTCA<br>ATTAGTCTTCTTTATCCGGAGATGCTAGGTCTGCTGGTAA<br>AAAAA |
| 99 | N14681-001-Q001<br>TTTAATACGAAAAAGAAAATTCAGTTTTTAACAAATAACG<br>ACCATAAAAATACTAAAATAAAAACAAGAAACATTATTT<br>AACATTTCACTTTTTGTCTATACTTTATTAAATTTGNAAC<br>ATGTTCTCATACATAGAGGAAAAACAAATTNCAAATACA<br>TAGTTAATTTTAACGTGCAAACATGTCATTATTTTAANTA |
| | TTTCACTCTGCACAGGGCGCGGATTATTATTATGAATGAG<br>ATAAGTATGTTTGATACGATCATTCATATTTATGCAATTA<br>GTATATTTTTGGTATACGGTTTATATTATATGCATTCTTT<br>GTTTGGGATATGAATATTAAATAACTAGCCAGAAAACATT<br><u>ATCATAATGTCATGACTGCCTGGTTT</u>TAATTAACATGATA<br>[A/C]ACATATGGGATGTGTAAGACCAATCNAATT<u>AACGA<br>TGTGTGTAGTTGGTTTTT</u>AAGANTGGTNTGGTCCAATGGT<br>TTTAATCTTTTATTGAATTAGAAATCTAATTTGATTGGAT<br>TTTAATAATAAGTAAAGACTATCTGATTAGTAATTAAAA<br>ATTAATAATTTTAATACGATTAAAATTAGTTTAATTATTT<br>ATAATTCAGTTAAAATACATAAAAGATTTGTATTAGTTAT<br>ATTTATATTTTATATTATATAAATTTTAAATGTAAAAT<br>TAAATTAGATTAAAATTGTTTCCTCAATTGATTTCAAGTA<br>TTTTTTATGTTTACACAGTCTTATCAACTATCAAAGCTCG<br>TTTCGTTGTAAGATGANTTTGGCAAAGNAAGGTGTCGTTA<br>GTTAC |
| 100 | N11636-001-Q001<br>AATTAATTTGTATAGTTACATTTTTTAGTTGTATTACAA<br>ATCTCATAACGTAAAATCATTAATGAATCTTTAGTTAAAT<br>TATTAGACTAGACTCGCTAGATAGATTTCCACAAACCCTA<br>TTACATTTTCTTTATAATAACAGTGAAAATTACATGAAAA<br>TGTGAAAGGCTACTGCACATTTTCTTTATGTGGTATAAAA<br>TATTAAATTATAAATTTGGTATATATGCCGAAACTATTTA<br>TGTTGGTTCATATACGGTTACATATAAATACTTTTTATCG<br>GTATATTCCACTAAACACTAAAATATTGAAGATATTAAAT<br>ATTTAAGATATCATTGTCCGTTTAGAATTTCAAAGTTAAG<br>CGT<u>GTTCGACCTGGAATATCGGAAGA</u>ATAGATGACTTATC<br>[A/G]GAAAGT<u>GATTCGCGATATCGTGCAAGT</u>GAATCNAA<br>AACACGGAGAAAAGTCACGTGGTNAACGGGTGGATAGTTT<br>GGTAGGCGGTCGGGCCGTTACATCTACCACGTCCTGTAAC<br>ACAGGTGCAGCCTCTGTGAANAAAAATGCTGGTTCCATAC<br>GGACAGGTGCAGCCAGTGGTATGGACGGGCAGGGCCGGGT<br>CTGAATAGAAGTNCATCGAGCATGTGTTTGGAGCCTGACG<br>AATATATAGATATTTTGGGGCCAATTATTTTTCATACAGA<br>ACATGCAGCTCTATTGGCTTGGGGTCCAACGAAAATATAG<br>ATGGACCTCTGTTCGCTTCTCCGCAATCGCATCTTATATT<br>ATTATCACTATTTTTTAGAAACAAGGGTCAAAAATATTT<br>TTTAG |
| 101 | N13732-001-Q001<br>CTTGACTATTTTTATGTGAATTTAAGAAAAAAAATAAAAG<br>TAAAAAATTATTATTTTTATTGTTTTCAGTTATTGTCTA<br>ATGAGTGATAACTCCTAACTTCTTAAGAAGTCTTAAATAA<br>GAATAATTATGAAAGCTAGTTATTTTTTTGTCAACCGGA<br>TGTTTATTAAACAAGGTCTATAATATAAAACAGGTCCAAG<br>AAGATGGGCAGTAAAACTATTACAAAAAGNTCCAACTGAA<br>AGGCAAATAAAACATAAATGAAAGGCCTANCATATAAAGC<br>CCAATATACAAAGCATCTTGAGGCCTTAAGCCCACGAGAG<br>AAAGATCTGTTGGGGAAGAGGGTCACACGACGCCATATAC<br>GATCACCCAAC<u>GATCAATGTACACGCGTCAAGAC</u>GCGGTT<br>[C/T]CAACATTCTTCCTCCGGAGCCAGC<u>GAAGAGGCGTG<br>ATGGAACTCC</u>GACGTCGACCAAGCCTATTAGATCGTTGAA<br>CGAAAACATCAATCGNCTGTAATCGATCAGAAATCCAATT<br>TTCTTGCATGCGCAAAACTCCATCTTTGATGATTTATATA<br>AGCTTGAAAATGGNGACAACCCTAACCGAGGGGAGGAAAG<br>AGACATTGAACCTTCAGATCAAGAGGTACGGTGCTATAGA<br>AGCCACCACTTCCCGTAAACCTAAAGCCGGCGAAGATGGT<br>GATAAGGGATCCACCGCTTCCAGAGGCAGAAACCCGACCA<br>TTGGGAGACTGAGTCCAAAGAGATCCGACAAACAAAACTC<br>GACGCTCTCTCN<u>CTGAAAGATAGGA</u>NAGAGATAAGAGAGA<br>GCAGA |
| 102 | N11255-001-Q001<br>AGATCTCTTGTCCGAAGCAGAGCATTTTTTCGCTGAAATA<br>TGCTCTAAGAAGTTTTTTCGCCCTGATGTTCCAACGTATC<br>GAACGATGATGGATGCATATGTGAAGAAGGGTAGAGTCAG<br>CGATGCTGTCAAAACTGTGAACCAAACTTTGGATGCCTCT<br>CTAACCTATATTGCTAAGAAGGTCTTAGTAATGTAACTTC<br>CGTTTATGTGCATCACTATGCAATTCAGATTCTTAGTTGC<br>ATACCAACTGTTGTTTATCCACAAATCTGGTGGAACTTNA<br>TTAGTAGTGCTTAATCTTGATTGTTTATCTTTTAAGTCTA<br>GTTAACAAGATCGTTAATACTCCTTTCTTAAAGCTAG<u>CAA<br>TAAAACAAAACAATAATCTGACGCACATATTTGAACTTA</u> |

TABLE 7-continued

Markers of QTLs significantly associated with shatter resistance (P ≤ 0.01)

| SEQ ID NO: | Marker Name and Sequence |
|---|---|
|  | [C/T]CAAACTATGAAGCGGGCTTCCAGACTTTT<u>AATTGG</u><br><u>GGCTATCAATCTGAGACTC</u>GTCATAATCTGCCCA<br>CCATTAATTGGGCGTATAATGGCTCTTGAGGGAGAGTATA<br>GTTTATATTATNAGCAGTCACAATGAACCTTCTGCATATT<br>GAGTCAAGCTATAATGTGGTTTCATGTGTTCATAACGCAG<br>AAGGAGCTCGAAATGGGTCTATCCGAAAGCAACTGTTGTA<br>CCTAACTTCCATCTCCCAGTGCGCAGCTTTGGGNTTAATG<br>TAGAATATTTTGTTTTCAACGACGCGCGTGTTTGGTTCTA<br>CTATATGAAACGGCGCACATGTTTGATTATGTTGATAGAA<br>ACGGCATGGCTTTGCCGTCTTCGAACGGTCACGGCATGGC<br>CATGT |
| 103 | N15511-001-Q001<br>TCTCTGGTAAAATCACATATATACTATAAATAAATAGTAA<br>TCTCTCCGCTTCATAATATATGATGTGTTAGAAGANNNNN<br>NNNNNNNNNNNNNNNNNNNNNNNNNNNNNNNNNNNNNN<br>NNNNNNNNNNNNNNNNNNNNNNNNNNNNNNNNNNNNNN<br>NNNNNNNNNNNNNNATCTATTCTTCCCTCCTTAGTCATG<br>AAAATAAACTTTAGAAATGTTAGTTTATAGTATATAAATA<br>AACTTTTGTTATCGTATATTAAGATTGTTAGTGACTATAG<br>TAAATGTTATTCTGTAAAGATTTAGTGTTTATTAGAAGAA<br>ATGAGACCCACCTGTGTTTTTAG<u>AGCCTGGTGCGTATGTA</u><br><u>TCATAAAAT</u>ATTGTTGGCACGAAACAACTCTAAAACTGTG<br>[A/G]TGGTTTAAACTAATAAACTAGAG<u>ATGGTTATTAAT</u><br><u>CATTACTCTATGCATCTTTCGATG</u>TATATTAAGATGGTTN<br>ANGTCCAAANAAAGAGGATTCTACGTAAAACGTTGAGTGT<br>TGCGTAAAGNATGTAACCTACAATACAGCATTAAAATATG<br>CATTCACTAGTGTTGGGGTGTAATAATATGATTAACACGT<br>ATTATAAGGAAAAGAAATTAAAAATCTTGCCCCNAGATN<br>TAGGTTATTCGATAACAAAAAGAGTATGCGTTAACTCTGA<br>ACATTGGTGTATCAGGAAATCCTTAGACGAAATTGGTGTT<br>AGTTTAGGATTTTATGTAATTTTCTCAATGCTTATAAGGC<br>CTCTAAGAATGCGAGAAGGAGATAATATAAATATTACATT<br>CGTAT |
| 104 | N10536-001-Q001<br>NNNNNNNNNNNNNNNNNNNNNNNNNNNNNNNNNNNNNN<br>NNNNNNNNNNNNNNNNCTTGTCATGTTATGATCAAGCAT<br>CTGGTCAAGAGAAGCGACCATATGAATGTACTTCTTTCTT<br>GGNAAACACTTTAACAAGCTTTTGGCTCTT<br>CTATCATCTGTCCCAAAGAAGCCGATTTGGAGGAGATTTC<br>GGATAGCTTCCCGGAAAAGGTATCGATTGTATCTTCATAT<br>TTCATCTTGA[G/T]TCTATTG<u>AATTCTGTCTTTAGGGTT</u><br><u>TGAAGCGTAG</u>CCTATTTTACCCTCTCAGCTCCTACATGTC<br>TTGTNTTTATAGCATCCCATATCGCTTTTGTTGTGTCTAA<br>GTCGCCAACTTGCATAATCAAACCCTCCGGTATAGACTGG<br>AACAAAAGCACAGTGGCCATACTGTTTTTCTTCTCGTCTT<br>TGGTNCCAGGGTCTATTGCTTCCCAAACTTCGCTAACCTT<br>GAGTGCAATCTTCATTCTCA |
| 105 | N09862-001-Q001<br>CTTTAAGTAGTTGTACTATGACTTCTTAATAGTAGATAAA<br>AATAGGACCCTAAACTAATAGATTAGATATATTGTTATTT<br>ATAATAATGATAAAAAGATAAAACATTATTCGAAATTTA<br>GAGATTTAAATGAATCATGGAAATGCAAGACCTATTTGG<br><u>ACCAGGATCGATTTGAGATGAAAGCT</u>AAGGATATAGCTAG<br>[A/G]CAATTCAATTGTTGAATGTT<u>ACCTTTTTTGTTCAA</u><br><u>AAGTTGACTGTTG</u>AACAATCTATTGATTATTCAAGCCAAG<br>ATTAATACAAAACAAATCATCTTTGGCATCAACAGCTTCT<br>AGGATTTTAGATGCTTACATATTTTGTGCAAGGACCGCCA<br>GTGTTTTTGATAACAGTGTTGAAACACAAGTGGTCATCAA<br>AAACG |
| 106 | N23033-001-Q001<br>CTTTAAAGAATTCAATTTAAGGAATATCTGAAGAAGAAA<br>TCAAAATGACTATGGATACTAGAAAGAATTAGAGAAGCAA<br>AGTGAGAAAATTCAAAATTGTAACGCTTTATGGTCTGAAA<br>ATATAAAATTTGACGCTGAAATGATCAAAGTTGACTCAAA<br>AGGTNNATAAAAGTCTTGAAAATTATGATAAATAAATAGTAGAA<br>AGAATAGTTATGATTGATGTGAAATAATGTCTACAAATAA<br>AAGAGAATATGATGTTTTCGGTGAATGAATGTCATATTTA<br>TATATTTTTACCTTGATGAGGCTGAACTGAATTCGAGTCAT<br>GAAATTATTATTCTCATTGGATTTGGAGTTT<u>CGGTAAACC</u><br><u>AGTACAAAATATCCAAATG</u>TTTTTCATCTATCACTTGTGC |
| 107 | N06039-1-Q1<br>GTCTTCAGGACTTCAAAATCACTC<u>CCCAGTACCCAATGCT</u><br><u>CATCT</u>CTTTTGCCAAGAAATGAAGAGAAACTGCCT[G/T]<br>TGTTTTGTTTGTCTTTTAAGATGATGACAGTGAGA<u>CTTGG</u><br><u>TGTGTATAACC</u>GACGGTTTAATGTTTCGGTTCGAT |
| 108 | N10016-001-Q001<br>GAGGAATTATATACGCGAAAGCAATAAGCAACCAGACAGA<br>CACCTTACCACCACAGGGTGTATTTATTCATTTAATCTAT<br>TTTTTTAGTTAAACCTTGCAAGGTTTAACGAAACTTCTGG<br>TGTCTATCTGGCTTGACCGGCAGGGGCCAAGCGGTTATT<br>TCCATG<u>CTTTGCCTAAGAGATTGCTTCATG</u>TGCAGCTAAT<br>[C/T]TTCGTTCAACCATAG<u>TCAGATGACTACAAGCACAA</u><br><u>GCAC</u>AGTGCGGAAGAGTGTGACGCCGCTGTCCCTGCAAAA<br>GAATTGCAATCAAACTATAATTATGTTAAGATAGTATTGG<br>TTATAGAGGAAATTAAATAAAAAGTACCAAAAAGGGTATG<br>AGACAAGTCCTTGGAGATCGGTTTCAGCATGAAAAAACAT<br>GGGTA |
| 109 | N22743-001-Q001<br>TTCTTTCCCTCTAGTACTTGTCTCCTGAACCTAATCGTAT<br>GTATCTTTGACCAGGTGAAAGGTGTTAAGAGTGGTATGGT<br>TTAGTAAGGTCTACTAAACCAAACCGAGACTCGGGTTGTT<br>AAGGTTGTTGAGATAAGTACAATGTATTAGAAGATAAAA<br>TGCACGGTAGATGTAGATAAAGTAGAATCTCCTTGTAAAG<br>ATACGAAGGTCGAGTATATGTATCCAACGTGATCAATGAG<br>ATCCACACACAGTTTACTAAATACAGTTTCTCTCTGAGTT<br>TACATGGTATCAAAGCGGGCCCAACATTTCCATATTCATC<br>TCCTCAGGAAACATCTTGATCATGATCAGAAGAAAAGCTT<br>CGGGGAGGATTTGTTATACCATTGCATCAAGCAATNAGCC<br>[A/T]TTGAGAAGTGTGCTACC<u>GTTGTCCAACGACCCTCT</u><br><u>GTTT</u>CCTCGGAGATCAGTAAAGGAAATGCTTTTGCAGTCT<br>TAAAATGTTAATGGCAATCAAAGTTGCCTCCTCATGAAAA<br>TATTATACGAGGCCTAAGTAGGTCCATATCTTTCAGTTAA<br>CAAGTTTGAAGTTCACCCTTTTGCATATGGAGTCTGAATG<br>ATCAACACCAAAATTTCATGTGGTTTCAGATTTATAGCGT<br>AATCCTTGATAAACAATATCAACAAGAATCATTTTTAAGC<br>AAGTTTTCAAAACTCTGCTTCCTGCTTTCTGATCTAATCA<br>GTGCTAAGATCATCACTTGTTAAGTAGTTCAACATCAAGC<br>TTTTCTGAAAATGAGAAACATCTCACATGTTCTGCCTGCT<br>TTCAG |
| 110 | N22953-001-Q001<br>TGTATCGATCGACGGCACTGGATGTGCATCGATCGATTGC<br>GTCTTCTTCGTATCGACCTCTAATGGTCAGCTCGGATGAA<br>ATCTATTTAAGCTCCTAAATGCTCCATAGTCATCACTTT<br>ACTCCAAAATACTCCTGAACCTGAAAACATACCTAATATG<br>ATAGAATATATAATATATAGATAGTAAAACACTTATATAC<br>CATGGATGAAAATGGGTCAAATCCATGGTATATCAAGCAT<br>CCCAAATACTTCGTCAAATCCAACCTCANTGGTATTGGGG<br>AATACACTCAGTGCTGCTTTGTATGTCNTGTATTTCAATG<br>TAATACATCTAAGAATTTTCTTC<u>ACTAGTTTCTTTCCTTG</u><br><u>TACTT</u>CCTTCCAGGATAAGAGCCTATTCTGACAAGGAAC<br>[A/T]AAGTTTAGAGTGTGGGAACCGAAATNCGC<u>ACTGTC</u><br><u>AATTTCCGATAAAAATAGG</u>AAAGCTAAGTAATCCTAACTT<br>TCCCAGAGGTCCCGGATATCTGCTAAACCACACGCCAAGC<br>GATCAAACAATGAGAACAAGAACANAATAAAAAATAGTAGAA<br>AACGAAAAGAGAGCAGAGAAGATCTTATTCCGAATTGANT<br>GAACGAGCATTACAACAGATAAAGCCTCGGCGGTTAGAGA<br>TGTCGGNGAGTTCCTAGTTCTAACCTTGTGAGACTTGATT<br>AACCTAGTTGAGTCGCAGCTCGAAAACAGAAAACGGAAAT<br>ATGCCTAAGTTTCCCTAAGTGCTATGCTTTGTTCTNAATA |

TABLE 7-continued

Markers of QTLs significantly associated with shatter resistance (P ≤ 0.01)

| SEQ ID NO: | Marker Name and Sequence |
|---|---|
|  | AAAAATGCNTCCCTTCAGCATCTGCAACCTCGACATCCTT ATATA |
| 111 | N09987-001-Q001<br>TTTATTGATGAAATTCCCAAGAATCATTAAGCTTTTGTTA ATGTACTTCCCTTCCGTCAAGCGTACTCCACCAGCACCAG TTTTGGCAATTCTTTCAGATCCAGCCAAATCAACCAGATT CTAGAATCCATTAAAAGAAGGCACATAAG<u>AGAATAAACAG CTTTCTACACCCGTAGA</u>GAAAATGATCACTCACCAAGACT [A/G]AGACACGGATAGGATCCATAGAATTGTTTCCTTTC CCCCTGC<u>TCTCAATCACCTTATCCCACC</u>AGAGATATTGTA TCAGAACAAATACTTCAAAAAAAAAAACAGTTGAAGGTTT CATTCATAGGTTTCGAAAACCCCACCATTCTGAAGATGGT GTGGGACGTGCTACTGTGAACGTTCATGTTTGTCTCACCA AAGTG |
| 112 | N10092-001-Q001<br>GGCTCCCAACCACTCACCCGAGACCAGCAAACATCAATCA AGAAAAATCTCTACCCAAATATCACGGTGGATTCTCTTAT CGATTCAACATCCCACACGTGGAATTCCAAGGTTATTCGG TCATTGGTGGAACCAGAGGACGCAAAGATCATAGAAAGCA TACCT<u>GGCATCGTCTGGTTGATCAAGA</u>TGCATGACATTTT [A/G]CCATTAATGGAAAATATACGATA<u>AAAATCGGGTTAT CAAGTGGAATGGG</u>TATACCCAGATAGGGAGAAATCGTTGC CGGTATTTGGACCTACAATAAACCTTTTAAAAGCATACTC TTGGAAAATACGTTGTCCACCAAAAATAAAACATTTTTA TGGCAGTTAGTGTCGGGCTGTATATCAGTAAAGAAAAATT TACGG |
| 113 | N10096-001-Q001<br>GACTATTTTAAGAGCTTCTAAAGGATGTCACATGGGCAGA AATATTCTCACCAATCATTTTGCCATGTCGTTACGGGCTG GGTTTCAAACTAATTTAAATAATTCCAGCCCAACCTTGCC CCATTCCGATCCAACCTAGTTAATAAAGTTACATTTTATT TCTT<u>CATAGACCTCCACATCACCAAGAAAA</u>AGGGAGACAC [A/G]TGTCATTAAAAAATATTCACCAAAA<u>ACTTTATTGTG TTTGGGTTTTTGCTTTAC</u>ACTTACGCATGGGCTTCAGACC CATCGTAAAATTAAGTTTCCTTGCCTTCTCGCCTAAGGAC AGGATTATCGGGGGTTTAGTGAGGTTTTAGTGGGTTTTT TAAGAGGAGGAGGGACCTACAGGAAGGAAAAACCGGTGGCA GAAAG |
| 114 | N22728-001-Q001<br>GTATGATCAAGGGTCGACTAAATAAAAATGTTGGCTTGAA GAGCTTCAGCTGGGATCCGGTTAACGTTCGGAATGATCCT ATAGGATCGGAGTTTGTTCTGTTTCCAATTGAGTTGTTGA TTGTTTTACGAAGCTGACGAGCTCGAGTAAAACATGATGT GTGCGTTATGACCTTCGAATCTTCGTCGCAATCAATTAAT ATCAGTTTCTCTTGAGTTCCATAACTTCAACTTCAATGTT TTTATTCTCTGCTTCTTATTCTTTCATTTAAATAATCGAG ACACGTTACTTAACCAAAAGTATGGCTCGTTATACTGCAC TACTGACAAATTGCTAAGAGTAAAGCACACAAAGGTTTCT TAGGAAGATTATTATTAGACTCTCATGAGAATTAGGTCTG [C/G]CATTCGGGTTTCTGCCNAGTCGGG<u>TCTTTCGTG TCCTAAACATTT</u>GAACCTGACTAGGTATTTAAAAATTTTG GTTCGGGTTCGGATCATTCTTGTGGGTCCGAATCGGTTCT AATTCATATACCCGTAAAACCCTAATTTTCGGGTAATTTT GAGTTCCGTTCGGTTTGGGTATTTAGGACCCGAAGTAAAG TATCCGAACTGGATTTGAAAACCCGAAAATACCTTAAAAC CAACAAAAAAATCCGGAAAATACCCAATTTTTTTACCA TTAATCTAACACAAAGATCTAAAAATACCAAATTTTTTAT TCAAATACACGAATTATATTTCTGAAAATTTTAAATTTTN ACCTGAAACCTGAAACTATACACGAAAACCTGAACCCAAA ACTNA |
| 115 | N22747-001-Q001<br>NNNNNNNNNNNNNNNNNNNNNNNNNNNNNNNNNNNNNNN NNNNNNNNNNNNNNNNNNNNNNNNNNNNNNNNNNNGCAG AAAAAAGAAACCGTTTCTAAATACACCTCTCTCTCTCTC TCTCCGGATTTGCTTACTTGAAGTTTTTGAATCGCGTCTC GTTGAAGTTATGGATGATTTTGCAGTCCCCCTTGAAAAGC AATTTTGACCAAATATAGTATAATATATAATTCCTATTTT ACAATATTCTAATATACACCGTTATTTTTTTTCAGTAAA TTGATGAAGAAGGATTATCCATATTGCATTTCAAGATTTT |
|  | TAGATATCCTTAAGACTCATAAAAATCTAACATAAATTAC ATCTATTCCCAGAGAATACGTTTTTTCG<u>AAATCAATTCCT [C/G]GTCTCTGAACTAATCGGGTTTTATATNGTGTTACC TCATTCTTTTCACTAGGGG</u>CATTGCTGGACAGAGTTCTTG TTTCATCTTAATATTTGCTAANGTTATTGTAGTTGTGAAT TTTGCGTTTTGAGTTGTTTTTCAAGTTTTTTTTATTGTTA TGGGATTAGAGTTGTGATGATGATCTGTGTATGCTTTGTT CTCCCACTTATGAAGGACTAAACTGTGTTAGNNNNNNNNNN NNNNNNNNNNNNNNNNNNNNNNNNNNNNNNNNNNNNNNN NNNNNNNNNNNNNNNNNNNNNNNNNNNNNNNNNNNNNNN NNNNNNNNNAAAAGTTTCTTCATTTTTTCTTTTCTTGAT GATTTCTGGGAAGAGGAAGAGGTAGTTGAACTTGTTGGGC TTGAT |
| 116 | N22840-001-Q001<br>TGNATATGTTGATGTGGTCGTGTTCAAGTTTCGAAGTTTC GAACTCATTATCTAGATTGTTGTTTCTGGACATATTTTTT TTTGTAACCGATTGNTGTGTTGATAATGAGTAATCAATCT ACCTACATTACATTTTNAAAGGATGATAACATGATCATTG ATCACTAACATACGTGTGTAGTTTGATGATTGGTTATGTC ATGTTACATTGAGTNTTTACTTGTTACAAATGTTCTCGAA TGGTGTACAAAAACGAGCTTCGACTCATCAATATGAAAAC TNTATCCAAGGATTATGTTCATGAAATAACAGATCCGAAC TAACTCTAATCGTGATCAATGTATTAAAATCGGATAATGC TTACCC<u>ACCTCCATTCATCATTCCCAATCCC</u>AACACCAAG [A/T]TCTTAC<u>TTTCAGTGTGATTCTTAGCCGAGC</u>AGGCT CTCGGCTAATAAAATGCACAAATCACTAATAAAATCTGTA AACTAATAAAATTCCAAAATTGAAAAAAAATTTAACCTAT CCAAAATTGCATTATTTATAATACAACACTAAATTTAAAA GTTATTAATTGTATTGAAGATTTATCATTTTAATCAAAGT TATTAATCTACACACTCACCTCAAATATTTTTTAAATACACAT AAACGTAAAATTCAATTAAAAGTATTTAATGTTTTAGAAA CTTTTCTTGTAAACAACACATTTTGTTTTCTATTGTGATC GCAATACTAAGTGAAAATTGTAGGTGCCACATTTTAAAA GAAACCTTGTTTTTGGCCGAGGAATAAACATCATAAGTAT TAAAA |
| 117 | N23027-001-Q001<br>TTCCATGTTTGGCTCATAAGCCACCTATGTGTGTTTAGTG GTTTTCCATTTTGTATTTTCAACAGGTAGAACAAACTTAA CCAAGTATAATCTATTCTACTTTAGTTTTACTTTTACAAC AAGTCCATTTACTCATTCAGTCAGTGACGGTCCTAAAAAA ATTTGGGCTGGACGCAAATTATAAATTGTGTGACCTATAA ATTTATAATAAAACAAAAATATGCTAATTATATCCCACAA AAGGTTCGAACCTCTCCATACTTTTTNAAAAAATATACG ATTAACCAACAACGCTACTAAAGGTTTGGTGCAAAACACG GCCAAAATATTACATACTGTAAACCGGGCNGGAAGCACAT GNTTCTGCCGCTTTGCCCATGGCCGATATTGCATTCAGT [A/T]GTTGAATAATAAATTTAAAATCCAAGTGTATTCTT AACGTTGGTAGTATAATGCTTTATCTTTTCTCTCTTTTAAA TNTTATTGAAAATGAGTTATTTTAAAAGTACTTCTAAGTG TCTTACAAATTGTTTAGGTTTTTCTGGAGCAAGGTGACG AGTATGGTGGCTTCCATATGTGAACACAATATTCTTTTGN ATTTTGTTCTCTTTTTGATGTTATCACTTCTTGGTAATAG ATTAACCGGCTTCATCTCNTTTCTGTTTTGCTATGCCATC ATTTCTTTTCTGGACTGTTTGTATATAGTCCCAACCGATC CCTGCACAACGAAATCATGAATTTTCTTTTCTGAAAATC AACTTGTTGGATCTGTAAAATGATGATAAGAATAGACAAA GGAAA |
| 118 | N22777-001-Q001<br>NNNNNNNNNNNNNNNNNNNNNNNNNNNNNNNNNNNNNNN NNNNNNNNNNNNNNNNNNNNCAAGTTTCTAGTTTCTT GTTTAATTCTGAAAAGGGATAAAGATTTCTTGTCGACTGA GAAAGAAGAGTCGAAGACAACGNTAGAGTTCTGTTTCTTT TTTTTCTTAATGTTTTTACTTTGTATTTCATTATAGTTT AAAGTAAAATGTTAATTTTATTAACTGTATTTAAAGAAA ATGACAAAACTGGATTATTATTATTATTTATACTAAAGGA ACAATGATTTTGGTTTTGGTTAGTTCTAAGATGATAAGAGTNTA GTTGTTTTGTTACTTTTTACCAAATTTCCTTTTATAATAC ATTGAACAACAGTTTGCCATTTCCTTACTATTTTACTTTC [C/G]CTTTTACGGAAAGGTCGNGTCAACATAAACATCCA AGAAATTGATAGGTAATGGATGCCTTTTNTAATGAACTGG ACCNCTCCTTGAGGCATTTGTCTACTTTTGACAAAATATT |

TABLE 7-continued

Markers of QTLs significantly associated with shatter resistance (P ≤ 0.01)

| SEQ ID NO: | Marker Name and Sequence |
|---|---|
|  | CACATGGTTTTGTTTATGGTTTTAAGAGCATGATTAACCC TAGAATTCCATTAGAGTCTCTTAATGATTTTTTAAGTATT AAATGTTAGTTAAGAACCTTAGTTAAGAGACATCTAGTTT TTGTTGCTCCAATGCTATTCTTTTTAATTAAGGGTTCTTA AAACACAACTAGATTTTNNNNNNNNNNNNNNNNNNNNNN NNNNNNNNNNNNNNNNNNNNNNNNNNNNNNNNNNNNNNNN NNNNNNNNNNNNNNNNNNNNNNNNNNNNNNNNNNNNAAG TGGGG |
| 119 | N09636-001-Q001<br>ATTTGACACTCTAACTAAAACAACTAAGTTTTTTTGTCAT TTGTTGGATTAATAATCAAAATAGAAATGAGAGTTACACC AAGCCGGCAAAGGTACACAACATTTACAGAGCCATAAGCT AACATTTATATATGATTTAAA<u>AGCGAAAAGATTACACTTT GTTTCTTT</u>GAAATATTTCAACGATCTTGTTTTTGGTTTTTC [G/T]GGTTTATG<u>ATTTGGCAATGAAACTAGAGTATACTA AGGCT</u>GAAAAGATTGTGTATGATACTTTAGCTTTTAATT TTCAAGATCTTGTTTTCGTTTTCGAGTTTATGAATTTCA TCCCAATTAAATTTTGGATTTTTGGGTTTTTTGAATTTCG GCCTCATGAAAATACTATAAAATTTTTATTCAAATTTAGT TCGGG |
| 120 | N09879-001-Q001<br>TCCATGGTATATTTTGATTTAGGATTGATTTATCTTAGAA TATAGAATTTGGTATGGTCGATTTTTGCAGATATAAGATA TTTATAGTAAAGATCAGTCGCAAACCGGATATGTTTTTAT TATTGGTGGAACCACAATTAATAGAGTTCCCAAAAATAAA <u>CTCCAGTTGCAACTTCTTCAAATCATAC</u>GGAAACAATAGC [A/G]TTTCATTAAACATGTATAGAATGT<u>ATATGGCTTTG GTCTATGGGTCATC</u>ACATATAAGAAGCAAGCAAAATAGTT ACAAAAAGAGCCAACAAAATTGTTTGAAGATAATTGGCT TGTGACGTTCAACTCAAAGAAAGTTATGTTAAGAATGATA GAACAAAGCATATTCCTAAATATGAGATATCAAGAAAAAT AAGAA |
| 121 | N10123-001-Q001<br>TCTTGAGAAGTGCGTGTATGCGCTTGGTATGCTAAACCCT CCACAGATTCAGGAACACCTAACATTTCTTGCTTCGAATT CAAATCGCACCCTGTAACAGAATCCTAGTGGAGATACAAG ACATCAGTCATATACGTTACTAATCTACCAATGGAAGGAT TCAGT<u>CAAATGACTAACCTGCGCAAGTGGCGGCCCGGTTG</u> [A/G]<u>TTCGACACAGATATCTACTTTCCCACTCCCTTGAC TAG</u>TAACAGAGAACACAGTAGTCGAACACGAACCATTATC AACAGAGAAGTGAATAATCTTCTTCCGCATTGTTGCTT TCACGAAAATCCTGCTCTTTCTCATCGAGATACTGCAATG TAGGAGAGGCAACAAGCGGAGTTTCCAATATCGAATCGCT ATCTA |
| 122 | N10316-001-Q001<br>TTTCGGAAGACATCTCTTCGTAAAGGTGAATTCAAAGCTA TGATTAGTCTCAGTGGTCAACAATCAAAGTTTTATACAAG TAAACATTTGTTTCAATATACCCAACCTTTACACCATTT CTTTGTACCAAAACTATCAATAATGATCGGGAAAAATACA CTT<u>ACCAGGAAGGAGGTCAAGATCTTAAATTATTTGTTAA</u> [C/T]<u>GGAGCATTAGTATAAATGATAAATATAAAAAGAGA ACATAATGTAGAAAGTCGATGCTAG</u>AGCATGATTATCGGT TCAGGTGGGTTTTAGTAGTAATTAGAAATTAAAAAAAAA AAAAACGGGAAAATAACTTAAGCGACGTATTCTAATTAAG GCACAAGAACCCTCTCTTGTAAGACACGCGTCACGTGGGA GGAGA |
| 123 | N10507-001-Q001<br>ATGATCGACCGCTTATTTTGTGCATAACTTAGAGAGAGTT TTTTTAATGAAATTATTTGATGATATTTCNCAATGGGGGT ACACACATATTTATAAGCAAGGATAAGGCGCTGACATAAG CGCTTACCTCAGCGATTACATCATCGCTTACATCACGCTT ACATAAGCTTATAGCGATTACATCAT<u>CGCTTACATCATTA TTCATTTTTTAGACACACTT</u>ATTTTATATGATATTTTACA TAATTAAACA[C/T]CGATAATGGTGTGCTTAATGATCCA TCTCGAANTCGAN<u>GATGTGCTTGTCGCAACTACC</u>GTAGTG ATCTTCTGGACATATGTAGTCTTCCTCTGGATATTCATTT TGGGTNTTTTTTTTGACTTCAATGTTGAACATTTTTCTG ATTTCATCAATATTCATTGAGTCACTGGGAGCTGCGAGTC ATGGAAGTATTCTGGTGGGCATTCTTGGGACAGAGATTCG TGCNTTACTATCTTCTGANA |
| 124 | N09834-001-Q001<br>TGTCCGTGTAATAAAAAACGGGTTTTAAGAACAATAAACG GCCAAGCCCATTTAAGACCTCTTTTTTTGAAAATACAAGA ATTATTAGTTTGATGTTCTAGGTTAAACAAATATAATCAT CTCAAATCGTCAGCCCTAGAAACTGACAAGACCCTTT<u>TGC TCCACTGTCTCTTCAGAAACGGAGAGACGGAGGTGGAATC</u> [C/T]<u>AGCGAATCC</u>GAGTCCAGGTTTCAGTTAAGGATTTG AGATTAGGTTATGATTACTGCACCAAGCTTATTCTGTTAA AATTTTAAGCTTTGTGGATTTGAGCTTATTTCTCTCTA GAAATAGGTGATTACTGATCTGGCAGAGGTGTCTTCCAAA ACTAGGGCAGACAACGAGGTATCATCAGAACCACTGTCTC CGATT |
| 125 | N22934-001-Q001<br>GGAAAAAGCCTCTGTAACTCCTCGAGAACATCGCCTGAGA GCGTTTTACATTTTTTCCTTTTGGTATTTTAGTCAAAAG AAAATTAACCAAATCTTTTAAATATTTTTAAAATCCTNN NNNNNNNNNNNNNNNNNNNNNNNNNNNNNNNNNNNNNNNN NNNNNNNNNNNNNNNNNNNNNNNNNNNNNNNNNNNNNNNN NNNNNNNNNNNNNNNNNNNTATTGAAAACGTGTTTTAACAG ATATGGCAATGTTTCTCATTTTAATTTCCAGAGTTTCTTG CTCCTCGTTCTCTCTCTTATTTCTCTCTGTATCGAGCTTT GCTTCAGGTTTGGGTGAAGGAGAAGGTTGTAGAGAGNGAT GACCAGAGTTGATCCAGGAATGTAAGAGACACTGAGCTCA [A/T]AGGCCAGAAACGGAGTCTTCT<u>GATGTGTCCAAGAT CACCGTGCC</u>TGTTGAACCTCCTAAAGCTATCTGCAAGACA CAACAGAGAAAGAGTTGGAGTTTAGACGGTCTAGAATGGT TGGAAGTAGTTCAACANAAGCCTGCTAATGATTCTATTAC CTTGCGTGGCATCATTCCTAGAAGCTCCATCATCAAAGGC AAGTGCTCCTGTTAGACGCAACAAGTGAAGTGAATTAGCT CACAAGCAACAGCCTATAGCTACAATAATGTTTCATGACA GAATCAAGAAACCAAACCACAGTTACCTCATCTCTATCAT AGTTGTCTCNCNCTATGGGGATCGAACAGTACATCTCCAGT GGCAAGTTCAANACATATACACGTAAACGACCAGAATCAG CCGAT |
| 126 | N22700-001-Q001<br>TCAAAATTAATATGACCTAGTTGTGAATGTTATCTTCTTG ACTCATTCTCAGTTGATGCTTGGAGACATGTGGTTGGCTT TATAACCATATGAACTTTATACAATCTGTTTCGTGATCTT CNAGCTTTGACAGCACAATTTTCTGTACTGATCTTGCATCA TTAATTCTTCCCCTCTCATCCTGATGTGACACCCTGCTTT TGTAGCTTACCCCAAGCTTATAATATTACTCTTTAGGTTA GNAATGAAATACACGTCAGTCATCTTTCTCGAGTCNCTGT TCATGTCGGTGAAGTATATTGTGCCTTTTCTTTTAATGTC TCTANGAGAANCGTCAC<u>CAAACCGTACTTTCCCTATGATG GT</u>ACTATCAATCNGTGAGAAGTACCTTCGATCTCCTGTCA [A/T]ATGATT<u>ACTAGCTCCATTGTCGAGATACC</u>ATATGT TCTCCCCTCTCAAGATTTGTCTCATATTTCTCAAGGAGAAC ATTCTTTTCGTTCAAAATACTTCTTCATACATCATAAGTT CATCAGCTTCTTGCGATCTCAGTGTTTCGGTCTCTTGAGCC TCCTGTAACTTAAGCTTGANCTCCGGACATTGAGCCACGA AGTGTCCAATTTTATCACACTGATAGCAAGTTATTCTCAT TGCNTTTCGTCCANCATTAAAACGTCTTNGACCTCTTCCT CTGTAATAGTTTGATCGACCGCCTCTGCCTCGACCTCTGT ATGTATCTCCATTGTAATCTAGGTTTGCTTGTTCTTGATA AGATCAGTTTGGTTGATCTTGAGAAGAACGATTTTGGTTG ACTTG |
| 127 | N22725-001-Q001<br>ATCGTTATTTCCTTTTTTTCATTATGACGTATTATNATAT CCTTTTCCTTATTNGGTTTGTCCAATCGAAGGGATATATA AACAGAGCTTTGTTTCTTGTTTGAAGATACGTTTGATTTA ATAGAAAGAGCTTTGCTTTATACCTTGTTTAGATTNGATT AAATTCATCAAAACAGAAGTTGGTCTCAAGAAGCTATCGA AAGAAANTTTTTGATGATCCAAGAACAGTCTCGAAGAAC CCTAAATTCTTATATCGAGCGTTCACCCATTCGTACGCTG CGCCATTATGAGATGCTTACTCTTATCCATGCCGGTCAGT CTAGTACGTCTCGTTTTCATCAATTTCTCTGTTCCAGAGT ACCT<u>GCATTGGCAGGTTTTAAATCTCAG</u>ATTTGTGCATAA [A/T]GACACCCNAGTAAGAAACACAAAGATTGTTTGTGC |

TABLE 7-continued

Markers of QTLs significantly associated with shatter resistance (P ≤ 0.01)

| SEQ ID NO: | Marker Name and Sequence |
|---|---|
|  | GTTATGTTNATCT<u>ACAGTAACACTTCCATTGGTTTTGAGC</u> AAGGCCAAGTNATACTTATCAGTTNTCTCTTCAGAACTGG AAAAATCTTTGTCGCTACTATTAGACACCAGAATGGGACC GATACGTAAGTTAGATGACTCAGAGAAAACCACTTAGACG ACAAGTTGCATATAAGAAAGCCGAATAATAAGAATGCATT TTCAAGGGATGCTACTAAAAATGAATGGAGGTCAATTTTGG GAGTTGAATGCTTTCTAAAGCAAAACAAGACTTATAATA TTCTACAGCTTTGCATACCATTTCAGATATAGAACAGCCA AATTCAGTCAGGTCGTACAAAGCGATCAAACCAATAGAAT TCAAA |
| 128 | N22881-001-Q001<br>ATTCGTCCAAGACTTCAGGCAAGATATTTAAATTAGTCTC ACACCTTTAGTTGCTTCAGTTTTCCTGTCCATGATTTCTT GTCCATGATTTTCTGTCCATGATCAATCAGGTTCTTCATG TTTTTAGTCTTGCTCTTTATTCTCTTCACGTCAACAGAAA CCAGCTACTTAGGCAGTTAATCAATGTATTGAACATGNAG AGATCATTTCGAATCCNTACAGCTTCCATCTTTTTCCACA GAGAGATGACGACNTCGTACTTCTTCAGTTTGANAATGAC GTTCAACAGTTTATTGAGATCGATGATTGAAGGGAAGGGG CGAGATTTGGCCATGTCGTTGAACAAATCGATAGCGTCAT CTAGTTT<u>GATATCACGACGACGGTTTCTGCTCAGTCTCTC</u> [A/T]<u>C</u>GGAGATC<u>AATCACGCTGGAGAAAGCTC</u>GTACCCA GCAACCNAGAGAAGGGAGCGCTTTTGCGTTTACTATTT TCGAAAAGATTCCGATGAAGCAATGTCTTCGCCGTCATCG CAATNGATCTCTGCATCGTTTTGCGATNGTCTCTCTGATT CCGAATCCTAAAACGAGACATGTTTATGGAGAGAGAGAGA GAGAGANNNNNNNNNNNNNNNNNNNNNNNNNNNNNNNNNN NNNNNNNNNNNNNNNNNNNNNNNNNNNNNNNNNNNNNNNN NNNNNNNNNNNNNNNNNNNNNNNNNNATTCTCAGGGGTAA ACTCTTTGCCGCTTGGAATAATTAAACTGTTCCTTGCGTT GCAAGTAATCATGTTATGAAAGTTAATTCACGCAAATCCA AAGTC |
| 129 | N23032-001-Q001<br>TGTGCAGGATAGAACGTTATATGGGGAGTTGGAATACTTT CATTTGTTTGAAGCTGCCAATGAAGGAGGATGGTTGGGAC ACTACTGTTTATAGATGNTCTGCTTTCTTTCTACAACGGA ATACCCCTGCGTTACTGCCTTGACAATGAGTCTGACCTCA AGACCTATCCCGACATTAGCCAAGCTGCGTCATGTAACAG CAGACGTATCTTTGTTTCGGTAAAGGGATGTCTATCGTTA ATTATTATCTTATATATAATACTATTGGTAATTCTATTTG GCTATGAATGTTTTCGTTGCTTTATCAACCACAAAACGAA CCTGAATTCTGCAAATGAATAAATATCTTATATAAGTATT <u>TGAAATCCTACACGATTTTAAGCATGTCAATTTTTAAGCC</u> [A/T]<u>G</u>GGGTGTATCGCGAGAC<u>GGAATGAGGGTGATGCGC</u> CTGTTCTCAAACGAGAAGGAGTATGTGTTAGCCAAGAAGA AGGTGACACGCATCCATTGGGACAAGCTCGCAACAGATCA CATCACTGATAGTTCTGTCCAACAGAATGGGACTTTGC AACGACGTGATGTACGAATATCTGTCTGTTTATTCAGNCA CACCAGTTTGTAAGGTGTTGGGTGTGGTTCGGCAAATAAG GCAAGCTTGGCCACAGTCTTCNGAGATAACATTGGTGC AGCTACCGAAATCGATCACGAAACGACAAACCTTTCCCCG GATGGTCAAGAGGAGCGCGATTCGTCAATCACCTGAGGA GTCAGCATATTTCGACGAATAACCAATAGTTGTCCAATAT CTCCA |
| 130 | N22786-001-Q001<br>ATCGAACCATCGACGAAACCGAGCTTCTTCCTTGCTTTAA GCGCCATACGCAAGTTAGTAGCCCATTCATTGTAGTTAGG TCCTTTGAGNAATNGCTGGAAATCACCGAGCCTGGATTG TCANTAGAAGATAAGCTCATACAGAATATCCTCCTTCGTT GGACTTCAACACTGAGATTGTGAAGAAGCAGATTTCGTAGC CGAAGCGTTAGTCAAATCGTCACCATCATTACTACCCATA TTGGCAAACTTAGAGAAGAACAAAAGAGGATGAAAAACCC CAAGAACAAAGAAATTTTTTGTGTTTAATGCTCTGATAC CATGTCAAGAAACCAGAGAAAGCATAGA<u>AGAGTTTCTTGT</u> <u>ATTCATCTAGGTCAACG</u>ACCATAAGTATATATACATGCTA [C/G]GTTACCTAATACCGTAAGATATGTACATCGAGATA AAAGGAATATTAACATAATAGATTACANC<u>CAAATATATGG</u> <u>CAAGATATGCATGTATATCCT</u>CAATATTGCCGCTCTTCCA GCTGAAGTATAGCTGCATTGACCTCATCAATAGTCGTGTA ACGGGTCATATTGGTCTCAAATTGGCAAATAGATCCTGCG TTGAGACAGAAGTTGACACATTAATTTGTTACAGATATGC GGAACCNAAGTGAAAACTGAATAAACAAATGTTTTAAGAA CTAACCTGCAAGTCAAATTCAATATCCAGAGGAAGATGAC CCTTGCTCAGTATGTATCTCTGGAAATGTATCAAAAAATT GATCAATCCTTTTCTTTGAAGAACCTTATATGATGTTGAA GTTAA |
| 131 | N23014-001-Q001<br>ACTCAAGAAGTATCTTCTCAGCGCAGGTTTTCATANCTCT CTTGCTGATACGTCTCTATTCATTCTCCGCCATGAAGGAC AGTATGTCTACTTCTGGTTTATGTGGACGATATTCTCGT TACTGGTACTGATAGCACTCTGGTTCAACGAGGNATCNAA CGTCTGGCTGCAAAGATCTCTATCAAGGATATGGGTCATC TCAGTTATTTTCTCGGAATCGAGGTGATACGAACGAAACA AGGACTCCATCTAATGCAGCGGANATATGTTACAGACTTN CTGCAGAAGACAAATCATTCATGCAAAACCGGTTGCTA CGCCTCTCCCTTCCT<u>CACCAAAGCTAACTCTGCACTCTGG</u> TCCTCTNTTGTATGATCCTTNGACTATCGACGTGTAGTA [C/G]GCAGTCTACAAT<u>ACCTTGCCTTAACTCGTCCTGAT</u> GTTTCATATGATGTTAACCGACTCTCGCAGTTTATGCACA AGCCATCGGTGGACCATTGGAATGCAGTCAAGNGTATGCT ATGCTACCTTGCCGGAACTCTAAGCCATGGGATCTTCCTT CGCAAACAATCATCTCCTCAGCTCCATGCATTATCTGACG CCGACTTGGCCGGNGACACAGATGATTATGGGGGTGATTG GTTGGGCTGTAACTGTAGTAAATTTACTTTAGAATTTAGT CTGTAGGATTTTTGATTTACCTTTAAGGGATGTAGCTTTA AAATTTCCTACACCTAAAAAGATGGGGCTTTAGAAAATAA GATATTTACAACCATTTTTTGTTTGTTTTGTTGNNNNNN NNNNN |
| 132 | N10471-001-Q001<br>CAAGTTGATATGGATCTTGTTATTTCATCCATAAAGGGTC AATTGATAACTATTATTGGACTACCAAAGCAAGTGTATCC TTCTCATGCCTCGCTAACAAACTACTAAAGCTCAAGGACA TAGTCTTTCCTCTCATTAAGCAAAGGCTGGAAAATGGCCT CTCAGCTAGGTTCTGGTTCAATAATTGGA<u>GACATCTTTTGGG</u> <u>ACCTTAGC</u>ATCTTNCCTTGACTCCTCTACTACTAGGCTAG GGATTCTTCT[C/T]ATTGAGTTGCTTCTATTT<u>GTAGGAA</u> <u>TGGAACTTGGCTAATCCC</u>ACCTTCAAGACAGACAACTAG CTTCAAATTCAGGCTTTTTGACCACTATCAACTTTTTTN ACCACTATCAACTTCTTGCAAAACTAGGGGTGGGCGTTCG GTTCTTCGGTTCAGTTCGGGTCGGTTCTTTCGGTTCTCGG TTCTCGGTTCTTTCGGTTCCTGNNNNNNNNNNNNNNNNN NNNNNNNNNNNNNNNNNNNNN |
| 133 | N11419-001-Q001<br>ACTTCCGTGTGGCAATAAGCGCTCGGAAAAAGTTTGCTTT TANCAACGGATCTATACCAAAACCTGCACGACTCACCCGA CCTTGAAGATTGGATAGCTAACAATCACCTACTGGTGAAT TGGATCAAATAACAATCGAACCAAAACTTCGATCGAATA TCTCTCACAAAGAAATCACTCGAGACCTCTGGGACCACAT CAAAAAGCGATTTNCTCTTAAAAGTGGAGCTCGTTACCAA CAACTACGAGCTTCCCTGGCAACTTGTCGACATGTGGGAT CTACGGTCGAAGACTACTTTGGACGCTTGACAAGAATCTG GGATTCTATGGCTAAATGTATGTCAACCAAGACATGTGAC TGCGGAAAGTGTGAA<u>TGCAACTTGGTCAGCACTCATGAAA</u> [C/T]AGAGCGCGAGATC<u>ATTCGTGCTCATGATTTCCTAT</u> <u>ATGGT</u>GTTCAATTTCAATTAATTTAGAGGACACTTCCAAA ATTCTGAGCTTCCCCGGAGTTTGGCTGTGATCCCTACATC TGGAAACCAAAGCATACTTAGTCTCAACAATCTAACACAN AATGAAAAATGTATTAAAGTAAATGCACTTTGTAAGAAAC AGGGGACTGTTATATATTTAAGTGAATGGGTGCAATATTA TATATGAACCATTGCAATTGTTTATATGAACAATTGCAAC TATATAATGAAACCTTGCAACCATTAATGATTGCAACATT TGNTAATTAACCATATTGATAATTGCAACCCTTGGTGATT AACCATTGCAACTTTTGGTTTAACCATTGCAACTATTGGT TGCAA |
| 134 | N22724-001-Q001<br>TGAATTTGTTCACCAGAAATATATTAAACNAGATTACTGA ACCAGGTTTACCAGGTCAAACCATATTGAACCGTGACCC AAAAATTATCCGGTTCAGCTNCCGGTCCGGTTTTAAAAAC ACTGTCCAAAACTGATTAATAACGAGTTTCAGATTGTTAT TAATAACGATATCTAATGTTTGCCAGCAGAGGACTTCTGT ATATCACGGTGATCTTTATTTATTTTAAGAATATTTTCA |

TABLE 7-continued

Markers of QTLs significantly associated with shatter resistance (P ≤ 0.01)

| SEQ ID NO: | Marker Name and Sequence |
|---|---|
| | TGCGACTGCTTACTTAGTTATATAAAATATCGAAGTCGAA GACCCATATAAGATTTTTTTTTGGCCAACAATAACTAATC TGCTACGAAATACTCAC<u>CGATTCGGAATGATCATATAAGA TCAAACTTC</u>AAAGTATGGTGATATGTTAATGTCTGCACTA [A/T]ATCTATCCGCTTATTTTATTAACGNTTTAACCTAA AATATTTAAA<u>AACTATAAAGTCTTGCATCCGTAATTACCC</u> AGCTAAATTCATGAAATTGAATTTGATTAAAGTCTTTAAT TATTTGAATAGTCTTAAAAGATGGTACATAGCTGATGTAA AAAAGCGCGTTCTTGAAGAGAACAGGAAGTCGTACAAGCT TTTAGTCAAAAAAAAAAAGTCGTACAAGCTTAATACTTCA ATGTTTTTTTATTCNCGAGACGGTTGATTATGTCTGCTTA AAACTATATATATACTCACTGCTGGTCAAGACAAGAACAA CAACGAAACAATGACAAAGATTCTTCTAAGCTTGCTCCAT ATACTTTTATGTGTGTCTTTACATGGTGTGGCAGAGGCTA GTTTC |
| 135 | N12785-001-Q001<br>GACTNGTAAAAGCCTGCCCGGAGAATGTTTTTGACATTGA AGACATGGGCAATGGTAAAAGTAAAATCCTTCCTTTAAAC AATAGGAGAGGATGCNNNNNNNNNNNNNNNNNNNNNNNNN NNNNNNNNNNNNNNNNNNNNNNNNNNNNNNNNNNNNNNNN NNNNNNNNNNNNNNNNNNNNNNNNNNNNNNNNNNNGAATG TCTGTAACAAGCTTGGGTTTATTGATGGAACGGTGATTCA ACCGGCGTCTACTTACCGTGANTATGGTGCTTGGTCTCGT TGCAATGATATGGTNGCAATATGGCTGATGAACTCTGTAT CCAAGAANATTGGTCAGAGCTTGTTATTCATCAATA<u>CCGC TGAAGGTATATCGAAGAATCT</u>CTTGGCTCGTTTCAAACCG [A/G]ATGATGCACCGANGGNTTTTGATATTAAA<u>CAAAAG CTGAGTAAGACTGAACAAGG</u>TTCAATGGATGTATCAACAT ATTATACTGAACTTGTGACTTTGTGGGAAGAGCACCGACC CGCGACGAGTCGGTCGCTACCTAGCGACCGACCAAACCT TTCGTTCGGTCGATACGTAGCGACCGATCCAGCGCGGACC AGGTCGCTACGTAGCGACCGAACTATCTCGGACATCGATC AACGGGTACGACCCAAATCTGTGCATTCTCGTTTATTCAT CAATGCTATCTCCCATGTACCGCATCCATATCATTTCTCA GATCATTCCGATCAAAGTTACCGTTGAACTTTACGATAA AAACCGCGAGAACTTGTTTTTGTCGAAAAGAAAATCGTAA CAAAC |
| 136 | N09910-001-Q001<br>TTACTATTTTGGTTTATTGATACTTTGATTCAAAATTTTA GTAGTTCGGTTTAATTTTTTTTAATTAGAATTGAAATAA TTAGGGTTTTGTGCCTTTAGTTAACAATCTATCGACAGCC CCTCTGGAAGGAAAAAAGCAACCAAAGAAGTGTTTGATAT <u>AACTTATTTTTATTCGTACTTTTTGTTTTTAACTTGAAC</u> [A/T]ATATGGACGATATGATT<u>TTAAGTCTTCCCATGGAT TGATGGAGG</u>AGATTCTCTCAAGGGTTCCGGTGAAATCTAT TGGAGCAGTACGATCAACTTGTAGAAACTGGAACGCTTTA TCTAAAGATCAAAGTTTTGTCAATAAGCATATTGACAAAG CAGCAGCATCATCAAGAGAAACGGAGGTTCATGTGATCAC GGTGA |
| 137 | N21146-001-Q001<br>TTTGGTGGTTGTTTGGAATTGAATCGTGTGTAATAAATGG TTAGGTTAGTGTTAGATTATGGTTGGTGTTAGTAATAAAT AGAAGTGATGAATGAGTTAGATAAAGGTCTAGTATATTTG TTGGGTTATGAATTCACT<u>CGATGGTTGTTAGATATATGTC TAGTCCTAAGT</u>ATATTTATTACATATATTCAACGTTCAC [A/C]ATCTCTACTCGGTTAAACAC<u>AAAAGTCTTCCTCTT GTTCTTCTCTTCC</u>ATCAAAACACCTTCGTTCATCTTCTTC TTCTCTTTTTCTCATATTTCACACACTAGAAATATGGATTA TAATCCATAAACGAGTGGGAAAATTTTGTTGCTCTTTTT CAAAGTCAACAACAAAGTGTCTTCGGTTCATCACAAGTTC CTTTT |
| 138 | N17618-001-Q001<br>AAAGTTTCACCGCCANACGAATGAGTTTGAATGGCCAGGA GCCCCGATACGGGATGGCCCCTAGTACCAGCCAGATTCGA CCAATCACGAGCCAGAGTGGTGCCGGTTAAGCGGGACA GGGTCGTCCCAGGAAGGATAAGCGCGCCCGGCATAGAG TGGGTCCCTGAGCCACCTGTATAGGAGCCACCCAAGAAGA AAAGGGGGCGTCCGCGCAAGGCCGCTGCCCCCAAGGAAGA CGCTTCAAAAAAGAGTTTGGAATCGTGTGGGAGTGATGTC ACGGTCCCAAAGTCTTGCTCAGTGGGTGAATACTTGGAGG |
| | GGTTCCTGAATACGACTAAGGGGTGCGCACCCAAGCT<u>CGT ATAAGTGTGGTGCCAATTGTTTAAGGCAGGGATCCGCAAG</u> [A/G]ACATTCGGGGGAGCC<u>GGAGAGCGCCAAGGATCCC</u> CTGGAGTTCTTGCTGATGAAAAGGATAGTCGGGCAAACAA TAACCGCAGGGGAGTGGATCGTGGGGTTGGGCGAAGAGGA TCGAAGATNCGCACTTCGTCAGACAGAGGAGAACCCAGAG CCGAGAATNCGACCTAGGACCTACACCTCGCGATGCNG GGATGGTTGGTTTAGGACCGGAGGCCGACCGTGTATTTCC ACATCCTTGTGGCTAGTTGAGGCTTTATGATCACTTCGTA GGAGTAGGACGTGAGCTTTCTATTGGATTTATTCTAACT ATTGAGTGGTTGCTTTGGTGTTGTTTCTCCATTTCTAAAG GCATTTTGTGTNTGTACATATGCCTTGANCTTTTCAAATT ATTGT |
| 139 | N09776-001-Q001<br>AAACCGGAGTTCCAAACATAGACAACAGAAGCTCGGCTCC AGCGTAAAATCCAAACTACAGAGGCCATGGGAGATCTTCT TACAGAGGCAGAGGAGGCTACACCTCCAGAGGAAGAGGCT TTATTCAACATCAGTCACAACCAACATCCTCTGGAGA<u>GCG TCTTGTTTGCCAAATCTGT</u>GGTCGCACTGGTTATACAGCT [A/C]TGAAGTGCTA<u>CAACAGATTCAACAACAACTACCAA AGTAATGAAGCTTATACGGTTGTTCGTGTTGCTGATGAAC ACGGAAGAGAATGGTACCCTGATTCTGGTTCCTCAGTTCA TGTCACCTCGTCGACTCAGAATCTACAAACCTCCCACCCC TACGAAGCTCATGATGCTGTCATGGTGGGAGATGGAGCTT TCCTT |
| 140 | N19296-001-Q001<br>ACGAACTTATCATACAAGATGATTCGGAAATAGTATCACA CTCACGAGGGTCATGGAAATCAAAAATATAATGGTCGAGA TCCGAGAACTACATATAATTAACGTGGATGAGTTGCTCAA AAGCATATGTACAGCTTG<u>CAACGAACAAAATAAAAGATGG AGATGTAA</u>CATTTTATAGAGATAAAATAAAAGGCTGAATC [A/C]GTTTTTCAGAAA<u>TTGGAAGGGCTTAAAAGAAAGTA CAGA</u>CAGATCGAGACTGGTTTCTTTATGTGCGGCAGATCC AAACACTGTGGTCGCCATTAAACAATCTTTGTAATAATCG CAAGTTCACAACATTTACACATAAATTTCCACATTATCAA AGAATTAATTAGATGTTGAGAAAAGAAAATCAAAGTACTA ATTAA |
| 141 | N05205-1-Q1<br>TACCTCAAACTTGAAGAATCCATCAAGAACATCAAGAAGG AG<u>TGGTTTGCTACCTCCGTTTCT</u>GTTGAGCTCATA[G/T] CCACTGTTGCTACTAAAGTCGNGTAACTCAGACTTCC<u>ATG AATCTTTTGCCTTTTGCA</u>TAGGTTTCCAGAATGTT |
| 142 | N10406-001-Q001<br>CACATTAATGGAGTCATGCCGGAAGCCTTGATTTCACTCC ACAGCCAAATACTTCCTCTTCTCCAACATGAAATCATGTT TCTTGATGAACTAGAATGCAATATCGACATCTACTGGAGG GTGTGTTTGCATATGTTGATCCTGTTCGTACAGTGTTCAN TGGCAGAACAACAATTCTTTGTGGCGATGTTGTTGGACG <u>GCTCATGTTGGATCGTGGGGTTTTGATAGCTTTTCTTTCN</u> ACGAAAAAGG[C/G]AAAACAAAAT<u>ATTTGTGGCGACCAT GGGT</u>TTATGAATTCTTCATGGTTCTTCTTCAAACATTCTC AGTTGAGTGGCAGTTCATACTTTTCTATTGGAGAGTTGGA GACGTTGCTCAAGAGTTGGATTGTTATAGTAATGGTGCTT GCGAATCTAACAACGTGTTGTGCATTCTGGTTTCGAATAT TGTACCAAAACCTGTTTGGAAGTGCATGTCTTTGAGTACA GCTGGCAAGAAGGTCGTGAT |
| 143 | N22941-001-Q001<br>TCTGTGAGCTCTTCATTGTCAACNACCCAGACATAGGTGT CCTCAATTGTTGATAGAGAGGGTAGTTGCAGATAAGTCAA ATATATAAGGTTCCTCAGCCGCCTCTGATCGAGCACCA GGGAATATCCAACCAGCTCTGTTGCAAGCGTCAGAGACTG TTGCTGTGTTTGGGATTGAAGTTCCCTTGGGGCCAAGAT CCCCAAACCTGTGAAAGAGCGGTCCTAGCGGTGTCCAACA ATCATGCCAAGAGTTATGACNCTGCCATTTCCCAGATTT CCATGTTGAGGAGGAAGCGTTGTTTTCATCAACAGCCCAT AGATTTTCACCCTTCAGTCTGTATTCNCGAGTCCAN<u>TCTG CCCAAAGTGAATCAGTATTCAAAAATAGTTTCCATAAAAG</u> [C/G]TTCAGGCAGA<u>GAGTTCTGTGACATATCCTCTTGCA</u> CAAATTTAGGCCCTGTGCAAGCTAATTCCTTACGTTTGGA |

TABLE 7-continued

Markers of QTLs significantly associated with shatter resistance (P ≤ 0.01)

| SEQ ID NO: | Marker Name and Sequence |
|---|---|
| | AGAAGCAAGAAAGTGGTTCAGCCCAGGATTGAAATGCCTA ANTAATAAAAATTTGAGAAGAGAGACTTCACTATGACATA TCCTCTTGTGTAAACAGGGGGGATTGCAAGAGCAGATTTG AAGCGAGAAAGATTTGTTGCTAGGAATAGCCAAGAATCTG CTTCAGAAAACAATAGATTGAACAAAATCATTTTGAATCT GAGATCAAATGAAATTTAAAGAAAAAACATAAGTCACATT AGACTCAACTGAAGCTCTCTAGGCAGGTATATATAGTCAT GAAATATATTACTTTTTGTCTNTTAATATATAGNCTTCGA AAGTG |
| 144 | N22875-001-Q001 TAAACACAACAAAGATCACAAAAATATGCTGAAAAACAGA ATATAATTAAATCACATCGTAAACTGGTAGCAAATATAAA TATGCAATTTCAAAACCATTTGCTATAAATTAGAAATGTA AATAAAGCTTAAATAAACATAACAATATCAGATAAAGCAT TTTCTAATTAGAGTACTAAAATCCATTTAATCAAATTACT TTCACAGGGAGATAATTAGATAAGAAGATAACAAACTTGT GACCAAAACTAGACGCGAGACAAGATTTCTTAGAATCTAC TGTCAATACCATTCAATAGCGATCCTACAGCTGCAAATAC AAATCGTCTAATTAACTAGAACAAAACAAAAGAAGGTTTG AATCGAGCATTAATGACTTACCATCCTTCAATCAAACCAG [C/G]GTTACTACTCTGCTTCTGATGTTCCTGAGGCTGTG GGTATTGCGGTGCATACGGAGGTGGATAGCCTTGCTGAGG ATATCCCTGCGGTGGTGGATAACATTGTTGAGGATAGGGT TGTTGTTGTGCCGGAGGATTTTCTGGAGGCGTNGGAGAAG CGTCCTAGGGTTAGGGTGTCCATCTGACGGATTACCTGT TCAACCATAATATGAAATAAACTAATCAGAAGAAAAAACG ATTAGAAGTTAGGATGGAACATTTAAATTGACCCCCTCCC CCCCCCCCCCAAAAGAGTTATTATATGATATATAGATGT CATGACACCTAATTATCAAAAAATTAATTTATATAAGCC TAAAAATGTTTATGATCTATGCAACAATACTTATATCTG TCTTG |
| 145 | N13286-001-Q001 TTAAAATTAANAATTAACCTTTCTTTTATGGAAAAACTGTC CTGGTCGAACTTGGGAGACTTTTTGAGTTCGCCTAGAATG GGTGAGAGGTAAAGAACATGATTGGTTTGTAACGAATGAA AATAATTGATTTNGAAAGAAAAAAACATAGTTATATATGA TCTTTGGGAATTTTAAATGTTAGACTGTGGCCTACCAATA TGTAGTATTAAAGTTTAATTGGTTAAAGATGCTTTAGGTA CATTATGCATCCTCTGTATAAAATGTTTATCAGTTGCACC TAAGCCGGACGTATGTGGATTTTCGTTCACATTAACAAGT AAANTGAATAAGCCATTACTTGTATCGACCGTGTTAAGCT GTAAATCGATAACAAACTAAAACGTTTTTTTTATTATGAA [A/G]GTCATGCAAGTGAGATACATTTCTTCACTACTAGT TACTTATTTTAAGAGACCAGTTTCAAACATTCCACCAAGC TTTTCCATTAGTNATATATATTGTCCAAAAACACTAACAA TCACCCACCAAATAATTTTATTTTCATCTAAATCTAC CTTTACTATATACATTCATGGACGAATTAGTTTGGAGTTA AAATCCTAATCGTACCACCACATTTTCCCAAGCATAAATA AACAACGAACGAAGTTGATGCTACTTTGTGGTAAACCAGT GGTAGAGTTGATTTGAATTAAAGCGAAAATTCCATCGATT CTGTATTNAAGTTTTGGTAAAACGAAATTACTGTCAATCA GACGAAGATGGGATTATACTTTAGACCTCGTTAAAAATCT GTACC |
| 146 | N04503-1-Q1 TTTTTTTTTTTTTTTTTTTTTTTTTGAAAATTAATT ATTCGTGACCATTTTATTTTGAAACAAAAGAACGACAGAG ACATAACGAGATTACATTTATTACAAGCGAAAATACTACT AGTCTACTACTACAAAACATCTATAACAACAATATACAT GGGAATAACAAAATGGTAGTAAAAAGAATAATAAGCCGAG CCACCAAGTAAACCAAGCTTCT[C/G]TCGCTTACACAAG AATCTCAACACGCCATCTGAACATTTCCTCCCTCGTCACA GGTAGGTTCAACGTCACAAGCCCAACCTCCGNGTCGTAGT TGAACTCAGTCTCGGTNCNATCAACACCGCATCTNAGNGG ACGCTGAGAAGAGTAAGCCCCAAAACGACCACAACCTCTA ACACCTAGAGATATCAGAGCTGTTGGAGAACGGNTTTCGC TGACCACTGAAGAAGAAGAGACTCAGGTTTCTGTCTGT CACGGTATTGATCTCCATGGACTGGATAGCTCCACTTGAG TTGAACATGTCCAGGAGTCCAATAGGTGCGAATGAGATGC TTGCAGTGATTTCCTTTAGAGGAGAGATGTGGAAGAGTTC ATATTCAAGAACCTTGAGAGTGAGTGGGATTGATGCACCC TTTGGTAGTCTAACCAGCTCCCCTGATTTGTAAGCGTAGA CTATTGAATCTCCACTCCAGTCTTCACCAGCCACTTCAGA GATGAGA |
| 147 | N22925-001-Q001 GCTTTTTGTGAAATGAATGGTTGGCTGGTTTTTGCAAGTC ATGCTTCTGAAGATAACCTTGCTTTCATTAGGTAGCCGCG AATCACCCCTCTTGGACATTGTGGCATATGCAGGCTATGC TTTCACTGGTCTCTTCTTGGCAAGATCATTTGGGGATATT CTTACTATGTTTTGATTCCGTGGACTTGCTTATGCACCGG AGTTCTCTTGGTGAAGACAATGAAGCGAGTTCTCTTTGCA GAAGCTAGGAGTTTATGACTCAAGCAGAAAATCATTACCTC TTGATTTTTTAGCATTAGCACAGTTTCCTCTTTTGATCTG GCTTGGTAACATTAGTGTCGATTGGCTCTTTTGAGATTCA TTAGTTGTGAATNAAAAGAACACTTATGATGTTATGAGAT [C/G]TACGATACTCCTGATGAAGTAGTACACCTCTCTCT TTTCATAACTTCTTTTTAATGTCAATTTTTTTGCATAGA CTACATTTCCAACATGATTTNAAACCAAACAAGGACATGA ACTTTGGTCATATAGTATTATTATCTATACTCCAAGCCCT CCTNTTGCATTGGTGCATTGTGATACTCCTTGGCA GATGGTTCNTTTTAAACCTGAATGAAAGACATGGAACCCT TTCNTTTAAAGATAGTATTCTTATACAAAGAAAAAGAAGA AGNAGGTCGTCGTGTTGAACCTAATTAGGATCTAATATGC TTCCCATCTTTGTAGCGTTGTTGATAAGTTACATCAAANC AAATATTGACCGACCTCAAAAACTAGTTTTAAATCATTTT CACTT |
| 148 | N05656-1-Q1 CGCTGTAACTTCTCAAGAGTTTCTCGCTAACATCACCGTT GCTTTCTCCTTTAGCCACTCTCCTAAGCTTCAAGAGAGAC TCNGCNAGAGAACCCTCCANTGCATTTCCTCCAAGTTTCA AACTTTTGCTCGGTTTTAACCTCGTTGTTCTTCGCT[G/T] TATCACCTTTCCTCTGAATCAACCCCCAAAGANTCCATCC TTTCCCCCATTTCTTTCCANNCTTCTTCAAACCAAAACCA TCCTGCTTCACCTCNCCACNACCAGCAACACAAACTACGC CTTTGGAAGCTAACTCTAAGCTCTCCGGTTTGTAGTTTTT GATGGAATACCAATTCGAATCNTCCAGTTCNCTCTCNGTA ACAAGCAACTTAGCTCCATGAAACAAACCAACACCTTCAG GTGACAACTTNGNTTTNACATCCACCAATCCATGCNTNGA TGACCGATCAAAGCTTCTTCTCCGCCGTGANTCCAAGTAN TAATCCCTCGTCTGAGCTGTCCNCCTGGCTTCTTCTCCG GCGAGGCTTNCATCTTCGGTCACGGATGANAAAGGTAN CAGCTTTGGATACGTCTTCCCGATCAAGCATCCGTCCCAT GACGCTCTANGCTCCTCGAAAGAGACTCGNCACAACCTNG GATCNACATCACATGANCGA |
| 149 | N17581-001-Q001 ATATTTAATTATTATATATATGGAGTAAAAGTATAAGAGT CTTTTTCCTCTTAATGAAGTAGATATTTTTGAAAATATTT ATTTAGTGATGATAAACATGAATAATGATACGAGCAAAGT GTTAAACATGAAAATTCCCCTTAAATATTCTCTTTGTTTT ACAAAGTATTATTATTATTTTGACATATTTTTTGTTACA CAAAGAATATCATTTTAGAATTTAAGTGTGATTTATATTT ATTTTAAACTTAATCTTTATTTCTAAATGCATTGATTTTA TAAANTATTTTACTTATCTCAAATATGATTTGTTAGATAA ATATGATTAATAAAAATATAATTTTTTGTTTGAATAACC TGAAGGTTTCCTCGTGGAATGACTCCGATTAATCCCTAAG [A/C]AGAGAAGTAACCCAAAAATAAACTATTNCTTCGTG TATTTAAATAGACCGCAAGGACCCATATCTATATAGGTGT CTAGGATAATGTAACTTAATTTCACACATAAGATATATCG AATTTGAAATGTGTTGGCATTCTAATTCATTTNTCCTCGT CACTCGACCACACAAAACATAAATATTCAAATCATATNT TTAACCGGTGTGAGAATTAAAATTGAGAAATTGCCACAAA TACCACATTCATAGTACCACTTTTNATGTNTACACTAATC ACTTTTATCCTCAATTTTAATAAAGGGTAAAAGACATTTA TACCNCTATGGTTAACTAATCTAAACTTAGGGTTTAGAGT TGAGAGANGGTAGGTTTTTGGCATCTGAAATTTAGGATT CTAAT |
| 150 | N001NVH-001-Q001* AATACGTCTACAATTTCATTAGTCTCAAGAAAAACAATAT AAAAACAAAATAAATAGCCA[A/G]ATTACATCCCAAATT CATCAAGTAGNCTTGAGTGGNGCCCCAATCCAATTATCCA GAAGC |

TABLE 7-continued

Markers of QTLs significantly associated with shatter resistance (P ≤ 0.01)

| SEQ ID NO: | Marker Name and Sequence |
|---|---|
| 151 | N22928-001-Q001<br>TGTGTTTTGCTTGTGCAAATGTGCANCTTTGAGTCTGTGT<br>GATGGACCTTTAGGGTTTGATAANGGGAAGGGAAAGATGG<br>TAGATGCAGGGGTGTTGCAGGACAGCCAAGGAGCAAGGGC<br>TTATGAAGGTTCTTCCCAACTTCATGGCAGGTTTGCGCAT<br>GGGGGAAAACTGACCATCGCAGAATGTACGGCCATGNATA<br>ATTTGTGAAATTTCATGCATCTTCAGTCAATAAATTCCCG<br>TAACTGTCATTACAACTTACTGTACTGGGACATCAGTTGG<br>CCNTCTTCTACTCGGCTTCATGAGTATAAGTATGAGTTTG<br>TTGAGATCTCGTCAGAATACGCTGAAGAGTTGCCAATAAC<br>GATTGCGTTTTTGCGTGAAGTCAAAGGCTTTGCAAGTGTC<br>[A/T]TTCATGACTGGTGGTGGTGGTAGATCAAACACGTT<br>TCAGTATGAGTTGCTTAGATTCTCTCNCAGCATCCCTTCA<br>ACTAAATTGANAGGGAAAGAAAGGAACTGTGTTCCTGTTG<br>GTTCTTATGAGCTTGATACAGCTGCGTTACCACAAATGAT<br>AGAAGATGGTGAAGAGGAAGACTGGTGATATTTGGGCAAT<br>GTACANNAACTGGAGGAATGAAATCAGGGTAGGGANCTTG<br>AAGAAGTGTGCTTACGAGGTTGTTGATGTTGGAGTGGGTG<br>GACGGGTTTGTATATTGTGCAAAGTCTCTAGCTTTTAATG<br>TTTTAGATTCAGACATTAACTTGCATCGGATCTGTCTTTT<br>GACTCTAGTTTTAGTCAATCTGGTGAAATGTTCTTTTACC<br>TCTTC |
| 152 | N08219-1-Q001<br>GACCGACGGCGTTCTTCAAGAGCTTAGGNGGACAGGTGGA<br>CATCGTCAAAGACGGGAAGCCTTACGTGATGTTCGGAGAC<br>GGGAAGCTNTGCAAGCCCATCAGCGAGGAGGATT<br>TAGCTTCGTTCATAGCGGACTGTGTCTTGGAAGAGGATAA<br>GATCAATAAGGTTTTGCCTATCGGTGGACCGGGGAAGGCC<br>TTGACGCCNTTGGAGCAAGGNGAGATTCTGTTTAGGATAC<br>TTGGGAGAGAGCCTAAGTTTCTGANAGTNCCTATTGAGAT<br>TATGGACTTTGTGATTGGGGT[G/T]CTTGATGGTGTGGC<br>GAAGGTGTTTCCTAGTGTTGCGGAGGCTGCTGAGTTTGGG<br>AAGATTGGGAGGTATTATGCTGCGGAGAGTATGTTGATTC<br>TTGATCCNGAGACTGGGGAGTATAGTGAGGAGAAGACTCC<br>GAGCTATGGGAAGGATACTCTTGAGGACTTCTTTGAGAAA<br>GTGGTTAGAGAAGGGATGGCTGGTCAAGAGCTTGGTGAAC<br>AGTTCTTCTAGTGGGGAGAAGTTTTTATGCTAATGAGTTT<br>GAGCTGTGTTGAGTGTTGTTAGCTGTTGAGATTATAAAAA<br>CTGTGAATTTGAGAGATTTGTTGATCCAAAAAAACAGTT<br>ATAAAACACATATTTCACANGTNCAAAAAAAAAAAAAAAA<br>AAAAAAAAAAAA |
| 153 | N05710-1-Q1<br>GAAACAATATGTTCATCTACATTTACACTTCCATTTGTTT<br>TGAGATAGTAATCTCTTCAAAACTGGAAAAGCATTGTCGC<br>TACTGTTAGACACCAGAATGGGACCGATATATAAGTTAGA<br>TGACTCAAAGAAACAACACTTAGACGACAAGTTGCACAAC<br>AAAGACCTATAATAAGAATGCATTTTCGAGGGGTGTTCTA<br>AAAATGTGAACCAAGAAGCGTGATCTGATATAAGTAGACA<br>TAAATTNNACCTCAAGCGTCGACCGAGATGAGGAGGAGGT<br>TGATGAAGAAAGCTTATCGGCACCAGATATAGCGCTGATT<br>ATGATGATGCTGANGGCAAAGCGTAAAACNCTTNTGGAGG<br>ATCCCTTTGATANGCAAAGTCCATATACAGAATCTCTAAC<br>TTGGAGTGAAGCGATTGAGCATCTCTCAACTCNANATCTC<br>GAATTAGAGACATANCCAAGTGCCAGTGATTCCATCACCA<br>CTGAAACAGATGTGTTCCCA[A/G]GACAAAACCCAAGCA<br>TAACATCATAGTGGAAATGCAAAACCCACAGTAATAGTTA<br>CAAGAGAGAAACAGCNTTTTTGCANCCCCCGGATGGTGCA<br>TAGCCACGGCTCAACATTTCTTTGATAAGCTCGGCCGATA<br>AGNTTATATCACCATCTCTAAGACATAGCGTGCCATCATT<br>CAGCATAAGCCCATCTCCTTTCATCTTTGT |
| 154 | N15338-001-Q001<br>TAGAGCGTAATAAATGTAGATCTGTTGAGGTTCTTTTTATA<br>TATATTTTCCGTATTTGGTCGGTCTTTGAGATGAGTTTGT<br>TTAAGAAAAACGTAAATGAAGTTGCTTGGGGTCTANGTG<br>ATTNCCTGATTGGCACGAAGAGCGACGCATCCCCGAAGCG<br>CGGCACTCTCCACGTGCTCTTGTGATCCATCTCAACAAGC<br>CATACTAATATAAAGTCATCTTAAAACCGACGCTGCATAA<br>TCTTTAGGTTCATGCACATTCTTGAATAGATTTCGAGGAA<br>CATACTGTAGTTAATATTTNAGCCTGGACCAGAAATAATA<br>TACTCGGATTGCATCTCAATAAAGAGTATTAAAAAACAAA<br>AACAAAAACAAAATCATTCTGAGACTTTGAAACGAAAAAG |

TABLE 7-continued

Markers of QTLs significantly associated with shatter resistance (P ≤ 0.01)

| SEQ ID NO: | Marker Name and Sequence |
|---|---|
| | [C/T]AATTAGTTTATTGAGCGCGGGGAAGAGTATATACA<br>TTATTAAACATACATCTCTCACTTNCTTTTCTATACGGCG<br>AGTTCATCTTCAAGATAACTGTATTCAAACGTGAACTCGT<br>TTTTGATCCTTTGAACCCTACACAGAGTTTTCATAAAGAA<br>AAAAGATTAGGATCATCACCTCGAACGACAAAGAGAACAA<br>GNAGACGAGAAATCGATAGATCATACCATCCTCCTTCTTG<br>GCTCTCATCTTTGGGGGTTTGGAAATCAAAGTAAACATAG<br>GCTCCTTGTTCATACTTCATCAGTTGCAATCTTTGGCTCCT<br>TGTGTCTCTGAAACCATGTGTTGAACTTTCTGTGGTATCT<br>CCACNNNNNNNNNNNNNNNNNNNNNNNNNNNNNNNNNNN<br>NNNNN |
| 155 | N10424-001-Q001<br>CTTGTTCTCGCTGAGACTGTCTTTCTTTTCTAGGAAGAAG<br>ACGCTAATACCGCGGACGCCGCCACCTCCTCTTCCTTGCCG<br>ATACAGGTCTCTGCGGAGCCTGTTTAAAACTTGTCCTCTA<br>CTCGGCTGTTTCCTGAAAGTTGAGCAAAATCGCAGCCACT<br>GCTGCTACGGCCATTTTCAGTTGGCACGAGAATTTGCCCA<br>ACGAGCTGTGGCTTTTCATTACTTCGACGGATTCCTTGAT<br>GGAAACATC[A/G]AAAGAGGGTTTGTATCTTGGCTCTG<br>CTGAACAGTGTCCGAGGCTTACAAACAGGTGTTCCAAATC<br>TGGATCACGTTGCTGGATTATTCACCACACTTCCTTGGCA<br>GCTAAAGATCATACCAGAAAATGCAGNAAATTGGCTATTT<br>TTCAAGACACCCCCACTACGCTACACATCGATGAGCTACA<br>CANCGACGAACTGTGGCANTAAGCCGNCGNCCATCTGGTG<br>GAAAAAAAATCCATTCCTAA |
| 156 | N16006-001-Q001<br>TTCTNTGCAATATGGGAAGTTGTATCTCTCTCGCTATC<br>ATGTGATCAGTGTACGAATCAAGTCTTTCAGTGGTTATGC<br>ATCAGAAGGGGTTATATTCACAATCTCGAGGAGAATCTCA<br>AGGCTTTGGAGACAACCATGGAGGAGCTTCAGGCAAATCG<br>GGATGATTTGTCAAAAAGGGNGGAGAGAGGAGGGTAAA<br>GGACTAAAAAGGCTNTCCCAAATCCAGGTATGGCTTACGA<br>GAGTCGACACAATCAAAACACANGTGAATGCTATATTTNG<br>TGCAATACCTGTTGGAAGTCAAAGGTTGTCTCTCTGTGGG<br>TTTTGCTCTANGAATTTAAAATCTAGATATCGTTACGGGG<br>AAAGGGTTTTTCTGATGTTGAAGGAGGTTGAGAATCTAAA<br>[C/T]TCTGGTGGAGACTTTGAAGTCNTTGCCGAGCAAGC<br>TCAAGCATCNGAGGTAGAGGAGCGGNCTATCCAACCGGGA<br>ATTGTTGGTCGGGACACGATGCTCAAAAAGGCATGGGTGT<br>AGAAGAATTTAGCTTAGGTTACTTAGGTTTCAAGTTAGCC<br>TTAGAACAGTAAATACATAATCAATTTAACGAGTTCCCGG<br>CCCTCGGCACGGTACGTCTCGTGGGAGAACTTCTGCTCCC<br>AAACTTGACTAGATCAAAAGAGTCACCAGCCACACCAAAT<br>AAGTGTGCTAGTTAGTTTACAATGAACCAAATACTCCAAG<br>CTAGAGAATACAACAAGCCCTTAGATAATAGACTTAAGCC<br>TAAGCTAGTTATCTTGTATGTTGTCTTCTTTCTCTTGCTA<br>ATCTC |
| 761 | N07278-1-Q1<br>AGTGTCAATATCAAAYGAGYCCTGATTCAAGAAGTCGCAG<br>AGTTTCTGTGAATAYCCAACSGAGTTCTTAGTTTC[A/G]<br>TCTGTATTCTTCCCATTTGCATATCCCTTGTCTAGCTTGA<br>GCTTGGGAATGTAGGTGGTGGATCTTATCGGAATC |
| 762 | N16343-001-Q001<br>CTAAGCATGATACAAGAGTCTGCCTTTCGGTCCTTTTCTT<br>TCAAGTGGGCCACTTTTTTTTCCCGAACGCAGTCCGAATA<br>TGAAGCGCATGGATACAAGTTATGACTTGGAATGAAAGAC<br>AATTCCTTTAGCTTTGATTTGGTTTGTTTCTTACGAATAT<br>TTTATATTATTATTTGATTGTTTTTACAATTACGAATAT<br>CCATATTTTTTATTCGAATCGAAATGGATAATGAATCAA<br>ATCAAAAWWTTTGAATATTCCGCCTAGTCCTAGTTTGGAG<br>CCTAGTGAAAATTAAAATAGCTTGACATTAGTTCTCAACA<br>TTTACGTAATGATTATTAAGGACAATCGAACTTTTCAAT<br>ATAGACGATTACCAATTTACCATATAGGGATATATAGAGC<br>[A/C]GAAGACTCAAAACCTTTAGTTGGACAAATGGTTAA<br>GTCACGAGTGCAATACATATTTTATATACAAATGTCAAC<br>AATTCTGTTAGTAGTCGTTCGTGCCACATAATTTATATATC<br>TTTGTGATTTTCTGTTTCGATTAATCTGTCTCATAGTTGC<br>AGTCGTTAGCTAGTATTAAGATCAACAAATTTTCGGGTGC<br>ATATTTTTTAAGTTTCTTAATTAAGGATATAAAGTACGC<br>GCGCTCAACTATTTGTAAATTAAAACATCACTGCAAGAGT |

TABLE 7-continued

Markers of QTLs significantly associated with shatter resistance (P ≤ 0.01)

| SEQ ID NO: | Marker Name and Sequence |
|---|---|
|  | TCAGTCAAACAGGGGCAGACCCCCACTATGGTCCAAGGGA GTCACTTGACACCCCTAAAATAGTTAAATAAATGAATTGC ATAGAATATCCAATGGATTTTTGTAGCAGAAATAGTTACT TTGWA |
| 763 | N23417-001-Q001<br>AAACTATGGTTCTGTTACACTTGTGTGTTCTTTAACTTGA AGCATACGAGTCTCCAACGAGTTAGGAGCAGGAAATCCAN AAGTGGCAAAACTGGCTGTATATGTCATTGTAGGCATAGC AGTTGCCCAAGGTATCGTGGTGGTAACGGTTTTGTTGTCG GTTCGAAAGGTCCTAGGCCGAGCTTTTAGCAGTGACCCGA AAATCATCTCTTATGCTGCATCGATGATACCTATTGTCGC ATGTGGAAACTTCCTTGATGGTCT<u>CCAATGCGTTCTCTCA</u><u>GGTTCTTATT</u>GCTTGCA[C/G]ACTCGACCATATGTTTCT GGAACAAGAAA<u>ATATTGGTTTAGGCTCCTCCTAGCTTATA</u> TATATATATGTCCGGTTAATCCTGGTTTGGTATGGTTTAG GGGTTGCTAGAGGATGTGGATGGCAGAAAATTGGAGCGTG TGTAAATCTTGGTTCATATTATCTCGTTGGAGTTCCGTTA GGGCTATTACTTGGTTTCCATTTCCACATCGGTGGTCGGG TAATAATCTTT |
| 764 | N22902-001-Q001<br>AAATTCATATTATTTACTTTGTTATTTATTTTTATTTTTC TACAATTTTTATGTATTNTGGAACAAGTATAATTTTAATA AAATATGACGATATAAGTTTGATAATACGANAAGTTTGTC AACCATAATAAAATTATTGTTATTCAGATACTCCGGTAAT TTTATTTTTTGACTGAAAATTCCAGTAAGGTTCCAATCCC AGATTAGATAATTTTATTTGCATTAATCTGTATATCAAAC ATTACTTTTGCTAATCTATACCTTGTATAATATGTCANAA TTGCTTTTATCTTTTCAATATCTATAGATTAAAATTTATA ATCTTTTATAGTCTATTCAACTTGCGCAGCATCATCTCGT AGGTGTTAAA<u>ACCCTCTGGGTTTTCTGAACTTTGTTAAACC</u> [C/G]TCTTTATACGATAG<u>ACTAGTAGTGCGCACCAAAAT</u> <u>CTT</u>GAACATTATTTTATAAAATCAAAACAAAATAACCAC CACCTTATCTCGGTCTTGTATCTGCAGATGACCCGGTTTA AGTGCAGAAGGATTAGCTTTCGGCCTGAGCTGGGCCAACAT CATGGGAGATTCNTTCTCTTTATTCTATGCCTTCAACTTA TGGGTTAAGGTCCTTTCAGGAGAAAAAATCTATGCCCCGG AAACTTCTATNATAGACAGAAGGTTTCAGAATCCAAATCC AACGGTGAAAGACCCGGAATCAATAAAACAGGTTGACCCG GTTGGAGATCTATGGATCACTCCAAGCAACAAGAAAATGG TGAGTTACTGTTTCAACCTCACCGTCNCCGACCAGATGTC ACCGC |
| 765 | N23063-001-Q001<br>GGGTAAGCTCAAGCAACTAGAGACTGAGGCAAAAGCTAAA AAGGAGAGGGTCAAAGAGCTCGAGGATTCTAAATATGGTA TCCGAGCTTGCATCAATGTCGTAAGGAGGGCTCTATCAGA CCAAGGTTGCAGCTGAGAATTTTGACACCGATGTCATAAA GGATCTAGCAGACACTCAGAGGGAAAGTAAGAAGCTCGTT AACCGGCTTAAACTGGCGCAAAGAGCTCATAAGGAGGAGT TCCAGAGGCTGAATGAATCAAGATCCAGAAGGTTTAGAAA AANGGCTTGTCAAGCTGCAGNGGTGAAATACCAGTCGCAT TTTGATCAGATATGTGAGCTTTGGCCGATTCTAAGATCGT <u>AAAGGAGAATGCCTTGTTGATGTCTC</u>AGGCGGCTAGTCAG [A/T]CAGGTTTG<u>ATCGATAAGATGACACAAAGGGGACTC</u> GTGGGTCATGTGGCAGATCAGGAGATATGGGTGCAGTCTC TCAAGAATTTCTAAGTGAAGATCGACGAGATAGACATCGT CCAACTAGATCCATAAAAGGATCTAAGNGTCTCACCCGTT TCTGATGTCTCCAGCTGAAATAGCCTCCCTTTGGGGCCAA TTCCTGAGCTAAATCCTATCGATGATTAAGAGGTCAGGAA TTAGACNGTCATGTCAGAAACTGTGACCATTCCAGGATGG TCGAGTTGAGGATCCTCCTGCTGACCAGAAGAAGACCGAT GCAACAACNGCTGAGGAGCCTCGGATATAGATCAGTTTG ACTCGAAACTCGTCTGTAACTCCGTTGTGGATGTTTCGGG CGCTG |
| 766 | N22723-001-Q001<br>CACTTATGCAGTTTGCGATCTTTGTGGAGACAGGGCAGTC TCTAGACTCAGACNACACTTTGCCCACAAGAGCTCTTACC TCTTCATTGTGGCGTAATCTCCTATCGTAGCAGAAACTAT ACGGTCGTTTCTTCCCTGTAGCAGTGAAGGACGAGATAAG AGGCCTGTGATCAGAGCCTTCAAAAGGGAGATAGACACNG TTTCCTTTCGGGAAACAGTCAGACCAGGAGATATTGGCTA GAGCTTGATCCAGTCTGCAGTGCACTCGATGAGTATGTCT CGTTCCTCTCCAGGAGGAGAAAATTTCCACGGTGTCTCAGA TCAAAGAGATCATTCGTTGCGAGGAAAGTCCTAAAGTTAC TGA<u>AGGAGCTTTCCGGTCTATCTCTGCCTCCAGTTTTCTC</u> [C/G]GAGTTGTCAGTGATTTCGTTGAA<u>ATCTCCAGTCAT</u> <u>TAACCAAGG</u>ATCGCTTCTCGAACCACCTAGCTGTGTAAGT TGGTCCCATACTTCTTGTCTATGGGATACTTCAAGAGCTC CATAAACGAAGGAACTGAAGAAGTTTGAATTTTTGTAGGA GATATGGGTATNTATGTAGTTAGGAGTCGCCGTCAGCACC TGGACCTTTACGTCAGACTTCCAGAGCAGGCAGAGCCCCC CTGAGCTTGGACTGTTGGACTGTTGAAACAAGGAAGTGAAACTC AAGAAGTAAAGGTTCCAGGTCTTTAAGGACAAAGGCATCT GGATTCTTTGTTTCCTGGATAAAGATGATATCTGGAGAGA ATTTTTTGTTGAGAGCAATGAGCCTTTGGACTGTTCTGGG ATTCN |
| 767 | N23049-001-Q001<br>AAAAAAATGGAGAATAACGACTAAAATGTCCGTGAGTAAA CATCAAATCAACATACTATTTAGATGTTTTAACGTGCGGT TGGATTTGGCCTTACCTCCGCCCAGATCCCCCCTTTTTGT AACTGTGATTGCCCATCAACACCTTTCTGACCTGACCCGA CATATTAACATAACTTT[A/T]ATTTGGGGGTAAACTAAA <u>ATTGGGTTTTGGATCCGTTTATTTCTCAGTTACAGACATGA</u> CGAAGAACATAAGAAGAGAGAGAGAGAGGACGTACAAC AGAGAAGACGATGACGAAGAGTCGAAGACCAGTAACAGAG AGAGAGAGACGATGACGACGACCAGTAACAGAGAGACG ACGTAGNAGAGAGAGAAAGACGACTTAGAACAGACAGA GAGAGAGACGACAACCAAGAACAAAGAGAGAGATGACAATGA ACGACGAAACGTGGAGAGCGAGACGAAGCCAGAGAGAG |
| 768 | N10321-001-Q001<br>TGGAAAATTCTATAGGTTTTATTGTAATCTTTTGTTTGAA AATCATTTGTGTGTCCATAATTGCTCTTTGAGAGAATTGT TTTCTTGAATGCTTTGATGGAACACTTTGCCGCATATGAA AAGGGATGTAGAGAGGATATGTGGCCGGAGTACCGTTTGC AAAACAACCATGGCAAGGCCAACAACACCATGTAAGTACAC [A/T]TCTTTG<u>TCAATACCTAACGAGCCTTCAAACTGATA</u> TCTCATTGAATTTCGTATTAGGCTTGCCTAGAATCAGGGA AGGGAAGGACTCAATCTATGTAGTCGTACATAAAATGACA CATTTTATTCCTTGTTAAAACGCCAACGAATAATTGAATC GCACGCGAGAACACTTTCTTTAAAAAGTATTTTGACTCTA TTCCA |
| 769 | N15374-001-Q001<br>CCTAATTTCCCTAATTTTTACTATGTAATACACCAAACTA TAAAAGTTTTATCAAACGGACAATGTTGAGATTATTAT TCTAAATAGATGTTTGTCTCCCTACATTTTCATATTTTGT ACCGAAACATTTATTTAAAAGATATGCAAAGTAGTGTGTA GCCAAATGCTATCATGTTTAAATTTGCCAAGAGCATATCC ACCTATACAGTGCAGATAATTGTTTACTTTTGTTAAGCTA CAAAAAGATGTTAAGCTGTAAGAGTGATTCGCATGAAAAA TCTATTACAATAAAAGAGAGTTACCTCTCTCTAYATGYCA CCACGTCATCAGGAAATATAAGACGTTTTTGGAC<u>ACTTGG</u> <u>CACTTCACCAAACCAGCCCGCTCGATTTGATTTTGTAT</u> [A/C]ATCCGGTTTW<u>TCTCATGCCTCTATCCTGGACTGGG</u> CCATTATTACAACTTTTCCTTGGGCCTTTAAAAACACTAT GACAAGCTCACTAGAATTTTATGTTTCTTCTTCTTCTTTG CGGTTGCGACAGTGGACAATTTTTTTTTCAGAACTAAAGG GACGTTCCAATCTCTCCCGTAACGTATCAATACTTCATTA ATCTGTTCTTAACTCTGAGGTTTTGCGTGATTAGCCMACT CCTCCCACTGGAAAGCATTCAATCGACATCTTTAATCTAA CTTTAAGATGATATYGTTTATTTTTCTTCKTGACCTTTGT GATTTCTCCATCTTCTTCCACTCACTTCATCTGTTATTGA CATCATAATTCCTCTTCAACCCYCATTCTCTCTATAGAAA GCCAG |
| 770 | N22802-001-Q001<br>GCATCTTGGCATTACTAGTTTGTATTTTTATTTTGCAAAG AGAACCAAANCTTAGTTATTACAATAGATTATCTTGCAA CAGTATTTCCAACAGCGTTATTTTAGAGTACTAATACTCA TGGCTGCTTTTTGGAGTGTCTCTCTGCAAAGTTATTTAGC TGGAAAATCAGTTTATGATGAGGTCAGTATCAACCGCAAA GGTGATACATAACCAGTTCTTAAGCAACAGCTCGACCTGC CAAACCACCATCTGTTATTTTAAATGTCAAACAAAGCTCG |

TABLE 7-continued

Markers of QTLs significantly associated
with shatter resistance (P ≤ 0.01)

| SEQ ID NO: | Marker Name and Sequence |
|---|---|
|  | TTAGCAAGACACAAATATANTTACCGGGTAGAATGATTAC GGCAACTNTAAGCCTGCAGCAAACCAACACGAAGTCTCAT TGTTCACATTAATGAAGAACACGCCGCCTTTTCTGCTGAA [C/G]TTGTACTTCCATTTGTCTTCAAAGAAATTGGTATG AAGACAATAAGCAAAGATGTGATGGAGTCGTGCTTTAGAA ACAATTGTCAAAGCCCAAAAACTAAGAACAACAAATGCCA AAATTGTGAAAGAACAACGAACTGGTTTTGCNAGCCAGGA AATCTGATCATGACAGTTGTCCAACACAGCTGACGCCAAC CGCTTGCATTGTGTGTTTGAGAAACAGCCGCNTCGTCAA ACATTGTCCATGAGAAGAGACATCAATGTGTATGAATGTG GTGGAGCAATGAAATAATTACCAAGTGATAAACTCCCAGT GGATATGCTGATAATTATTATGAAANTCAAATTGAGAACC AGCTTTCTCAAACCCATGCTCTCAGTTTCTTGCCACCAAA CATTA |
| 771 | N22803-001-Q001<br>TAGATTGTTATGTTTTGATATCATCACAACCAAATAACAT GCCATGTATTTCCATCATCATTATCGTTATCATTATTTTG CCAACATTATTATCAATTTATCACTGTTTTGTTAAATAAC GTATTTCCATTATACGGTTCCTTTGTTGTTGATATTATAT AATATAAAAGGTCACATGTATTACTATTATCGAACATGAC ATAATATAAGGATTATTAGAGCGGAAGCTAAATAAAATTT NGCTNGATATTGTAATGGTGCTGCATCATGTTTTCTTTTT TGGTAAAATTTTAATTGATTACACCAAAATGTTCGTATGT TACAACTTACAAGGTTGGGACTGAAATGGCTCGTTGCTTC TCTTTCCAAAGAGGCATCTTAGCTCTCCTAAAATCGCTAT [A/T]CTTGGGCAGATGATCATCATGAGGATGGTTTCACT TTTGATTTCCTCCTGCTCTGTTTTATGCTTTTTGCCCACT TGTTTTGGGTTATTATTGNCTATTGGCATTTGTTTTTGCT TGAACTACCTCTAGTCGTTTTGACTAGAATACTTTATGAT TTTTAATCAATGANAAAAAAAACAGTTACAAAAGGATATT AATAGCAGAAAACTGGATGAAACTAAACAACAGAGCTACT CAACCACATCTTAACTTTGAACAAAGACTAGAAGGTAGAC AGTAGAGAGGGAAACCAACGAAACAAGCTTAGACCAAGGA ATTGGTAAGGACCGCAAGAACAAATGGGTCGCAGCGAGAA AGAGAGAGNTGGATGCCCTCAAACCATGTTGCAACACCTT CCTAC |
| 772 | N18929-001-Q001<br>TAAGACATTGTTTTATAATTTATTCAAACAATTATTTCCA TTTTAACCAAAGTTGAGCAATTATTGTGGAAGTTTGAAAA ATTGGTAGATTTGTCAGTAATGTACTATCTAAACCCATCA ATAGAGTGATGGTTGAAGAGAGTATTGGTTTCCACCCGCA ATGCAAGGAAATCAACTTATCTCATTTGAGTTTTGCCGAT GATATTGTGGTTTTTAC[A/G]GATGGTTCTCCAATGTCG CTTCAGGGTACTCTAAAGGTCTTTGAAGACTTCACTGCTA TGTCTGGTTTGCAGATAAACATAGCAAAGTCCACGGTCTT AACTGCTGGTAGAGGAAAGCATGTACTAGAGGATGCAGCA GCTGATGCGGGTCTCTCCGTTTCTGCCCTGCCTATTAGGT ATCTTGGACTACCGCTTACCACCAAGATAATGTGCAGGGA TGATTATGAGCCGCTTATTACTAAGATCAGGAACYGGTTC CTCTCTTGGACGAGCAAAGCTCTCTCATATGCAGGTCGAT TACAACTTATAAAATCAGTTATTGCTAGTATCACAAACTT TTGGTGTGCTGCGTTCTGTCTTCCGCAAAACTGTATAGCG GAAATCGAGAGTATGTGCTCTG |
| 773 | N16041-001-Q001<br>CCATTAACATTAGGACATTACATCTTTTCTTTTTTGTTGC TTTTTGTCCGTACGTTATCGTCGTCCGTTTGAAACTTTTT AATCTTATCCCTAATTTTTTATCATCGTAAGCAAATCTAG TTTTATGTTCGAGATATGATGGTTATTGAAATATATATGG GTTGTGCTTTCAATAATCTTGTCCATAGTTTTTTTGTCAA AAAAACCCATCCATAATCACCAGCTACCGCCACAAAATCT TTATACGTTAGCTTGTTGCAGTGAACTTTAAAAAAAATAT TGTTGTTATTTCAATAAACACGGACATGGGCCATTATGCT TAATAGACTTTAGTCTACAGCTTTATCTCTCAAAACCCAT AGTAAAACACAAGTCTAATGATACAAGCT[C/T]AGAGCC TAAGCATTTACAAATAGAAATTTAAGGTTAACTTTTATAA TTGTTATCAAACATTTCATAGGCAAAAGATAGAAAATGGA CAAATTAACAGGTAGTATACGATTTCTACATTTTAGCAGT ATTTTATATTAATCATGCTATTAATTTAGCTGATTAAATC ATTTTATGTAGTTTATCTTCTTTTTATCAACTTATAGTTT ATCTTTGTTGGCAAATAATTTGTTTTCTTTTTAAATCAAA ATCGTTGATTTTATCCATGGTAAACTTTGAGTATCTAACG CATTATAATTTTTTAAGGTCTGGGAAATAAATCGAATCC AAAAATCCAAGCCGAACCCGATCCAATAAAAATGAATATC AAATGGATCTTATTTTATGATATTTTGGATTATG |
| 774 | N18401-001-Q001<br>CTTGTCTTTCTTTTTTGATAGAGAGAATATTGCTCTGCTT TCTKATTAGAGGCTTTGATWACATACTTTAGGTGGTAAAG GGTCTGATCCAGATTTTCTGAAGAGGTAACTTGTATTGAT TACATACTTTAGATCCAGGGTGCGTTTATAACTGATACCT TTGCTTGTGGTGGATTTTCTTTTGCCAGCGAAGAGCTGTA AGTTTTGTACTTTAGTCAATTTTGCAGCTCTACAGAACCT TCTAAGAAGCTACCTCACTAGACAGGTGATTYTAAAGATT CTCTTGYGTCTGCTACTGTTCACTCTTAGATCTCAGTCTT TCCTGTTTCTGAAGTTACCTTTGCCAACTCTACTTATTCT CGTCTTTCTCGCTTTCTCACTTTTTTTGTTCTTAGCTTTG [C/T]AGACGGGTTAGGTTAGTAAAAGCCAGTGGTAAAAA ATATGACTCTGTAGAAAGGAGTATTATATCAGTAACAAGG AGATGCCTTTTCATTCTGAGGACGACAARAGTGAAGACTA CCTCTTCAAGATTCTGCAGCTCGGAAATCAAATTTTGCTC GCAAGATTTGCTAGGGATTAGTTATACCCCAGTTAAAAGT CGACGACTAGAGTGGAGTTTCAGACGGAGATCAAATAACA GATATGGACACAGCAGAGGTGCTGTTGGAGCTCTTCTGGTTC ACAACATCAGCAGACAGAAAACTTTTCAGAGCATTGGTAG ATGGCTTTAACTAGCTGCATAGTAAGAAAACTACTCGTGG GTAACAAGTCGGATCTAAAGTACATAAGCACTAAACATCG GAAGG |

Table 8 below sets forth exemplary sets of forward and reverse primer sequences for each polymorphic region in the above-listed markers. For genotyping carried out via the KASP genotyping assay (LGC Genomics, Boston Mass.), two forward primers with alternative 3' ends are shown. For genotyping carried out via the TaqMan SNP genotyping assay (Life Technologies, Inc., Grand Island N.Y.), additional differentially dye labeled probes (VIC and FAM) are shown as well as the forward and reverse primers.

TABLE 8

List of SNP markers and primer sequences used for amplification of loci associated with resistance to shatter

| Marker | SNP | Forward Primer Sequence | Seq ID NO | Reverse Primer Sequence | Seq ID NO | FAM Probe | Seq ID NO | VIC Probe | Seq ID NO |
|---|---|---|---|---|---|---|---|---|---|
| N20003-001-Q001 | G/T | ACGTCGGTACTCTT TTCTGTTGTC | 157 | CCCTTACTCTAGG ATGGGTGATACA | 158 | AACTCAGGAATT AATGAT | 159 | ACTCAGGAATGA ATGAT | 160 |
| N03491-1-Q1 | C/G | TTCGGGGATTAGA GCTTTCC | 161 | TCATCAGTACCGT TTGATTTCG | 162 | TCGATCTCTCAC TACGG | 163 | TCTCTCACTAGG GACTAC | 164 |

TABLE 8-continued

List of SNP markers and primer sequences
used for amplification of loci
associated with resistance to shatter

| Marker | SNP | Forward Primer Sequence | Seq ID NO | Reverse Primer Sequence | Seq ID NO | FAM Probe | Seq ID NO | VIC Probe | Seq ID NO |
|---|---|---|---|---|---|---|---|---|---|
| N0017NR-001-Q001* | A/G | TAGCTATTCATAAT TAATCAAAAGGTG GTCC | 165 | GCAGTATCATATG TTCCACTCTAGAG ATG | 166 | ATTTTACACCTT AGTGCTGTGA | 167 | AATTTTACACCTT AGTGCTATGA | 168 |
| N10336-001-Q001 | A/G | CCGCTTAGCTCTCT TCGGTTATTTT | 169 | AACAGCACATGAC GAGATGACATAT | 170 | CTGAATGTGGTC TATCAC | 171 | CTGAATGTGGTT TATCAC | 172 |
| N23133-001-Q001 | C/T | AACAAGCCCTCTC ATGTACAATGT | 173 | ACCACCGCTATG CATCAAATCT | 174 | ACTAGTTGATTA TGAAGAAA | 175 | CTAGTTGATTGT GAAGAAA | 176 |
| N16487-001-Q001 | G/T | CCGTACGATGAAT CAGACGAAAGTA | 177 | GAAACGAATAAAT TATAGAACGAAGC TACTAATGG | 178 | AACAGAGAGATT AATTGG | 179 | ACAGAGAGATGA ATTGG | 180 |
| N23426-001-Q001 | A/G | TGATGCTTCCCTTC AAAGAAAGACA | 181 | ACATGTTACCAAT CAAAGCCTATATT ACATTTACA | 182 | TTTTTGTGCAAC TTC | 183 | CTTGTTTTGTA CAACTTC | 184 |
| N05671-1-Q1 | C/T | CCCATCAAATGAAA AGGAGGA | 185 | CTATGGCGATGTT GCTCAAA | 186 | ATGGTTCCATAA CTC | 187 | CATGGTTCCGTA ACT | 188 |
| N12643-001-Q001 | A/C | CCTCTTTGAGCTAA CACTAGTCACA | 189 | ATCCAAGGGACA AAATGCTACCAA | 190 | ACCCATGGTGG TTCT | 191 | CAAACCCATGTT GGTTCT | 192 |
| N05943-1-Q1 | A/C | TTGCAAAACTCCAG GTCAGA | 193 | AAAGCTTGTGTCG AAGCAAAT | 194 | ACGTACATAACA CGCTT | 195 | AACGTACACAAC ACG | 196 |
| N06007-1-Q1 | C/T | CACAATAAAACCAG AGCTTCCA | 197 | GCAACGAACCAA AAATCACA | 198 | CTTTTCCAAATG ATTACAC | 199 | CTTTTCCAGATG ATTAC | 200 |
| N10105-001-Q001 | A/T | CACCTGACCGAAA GAAACACTAGTT | 201 | TCTTTCTGTAAGA ATTATTCTTCATTT AGCTATGCT | 202 | AAGATAAAATTA CTGTTATTAGC | 203 | AAGATAAAATTA CTGATATTAGC | 204 |
| N08181-1-Q1 | G/T | TCTTTTGTTGAATG GGGATTTT | 205 | CGTCAAAAGAAAA TAGAAAAAGACAG | 206 | TCCAACTTCCAA ATTA | 207 | TCCAACTTCCAA AGTAT | 208 |
| N06675-1-Q1 | C/T | AACGACATAGACG ATCGTTGG | 209 | TCTCCATCACTTC GTTAGTATTCG | 210 | CACAAGAATCCA CAACT | 211 | ACACAAGAGTCC ACAAC | 212 |
| NO01K1-12-001-Q001* | A/G | GAGAGAAAGAGTG GGAAAGAAAAGAG T | 213 | GCTCTCTGAAGAT GGGAAGAAATGA | 214 | CTCCACGCCTTA GCT | 215 | TCTCCACGCTTT AGCT | 216 |
| N29313-001-Q001 | G/T | ACAATCTGGCCAC ACAGACG | 217 | GTTATTCATAAAG CCAAGGTTTTCAC TTCT | 218 | AGAGAAGAATCA ACTAGAAGTA | 219 | AGAAGAATCAAC GAGAAGTA | 220 |
| N88512-001-K001 | A/C | GAAGGTGACCAAG TTCATGCTCAACAA CTAGCAAATCAAA GTGACC and GAAGGTCGGAGTC AACGGATTGATCAA CAACTAGCAAATCA AAAGTGACA | 221 and 222 | GGTGGAATAAAGT GTTCTTTGACGAA CTT | 223 | 0 |  | 0 |  |
| N88514-001-K001 | C/G | GAAGGTGACCAAG TTCATGCTAATGTA AAGGAGAAGAAGA AGAGCAC and GAAGGTCGGAGTC AACGGATTAATGTA AAGGAGAAGAAGA AGAGCAG | 224 and 225 | TCCCAACCAATTG GTCGCCAGTAA | 226 | 0 |  | 0 |  |

TABLE 8-continued

List of SNP markers and primer sequences used for amplification of loci associated with resistance to shatter

| Marker | SNP | Forward Primer Sequence | Seq ID NO | Reverse Primer Sequence | Seq ID NO | FAM Probe | Seq ID NO | VIC Probe | Seq ID NO |
|---|---|---|---|---|---|---|---|---|---|
| N88515-001-K001 | A/G | GAAGGTGACCAAG TTCATGCTAACAGA TCATTCTAACTCAT TGCCG and GAAGGTCGGAGTC AACGGATTGTAACA GATCATTCTAACTC ATTGCCA | 227 and 228 | GAGGTAATCTACA CCGCCCCTTATA | 229 | 0 | | 0 | |
| N88516-001-K001 | A/T | GAAGGTGACCAAG TTCATGCTGTCGTG AAAAAATAATTTTC TATATTTCCAA and GAAGGTCGGAGTC AACGGATTCTGTC GTGAAAAAATAATT TTCTATATTTCCAT | 230 and 231 | GTACCATTTTATT GTAATGAACTATC TTTT | 232 | 0 | | 0 | |
| N88517-001-K001 | A/G | GAAGGTGACCAAG TTCATGCTGTTGAG CTGATCTTACAGGT CCATTA and GAAGGTCGGAGTC AACGGATTGAGCT GATCTTACAGGTC CATTG | 233 and 234 | TCAGCTCCGGTG AAGAAAACAGAGA | 235 | 0 | | 0 | |
| N88518-001-K001 | A/G | GAAGGTGACCAAG TTCATGCTTTAAAG TTTACTTTTATACAT CACGAGATTAA and GAAGGTCGGAGTC AACGGATTGAGCT GATCTTACAGGTC CATTG | 236 and 237 | CTCAACTAGTTTC TTTTAATTTCTGTT GAA | 238 | 0 | | 0 | |
| N88519-001-K001 | A/G | GAAGGTGACCAAG TTCATGCTGAGATA ATTCAAGGTGATTA AGTGATATTG and GAAGGTCGGAGTC AACGGATTATGAG ATAATTCAAGGTGA TTAAGTGATATTA | 239 and 240 | CAGCCCATTTCCA AAAGTTTTTGGGT TTT | 241 | 0 | | 0 | |
| N88520-001-K001 | G/T | GAAGGTGACCAAG TTCATGCTGAATCG ATCAGAATCTAAAC GGTTATG and GAAGGTCGGAGTC AACGGATTCGAAT CGATCAGAATCTAA ACGGTTATT | 242 and 243 | GAGATCTGATCAA AATTGACTTTGCA CTTA | 244 | 0 | | 0 | |
| N88521-001-K001 | A/G | GAAGGTGACCAAG TTCATGCTCCAATA TAGAAAAAAACAAA ACACTCTTCG and GAAGGTCGGAGTC AACGGATTAAACCA ATATAGAAAAAAC AAAACACTCTTCA | 245 and 246 | GTTGGAAGCTTTA ACGGTTATGGAAT GTA | 247 | 0 | | 0 | |

TABLE 8-continued

List of SNP markers and primer sequences used for amplification of loci associated with resistance to shatter

| Marker | SNP | Forward Primer Sequence | Seq ID NO | Reverse Primer Sequence | Seq ID NO | FAM Probe | Seq ID NO | VIC Probe | Seq ID NO |
|---|---|---|---|---|---|---|---|---|---|
| N001KFE-001-Q001* | A/G | CAACGCGTTGCCCGAAAA | 248 | TTGAAGTACTAAAGTGGATAGCGGAAAA | 249 | TTTAAAGAAGGAAAATTC | 250 | TGATTTAAAGAAAGAAAATTC | 251 |
| N88522-001-K001 | A/C | GAAGGTGACCAAGTTCATGCTTTTATTTTCTTCTGGATACAGATAAGAATAA and GAAGGTCGGAGTCAACGGATTTTATTTTCTTCTGGATACAGATAAGAATAC | 252 and 253 | CTCAGACTTCATTGCAAAGCTGAATAGAA | 254 | 0 | | 0 | |
| N88523-001-K001 | A/G | GAAGGTGACCAAGTTCATGCTACAAGTCATGTATTTGTAACGACTTGAAAA and GAAGGTCGGAGTCAACGGATTCAAGTCATGTATTTGTAACGACTTGAAAG | 255 and 256 | GGAGTCCGGACTGAAATGCAGATTA | 257 | 0 | | 0 | |
| N88524-001-K001 | G/T | GAAGGTGACCAAGTTCATGCTCTGAAGAGCTGATGTCTTTTGGTG and GAAGGTCGGAGTCAACGGATTCTGAAGAGCTGATGTCTTTTGGTT | 258 and 259 | CAATGTTTCTGAACAGAAACTTCTCAGTTT | 260 | 0 | | 0 | |
| N88525-001-K001 | A/T | GAAGGTGACCAAGTTCATGCTCAATAGCCTTTTAAGAGTTTTCTAACCA and GAAGGTCGGAGTCAACGGATTCAATAGCCTTTTAAGAGTTTTCTAACCT | 261 and 262 | CCTTTTGTGTTATTAAAAGCGGGAGTGTT | 263 | 0 | | 0 | |
| N88529-001-K001 | C/T | GAAGGTGACCAAGTTCATGCTCCTCAACAGCCTGAAAAATATAACATAAT and GAAGGTCGGAGTCAACGGATTCCTCAACAGCCTGAAAAATATAACATAAC | 264 and 265 | GTCCCGGATATATAACTGCTGTATACATA | 266 | 0 | | 0 | |
| N88530-001-K001 | C/T | GAAGGTGACCAAGTTCATGCTCATTGTTGCGTATGACAAGCTCGT and GAAGGTCGGAGTCAACGGATTGTTGCGTATGACAAGCTCGC | 267 and 268 | GGTATCGTTCGTGAGAGATTGGCTA | 269 | 0 | | 0 | |
| N88531-001-K001 | A/G | GAAGGTGACCAAGTTCATGCTCAATAAGACAAAAATTCAAAACAAGAAAAAATG and | 270 and 271 | GGCTTTGTAAATTTCCGTTTTCAAACGTTT | 272 | 0 | | 0 | |

TABLE 8-continued

List of SNP markers and primer sequences
used for amplification of loci
associated with resistance to shatter

| Marker | SNP | Forward Primer Sequence | Seq ID NO | Reverse Primer Sequence | Seq ID NO | FAM Probe | Seq ID NO | VIC Probe | Seq ID NO |
|---|---|---|---|---|---|---|---|---|---|
| | | GAAGGTCGGAGTC AACGGATTCAATAA GACAAAAATTCAAA ACAAGAAAAAATA | | | | | | | |
| N88533-001-K001 | A/G | GAAGGTGACCAAG TTCATGCTGATTAC ACGCACAAATTCG AGAAATG and GAAGGTCGGAGTC AACGGATTACACG CACAAATTCGAGAA ATA | 273 and 274 | ATCTCGCTGATCC AGTTTGTTCTTGA TTT | 275 | 0 | | 0 | |
| N88535-001-K001 | A/C | GAAGGTGACCAAG TTCATGCTTGGTTC ATTTTATTTAATGG ACCTTTGC and GAAGGTCGGAGTC AACGGATTCTTGGT TCATTTTATTTAAT GGACCTTTGA | 276 and 277 | GAACCACTGTGTT AACAAAACAACAA CGTT | 278 | 0 | | 0 | |
| N88536-001-K001 | C/G | GAAGGTGACCAAG TTCATGCTCCCATT ATCATTGTGCAATT TCCGAG and GAAGGTCGGAGTC AACGGATTCCCATT ATCATTGTGCAATT TCCGAC | 279 and 280 | CCTTTCTTGCTTC TCCAGATACAATT TGTT | 281 | 0 | | 0 | |
| N88537-001-K001 | C/G | GAAGGTGACCAAG TTCATGCTGTTTGA TCCTCAGTTCGCTC GTC and GAAGGTCGGAGTC AACGGATTGTTTGA TCCTCAGTTCGCTC GTG | 282 and 283 | TCCCCTTCCGATC CTCATCATCTTA | 284 | 0 | | 0 | |
| N07541-1-Q1 | C/G | TTCTTCCATCGTCT CTCCTGA | 285 | TGCAATTCAGTGT TTCGATTTT | 286 | CTCCCACCTATC AAA | 287 | CTCCCAGCTATC AAA | 288 |
| N23413-001-Q001 | A/T | ACTTAAAGACCTCT CCTTACTCTCCAA | 289 | GCTGGTAATTGAA AAGGATTGATCTT TGA | 290 | CAAGCCAAAGT CTTAAC | 291 | CAAGCCAAAGAC TTAAC | 292 |
| N08344-1-Q1 | A/C | CTCGTCTCCGTTG GTGGT | 293 | GGCAACCCTTTCA AAACAGA | 294 | ACAGGTCTCCTC CAC | 295 | ACAGGTCGCCTC C | 296 |
| N23533-001-Q011 | C/T | GGAAAGTTGAATTT GATTCGCC | 297 | CATTCCTCAACAA CAACCCCTAA | 298 | CTTGATCATCAC AAAAC | 299 | TCACGAAACTCG ACTGG | 300 |
| N14649-001-Q001 | A/C | TCCTGTACACACAA ATTCAAGACATCA | 301 | GGGTCTTTGAAGT TTAATACTTGTTTA GTTCTC | 302 | CAAAGAGCAAC AACG | 303 | CACAAAGAGAAA CAACG | 304 |
| N23310-001-Q001 | A/G | TGCGCTTGTTTCTA AGACTCCAA | 305 | GGGTCTTCCTAG GAGTGCACTA | 306 | CCTGAAACCGC ATTGC | 307 | CCTGAAACCACA TTGC | 308 |
| N10526-001-Q001 | G/T | CAATCTCAAACTGC CACTCTTGGTA | 309 | TCCTGTCATGTGA GCTTTGCA | 310 | CCATCACGTTAC TACCG | 311 | CATCACGTGACT ACCG | 312 |
| N23373-001-Q001 | C/G | TTCTGGCCATTCAC AGTTAATACGT | 313 | AATTAAAGCACCA ACTATCTTACAAT GTTGAAC | 314 | CCGAGTGA CAACGAATTGAA | 315 | CGGAGTGA CAACGAATTGAA | 316 |

TABLE 8-continued

List of SNP markers and primer sequences used for amplification of loci associated with resistance to shatter

| Marker | SNP | Forward Primer Sequence | Seq ID NO | Reverse Primer Sequence | Seq ID NO | FAM Probe | Seq ID NO | VIC Probe | Seq ID NO |
|---|---|---|---|---|---|---|---|---|---|
| N23353-001-Q001 | C/G | CCTATCTGGAAGTTTGAGCTTGCT | 317 | CTCAACAAGATGTCACCGTCATAGA | 318 | AAGTTGAGCTAAGAATATA | 319 | AAGTTGAGCTAACAATATA | 320 |
| N23206-001-Q001 | C/T | CAGTTTTTCAGTTTAAGAAATATATAAACCGCTTAGAT | 321 | GATAGTTCATGGTAGACCTCAGCAT | 322 | CGAAAAGTAAACTAAACCGA | 323 | CGAAAAGTAAACTGAACCGA | 324 |
| N11025-001-Q001 | A/G | CCACTGCACCCCGTAATCT | 325 | GGGACCAGAGACGTCTGAG | 326 | AACATCTGCGTCGCTAG | 327 | TTGAACATCTGCATCGCTAG | 328 |
| N09969-001-Q001 | C/T | CGGCTCCAAGTTGCTTTTAGTTTG | 329 | GCTATACTTACGTAAAAAAAGCCTTGAGA | 330 | TTATCAAACAGAGTAAATG | 331 | ATCAAACGGAGTAAATG | 332 |
| N09882-001-Q001 | A/C | AGATCTTGTTGACTTCTCGGTTAACTC | 333 | AGGGTCTTGGCATGTTCCTTTT | 334 | TCGGTGACACTTTTA | 335 | ATTTCGGTGAAACTTTTA | 336 |
| N10389-001-Q001 | C/T | ACCTTTTTATATAGAGTAGTCGAGATGGTTTGA | 337 | GTTGACTCTGTGAAGTTAGATGGATCTAAA | 338 | TTTGCTTATGTTATTCTC | 339 | TTGCTTATGCTATTCTC | 340 |
| N09940-001-Q001 | A/G | AAATGTTATATTTTCGTTTAATTGTCTGCTGGTT | 341 | AAAACGTGGGCTTTTTCACAGG | 342 | ACTTGCGACGGTCAA | 343 | TGACTTGCGATGGTCAA | 344 |
| N23409-001-Q001 | C/G | AACCAACACAACTATTACCCAAACCT | 345 | CCGCGTTTTAGAACATGGAGTAGAA | 346 | CAATGAGAGTCTCCACTTT | 347 | CAATGAGAGTGTCCACTTT | 348 |
| N23119-001-Q001 | A/G | CAATGTTAAATTCTGGTGGCCAACA | 349 | GTAGCACTTGAGGAATAACCCTGAT | 350 | ACTGCAGGTTCACCG | 351 | AACTGCAGATTCACCG | 352 |
| N09861-001-Q001 | A/G | AACTGGATGATCGTTTACCACTGAAA | 353 | TCGATTGTTCATAGCTGCCTTTGA | 354 | CCTAATTTAGGATATGTCCCAC | 355 | CCCTAATTTAGGATATATCCCAC | 356 |
| N04807-1-Q1 | A/G | TATCTTCACCGACGGCTTTC | 357 | GAAGTGCCGACTCACCAAGT | 358 | CTCTTTTGTTTCTCC | 359 | ACTCTTTCGTTTCTC | 360 |
| N06778-1-Q1 | C/G | CGATGCACCATCATGTGAG | 361 | CCTCTAATTTCACTGACACTCTTGA | 362 | CAGTTCTCCTTTCCTATT | 363 | CAGTTCTCGTTTCCT | 364 |
| N09897-001-Q001 | C/T | TGGTAGAGCTGAAAGATGATGTTCTC | 365 | AGCCAACCGCTTATTACCACTATG | 366 | TTCGGTATGACAAGATAA | 367 | CTTCGGTATGACGAGATAA | 368 |
| N10499-001-Q001 | A/C | TGGTCTCTGCATCTTCGAATCTG | 369 | CGATATACCAAGGTTGCTGATGCT | 370 | CCAGAAGCATTTGC | 371 | AACCAGAAGAATTTGC | 372 |
| N23447-001-Q001 | A/G | GAACCTAAACCAATGGATAGAAACTTGACT | 373 | TCGAACTAAAACTAGATGATTATGATTAAAGCAGTAAA | 374 | CTTAGGGTGTAGGTTAAT | 375 | CCTTAGGGTGTAAGTTAAT | 376 |
| N19834-001-Q001 | A/G | GTAGACTTTTCCAAGCTAATCTTCAGACAA | 377 | GGTGTTATTGAAGGCACTAGAAGATCA | 378 | CAAATACTTTCAGTATCCC | 379 | CAAATACTTTCAATATCCC | 380 |
| N23362-001-Q001 | A/G | GGCCTTGGGATTAAGAATCTTTCGA | 381 | CGAGCCTGCCTGAAAGAAAAGTA | 382 | CAGATCAACCTAAGGCA | 383 | CCAGATCAACTTAAGGCA | 384 |
| N23266-001-Q001 | C/G | GCAGCTCTTTGTTTCAAACCCATTA | 385 | GTACCGATGAAACGCGAGAAG | 386 | CACATCAATTCAGTTTTT | 387 | CACATCAATTGAGTTTTT | 388 |
| N19862-001-Q001 | A/C | GTGGCACAAGATGCGATGAG | 389 | AAGTTTCATTAGTTTTGATGGGTAGTGCTA | 390 | AAGATCCGCATGGCT | 391 | AAGAAGATCAGCATGGCT | 392 |
| N22187-001-Q001 | A/G | CATCTGGATCACCGGTTGGT | 393 | CCGTCACTGTCTCAGGAGGAA | 394 | AACGCCCGCCAGAGA | 395 | CAACGCCCGCTAGAGA | 396 |
| N08651-1-Q1 | A/T | GATAACTATATTCATCGACTCCCAAAC | 397 | GGACCATCTGCGTGGTAGA | 398 | ACATAAGTTACCACCAGTT | 399 | ACAAAAGTTACCACCAGTT | 400 |

TABLE 8-continued

List of SNP markers and primer sequences used for amplification of loci associated with resistance to shatter

| Marker | SNP | Forward Primer Sequence | Seq ID NO | Reverse Primer Sequence | Seq ID NO | FAM Probe | Seq ID NO | VIC Probe | Seq ID NO |
|---|---|---|---|---|---|---|---|---|---|
| N23296-001-Q001 | A/G | CTTATACACTTAAGTCTTTGAATTTCAAACTATGCA | 401 | CCACAACAAACAGCTCTACTTACAATAC | 402 | CTTCGCATCCTAATCG | 403 | CTTCGCATCTTAATCG | 404 |
| N17314-001-Q001 | G/T | CGCTTGAGAGCTTTTAAAGAGAGATAGT | 405 | GCCCATTTAAGCACCATACCAATC | 406 | ACTGCATGCAATTATATAT | 407 | CTGCATGCAATGATATAT | 408 |
| N20380-001-Q001 | A/C | AAACTGTGAGTCCCTGGAGAGA | 409 | GTATGGCTTCTTGATTAAGTTTGAAGCA | 410 | CACAACCTGAACTCTACT | 411 | CACAACCTGAAATCTACT | 412 |
| N05490-1-Q1 | C/G | CAGATTGGTAATGGTTCCCTGT | 413 | CATGGATTTTCCTGCCCTAA | 414 | TTGCATATCATCCCCA | 415 | TTGCATATCATCGCC | 416 |
| N18849-001-Q001 | G/T | CCATGCAACGTAGGAAACAAGTATC | 417 | CGAGGTCGAATTGTTTTGGTATGTG | 418 | AACTTCTCTATATTTTCC | 419 | TGAACTTCTCTATCTTTTCC | 420 |
| N08200-1-Q1 | C/G | AAGAGAAGCGTCTCCTCGTTC | 421 | TCGACGTCTATCCCCAAGAT | 422 | ACGCAACCACCGAT | 423 | ACGCAACGACCGAT | 424 |
| N19827-001-Q001 | A/G | GAAAGATAATTAAATAAAACGAACCAACAAACAACA | 425 | CCAAACATTTATTACTAGGATTTTCCTCCCT | 426 | AATAGCCACGAATGAA | 427 | AGAAATAGCCACAAATGAA | 428 |
| N001R9W-001-Q001* | A/C | CGGAGACCTTCAGTGTGTTAGAC | 429 | GTTCCCAATGTAAGCACAAAGGTT | 430 | ACGTGATAACCAACTAC | 431 | ACGTGATAACAAACTAC | 432 |
| N08264-1-Q1 | C/T | TCAACAACTGGTTCATCTGGAA | 433 | CCAGTGAAGATGGATGCAAAG | 434 | CTACCACAGACTTATC | 435 | TCTACCACAGACTTGTC | 436 |
| N23132-001-Q001 | A/G | CTTACTGATCATGTTAGTTGGCAGTTTT | 437 | GAGCCATTGTTTGTAAGAGAAATTGAATATGA | 438 | TTGAGTATGCAGGTATGTC | 439 | TTGAGTATGCAGATATGTC | 440 |
| N03615-1-Q1 | A/T | CGTCTCTGCTTACCTCACTATGAA | 441 | GCAGTAGACAACAGCTTTTGGAA | 442 | ACATAAACATGGTCTGC | 443 | ACATAATCATGGTCTGC | 444 |
| N001RWT-001-Q001* | A/G | TGATTTGCCTAGACCAATTTTTAGAACAC | 445 | GGTTAAAACATGAACCGTTAAGCTGAA | 446 | TTTGTCTTTGGTTGTAGTTG | 447 | TGTTTGTCTTTGGTTATAGTTG | 448 |
| N08465-1-Q1 | A/G | TCCTTCTCCTCCGAGAAAGTT | 449 | CCTCCGTATCCGTAGACATCA | 450 | ACGTTAAATCGTTTAGTTG | 451 | CAACGTTAAGTCGTTTAG | 452 |
| N1C774-001-Q001 | A/C | CACTAATTTATATAGAAAATATGTAAAACTTTTTCCATCA | 453 | GATGGGTGCCATAATAATCTATTTATACTTTTTTTGT | 454 | TTTCTAACATCGTGGAAAT | 455 | CCATTTCTAACATAGTGGAAAT | 456 |
| N17035-001-Q001 | A/G | TGTGAAAATATAAGTTTCACATCGAGATCGA | 457 | TCATGTTAAGTTTGGATTTATCATGAGTTTTCAAATT | 458 | TCAATCCACGTATTACC | 459 | ATCAATCCACATATTACC | 460 |
| N20834-001-Q001 | C/T | AAACGCCAAAACTGGTCATCTTG | 461 | ACCGTAACCAGCTCTCTCTGTAATA | 462 | ACGTGTCGTAATTCATGT | 463 | ACGTGTCGTAGTTCATGT | 464 |
| N22903-001-Q001 | C/G | CCGCCAAGTTTTAAACAAAATCAATAAATCATATT | 465 | TGTGCAGTTAATAGTTGTATAGTGTATCTTTG | 466 | TGAAGTTTCAACCACCATT | 467 | TGAAGTTTCAAGCACCATT | 468 |
| N09920-001-Q001 | A/T | AGCCAATTTTAAGTAAATCATTGAATATTGTTAGTGT | 469 | CGGAGGGATTTCGAAATAGTATGTT | 470 | CCTCTCTGAGTTAATTGA | 471 | CCTCTCTGAGTAAATTGA | 472 |
| N22822-001-Q001 | C/G | GTAGGGTATCATTTTATTTTCTATCGACTGAGT | 473 | CGCGTGCTTAGTGGTTACCA | 474 | AGTGCTTGTGTCTCATG | 475 | CAGTGCTTGTGTGTCATG | 476 |
| N22688-001-Q001 | C/G | GCATGAATAGTAGTAGCTTTCTTTTTTTAAATGTGTATA | 477 | AAATTAACAACAGTGTTACCTAATTATTATAAAGAATTA | 478 | TTGAGAAGTCTCGAAAAT | 479 | TTGAGAAGTCTGGAAAAT | 480 |

TABLE 8-continued

List of SNP markers and primer sequences used for amplification of loci associated with resistance to shatter

| Marker | SNP | Forward Primer Sequence | Seq ID NO | Reverse Primer Sequence | Seq ID NO | FAM Probe | Seq ID NO | VIC Probe | Seq ID NO |
|---|---|---|---|---|---|---|---|---|---|
| N10074-001-Q001 | G/T | CGCCAACTACACAAGAGCATAATTT | 481 | GAAGCTGTGGAAGTTACAATGCAAA | 482 | CCTCAAGTCTTAAACTT | 483 | CTCAAGTCTGAAACTT | 484 |
| N10057-001-Q001 | C/T | TCCACAATCTCTCCTTCCAAATTCAC | 485 | ACTCGGGTCTGTACGTTGAGA | 486 | CGGAGACAAGGAAG | 487 | ACCGGAGACGAGGAAG | 488 |
| N10086-001-Q001 | C/T | TCACCTCTCATGTTGCTATAAGGTTATCT | 489 | CTGAAGCAATCACAAATTGAACTAAAGGA | 490 | AACTTCTCACATTGCC | 491 | AACTTCTCGCATTGCC | 492 |
| N11084-001-Q001 | A/G | TTTTCTCACAAAGATCATGTACTCATTACTTCTT | 493 | AAGCTTGCAAGCCAAAAGAGATG | 494 | CGCAACACAAGATT | 495 | ACCGCAACATAAGATT | 496 |
| N22814-001-Q001 | A/T | CTCCTTCTAGAGTCTGGGAATCGAA | 497 | GCAGAAAATTTGGACCCCCATTAAA | 498 | TTTGCGTCATTAAAAT | 499 | TTTGCGTCAATAAAAT | 500 |
| N01564-2-Q1 | A/C | AAGTTCATCTACACTTAATCCGACACA | 501 | GAGTTCATTCCACAGATCTGACCAT | 502 | CCTATCAAAGCACGTCT | 503 | CTATCAAAGCAAGTCT | 504 |
| N12902-001-Q001 | C/T | CGATCGAGAGAAACTTCGAGACTT | 505 | CCGATAAAACAATCAACACCAAAACAATTAA | 506 | CCCAACAAAAGAGGCA | 507 | CCCAACAAGGAGGCA | 508 |
| N21144-001-Q001 | A/C | AGTAGAATACTTAATGTTTATAATCACGAGATATAATTGTTTTCA | 509 | CCTGGTGGCCATGTATAATATCACA | 510 | ATCCCCACATGATGC | 511 | CATCCCCAAATGATGC | 512 |
| N07534-1-Q1 | G/T | TAGAGACCAAGGCCCAACAG | 513 | TTATTTGTGTGGTGCGGTTC | 514 | TCCACAACTAGCAACC | 515 | CCACCACTAGCAAC | 516 |
| N22993-001-Q001 | C/G | CTGAGTAATTATAGTATTGTGCCAACCCT | 517 | GGGCTTTTGTTTGACTTGTGCAA | 518 | CAAAGAAGTCCGTCTAAC | 519 | CAAAGAAGTCGGTCTAAC | 520 |
| N09963-001-Q001 | G/T | GCATCAACCATCAATCTGAATGGTATG | 521 | GGCATCCTACTGACCTGTATGTTAA | 522 | ATTTGCAAAAATTTCTCT | 523 | AATTTGCAAAAAGTTCTCT | 524 |
| N115C2-001-Q001 | C/T | GTCCCATGCATTGTATTTGAAGTTGA | 525 | TGCATACATATGATCATCAAATTTCCCAATG | 526 | CTAGATGCACACTTCTA | 527 | CTAGATGCACGCTTCTA | 528 |
| N14681-001-Q001 | A/C | ATCATAATGTCATGACTGCCTGGTTT | 529 | TCTTAAAAACCAACTACACACATCGTT | 530 | TCCCATATGTGTATCATG | 531 | CATCCCATATGTTTATCATG | 532 |
| N11636-001-Q001 | A/G | GTTCGACCTGGAATATCGGAAGA | 533 | CACTTGCACGATATCGCGAATC | 534 | TAGATGACTTATCGGAAAGT | 535 | ATAGATGACTTATCAGAAAGT | 536 |
| N13732-001-Q001 | C/T | GATCAATGTACACGCGTCAAGAC | 537 | GGAGTTCCATCACGCCTCTTC | 538 | AAGAATGTTGAAACCGC | 539 | AAGAATGTTGGAACCGC | 540 |
| N11255-001-Q001 | C/T | CAATAAAACAAAACAATAATCTGACGCACAT | 541 | GAGTCTCAGATTGATAGCCCCAATT | 542 | CTTCATAGTTTGATAAGTTC | 543 | TTCATAGTTTGGTAAGTTC | 544 |
| N15511-001-Q001 | A/G | AGCCTGGTGCGTATGTATCATAAAA | 545 | ATCGAAAGATGCATAGAGTAATGATTAATAACCA | 546 | CTAAAACTGTGGTGGTTTA | 547 | CTCTAAAACTGTGATGGTTTA | 548 |
| N10536-001-Q001 | G/T | CTTCCCGGAAAAGGTATCGATTGTA | 549 | ACGCTTCAAACCCTAAAGACAGAAT | 550 | ATTTCATCTTGATTCTATTG | 551 | ATTTCATCTTGAGTCTATTG | 552 |
| N09862-001-Q001 | A/G | CCAGGATCGATTTGAGATGAAAGCT | 553 | TCAACAGTCAACTTTTGAACAAAAAGGT | 554 | ATATAGCTAGGCAATTCA | 555 | AGGATATAGCTAGACAATTCA | 556 |
| N23033-001-Q001 | A/T | CGGTAAACCAGTACAAAATATCCAAATGTT | 557 | CGGATTTAAAATAGTTTGAAGATAAATAATGGCTTGT | 558 | ACTTGTGCTAATCTCT | 559 | CTTGTGCAAATCTCT | 560 |

TABLE 8-continued

List of SNP markers and primer sequences used for amplification of loci associated with resistance to shatter

| Marker | SNP | Forward Primer Sequence | Seq ID NO | Reverse Primer Sequence | Seq ID NO | FAM Probe | Seq ID NO | VIC Probe | Seq ID NO |
|---|---|---|---|---|---|---|---|---|---|
| N06039-1-Q1 | G/T | CCCAGTACCCAATGCTCATC | 561 | CCGTCGGTTATACACACCAAG | 562 | AACTGCCTTTGTTTTGT | 563 | CTGCCTGTGTTTTGT | 564 |
| N10016-001-Q001 | C/T | GCTTTGCCTAAGAGATTGCTTCATG | 565 | TGCTTGTGCTTGTAGTCATCTGA | 566 | TTGAACGAAAATTAGC | 567 | TTGAACGAAGATTAGC | 568 |
| N22743-001-Q001 | A/T | GGATTTGTTATACCATTGCATCAAGCA | 569 | ACAGAGGGTCGTTGGACAAC | 570 | ACACTTCTCAAAGGCT | 571 | CACACTTCTCAATGGCT | 572 |
| N22953-001-Q001 | A/T | CTAGTTTCTTTCCTTGTACTTCCTTCCA | 573 | GCTTTCCTATTTTTATCGGAAATTGACAGT | 574 | TGACAAGGAACTAAGTTTA | 575 | TGACAAGGAACAAAGTTTA | 576 |
| N09987-001-Q001 | A/G | AGAATAAACAGCTTTCTACACCCGTAG | 577 | TCTGGTGGGATAAGGTGATTGAGA | 578 | CACCAAGACTGAGACAC | 579 | TCACCAAGACTAAGACAC | 580 |
| N10092-001-Q001 | A/G | GGCATCGTCTGGTTGATCAAGA | 581 | CCCATTCCACTTGATAACCCGATTT | 582 | CATGACATTTGCCATTAA | 583 | TGCATGACATTTTACCATTAA | 584 |
| N10096-001-Q001 | A/G | CATAGACCTCCACATCACCAAGAAA | 585 | TGTAAAGCAAAACCCAAACACAATAAAGT | 586 | AGGGAGACACGTGTCAT | 587 | AAGGGAGACACATGTCAT | 588 |
| N22728-001-Q001 | C/G | AGCACACAAAGGTTTCTTAGGAAGATTATT | 589 | GGTTCAAATGTTTAGGACACGAAAGAC | 590 | CCCGAATGCCCAGACC | 591 | CCGAATGCGCAGACC | 592 |
| N22747-001-Q001 | C/G | ATCTATTCCCAGAGAATACGTTTTTCGA | 593 | GCCCCTAGTGAAAAGAATGAGGTAA | 594 | TCAGAGACCAGGAATT | 595 | TCAGAGACGAGGAATT | 596 |
| N22840-001-Q001 | A/T | ACCTCCATTCATCATTCCCAATCC | 597 | GCTCGGCTAAGAATCACACTGAAA | 598 | CAACACCAAGTTCTTAC | 599 | CAACACCAAGATCTTAC | 600 |
| N23027-001-Q001 | A/T | CCGCTTTTGCCCATGGC | 601 | ACTACCAACGTTAAGAATACACTTGGATTT | 602 | ATTGCATTCAGTTGTTGAA | 603 | ATTGCATTCAGTAGTTGAA | 604 |
| N22777-001-Q001 | C/G | GAACAACAGTTTGCCATTTCCTTACT | 605 | GGCATCCATTACCTATCAATTTCTTGGA | 606 | CGTAAAAGCGAAAGTA | 607 | CCGTAAAAGGGAAAGTA | 608 |
| N09636-001-Q001 | G/T | AGCGAAAAGATTACACTTTGTTTCTTTGAA | 609 | GCCTTAGTATACTCTAGTTTCATTGCCAAA | 610 | TTTTGGTTTTTCTGGTTTAT | 611 | TTGGTTTTTCGGGTTTAT | 612 |
| N09879-001-Q001 | A/G | CTCCAGTTGCAACTTCTTCAAATCAT | 613 | GATGACCCATAGACCAAAGCCATAT | 614 | TGTTTAATGAAACGCTATTG | 615 | CATGTTTAATGAAATGCTATTG | 616 |
| N10123-001-Q001 | A/G | CAAATGACTAACCTGCGCAAGTG | 617 | AGTCAAGGGAGTGGGAAAGTAGAT | 618 | CCGGTTGGTTCGACA | 619 | CCCGGTTGATTCGACA | 620 |
| N10316-001-Q001 | C/T | ACCAGGAAGGAGGTCAAGATCTTAA | 621 | AGCATCGACTTTCTACATTATGTTCTCTTTT | 622 | AATGCTCCATTAACAAA | 623 | ATGCTCCGTTAACAAA | 624 |
| N10507-001-Q001 | C/T | CGCTTACATCATTATTCATTTTTTAGACACACT | 625 | GGTAGTTGCGACAAGCACATC | 626 | CACCATTATCGATGTTTAA | 627 | ACCATTATCGGTGTTTAA | 628 |
| N09834-001-Q001 | C/T | TGCTCCACTGTCTCTTCAGAAAC | 629 | AATCCTTAACTGAAACCTGGACTCG | 630 | ATTCGCTAGATTCCA | 631 | ATTCGCTGGATTCCA | 632 |
| N22934-001-Q001 | A/T | GACCAGAGTTGATCCAGGAATGTAA | 633 | GCACGGTGATCTTGGACACAT | 634 | TTTCTGGCCTATGAGCTCA | 635 | TTTCTGGCCTTTGAGCTCA | 636 |
| N22700-001-Q001 | A/T | CAAACCGTACTTCCCTATGATGGT | 637 | TGGTATCTCGACAATGGAGCTAGT | 638 | ATCTCCTGTCATATGATT | 639 | TCTCCTGTCAAATGATT | 640 |
| N22725-001-Q001 | A/T | GCATTGGCAGGTTTTAAATCTCAGA | 641 | CTCAAAACCAATGGAAGTGTTACTGT | 642 | TTGTGCATAATGACACCC | 643 | TGTGCATAAAGACACCC | 644 |

TABLE 8-continued

List of SNP markers and primer sequences used for amplification of loci associated with resistance to shatter

| Marker | SNP | Forward Primer Sequence | Seq ID NO | Reverse Primer Sequence | Seq ID NO | FAM Probe | Seq ID NO | VIC Probe | Seq ID NO |
|---|---|---|---|---|---|---|---|---|---|
| N22881-001-Q001 | A/T | TGATATCACGACG ACGGTTTCTG | 645 | GAGCTTTCTCCAG CGTGATTG | 646 | CTCAGTCTCTCT CGGAGAT | 647 | CTCAGTCTCTCA CGGAGAT | 648 |
| N23032-001-Q001 | A/T | GAAATCCTACACG ATTTTAAGCATGTC AA | 649 | GCGCATCACCCT CATTCC | 650 | TACACCCCAGG CTTAA | 651 | ACACCCCTGGCT TAA | 652 |
| N22786-001-Q001 | C/G | GAGTTTCTTGTATT CATCTAGGTCAAC GA | 653 | TGAGGATATACAT GCATATCTTGCCA TATATTTG | 654 | CGGTATTAGGTA ACCTAGCAT | 655 | CGGTATTAGGTA ACGTAGCAT | 656 |
| N23014-001-Q001 | C/G | CACCAAAGCTAACT CTGCACTCT | 657 | CAGGACGAGTTA AGGCAAGGT | 658 | ATTGTAGACTGC CTACTAC | 659 | ATTGTAGACTGC GTACTAC | 660 |
| N10471-001-Q001 | C/T | GACATCTTTTGGGA CCTTAGCATCT | 661 | GGATTAGCCAAGT TCCATTCCTACA | 662 | AAGCAACTCAAT AAGAAGA | 663 | AAGCAACTCAAT GAGAAGA | 664 |
| N11419-001-Q001 | C/T | TGCAACTTGGTCA GCACTCA | 665 | CACCATATAGGAA ATCATGAGCACGA A | 666 | TCGCGCTCTATT TCA | 667 | TCGCGCTCTGTT TCA | 668 |
| N22724-001-Q001 | A/T | CGATTCGGAATGA TCATATAAGATCAA ACTTC | 669 | GGGTAATTACGG ATGCAAGACTTTA TAGTT | 670 | ATGTCTGCACTA TATCTAT | 671 | TGTCTGCACTAA ATCTAT | 672 |
| N12785-001-Q001 | A/G | CCGCTGAAGGTAT ATCGAAGAATCT | 673 | CCTTGTTCAGTCT TACTCAGCTTTTG | 674 | CAAACCGGATG ATGC | 675 | TTCAAACCGAAT GATGC | 676 |
| N09910-001-Q001 | A/T | AAAGCAACCAAAG AAGTGTTTGATATA ACTTATTTTA | 677 | CTCCATCAATCCA TGGGAAGACTTA | 678 | TCGTCCATATAG TTCAAG | 679 | ATCGTCCATATT GTTCAAG | 680 |
| N21146-001-Q001 | A/C | CGATGGTTGTTAG ATATATGTCTAGTC CTAAGT | 681 | GGAAGAGAAGAA CAAGAGGAAGAC TTT | 682 | AACGTTCACCAT CTCT | 683 | AACGTTCACAAT CTCT | 684 |
| N17618-001-Q001 | A/G | CGTATAAGTGTGG TGCCAATTGTTT | 685 | GGATCCTTGGCG CTCTCC | 686 | CGCAAGGACAT TC | 687 | CCGCAAGAACAT TC | 688 |
| N09776-001-Q001 | A/C | GCGTCTTGTTTGC CAAATCTGT | 689 | CTTTGGTAGTTGT TGTTGAATCTGTT GT | 690 | CTGGTTATACAG CTCTGAAGT | 691 | CTGGTTATACAG CTATGAAGT | 692 |
| N19296-001-Q001 | A/C | GCAACGAACAAAA TAAAAGATGGAGAT GTAA | 693 | TCTGTACTTTCTT TTAAGCCCTTCCA | 694 | AAAGGCTGAATC CGTTTT | 695 | AAGGCTGAATCA GTTTT | 696 |
| N05205-1-Q1 | G/T | TGGTTTGCTACCTC CGTTTC | 697 | TGCAAAAGGCAAA AGATTCA | 698 | CTCATATCCACT GTTGC | 699 | CTCATAGCCACT GTTG | 700 |
| N10406-001-Q001 | C/G | ACGGCTCATGTTG GATCGT | 701 | ACCCATGGTCGC CACAAAT | 702 | ATTTTGTTTTCC CTTTTTC | 703 | TTTTGTTTTGCCT TTTTC | 704 |
| N22941-001-Q001 | C/G | TCTGCCCAAAGTG AATCAGTATTCA | 705 | TGCAAGAGGATAT GTCACAGAACTC | 706 | CTGCCTGAACCT TTTA | 707 | CTGCCTGAAGCT TTTA | 708 |
| N22875-001-Q001 | C/G | CGAGCATTAATGA CTTACCATCCTTCA | 709 | ACAGCCTCAGGA ACATCAGAAG | 710 | CAGAGTAGTAAC CCTGGTTT | 711 | CAGAGTAGTAAC GCTGGTTT | 712 |
| N11286-001-Q001 | A/G | GACCGTGTTAAGC TGTAAATCGATAAC | 713 | GGTCTCTTAAAAT AAGTAACTAGTAG TGAAGAAATGT | 714 | ACTTGCATGACC TTCATA | 715 | CACTTGCATGAC TTTCATA | 716 |
| N04503-1-Q1 | C/G | TAATAAGCCGAGC CACCAAG | 717 | GACGAGGGAGGA AATGTTCA | 718 | ACCAAGCTTCTC TC | 719 | CCAAGCTTCTGT CGC | 720 |
| N22925-001-Q001 | C/G | TGTCGATTGGCTCT TTTGAGATTCA | 721 | AGAAGTTATGAAA AGAGAGAGGTGT ACTACT | 722 | AGGAGTATCGTA CATCTCA | 723 | AGGAGTATCGTA GATCTCA | 724 |

TABLE 8-continued

List of SNP markers and primer sequences used for amplification of loci associated with resistance to shatter

| Marker | SNP | Forward Primer Sequence | Seq ID NO | Reverse Primer Sequence | Seq ID NO | FAM Probe | Seq ID NO | VIC Probe | Seq ID NO |
|---|---|---|---|---|---|---|---|---|---|
| N05656-1-Q1 | G/T | TTGCTCGGTTTTAACCTCGT | 725 | AAGAAATGGGGGAAAGGATG | 726 | TCTTCGCTTTATCACC | 727 | CTTCGCTGTATCACC | 728 |
| N17581-001-Q001 | A/C | GAAGGTTTCCTCGTGGAATGACT | 729 | GATATGGGTCCTTGCGGTCTATTT | 730 | TCCCTAAGCAGAGAAG | 731 | ATTAATCCCTAAGAAGAGAAG | 732 |
| N001NVH-001-Q001* | A/G | CGTCTACAATTTCATTAGTCTCAAGAAAAACA | 733 | GCTTCTGGATAATTGGATTGGG | 734 | TGGGATGTAATCTGGCTAT | 735 | TTTGGGATGTAATTTGGCTAT | 736 |
| N22928-001-Q001 | A/T | GATTGCGTTTTTGCGTGAAGTC | 737 | GCAACTCATACTGAAACGTGTTGA | 738 | TTGCAAGTGTCTTTCATG | 739 | TGCAAGTGTCATTCATG | 740 |
| N08219-1-Q001 | G/T | TGGGAGAGAGCCTAAGTTTCTG | 741 | CGCAACACTAGGAAACACCTT | 742 | ACACCATCAAGAAC | 743 | ACACCATCAAGCAC | 744 |
| N05710-1-Q1 | A/G | TTCCATCACCACTGAAACAGA | 745 | CGTGGCTATGCACCATCC | 746 | TTCCCAAGACAAAAC | 747 | CCCAGGACAAAAC | 748 |
| N15338-001-Q001 | C/T | AAACAAAAACAAAATCATTCTGAGACTTTGAAAC | 749 | TGAAGATGAACTCGCCGTATAGAAAAG | 750 | TCAATAAACTAATTACTTTTC | 751 | CAATAAACTAATTGCTTTTTC | 752 |
| N10424-001-Q001 | A/G | CTTCGACGGATTCCTTGATGGA | 753 | CTGTTCAGCAGAGCCAAGATACA | 754 | CCCTCTTTCGATGTTC | 755 | AACCCTCTTTTGATGTTC | 756 |
| N16006-001-Q001 | C/T | GTTTTTCTGATGTTGAAGGAGGTTGA | 757 | GTGTCCCGACCAACAATTCC | 758 | TCCACCAGAATTTAGA | 759 | CTCCACCAGAGTTTAGA | 760 |
| N07278-1-Q1 | A/G | CCTGATTCAAGAAGTCGCAGA | 775 | TCCCAAGCTCAAGCTAGACAA | 776 | CTTAGTTTCATCTGTATTC | 777 | CTTAGTTTCGTCTGTATTC | 778 |
| N16343-001-Q001 | A/C | AGGACAATCGAACTTTTCAATATAGACGATT | 779 | TCGTGACTTAACCATTTGTCAACT | 780 | TAGAGCCGAAGACTC | 781 | ATATATAGCAGAAGACTC | 782 |
| N23417-001-Q001 | C/G | CCAATGCGTTCTCTCAGGTTCTTAT | 783 | AGCTAGGAGGAGCCTAAACCAATAT | 784 | ATGGTCGAGTCTGCAAG | 785 | ATGGTCGAGTGTGCAAG | 786 |
| N22902-001-Q001 | C/G | ACCCTCTGGGTTTTCTGAACTTTG | 787 | AAGATTTGGTGCGCACTACTAGT | 788 | TCGTATAAAGACGGTTTAA | 789 | CTATCGTATAAAGAGGGTTTAA | 790 |
| N23063-001-Q001 | A/T | GGAGAATGCCTTGTTGATGTCTCA | 791 | GTCCCCTTTGTGTCATCTTATCGAT | 792 | CTAGTCAGTCAGGTTTG | 793 | CTAGTCAGACAGGTTTG | 794 |
| N22723-001-Q001 | C/G | AAGGAGCTTTCCGGTCTATCTCT | 795 | CGATCCTTGGTTAATGACTGGAGAT | 796 | CAGTTTTCTCGGAGTTGT | 797 | CCAGTTTTCTCCGAGTTGT | 798 |
| N23049-001-Q001 | A/T | TTGCCCATCAACACCTTTCTGA | 799 | CTGAGAAATAAACGGATCAAAACCCAAT | 800 | CATATTAACATAACTTTTATTTGG | 801 | CATATTAACATAACTTTAATTTGG | 802 |
| N10321-001-Q001 | A/T | CCATGGCAAGGCACAAACAC | 803 | CAGTTTGAAGGCTCGTTAGGTATTGA | 804 | ATGTAAGTACACTTCTTTG | 805 | ATGTAAGTACACATCTTTG | 806 |
| N15374-001-Q001 | A/C | ACTTGGCACTTCACCAAACCA | 807 | CAGTCCAGGATAGAGGCATGAGA | 808 | ATTTGATTTTGTATCATCCG | 809 | ATTTGATTTTGTATAATCCG | 810 |
| N22802-001-Q001 | C/G | GAAGAACACGCCGCCTTTTC | 811 | TCACATCTTTGCTTATTGTCTTCATACCA | 812 | ATGGAAGTACAACTTCAGC | 813 | ATGGAAGTACAAGTTCAGC | 814 |
| N22803-001-Q001 | A/T | GCTCGTTGCTTCTCTTTCCAAAG | 815 | CAGGAGGAAATCAAAAGTGAAACCA | 816 | CTAAAATCGCTATTCTTGG | 817 | CCTAAAATCGCTATACTTGG | 818 |
| N18929-001-Q001 | A/G | ACTTATCTCATTTGAGTTTTGCCGATGA | 819 | GTACCCTGAAGCGACATTGGA | 820 | TGGTTTTACGGATGGTT | 821 | TGTGGTTTTTACAGATGGTT | 822 |
| N16041-001-Q001 | C/T | TCTCAAAACCCATAGTAAAACACAAGTCT | 823 | TGCCTATGAAATGTTTGATAACAATTATAAAAGTTAACC | 824 | TTAGGCTCTAAGCTTG | 825 | CTTAGGCTCTGAGCTTG | 826 |

TABLE 8-continued

List of SNP markers and primer sequences used for amplification of loci associated with resistance to shatter

| Marker | SNP | Forward Primer Sequence | Seq ID NO | Reverse Primer Sequence | Seq ID NO | FAM Probe | Seq ID NO | VIC Probe | Seq ID NO |
|---|---|---|---|---|---|---|---|---|---|
| N18401-001-Q001 | C/T | TCGTCTTTCTCGCTTTCTCACTTTT | 827 | CAGAGTCATATTTTTTACCACTGGCTTTT | 828 | CCCGTCTACAAAGC | 829 | ACCCGTCTGCAAAGC | 830 |

While the foregoing invention has been described in some detail for purposes of clarity and understanding, it will be clear to one skilled in the art from a reading of this disclosure that various changes in form and detail can be made without departing from the true scope of the invention. For example, all the techniques, methods, compositions, apparatus and systems described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of BB2360sequencelisting.txt, created on Jul. 10, 2015 and having a size of 307 kilobytes. The sequence listing filed via EFS-Web is part of the specification and is hereby incorporated in its entirety by reference herein.

Standard IUPAC notation is used in the text file submitted via EFS-Web. Standard IUPAC notation is shown in Table 9.

TABLE 9

Standard IUPAC notations.

| IUPAC nucleotide code | Base |
|---|---|
| A | Adenine |
| C | Cytosine |
| G | Guanine |
| T (or U) | Thymine (or Uracil) |
| R | A or G |
| Y | C or T |
| S | G or C |
| W | A or T |
| K | G or T |
| M | A or C |
| B | C or G or T |
| D | A or G or T |
| H | A or C or T |
| V | A or C or G |
| N | Any base |
| . or - | Gap |

What is claimed is:

1. A method of producing a *Brassica* plant or germplasm that exhibits pod shatter resistance, the method comprising crossing a first plant comprising a pod shatter resistance locus with a second plant lacking the pod shatter resistance locus to produce progeny seed for a nucleic acid, screening a population of progeny seed or a progeny plant grown therefrom, wherein the first plant comprises a quantitative trait locus (QTL) on linkage group N4 and detecting in the progeny plant or germplasm at least one allele of the at least one QTL that is associated with the shatter resistance, wherein the QTL is localized to linkage group N4, wherein said linkage group comprises at least one marker that is associated with the resistance to shatter with a statistical significance of p≤0.01, wherein the QTL is localized to a chromosomal interval flanked by and including markers N88514-001-K001 and N88537-001-K001 on linkage group N4; and wherein the marker comprises an allele selected from the group consisting of a C at a position corresponding to 201 of SEQ ID NO: 17, a G at a position corresponding to 151 of SEQ ID NO: 15, an A at a position corresponding to 201 of SEQ ID NO: 25, an A at a position corresponding to 201 of SEQ ID NO: 23, and A at a position corresponding to 101 of SEQ ID NO: 26, an A at a position corresponding to 201 of SEQ ID NO: 22, an A at a position corresponding to 201 of SEQ ID NO: 30, a C at a position corresponding to 201 of SEQ ID NO: 32, a G at a position corresponding to 201 of SEQ ID NO: 37, and a T at a position corresponding to 501 of SEQ ID NO: 14, thereby producing the *Brassica* plant or germplasm that will exhibit shatter resistance.

2. The method of claim 1, wherein the marker comprises at least five alleles selected from the group consisting of a C at a position corresponding to 201 of SEQ ID NO: 17, a G at a position corresponding to 151 of SEQ ID NO: 15, an A at a position corresponding to 201 of SEQ ID NO: 25, an A at a position corresponding to 201 of SEQ ID NO: 23, an A at a position corresponding to 101 of SEQ ID NO: 26, an A at a position corresponding to 201 of SEQ ID NO: 22, an A at a position corresponding to 201 of SEQ ID NO: 30, a C at a position corresponding to 201 of SEQ ID NO: 32, a G at a position corresponding to 201 of SEQ ID NO: 37, and a T at a position corresponding to 501 of SEQ ID NO: 14.

3. The method of claim 1, further comprising detecting at least one marker selected from the group consisting of: N05943-1-Q1 (SEQ ID NO:10); N06007-1-Q1 (SEQ ID NO:11); N10105-001-Q-001 (SEQ ID NO:12); N08181-1-Q1 (SEQ ID NO:13); N06675-1-Q1 (SEQ ID NO:14); N001KH2-001-Q001 (SEQ ID NO:15); N29313-001-Q001 (SEQ ID NO:16); N88512-001-K001 (SEQ ID NO:17); N88514-001-KO01 (SEQ ID NO:18); N88515-001-K01 (SEQ ID NO:19); N88516-001-KO01 (SEQ ID NO:20); N88517-001-K01 (SEQ ID NO:21); N88518-001-K001 (SEQ ID NO:22); N88519-001-K001 (SEQ ID NO:23); N88520-001-K001 (SEQ ID NO:24); N88521-001-K001 (SEQ ID NO:25); N001KFE-001-Q001 (SEQ ID NO:26); N88522-001-K001 (SEQ ID NO:27); N88523-001-K001 (SEQ ID NO:28); N88524-001-K001 (SEQ ID NO:29); N88525-001-K001 (SEQ ID NO:30); N88529-001-K001 (SEQ ID NO:31); N88530-001-K001 (SEQ ID NO:32); N88531-001-K001 (SEQ ID NO:33); N88533-001-K001 (SEQ ID NO:34); N88535-001-K001 (SEQ ID NO:35); N88536-001-K001 (SEQ ID NO:36); N88537-001-K001 (SEQ ID NO:37).

4. The method of claim 3, wherein the detecting comprises detecting at least one marker selected from the group consisting of: N88514-001-K001 (SEQ ID NO:18); N88515-001-K001 (SEQ ID NO:19); N88516-001-K001 (SEQ ID NO:20); N88517-001-K001 (SEQ ID NO:21); N88518-001-K001 (SEQ ID NO:22); N88519-001-K001 (SEQ ID NO:23); N88520-001-K001 (SEQ ID NO:24); N88521-001-K001 (SEQ ID NO:25); N001KFE-001-Q001 (SEQ ID NO:26); N88522-001-K001 (SEQ ID NO:27); N88523-001-K001 (SEQ ID NO:28); N88524-001-K001 (SEQ ID NO:29); N88525-001-K001 (SEQ ID NO:30); N88529-001-K001 (SEQ ID NO:31); N88530-001-K001 (SEQ ID NO:32); N88531-001-K001 (SEQ ID NO:33); N88533-001-K001 (SEQ ID NO:34); N88535-001-K001 (SEQ ID NO:35); N88536-001-K001 (SEQ ID NO:36); and N88537-001-K001 (SEQ ID NO:37).

5. The method of claim 3, further comprising detecting a second marker located in a different linkage group.

6. The method of claim 1, wherein the plant is *Brassica napus; Brassica juncea; Brassica rapa; Brassica oleracea;* or *Brassica carinata*.

7. The method of claim 6, wherein the plant is *Brassica napus* (canola).

8. The method of claim 7, wherein the plant is spring canola.

9. The method of claim 7, wherein the plant is winter canola.

10. The method of claim 7, wherein the plant is semi-winter canola.

11. A method of producing an F1 hybrid seed, wherein the F1 hybrid plant derived from the F1 hybrid seed is exhibits shatter resistance, the method comprising cross pollinating the identified plant or progeny thereof of claim 1 with a second plant, wherein the second plant lacks the at least one allele of the at least one QTL detected in the identified plant.

12. A method of marker assisted selection (MAS) of a quantitative trait locus (QTL) associated with shatter resistance in *Brassica*, the method comprising the steps of:
 (a) producing the *Brassica* plant according to claim 1;
 (b) crossing the *Brassica* plant with a different *Brassica* plant to produce progeny;
 (c) evaluating the progeny for the allele associated with the shatter resistance; and
 (d) selecting progeny plants that possess the allele.

13. The method of claim 12, wherein the *Brassica* plant of step (a) is a member of a segregating population.

14. The method of claim 12, wherein the marker assisted selection is performed using high throughput screening.

15. A method of producing a *Brassica* plant or germplasm that exhibits pod shatter resistance, the method comprising:
 a) isolating at least one nucleic acid from a *Brassica* plant selected from a population of *Brassica* plants;
 b) detecting by way of amplifying marker loci or portions thereof from the nucleic acid of a), thereby producing a plurality of amplicons for pod shatter resistance alleles located on maize chromosome 4 and further located within and including markers N05943-1-Q1 and N06675-1-Q1, wherein the amplicons comprise at least five alleles favorable for shatter resistance selected from the group consisting of a C at a position corresponding to 201 of SEQ ID NO: 17, a G at a position corresponding to 151 of SEQ ID NO: 15, an A at a position corresponding to 201 of SEQ ID NO: 25, an A at a position corresponding to 201 of SEQ ID NO: 23, an A at a position corresponding to 101 of SEQ ID NO: 26, an A at a position corresponding to 201 of SEQ ID NO: 22, an A at a position corresponding to 201 of SEQ ID NO: 30, a C at a position corresponding to 201 of SEQ ID NO: 32, a G at a position corresponding to 201 of SEQ ID NO: 37, and a T at a position corresponding to 501 of SEQ ID NO: 14;
 c) selecting a first plant from the population of a) based on the presence of the at least five alleles detected in b);
 d) crossing the first plant with a second plant, wherein the second maize plant does not have in its genome at least one of the at least five alleles favorable for shatter resistance; and
 e) producing a progeny plant having improved pod-shatter resistance from the cross of d) wherein said progeny plant comprises the at least five alleles favorable for shatter resistance detected in b).

* * * * *